(12) United States Patent
Katz et al.

(10) Patent No.: US 12,134,611 B2
(45) Date of Patent: Nov. 5, 2024

(54) COMPOUNDS AND COMPOSITIONS FOR TREATING CONDITIONS ASSOCIATED WITH NLRP ACTIVITY

(71) Applicant: Novartis AG, Basel (CH)

(72) Inventors: Jason Katz, Newton, MA (US); William Roush, Boston, MA (US); Hans Martin Seidel, Concord, MA (US); Dong-Ming Shen, Edison, NJ (US); Shankar Venkatraman, Lansdale, PA (US)

(73) Assignee: Novartis AG, Basel (CH)

( * ) Notice: Subject to any disclaimer, the term of this patent is extended or adjusted under 35 U.S.C. 154(b) by 640 days.

(21) Appl. No.: 17/292,887

(22) PCT Filed: Nov. 11, 2019

(86) PCT No.: PCT/US2019/060775
§ 371 (c)(1),
(2) Date: May 11, 2021

(87) PCT Pub. No.: WO2020/102100
PCT Pub. Date: May 22, 2020

(65) Prior Publication Data
US 2023/0024859 A1    Jan. 26, 2023

Related U.S. Application Data

(60) Provisional application No. 62/760,244, filed on Nov. 13, 2018, provisional application No. 62/760,248, filed on Nov. 13, 2018, provisional application No. 62/760,279, filed on Nov. 13, 2018, provisional application No. 62/795,373, filed on Jan. 22, 2019, provisional application No. 62/796,361, filed on Jan. 24, 2019, provisional application No. 62/796,356, filed on Jan. 24, 2019.

(51) Int. Cl.
| | |
|---|---|
| *C07D 417/12* | (2006.01) |
| *A61K 45/06* | (2006.01) |
| *A61P 35/00* | (2006.01) |
| *C07D 275/06* | (2006.01) |
| *C07D 279/02* | (2006.01) |
| *C07D 281/10* | (2006.01) |
| *C07D 285/18* | (2006.01) |
| *C07D 285/36* | (2006.01) |
| *C07D 513/04* | (2006.01) |
| *C07D 513/10* | (2006.01) |

(52) U.S. Cl.
CPC .......... *C07D 417/12* (2013.01); *A61K 45/06* (2013.01); *A61P 35/00* (2018.01); *C07D 275/06* (2013.01); *C07D 279/02* (2013.01); *C07D 281/10* (2013.01); *C07D 285/18* (2013.01); *C07D 285/36* (2013.01); *C07D 513/04* (2013.01); *C07D 513/10* (2013.01)

(58) Field of Classification Search
CPC .. C07D 415/12; C07D 275/06; C07D 279/02; C07D 281/10; C07D 285/18; C07D 513/04; C07D 513/10; A61P 35/00
See application file for complete search history.

(56) References Cited

U.S. PATENT DOCUMENTS

2020/0216389 A1    7/2020    Miller et al.

FOREIGN PATENT DOCUMENTS

| | | |
|---|---|---|
| EP | 0552553 A1 | 7/1993 |
| WO | 9957101 A1 | 11/1999 |
| WO | 2005009973 A1 | 2/2005 |
| WO | 2008114023 A2 | 9/2008 |
| WO | 2016/131098 A1 | 8/2016 |
| WO | 2017/184604 A1 | 10/2017 |
| WO | 2017184623 A1 | 10/2017 |
| WO | 2017184746 A1 | 10/2017 |
| WO | 2017218617 A1 | 12/2017 |
| WO | 2018136890 A1 | 7/2018 |
| WO | 2018225018 A1 | 12/2018 |
| WO | 2019/023145 A1 | 1/2019 |
| WO | 2019023147 A1 | 1/2019 |
| WO | 2020018975 A1 | 1/2020 |
| WO | 2020035466 A1 | 2/2020 |
| WO | 2020053282 A1 | 3/2020 |
| WO | 2020150674 A1 | 7/2020 |
| WO | 2020254697 A1 | 12/2020 |

OTHER PUBLICATIONS

Nandi et al., "Direct Synthesis of N-Acyl Sulfonimidamides and N-Sufonimidoyl Amidines from Sulfonimidoyl Azides," Adv Synth and Catal. 360:2465-9 (2018).

(Continued)

*Primary Examiner* — Alicia L Otton

(74) *Attorney, Agent, or Firm* — Timothy P. O'Dea

(57) ABSTRACT

In one aspect, compounds of Formula AA, or a pharmaceutically acceptable salt thereof, are featured or a pharmaceutically acceptable salt thereof, wherein the variables shown in Formula A can be as defined anywhere herein.

(AA)

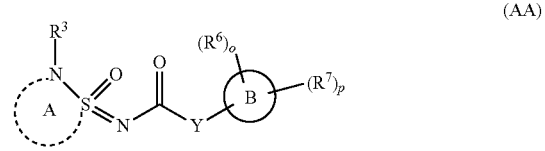

20 Claims, 5 Drawing Sheets

(56) References Cited

OTHER PUBLICATIONS

Izzo et al., "Exploration of Novel Chemical Space: Synthesis and in vitro Evaluation of N-Functionalized Tertiary Sulfonimidamides," Chemistry. A European Journal 24(37):9295-304 (2018).
Toth et al., "Sulfonimidamide analogs of oncolytic sulfonylureas," J. Med. Chem. 40(6):1018-25 (1997).
International Search Report and Written Opinion for PCT/US2019/060775, mailed Feb. 18, 2020 (10 pages).
Wakchaure, et al., Synthesis of Vinyl- and Aryl-Acyl Sulfonimidamides Through Pd-Catalyzed Carbonylation Using Mo(CO)6 as ex situ CO Source, European Journal of Organic Chemistry, 2015, 213-219.

FIG. 5

COMPOUNDS AND COMPOSITIONS FOR TREATING CONDITIONS ASSOCIATED WITH NLRP ACTIVITY

TECHNICAL FIELD

This disclosure features chemical entities (e.g., a compound that modulates (e.g., antagonizes) NLRP3, or a pharmaceutically acceptable salt, and/or hydrate, and/or cocrystal, and/or drug combination of the compound) that are useful, e.g., for treating a condition, disease or disorder in which a decrease or increase in NLRP3 activity (e.g., an increase, e.g., a condition, disease or disorder associated with NLRP3 signaling) contributes to the pathology and/or symptoms and/or progression of the condition, disease or disorder in a subject (e.g., a human). This disclosure also features compositions as well as other methods of using and making the same. The present disclosure also relates to, in part, methods and compositions for treating anti-TNFα resistance in a subject with an NLRP3 antagonist. The present disclosure also relates, in part, to methods, combinations and compositions for treating TFNα related diseases and anti-TNFα resistance in a subject that include administration of an NLRP3 antagonist, an NLRP3 antagonist and an anti-TNFα agent, or a composition encompassing an NLRP3 antagonist and an anti-TNFα agent.

BACKGROUND

The NLRP3 inflammasome is a component of the inflammatory process and its aberrant activation is pathogenic in inherited disorders such as the cryopyrin associated periodic syndromes (CAPS). The inherited CAPS Muckle-Wells syndrome (MWS), familial cold autoinflammatory syndrome (FCAS) and neonatal onset multi-system inflammatory disease (NOMID) are examples of indications that have been reported to be associated with gain of function mutations in NLRP3.

NLRP3 can form a complex and has been implicated in the pathogenesis of a number of complex diseases, including but not limited to metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as Osteoarthritis, osteoporosis and osteopetrosis disorders eye disease, such as glaucoma and macular degeneration, diseased caused by viral infection such as HIV and AIDS, autoimmune disease such as Rheumatoid Arthritis, Systemic Lupus Erythematosus, Autoimmune Thyroiditis, Addison's disease, pernicious anemia, cancer and aging.

In light of the above, it would be desirable to provide compounds that modulate (e.g., antagonize) NLRP3.

Several patients having inflammatory or autoimmune diseases are treated with anti-TNFα agents. A subpopulation of such patients develop resistance to treatment with the anti-TNFα agents. It is desirable to develop methods for reducing a patient's resistance to anti-TNFα agents. In light of the this, it would also be desirable to provide alternative therapies for treating inflammatory or autoimmune diseases (for example NLRP3 inflammasome inhibitors) to avoid or minimise the use of anti-TNFα agents.

Intestinal bowel disease (IBD), encompassing Ulcerative Colitis (UC) and Crohn's disease (CD), are chronic diseases characterized by barrier dysfunction and uncontrolled inflammation and mucosal immune reactions in the gut. A number of inflammatory pathways have been implicated in the progression of IBD, and anti-inflammatory therapy such as tumor necrosis factor-alpha (TNF-α) blockade has shown efficacy in the clinic (Rutgeerts P et al *N Engl J Med* 2005; 353:2462-76). Anti-TNFα therapies, however, do not show complete efficacy, however, other cytokines such as IL-10, IL-6, IL-12, IL-18, IL-21, and IL-23 have been shown to drive inflammatory disease pathology in IBD (Neurath M F *Nat Rev Immunol* 2014; 14; 329-42). IL-1β and IL-18 are produced by the NLRP3 inflammasome in response to pathogenic danger signals, and have been shown to play a role in IBD. Anti-IL-1β therapy is efficacious in patients with IBD driven by genetic mutations in CARD8 or IL-10R (Mao L et al, *J Clin Invest* 2018; 238:1793-1806, Shouval D S et al, *Gastroenterology* 2016; 151:1100-1104), TL-18 genetic polymorphisms have been linked to UC (Kanai T et al, *Curr Drug Targets* 2013; 14:1392-9), and NLRP3 inflammasome inhibitors have been shown to be efficacious in murine models of IBD (Perera A P et al, *Sci Rep* 2018; 8:8618). Resident gut immune cells isolated from the lamina propria of IBD patients can produce IL-10, either spontaneously or when stimulated by LPS, and this IL-1β production can be blocked by the ex vivo addition of a NLRP3 antagonist. Based on strong clinical and preclinical evidence showing that inflammasome-driven IL-1β and IL-18 play a role in IBD pathology, it is clear that NLRP3 inflammasome inhibitors could be an efficacious treatment option for UC, Crohn's disease, or subsets of IBD patients. These subsets of patients could be defined by their peripheral or gut levels of inflammasome related cytokines including IL-10, IL-6, and IL-18, by genetic factors that pre-dispose IBD patients to having NLRP3 inflammasome activation such as mutations in genes including ATG16L1, CARD8, IL-10R, or PTPN2 (Saitoh T et al, *Nature* 2008; 456:264, Spalinger M R, *Cell Rep* 2018; 22:1835), or by other clinical rationale such as non-response to TNF therapy.

Though anti-TNF therapy is an effective treatment option for Crohn's disease, 40% of patients fail to respond. One-third of non-responsive CD patients fail to respond to anti-TNF therapy at the onset of treatment, while another third lose response to treatment over time (secondary non-response). Secondary non-response can be due to the generation of anti-drug antibodies, or a change in the immune compartment that desensitizes the patient to anti-TNF (Ben-Horin S et al, *Autoimmun Rev* 2014; 13:24-30, Steenholdt C et al *Gut* 2014; 63:919-27). Anti-TNF reduces inflammation in IBD by causing pathogenic T cell apoptosis in the intestine, therefore eliminating the T cell mediated inflammatory response (Van den Brande et al *Gut* 2007:56:509-17). There is increased NLRP3 expression and increased production of IL-1β in the gut of TNF-non-responsive CD patients (Leal R F et al *Gut* 2015; 64:233-42) compared to TNF-responsive patients, suggesting NLRP3 inflammasome pathway activation. Furthermore, there is increased expression of TNF-receptor 2 (TNF-R2), which allows for TNF-mediated proliferation of T cells (Schmitt H et al *Gut* 2018; 0:1-15). IL-1β signaling in the gut promotes T cell differentiation toward Th1/17 cells which can escape anti-TNF-α mediated apoptosis. It is therefore likely that NLRP3 inflammasome activation can cause non-responsiveness in CD patients to anti-TNF-α therapy by sensitizing pathogenic T cells in the gut to anti-TNF-α mediated apoptosis. Experimental data from immune cells isolated from the gut of TNF-resistant Crohn's patients show that these cells spontaneously release IL-10, which can be inhibited by the addition of an NLRP3 antagonist. NLRP3 inflammasome antagonists—in part by blocking IL-16 secretion—would be expected to inhibit the mechanism leading to anti-TNF non-responsiveness, re-sensitizing the patient to anti-TNF therapy. In IBD patients who are naive to anti-TNF therapy, treatment with an NLRP3 antagonist would be expected to prevent primary- and secondary-non responsiveness by blocking the mechanism leading to non-response.

NLRP3 antagonists that are efficacious locally in the gut can be efficacious drugs to treat IBD; in particular in the treatment of TNF-resistant CD alone or in combination with anti-TNF therapy. Systemic inhibition of both IL-1β and TNF-α has been shown to increase the risk of opportunistic infections (Genovese M C et al, Arthritis Rheum 2004; 50:1412), therefore, only blocking the NLRP3 inflammasome at the site of inflammation would reduce the infection risk inherent in neutralizing both IL-1β and TNF-α. NLRP3 antagonists that are potent in NLRP3-inflammasome driven cytokine secretion assays in cells, but have low permeability in vitro in a permeability assay such as an MDCK assay, have poor systemic bioavailability in a rat or mouse pharmacokinetic experiment, but high levels of compound in the colon and/or small intestine could be a useful therapeutic option for gut restricted purposes.

In light of the above, the present invention also provides alternative therapies for the treatment of inflammatory or autoimmune diseases, including IBD, that solves the above problems associated with anti-TNFα agents.

SUMMARY

This disclosure features chemical entities (e.g., a compound that modulates (e.g., antagonizes) NLRP3, or a pharmaceutically acceptable salt, and/or hydrate, and/or cocrystal, and/or drug combination of the compound) that are useful, e.g., for treating a condition, disease or disorder in which a decrease or increase in NLRP3 activity (e.g., an increase, e.g., a condition, disease or disorder associated with NLRP3 signaling).

In some embodiments, provided herein is a compound of Formula AA

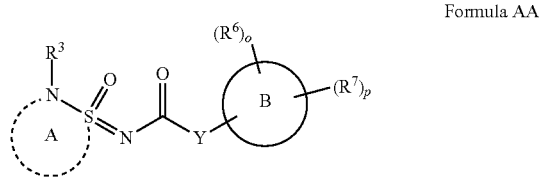

Formula AA or a pharmaceutically acceptable salt thereof, wherein the variables in Formula AA can be as defined anywhere herein.

This disclosure also features compositions as well as other methods of using and making the same.

The present invention is also relates to the Applicant's discovery that inhibition of NLRP3 inflammasomes can increase a subject's sensitivity to an anti-TNFα agent or can overcome resistance to an anti-TNFα agent in a subject, or indeed provide an alternative therapy to anti-TNFα agents.

Provided herein are methods of treating a subject that include: (a) identifying a subject having a cell that has an elevated level of NLRP3 inflammasome activity and/or expression as compared to a reference level; and (b) administering to the identified subject a therapeutically effective amount of a compound of Formula I or a pharmaceutically acceptable salt, solvate, or co-crystal thereof.

Provided herein are methods for the treatment of inflammatory or autoimmune disease including IBD, such as UC and CD in a subject in need thereof, comprising administering to said subject a therapeutically effective amount a compound for Formula I or a pharmaceutically acceptable salt, solvate, or co-crystal thereof, wherein the NLRP3 antagonist is a gut-targeted NLRP3 antagonist.

Provided herein are methods of treating a subject in need thereof, that include: (a) identifying a subject having resistance to an anti-TNFα agent; and (b) administering a treatment comprising a therapeutically effective amount of a compound for Formula I, or a pharmaceutically acceptable salt, solvate, or co-crystal thereof to the identified subject.

Provided herein are methods of treating a subject in need thereof, that include: administering a treatment comprising a therapeutically effective amount of a compound for Formula I or a pharmaceutically acceptable salt, solvate, or co-crystal thereof to a subject identified as having resistance to an anti-TNFα agent.

Provided herein are methods of selecting a treatment for a subject in need thereof, that include: (a) identifying a subject having resistance to an anti-TNFα agent; and (b) selecting for the identified subject a treatment comprising a therapeutically effective amount of a compound for Formula I or a pharmaceutically acceptable salt, solvate, or co-crystal thereof.

Provided herein are methods of selecting a treatment for a subject in need thereof, that include selecting a treatment comprising a therapeutically effective amount of a compound for Formula I or a pharmaceutically acceptable salt, solvate, or co-crystal thereof for a subject identified as having resistance to an anti-TNFα agent.

In some embodiments of any of the methods described herein, the treatment further includes a therapeutically effective amount of an anti-TNFα agent, in addition to the NLRP3 antagonist.

An "antagonist" of NLRP3 includes compounds that inhibit the ability of NLRP3 to induce the production of IL-1β and/or IL-18 by directly binding to NLRP3, or by inactivating, destabilizing, altering distribution, of NLRP3 or otherwise.

In one aspect, pharmaceutical compositions are featured that include a chemical entity described herein (e.g., a compound described generically or specifically herein or a pharmaceutically acceptable salt thereof or compositions containing the same) and one or more pharmaceutically acceptable excipients.

In one aspect, methods for modulating (e.g., agonizing, partially agonizing, antagonizing) NLRP3 activity are featured that include contacting NLRP3 with a chemical entity described herein (e.g., a compound described generically or specifically herein or a pharmaceutically acceptable salt thereof or compositions containing the same). Methods include in vitro methods, e.g., contacting a sample that includes one or more cells comprising NLRP3, as well as in vivo methods.

In a further aspect, methods of treatment of a disease in which NLRP3 signaling contributes to the pathology and/or symptoms and/or progression of the disease are featured that include administering to a subject in need of such treatment an effective amount of a chemical entity described herein (e.g., a compound described generically or specifically herein or a pharmaceutically acceptable salt thereof or compositions containing the same).

In a further aspect, methods of treatment are featured that include administering to a subject a chemical entity described herein (e.g., a compound described generically or specifically herein or a pharmaceutically acceptable salt thereof or compositions containing the same), wherein the chemical entity is administered in an amount effective to treat a disease in which NLRP3 signaling contributes to the pathology and/or symptoms and/or progression of the disease, thereby treating the disease.

Embodiments can include one or more of the following features.

The chemical entity can be administered in combination with one or more additional therapies with one or more agents suitable for the treatment of the condition, disease or disorder.

Examples of the indications that may be treated by the compounds disclosed herein include but are not limited to metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as osteoarthritis, osteoporosis and osteopetrosis disorders, eye disease, such as glaucoma and macular degeneration, diseases caused by viral infection such as HIV and AIDS, autoimmune disease such as rheumatoid arthritis, systemic Lupus erythematosus, autoimmune thyroiditis; Addison's disease, pernicious anemia, cancer and aging.

The methods can further include identifying the subject.

Other embodiments include those described in the Detailed Description and/or in the claims.

Additional Definitions

To facilitate understanding of the disclosure set forth herein, a number of additional terms are defined below. Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs. Each of the patents, applications, published applications, and other publications that are mentioned throughout the specification and the attached appendices are incorporated herein by reference in their entireties.

As used herein, the term "NLRP3" is meant to include, without limitation, nucleic acids, polynucleotides, oligonucleotides, sense and antisense polynucleotide strands, complementary sequences, peptides, polypeptides, proteins, homologous and/or orthologous NLRP3 molecules, isoforms, precursors, mutants, variants, derivatives, splice variants, alleles, different species, and active fragments thereof.

The term "acceptable" with respect to a formulation, composition or ingredient, as used herein, means having no persistent detrimental effect on the general health of the subject being treated.

"API" refers to an active pharmaceutical ingredient.

The terms "effective amount" or "therapeutically effective amount," as used herein, refer to a sufficient amount of a chemical entity (e.g., a compound exhibiting activity as a modulator of NLRP3, or a pharmaceutically acceptable salt and/or hydrate and/or cocrystal thereof;) being administered which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is determined using any suitable technique, such as a dose escalation study.

The term "excipient" or "pharmaceutically acceptable excipient" means a pharmaceutically-acceptable material, composition, or vehicle, such as a liquid or solid filler, diluent, carrier, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, e.g., *Remington: The Science and Practice of Pharmacy*, 21st ed.; Lippincott Williams & Wilkins: Philadelphia, PA, 2005; *Handbook of Pharmaceutical Excipients*, 6th ed.; Rowe et al., Eds.; The Pharmaceutical Press and the American Pharmaceutical Association: 2009; *Handbook of Pharmaceutical Additives*, 3rd ed.; Ash and Ash Eds.; Gower Publishing Company: 2007; *Pharmaceutical Preformulation and Formulation*, 2nd ed.; Gibson Ed.; CRC Press LLC: Boca Raton, FL, 2009.

The term "pharmaceutically acceptable salt" may refer to pharmaceutically acceptable addition salts prepared from pharmaceutically acceptable non-toxic acids including inorganic and organic acids. In certain instances, pharmaceutically acceptable salts are obtained by reacting a compound described herein, with acids such as hydrochloric acid, hydrobromic acid, sulfuric acid, nitric acid, phosphoric acid, methanesulfonic acid, ethanesulfonic acid, p-toluenesulfonic acid, salicylic acid and the like. The term "pharmaceutically acceptable salt" may also refer to pharmaceutically acceptable addition salts prepared by reacting a compound having an acidic group with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like, or by other methods previously determined. The pharmacologically acceptable salt s not specifically limited as far as it can be used in medicaments. Examples of a salt that the compounds described hereinform with a base include the following: salts thereof with inorganic bases such as sodium, potassium, magnesium, calcium, and aluminum; salts thereof with organic bases such as methylamine, ethylamine and ethanolamine; salts thereof with basic amino acids such as lysine and ornithine; and ammonium salt. The salts may be acid addition salts, which are specifically exemplified by acid addition salts with the following: mineral acids such as hydrochloric acid, hydrobromic acid, hydroiodic acid, sulfuric acid, nitric acid, and phosphoric acid:organic acids such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; acidic amino acids such as aspartic acid and glutamic acid.

The term "pharmaceutical composition" refers to a mixture of a compound described herein with other chemical components (referred to collectively herein as "excipients"), such as carriers, stabilizers, diluents, dispersing agents, suspending agents, and/or thickening agents. The pharmaceutical composition facilitates administration of the compound to an organism. Multiple techniques of administering a compound exist in the art including, but not limited to: rectal, oral, intravenous, aerosol, parenteral, ophthalmic, pulmonary, and topical administration.

The term "subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

As used herein, the term "prevent", "preventing" or "prevention" in connection to a disease or disorder refers to the prophylactic treatment of a subject who is at risk of developing a condition (e.g., specific disease or disorder or clinical symptom thereof) resulting in a decrease in the probability that the subject will develop the condition.

The terms "treat", "treating", and "treatment", in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof.

The terms "hydrogen" and "H" are used interchangeably herein.

The term "halo" refers to fluoro (F), chloro (Cl), bromo (Br), or iodo (I).

The term "alkyl" refers to a hydrocarbon chain that may be a straight chain or branched chain, saturated or unsaturated, containing the indicated number of carbon atoms. For example, $C_{1-10}$ indicates that the group may have from 1 to 10 (inclusive) carbon atoms in it. Non-limiting examples include methyl, ethyl, iso-propyl, tert-butyl, n-hexyl.

The term "haloalkyl" refers to an alkyl, in which one or more hydrogen atoms is/are replaced with an independently selected halo.

The term "alkoxy" refers to an —O-alkyl radical (e.g., —OCH$_3$).

The term "carbocyclic ring" as used herein includes an aromatic or nonaromatic cyclic hydrocarbon group having 3 to 10 carbons, such as 3 to 8 carbons, such as 3 to 7 carbons, which may be optionally substituted. Examples of carbocyclic rings include five-membered, six-membered, and seven-membered carbocyclic rings.

The term "heterocyclic ring" refers to an aromatic or nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, or 3 atoms of each ring may be substituted by a substituent. Examples of heterocyclic rings include five-membered, six-membered, and seven-membered heterocyclic rings.

The term "cycloalkyl" as used herein includes an nonaromatic cyclic, bicyclic, fused, or spiro hydrocarbon radical having 3 to 10 carbons, such as 3 to 8 carbons, such as 3 to 7 carbons, wherein the cycloalkyl group which may be optionally substituted. Examples of cycloalkyls include five-membered, six-membered, and seven-membered rings. Examples include cyclopropyl, cyclobutyl, cyclopentyl, cyclopentenyl, cyclohexyl, cyclohexenyl, cycloheptyl, and cyclooctyl.

The term "heterocycloalkyl" refers to an nonaromatic 5-8 membered monocyclic, 8-12 membered bicyclic, or 11-14 membered tricyclic ring, fused, or spiro system radical having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, or 3 atoms of each ring may be substituted by a substituent. Examples of heterocycloalkyls include five-membered, six-membered, and seven-membered heterocyclic rings. Examples include piperazinyl, pyrrolidinyl, dioxanyl, morpholinyl, tetrahydrofuranyl, and the like.

The term "aryl" is intended to mean an aromatic ring radical containing 6 to 10 ring carbons. Examples include phenyl and naphthyl.

The term "heteroaryl" is intended to mean an aromatic ring system containing 5 to 14 aromatic ring atoms that may be a single ring, two fused rings or three fused rings wherein at least one aromatic ring atom is a heteroatom selected from, but not limited to, the group consisting of O, S and N. Examples include furanyl, thienyl, pyrrolyl, imidazolyl, oxazolyl, thiazolyl, isoxazolyl, pyrazolyl, isothiazolyl, oxadiazolyl, triazolyl, thiadiazolyl, pyridinyl, pyrazinyl, pyrimidinyl, pyridazinyl, triazinyl and the like. Examples also include carbazolyl, quinolizinyl, quinolinyl, isoquinolinyl, cinnolinyl, phthalazinyl, quinazolinyl, quinoxalinyl, triazinyl, indolyl, isoindolyl, indazolyl, indolizinyl, purinyl, naphthyridinyl, pteridinyl, carbazolyl, acridinyl. phenazinyl, phenothiazinyl, phenoxazinyl, benzoxazolyl, benzothiazolyl, 1H-benzimidazolyl, imidazopyridinyl, benzothienyl, benzofuranyl, isobenzofuran and the like.

The term "hydroxy" refers to an OH group.

The term "amino" refers to an NH$_2$ group.

The term "oxo" refers to O. By way of example, substitution of a CH$_2$ group with oxo gives a C=O group.

As used herein, the terms "the ring A" or "A" are used interchangeably to denote

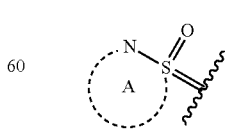

in formula AA wherein the bond that is shown as being broken by the wavy line ∫ connects A to the NC(O) group of Formula AA.

As used herein, the terms "the ring B" or "B" are used interchangeably to denote

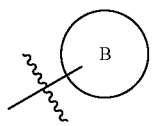

in formula AA wherein the bond that is shown as being broken by the wavy line / connects B to the YC(O) group of Formula AA.

As used herein, the term "the substituted ring B" is used to denote

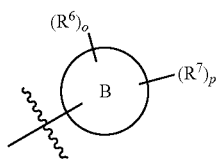

in formula AA, wherein the bond that is shown as being broken by the wavy line / connects B to the YC(O) group of Formula AA.

As used herein, the recitation "S(O$_2$)", alone or as part of a larger recitation, refers to the group

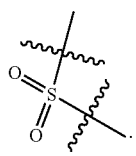

In addition, atoms making up the compounds of the present embodiments are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

The scope of the compounds disclosed herein includes tautomeric form of the compounds. Thus, by way of example, a compound that is represented as containing the moiety

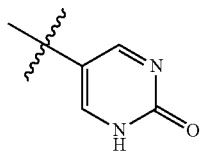 [SMILES: *c1cnc(=O)[nH]c1]

is also intended to include the tautomeric form containing the moiety

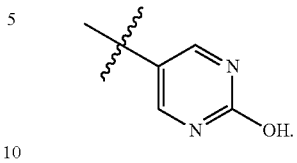

Non-limiting exemplified compounds of the formulae described herein include a stereogenic sulfur atom and optionally one or more stereogenic carbon atoms. This disclosure provides examples of stereoisomer mixtures (e.g., racemic mixture of enantiomers; mixture of diastereomers). This disclosure may describe and exemplify methods for separating individual components of said stereoisomer mixtures (e.g., resolving the enantiomers of a racemic mixture). In cases of compounds containing a stereogenic sulfur atom, resolved enantiomers are graphically depicted using one of the two following formats: formulas A/B (hashed and solid wedge three-dimensional representation); and formula C ("flat structures with *-labelled stereogenic sulfur).

Formula A

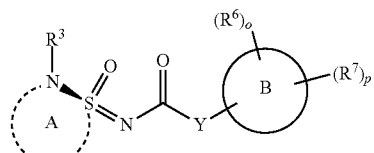

Formula B

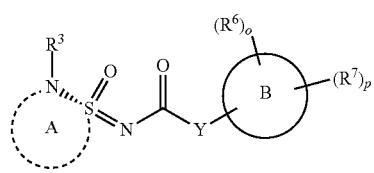

Formula C

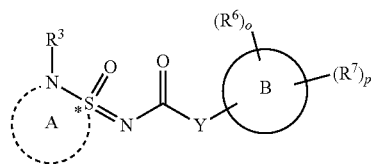

In reaction schemes showing resolution of a racemic mixture, Formulas A/B and C are intended only to convey that the constituent enantiomers were resolved in enantiopure pure form (about 98% ee or greater). The schemes that show resolution products using the formula A/B format are not intended to disclose or imply any correlation between absolute configuration and order of elution. Some of the compounds shown in the tables below are graphically represented using the formula A/B format.

The details of one or more embodiments of the invention are set forth in the accompanying drawings and the description below. Other features and advantages of the invention will be apparent from the description and drawings, and from the claims.

DESCRIPTION OF THE DRAWINGS

FIG. 5: Layout of the microplate to measure activity of compounds in the THP-1 stimulation assay.

DETAILED DESCRIPTION

Figure 1:
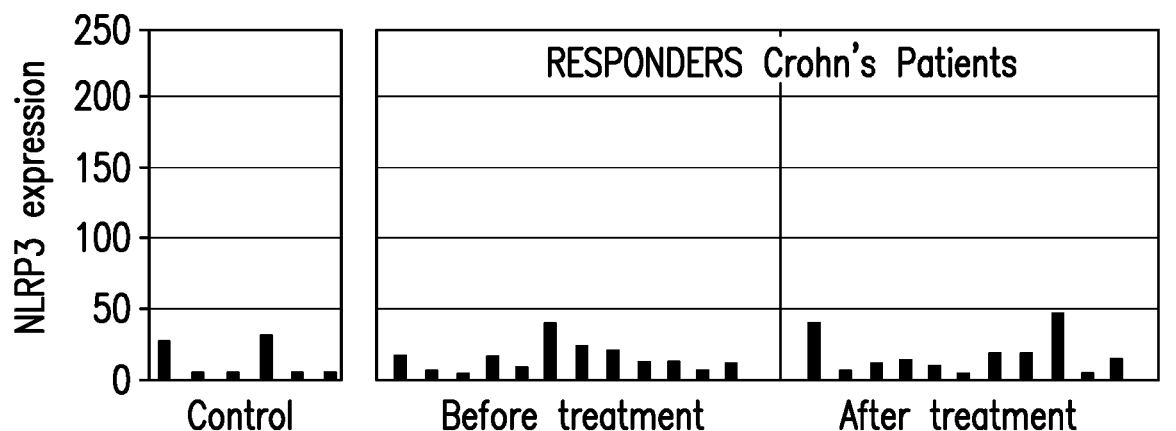
FIG. 1: Expression levels of RNA encoding NLRP3 in Crohn's Disease patients who are responsive and non-responsive to infliximab.
Figure 1:
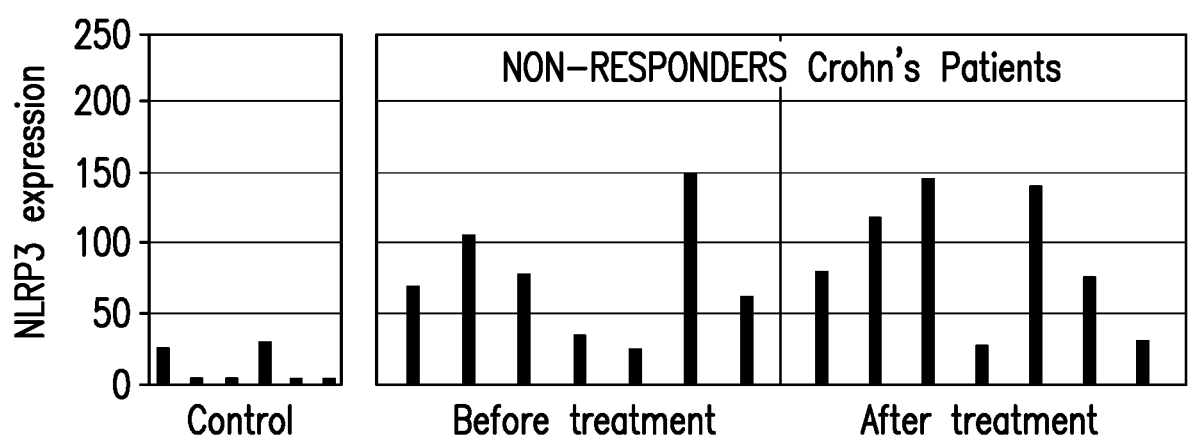

In some embodiments, provided herein is a compound of Formula AA

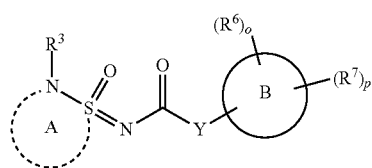

Formula AA wherein
o=1 or 2;
p=0, 1, 2, or 3;
Y is —$CR^{15}R^{15}$— or —$NR^{16}$—;
ring A is:
(i) a saturated or unsaturated monocyclic ring that includes from 5-8 ring atoms (inclusive of N—$R^3$ and S(O)); or
(ii) a saturated or unsaturated bicyclic or tricyclic ring that includes from 8-20 ring atoms (inclusive of N—$R^3$ and S(O)),
wherein the dotted, circular line connecting N—$R^3$ and S is a divalent group that includes from 3-6 ring atoms; wherein:
(a) from 0-2 of the divalent group's ring atoms are ring heteroatoms, which are each independently selected from the group consisting of O, N, NH, $NR^{13}$, S, S(O), and $S(O)_2$; and
(b) from 1-6 of the divalent group's ring atoms are ring carbon atoms, which are each independently selected from the group consisting of C, CH, $CH_2$, C(O), $CR^1$, $C(R^1)_2$, and $CHR^1$;
wherein:
(1) when ring A is a monocyclic ring, then each of the divalent group's 1-6 ring carbon atoms is independently selected from the group consisting of CH, $CH_2$, C(O), $CR^1$, $C(R^1)_2$, and $CHR^1$; and
(2) when ring A is a bicyclic or tricyclic ring, then (A) or (B) applies:
(A) two or three adjacent ring carbon atoms of the divalent group are each independently selected from the group consisting of C, CH, and $CR^1$, and are fused to a second ring that is selected from the group consisting of:
(a) $C_{6-10}$ aryl optionally substituted with from 1-5 independently selected $R^a$;
(b) heteroaryl including from 5-10 ring atoms, wherein from 1-4 ring atoms are each independently selected from the group consisting of N, $N(R^N)$, O, and S, wherein the heteroaryl is optionally substituted with from 1-3 independently selected $R^a$;
(c) $C_{3-10}$ cycloalkyl optionally substituted with from 1-4 independently selected $R^b$.
(d) heterocycloalkyl including from 3-10 ring atoms, wherein from 1-3 ring atoms are each independently selected from the group consisting of $N(R^N)$, O, and S, wherein the heterocycloalkyl is optionally substituted with from 1-4 independently selected $R^b$; or
(B) one of the divalent group's ring carbon atoms is C and is spiro-fused to a second ring that is selected from the group consisting of:
(a) $C_{3-10}$ cycloalkyl optionally substituted with from 1-4 independently selected $R^b$;
(b) heterocycloalkyl including from 3-10 ring atoms, wherein from 1-3 ring atoms are each independently selected from the group consisting of $N(R^N)$, O, and S, wherein the heterocycloalkyl is optionally substituted with from 1-4 independently selected $R^b$;
each $R^1$ is independently selected from the group consisting of: $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOC_1$-$C_6$ alkyl, NH—(C=$NR^{13}$)$NR^{11}R^{12}$, $CONR^8R^9$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $C_3$-$C_7$ cycloalkyl, and 3- to 7-membered heterocycloalkyl,
wherein the $C_1$-$C_6$ alkyl, $C_6$-$C_{10}$ aryl, 5- to 10-membered heteroaryl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO (5- to 10-membered heteroaryl), NHCO(3- to 7-membered heterocycloalkyl), and $NHCOC_2$-$C_6$ alkynyl;
wherein when $R^1$ is $C_3$-$C_7$ cycloalkyl, 3- to 7-membered heterocycloalkyl, $C_6$-$C_{10}$ aryl, or 5- to 10-membered heteroaryl, each $C_1$-$C_6$ alkyl substituent and each $C_1$-$C_6$ alkoxy substituent on $R^1$, when present, is further optionally independently substituted with one to three hydroxy, $C_1$-$C_6$ alkoxy, halo, $NR^8R^9$, or oxo;
wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) substituents on $R^1$ are optionally substituted with one or more substituents independently selected from halo, $C_1$-$C_6$ alkyl, and $OC_1$-$C_6$ alkyl;
each $R^a$ is independently selected from hydroxy, halo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, =$NR^{10}$, CN, $COOC_1$-$C_6$ alkyl, $OS(O_2)$ $C_6$-$C_{10}$ aryl, $S(O_2)C_6$-$C_{10}$ aryl, $C_6$-$C_{10}$ aryl, $OC_6$-$C_{10}$ aryl, 5- to 10-membered heteroaryl, $C_3$-$C_{10}$ cycloalkyl, 3- to 10-membered heterocycloalkyl, $CO_2H$, and $CONR^8R^9$,
wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents each independently selected from hydroxy, halo, $C_1$-$C_6$ alkyl, $C_{1\text{-}4}$ haloalkyl, $C_2$-$C_6$ alkenyl, $C_2$-$C_6$ alkynyl, $C_3$-$C_{10}$ cycloalkyl, 3- to 10-membered heterocycloalkyl, $C_1$-$C_6$ alkoxy, oxo, $NR^8R^9$, $=NR^{10}$, $COOC_1$-$C_6$ alkyl, $C_6$-$C_{10}$ aryl, $CO_2H$, and $CONR^8R^9$, each $R^b$ is independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, $=NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, $OC_6$-$C_{10}$ aryl, 5- to 10-membered heteroaryl, $C_3$-$C_{10}$ cycloalkyl, 3- to 10-membered heterocycloalkyl, $CO_2H$, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents each independently selected from hydroxy, halo, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, $=NR^{10}$, $COOC_1$-$C_6$ alkyl, $C_6$-$C_{10}$ aryl, $CO_2H$, and $CONR^8R^9$;

each $R^N$ is independently selected from hydrogen, $C_1$-$C_6$ alkyl, $(C=NR^{13})NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$;

wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl, or 3- to 7-membered heterocycloalkyl;

ring B is a 5-10-membered heteroaryl or a $C_6$-$C_{10}$ aryl;

$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_{10}$ cycloalkyl and 3- to 10-membered heterocycloalkyl, and a $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$;
wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;
OR
at least one pair of $R^6$ and $R^7$ on adjacent carbon atoms taken together with the carbon atoms to which each is attached form a $C_4$-$C_8$ carbocyclic ring or a 5- to 8-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$, each occurrence of $R^8$ and $R^9$ is independently selected from hydrogen, $C_1$-$C_6$ alkyl, $(C=NR^{13})NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$;

wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl, or 3- to 7-membered heterocycloalkyl; or $R^8$ and $R^9$ taken together with the nitrogen atom to which each is attached form a 3- to 7-membered ring optionally containing one or more additional heteroatoms;

$R^{10}$ is $C_1$-$C_6$ alkyl;

$R^{13}$ is $C_1$-$C_6$ alkyl, $C_6$-$C_{10}$ aryl, or 5- to 10-membered heteroaryl;

each of $R^{11}$ and $R^{12}$ at each occurrence is independently selected from hydrogen and $C_1$-$C_6$ alkyl;

$R^3$ is selected from hydrogen, cyano, hydroxy, $C_1$-$C_6$ alkoxy, $C_1$-$C_6$ alkyl, and

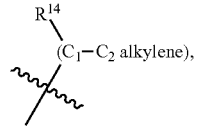

wherein the $C_1$-$C_2$ alkylene group is optionally substituted by oxo; $R^{14}$ is hydrogen, $C_1$-$C_6$ alkyl, 5- to 10-membered monocyclic or bicyclic heteroaryl or $C_6$-$C_{10}$ monocyclic or bicyclic aryl, wherein each $C_1$-$C_6$ alkyl, aryl, or heteroaryl is optionally independently substituted with 1 or 2 $R^6$;

each occurrence of $R^5$ is independently selected from hydrogen and $C_1$-$C_6$ alkyl; and $R^{16}$ is selected from hydrogen and $C_1$-$C_6$ alkyl;

or a pharmaceutically acceptable salt thereof.

In some embodiments the variables shown in the formulae herein are as follows:

The Ring A and Substitutions on the Ring A

In some embodiments, ring A is a saturated or unsaturated bicyclic or tricyclic ring that includes from 6-14 ring atoms.

In some embodiments, ring A is a bicyclic or tricyclic ring that includes from 8-14 ring atoms.

In certain embodiments (when ring A is a saturated or unsaturated bicyclic or tricyclic ring that includes from 6-14 (e.g., 8-14) ring atoms), (A) applies.

In certain embodiments (when ring A is a saturated or unsaturated bicyclic or tricyclic ring that includes from 6-14 (e.g., 8-14) ring atoms (e.g., when (A) applies), ring A has Formula (A1):

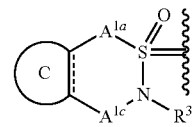

(A1)

wherein:
⫽ represents a single bond or a double bond;
ring C is selected from the group consisting of:
(a) $C_{6\text{-}10}$ aryl optionally substituted with from 1-5 independently selected $R^a$;
(b) heteroaryl including from 5-10 ring atoms, wherein from 1-4 ring atoms are each independently selected from the group consisting of N, N($R^N$), O, and S, wherein the heteroaryl is optionally substituted with from 1-3 independently selected $R^a$;

(c) $C_{3-10}$ cycloalkyl optionally substituted with from 1-4 independently selected $R^b$; and (d) heterocycloalkyl including from 3-10 ring atoms, wherein from 1-3 ring atoms are each independently selected from the group consisting of N($R^N$), O, and S, wherein the heterocycloalkyl is optionally substituted with from 1-4 independently selected $R^b$; and each of $A^{1a}$ and $A^{1c}$ is independently selected from: a bond, $CH_2$, $CHR^1$, $C(R^1)_2$, $C(O)$, N, NH, $NR^{13}$, O, $S(O)_2$, and $A^{1d}$-$A^{1e}$-$A^{1f}$-;

provided that one or more of $A^{1a}$ and $A^{1e}$ is other than a bond;

wherein each of $A^{1d}$, $A^{1e}$, and $A^{1f}$ is independently a bond, $CH_2$, $CHR^1$, $C(R^1)_2$, $C(O)$, $S(O)_2$, NH, $NR^{13}$, and O, provided that from 2-3 of $A^{1d}$, $A^{1e}$, and $A^{1f}$ are other than a bond, and provided that $A^{1d}$ and $A^{1e}$ are not both O or not both $S(O)_2$, and $A^{1e}$ and $A^{1f}$ are not both O or not both $S(O)_2$.

In some embodiments of Formula (A1), $A^1$a is selected from a bond, $CH_2$, $CHR^1$, $C(R^1)_2$, and $A^{1d}$-$A^{1e}$-$A^{1f}$.

In certain of the foregoing embodiments, each of Aid, $A^{1e}$, and $A^{1f}$ is independently selected from a bond, $CH_2$, $CHR^1$, and $C(R^1)_2$.

As a non-limiting example, each of Aid, $A^{1e}$, and $A^{1f}$ can be independently selected from a bond and $CH_2$.

In certain embodiments of Formula (A1), $A^{1a}$ is a bond.

In certain embodiments of Formula (A1), $A^{1a}$ is selected from $CH_2$, $CHR^1$, and, $C(R^1)_2$.

In certain embodiments of Formula (A1), $A^{1a}$ is $A^{1d}$-$A^{1e}$-$A^{1f}$.

In certain of the foregoing embodiments, one of $A^{1d}$, $A^{1e}$, and $A^{1f}$ is a bond.

In certain embodiments (when $A^1$a is $A^{1d}$-$A^{1e}$-$A^{1f}$), one of $A^{1d}$, $A^{1e}$, and $A^{1f}$ is selected from $CH_2$, $CHR^1$, and, $C(R^1)_2$.

As a non-limiting example of the foregoing embodiments, one of $A^{1d}$, $A^{1e}$, and $A^{1f}$ can be a bond; and each of the remaining $A^{1d}$, $A^{1e}$, and $A^{1f}$ can be $CH_2$.

In some embodiments of Formula (A1), $A^{1e}$ is selected from the group consisting of: $CH_2$, $CHR^1$, $C(R^1)_2$, $C(O)$, $S(O)_2$, and $A^{1d}$-$A^{1e}$-$A^{1f}$.

In certain embodiments of Formula (A1), $A^{1c}$ is $C(O)$.

In certain embodiments of Formula (A1), $A^{1c}$ is selected from the group consisting of: $CH_2$, $CHR^1$, and $C(R^1)_2$.

In certain embodiments of Formula (A1), $A^{1e}$ is $A^{1d}$-$A^{1e}$-$A^{1f}$.

In certain of the foregoing embodiments, each of $A^{1d}$, $A^{1e}$, and $A^{1f}$ is independently selected from a bond, $C(O)$, NH, $NR^{13}$, $CH_2$, $CHR^1$, and $C(R^1)_2$.

In certain of the foregoing embodiments, each of $A^{1d}$, $A^{1e}$, and $A^{1f}$ can be independently selected from a bond, $C(O)$, and $CH_2$.

In certain embodiments, one of $A^{1d}$, $A^{1e}$, and $A^{1f}$ is $C(O)$.

In some embodiments of Formula (A1), $A^{1a}$ is a bond; and $A^{1c}$ is selected from $CH_2$, $CHR^1$, $C(R^1)_2$, $C(O)$, and $A^{1d}$-$A^{1e}$-$A^{1f}$.

In certain of the foregoing embodiments, $A^{1e}$ is $C(O)$.

In certain other embodiments (when $A^{1a}$ is a bond; and $A^{1e}$ is selected from $CH_2$, $CHR^1$, $C(R^1)_2$, $C(O)$, and $A^{1d}$-$A^{1e}$-$A^{1f}$), $A^{1c}$ is $CH_2$, $CHR^1$, or $C(R^1)_2$ (e.g., $A^{1e}$ is $CH_2$).

In certain embodiments (when $A^{1a}$ is a bond; and $A^{1c}$ is selected from $CH_2$, $CHR^1$, $C(R^1)_2$, $C(O)$, and $A^{1d}$-$A^{1e}$-$A^{1f}$), ring A is selected from:

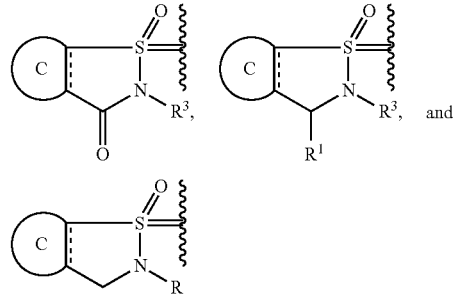

(e.g., $R^3$ is H or $C_{1-3}$ alkyl (e.g., H or methyl)).

As a non-limiting example of the foregoing embodiments, ring A is:

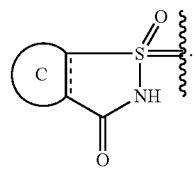

In certain embodiments (when $A^{1a}$ is a bond; and $A^{1c}$ is selected from $CH_2$, $CHR^1$, $C(R^1)_2$, $C(O)$, and $A^{1d}$-$A^{1e}$-$A^{1f}$), $A^{1c}$ is $A^{1d}$-$A^{1e}$-$A^{1f}$, wherein one of Aid, $A^{1e}$, and $A^{1f}$ is $C(O)$ or $CH_2$ (e.g., $A^{1d}$ is $C(O)$; or $A^{1d}$ is $CH_2$).

In certain of the foregoing embodiments, each of the remaining Aid, $A^{1e}$, and $A^{1f}$ is independently selected from: a bond, NH, $NR^{13}$, $CH_2$, $CHR^1$, and $C(R^1)_2$.

In certain of the foregoing embodiments, ring A is:

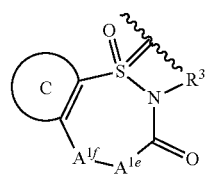

(e.g., $R^3$ is H or $C_{1-3}$ alkyl (e.g., H or methyl)).

In certain embodiments (when ring A is

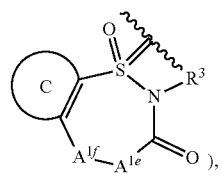

$A^{1e}$ is selected from $CH_2$, $CHR^1$, and $C(R^1)_2$ (e.g., $A^{1e}$ is $CH_2$).

In certain other embodiments (when ring A is

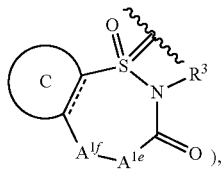

), $A^{1e}$ is selected from NH and $NR^{13}$ (e.g., NH and NMe (e.g., NH)).

In certain embodiments (when $A^1a$ is a bond; and $A^{1c}$ is $A^{1d}$-$A^{1e}$-$A^{1f}$, wherein one of Aid, $A^{1e}$, and $A^{1f}$ is C(O) or $CH_2$ (e.g., $A^{1d}$ is C(O); or $A^{1d}$ is $CH_2$)), ring A is selected from:

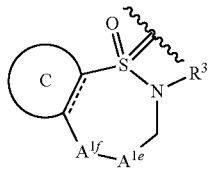

(e.g., $R^3$ is H or $C_{1-3}$ alkyl (e.g., H or methyl)).

In certain embodiments (when ring A is selected from:

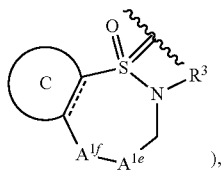

), $A^{1e}$ is selected from $CH_2$, $CHR^1$, and $C(R^1)_2$ (e.g., $A^{1e}$ is $CH_2$).

In certain embodiments when ring A is

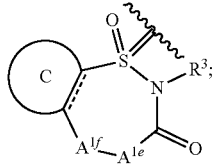

or when ring A is

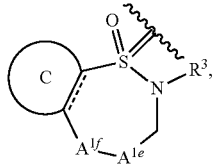

$A^{1f}$ is a bond.

In certain other embodiments when ring A is

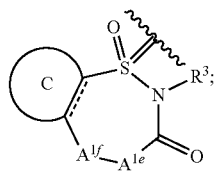

or when ring A is

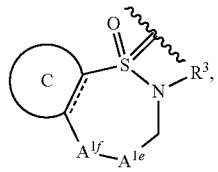

$A^{1f}$ is selected from $CH_2$, $CHR^1$, and $C(R^1)_2$ (e.g., $A^{1f}$ is $CH_2$).

In some embodiments of Formula (A1), $A^{1a}$ is selected from $CH_2$, $CHR^1$, and, $C(R^1)_2$; and $A^{1c}$ is selected from $CH_2$, $CHR^1$, $C(R^1)_2$, C(O), and $A^{1d}$-$A^{1e}$-$A^{1f}$.

In certain of the foregoing embodiments, $A^{1c}$ is selected from is selected from the group consisting of: $CH_2$, $CHR^1$, C(O), and $A^{1d}$-$A^{1e}$-$A^{1f}$.

In certain embodiments (when $A^{1a}$ is selected from $CH_2$, $CHR^1$, and, $C(R^1)_2$; and $A^{1c}$ is selected from $CH_2$, $CHR^1$, $C(R^1)_2$, C(O), and $A^{1d}$-$A^{1e}$-$A^{1f}$ (e.g., when $A^{1c}$ is selected from is selected from the group consisting of: $CH_2$, $CHR^1$, C(O), and $A^{1d}$-$A^{1c}$-$A^{1f}$)), $A^{1c}$ is C(O).

In certain embodiments, ring A is selected from:

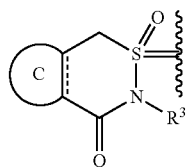

(e.g., $R^3$ is H or $C_{1-3}$ alkyl (e.g., H or methyl)).

In certain embodiments (when $A^{1a}$ is selected from $CH_2$, $CHR^1$, and, $C(R^1)_2$; and $A^{1c}$ is selected from $CH_2$, $CHR^1$, $C(R^1)_2$, C(O), and $A^{1d}$-$A^{1e}$-$A^{1f}$ (e.g., when $A^{1e}$ is selected from is selected from the group consisting of: $CH_2$, $CHR^1$, C(O), and $A^{1d}$-$A^{1e}$-$A^{1f}$)), $A^{1c}$ is $A^{1d}$-$A^{1c}$-$A^{1f}$.

In certain of the foregoing embodiments, $A^{1f}$ is a bond.

In certain embodiments (when $A^1a$ is selected from $CH_2$, $CHR^1$, and, $C(R^1)_2$; and $A^{1c}$ is $A^{1d}$-$A^{1e}$-$A^{1f}$ (e.g., $A^{1f}$ is a bond)), each of $A^{1d}$ and $A^{1e}$ is independently selected from C(O), $CH_2$, $CHR^1$, and $C(R^1)_2$.

In certain of the foregoing embodiments, each of $A^{1d}$ and $A^{1e}$ is independently C(O) and $CH_2$.

As a non-limiting example, ring A is:

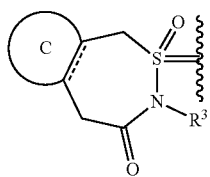

(e.g., $R^3$ is H or $C_{1-3}$ alkyl (e.g., H or methyl)).

In some embodiments of Formula (A1), $A^{1a}$ is $A^{1d}$-$A^{1e}$-$A^{1f}$; and $A^{1c}$ is selected from $CH_2$, $CHR^1$, $C(R^1)_2$, $C(O)$, and $A^{1d}$-$A^{1e}$-$A^{1f}$.

In certain of the foregoing embodiments, $A^{1c}$ is selected from the group consisting of: $CH_2$, $CHR^1$, $C(O)$, and $A^{1d}$-$A^{1e}$-$A^{1f}$.

As a non-limiting example, $A^{1c}$ is $C(O)$.

In certain embodiments (when $A^{1a}$ is $A^{1d}$-$A^{1e}$-$A^{1f}$; and $A^{1c}$ is selected from $CH_2$, $CHR^1$, $C(R^1)_2$, $C(O)$, and $A^{1d}$-$A^{1e}$-$A^{1f}$), each of $A^{1d}$, $A^{1e}$, and $A^{1f}$ of $A^{1a}$ is independently a bond, $CH_2$, $CHR^1$, and $C(R^1)_2$.

In certain of the foregoing embodiments, one of $A^{1d}$, $A^{1e}$, and $A^{1f}$ is a bond.

In certain of the foregoing embodiments, each of the remaining $A^{1d}$, $A^{1e}$, and $A^{1f}$ is $CH_2$.

As a non-limiting example of the foregoing embodiments, ring A is:

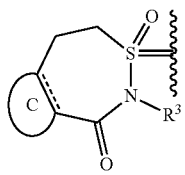

(e.g., $R^3$ is H or $C_{1-3}$ alkyl (e.g., H or methyl)).

In some embodiments (e.g., when ring A has Formula (A1)), each $R^1$ when present is independently selected from the group consisting of: $C_1$-$C_6$ alkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $C_3$-$C_7$ cycloalkyl, and 3- to 7-membered heterocycloalkyl.

In certain of the foregoing embodiments, each $R^1$ when present is $C_1$-$C_6$ alkyl.

In some embodiments of Formula (A1), ring C is $C_{6-10}$ aryl optionally substituted with from 1-5 independently selected $R^a$.

In certain embodiments of Formula (A1), ring C is C aryl optionally substituted with from 1-3 (e.g., 1-2, e.g., 1) independently selected $R^a$.

As a non-limiting example of the foregoing embodiments, ring C is selected from:

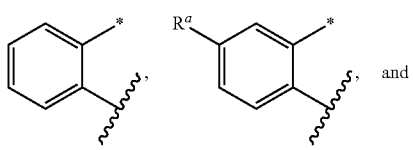

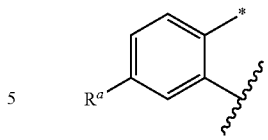

and (e.g., ring C is

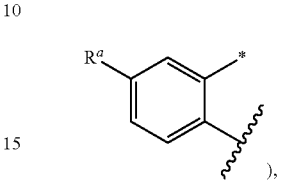

), wherein the asterisk represents point of attachment to $A^{1a}$.

In some embodiments of Formula (A1), ring C is heteroaryl including from 5-10 ring atoms, wherein from 1-4 ring atoms are each independently selected from the group consisting of N, $N(R^N)$, O, and S, wherein the heteroaryl is optionally substituted with from 1-3 independently selected $R^a$.

In certain embodiments of Formula (A1), ring C is heteroaryl including from 5-6 ring atoms, wherein from 1-4 ring atoms are each independently selected from the group consisting of N, $N(R^N)$, O, and S, wherein the heteroaryl is optionally substituted with from 1-3 independently selected $R^a$.

In certain embodiments of Formula (A1), ring C is heteroaryl including from 6 ring atoms, wherein from 1-3 (e.g., 1-2, e.g., 1 or 2) ring atoms are each independently selected from the group consisting of N, $N(R^N)$, O, and S, wherein the heteroaryl is optionally substituted with from 1-2 independently selected $R^a$.

As a non-limiting example of the foregoing embodiments, ring C is selected from:

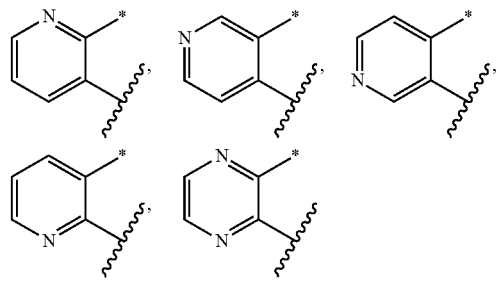

each of which is optionally substituted with from 1-2 independently selected $R^a$ (e.g., unsubstituted), wherein the asterisk represents point of attachment to $A^{1a}$.

In certain embodiments of Formula (A1), ring C is heteroaryl including from 5 ring atoms, wherein from 1-3 (e.g., 1-2, e.g., 1) ring atoms are each independently selected from the group consisting of N, $N(R^N)$, O, and S, wherein the heteroaryl is optionally substituted with from 1-2 independently selected $R^a$.

In certain of the foregoing embodiments, ring C is thiophenyl optionally substituted with from 1-2 (e.g., 1) independently selected $R^a$.

As a non-limiting example of the foregoing embodiments, ring C is selected from:

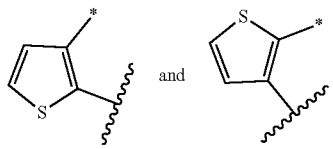 [SMILES: *c1ccsc1* ; *c1ccsc1*]

each of which is optionally substituted with from 1-2 independently selected $R^a$ (e.g., substituted with 1 $R^a$; or unsubstituted), wherein the asterisk represents point of attachment to $A^{1a}$.

In some embodiments of Formula (A1), ring C is heteroaryl including from 8-10 ring atoms, wherein from 1-3 (e.g., 1-2, e.g., 1 or 2) ring atoms are each independently selected from the group consisting of N, $N(R^N)$, O, and S, wherein the heteroaryl is optionally substituted with from 1-2 independently selected $R^a$.

As a non-limiting example of the foregoing embodiments, ring C is selected from:

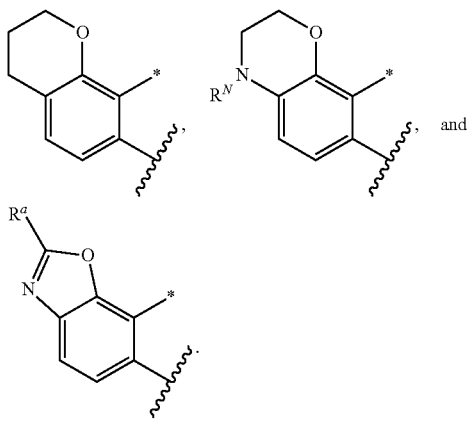

In some embodiments of Formula (A1), each $R^a$ when present is independently selected from:

hydroxy, halo, $C_1$-$C_6$ alkyl, $C_2$-$C_6$ alkenyl, $C_1$-$C_6$ alkoxy, $OC_3$-$C_{10}$ cycloalkyl, $NR^8R^9$, CN, $COOC_1$-$C_6$ alkyl, $OS(O_2)$ $C_6$-$C_{10}$ aryl, $S(O_2)C_6$-$C_{10}$ aryl, $C_6$-$C_{10}$ aryl, $OC_6$-$C_{10}$ aryl, 5- to 10-membered heteroaryl, $C_3$-$C_{10}$ cycloalkyl, 3- to 10-membered heterocycloalkyl, $CO_2H$, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents each independently selected from hydroxy, halo, $C_1$-$C_6$ alkyl, $C_{1-4}$ haloalkyl, $C_3$-$C_{10}$ cycloalkyl, 3- to 10-membered heterocycloalkyl, $C_1$-$C_6$ alkoxy, oxo, $NR^8R^9$, $COOC_1$-$C_6$ alkyl, $C_6$-$C_{10}$ aryl, $CO_2H$, and $CONR^8R^9$.

In certain of the foregoing embodiments, one or more occurrences of $R^a$ is $C_1$-$C_6$ alkyl which is optionally substituted with one or more substituents each independently selected from hydroxy, halo, $C_3$-$C_{10}$ cycloalkyl, 3- to 10-membered heterocycloalkyl, $C_1$-$C_6$ alkoxy, oxo, $NR^8R^9$, $COOC_1$-$C_6$ alkyl, $C_6$-$C_{10}$ aryl, $CO_2H$, and $CONR^8R^9$.

In certain of the foregoing embodiments, one or more occurrences of $R^a$ is $C_1$-$C_6$ alkyl which is optionally substituted with one or more substituents each independently selected from hydroxy, halo, $C_3$-$C_{10}$ cycloalkyl, 3- to 10-membered heterocycloalkyl, $C_1$-$C_6$ alkoxy, $NR^8R^9$, $COOC_1$-$C_6$ alkyl, $C_6$-$C_{10}$ aryl, $CO_2H$, and $CONR^8R^9$.

In certain of the foregoing embodiments, one or more occurrences of $R^a$ is $C_1$-$C_6$ alkyl which is optionally substituted with one or more substituents each independently selected from halo, hydroxy and $NR^8R^9$, In certain embodiments, one or more occurrences of $R^a$ is $OC_6$-$C_{10}$ aryl, $C_2$-$C_6$ alkenyl, 3- to 10-membered heterocycloalkyl, $C_6$-$C_{10}$ aryl, or 5- to 10-membered heteroaryl, each of which is optionally substituted as defined herein.

In certain embodiments, one or more occurrences of $R^a$ is CN, halo, $CO_2H$, $CONR^8R^9$, or $COOC_1$-$C_6$ alkyl.

In some embodiments of Formula (A1), ring C is selected from:

(c) $C_{3-10}$ cycloalkyl optionally substituted with from 1-4 independently selected $R^b$; and (d) heterocycloalkyl including from 3-10 ring atoms, wherein from 1-3 ring atoms are each independently selected from the group consisting of $N(R^N)$, O, and S, wherein the heterocycloalkyl is optionally substituted with from 1-4 independently selected $R^b$.

In certain of the foregoing embodiments, ring C is $C_{5-8}$ (e.g., $C_{5-6}$, e.g., $C_5$) cycloalkyl optionally substituted with from 1-2 independently selected $R^b$.

In certain other of the foregoing embodiments, ring C is heterocycloalkyl including from 5-8 (e.g., 5 or 6, (e.g., 5)) ring atoms, wherein from 1-3 (e.g., 1) ring atoms are each independently selected from the group consisting of $N(R^N)$, O, and S, wherein the heterocycloalkyl is optionally substituted with from 1-4 independently selected $R^b$.

In certain embodiments, each $R^b$ is independently selected from hydroxy, halo, oxo, $C_1$-$C_6$ alkyl, $C_1$-$C_6$ alkoxy, $OC_3$-$C_{10}$ cycloalkyl, $NR^8R^9$, CN, $COOC_1$-$C_6$ alkyl, $C_6$-$C_{10}$ aryl, $OC_6$-$C_{10}$ aryl, 5- to 10-membered heteroaryl, $C_3$-$C_{10}$ cycloalkyl, 3- to 10-membered heterocycloalkyl, $CO_2H$, and $CONR^8R^9$.

In certain of the foregoing embodiments, each $R^b$ is independently $C_{1-3}$ alkyl.

In some embodiments of Formula (A1), ring A is as defined in any of the embodiments described herein; and ring C is as defined in any of the embodiments described herein.

In certain embodiments (when ring A is a saturated or unsaturated bicyclic or tricyclic ring that includes from 6-14 ring atoms), (B) applies.

In certain of the foregoing embodiments, ring A has Formula (A2):

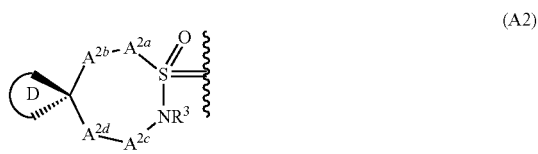

(A2)

wherein ring D is selected from the group consisting of:
(a) $C_{3-10}$ cycloalkyl optionally substituted with from 1-4 independently selected $R^b$; and
(b) heterocycloalkyl including from 3-10 ring atoms, wherein from 1-3 ring atoms are each independently selected from the group consisting of $N(R^N)$, O, and S, wherein the heterocycloalkyl is optionally substituted with from 1-4 independently selected $R^b$; and
each of $A^{2a}$, $A^{2b}$, $A^{2c}$, and $A^{2d}$ is independently selected from: a bond, NH, $NR^{13}$, O, $CH_2$, $CH(R^1)$, $C(R^1)_2$, C(O), and S(O)$_2$; provided that one or more of $A^{2a}$, $A^{2b}$, $A^{2c}$, and $A^{2d}$ are other than a bond, and provided that $A^{2c}$ and $A^{2d}$ are not both O or not both S(O)$_2$; and $A^{2a}$ and $A^{2b}$ are not both O or not both S(O)$_2$.

In some embodiments of Formula (A2), $A^{2a}$ is CH$_2$, CH(R$^1$), or C(R$^1$)$_2$ (e.g., CH$_2$); and $A^{2b}$ is a bond.

In some embodiments of Formula (A2), each of $A^{2a}$ and $A^{2b}$ is independently selected from the group consisting of CH$_2$, CH(R$^1$), and C(R$^1$)$_2$ (e.g., each of $A^{2a}$ and $A^{2b}$ is CH$_2$).

In some embodiments of Formula (A2), $A^{2c}$ is C(O).

In certain embodiments (when $A^{2c}$ is C(O)), $A^{2d}$ is selected from a bond, NH, NR$^{13}$, CH$_2$, CH(R$^1$), and C(R$^1$)$_2$.

In certain embodiments (when $A^{2c}$ is C(O)), $A^{2d}$ is a bond.

In certain embodiments (when $A^{2c}$ is C(O)), $A^{2d}$ is selected from CH$_2$, CH(R$^1$), and C(R$^1$)$_2$.

In some embodiments of Formula (A2), $A^{2a}$ is CH$_2$, CH(R$^1$), or C(R$^1$)$_2$ (e.g., CH$_2$); $A^{2b}$ is a bond; and $A^{2c}$ is C(O).

In certain of the foregoing embodiments, $A^{2d}$ is a bond (e.g., ring A is

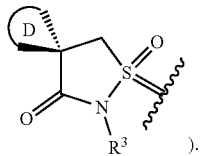

).

In certain other embodiments, $A^{2d}$ is selected from CH$_2$, CH(R$^1$), and C(R$^1$)$_2$ (e.g., CH$_2$ (e.g., ring A is

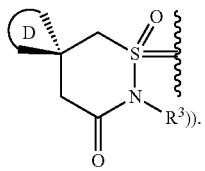

)).

In some embodiments of Formula (A2), each of $A^{2a}$ and $A^{2b}$ is independently selected from the group consisting of CH$_2$, CH(R$^1$), and C(R$^1$)$_2$ (e.g., each of $A^{2a}$ and $A^{2b}$ is CH$_2$); and $A^{2c}$ is C(O).

In certain of the foregoing embodiments, $A^{2d}$ is a bond (e.g., ring A is


).

In some embodiments of Formula (A2), ring D is heterocycloalkyl including from 3-10 ring atoms, wherein from 1-3 ring atoms are each independently selected from the group consisting of N(R$^N$), O, and S, wherein the heterocycloalkyl is optionally substituted with from 1-4 independently selected R$^b$.

In certain of the foregoing embodiments, ring D is heterocycloalkyl including from 4-6 (e.g., 5) ring atoms, wherein from 1-3 (e.g., from 1-2 (e.g., 1)) ring atoms are each independently selected from the group consisting of N(R$^N$), O, and S, wherein the heterocycloalkyl is optionally substituted with from 1-4 independently selected R$^b$.

As non-limiting examples of the foregoing embodiments, ring D is

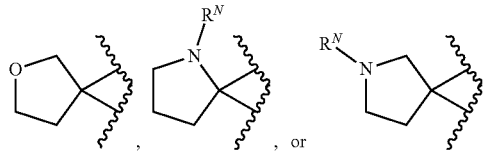

each of which is optionally substituted with from 1-2 R$^b$ (e.g., unsubstituted).

In some embodiments of Formula (A2), ring D is C$_{3-10}$ cycloalkyl optionally substituted with from 1-4 independently selected R$^b$.

In certain of the foregoing embodiments, ring D is C$_{3-6}$ cycloalkyl optionally substituted with from 1-2 (e.g., 1) independently selected R$^b$.

As non-limiting examples of the foregoing embodiments, ring D is

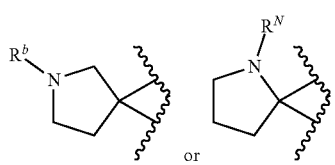

In some embodiments of Formula (A2), each R$^b$ is independently selected from hydroxy, halo, oxo, C$_1$-C$_6$ alkyl, C$_1$-C$_6$ alkoxy, OC$_3$-C$_{10}$ cycloalkyl, NR$^8$R$^9$, CN, COOC$_1$-C$_6$ alkyl, C$_6$-C$_{10}$ aryl, OC$_6$-C$_{10}$ aryl, 5- to 10-membered heteroaryl, C$_3$-C$_{10}$ cycloalkyl, 3- to 10-membered heterocycloalkyl, CO$_2$H, and CONR$^8$R$^9$, wherein the C$_1$-C$_6$ alkyl, C$_1$-C$_6$ alkoxy, C$_6$-C$_{10}$ aryl, 5- to 10-membered heteroaryl, C$_3$-C$_{10}$ cycloalkyl, and 3- to 10-membered heterocycloalkyl are optionally substituted with one or more substituents each independently selected from hydroxy, halo, C$_1$-C$_6$ alkyl, C$_2$-C$_6$ alkenyl, C$_2$-C$_6$ alkynyl, C$_3$-C$_{10}$ cycloalkyl, C$_1$-C$_6$ alkoxy, oxo, NR$^8$R$^9$, COOC$_1$-C$_6$ alkyl, C$_6$-C$_{10}$ aryl, CO$_2$H, and CONR$^8$R$^9$.

In certain of these embodiments, R$^b$ is C$_1$-C$_6$ alkyl optionally substituted with one or more substituents each independently selected from hydroxy, halo, C$_1$-C$_6$ alkyl, C$_2$-C$_6$ alkenyl, C$_2$-C$_6$ alkynyl, C$_3$-C$_{10}$ cycloalkyl, C$_1$-C$_6$ alkoxy, oxo, NR$^8$R$^9$, COOC$_1$-C$_6$ alkyl, C$_6$-C$_{10}$ aryl, CO$_2$H, and CONR$^8$R$^9$.

In some embodiments, ring A is a saturated or unsaturated monocyclic ring that includes from 5-8 ring atoms.

In certain of the foregoing embodiments, ring A is a saturated monocyclic ring that includes from 5-8 ring atoms.

In certain of the foregoing embodiments, ring A has Formula (A3):

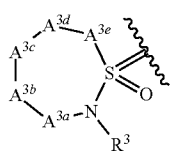

(A3)

wherein:

each of $A^{3a}$, $A^{3b}$, $A^{3c}$, $A^{3d}$, and $A^{3e}$ is independently selected from: a bond, $CH_2$, $CHR^1$, $C(R^1)_2$, $C(O)$, N, NH, $NR^{13}$, O, and, $S(O)_2$; provided that three or more of $A^{3a}$, $A^{3b}$, $A^{3c}$, $A^{3d}$, and $A^{3e}$ are other than a bond, and $A^{3a}$ and $A^{3b}$ are not both O or not both $S(O)_2$;
$A^{3b}$ and $A^{3c}$ are not both O or not both $S(O)_2$;
$A^{3c}$ and $A^{3d}$ are not both O or not both $S(O)_2$; and
$A^{3d}$ and $A^{3e}$ are not both O or not both $S(O)_2$.

In some embodiments of Formula (A3), $A^{3a}$ is C(O).

In some embodiments of Formula (A3), $A^{3a}$ is selected from the group consisting of $CH_2$, $CHR^1$, and $C(R^1)_2$.

In some embodiments of Formula (A3), $A^{3b}$ is selected from the group consisting of $CH_2$, $CHR^1$, and $C(R^1)_2$.

In some embodiments of Formula (A3), $A^{3b}$ is selected from the group consisting of NH and $NR^3$.

In some embodiments of Formula (A3), $A^{3c}$ is selected from the group consisting of $CH_2$, $CHR^1$, and $C(R^1)_2$.

In some embodiments of Formula (A3), $A^{3c}$ is selected from the group consisting of NH and $NR^{13}$.

In some embodiments of Formula (A3), $A^{3d}$ is a bond.

In some embodiments of Formula (A3), $A^{3d}$ is selected from the group consisting of $CH_2$, $CHR^1$, and $C(R^1)_2$ (e.g., $A^{3d}$ is $CH_2$ or $CHR^1$).

In some embodiments of Formula (A3), $A^{3e}$ is a bond.

In some embodiments of Formula (A3), $A^{3e}$ is selected from the group consisting of $CH_2$, $CHR^1$, and $C(R^1)_2$ (e.g., $A^{3e}$ is $CH_2$ or $CHR^1$).

In some embodiments of Formula (A3), $A^{3a}$ is C(O); $A^{3e}$ is a bond; and $A^{3d}$ is a bond.

In certain of the foregoing embodiments, each of $R^{3b}$ and $R^{3c}$ is selected from the group consisting of $CH_2$, $CHR^1$, and $C(R^1)_2$.

In certain embodiments, each of $R^{3b}$ and $R^{3c}$ is $CH_2$ (e.g., ring A is

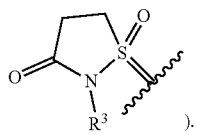

).

In certain embodiments (when $A^{3a}$ is C(O); $A^{3e}$ is a bond; and $A^{3d}$ is a bond), one of $R^{3b}$ and $R^{3c}$ is selected from the group consisting of $CHR^1$ and $C(R^1)_2$.

As non-limiting examples of the foregoing embodiments, ring A is selected from:

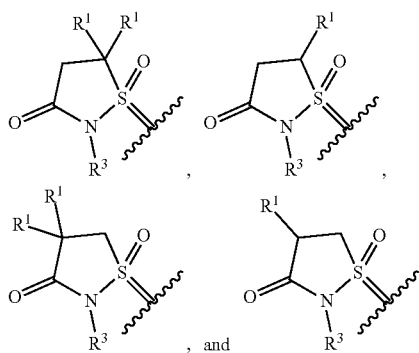

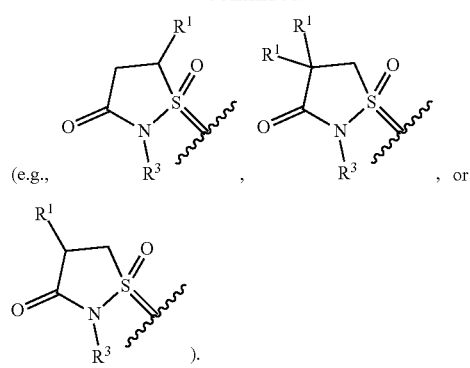

In some embodiments of Formula (A3), $A^{3a}$ is $CH_2$, $CHR^1$, or $C(R^1)_2$; $A^{3c}$ is a bond; and $A^{3d}$ is a bond.

In certain of the foregoing embodiments, each of $R^{3b}$ and $R^{3c}$ is selected from the group consisting of $CH_2$, $CHR^1$, and $C(R^1)_2$.

In certain of these embodiments, each of $R^{3b}$ and $R^{3c}$ is $CH_2$ (e.g., ring A is

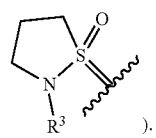

).

In certain other of these embodiments, one of $R^{3b}$ and $R^{3c}$ is selected from the group consisting of $CHR^1$ and $C(R^1)_2$.

As non-limiting examples of the foregoing embodiments, ring A is selected from the group consisting of:

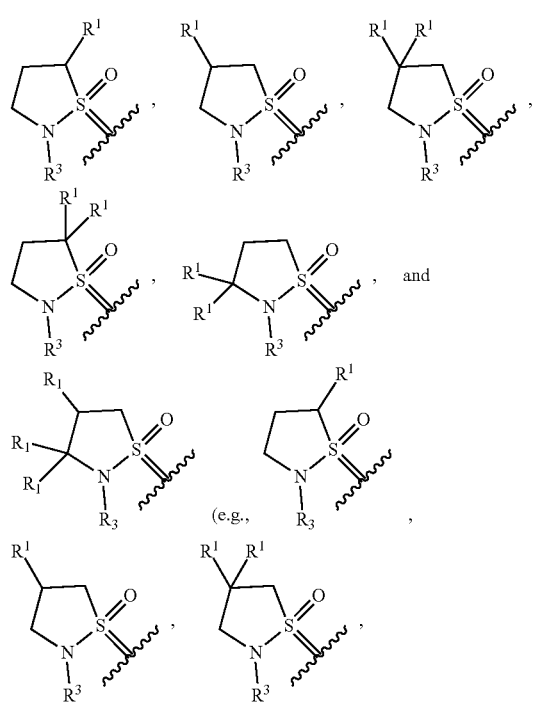

-continued

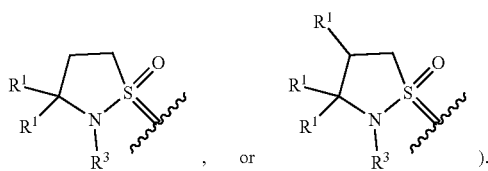

In some embodiments of Formula (A3), $A^{3a}$ is C(O); $A^{3e}$ is a bond; and $A^{3d}$ is other than a bond.

In certain of the foregoing embodiments, each of $A^{3b}$, $A^{3c}$, and $A^{3d}$ is selected from the group consisting of $CH_2$, $CHR^1$, and $C(R^1)_2$.

In certain of these embodiments, each of $A^{3b}$, $A^{3c}$, and $A^{3d}$ is $CH_2$ (e.g., ring A is

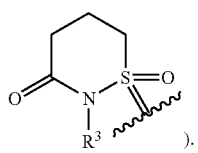
).

In certain other of these embodiments, one of $A^{3b}$, $A^{3c}$, and $A^{3d}$ is selected from the group consisting of $CHR^1$ and $C(R^1)_2$.

As non-limiting examples of the foregoing embodiments, ring A is selected from:

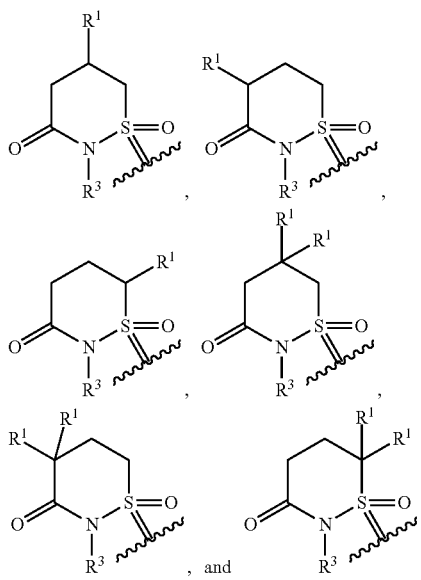

In certain embodiments (when $A^{3a}$ is C(O); $A^{3e}$ is a bond; and $A^{3d}$ is other than a bond), $A^{3b}$ is NH or $NR^{13}$.

In certain of the foregoing embodiments, each of $A^{3c}$ and $A^{3d}$ is selected from the group consisting of $CH_2$, $CHR^1$, and $C(R^1)_2$.

In certain embodiments, each of $A^{3c}$ and $A^{3d}$ is $CH_2$.

As non-limiting examples of the foregoing embodiments, ring A is selected from:

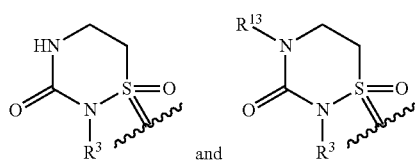

In some embodiments of Formula (A3), $A^{3a}$ is $CH_2$, $CHR^1$, or $C(R^1)_2$; $A^{3e}$ is a bond; and $A^{3d}$ is other than a bond.

In certain of the foregoing embodiments, each of $A^{3b}$, $A^{3c}$, and $A^{3d}$ is selected from the group consisting of $CH_2$, $CHR^1$, and $C(R^1)_2$.

In certain of these embodiments, each of $A^{3b}$, $A^{3c}$, and $A^{3d}$ is $CH_2$ (e.g., ring A is

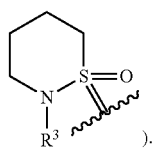
).

In certain other of these embodiments, one of $A^{3b}$, $A^{3c}$, and $A^{3d}$ is selected from the group consisting of $CHR^1$ and $C(R^1)_2$.

As non-limiting examples to the foregoing embodiments, ring A is selected from:

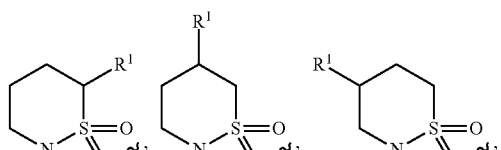

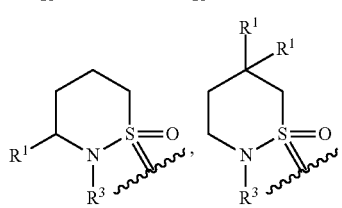

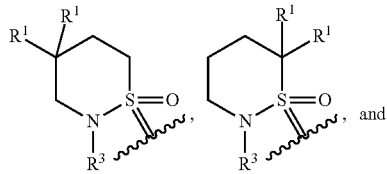

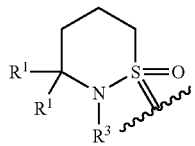

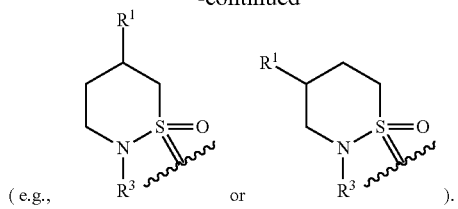

(e.g., ... or ...).

In some embodiments of Formula (A3), $A^{3a}$ is C(O); and $A^{3e}$ is $CH_2$; and $A^{3d}$ is other than a bond.

In certain of the foregoing embodiments, each of $A^{3b}$ and $A^{3d}$ is independently selected from the group consisting of $CH_2$, $CHR^1$, and $C(R^1)_2$.

In certain of these embodiments, each of $A^{3b}$ and $A^{3d}$ is $CH_2$.

In certain embodiments, $A^{3c}$ is selected from NH, $NR^{13}$, $CH_2$, $CHR^1$, and $C(R^1)_2$.

As non-limiting examples of the foregoing embodiments, ring A is selected from:

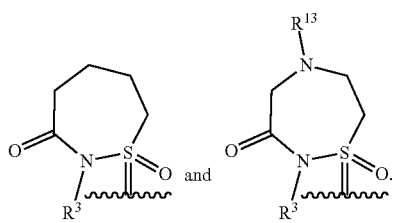

and

In some embodiments of Formula (A3), each $R^1$ is independently selected from the group consisting of: $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_8$ cycloalkyl, $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $CONR^8R^9$, $S(O_2)C_1$-$C_6$ alkyl, $S(O)C_1$-$C_6$ alkyl, $S(O_2)NR^{11}R^{12}$, $C_3$-$C_7$ cycloalkyl, and 3- to 7-membered heterocycloalkyl, wherein the $C_1$-$C_6$ alkyl, $C_6$-$C_{10}$ aryl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein when $R^1$ is $C_3$-$C_7$ cycloalkyl, 3- to 7-membered heterocycloalkyl, $C_6$-$C_{10}$ aryl, or 5- to 10-membered heteroaryl, each $C_1$-$C_6$ alkyl substituent and each $C_1$-$C_6$ alkoxy substituent on $R^1$, when present, is further optionally independently substituted with one to three hydroxy, $C_1$-$C_6$ alkoxy, halo, $NR^8R^9$, or oxo; and wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) substituents on $R^1$ are optionally substituted with one or more substituents independently selected from halo, $C_1$-$C_6$ alkyl, and $OC_1$-$C_6$ alkyl.

In some embodiments of Formula (A3), one or more occurrences of $R^1$ is $C_1$-$C_6$ alkyl, optionally substituted with one or more substituents each independently selected from hydroxy, halo, CN, oxo, $C_1$-$C_6$ alkoxy, $NR^8R^9$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), and NHCO(3- to 7-membered heterocycloalkyl), wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) substituents on $R^1$ are optionally substituted with one or more substituents independently selected from halo, $C_1$-$C_6$ alkyl, and $OC_1$-$C_6$ alkyl.

In some embodiments of Formula (A3), one or more occurrences of $R^1$ is $C_1$-$C_6$ alkyl, optionally substituted with one or more substituents each independently selected from hydroxy, halo, CN, $C_1$-$C_6$ alkyl, $C_1$-$C_6$ alkoxy, $NR^8R^9$, $C_6$-$C_{10}$ aryl, and 5- to 10-membered heteroaryl;

wherein the $C_6$-$C_{10}$ aryl and 5- to 10-membered heteroaryl substituents on $R^1$ are optionally substituted with one or more substituents independently selected from halo, $C_1$-$C_6$ alkyl, and $OC_1$-$C_6$ alkyl.

In some embodiments of Formula (A3), one or more occurrences of $R^1$ is $C_6$-$C_{10}$ aryl or 5- to 10-membered heteroaryl, each of which is optionally substituted with one or more substituents each independently selected from hydroxy, halo, CN, oxo, $C_1$-$C_6$ alkyl, $C_1$-$C_6$ alkoxy, $NR^8R^9$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), and NHCO(3- to 7-membered heterocycloalkyl);

wherein each $C_1$-$C_6$ alkyl substituent and each $C_1$-$C_6$ alkoxy substituent on R, when present, is further optionally independently substituted with one to three hydroxy, $C_1$-$C_6$ alkoxy, halo, $NR^8R^9$, or oxo; and wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) substituents on $R^1$ are optionally substituted with one or more substituents independently selected from halo, $C_1$-$C_6$ alkyl, and $OC_1$-$C_6$ alkyl.

In some embodiments of Formula (A3), one or more occurrences of $R^1$ is $C_6$-$C_{10}$ aryl optionally substituted with one or more substituents each independently selected from hydroxy, halo, CN, $C_1$-$C_6$ alkyl, $C_1$-$C_6$ alkoxy, $NR^8R^9$, $COOC_1$-$C_6$ alkyl, and $CONR^8R^9$;

wherein each $C_1$-$C_6$ alkyl substituent and each $C_1$-$C_6$ alkoxy substituent on $R^1$, when present, is further optionally independently substituted with one to three hydroxy, $C_1$-$C_6$ alkoxy, halo, $NR^8R^9$, or oxo.

In some embodiments of Formula (A3), one or more occurrences of $R^1$ is hydroxyl, $C_1$-$C_6$ alkoxy, $C_1$-$C_6$ haloalkoxy, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), NHCOC$_2$-C$_6$ alkynyl, CONR$^8$R$^9$, S(O$_2$)C$_1$-C$_6$ alkyl, S(O)C$_1$-C$_6$ alkyl, or S(O$_2$)NR$^{11}$R$^{12}$.

The Group R$^1$

In some embodiments, R$^1$ is C$_1$-C$_6$ alkyl optionally substituted with one or more hydroxy.
In some embodiments, R$^1$ is 1-hydroxy-2-methylpropan-2-yl.
In some embodiments, R$^1$ is 2-hydroxyethyl.
In some embodiments, R$^1$ is C$_1$-C$_6$ alkyl.
In some embodiments, R$^1$ is methyl.
In some embodiments, R$^1$ is isopropyl.
In some embodiments, R$^1$ is isopropyl.
In some embodiments, R$^1$ is C$_1$-C$_6$ alkyl substituted with hydroxy at the carbon directly connected to ring A.
In some embodiments, R$^1$ is 2-hydroxy-2-propyl.
In some embodiments, R$^1$ is hydroxymethyl.
In some embodiments, R$^1$ is 1-hydroxyethyl.
In some embodiments, R$^1$ is 1-hydroxy-2-propyl.
In some embodiments, R$^1$ is C$_1$-C$_6$ alkyl substituted with two or more hydroxy groups.
In some embodiments, R$^1$ is C$_1$-C$_6$ alkyl substituted with two or more hydroxy groups, wherein one of the two or more hydroxy groups is bonded to the carbon directly connected to ring A.
In some embodiments, R$^1$ is 1,2-dihydroxy-prop-2-yl.
In some embodiments, R$^1$ is C$_3$-C$_7$ cycloalkyl optionally substituted with one or more hydroxy.
In some embodiments, R$^1$ is C$_3$-C$_7$ cycloalkyl.
In some embodiments, R$^1$ is C$_3$-C$_7$ cycloalkyl substituted with hydroxy at the carbon directly connected to ring A.
In some embodiments, R$^1$ is 1-hydroxy-1-cyclopropyl.
In some embodiments, R$^1$ is 1-hydroxy-1-cyclobutyl.
In some embodiments, R$^1$ is 1-hydroxy-1-cyclopentyl.
In some embodiments, R$^1$ is 1-hydroxy-1-cyclohexyl.
In some embodiments, R$^1$ is 3- to 7-membered heterocycloalkyl optionally substituted with one or more hydroxy.
In some embodiments, R$^1$ is 3- to 7-membered heterocycloalkyl.
In some embodiments, R$^1$ is morpholinyl (e.g., 1-morpholinyl).
In some embodiments, R$^1$ is 1,3-dioxolan-2-yl.
In some embodiments, R$^1$ is 3- to 7-membered heterocycloalkyl optionally substituted with one or more C$_1$-C$_6$ alkyl.
In some embodiments, R$^1$ is 1-methylpyrrolidin-2-yl.
In some embodiments, R$^1$ is 3- to 7-membered heterocycloalkyl substituted with hydroxy at the carbon directly connected to ring A.
In some embodiments, R$^1$ is C$_1$-C$_6$ alkyl optionally substituted with one or more oxo.
In some embodiments, R$^1$ is COCH$_3$.
In some embodiments, R$^1$ is COCH$_2$CH$_3$.
In some embodiments, R$^1$ is C$_3$-C$_7$ cycloalkyl optionally substituted with one or more oxo.
In some embodiments, R$^1$ is 3- to 7-membered heterocycloalkyl optionally substituted with one or more oxo.
In some embodiments, R$^1$ is C$_1$-C$_6$ alkyl optionally substituted with one or more C$_1$-C$_6$ alkoxy.
In some embodiments, R$^1$ is 2-methoxy-2-propyl.
In some embodiments, R$^1$ is methoxymethyl.
In some embodiments, R$^1$ is C$_3$-C$_7$ cycloalkyl optionally substituted with one or more C$_1$-C$_6$ alkoxy.
In some embodiments, R$^1$ is 3- to 7-membered heterocycloalkyl optionally substituted with one or more C$_1$-C$_6$ alkoxy.
In some embodiments, R$^1$ is C$_1$-C$_6$ alkyl optionally substituted with one or more NR$^8$R$^9$.
In some embodiments, R$^1$ is C$_1$-C$_6$ alkyl substituted with NR$^8$R$^9$ at the carbon directly connected to ring A.
In some embodiments, R$^1$ is (methylamino)methyl.
In some embodiments, R$^1$ is (dimethylamino)methyl.
In some embodiments, R$^1$ is aminomethyl.
In some embodiments, R$^1$ is N-methylacetamidomethyl.
In some embodiments, R$^1$ is 1-(dimethylamino)eth-1-yl.
In some embodiments, R$^1$ is 2-(dimethylamino)prop-2-yl.
In some embodiments, R$^1$ is (2-methoxy-eth-1-yl)(methyl) aminomethyl.
In some embodiments, R$^1$ is (methyl)(acetyl)aminomethyl.
In some embodiments, R$^1$ is (methyl)(cyclopropylmethyl) aminomethyl.
In some embodiments, R$^1$ is (methyl)(2,2-difluoroeth-1-yl) aminomethyl.
In some embodiments, R$^1$ is C$_3$-C$_7$ cycloalkyl optionally substituted with one or more NR$^8$R$^9$.
In some embodiments, R$^1$ is 3- to 7-membered heterocycloalkyl optionally substituted with one or more NR$^8$R$^9$.
In some embodiments, R$^1$ is C$_1$-C$_6$ haloalkyl optionally substituted with one or more hydroxy.
In some embodiments, R$^1$ is C$_1$-C$_6$ alkoxy.
In some embodiments, R$^1$ is C$_1$-C$_6$ haloalkoxy.
In some embodiments, R$^1$ is C$_1$-C$_6$ alkyl optionally substituted with 3- to 7-membered heterocycloalkyl, wherein the 3- to 7-membered heterocycloalkyl is further optionally substituted as defined elsewhere herein.
In some embodiments, R$^1$ is pyrrolidinylmethyl (e.g., pyrrolidin-1-ylmethyl).
In some embodiments, R$^1$ is optionally substituted pyrrolidinylmethyl (e.g., 3,3-difluoropyrrolidin-1-ylmethyl).
In some embodiments, R$^1$ is azetidinylmethyl (e.g., azetidin-1-ylmethyl).
In some embodiments, R$^1$ is optionally substituted azetidinylmethyl (e.g., 3-methoxyazetidin-1-ylmethyl).
In some embodiments, R$^1$ is morpholinylmethyl (e.g., morpholin-4-ylmethyl).
In some embodiments, R$^1$ is C$_1$-C$_6$ alkyl optionally substituted with C$_6$-C$_{10}$ aryl, wherein the C$_6$-C$_{10}$ aryl is further optionally substituted as defined elsewhere herein.
In certain embodiments, R$^1$ is C$_1$-C$_6$ alkyl optionally substituted with unsubstituted C$_6$-C$_{10}$ aryl (e.g., benzyl).
In some embodiments, R$^1$ is halo.
In some embodiments, R$^1$ is fluoro.
In some embodiments, R$^1$ is chloro.
In some embodiments, R$^1$ is CN.
In some embodiments, R$^1$ is NO$_2$.
In some embodiments, R$^1$ is COC$_1$-C$_6$ alkyl.
In some embodiments, R$^1$ is CO—C$_6$-C$_{10}$ aryl.
In some embodiments, R$^1$ is CO(5- to 10-membered heteroaryl).
In some embodiments, R$^1$ is CO$_2$C$_1$-C$_6$ alkyl.
In some embodiments, R$^1$ is CO$_2$C$_3$-C$_8$ cycloalkyl.
In some embodiments, R$^1$ is OCOC$_1$-C$_6$ alkyl.
In some embodiments, R$^1$ is OCOC$_6$-C$_{10}$ aryl.
In some embodiments, R$^1$ is OCO(5- to 10-membered heteroaryl).
In some embodiments, R$^1$ is OCO(3- to 7-membered heterocycloalkyl).
In some embodiments, R$^1$ is C$_6$-C$_{10}$ aryl, wherein the C$_6$-C$_{10}$ aryl is optionally substituted as described elsewhere herein.
In some embodiments, R$^1$ is phenyl wherein the phenyl is substituted with C$_{1-6}$ alkyl, wherein the C$_{1-6}$ alkyl is further optionally substituted (e.g., with hydroxy) as defined elsewhere herein.
In some embodiments, R$^1$ is phenyl
In some embodiments, R$^1$ is 5- to 10-membered heteroaryl.

In some embodiments, $R^1$ is pyridyl (e.g., 4-pyridyl).
In some embodiments, $R^1$ is pyrazolyl (e.g., 1-pyrazolyl).
In some embodiments, $R^1$ is $NH_2$.
In some embodiments, $R^1$ is $NHC_1$-$C_6$ alkyl.
In some embodiments, $R^1$ is $N(C_1$-$C_6$ alkyl$)_2$.
In some embodiments, $R^1$ is $CONR^8R^9$.
In some embodiments, $R^1$ is $SF_5$.
In some embodiments, $R^1$ is $SC_1$-$C_6$ alkyl,
In some embodiments, $R^1$ is $S(O_2)C_1$-$C_6$ alkyl.
In some embodiments, $R^1$ is $S(O_2)CH_3$.
In some embodiments, $R^1$ is $S(O_2)NR^{11}R^{12}$.
In some embodiments, $R^1$ is $S(O_2)N(CH_3)_2$.
In some embodiments, $R^1$ is $S(O)C_1$-$C_6$ alkyl.
In some embodiments, $R^1$ is $S(O)CH_3$.

The group $R^a$
In some embodiments, $R^a$ is $C_1$-$C_6$ alkyl optionally substituted with one or more hydroxy.
In some embodiments, $R^a$ is 1-hydroxy-2-methylpropan-2-yl.
In some embodiments, $R^a$ is 2-hydroxyethyl.
In some embodiments, $R^a$ is $C_1$-$C_6$ alkyl.
In some embodiments, $R^a$ is methyl.
In some embodiments, $R^a$ is isopropyl.
In some embodiments, $R^a$ is isopropyl.
In some embodiments, $R^a$ is $C_1$-$C_6$ alkyl substituted with hydroxy at the carbon directly connected to ring A.
In some embodiments, $R^a$ is 2-hydroxy-2-propyl.
In some embodiments, $R^a$ is hydroxymethyl.
In some embodiments, $R^a$ is 1-hydroxyethyl.
In some embodiments, $R^a$ is 1-hydroxy-2-propyl.
In some embodiments, $R^a$ is $C_1$-$C_6$ alkyl substituted with two or more hydroxy groups.
In some embodiments, $R^a$ is $C_1$-$C_6$ alkyl substituted with two or more hydroxy groups, wherein one of the two or more hydroxy groups is bonded to the carbon directly connected to ring A.
In some embodiments, $R^a$ is 1,2-dihydroxy-prop-2-yl.
In some embodiments, $R^a$ is $C_3$-$C_7$ cycloalkyl optionally substituted with one or more hydroxy.
In some embodiments, $R^a$ is $C_3$-$C_7$ cycloalkyl.
In some embodiments, $R^a$ is $C_3$-$C_7$ cycloalkyl substituted with hydroxy at the carbon directly connected to ring A.
In some embodiments, $R^a$ is 1-hydroxy-1-cyclopropyl.
In some embodiments, $R^a$ is 1-hydroxy-1-cyclobutyl.
In some embodiments, $R^a$ is 1-hydroxy-1-cyclopentyl.
In some embodiments, $R^a$ is 1-hydroxy-1-cyclohexyl.
In some embodiments, $R^a$ is 3- to 7-membered heterocycloalkyl optionally substituted with one or more hydroxy.
In some embodiments, $R^a$ is 3- to 7-membered heterocycloalkyl.
In some embodiments, $R^a$ is morpholinyl (e.g., 1-morpholinyl).
In some embodiments, $R^a$ is 1,3-dioxolan-2-yl.
In some embodiments, $R^a$ is 3- to 7-membered heterocycloalkyl optionally substituted with one or more $C_1$-$C_6$ alkyl.
In some embodiments, $R^a$ is 1-methylpyrrolidin-2-yl.
In some embodiments, $R^a$ is 3- to 7-membered heterocycloalkyl substituted with hydroxy at the carbon directly connected to ring A.
In some embodiments, $R^a$ is $C_1$-$C_6$ alkyl optionally substituted with one or more oxo.
In some embodiments, $R^a$ is $COCH_3$.
In some embodiments, $R^a$ is $COCH_2CH_3$.
In some embodiments, $R^a$ is $C_3$-$C_7$ cycloalkyl optionally substituted with one or more oxo.
In some embodiments, $R^a$ is 3- to 7-membered heterocycloalkyl optionally substituted with one or more oxo.
In some embodiments, $R^a$ is $C_1$-$C_6$ alkyl optionally substituted with one or more $C_1$-$C_6$ alkoxy.
In some embodiments, $R^a$ is 2-methoxy-2-propyl.
In some embodiments, $R^a$ is methoxymethyl.
In some embodiments, $R^a$ is $C_3$-$C_7$ cycloalkyl optionally substituted with one or more $C_1$-$C_6$ alkoxy.
In some embodiments, $R^a$ is 3- to 7-membered heterocycloalkyl optionally substituted with one or more $C_1$-$C_6$ alkoxy.
In some embodiments, $R^a$ is $C_1$-$C_6$ alkyl optionally substituted with one or more $NR^8R^9$.
In some embodiments, $R^a$ is $C_1$-$C_6$ alkyl substituted with $NR^8R^9$ at the carbon directly connected to ring A.
In some embodiments, $R^a$ is (methylamino)methyl.
In some embodiments, $R^a$ is (dimethylamino)methyl.
In some embodiments, $R^a$ is aminomethyl.
In some embodiments, $R^a$ is N-methylacetamidomethyl.
In some embodiments, $R^a$ is 1-(dimethylamino)eth-1-yl.
In some embodiments, $R^a$ is 2-(dimethylamino)prop-2-yl.
In some embodiments, $R^a$ is (2-methoxy-eth-1-yl)(methyl)aminomethyl.
In some embodiments, $R^a$ is (methyl)(acetyl)aminomethyl.
In some embodiments, $R^a$ is (methyl)(cyclopropylmethyl)aminomethyl.
In some embodiments, $R^a$ is (methyl)(2,2-difluoroeth-1-yl)aminomethyl.
In some embodiments, $R^a$ is $C_3$-$C_7$ cycloalkyl optionally substituted with one or more $NR^8R^9$.
In some embodiments, $R^a$ is 3- to 7-membered heterocycloalkyl optionally substituted with one or more $NR^8R^9$.
In some embodiments, $R^a$ is $C_1$-$C_6$ haloalkyl optionally substituted with one or more hydroxy.
In some embodiments, $R^a$ is $C_1$-$C_6$ alkoxy.
In some embodiments, $R^a$ is $C_1$-$C_6$ haloalkoxy.
In some embodiments, $R^a$ is $C_1$-$C_6$ alkyl optionally substituted with 3- to 7-membered heterocycloalkyl, wherein the 3- to 7-membered heterocycloalkyl is further optionally substituted as defined elsewhere herein.
In some embodiments, $R^a$ is pyrrolidinylmethyl (e.g., pyrrolidin-1-ylmethyl).
In some embodiments, $R^a$ is optionally substituted pyrrolidinylmethyl (e.g., 3,3-difluoropyrrolidin-1-ylmethyl).
In some embodiments, $R^a$ is azetidinylmethyl (e.g., azetidin-1-ylmethyl).
In some embodiments, $R^a$ is optionally substituted azetidinylmethyl (e.g., 3-methoxyazetidin-1-ylmethyl).
In some embodiments, $R^a$ is morpholinylmethyl (e.g., morpholin-4-ylmethyl).
In some embodiments, $R^a$ is halo.
In some embodiments, $R^a$ is fluoro.
In some embodiments, $R^a$ is chloro.
In some embodiments, $R^a$ is CN.
In some embodiments, $R^a$ is $CO_2C_1$-$C_6$ alkyl.
In some embodiments, $R^a$ is $CO_2C_3$-$C_8$ cycloalkyl.
In some embodiments, $R^a$ is $C_6$-$C_{10}$ aryl.
In some embodiments, $R^a$ is phenyl.
In some embodiments, $R^a$ is 5- to 10-membered heteroaryl.
In some embodiments, $R^a$ is pyridyl (e.g., 4-pyridyl).
In some embodiments, $R^a$ is pyrazolyl (e.g., 1-pyrazolyl).
In some embodiments, $R^a$ is $NR^8R^9$.
In some embodiments, $R^a$ is $CONR^8R^9$.

The Variables o and p
In some embodiments, o=1 or 2.
In some embodiments, o=1.
In some embodiments, o=2.
In some embodiments, p=0, 1, 2, or 3.
In some embodiments, p=0.

In some embodiments, p=1.
In some embodiments, p=2.
In some embodiments, o=1 and p=0.
In some embodiments, o=2 and p=0.
In some embodiments, o=1 and p=1.
In some embodiments, o=1 and p=2.
In some embodiments, o=2 and p=1.
In some embodiments, o=2 and p=2.
In some embodiments, o=2 and p=3.

The Ring B and Substitutions on the Ring B

In some embodiments, B is a 5- to 10-membered monocyclic or bicyclic heteroaryl or a $C_6$-$C_{10}$ monocyclic or bicyclic aryl, such as phenyl.
In some embodiments, B is a 5- to 6-membered monocyclic heteroaryl or a $C_6$ monocyclic aryl.
In some embodiments, B is a 5- to 10-membered monocyclic or bicyclic heteroaryl.
In some embodiments, B is a $C_6$-$C_{10}$ monocyclic or bicyclic aryl.
In some embodiments, B is a 5-membered heteroaryl.
In some embodiments, B is a 7-10 membered monocyclic or bicyclic heteroaryl.
In some embodiments, B is phenyl substituted with 1 or 2 $R^6$ and optionally substituted with 1, 2, or 3 $R^7$.
In some embodiments, B is pyridyl substituted with 1 or 2 $R^6$ and optionally substituted with 1, 2, or 3 $R^7$.
In some embodiments, B is indazolyl substituted with 1 or 2 $R^6$ and optionally substituted with 1, 2, or 3 $R^7$.
In some embodiments, B is pyrazolyl substituted with 1 or 2 $R^6$ and optionally substituted with 1 or 2 $R^7$.
In some embodiments, B is phenyl, o is 1 or 2, and p is 0, 1, 2, or 3.
In some embodiments, B is phenyl, o is 1, and p is 0, 1, 2, or 3.
In some embodiments, B is phenyl, o is 2, and p is 0, 1, 2, or 3.
In some embodiments, B is one of the rings disclosed hereinbelow, substituted as disclosed hereinbelow, wherein in each case the bond that is shown as being broken by the wavy line / connects B to the Y(CO) group of Formula AA.

In some embodiments, the substituted ring B

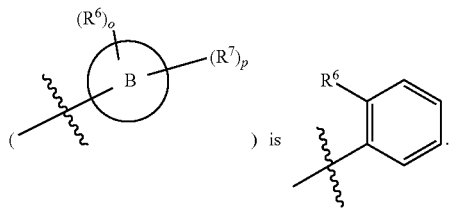) is 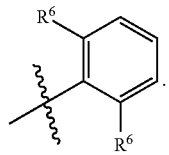

In some embodiments, the substituted ring B

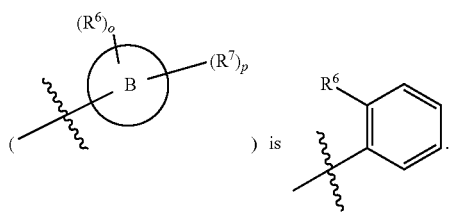) is 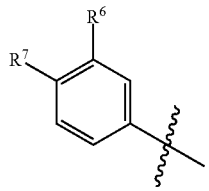

In some embodiments, the substituted ring B is

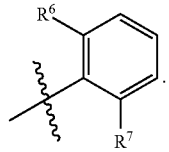

In some embodiments, the substituted ring B is

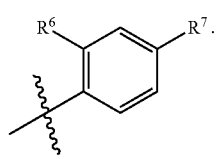

In some embodiments, the substituted ring B is

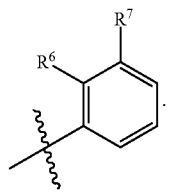

In some embodiments, the substituted ring B is

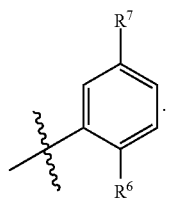

In some embodiments, the substituted ring B is

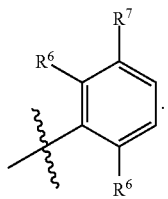

In some embodiments, the substituted ring B is

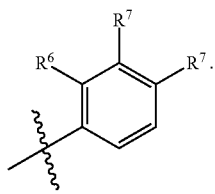

In some embodiments, the substituted ring B is

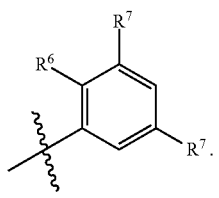

In some embodiments, the substituted ring B is

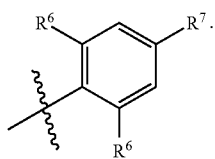

In some embodiments, the substituted ring B is

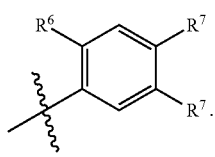

In some embodiments, the substituted ring B is

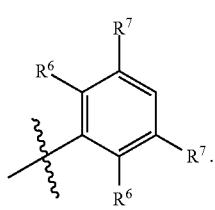

In some embodiments, the substituted ring B is

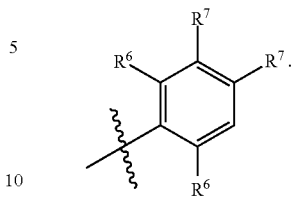

In some embodiments, the substituted ring B is

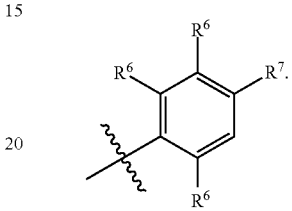

In some embodiments, the substituted ring B is

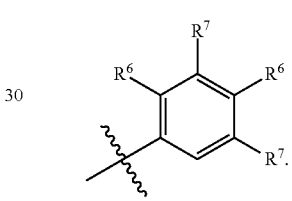

In some embodiments, the substituted ring B is

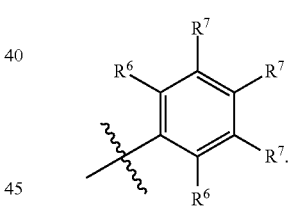

In some embodiments, the substituted ring B is

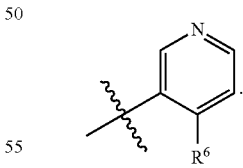

In some embodiments, the substituted ring B is

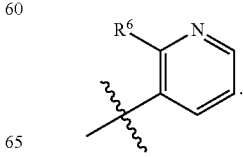

In some embodiments, the substituted ring B is

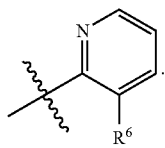

In some embodiments, the substituted ring B is

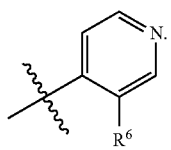

In some embodiments, the substituted ring B is

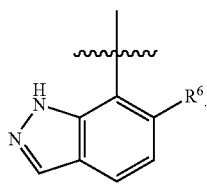

In some embodiments, the substituted ring B is

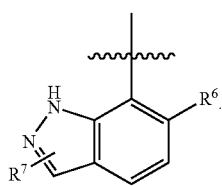

In some embodiments, the substituted ring B is

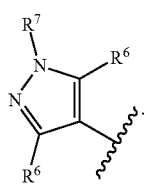

In some embodiments, the substituted ring B is

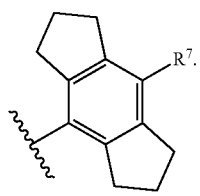

In some embodiments, the substituted ring B is

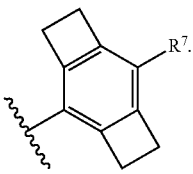

In some embodiments, the substituted ring B is

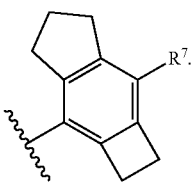

In some embodiments, the substituted ring B is

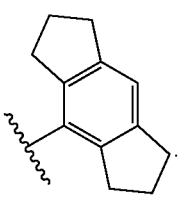 [SMILES: *c1c2c(cc3c1CCC3)CCC2]

In some embodiments, the substituted ring B is

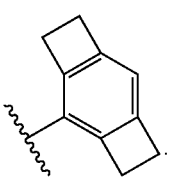 [SMILES: *c1c2c(cc3c1CC3)CC2]

In some embodiments, the substituted ring B is

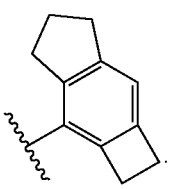 [SMILES: *c1c2c(cc3c1CC3)CCC2]

In some embodiments, the substituted ring B is

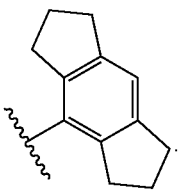 [SMILES: *c1c2c(cc3c1CCC3)CCC2]

In some embodiments, the substituted ring B is

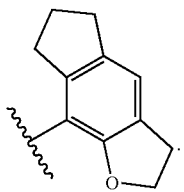 [SMILES: *c1c2c(cc3c1OCC3)CCC2]

In some embodiments, the substituted ring B is

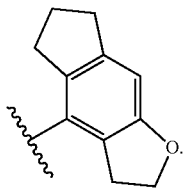 [SMILES: *c1c2c(cc3c1CCO3)CCC2]

In some embodiments, the substituted ring B is

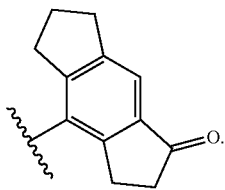 [SMILES: *c1c2c(cc3c1CCC3=O)CCC2]

In some embodiments, the substituted ring B is

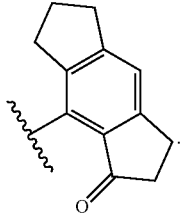 [SMILES: *c1c2c(cc3c1C(=O)CC3)CCC2]

In some embodiments, the substituted ring B is

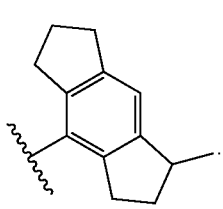 [SMILES: *c1c2c(cc3c1CCC3C)CCC2]

In some embodiments, the substituted ring B is

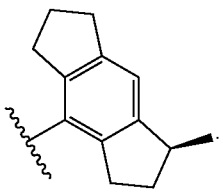 [SMILES: *c1c2c(cc3c1CC[C@@H]3C)CCC2]

In some embodiments, the substituted ring B is

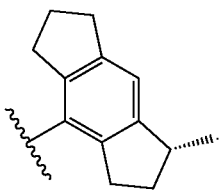 [SMILES: *c1c2c(cc3c1CC[C@H]3C)CCC2]

In some embodiments, the substituted ring B is

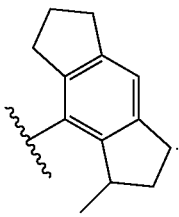 [SMILES: *c1c2c(cc3c1C(C)CC3)CCC2]

In some embodiments, the substituted ring B is

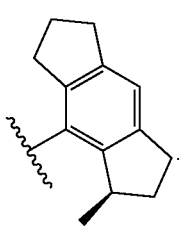 [SMILES: *c1c2c(cc3c1[C@H](C)CC3)CCC2]

In some embodiments, the substituted ring B is

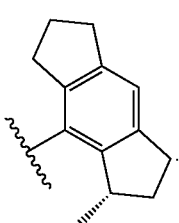

In some embodiments, the substituted ring B is

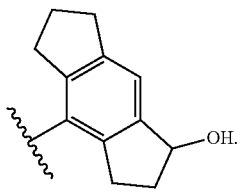 [SMILES: *c1c2c(cc3c1CCC3O)CCC2]

In some embodiments, the substituted ring B is

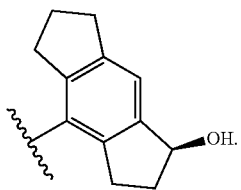 [SMILES: *c1c2c(cc3c1CC[C@@H]3O)CCC2]

In some embodiments, the substituted ring B is

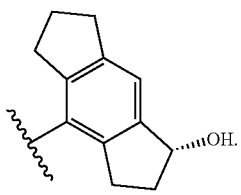 [SMILES: *c1c2c(cc3c1CC[C@H]3O)CCC2]

In some embodiments, the substituted ring B is

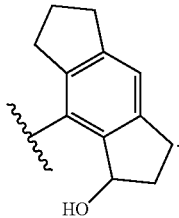 [SMILES: *c1c2c(cc3c1C(O)CC3)CCC2]

In some embodiments, the substituted ring B is

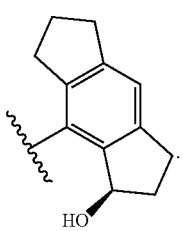 [SMILES: *c1c2c(cc3c1[C@H](O)CC3)CCC2]

In some embodiments, the substituted ring B is

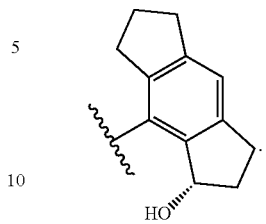

In some embodiments, the substituted ring B is

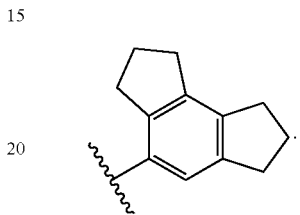

In some embodiments, the substituted ring B is

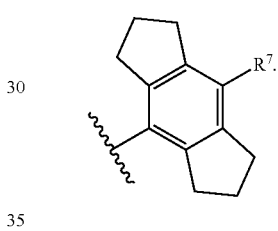

In some embodiments, B is phenyl substituted with 1 or 2 $R^6$ and optionally substituted with 1 or 2 $R^7$.

In certain of the foregoing embodiments, B is

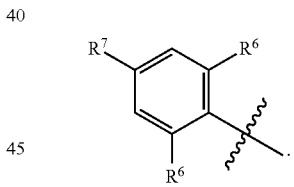

In certain embodiments (when B is

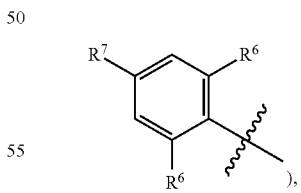

), each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CONR$^8$R$^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy.

In certain embodiments (when B is

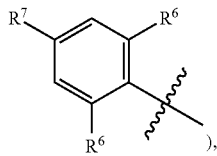

each $R^6$ and $R^7$ is independently selected from $C_1$-$C_6$ alkyl optionally substituted with hydroxy, $C_3$-$C_7$ cycloalkyl, $C_1$-$C_6$ haloalkyl, and halo.

In certain embodiments (when B is

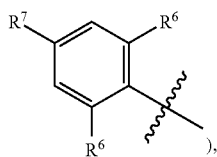

each $R^6$ and $R^7$ is independently selected from methyl, 2-hydroxy-2-propyl, cyclopropyl, trifluoromethyl, difluoromethyl, and fluoro.

In certain embodiments (when B is phenyl substituted with 1 or 2 $R^6$ and optionally substituted with 1 or 2 $R^7$), o=2 and p=2.

In certain of the foregoing embodiments, B is

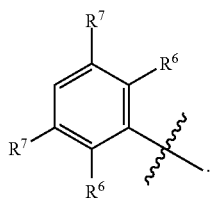

In certain embodiments (when B is

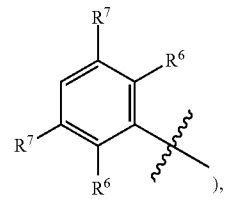

each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or at least one pair of $R^6$ and $R^7$ on adjacent atoms, taken together with the atoms connecting them, independently form at least one $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In certain embodiments (when B is

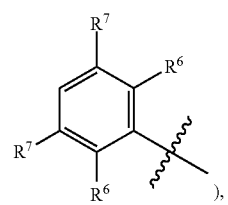

each $R^6$ and $R^7$ is independently selected from $C_1$-$C_6$ alkyl optionally substituted with hydroxy, $C_3$-$C_7$ cycloalkyl, $C_1$-$C_6$ haloalkyl, and halo;

or at least one pair (e.g., two pairs) of $R^6$ and $R^7$ on adjacent atoms, taken together with the atoms connecting them, independently form a $C_4$-$C_5$ carbocyclic ring or a 5-membered heterocyclic ring containing 1 O, wherein the carbocyclic ring or heterocyclic ring is optionally independently substituted with one or more substituents independently selected from $C_1$-$C_6$ alkyl.

In certain embodiments (when B is R

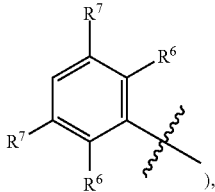

), each $R^6$ and $R^7$ is independently selected from methyl, 2-hydroxy-2-propyl, cyclopropyl, trifluoromethyl, difluoromethyl, and fluoro;

or at least one pair (e.g., two pairs) of $R^6$ and $R^7$ on adjacent atoms, taken together with the atoms connecting them, independently form a $C_4$-$C_5$ carbocyclic ring or a 5-membered heterocyclic ring containing 1 O, wherein the carbocyclic ring or heterocyclic ring is optionally independently substituted with one or more methyl.

In certain embodiments (when B is phenyl substituted with 1 or 2 $R^6$ and optionally substituted with 1 or 2 $R^7$; and o=2 and p=2), B is R

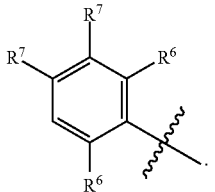

.

In certain embodiments (when B is R

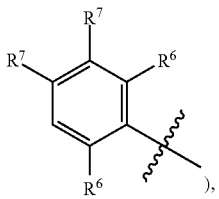

), each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;

wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In certain embodiments (when B is R

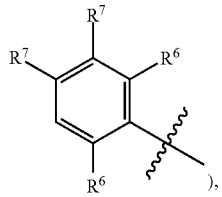

), each $R^6$ and $R^7$ is independently selected from $C_1$-$C_6$ alkyl optionally substituted with hydroxy, $C_3$-$C_7$ cycloalkyl, $C_1$-$C_6$ haloalkyl, and halo;

or at least one pair (e.g., two pairs) of $R^6$ and $R^7$ on adjacent atoms, taken together with the atoms connecting them, independently form a $C_4$-$C_5$ carbocyclic ring or a 5-membered heterocyclic ring containing 1 O, wherein the carbocyclic ring or heterocyclic ring is optionally independently substituted with one or more substituents independently selected from $C_1$-$C_6$ alkyl.

In certain embodiments (when B is

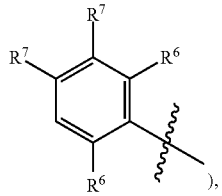

), each $R^6$ and $R^7$ is independently selected from methyl, 2-hydroxy-2-propyl, cyclopropyl, trifluoromethyl, difluoromethyl, and fluoro; or at least one pair (e.g., two pairs) of $R^6$ and $R^7$ on adjacent atoms, taken together with the atoms connecting them, independently form a $C_4$-$C_5$ carbocyclic ring or a 5-membered heterocyclic ring containing 1 O, wherein the carbocyclic ring or heterocyclic ring is optionally independently substituted with one or more methyl.

In certain embodiments (when B is phenyl substituted with 1 or 2 $R^6$ and optionally substituted with 1 or 2 $R^7$; and o=2 and p=2), B is

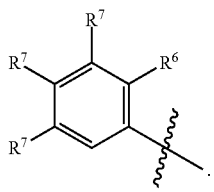

In certain embodiments (when B is

), each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CONR$^8$R$^9$, and 4- to 6-membered heterocycloalkyl,
wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, NR$^8$R$^9$, =NR$^{10}$, COOC$_1$-$C_6$ alkyl, CONR$^8$R$^9$, 4- to 6-membered heterocycloalkyl, $C_6$-$C_{10}$ aryl, 5- to 10-membered heteroaryl, OCOC$_1$-$C_6$ alkyl, OCOC$_6$-$C_{10}$ aryl, OCO(5- to 10-membered heteroaryl), OCO(4- to 6-membered heterocycloalkyl), NHCOC$_1$-$C_6$ alkyl, NHCOC$_6$-$C_{10}$ aryl, NHCO(5- to 10-membered heteroaryl), NHCO(4- to 6-membered heterocycloalkyl), and NHCOC$_2$-$C_6$ alkynyl;
wherein each $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, COC$_1$-$C_6$ alkyl, CO$_2$C$_1$-$C_6$ alkyl, CO$_2$C$_3$-$C_6$ cycloalkyl, OCOC$_1$-$C_6$ alkyl, OCOC$_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, CONR$^8$R$^9$, SF$_5$, S(O$_2$)C$_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;
or $R^6$ and $R^7$, taken together with the atoms connecting them, independently form $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, NR$^8$R$^9$, =NR$^{10}$, COOC$_1$-$C_6$ alkyl, $C_6$-$C_{10}$ aryl, and CONR$^8$R$^9$.

In certain embodiments (when B is

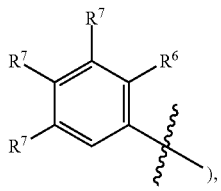
), each $R^6$ and $R^7$ is independently selected from $C_1$-$C_6$ alkyl optionally substituted with hydroxy, $C_3$-$C_7$ cycloalkyl, $C_1$-$C_6$ haloalkyl, and halo;
or at least one pair (e.g., two pairs) of $R^6$ and $R^7$ on adjacent atoms, taken together with the atoms connecting them, independently form a $C_4$-$C_5$ carbocyclic ring or a 5-membered heterocyclic ring containing 1 O, wherein the carbocyclic ring or heterocyclic ring is optionally independently substituted with one or more substituents independently selected from $C_1$-$C_6$ alkyl.

In certain embodiments (when B is

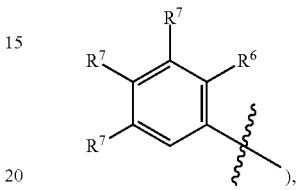
), each $R^6$ and $R^7$ is independently selected from methyl, 2-hydroxy-2-propyl, cyclopropyl, trifluoromethyl, difluoromethyl, and fluoro;
or at least one pair (e.g., two pairs) of $R^6$ and $R^7$ on adjacent atoms, taken together with the atoms connecting them, independently form a $C_4$-$C_5$ carbocyclic ring or a 5-membered heterocyclic ring containing 1 O, wherein the carbocyclic ring or heterocyclic ring is optionally independently substituted with one or more methyl.

In some embodiments, B is pyridyl substituted with 1 or 2 $R^6$ and optionally substituted with 1 or 2 $R^7$.

In certain of the foregoing embodiments, B is R

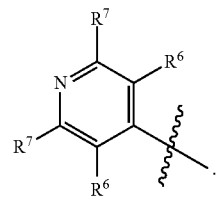

In certain embodiments (when B is

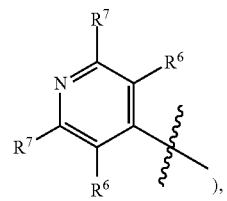
), each $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CONR$^8$R$^9$, and 4- to 6-membered heterocycloalkyl,
wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, NR$^8$R$^9$, =NR$^{10}$, COOC$_1$-$C_6$ alkyl, CONR$^8$R$^9$, 4- to 6-membered heterocycloalkyl, $C_6$-$C_{10}$ aryl, 5- to 10-membered heteroaryl, OCOC$_1$-C$_6$ alkyl, OCOC$_6$-C$_{10}$ aryl, OCO(5- to 10-membered heteroaryl), OCO(4- to 6-membered heterocycloalkyl), NHCOC$_1$-C$_6$ alkyl, NHCOC$_6$-C$_{10}$ aryl, NHCO(5- to 10-membered heteroaryl), NHCO(4- to 6-membered heterocycloalkyl), and NHCOC$_2$-C$_6$ alkynyl;

wherein each R$^7$ is independently selected from C$_1$-C$_6$ alkyl, C$_1$-C$_6$ haloalkyl, C$_1$-C$_6$ alkoxy, C$_1$-C$_6$ haloalkoxy, halo, CN, COC$_1$-C$_6$ alkyl, CO$_2$C$_1$-C$_6$ alkyl, CO$_2$C$_3$-C$_6$ cycloalkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, CONR$^8$R$^9$, SF$_5$, S(O$_2$)C$_1$-C$_6$ alkyl, C$_3$-C$_7$ cycloalkyl and 4- to 6-membered heterocycloalkyl, wherein the C$_1$-C$_6$ alkyl is optionally substituted with one to two C$_1$-C$_6$ alkoxy;

or at least one pair of R$^6$ and R$^7$ on adjacent atoms, taken together with the atoms connecting them, independently form at least one C$_4$-C$_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, C$_1$-C$_6$ alkyl, C$_1$-C$_6$ alkoxy, NR$^8$R$^9$, =NR$^{10}$, COOC$_1$-C$_6$ alkyl, C$_6$-C$_{10}$ aryl, and CONR$^8$R$^9$.

In certain embodiments (when B is

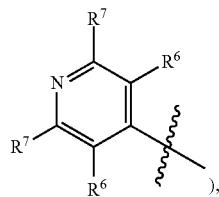

each R$^6$ and R$^7$ is independently selected from C$_1$-C$_6$ alkyl optionally substituted with hydroxy, C$_3$-C$_7$ cycloalkyl, C$_1$-C$_6$ haloalkyl, and halo;

or at least one pair (e.g., two pairs) of R$^6$ and R$^7$ on adjacent atoms, taken together with the atoms connecting them, independently form a C$_4$-C$_5$ carbocyclic ring or a 5-membered heterocyclic ring containing 1 O, wherein the carbocyclic ring or heterocyclic ring is optionally independently substituted with one or more substituents independently selected from C$_1$-C$_6$ alkyl.

In certain embodiments (when B is

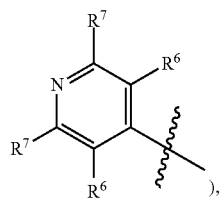

each R$^6$ and R$^7$ is independently selected from methyl, 2-hydroxy-2-propyl, cyclopropyl, trifluoromethyl, difluoromethyl, and fluoro;

or at least one pair (e.g., two pairs) of R$^6$ and R$^7$ on adjacent atoms, taken together with the atoms connecting them, independently form a C$_4$-C$_5$ carbocyclic ring or a 5-membered heterocyclic ring containing 1 O, wherein the carbocyclic ring or heterocyclic ring is optionally independently substituted with one or more methyl.

The Groups R$^6$ and R$^7$

In any of the formulae disclosed herein, unless otherwise specified, the definitions of R$^6$ and R$^7$ encompass situations wherein:

(a) each occurrence of R$^6$ and each occurrence of R$^7$ is a monovalent substituent as described elsewhere herein;

(b) when o=p, and each pair of R$^6$ and R$^7$ are on adjacent carbon atoms, each pair of R$^6$ and R$^7$ taken together with atom to which each is attached forms an independently selected carbocyclic or heterocyclic ring as described elsewhere herein;
and (c) one or more pairs of R$^6$ and R$^7$ on adjacent carbon atoms, taken together with the atom to which each is attached, form one or more independently selected carbocyclic or heterocyclic ring as described elsewhere herein; and each remaining occurrences of R$^6$ and R$^7$ (inclusive of pair(s) of R$^6$ and R$^7$ on adjacent atoms) is independently a monovalent substituent as described herein.

In some embodiments,

R$^6$ and R$^7$ are each independently selected from C$_1$-C$_6$ alkyl, C$_1$-C$_6$ haloalkyl, C$_1$-C$_6$ alkoxy, C$_1$-C$_6$ haloalkoxy, halo, CN, NO$_2$, COC$_1$-C$_6$ alkyl, CO$_2$C$_1$-C$_6$ alkyl, CO$_2$C$_3$-C$_8$ cycloalkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, NH$_2$, NHC$_1$-C$_6$ alkyl, N(C$_1$-C$_6$ alkyl)$_2$, CONR$^8$R$^9$, SF$_5$, S(O$_2$)C$_1$-C$_6$ alkyl, C$_3$-C$_{10}$ cycloalkyl and 3- to 10-membered heterocycloalkyl, and a C$_2$-C$_6$ alkenyl, wherein R$^6$ and R$^7$ are each optionally substituted with one or more substituents independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 3- to 7-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO(5- to 10-membered heteroaryl), OCO(3- to 7-membered heterocycloalkyl), NHCOC$_1$-C$_6$ alkyl, NHCOC$_6$-C$_{10}$ aryl, NHCO(5- to 10-membered heteroaryl), NHCO(3- to 7-membered heterocycloalkyl), NHCOC$_2$-C$_6$ alkynyl, C$_6$-C$_{10}$ aryloxy, and S(O$_2$)C$_1$-C$_6$ alkyl; and wherein the C$_1$-C$_6$ alkyl or C$_1$-C$_6$ alkoxy that R$^6$ or R$^7$ is substituted with is optionally substituted with one or more hydroxyl, C$_6$-C$_{10}$ aryl or NR$^8$R$^9$, or wherein R$^6$ or R$^7$ is optionally fused to a five-to-seven-membered carbocyclic ring or heterocyclic ring containing one or two heteroatoms independently selected from oxygen, sulfur and nitrogen;

wherein the 3- to 7-membered heterocycloalkyl, C$_6$-C$_{10}$ aryl, 5- to 10-membered heteroaryl, NHCOC$_6$-C$_{10}$ aryl, NHCO(5- to 10-membered heteroaryl) and NHCO(3- to 7-membered heterocycloalkyl) are optionally substituted with one or more substituents independently selected from halo, C$_1$-C$_6$ alkyl, and OC$_1$-C$_6$ alkyl;

or at least one pair of R$^6$ and R$^7$ on adjacent atoms, taken together with the atoms connecting them, independently form at least one C$_4$-C$_5$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, C$_1$-C$_6$ alkyl, C$_1$-C$_6$ alkoxy, NR$^8$R$^9$, CH$_2$NR$^8$R$^9$, =NR$^1$, COOC$_1$-C$_6$ alkyl, C$_6$-C$_{10}$ aryl, and CONR$^8$R$^9$.

In some embodiments,

R$^6$ and R$^7$ are each independently selected from C$_1$-C$_6$ alkyl, C$_1$-C$_6$ haloalkyl, C$_1$-C$_6$ alkoxy, C$_1$-C$_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_{10}$ cycloalkyl and 3- to 10-membered heterocycloalkyl, and a $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$, or wherein $R^6$ or $R^7$ is optionally fused to a five-to-seven-membered carbocyclic ring or heterocyclic ring containing one or two heteroatoms independently selected from oxygen, sulfur and nitrogen;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_6$ aliphatic carbocyclic ring or at least one 5- to 6-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl, wherein the $C_3$-$C_7$ cycloalkyl, $C_1$-$C_6$ haloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO (5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

or at least one pair of $R^6$ and $R^7$ on adjacent atoms, taken together with the atoms connecting them, independently form at least one $C_4$-$C_8$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, $=NR^{10}$, $COOC_1$-$C_6$ alkyl, $C_6$-$C_{10}$ aryl, and $CONR^8R^9$.

In some embodiments, $R^6$ and $R^7$ are each independently selected from $C_1$-$C_6$ alkyl, halo, CN, $NO_2$, $COC_1$-$C_6$ alkyl, $CO_2C_1$-$C_6$ alkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO (5- to 10-membered heteroaryl), NHCO(3- to 7-membered heterocycloalkyl), and $NHCOC_2$-$C_6$ alkynyl;

wherein the 3- to 7-membered heterocycloalkyl, $C_6$-$C_{10}$ aryl, 5- to 10-membered heteroaryl, NHCOC$_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and OC$_1$-$C_6$ alkyl;

or at least one pair of $R^6$ and $R^7$ on adjacent atoms, taken together with the atoms connecting them, independently form at least one $C_4$-$C_5$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, NR$^8$R$^9$, CH$_2$NR$^8$R$^9$, =NR$^{10}$, COOC$_1$-$C_6$ alkyl, $C_6$-$C_{10}$ aryl, and CONR$^8$R$^9$.

In some embodiments, $R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, NO$_2$, COC$_1$-$C_6$ alkyl, CO$_2$C$_1$-$C_6$ alkyl, CO$_2$C$_3$-$C_8$ cycloalkyl, OCOC$_1$-$C_6$ alkyl, OCOC$_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, NH$_2$, NHC$_1$-$C_6$ alkyl, N(C$_1$-$C_6$ alkyl)$_2$, CONR$^8$R$^9$, SF$_5$, SC$_1$-$C_6$ alkyl, S(O$_2$)C$_1$-$C_6$ alkyl, $C_3$-$C_7$ cycloalkyl and 3- to 7-membered heterocycloalkyl, wherein the $C_1$-$C_6$ alkyl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, NR$^8$R$^9$, =NR$^{10}$, COOC$_1$-$C_6$ alkyl, CONR$^8$R$^9$, 3- to 7-membered heterocycloalkyl, $C_6$-$C_{10}$ aryl, 5- to 10-membered heteroaryl, OCOC$_1$-$C_6$ alkyl, OCOC$_6$-$C_{10}$ aryl, OCO (5- to 10-membered heteroaryl), OCO(3- to 7-membered heterocycloalkyl), NHCOC$_1$-$C_6$ alkyl, NHCOC$_6$-$C_{10}$ aryl, NHCO(5- to 10-membered heteroaryl), NHCO(3- to 7-membered heterocycloalkyl), and NHCOC$_2$-$C_6$ alkynyl;

wherein the 3- to 7-membered heterocycloalkyl, $C_6$-$C_{10}$ aryl, 5- to 10-membered heteroaryl, NHCOC$_6$-$C_{10}$ aryl, NHCO(5- to 10-membered heteroaryl) and NHCO(3- to 7-membered heterocycloalkyl) are unsubstituted;

or at least one pair of $R^6$ and $R^7$ on adjacent atoms, taken together with the atoms connecting them, independently form at least one $C_4$-$C_5$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, NR$^8$R$^9$, CH$_2$NR$^8$R$^9$, =NR$^{10}$, COOC$_1$-$C_6$ alkyl, $C_6$-$C_{10}$ aryl, and CONR$^8$R$^9$.

In some embodiments, $R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, NO$_2$, COC$_1$-$C_6$ alkyl, CO$_2$C$_1$-$C_6$ alkyl, CO$_2$C$_3$-$C_8$ cycloalkyl, OCOC$_1$-$C_6$ alkyl, OCOC$_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, NH$_2$, NHC$_1$-$C_6$ alkyl, N(C$_1$-$C_6$ alkyl)$_2$, CONR$^8$R$^9$, SF$_5$, SC$_1$-$C_6$ alkyl, S(O$_2$)C$_1$-$C_6$ alkyl, $C_3$-$C_7$ cycloalkyl and 3- to 7-membered heterocycloalkyl, wherein the $C_1$-$C_6$ alkyl, $C_3$-$C_7$ cycloalkyl and 3- to 7-membered heterocycloalkyl are each unsubstituted;

or at least one pair of $R^6$ and $R^7$ on adjacent atoms, taken together with the atoms connecting them, independently form at least one $C_4$-$C_5$ carbocyclic ring or at least one 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, $C_1$-$C_6$ alkyl, $C_1$-$C_6$ alkoxy, NR$^8$R$^9$, CH$_2$NR$^8$R$^9$, =NR$^{10}$, COOC$_1$-$C_6$ alkyl, $C_6$-$C_{10}$ aryl, and CONR$^8$R$^9$.

In some embodiments, $R^6$ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; CONR$^8$R$^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, NR$^8$R$^9$, =NR$^{10}$, COOC$_1$-$C_6$ alkyl, CONR$^8$R$^9$, 4- to 6-membered heterocycloalkyl, $C_6$-$C_{10}$ aryl, 5- to 10-membered heteroaryl, OCOC$_1$-$C_6$ alkyl, OCOC$_6$-$C_{10}$ aryl, OCO (5- to 10-membered heteroaryl), OCO(4- to 6-membered heterocycloalkyl), NHCOC$_1$-$C_6$ alkyl, NHCOC$_6$-$C_{10}$ aryl, NHCO(5- to 10-membered heteroaryl), NHCO(4- to 6-membered heterocycloalkyl), and NHCOC$_2$-$C_6$ alkynyl;

and $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, COC$_1$-$C_6$ alkyl, CO$_2$C$_1$-$C_6$ alkyl, CO$_2$C$_3$-$C_6$ cycloalkyl, OCOC$_1$-$C_6$ alkyl, OCOC$_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, CONR$^8$R$^9$, SF$_5$, S(O$_2$)C$_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;

or $R^6$ and $R^7$, taken together with the atoms connecting them, independently form $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, NR$^8$R$^9$, =NR$^{10}$, COOC$_1$-$C_6$ alkyl, $C_6$-$C_{10}$ aryl, and CONR$^8$R$^9$.

In some embodiments, $R^6$ and $R^7$ are each independently selected from $C_1$-$C_6$ alkyl, $C_1$-$C_6$ alkoxy, halo, CN, NO$_2$, COC$_1$-$C_6$ alkyl, CO$_2$C$_1$-$C_6$ alkyl, $C_6$-$C_{10}$ aryl, 5- to 10-membered heteroaryl, CONR$^8$R$^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_4$-$C_5$ carbocyclic ring, wherein the carbocyclic ring is optionally independently substituted with one or more hydroxy or oxo.

In some embodiments, $R^6$ and $R^7$ are each independently selected from $C_1$-$C_6$ alkyl, $C_1$-$C_6$ alkoxy, halo, CN, NO$_2$, COC$_1$-$C_6$ alkyl, CO$_2$C$_1$-$C_6$ alkyl, $C_6$-$C_{10}$ aryl, 5- to 10-membered heteroaryl, CONR$^8$R$^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo, or at least one pair of $R^6$ and $R^7$ on adjacent atoms, taken together with the atoms connecting them, independently form at least one $C_4$-$C_6$ aliphatic carbocyclic ring, wherein the carbocyclic ring is optionally independently substituted with one or more hydroxy or oxo.

In some embodiments,
$R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocycloalkyl is optionally substituted with one or more substituents each independently selected from hydroxy or oxo,
or at least one pair of $R^6$ and $R^7$ on adjacent atoms, taken together with the atoms connecting them, independently form at least one 5- to 8-membered heterocyclic ring containing 1 or 2 heteroatoms independently selected from O, N, and S, wherein the heterocyclic ring is optionally independently substituted with one or more hydroxy or oxo.

In some embodiments,
$R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl,
wherein the $C_1$-$C_6$ alkyl and 3- to 7-membered heterocycloalkyl is optionally substituted with one or more substituents each independently selected from hydroxy or oxo,
or at least one pair of $R^6$ and $R^7$ on adjacent atoms, taken together with the atoms connecting them, independently form at least one $C_4$-$C_5$ carbocyclic ring, wherein the carbocyclic ring is optionally independently substituted with one or more hydroxy or oxo.

In some embodiments,
at least one pair of $R^6$ and $R^7$ on adjacent atoms, taken together with the atoms connecting them, independently form at least one $C_4$-$C_6$ aliphatic carbocyclic ring, wherein the carbocyclic ring is optionally independently substituted with one or more hydroxy or oxo.

In some embodiments,
at least one pair of $R^6$ and $R^7$ on adjacent atoms, taken together with the atoms connecting them, independently form at least one $C_4$ aliphatic carbocyclic ring, wherein the carbocyclic ring is optionally independently substituted with one or more hydroxy or oxo.

In some embodiments,
at least one pair of $R^6$ and $R^7$ on adjacent atoms, taken together with the atoms connecting them, independently form at least one $C_5$ aliphatic carbocyclic ring, wherein the carbocyclic ring is optionally independently substituted with one or more hydroxy or oxo.

In some embodiments,
at least one pair of $R^6$ and $R^7$ on adjacent atoms, taken together with the atoms connecting them, independently form at least one $C_6$ aliphatic carbocyclic ring, wherein the carbocyclic ring is optionally independently substituted with one or more hydroxy or oxo.

In some embodiments,
at least one pair of $R^6$ and $R^7$ on adjacent atoms, taken together with the atoms connecting them, independently form at least one 5- to 6-membered heterocyclic ring containing 1 heteroatom independently selected from O, N, and S, wherein the heterocyclic ring is optionally independently substituted with one or more hydroxy or oxo.

In some embodiments,
at least one pair of $R^6$ and $R^7$ on adjacent atoms, taken together with the atoms connecting them, independently form at least one 5-membered heterocyclic ring containing 1 heteroatom independently selected from O, N, and S, wherein the heterocyclic ring is optionally independently substituted with one or more hydroxy or oxo.

In some embodiments,
at least one pair of $R^6$ and $R^7$ on adjacent atoms, taken together with the atoms connecting them, independently form at least one 6-membered heterocyclic ring containing 1 heteroatom independently selected from O, N, and S, wherein the heterocyclic ring is optionally independently substituted with one or more hydroxy or oxo.

In some embodiments,
at least one pair of $R^6$ and $R^7$ on adjacent atoms, taken together with the atoms connecting them, independently form at least one $C_4$ aliphatic carbocyclic ring, wherein the carbocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one $C_5$ aliphatic carbocyclic ring, wherein the carbocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one $C_6$ aliphatic carbocyclic ring, wherein the carbocyclic ring is optionally independently substituted with one or more $C_1$-$C_6$ alkyl.

In some embodiments,
at least one pair of $R^6$ and $R^1$ on adjacent atoms, taken together with the atoms connecting them, independently form at least one 5- to 6-membered heterocyclic ring containing 1 heteroatom independently selected from O, N, and S, wherein the heterocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one 5-membered heterocyclic ring containing 1 heteroatom independently selected from O, N, and S, wherein the heterocyclic ring is optionally independently substituted with one or more $C_1$-$C_6$ alkyl.

In some embodiments,
at least one pair of $R^6$ and $R^7$ on adjacent atoms, taken together with the atoms connecting them, independently form at least one 6-membered heterocyclic ring containing 1 heteroatom independently selected from O, N, and S, wherein the heterocyclic ring is optionally independently substituted with one or more $C_1$-$C_6$ alkyl.

In some embodiments, o=1; p=0; and
$R^6$ is selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl)$_2$, $CONR^8R^9$, $SF_5$, $SC_1$-$C_6$ alkyl, $S(O_2)C_1$-$C_6$ alkyl, $C_3$-$C_7$ cycloalkyl and 3- to 7-membered heterocycloalkyl,
wherein the $C_1$-$C_6$ alkyl, $C_1$-$C_6$ haloalkyl, $C_3$-$C_7$ cycloalkyl and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and NHCOC$_2$-C$_6$ alkynyl;
wherein the 3- to 7-membered heterocycloalkyl, C$_6$-C$_{10}$ aryl, 5- to 10-membered heteroaryl, NHCOC$_6$-C$_{10}$ aryl, NHCO(5- to 10-membered heteroaryl) and NHCO(3- to 7-membered heterocycloalkyl) are optionally substituted with one or more substituents independently selected from halo, C$_1$-C$_6$ alkyl, and OC$_1$-C$_6$ alkyl.

In some embodiments, o=1; p=1; and
R$^6$ and R$^7$ are each independently selected from C$_1$-C$_6$ alkyl, C$_1$-C$_6$ alkoxy, halo, CN, NO$_2$, COC$_1$-C$_6$ alkyl, CO$_2$C$_1$-C$_6$ alkyl, C$_6$-C$_{10}$ aryl, 5- to 10-membered heteroaryl, CONR$^8$R$^9$, and 3- to 7-membered heterocycloalkyl,
wherein the C$_1$-C$_6$ alkyl and 3- to 7-membered heterocycloalkyl is optionally substituted with one or more substituents each independently selected from hydroxy or oxo,
or at least one pair of R$^6$ and R$^7$ on adjacent atoms, taken together with the atoms connecting them, independently form at least one C$_4$-C$_5$ carbocyclic ring, wherein the carbocyclic ring is optionally independently substituted with one or more hydroxy or oxo.

In some embodiments, o=1 or 2; p=1, 2, or 3; and
R$^6$ and R$^7$ are each independently selected from C$_1$-C$_6$ alkyl, C$_1$-C$_6$ haloalkyl, C$_1$-C$_6$ alkoxy, C$_1$-C$_6$ haloalkoxy, halo, CN, NO$_2$, COC$_1$-C$_6$ alkyl, CO$_2$C$_1$-C$_6$ alkyl, CO$_2$C$_3$-C$_8$ cycloalkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, NH$_2$, NHC$_1$-C$_6$ alkyl, N(C$_1$-C$_6$ alkyl)$_2$, CONR$^8$R$^9$, SF$_5$, SC$_1$-C$_6$ alkyl, S(O$_2$)C$_1$-C$_6$ alkyl, C$_3$-C$_7$ cycloalkyl and 3- to 7-membered heterocycloalkyl,
wherein the C$_1$-C$_6$ alkyl, C$_1$-C$_6$ haloalkyl, C$_3$-C$_7$ cycloalkyl, and 3- to 7-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 3- to 7-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO (5- to 10-membered heteroaryl), OCO(3- to 7-membered heterocycloalkyl), NHCOC$_1$-C$_6$ alkyl, NHCOC$_6$-C$_{10}$ aryl, NHCO(5- to 10-membered heteroaryl), NHCO(3- to 7-membered heterocycloalkyl), and NHCOC$_2$-C$_6$ alkynyl;
wherein the 3- to 7-membered heterocycloalkyl, C$_6$-C$_{10}$ aryl, 5- to 10-membered heteroaryl, NHCOC$_6$-C$_{10}$ aryl, NHCO(5- to 10-membered heteroaryl) and NHCO(3- to 7-membered heterocycloalkyl) are optionally substituted with one or more substituents independently selected from halo, C$_1$-C$_6$ alkyl, and OC$_1$-C$_6$ alkyl.

In some embodiments, o=2; p=1; and
each R$^6$ is independently selected from C$_1$-C$_6$ alkyl, C$_3$-C$_7$ cycloalkyl, C$_1$-C$_6$ haloalkyl, C$_1$-C$_6$ alkoxy, C$_1$-C$_6$ haloalkoxy, halo, CN, C$_6$-C$_{10}$ aryl, 5- to 10-membered heteroaryl, CO—C$_1$-C$_6$ alkyl; CONR$^8$R$^9$, and 4- to 6-membered heterocycloalkyl,
wherein the C$_1$-C$_6$ alkyl, C$_1$-C$_6$ haloalkyl, C$_3$-C$_7$ cycloalkyl and 4- to 6-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 4- to 6-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO (5- to 10-membered heteroaryl), OCO(4- to 6-membered heterocycloalkyl), NHCOC$_1$-C$_6$ alkyl, NHCOC$_6$-C$_{10}$ aryl, NHCO(5- to 10-membered heteroaryl), NHCO(4- to 6-membered heterocycloalkyl), and NHCOC$_2$-C$_6$ alkynyl;
and R$^7$ is independently selected from C$_1$-C$_6$ alkyl, C$_1$-C$_6$ haloalkyl, C$_1$-C$_6$ alkoxy, C$_1$-C$_6$ haloalkoxy, halo, CN, COC$_1$-C$_6$ alkyl, CO$_2$C$_1$-C$_6$ alkyl, CO$_2$C$_3$-C$_6$ cycloalkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, CONR$^8$R$^9$, SF$_5$, S(O$_2$)C$_1$-C$_6$ alkyl, C$_3$-C$_7$ cycloalkyl and 4- to 6-membered heterocycloalkyl, wherein the C$_1$-C$_6$ alkyl is optionally substituted with one to two C$_1$-C$_6$ alkoxy;
or R$^6$ and R$^7$, taken together with the atoms connecting them, independently form C$_4$-C$_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, C$_1$-C$_6$ alkyl, C$_1$-C$_6$ alkoxy, NR$^8$R$^9$, =NR$^{10}$, COOC$_1$-C$_6$ alkyl, C$_6$-C$_{10}$ aryl, and CONR$^8$R$^9$.

In some embodiments, o=2; p=2 or 3; and
each R$^6$ is independently selected from C$_1$-C$_6$ alkyl, C$_3$-C$_7$ cycloalkyl, C$_1$-C$_6$ haloalkyl, C$_1$-C$_6$ alkoxy, C$_1$-C$_6$ haloalkoxy, halo, CN, C$_6$-C$_{10}$ aryl, 5- to 10-membered heteroaryl, CO—C$_1$-C$_6$ alkyl; CONR$^8$R$^9$, and 4- to 6-membered heterocycloalkyl,
wherein the C$_1$-C$_6$ alkyl, C$_1$-C$_6$ haloalkyl, C$_3$-C$_7$ cycloalkyl and 4- to 6-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 4- to 6-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO (5- to 10-membered heteroaryl), OCO(4- to 6-membered heterocycloalkyl), NHCOC$_1$-C$_6$ alkyl, NHCOC$_6$-C$_{10}$ aryl, NHCO(5- to 10-membered heteroaryl), NHCO(4- to 6-membered heterocycloalkyl), and NHCOC$_2$-C$_6$ alkynyl;
wherein each R$^7$ is independently selected from C$_1$-C$_6$ alkyl, C$_1$-C$_6$ haloalkyl, C$_1$-C$_6$ alkoxy, C$_1$-C$_6$ haloalkoxy, halo, CN, COC$_1$-C$_6$ alkyl, CO$_2$C$_1$-C$_6$ alkyl, CO$_2$C$_3$-C$_6$ cycloalkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, CONR$^8$R$^9$, SF$_5$, S(O$_2$)C$_1$-C$_6$ alkyl, C$_3$-C$_7$ cycloalkyl and 4- to 6-membered heterocycloalkyl, wherein the C$_1$-C$_6$ alkyl is optionally substituted with one to two C$_1$-C$_6$ alkoxy;
or at least one pair of R$^6$ and R$^7$ on adjacent atoms, taken together with the atoms connecting them, independently form at least one C$_4$-C$_7$ (e.g., C$_4$-C$_6$) carbocyclic ring (e.g., aliphatic carbocyclic ring) or at least one 5-to-7-membered (e.g., 5-to-6-membered) heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, C$_1$-C$_6$ alkyl, C$_1$-C$_6$ alkoxy, NR$^8$R$^9$, CH$_2$NR$^8$R$^9$, =NR$^{10}$, COOC$_1$-C$_6$ alkyl, C$_6$-C$_{10}$ aryl, and CONR$^8$R$^9$.

In some embodiments, o=1 or 2; p=1, 2, or 3; and
R$^6$ and R$^7$ are each independently selected from C$_1$-C$_6$ alkyl, C$_1$-C$_6$ alkoxy, halo, CN, NO$_2$, COC$_1$-C$_6$ alkyl, CO$_2$C$_1$-C$_6$ alkyl, C$_6$-C$_{10}$ aryl, 5- to 10-membered heteroaryl, CONR$^8$R$^9$, and 3- to 7-membered heterocycloalkyl,
wherein the C$_1$-C$_6$ alkyl and 3- to 7-membered heterocycloalkyl is optionally substituted with one or more substituents each independently selected from hydroxy or oxo,
or at least one pair of R$^6$ and R$^7$ on adjacent atoms, taken together with the atoms connecting them, independently form at least one $C_4$-$C_5$ carbocyclic ring, wherein the carbocyclic ring is optionally independently substituted with one or more hydroxy or oxo.

In some embodiments, o=1 or 2; p=1, 2, or 3; and
$R^6$ and $R^7$ are each independently selected from $C_1$-$C_6$ alkyl, $C_1$-$C_6$ alkoxy, halo, CN, $NO_2$, $COC_1$-$C_6$ alkyl, $CO_2C_1$-$C_6$ alkyl, $C_6$-$C_{10}$ aryl, 5- to 10-membered heteroaryl, $CONR^8R^9$, and 3- to 7-membered heterocycloalkyl, wherein the $C_1$-$C_6$ alkyl and 3- to 7-membered heterocycloalkyl is optionally substituted with one or more substituents each independently selected from hydroxy or oxo.

In some embodiments, o=1 or 2; p=1, 2, or 3; and
one $R^6$ and one $R^7$ are on adjacent atoms, and taken together with the atoms connecting them, form a $C_4$-$C_5$ carbocyclic ring or a 5- to 8-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=1 or 2; p=1, 2, or 3; and
one $R^6$ and one $R^7$ are on adjacent atoms, and taken together with the atoms connecting them, form a $C_6$ carbocyclic ring or a 5-to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=1 or 2; p=1, 2, or 3; and
one $R^6$ and one $R^7$ are on adjacent atoms, and taken together with the atoms connecting them, form a $C_4$-$C_5$ carbocyclic ring or a 5- to 8-membered heterocyclic ring containing 1 or 2 heteroatoms independently selected from O, N, and S, wherein the carbocyclic ring or heterocyclic ring is unsubstituted.

In some embodiments, o=2; p=2 or 3; and
two pairs, each of one $R^6$ and one $R^7$, are on adjacent atoms, and each pair of one $R^6$ and one $R^7$ taken together with the atoms connecting them independently form a $C_4$-$C_5$ carbocyclic ring or a 5- to 8-membered heterocyclic ring containing 1 or 2 heteroatoms independently selected from O, N, and S, wherein each carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^7$ taken together with the atoms connecting them independently form a $C_6$ carbocyclic ring or a 5-to-6-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^7$ taken together with the atoms connecting them independently form a $C_5$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^7$ taken together with the atoms connecting them independently form a $C_4$ carbocyclic ring, wherein the carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, one pair of one $R^6$ and one $R^7$ taken together with the atoms connecting them independently form a $C_4$ carbocyclic ring, and the other pair of one $R^6$ and one $R^7$ taken together with the atoms connecting them independently form a $C_5$ carbocyclic ring, wherein each of $C_4$ and $C_5$ carbocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, one pair of one $R^6$ and one $R^7$ taken together with the atoms connecting them independently form a $C_5$ carbocyclic ring, and the other pair of one $R^6$ and one $R^7$ taken together with the atoms connecting them independently form a 5- to 8-membered heterocyclic ring containing 1 or 2 heteroatoms independently selected from O, N, and S (e.g., a 5-membered heterocyclic ring, e.g., 5-membered heterocyclic ring containing 1 heteroatom), wherein each of carbocyclic and heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^7$ taken together with the atoms connecting them independently form a $C_4$-$C_5$ carbocyclic ring or a 5- to 8-membered heterocyclic ring containing 1 or 2 heteroatoms independently selected from O, N, and S, wherein the carbocyclic ring or heterocyclic ring is unsubstituted.

Particular embodiments wherein o=1; p=0:
In some embodiments, $R^6$ is $C_1$-$C_6$ alkyl.
In some embodiments, $R^6$ is isopropyl.
In some embodiments, $R^6$ is ethyl.
In some embodiments, $R^6$ is methyl.
In some embodiments, $R^6$ is $C_1$-$C_6$ alkyl substituted with one or more halo.
In some embodiments, $R^6$ is trifluoromethyl.
In some embodiments, $R^6$ is trifluoromethoxy.
In some embodiments, $R^6$ is $C_3$-$C_7$ cycloalkyl.
In some embodiments, $R^6$ is cyclopropyl.
In some embodiments, $R^6$ is halo.
In some embodiments, $R^6$ is chloro.
In some embodiments, $R^6$ is fluoro.
In some embodiments, $R^6$ is cyano.
In some embodiments, $R^6$ is attached to a carbon of an aryl ring B.
In some embodiments, $R^6$ is attached to a carbon of a heteroaryl ring B.
In some embodiments, $R^6$ is attached to a nitrogen of a heteroaryl ring B.

Particular embodiments wherein o=1 or 2: p=1, 2, or 3:

In some embodiments, at least one $R^6$ is $C_1$-$C_6$ alkyl, and at least one $R^7$ is $C_1$-$C_6$ alkyl optionally substituted with one or more halo.

In some embodiments, at least one $R^6$ is $C_1$-$C_6$ alkyl and at least one $R^7$ is $C_1$-$C_6$ alkyl.

In some embodiments, at least one $R^6$ is isopropyl and at least one $R^7$ is methyl.

In some embodiments, at least one $R^6$ is isopropyl and at least one $R^7$ is isopropyl.

In some embodiments, o=1; p=1; $R^6$ is isopropyl; and $R^7$ is isopropyl.

In some embodiments, at least one $R^6$ is $C_1$-$C_6$ alkyl, and at least one $R^7$ is $C_1$-$C_6$ alkyl substituted with one or more halo.

In some embodiments, at least one $R^6$ is isopropyl and at least one $R^7$ is trifluoromethyl.

In some embodiments, at least one $R^6$ is $C_1$-$C_6$ alkyl, and at least one $R^7$ is $C_3$-$C_7$ cycloalkyl.

In some embodiments, at least one $R^6$ is isopropyl and at least one $R^7$ is cyclopropyl.

In some embodiments, o=1; p=1; $R^6$ is isopropyl; and $R^7$ is cyclopropyl.

In some embodiments, at least one $R^6$ is $C_1$-$C_6$ alkyl, and at least one $R^7$ is halo.

In some embodiments, at least one $R^6$ is isopropyl and at least one $R^7$ is halo.

In some embodiments, at least one $R^6$ is isopropyl and at least one $R^7$ is chloro.

In some embodiments, at least one $R^6$ is isopropyl and at least one $R^7$ is fluoro.

In some embodiments, o=1; p=1; $R^6$ is isopropyl; and $R^7$ is chloro.

In some embodiments, o=2; p=1; at least one $R^6$ is isopropyl; and $R^7$ is chloro.

In some embodiments, o=1; p=1; $R^6$ is isopropyl; and $R^7$ is fluoro.

In some embodiments, o=2; p=1; at least one $R^6$ is isopropyl; and $R^7$ is fluoro.

In some embodiments, o=2; p=2; at least one $R^6$ is isopropyl; and at least one $R^7$ is fluoro.

In some embodiments, o=2; p=2; at least one $R^6$ is isopropyl; one $R^7$ is fluoro; and the other $R^7$ is cyano.

In some embodiments, o=2; p=3; at least one $R^6$ is isopropyl; two $R^7$ are fluoro; and one $R^7$ is chloro.

In some embodiments, o=2; p=1; at least one $R^6$ is ethyl; and $R^7$ is fluoro.

In some embodiments, o=2; p=1; one $R^6$ is isopropyl; the other $R^6$ is trifluoromethyl; and $R^7$ is chloro.

In some embodiments, at least one $R^6$ is $C_1$-$C_6$ alkyl, and at least one $R^7$ is cyano.

In some embodiments, at least one $R^6$ is isopropyl and at least one $R^7$ is cyano.

In some embodiments, o=1; p=1; $R^6$ is isopropyl; and $R^7$ is cyano.

In some embodiments, o=2; p=1; at least one $R^6$ is isopropyl; and $R^7$ is cyano.

In some embodiments, at least one $R^6$ is $C_3$-$C_7$ cycloalkyl, and at least one $R^7$ is $C_3$-$C_7$ cycloalkyl.

In some embodiments, at least one $R^6$ is cyclopropyl, and at least one $R^7$ is cyclopropyl.

In some embodiments, at least one $R^6$ is $C_3$-$C_7$ cycloalkyl, and at least one $R^7$ is halo.

In some embodiments, at least one $R^6$ is cyclopropyl and at least one $R^7$ is halo.

In some embodiments, at least one $R^6$ is cyclopropyl and at least one $R^7$ is chloro.

In some embodiments, at least one $R^6$ is cyclopropyl and at least one $R^7$ is fluoro.

In some embodiments, o=1; p=1; $R^6$ is cyclopropyl; and $R^7$ is chloro.

In some embodiments, o=1; p=1; $R^6$ is cyclopropyl; and $R^7$ is fluoro.

In some embodiments, at least one $R^6$ is $C_1$-$C_6$ alkyl, and at least one $R^7$ is $C_1$-$C_6$ alkoxy optionally substituted with one or more halo.

In some embodiments, at least one $R^6$ is isopropyl, and at least one $R^7$ is $C_1$-$C_6$ alkoxy.

In some embodiments, at least one $R^6$ is isopropyl, and at least one $R^7$ is methoxy.

In some embodiments, o=1; p=1; $R^6$ is isopropyl, and $R^7$ is methoxy.

In some embodiments, o=2; p=1; at least one $R^6$ is isopropyl, and $R^7$ is methoxy.

In some embodiments, at least one $R^6$ is $C_1$-$C_6$ alkyl, and at least one $R^7$ is $C_1$-$C_6$ alkoxy substituted with one or more halo.

In some embodiments, at least one $R^6$ is isopropyl, and at least one $R^7$ is trifluoromethoxy.

In some embodiments, at least one $R^6$ is isopropyl, and at least one $R^7$ is difluoromethoxy.

In some embodiments, at least one $R^6$ is halo, and at least one $R^7$ is $C_1$-$C_6$ haloalkyl optionally substituted with hydroxy.

In some embodiments, o=1; p=1; $R^6$ is chloro, and $R^7$ is trifluoromethyl.

In some embodiments, at least one $R^6$ is halo, and at least one $R^7$ is $C_1$-$C_6$ haloalkoxy.

In some embodiments, at least one $R^6$ is chloro, and at least one $R^7$ is trifluoromethoxy.

In some embodiments, o=1; p=1; $R^6$ is chloro, and $R^7$ is trifluoromethoxy.

In some embodiments, at least one $R^6$ is $C_1$-$C_6$ alkoxy; and at least one $R^7$ is halo.

In some embodiments, o=1; p=2; $R^6$ is $C_1$-$C_6$ alkoxy; and at least one $R^7$ is chloro.

In some embodiments, at least one $R^7$ is $C_1$-$C_6$ alkyl, and at least one $R^6$ is $C_1$-$C_6$ alkyl optionally substituted with one or more halo.

In some embodiments, at least one $R^7$ is isopropyl and at least one $R^6$ is methyl.

In some embodiments, at least one $R^7$ is $C_1$-$C_6$ alkyl, and at least one $R^6$ is $C_1$-$C_6$ alkyl substituted with one or more halo.

In some embodiments, at least one $R^7$ is isopropyl and at least one $R^6$ is trifluoromethyl.

In some embodiments, at least one $R^7$ is $C_1$-$C_6$ alkyl, and at least one $R^6$ is $C_3$-$C_7$ cycloalkyl.

In some embodiments, at least one $R^7$ is isopropyl and at least one $R^6$ is cyclopropyl.

In some embodiments, o=1; p=1; $R^7$ is isopropyl; and $R^6$ is cyclopropyl.

In some embodiments, at least one $R^7$ is $C_1$-$C_6$ alkyl, and at least one $R^6$ is halo.

In some embodiments, at least one $R^7$ is isopropyl and at least one $R^6$ is halo.

In some embodiments, at least one $R^7$ is isopropyl and at least one $R^6$ is chloro.

In some embodiments, at least one $R^7$ is isopropyl and at least one $R^6$ is fluoro.

In some embodiments, o=1; p=1; $R^7$ is isopropyl; and $R^6$ is chloro.

In some embodiments, o=2; p=1; $R^7$ is isopropyl; and at least one $R^6$ is chloro.

In some embodiments, o=1; p=1; $R^7$ is isopropyl; and $R^6$ is fluoro.
In some embodiments, o=2; p=1; $R^7$ is isopropyl; and at least one $R^6$ is fluoro.
In some embodiments, o=2; p=2; $R^7$ is isopropyl; and at least one $R^6$ is fluoro.
In some embodiments, o=2; p=2; at least one $R^7$ is isopropyl; one $R^6$ is fluoro; and the other $R^6$ is cyano.
In some embodiments, o=2; p=1; $R^7$ is ethyl; and at least one $R^6$ is fluoro.
In some embodiments, o=1; p=2; one $R^7$ is isopropyl; the other $R^7$ is trifluoromethyl; and $R^6$ is chloro.
In some embodiments, at least one $R^7$ is $C_1$-$C_6$ alkyl, and at least one $R^6$ is cyano.
In some embodiments, at least one $R^7$ is isopropyl and at least one $R^6$ is cyano.
In some embodiments, o=1; p=1; $R^7$ is isopropyl; and $R^6$ is cyano.
In some embodiments, o=2; p=1; $R^7$ is isopropyl; and at least one $R^6$ is cyano.
In some embodiments, at least one $R^7$ is $C_3$-$C_7$ cycloalkyl, and at least one $R^6$ is $C_3$-$C_7$ cycloalkyl.
In some embodiments, at least one $R^7$ is cyclopropyl, and at least one $R^6$ is cyclopropyl.
In some embodiments, at least one $R^7$ is $C_3$-$C_7$ cycloalkyl, and at least one $R^6$ is halo.
In some embodiments, at least one $R^7$ is cyclopropyl and at least one $R^6$ is halo.
In some embodiments, at least one $R^7$ is cyclopropyl and at least one $R^6$ is chloro.
In some embodiments, at least one $R^7$ is cyclopropyl and at least one $R^6$ is fluoro.
In some embodiments, o=1; p=1; $R^7$ is cyclopropyl; and $R^6$ is chloro.
In some embodiments, o=1; p=1; $R^7$ is cyclopropyl; and $R^6$ is fluoro.
In some embodiments, at least one $R^7$ is $C_1$-$C_6$ alkyl, and at least one $R^6$ is $C_1$-$C_6$ alkoxy optionally substituted with one or more halo.
In some embodiments, at least one $R^7$ is isopropyl, and at least one $R^6$ is $C_1$-$C_6$ alkoxy.
In some embodiments, at least one $R^7$ is isopropyl, and at least one $R^6$ is methoxy.
In some embodiments, o=1; p=1; $R^7$ is isopropyl, and $R^6$ is methoxy.
In some embodiments, o=2; p=1; $R^7$ is isopropyl, and at least one $R^6$ is methoxy.
In some embodiments, at least one $R^7$ is $C_1$-$C_6$ alkyl, and at least one $R^6$ is $C_1$-$C_6$ alkoxy substituted with one or more halo.
In some embodiments, at least one $R^7$ is isopropyl, and at least one $R^6$ is trifluoromethoxy.
In some embodiments, at least one $R^7$ is halo, and at least one $R^6$ is $C_1$-$C_6$ haloalkyl optionally substituted with one or more hydroxy.
In some embodiments, o=1; p=1; $R^7$ is chloro, and $R^6$ is trifluoromethyl.
In some embodiments, at least one $R^7$ is halo, and at least one $R^6$ is $C_1$-$C_6$ haloalkoxy.
In some embodiments, at least one $R^7$ is chloro, and at least one $R^6$ is trifluoromethoxy.
In some embodiments, o=1; p=1; $R^7$ is chloro, and $R^6$ is trifluoromethoxy.
In some embodiments, at least one $R^7$ is $C_1$-$C_6$ alkoxy; and at least one $R^6$ is halo.
In some embodiments, o=1; p=2; at least one $R^7$ is $C_1$-$C_6$ alkoxy; and $R^6$ is chloro.

In some embodiments, $R^6$ and $R^7$ are each attached to a carbon of an aryl ring B.
In some embodiments, $R^6$ and $R^7$ are each attached to a carbon of a heteroaryl ring B.
In some embodiments, $R^6$ is attached to a carbon and $R^7$ is attached to a nitrogen of a heteroaryl ring B.
In some embodiments, $R^7$ is attached to a carbon and $R^6$ is attached to a nitrogen of a heteroaryl ring B.
In some embodiments, one $R^6$ and one $R^7$ are on adjacent atoms, and taken together with the atoms connecting them, form a $C_5$ carbocyclic ring optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.
In some embodiments, $R^6$ and $R^7$ are on adjacent atoms, and taken together with the atoms connecting them, form a $C_5$ aliphatic carbocyclic ring.
In some embodiments, $R^6$ and $R^7$ are on adjacent atoms, and taken together with the atoms connecting them, form a $C_6$ carbocyclic ring optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.
In some embodiments, $R^6$ and $R^7$ are on adjacent atoms, and taken together with the atoms connecting them, form a $C_6$ aliphatic carbocyclic ring.
In some embodiments, $R^6$ and $R^7$ are on adjacent atoms, and taken together with the atoms connecting them, form a $C_6$ aromatic carbocyclic ring.
In some embodiments, $R^6$ and $R^7$ are on adjacent atoms, and taken together with the atoms connecting them, form a 5-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.
In some embodiments, $R^6$ and $R^7$ are on adjacent atoms, and taken together with the atoms connecting them, form a 5-membered aliphatic heterocyclic ring containing 1 or 2 heteroatoms independently selected from O, N, and S.
In some embodiments, $R^6$ and $R^7$ are on adjacent atoms, and taken together with the atoms connecting them, form a 5-membered heteroaromatic ring containing 1 or 2 heteroatoms independently selected from O, N, and S.
In some embodiments, $R^6$ and $R^7$ are on adjacent atoms, and taken together with the atoms connecting them, form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, =$NR^{10}$, $COOC_1$-$C_6$ alkyl, $C_6$-$C_{10}$ aryl, and $CONR^8R^9$.
In some embodiments, $R^6$ and $R^7$ are on adjacent atoms, and taken together with the atoms connecting them, form a 6-membered aliphatic heterocyclic ring containing 1 or 2 heteroatoms independently selected from O, N, and S.
In some embodiments, $R^6$ and $R^7$ are on adjacent atoms, and taken together with the atoms connecting them, form a 6-membered heteroaromatic ring containing 1 or 2 heteroatoms independently selected from O, N, and S.
In some embodiments, one $R^6$ and one $R^7$ are on adjacent atoms, and taken together with the atoms connecting them, form a $C_4$-$C_5$ carbocyclic ring or a 5- to 8-membered heterocyclic ring containing 1 or 2 heteroatoms independently selected from O, N, and S, wherein the ring is fused to the B ring at the 2- and 3-positions relative to the bond connecting the B ring to the Y(CO) group.

In some embodiments, o=1; p=2; and
one pair of one $R^6$ and one $R^7$, are on adjacent atoms; and said pair of one $R^6$ and one $R^7$ taken together with the atoms connecting them form form a $C_4$-$C_5$ carbocyclic ring or a 5- to 8-membered heterocyclic ring containing 1 or 2 heteroatoms independently selected from O, N, and S,
wherein the ring is fused to the B ring at the 2- and 3-positions relative to the bond connecting the B ring to the Y(CO) group.

In some embodiments, o=1; p=2; and
one pair of one $R^6$ and one $R^7$, are on adjacent atoms; and said pair of one $R^6$ and one $R^7$ taken together with the atoms connecting them form form a $C_4$-$C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=1; p=2; and
one pair of one $R^6$ and one $R^7$, are on adjacent atoms; and said pair of one $R^6$ and one $R^7$ taken together with the atoms connecting them form form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=1; p=2; and
one pair of one $R^6$ and one $R^7$, are on adjacent atoms; and said pair of one $R^6$ and one $R^7$ taken together with the atoms connecting them form form a $C_5$ aliphatic carbocyclic ring.

In some embodiments, o=2; p=2; and
one pair of one $R^6$ and one $R^7$, are on adjacent atoms; and said pair of one $R^6$ and one $R^7$ taken together with the atoms connecting them form form a $C_4$-$C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2; and
one pair of one $R^6$ and one $R^7$, are on adjacent atoms; and said pair of one $R^6$ and one $R^7$ taken together with the atoms connecting them form form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=1; p=2; and
one pair of one $R^6$ and one $R^7$, are on adjacent atoms; and said pair of one $R^6$ and one $R^7$ taken together with the atoms connecting them form form a $C_5$ aliphatic carbocyclic ring.

In some embodiments, o=2; p=2 or 3; and
two pairs, each of one $R^6$ and one $R^7$, are on adjacent atoms; one pair of one $R^6$ and one $R^7$ taken together with the atoms connecting them form a $C_4$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$; and the other pair of one $R^6$ and one $R^7$ taken together with the atoms connecting them form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms; one pair of one $R^6$ and one $R^7$ taken together with the atoms connecting them form a $C_4$ aliphatic carbocyclic ring and the other pair of one $R^6$ and one $R^7$ taken together with the atoms connecting them form a $C_5$ aliphatic carbocyclic ring.

In some embodiments, o=2; p=2 or 3; and
two pairs, each of one $R^6$ and one $R^7$, are on adjacent atoms, and each pair of one $R^6$ and one $R^7$ taken together with the atoms connecting them form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^7$ taken together with the atoms connecting them form a $C_5$ aliphatic carbocyclic ring.

In some embodiments, o=2; p=2 or 3; and
two pairs, each of one $R^6$ and one $R^7$, are on adjacent atoms, and each pair of one $R^6$ and one $R^7$ taken together with the atoms connecting them form a $C_6$ carbocyclic ring optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^7$ taken together with the atoms connecting them form a $C_6$ aliphatic carbocyclic ring.

In some embodiments, o=2; p=2 or 3; and
two pairs, each of one $R^6$ and one $R^7$, are on adjacent atoms, and each pair of one $R^6$ and one $R^7$ taken together with the atoms connecting them form a $C_6$ aromatic carbocyclic ring.

In some embodiments, o=2; p=2 or 3; and
two pairs, each of one $R^6$ and one $R^7$, are on adjacent atoms, and each pair of one $R^6$ and one $R^7$ taken together with the atoms connecting them form a 5-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^7$ taken together with the atoms connecting them form a 5-membered aliphatic heterocyclic ring containing 1 or 2 heteroatoms independently selected from O, N, and S.

In some embodiments, o=2; p=2 or 3; and
two pairs, each of one $R^6$ and one $R^7$, are on adjacent atoms, and each pair of one $R^6$ and one $R^7$ taken together with the atoms connecting them form a 5-membered heteroaromatic ring containing 1 or 2 heteroatoms independently selected from O, N, and S.

In some embodiments, o=2; p=2 or 3; and
two pairs, each of one $R^6$ and one $R^7$, are on adjacent atoms, and each pair of one $R^6$ and one $R^7$ taken together with the atoms connecting them form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms, and each pair of one $R^6$ and one $R^7$ taken together with the atoms connecting them form a 6-membered aliphatic heterocyclic ring containing 1 or 2 heteroatoms independently selected from O, N, and S.

In some embodiments, o=2; p=2 or 3; and
two pairs, each of one $R^6$ and one $R^7$, are on adjacent atoms, and each pair of one $R^6$ and one $R^7$ taken together with the atoms connecting them form a 6-membered heteroaromatic ring containing 1 or 2 heteroatoms independently selected from O, N, and S.

In some embodiments, o=2; p=2 or 3; and
two pairs, each of one $R^6$ and one $R^7$, are on adjacent atoms; one pair of one $R^6$ and one $R^7$ taken together with the atoms connecting them form a $C_{4-8}$ carbocyclic ring optionally independently substituted with one or more substituents independently selected from hydroxy, halo, oxo, $C_1$-$C_6$ alkyl, $C_1$-$C_6$ alkoxy, $NR^8R^9$, $—NR^{10}$, $COOC_1$-$C_6$ alkyl, $C_6$-$C_{10}$ aryl, and $CONR^8R^9$; and the other pair of one $R^6$ and one $R^7$ taken together with the atoms connecting them form a 5- to 8-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms; one pair of one $R^6$ and one $R^7$ taken together with the atoms connecting them form a $C_5$ aliphatic carbocyclic ring and the other pair of one $R^6$ and one $R^7$ taken together with the atoms connecting them form a 5-membered aliphatic heterocyclic ring containing 1 or 2 heteroatoms independently selected from O, N, and S.

In some embodiments, o=2; p=2 or 3; and
two pairs, each of one $R^6$ and one $R^7$, are on adjacent atoms; one pair of one $R^6$ and one $R^7$ taken together with the atoms connecting them form a $C_5$ carbocyclic ring optionally independently substituted with one or more substituents independently selected from hydroxy, halo, oxo, $C_1$-$C_6$ alkyl, $C_1$-$C_6$ alkoxy, $NR^8R^9$, $—NR^{10}$, $COOC_1$-$C_6$ alkyl, $C_6$-$C_{10}$ aryl, and $CONR^8R^9$; and the other pair of one $R^6$ and one $R^7$ taken together with the atoms connecting them form a 6-membered heterocyclic ring containing 1 or 2 heteroatoms independently selected from O, N, and S, optionally substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, o=2; p=2 or 3; and
two pairs, each of one $R^6$ and one $R^7$, are on adjacent atoms; one pair of one $R^6$ and one $R^7$ taken together with the atoms connecting them form a $C_5$ aliphatic carbocyclic ring and the other pair of one $R^6$ and one $R^7$ taken together with the atoms connecting them form a 5-membered aliphatic heterocyclic ring containing 1 or 2 heteroatoms independently selected from O, N, and S.

In some embodiments, o=2; p=2 or 3; and
two pairs, each of one $R^6$ and one $R^7$, are on adjacent atoms, and each pair of one $R^6$ and one $R^7$ taken together with the atoms connecting them independently form a $C_4$-$C_5$ carbocyclic ring or a 5- to 8-membered heterocyclic ring containing 1 or 2 heteroatoms independently selected from O, N, and S,
wherein one of the two rings is fused to the B ring at the 2- and 3-positions relative to the bond connecting the B ring to the YC(O) group, and the other of the two rings is fused to the B ring at the 5- and 6-positions relative to the bond connecting the B ring to the YC(O) group.

In some embodiments, o=2; p=2 or 3; and
two pairs, each of one $R^6$ and one $R^7$, are on adjacent atoms, and each pair of one $R^6$ and one $R^7$ taken together with the atoms connecting them independently form a $C_4$-$C_5$ carbocyclic ring or a 5- to 8-membered heterocyclic ring containing 1 or 2 heteroatoms independently selected from O, N, and S,
wherein one of the two rings is fused to the B ring at the 2- and 3-positions relative to the bond connecting the B ring to the YC(O) group, and the other of the two rings is fused to the B ring at the 4- and 5-positions relative to the bond connecting the B ring to the YC(O) group.

In some embodiments, o=2; p=2; and
two pairs, each of one $R^6$ and one $R^7$, are on adjacent atoms, and each pair of one $R^6$ and one $R^7$ taken together with the atoms connecting them form a $C_5$ aliphatic carbocyclic ring.

In some embodiments, o=2; p=2; and
two pairs, each of one $R^6$ and one $R^7$, are on adjacent atoms, one pair of one $R^6$ and one $R^7$ taken together with the atoms connecting them form a $C_4$ aliphatic carbocyclic ring, and the other pair of one $R^6$ and one $R^7$ taken together with the atoms connecting them form a $C_5$ aliphatic carbocyclic ring.

In some embodiments, o=2; p=2; and
two pairs, each of one $R^6$ and one $R^7$, are on adjacent atoms, and each pair of one $R^6$ and one $R^7$ taken together with the atoms connecting them form a $C_4$ aliphatic carbocyclic ring.

In some embodiments, o=2; p=2; and
two pairs, each of one $R^6$ and one $R^7$, are on adjacent atoms, one pair of one $R^6$ and one $R^7$ taken together with the atoms connecting them form a $C_5$ aliphatic carbocyclic ring, and the other pair of one $R^6$ and one $R^7$ taken together with the atoms connecting them form a 5-membered heterocyclic ring containing 1 or 2 heteroatoms independently selected from O, N, and S.

In some embodiments, o=2; p=3; and
two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is halo (e.g., Cl or F).

In some embodiments, o=2; p=3; and
two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is CN.

In some embodiments, one $R^7$ is pyrazolyl and is para to the bond connecting the B ring to the YC(O) group of Formula AA.

In some embodiments, one $R^7$ is 3-pyrazolyl and is para to the bond connecting the B ring to the YC(O) group of Formula AA.

In some embodiments, one $R^7$ is 4-pyrazolyl and is para to the bond connecting the B ring to the YC(O) group of Formula AA.

In some embodiments, one $R^7$ is 5-pyrazolyl and is para to the bond connecting the B ring to the YC(O) group of Formula AA.

In some embodiments, one $R^7$ is thiazolyl and is para to the bond connecting the B ring to the YC(O) group of Formula AA.

In some embodiments, one $R^7$ is 4-thiazolyl and is para to the bond connecting the B ring to the YC(O) group of Formula AA.

In some embodiments, one $R^7$ is 5-thiazolyl and is para to the bond connecting the B ring to the YC(O) group of Formula AA.

In some embodiments, one $R^7$ is furyl and is para to the bond connecting the B ring to the YC(O) group of Formula AA.

In some embodiments, one $R^7$ is 2-furyl and is para to the bond connecting the B ring to the YC(O) group of Formula AA.

In some embodiments, one $R^7$ is thiophenyl and is para to the bond connecting the B ring to the YC(O) group of Formula AA.
In some embodiments, one $R^7$ is 2-thiophenyl and is para to the bond connecting the B ring to the YC(O) group of Formula AA.
In some embodiments, one $R^7$ is phenyl and is para to the bond connecting the B ring to the YC(O) group of Formula AA.
In some embodiments, one $R^7$ is cycloalkenyl (e.g., cyclopentenyl, e.g., 1-cyclopentenyl) and is para to the bond connecting the B ring to the YC(O) group of Formula AA.
In some embodiments, one $R^7$ is phenyl optionally substituted with one or more $C_1$-$C_6$ alkyl (e.g., methyl or propyl, e.g., 2-propyl) optionally substituted with one or more hydroxyl, $NR^8R^9$ (e.g., dimethylamino), or $C_6$-$C_{10}$ aryl (e.g., phenyl, naphthyl, or methylenedioxyphenyl and is para to the bond connecting the B ring to the YC(O) group of Formula AA.
In some embodiments, one $R^7$ is phenyl optionally substituted with one or more $C_1$-$C_6$ alkoxy (e.g., methoxy) optionally substituted with one or more hydroxyl, $NR^8R^9$ (e.g., dimethylamino), or $C_6$-$C_{10}$ aryl (e.g., phenyl, naphthyl, or methylenedioxyphenyl and is para to the bond connecting the B ring to the YC(O) group of Formula AA.
In some embodiments, one $R^7$ is phenyl optionally substituted with one or more $C_6$-$C_{10}$ aryloxy (e.g., phenoxy) and is para to the bond connecting the B ring to the YC(O) group of Formula AA.
In some embodiments, one $R^7$ is phenyl optionally substituted with one or more CN and is para to the bond connecting the B ring to the YC(O) group of Formula AA.
In some embodiments, one $R^7$ is phenyl optionally substituted with one or more halo (e.g., F, Cl) and is para to the bond connecting the B ring to the YC(O) group of Formula AA and is para to the bond connecting the B ring to the YC(O) group of Formula AA.
In some embodiments, one $R^7$ is phenyl optionally substituted with one or more $COOC_1$-$C_6$ alkyl (e.g., $CO_2$t-Bu) and is para to the bond connecting the B ring to the YC(O) group of Formula AA.
In some embodiments, one $R^7$ is phenyl optionally substituted with one or more $S(O_2)C_1$-$C_6$ alkyl (e.g., $S(O_2)$methyl) and is para to the bond connecting the B ring to the YC(O) group of Formula AA.
In some embodiments, one $R^7$ is phenyl optionally substituted with one or more 3- to 7-membered heterocycloalkyl (e.g., morpholinyl) and is para to the bond connecting the B ring to the YC(O) group of Formula AA.
In some embodiments, one $R^7$ is phenyl optionally substituted with one or more $CONR^8R^9$ (e.g., unsubstituted amido) and is para to the bond connecting the B ring to the Y(CO) group of Formula AA.
In some embodiments, one $R^7$ is phenyl optionally substituted with one or more $C_1$-$C_6$ alkyl (e.g., methyl or propyl, e.g., 2-propyl) and with one or more halo (e.g., F, Cl) and is para to the bond connecting the B ring to the Y(CO) group of Formula AA and is para to the bond connecting the B ring to the Y(CO) group of Formula AA.
In some embodiments, $R^6$ and $R^7$ are each attached to a carbon of an aryl ring B.
In some embodiments, $R^6$ and $R^7$ are each attached to a carbon of a heteroaryl ring B.
In some embodiments, $R^6$ is attached to a carbon and $R^7$ is attached to a nitrogen of a heteroaryl ring B.
In some embodiments, $R^7$ is attached to a carbon and $R^6$ is attached to a nitrogen of a heteroaryl ring B.

In some embodiments of any of the formulae herein, each of $R^1$ and $R^2$ is independently selected from the group consisting of $C_1$-$C_6$ alkyl optionally substituted with one or more hydroxy, halo, oxo, or $C_1$-$C_6$ alkoxy; $C_3$-$C_7$ cycloalkyl optionally substituted with one or more hydroxy, halo, oxo, $C_1$-$C_6$ alkoxy, or $C_1$-$C_6$ alkyl; wherein the $C_1$-$C_6$ alkoxy or $C_1$-$C_6$ alkyl is further optionally substituted with one to three hydroxy, halo, $NR^8R^9$, or oxo; 3- to 7-membered heterocycloalkyl optionally substituted with one or more hydroxy, halo, oxo, or $C_1$-$C_6$ alkyl wherein the $C_1$-$C_6$ alkoxy or $C_1$-$C_6$ alkyl is further optionally substituted with one to three hydroxy, halo, or oxo; $C_1$-$C_6$ haloalkyl; $C_1$-$C_6$ alkoxy; $C_1$-$C_6$ haloalkoxy; halo; CN; CO—$C_1$-$C_6$ alkyl; CO—$C_6$-$C_{10}$ aryl; CO(5- to 10-membered heteroaryl); $CO_2C_1$-$C_6$ alkyl; $CO_2C_3$-$C_8$ cycloalkyl; $OCOC_1$-$C_6$ alkyl; $OCOC_6$-$C_{10}$ aryl; OCO(5- to 10-membered heteroaryl); OCO(3- to 7-membered heterocycloalkyl); $C_6$-$C_{10}$ aryl; 5- to 10-membered heteroaryl; $NH_2$; $NHC_1$-$C_6$ alkyl; $N(C_1$-$C_6$ alkyl)$_2$; $CONR^8R^9$; $SF_5$; $S(O_2)NR^{11}R^{12}$; $S(O)C_1$-$C_6$ alkyl; and $S(O_2)C_1$-$C_6$ alkyl.

In some embodiments of any of the formulae herein, $R^1$ is selected from the group consisting of 1-hydroxy-2-methylpropan-2-yl; methyl; isopropyl; 2-hydroxy-2-propyl; hydroxymethyl; 1-hydroxyethyl; 2-hydroxyethyl; 1-hydroxy-2-propyl; 1-hydroxy-1-cyclopropyl; 1-hydroxy-1-cyclobutyl; 1-hydroxy-1-cyclopentyl; 1-hydroxy-1-cyclohexyl; morpholinyl; 1,3-dioxolan-2-yl; $COCH_3$; $COCH_2CH_3$; 2-methoxy-2-propyl; fluoro; chloro; phenyl; pyridyl; pyrazolyl; $S(O_2)CH_3$; and $S(O_2)NR^{11}R^{12}$.

In some embodiments, $R^2$ is selected from the group consisting of fluoro, chloro, cyano, methyl; methoxy; ethoxy; isopropyl; 1-hydroxy-2-methylpropan-2-yl; 2-hydroxy-2-propyl; hydroxymethyl; 1-hydroxyethyl; 2-hydroxyethyl; 1-hydroxy-2-propyl; 1-hydroxy-1-cyclopropyl; $COCH_3$; COPh; 2-methoxy-2-propyl; $S(O_2)CH_3$; and $S(O_2)NR^{11}R^{12}$.

In some embodiments, the substituted ring B is

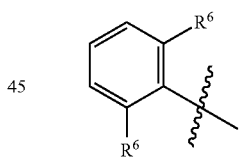

and each $R^6$ is independently selected from the group consisting of: $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl, wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl.

In some embodiments, the substituted ring B is

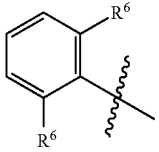

and each R⁶ is independently selected from the group consisting of: $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, wherein the $C_1$-$C_6$ alkyl, $C_1$-$C_6$ haloalkyl, and $C_3$-$C_7$ cycloalkyl is optionally substituted with one or more substituents each independently selected from hydroxy, halo, CN, or oxo.

In some embodiments, the substituted ring B is

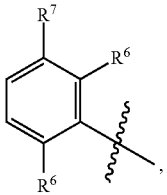

wherein each R⁶ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl,
wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;
wherein R⁷ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO (5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;
or R⁶ and R⁷, taken together with the atoms connecting them, independently form $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^1$, $COOC_1$-$C_6$ alkyl, $C_6$-$C_{10}$ aryl, and $CONR^8R^9$.

In some embodiments, the substituted ring B is

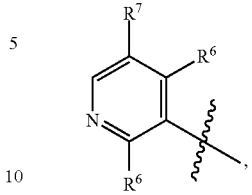

wherein each R⁶ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl,
wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO
(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;
wherein R⁷ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO (5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy;
or R⁶ and R⁷, taken together with the atoms connecting them, independently form $C_4$-$C_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, $C_1$-$C_6$ alkyl, $C_1$-$C_6$ alkoxy, $NR^8R^9$, $=NR^{10}$, $COOC_1$-$C_6$ alkyl, $C_6$-$C_{10}$ aryl, and $CONR^8R^9$.

In some embodiments, the substituted ring B is

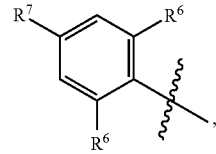

wherein each R⁶ is independently selected from $C_1$-$C_6$ alkyl, $C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl,
wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO (5- to 10-membered heteroaryl), OCO(4- to 6-membered heterocycloalkyl), NHCOC$_1$-C$_6$ alkyl, NHCOC$_6$-C$_{10}$ aryl, NHCO(5- to 10-membered heteroaryl), NHCO(4- to 6-membered heterocycloalkyl), and NHCOC$_2$-C$_6$ alkynyl;

wherein R$^7$ is independently selected from C$_1$-C$_6$ alkyl, C$_1$-C$_6$ haloalkyl, C$_1$-C$_6$ alkoxy, C$_1$-C$_6$ haloalkoxy, halo, CN, COC$_1$-C$_6$ alkyl, CO$_2$C$_1$-C$_6$ alkyl, CO$_2$C$_3$-C$_6$ cycloalkyl, OCOC$_1$-C$_6$ alkyl, OCOC$_6$-C$_{10}$ aryl, OCO (5- to 10-membered heteroaryl), OCO(3- to 7-membered heterocycloalkyl), C$_6$-C$_{10}$ aryl, 5- to 10-membered heteroaryl, CONR$^8$R$^9$, SF$_5$, S(O$_2$)C$_1$-C$_6$ alkyl, C$_3$-C$_7$ cycloalkyl and 4- to 6-membered heterocycloalkyl, wherein the C$_1$-C$_6$ alkyl is optionally substituted with one to two C$_1$-C$_6$ alkoxy.

In some embodiments, the substituted ring B is

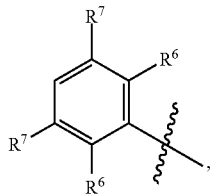

wherein each R$^6$ is independently selected from C$_1$-C$_6$ alkyl, C$_3$-C$_7$ cycloalkyl, C$_1$-C$_6$ haloalkyl, C$_1$-C$_6$ alkoxy, C$_1$-C$_6$ haloalkoxy, halo, CN, C$_6$-C$_{10}$ aryl, 5- to 10-membered heteroaryl, CO—C$_1$-C$_6$ alkyl; CONR$^8$R$^9$, and 4- to 6-membered heterocycloalkyl, wherein the C$_1$-C$_6$ alkyl, C$_1$-C$_6$ haloalkyl, C$_3$-C$_7$ cycloalkyl and 4- to 6-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 4- to 6-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO (5- to 10-membered heteroaryl), OCO(4- to 6-membered heterocycloalkyl), NHCOC$_1$-C$_6$ alkyl, NHCOC$_6$-C$_{10}$ aryl, NHCO(5- to 10-membered heteroaryl), NHCO(4- to 6-membered heterocycloalkyl), and NHCOC$_2$-C$_6$ alkynyl;

wherein each R$^7$ is independently selected from C$_1$-C$_6$ alkyl, C$_1$-C$_6$ haloalkyl, C$_1$-C$_6$ alkoxy, C$_1$-C$_6$ haloalkoxy, halo, CN, COC$_1$-C$_6$ alkyl, CO$_2$C$_1$-C$_6$ alkyl, CO$_2$C$_3$-C$_6$ cycloalkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, CONR$^8$R$^9$, SF$_5$, S(O$_2$)C$_1$-C$_6$ alkyl, C$_3$-C$_7$ cycloalkyl and 4- to 6-membered heterocycloalkyl, wherein the C$_1$-C$_6$ alkyl is optionally substituted with one to two C$_1$-C$_6$ alkoxy;

or at least one pair of R$^6$ and R$^7$ on adjacent atoms, taken together with the atoms connecting them, independently form at least one C$_4$-C$_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, C$_1$-C$_6$ alkyl, C$_1$-C$_6$ alkoxy, NR$^8$R$^9$, =NR$^{10}$, COOC$_1$-C$_6$ alkyl, C$_6$-C$_{10}$ aryl, and CONR$^8$R$^9$.

In some embodiments, the substituted ring B is

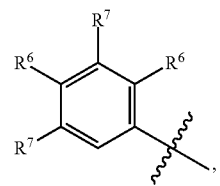

wherein each R$^6$ is independently selected from C$_1$-C$_6$ alkyl, C$_3$-C$_7$ cycloalkyl, C$_1$-C$_6$ haloalkyl, C$_1$-C$_6$ alkoxy, C$_1$-C$_6$ haloalkoxy, halo, CN, C$_6$-C$_{10}$ aryl, 5- to 10-membered heteroaryl, CO—C$_1$-C$_6$ alkyl; CONR$^8$R$^9$, and 4- to 6-membered heterocycloalkyl, wherein the C$_1$-C$_6$ alkyl, C$_1$-C$_6$ haloalkyl, C$_3$-C$_7$ cycloalkyl and 4- to 6-membered heterocycloalkyl is optionally substituted with one or more substituents each independently selected from hydroxy, halo, CN, oxo, C$_1$-C$_6$ alkyl, C$_1$-C$_6$ In some embodiments, the substituted ring B is

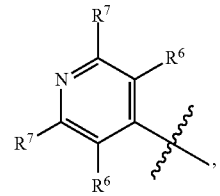

alkoxy, NR$^8$R$^9$, =NR$^{10}$, COOC$_1$-C$_6$ alkyl, CONR$^8$R$^9$, 4- to 6-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO (5- to 10-membered heteroaryl), OCO(4- to 6-membered heterocycloalkyl), NHCOC$_1$-C$_6$ alkyl, NHCOC$_6$-C$_{10}$ aryl, NHCO(5- to 10-membered heteroaryl), NHCO(4- to 6-membered heterocycloalkyl), and NHCOC$_2$-C$_6$ alkynyl;

wherein each R$^7$ is independently selected from C$_1$-C$_6$ alkyl, C$_1$-C$_6$ haloalkyl, C$_1$-C$_6$ alkoxy, C$_1$-C$_6$ haloalkoxy, halo, CN, COC$_1$-C$_6$ alkyl, CO$_2$C$_1$-C$_6$ alkyl, CO$_2$C$_3$-C$_6$ cycloalkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, CONR$^8$R$^9$, SF$_5$, S(O$_2$)C$_1$-C$_6$ alkyl, C$_3$-C$_7$ cycloalkyl and 4- to 6-membered heterocycloalkyl, wherein the C$_1$-C$_6$ alkyl is optionally substituted with one to two C$_1$-C$_6$ alkoxy;

or at least one pair of R$^6$ and R$^7$ on adjacent atoms, taken together with the atoms connecting them, independently form at least one C$_4$-C$_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, C$_1$-C$_6$ alkyl, C$_1$-C$_6$ alkoxy, NR$^8$R$^9$, =NR$^{10}$, COOC$_1$-C$_6$ alkyl, C$_6$-C$_{10}$ aryl, and CONR$^8$R$^9$.

In some embodiments, the substituted ring B is

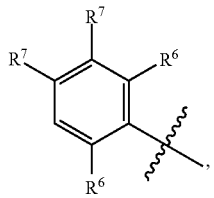

wherein each R$^6$ is independently selected from C$_1$-C$_6$ alkyl, C$_3$-C$_7$ cycloalkyl, C$_1$-C$_6$ haloalkyl, C$_1$-C$_6$ alkoxy, C$_1$-C$_6$ haloalkoxy, halo, CN, C$_6$-C$_{10}$ aryl, 5- to 10-membered heteroaryl, CO—C$_1$-C$_6$ alkyl; CONR$^8$R$^9$, and 4- to 6-membered heterocycloalkyl, wherein the C$_1$-C$_6$ alkyl, C$_1$-C$_6$ haloalkyl, C$_3$-C$_7$ cycloalkyl and 4- to 6-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 4- to 6-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO (5- to 10-membered heteroaryl), OCO(4- to 6-membered heterocycloalkyl), NHCOC$_1$-C$_6$ alkyl, NHCOC$_6$-C$_{10}$ aryl, NHCO(5- to 10-membered heteroaryl), NHCO(4- to 6-membered heterocycloalkyl), and NHCOC$_2$-C$_6$ alkynyl;

wherein each R$^7$ is independently selected from C$_1$-C$_6$ alkyl, C$_1$-C$_6$ haloalkyl, C$_1$-C$_6$ alkoxy, C$_1$-C$_6$ haloalkoxy, halo, CN, COC$_1$-C$_6$ alkyl, CO$_2$C$_1$-C$_6$ alkyl, CO$_2$C$_3$-C$_6$ cycloalkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, CONR$^8$R$^9$, SF$_5$, S(O$_2$)C$_1$-C$_6$ alkyl, C$_3$-C$_7$ cycloalkyl and 4- to 6-membered heterocycloalkyl, wherein the C$_1$-C$_6$ alkyl is optionally substituted with one to two C$_1$-C$_6$ alkoxy;

or R$^6$ and R$^7$, taken together with the atoms connecting them, independently form a C$_4$-C$_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, halo, oxo, C$_1$-C$_6$ alkyl, C$_1$-C$_6$ alkoxy, NR$^8$R$^9$, =NR$^{10}$, COOC$_1$-C$_6$ alkyl, C$_6$-C$_{10}$ aryl, and CONR$^8$R$^9$.

In some embodiments, the substituted ring B is

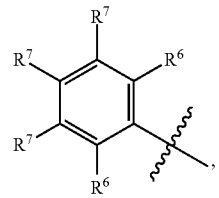

wherein each R$^6$ is independently selected from C$_1$-C$_6$ alkyl, C$_3$-C$_7$ cycloalkyl, C$_1$-C$_6$ haloalkyl, C$_1$-C$_6$ alkoxy, C$_1$-C$_6$ haloalkoxy, halo, CN, C$_6$-C$_{10}$ aryl, 5- to 10-membered heteroaryl, CO—C$_1$-C$_6$ alkyl; CONR$^8$R$^9$, and 4- to 6-membered heterocycloalkyl, wherein the C$_1$-C$_6$ alkyl, C$_1$-C$_6$ haloalkyl, C$_3$-C$_7$ cycloalkyl and 4- to 6-membered heterocycloalkyl is optionally substituted with one or more substituents each independently selected from hydroxy, halo, CN, oxo, C$_1$-C$_6$ alkyl, C$_1$-C$_6$ alkoxy, NR$^8$R$^9$, =NR$^{10}$, COOC$_1$-C$_6$ alkyl, CONR$^8$R$^9$, 4- to 6-membered heterocycloalkyl, C$_6$-C$_{10}$ aryl, 5- to 10-membered heteroaryl, OCOC$_1$-C$_6$ alkyl, OCOC$_6$-C$_{10}$ aryl, OCO (5- to 10-membered heteroaryl), OCO(4- to 6-membered heterocycloalkyl), NHCOC$_1$-C$_6$ alkyl, NHCOC$_6$-C$_{10}$ aryl, NHCO(5- to 10-membered heteroaryl), NHCO(4- to 6-membered heterocycloalkyl), and NHCOC$_2$-C$_6$ alkynyl;

wherein each R$^7$ is independently selected from C$_1$-C$_6$ alkyl, C$_1$-C$_6$ haloalkyl, C$_1$-C$_6$ alkoxy, C$_1$-C$_6$ haloalkoxy, halo, CN, COC$_1$-C$_6$ alkyl, CO$_2$C$_1$-C$_6$ alkyl, CO$_2$C$_3$-C$_6$ cycloalkyl, OCOC$_1$-C$_6$ alkyl, OCOC$_6$-C$_{10}$ aryl, OCO(5- to 10-membered heteroaryl), OCO(3- to 7-membered heterocycloalkyl), C$_6$-C$_{10}$ aryl, 5- to 10-membered heteroaryl, CONR$^8$R$^9$, SF$_5$, S(O$_2$)C$_1$-C$_6$ alkyl, C$_3$-C$_7$ cycloalkyl and 4- to 6-membered heterocycloalkyl, wherein the C$_1$-C$_6$ alkyl is optionally substituted with one to two C$_1$-C$_6$ alkoxy;

or at least one pair of R$^6$ and R$^7$ on adjacent atoms, taken together with the atoms connecting them, independently form at least one C$_4$-C$_7$ carbocyclic ring or at least one 5-to-7-membered heterocyclic ring containing 1 or 2 heteroatoms independently selected from O, N, and S, wherein the carbocyclic ring or heterocyclic ring is optionally independently substituted with one or more substituents independently selected from hydroxy, hydroxymethyl, halo, oxo, C$_1$-C$_6$ alkyl, C$_1$-C$_6$ alkoxy, NR$^8$R$^9$, CH$_2$NR$^8$R$^9$, =NR$^{10}$, COOC$_1$-C$_6$ alkyl, C$_6$-C$_{10}$ aryl, and CONR$^8$R$^9$;

The Group R$^3$

In some embodiments, R$^3$ is selected from hydrogen, C$_1$-C$_6$ alkyl, and

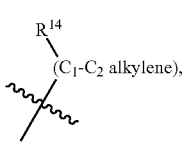

wherein the $C_1$-$C_2$ alkylene group is optionally substituted with oxo.

In some embodiments, $R^3$ is hydrogen.
In some embodiments, $R^3$ is $C_{1-3}$ alkyl (e.g., methyl).
In some embodiments, $R^3$ is cyano.
In some embodiments, $R^3$ is hydroxy.
In some embodiments, $R^3$ is $C_1$-$C_6$ alkoxy. In some embodiments, $R^3$ is $C_1$-$C_6$ alkyl.
In some embodiments, $R^3$ is methyl.
In some embodiments, $R^3$ is

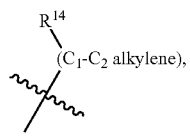

wherein the $C_1$-$C_2$ alkylene group is optionally substituted with oxo.

In some embodiments, $R^3$ is —$CH_2R^{14}$.
In some embodiments, $R^3$ is —$C(O)R^{14}$.
In some embodiments, $R^3$ is —$CH_2CH_2R^{14}$.
In some embodiments, $R^3$ is —$CHR^{14}CH_3$.
In some embodiments, $R^3$ is —$CH_2C(O)R^{14}$.
In some embodiments, $R^3$ is —$C(O)CH_2R^{14}$.
In some embodiments, $R^3$ is $CO_2C_1$-$C_6$ alkyl.

The Variable Y
In some embodiments, Y is —$CR^{15}R^{15}$— (e.g., —$CH_2$—).
In some embodiments, Y is —$NR^{16}$— (e.g., —NH—).

The Group $R^{14}$
In some embodiments, $R^{14}$ is hydrogen, $C_1$-$C_6$ alkyl, 5- to 10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1 or 2 $R^6$.
In some embodiments, $R^{14}$ is hydrogen or $C_1$-$C_6$ alkyl.
In some embodiments, $R^{14}$ is hydrogen, 5- to 10-membered monocyclic or bicyclic heteroaryl or $C_6$-$C_{10}$ monocyclic or bicyclic aryl, wherein each $C_1$-$C_6$ alkyl, aryl or heteroaryl is optionally independently substituted with 1 or 2 $R^6$.
In some embodiments, $R^{14}$ is hydrogen.
In some embodiments, $R^{14}$ is $C_1$-$C_6$ alkyl.
In some embodiments, $R^{14}$ is methyl.
In some embodiments, $R^{14}$ is 5- to 10-membered monocyclic or bicyclic heteroaryl optionally independently substituted with 1 or 2 $R^6$.
In some embodiments, $R^{14}$ is $C_6$-$C_{10}$ monocyclic or bicyclic aryl optionally independently substituted with 1 or 2 $R^6$.

The Moiety

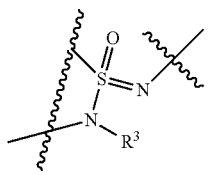

In some embodiments, the sulfur in the moiety

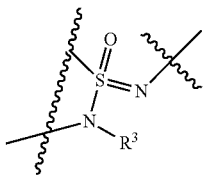

has (S) stereochemistry.

In some embodiments, the sulfur in the moiety

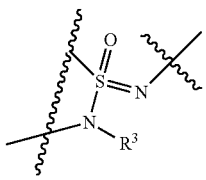

has (R) stereochemistry.

The Group $R^{10}$
In some embodiments, $R^{10}$ is $C_1$-$C_6$ alkyl.
In some embodiments, $R^{10}$ is methyl.
In some embodiments, $R^{10}$ is ethyl.

The Groups $R^1$ and $R^9$
In some embodiments, each of $R^8$ and $R^9$ at each occurrence is independently selected from hydrogen, $C_1$-$C_6$ alkyl, (C=$NR^{13}$)$NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to.
In some embodiments, each of $R^8$ and $R^9$ at each occurrence is independently selected from hydrogen, $C_1$-$C_6$ alkyl, (C=$NR^{13}$)$NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$; wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl or 3- to 7-membered heterocycloalkyl; or $R^8$ and $R^9$ taken together with the nitrogen they are attached to form a 3- to 7-membered ring optionally containing one or more heteroatoms in addition to the nitrogen they are attached to.
In some embodiments, each of $R^8$ and $R^9$ at each occurrence is hydrogen,
In some embodiments, each $R^8$ at each occurrence is hydrogen and each $R^9$ at each occurrence is $C_1$-$C_6$ alkyl.
In some embodiments, each $R^8$ at each occurrence is hydrogen and each $R^9$ at each occurrence is methyl.
In some embodiments, each $R^8$ at each occurrence is hydrogen and each $R^9$ at each occurrence is ethyl.
In some embodiments, each of $R^8$ and $R^9$ at each occurrence is methyl.
In some embodiments, each of $R^8$ and $R^9$ at each occurrence is ethyl.
In some embodiments, $R^8$ and $R^9$ taken together with the nitrogen they are attached to form a 3-membered ring.
In some embodiments, $R^8$ and $R^9$ taken together with the nitrogen they are attached to form a 4-membered ring.
In some embodiments, $R^8$ and $R^9$ taken together with the nitrogen they are attached to form a 5-membered ring.

In some embodiments, $R^8$ and $R^9$ taken together with the nitrogen they are attached to form a 6-membered ring optionally containing one or more oxygen atoms in addition to the nitrogen they are attached to.

In some embodiments, $R^8$ and $R^9$ taken together with the nitrogen they are attached to form a 6-membered ring optionally containing one or more nitrogen atoms in addition to the nitrogen they are attached to.

In some embodiments, $R^8$ and $R^9$ taken together with the nitrogen they are attached to form a 7-membered ring.

The Group $R^{13}$

In some embodiments, $R^{13}$ is $C_1$-$C_6$ alkyl.
In some embodiments, $R^{13}$ is methyl.
In some embodiments, $R^{13}$ is ethyl.
In some embodiments, $R^{13}$ is $C_6$-$C_{10}$ aryl.
In some embodiments, $R^{13}$ is phenyl.
In some embodiments, $R^{13}$ is 5- to 10-membered heteroaryl.

The groups $R^{11}$ and $R^{12}$

In some embodiments, each of $R^{11}$ and $R^{12}$ at each occurrence is independently selected from hydrogen and $C_1$-$C_6$ alkyl.
In some embodiments, each of $R^{11}$ and $R^{12}$ at each occurrence is hydrogen,
In some embodiments, each $R^{11}$ at each occurrence is hydrogen and each $R^{12}$ at each occurrence is $C_1$-$C_6$ alkyl.
In some embodiments, each $R^{11}$ at each occurrence is hydrogen and each $R^{12}$ at each occurrence is methyl.
In some embodiments, each $R^{11}$ at each occurrence is hydrogen and each $R^{12}$ at each occurrence is ethyl.
In some embodiments, each of $R^{11}$ and $R^{12}$ at each occurrence is methyl.
In some embodiments, each of $R^{11}$ and $R^{12}$ at each occurrence is ethyl.

In some embodiments of the compound of formula AA, the substituted ring B is

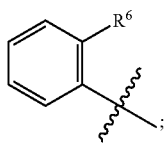

and $R^6$ is selected from:
$C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA, the substituted ring B is

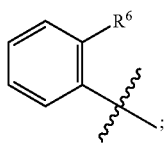

and $R^6$ is selected from:
isopropyl, ethyl, methyl, trifluoromethyl, trifluoromethoxy, cyclopropyl, halo, chloro, and fluoro.

In some embodiments of the compound of formula AA, the substituted ring B is

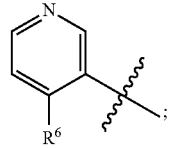

and $R^6$ is selected from:
$C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA, the substituted ring B is

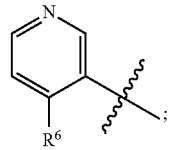

and $R^6$ is selected from:
isopropyl, ethyl, methyl, trifluoromethyl, trifluoromethoxy, cyclopropyl, halo, chloro, and fluoro.

In some embodiments of the compound of formula AA, the substituted ring B is

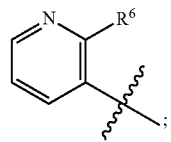

and $R^6$ is selected from:
$C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.

In some embodiments of the compound of formula AA, the substituted ring B is

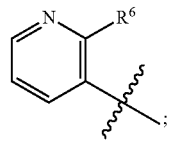

and $R^6$ is selected from:
isopropyl, ethyl, methyl, trifluoromethyl, trifluoromethoxy, cyclopropyl, halo, chloro, and fluoro.

In some embodiments of the compound of formula AA, the substituted ring B is

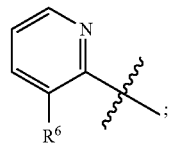

and $R^6$ is selected from:
$C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.
In some embodiments of the compound of formula AA, the substituted ring B is

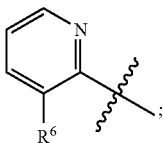

and $R^6$ is selected from:
isopropyl, ethyl, methyl, trifluoromethyl, trifluoromethoxy, cyclopropyl, halo, chloro, and fluoro.
In some embodiments of the compound of formula AA, the substituted ring B is

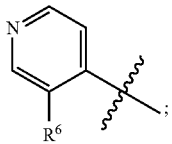

and $R^6$ is selected from:
$C_1$-$C_6$ alkyl, $C_1$-$C_6$ alkyl substituted with one or more halo, $C_1$-$C_6$ alkoxy, $C_1$-$C_6$ alkoxy substituted with one or more halo, $C_3$-$C_7$ cycloalkyl, halo, and cyano.
In some embodiments of the compound of formula AA, the substituted ring B is

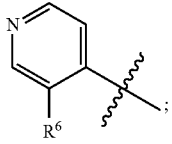

and $R^6$ is selected from:
isopropyl, ethyl, methyl, trifluoromethyl, trifluoromethoxy, cyclopropyl, halo, chloro, and fluoro.
In some embodiments of the compound of formula AA, the substituted ring B is

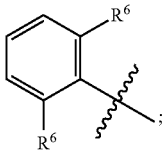

and the two $R^6$ are one of the following combinations:
One $R^6$ is $C_1$-$C_6$ alkyl, and the other $R^6$ is $C_1$-$C_6$ alkyl optionally substituted with one or more halo;
One $R^6$ is $C_1$-$C_6$ alkyl and the other $R^6$ is $C_1$-$C_6$ alkyl;
One $R^6$ is $C_1$-$C_6$ alkyl, and the other $R^6$ is $C_1$-$C_6$ alkyl substituted with one or more halo;
One $R^6$ is $C_1$-$C_6$ alkyl, and the other $R^6$ is $C_3$-$C_7$ cycloalkyl;
One $R^6$ is $C_1$-$C_6$ alkyl, and the other $R^6$ is halo;
One $R^6$ is $C_1$-$C_6$ alkyl, and the other $R^6$ is cyano;
One $R^6$ is $C_3$-$C_7$ cycloalkyl, and the other $R^6$ is $C_3$-$C_7$ cycloalkyl;
One $R^6$ is $C_3$-$C_7$ cycloalkyl, and the other $R^6$ is halo;
One $R^6$ is cyclopropyl and the other $R^6$ is halo;
One $R^6$ is $C_1$-$C_6$ alkyl, and the other $R^6$ is $C_1$-$C_6$ alkoxy optionally substituted with one or more halo;
One $R^6$ is $C_1$-$C_6$ alkyl, and the other $R^6$ is $C_1$-$C_6$ alkoxy;
One $R^6$ is $C_1$-$C_6$ alkyl, and the other $R^6$ is $C_1$-$C_6$ alkoxy substituted with one or more halo;
One $R^6$ is halo, and the other $R^6$ is $C_1$-$C_6$ haloalkyl;
One $R^6$ is halo, and the other $R^6$ is $C_1$-$C_6$ haloalkoxy;
One $R^6$ is $C_1$-$C_6$ alkoxy; and the other $R^6$ is halo;
One $R^6$ is $C_1$-$C_6$ alkoxy; and the other $R^6$ is chloro.
In some embodiments, of the compound of formula AA, the substituted ring B is

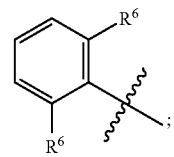

and the two $R^6$ are one of the following combinations:
One $R^6$ is isopropyl; and the other $R^6$ is methyl;
One $R^6$ is isopropyl; and the other $R^6$ is n-propyl;
One $R^6$ is isopropyl; and the other $R^6$ is isopropyl;
One $R^6$ is isopropyl; and the other $R^6$ is trifluoromethyl;
One $R^6$ is isopropyl; and the other $R^6$ is cyclopropyl;
One $R^6$ is isopropyl; and the other $R^6$ is chloro;
One $R^6$ is isopropyl; and the other $R^6$ is fluoro;
One $R^6$ is ethyl; and the other $R^6$ is fluoro;
One $R^6$ is isopropyl; and the other $R^6$ is cyano;
One $R^6$ is cyclopropyl; and the other $R^6$ is cyclopropyl;
One $R^6$ is cyclopropyl; and the other $R^6$ is chloro;
One $R^6$ is cyclopropyl; and the other $R^6$ is fluoro;
One $R^6$ is isopropyl; and the other $R^6$ is methoxy;
One $R^6$ is isopropyl; and the other $R^6$ is methoxy; or
One $R^6$ is isopropyl; and the other $R^6$ is trifluoromethoxy.
In some embodiments, of the compound of formula AA, the substituted ring B is

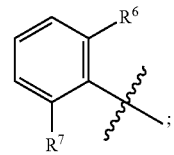

and $R^6$ and $R^7$ are one of the following combinations:
$R^6$ is $C_1$-$C_6$ alkyl, and $R^7$ is $C_1$-$C_6$ alkyl optionally substituted with one or more halo;
$R^6$ is $C_1$-$C_6$ alkyl and $R^7$ is $C_1$-$C_6$ alkyl;
$R^6$ is $C_1$-$C_6$ alkyl, and $R^7$ is $C_1$-$C_6$ alkyl substituted with one or more halo;
$R^6$ is $C_1$-$C_6$ alkyl, and $R^7$ is $C_3$-$C_7$ cycloalkyl;
$R^6$ is $C_1$-$C_6$ alkyl, and $R^1$ is halo;
$R^6$ is $C_1$-$C_6$ alkyl, and $R^7$ is cyano;
$R^6$ is $C_3$-$C_7$ cycloalkyl, and $R^7$ is $C_3$-$C_7$ cycloalkyl;
$R^6$ is $C_3$-$C_7$ cycloalkyl, and $R^7$ is halo;
$R^6$ is cyclopropyl and $R^7$ is halo;
$R^6$ is $C_1$-$C_6$ alkyl, and $R^7$ is $C_1$-$C_6$ alkoxy optionally substituted with one or more halo;

$R^6$ is $C_1$-$C_6$ alkyl, and $R^7$ is $C_1$-$C_6$ alkoxy;
$R^6$ is $C_1$-$C_6$ alkyl, and $R^7$ is $C_1$-$C_6$ alkoxy substituted with one or more halo;
$R^6$ is halo, and $R^7$ is $C_1$-$C_6$ haloalkyl;
$R^6$ is halo, and $R^7$ is $C_1$-$C_6$ haloalkoxy;
$R^6$ is $C_1$-$C_6$ alkoxy; and $R^7$ is halo;
$R^6$ is $C_1$-$C_6$ alkoxy; and $R^7$ is chloro;
$R^7$ is $C_1$-$C_6$ alkyl, and $R^6$ is $C_1$-$C_6$ alkyl optionally substituted with one or more halo;
$R^7$ is $C_1$-$C_6$ alkyl, and $R^6$ is $C_1$-$C_6$ alkyl substituted with one or more halo;
$R^7$ is $C_1$-$C_6$ alkyl, and $R^6$ is $C_3$-$C_7$ cycloalkyl;
$R^7$ is $C_1$-$C_6$ alkyl, and $R^6$ is halo;
$R^7$ is $C_1$-$C_6$ alkyl and $R^6$ is halo;
$R^7$ is $C_1$-$C_6$ alkyl, and $R^6$ is cyano;
$R^7$ is $C_3$-$C_7$ cycloalkyl, and $R^6$ is $C_3$-$C_7$ cycloalkyl;
$R^7$ is $C_3$-$C_7$ cycloalkyl, and $R^6$ is halo;
$R^7$ is $C_3$-$C_7$ cycloalkyl and $R^6$ is halo;
$R^7$ is $C_1$-$C_6$ alkyl, and $R^6$ is $C_1$-$C_6$ alkoxy optionally substituted with one or more halo;
$R^7$ is $C_1$-$C_6$ alkyl, and $R^6$ is $C_1$-$C_6$ alkoxy;
$R^7$ is $C_1$-$C_6$ alkyl, and $R^6$ is $C_1$-$C_6$ alkoxy substituted with one or more halo;
$R^7$ is halo, and $R^6$ is $C_1$-$C_6$ haloalkyl;
$R^7$ is halo, and $R^6$ is $C_1$-$C_6$ haloalkoxy;
$R^7$ is $C_1$-$C_6$ alkoxy; and $R^6$ is halo; or
$R^7$ is $C_1$-$C_6$ alkoxy; and $R^6$ is chloro.

In some embodiments, of the compound of formula AA, the substituted ring B is

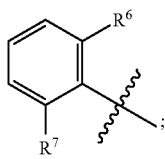

and $R^6$ and $R^7$ are one of the following combinations:
$R^6$ is isopropyl; and $R^7$ is methyl;
$R^6$ is isopropyl; and $R^7$ is isopropyl;
$R^6$ is isopropyl; and $R^7$ is trifluoromethyl;
$R^6$ is isopropyl; and $R^7$ is cyclopropyl;
$R^6$ is isopropyl; and $R^7$ is chloro;
$R^6$ is isopropyl; and $R^7$ is fluoro;
$R^6$ is ethyl; and $R^7$ is fluoro;
$R^6$ is isopropyl; and $R^7$ is cyano;
$R^6$ is cyclopropyl; and $R^7$ is cyclopropyl;
$R^6$ is cyclopropyl; and $R^7$ is chloro;
$R^6$ is cyclopropyl; and $R^7$ is fluoro; $R^6$ is isopropyl; and $R^7$ is methoxy;
$R^6$ is isopropyl; and $R^7$ is trifluoromethoxy;
$R^6$ is chloro; and $R^7$ is trifluoromethyl;
$R^6$ is chloro; and $R^7$ is trifluoromethoxy;
$R^7$ is isopropyl; and $R^6$ is methyl;
$R^7$ is isopropyl; and $R^6$ is trifluoromethyl;
$R^7$ is isopropyl; and $R^6$ is cyclopropyl;
$R^7$ is isopropyl; and $R^6$ is chloro;
$R^7$ is ethyl; and $R^6$ is fluoro;
$R^7$ is isopropyl; and $R^6$ is cyano;
$R^7$ is cyclopropyl; and $R^6$ is cyclopropyl;
$R^7$ is cyclopropyl; and $R^6$ is chloro;
$R^7$ is cyclopropyl; and $R^6$ is fluoro;
$R^7$ is isopropyl; and $R^6$ is methoxy;
$R^7$ is isopropyl; and $R^6$ is trifluoromethoxy;
$R^7$ is chloro; and $R^6$ is trifluoromethyl; or
$R^7$ is chloro; and $R^6$ is trifluoromethoxy.

In some embodiments, of the compound of formula AA, the substituted ring B is

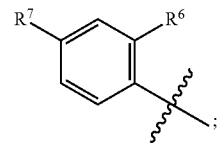

and $R^6$ and $R^7$ are one of the following combinations:
$R^6$ is $C_1$-$C_6$ alkyl, and $R^7$ is $C_1$-$C_6$ alkyl optionally substituted with one or more halo;
$R^6$ is $C_1$-$C_6$ alkyl and $R^7$ is $C_1$-$C_6$ alkyl;
$R^6$ is $C_1$-$C_6$ alkyl, and $R^7$ is $C_1$-$C_6$ alkyl substituted with one or more halo;
$R^6$ is $C_1$-$C_6$ alkyl, and $R^7$ is $C_3$-$C_7$ cycloalkyl;
$R^6$ is $C_1$-$C_6$ alkyl, and $R^7$ is halo;
$R^6$ is $C_1$-$C_6$ alkyl, and $R^7$ is cyano;
$R^6$ is $C_3$-$C_7$ cycloalkyl, and $R^7$ is $C_3$-$C_7$ cycloalkyl;
$R^6$ is $C_3$-$C_7$ cycloalkyl, and $R^7$ is halo;
$R^6$ is cyclopropyl and $R^7$ is halo;
$R^6$ is $C_1$-$C_6$ alkyl, and $R^7$ is $C_1$-$C_6$ alkoxy optionally substituted with one or more halo;
$R^6$ is $C_1$-$C_6$ alkyl, and $R^7$ is $C_1$-$C_6$ alkoxy;
$R^6$ is $C_1$-$C_6$ alkyl, and $R^7$ is $C_1$-$C_6$ alkoxy substituted with one or more halo;
$R^6$ is halo, and $R^7$ is $C_1$-$C_6$ haloalkyl;
$R^6$ is halo, and $R^7$ is $C_1$-$C_6$ haloalkoxy;
$R^6$ is $C_1$-$C_6$ alkoxy; and $R^7$ is halo;
$R^6$ is $C_1$-$C_6$ alkoxy; and $R^7$ is chloro;
$R^7$ is $C_1$-$C_6$ alkyl, and $R^6$ is $C_1$-$C_6$ alkyl optionally substituted with one or more halo;
$R^7$ is $C_1$-$C_6$ alkyl, and $R^6$ is $C_1$-$C_6$ alkyl substituted with one or more halo;
$R^7$ is $C_1$-$C_6$ alkyl, and $R^6$ is $C_3$-$C_7$ cycloalkyl;
$R^7$ is $C_1$-$C_6$ alkyl, and $R^6$ is halo;
$R^7$ is $C_1$-$C_6$ alkyl and $R^6$ is halo;
$R^7$ is $C_1$-$C_6$ alkyl, and $R^6$ is cyano;
$R^7$ is $C_3$-$C_7$ cycloalkyl, and $R^6$ is $C_3$-$C_7$ cycloalkyl;
$R^7$ is $C_3$-$C_7$ cycloalkyl, and $R^6$ is halo;
$R^7$ is $C_3$-$C_7$ cycloalkyl and $R^6$ is halo;
$R^7$ is $C_1$-$C_6$ alkyl, and $R^6$ is $C_1$-$C_6$ alkoxy optionally substituted with one or more halo;
$R^7$ is $C_1$-$C_6$ alkyl, and $R^6$ is $C_1$-$C_6$ alkoxy;
$R^7$ is $C_1$-$C_6$ alkyl, and $R^6$ is $C_1$-$C_6$ alkoxy substituted with one or more halo;
$R^7$ is halo, and $R^6$ is $C_1$-$C_6$ haloalkyl;
$R^7$ is halo, and $R^6$ is $C_1$-$C_6$ haloalkoxy;
$R^7$ is $C_1$-$C_6$ alkoxy; and $R^6$ is halo; or
$R^7$ is $C_1$-$C_6$ alkoxy; and $R^6$ is chloro.

In some embodiments, of the compound of formula AA, the substituted ring B is

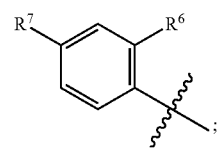

and $R^6$ and $R^7$ are one of the following combinations:
$R^6$ is isopropyl; and $R^7$ is methyl;
$R^6$ is isopropyl; and $R^7$ is isopropyl;

$R^6$ is isopropyl; and $R^7$ is trifluoromethyl;
$R^6$ is isopropyl; and $R^7$ is cyclopropyl;
$R^6$ is isopropyl; and $R^7$ is chloro;
$R^6$ is isopropyl; and $R^7$ is fluoro;
$R^6$ is ethyl; and $R^7$ is fluoro;
$R^6$ is isopropyl; and $R^7$ is cyano;
$R^6$ is cyclopropyl; and $R^7$ is cyclopropyl;
$R^6$ is cyclopropyl; and $R^7$ is chloro;
$R^6$ is cyclopropyl; and $R^7$ is fluoro;
$R^6$ is isopropyl; and $R^7$ is methoxy;
$R^6$ is isopropyl; and $R^7$ is trifluoromethoxy;
$R^6$ is chloro; and $R^7$ is trifluoromethyl;
$R^6$ is chloro; and $R^7$ is trifluoromethoxy;
$R^7$ is isopropyl; and $R^6$ is methyl;
$R^7$ is isopropyl; and $R^6$ is trifluoromethyl;
$R^7$ is isopropyl; and $R^6$ is cyclopropyl;
$R^7$ is isopropyl; and $R^6$ is chloro;
$R^7$ is ethyl; and $R^6$ is fluoro;
$R^7$ is isopropyl; and $R^6$ is cyano;
$R^7$ is cyclopropyl; and $R^6$ is cyclopropyl;
$R^7$ is cyclopropyl; and $R^6$ is chloro;
$R^7$ is cyclopropyl; and $R^6$ is fluoro;
$R^7$ is isopropyl; and $R^6$ is methoxy;
$R^7$ is isopropyl; and $R^6$ is trifluoromethoxy;
$R^7$ is chloro; and $R^6$ is trifluoromethyl; or
$R^7$ is chloro; and $R^6$ is trifluoromethoxy.

In some embodiments, of the compound of formula AA, the substituted ring B is

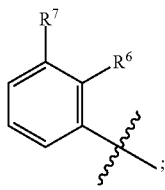

and $R^6$ and $R^7$ are one of the following combinations:
$R^6$ is $C_1$-$C_6$ alkyl, and $R^7$ is $C_1$-$C_6$ alkyl optionally substituted with one or more halo;
$R^6$ is $C_1$-$C_6$ alkyl and $R^7$ is $C_1$-$C_6$ alkyl;
$R^6$ is $C_1$-$C_6$ alkyl, and $R^7$ is $C_1$-$C_6$ alkyl substituted with one or more halo;
$R^6$ is $C_1$-$C_6$ alkyl, and $R^7$ is $C_3$-$C_7$ cycloalkyl;
$R^6$ is $C_1$-$C_6$ alkyl, and $R^7$ is halo;
$R^6$ is $C_1$-$C_6$ alkyl, and $R^7$ is cyano;
$R^6$ is $C_3$-$C_7$ cycloalkyl, and $R^7$ is $C_3$-$C_7$ cycloalkyl;
$R^6$ is $C_3$-$C_7$ cycloalkyl, and $R^7$ is halo;
$R^6$ is cyclopropyl and $R^7$ is halo;
$R^6$ is $C_1$-$C_6$ alkyl, and $R^7$ is $C_1$-$C_6$ alkoxy optionally substituted with one or more halo;
$R^6$ is $C_1$-$C_6$ alkyl, and $R^7$ is $C_1$-$C_6$ alkoxy;
$R^6$ is $C_1$-$C_6$ alkyl, and $R^7$ is $C_1$-$C_6$ alkoxy substituted with one or more halo;
$R^6$ is halo, and $R^7$ is $C_1$-$C_6$ haloalkyl;
$R^6$ is halo, and $R^7$ is $C_1$-$C_6$ haloalkoxy;
$R^6$ is $C_1$-$C_6$ alkoxy; and $R^7$ is halo;
$R^6$ is $C_1$-$C_6$ alkoxy; and $R^7$ is chloro;
$R^7$ is $C_1$-$C_6$ alkyl, and $R^6$ is $C_1$-$C_6$ alkyl optionally substituted with one or more halo;
$R^7$ is $C_1$-$C_6$ alkyl, and $R^6$ is $C_1$-$C_6$ alkyl substituted with one or more halo;
$R^7$ is $C_1$-$C_6$ alkyl, and $R^6$ is $C_3$-$C_7$ cycloalkyl;
$R^7$ is $C_1$-$C_6$ alkyl, and $R^6$ is halo;
$R^7$ is $C_1$-$C_6$ alkyl and $R^6$ is halo;
$R^7$ is $C_1$-$C_6$ alkyl, and $R^6$ is cyano;
$R^7$ is $C_3$-$C_7$ cycloalkyl, and $R^6$ is $C_3$-$C_7$ cycloalkyl;
$R^7$ is $C_3$-$C_7$ cycloalkyl, and $R^6$ is halo;
$R^7$ is $C_3$-$C_7$ cycloalkyl and $R^6$ is halo;
$R^7$ is $C_1$-$C_6$ alkyl, and $R^6$ is $C_1$-$C_6$ alkoxy optionally substituted with one or more halo;
$R^7$ is $C_1$-$C_6$ alkyl, and $R^6$ is $C_1$-$C_6$ alkoxy;
$R^7$ is $C_1$-$C_6$ alkyl, and $R^6$ is $C_1$-$C_6$ alkoxy substituted with one or more halo;
$R^7$ is halo, and $R^6$ is $C_1$-$C_6$ haloalkyl;
$R^7$ is halo, and $R^6$ is $C_1$-$C_6$ haloalkoxy;
$R^7$ is $C_1$-$C_6$ alkoxy; and $R^6$ is halo; or
$R^7$ is $C_1$-$C_6$ alkoxy; and $R^6$ is chloro;
$R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; or
$R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

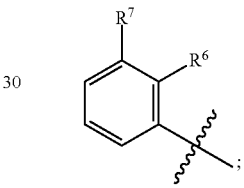

and $R^6$ and $R^7$ are one of the following combinations:
$R^6$ is isopropyl; and $R^7$ is methyl;
$R^6$ is isopropyl; and $R^7$ is isopropyl;
$R^6$ is isopropyl; and $R^7$ is trifluoromethyl;
$R^6$ is isopropyl; and $R^7$ is cyclopropyl;
$R^6$ is isopropyl; and $R^7$ is chloro;
$R^6$ is isopropyl; and $R^7$ is fluoro;
$R^6$ is ethyl; and $R^7$ is fluoro;
$R^6$ is isopropyl; and $R^7$ is cyano;
$R^6$ is cyclopropyl; and $R^7$ is cyclopropyl;
$R^6$ is cyclopropyl; and $R^7$ is chloro;
$R^6$ is cyclopropyl; and $R^7$ is fluoro;
$R^6$ is isopropyl; and $R^7$ is methoxy;
$R^6$ is isopropyl; and $R^7$ is trifluoromethoxy;
$R^6$ is chloro; and $R^7$ is trifluoromethyl;
$R^6$ is chloro; and $R^7$ is trifluoromethoxy;
$R^7$ is isopropyl; and $R^6$ is methyl;
$R^7$ is isopropyl; and $R^6$ is trifluoromethyl;
$R^7$ is isopropyl; and $R^6$ is cyclopropyl;
$R^7$ is isopropyl; and $R^6$ is chloro;
$R^7$ is ethyl; and $R^6$ is fluoro;
$R^7$ is isopropyl; and $R^6$ is cyano;
$R^7$ is cyclopropyl; and $R^6$ is cyclopropyl;
$R^7$ is cyclopropyl; and $R^6$ is chloro;
$R^7$ is cyclopropyl; and $R^6$ is fluoro;
$R^7$ is isopropyl; and $R^6$ is methoxy;
$R^7$ is isopropyl; and $R^6$ is trifluoromethoxy;
$R^7$ is chloro; and $R^6$ is trifluoromethyl;
$R^7$ is chloro; and $R^6$ is trifluoromethoxy;
$R^6$ and $R^7$ on adjacent atoms taken together with the atoms connecting them form a $C_4$ aliphatic carbocyclic ring;

R⁶ and R⁷ on adjacent atoms taken together with the atoms connecting them form a C₅ aliphatic carbocyclic ring;

R⁶ and R⁷ on adjacent atoms taken together with the atoms connecting them form a C₆ aliphatic carbocyclic ring;

R⁶ and R⁷ on adjacent atoms taken together with the atoms connecting them form a 5-membered heterocyclic ring containing 1 heteroatoms independently selected from O, N, and S;

R⁶ and R⁷ on adjacent atoms taken together with the atoms connecting them form a 6-membered heterocyclic ring containing 1 heteroatoms independently selected from O, N, and S; or R⁶ and R⁷ on adjacent atoms taken together with the atoms connecting them form a C₅ aliphatic carbocyclic ring.

In some embodiments, of the compound of formula AA, the substituted ring B is

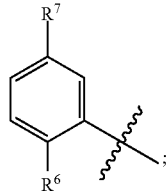

and R⁶ and R⁷ are one of the following combinations:
R⁶ is C₁-C₆ alkyl, and R⁷ is C₁-C₆ alkyl optionally substituted with one or more halo;
R⁶ is C₁-C₆ alkyl and R⁷ is C₁-C₆ alkyl;
R⁶ is C₁-C₆ alkyl, and R⁷ is C₁-C₆ alkyl substituted with one or more halo;
R⁶ is C₁-C₆ alkyl, and R⁷ is C₃-C₇ cycloalkyl;
R⁶ is C₁-C₆ alkyl, and R⁷ is halo;
R⁶ is C₁-C₆ alkyl, and R⁷ is cyano;
R⁶ is C₃-C₇ cycloalkyl, and R⁷ is C₃-C₇ cycloalkyl;
R⁶ is C₃-C₇ cycloalkyl, and R⁷ is halo;
R⁶ is cyclopropyl and R⁷ is halo;
R⁶ is C₁-C₆ alkyl, and R⁷ is C₁-C₆ alkoxy optionally substituted with one or more halo;
R⁶ is C₁-C₆ alkyl, and R⁷ is C₁-C₆ alkoxy;
R⁶ is C₁-C₆ alkyl, and R⁷ is C₁-C₆ alkoxy substituted with one or more halo;
R⁶ is halo, and R⁷ is C₁-C₆ haloalkyl;
R⁶ is halo, and R⁷ is C₁-C₆ haloalkoxy;
R⁶ is C₁-C₆ alkoxy; and R⁷ is halo;
R⁶ is C₁-C₆ alkoxy; and R⁷ is chloro;
R⁷ is C₁-C₆ alkyl, and R⁶ is C₁-C₆ alkyl optionally substituted with one or more halo;
R⁷ is C₁-C₆ alkyl, and R⁶ is C₁-C₆ alkyl substituted with one or more halo;
R⁷ is C₁-C₆ alkyl, and R⁶ is C₃-C₇ cycloalkyl;
R⁷ is C₁-C₆ alkyl, and R⁶ is halo;
R⁷ is C₁-C₆ alkyl and R⁶ is halo;
R⁷ is C₁-C₆ alkyl, and R⁶ is cyano;
R⁷ is C₃-C₇ cycloalkyl, and R⁶ is C₃-C₇ cycloalkyl;
R⁷ is C₃-C₇ cycloalkyl, and R⁶ is halo;
R⁷ is C₃-C₇ cycloalkyl and R⁶ is halo;
R⁷ is C₁-C₆ alkyl, and R⁶ is C₁-C₆ alkoxy optionally substituted with one or more halo;
R⁷ is C₁-C₆ alkyl, and R⁶ is C₁-C₆ alkoxy;
R⁷ is C₁-C₆ alkyl, and R⁶ is C₁-C₆ alkoxy substituted with one or more halo;

R⁷ is halo, and R⁶ is C₁-C₆ haloalkyl;
R⁷ is halo, and R⁶ is C₁-C₆ haloalkoxy;
R⁷ is C₁-C₆ alkoxy; and R⁶ is halo; or
R⁷ is C₁-C₆ alkoxy; and R⁶ is chloro.

In some embodiments, of the compound of formula AA, the substituted ring B is

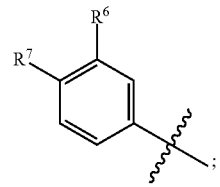

and R⁶ and R⁷ are one of the following combinations:
R⁶ is C₁-C₆ alkyl, and R⁷ is C₁-C₆ alkyl optionally substituted with one or more halo;
R⁶ is C₁-C₆ alkyl and R⁷ is C₁-C₆ alkyl;
R⁶ is C₁-C₆ alkyl, and R¹ is C₁-C₆ alkyl substituted with one or more halo;
R⁶ is C₁-C₆ alkyl, and R⁷ is C₃-C₇ cycloalkyl;
R⁶ is C₁-C₆ alkyl, and R⁷ is halo;
R⁶ is C₁-C₆ alkyl, and R⁷ is cyano;
R⁶ is C₃-C₇ cycloalkyl, and R⁷ is C₃-C₇ cycloalkyl;
R⁶ is C₃-C₇ cycloalkyl, and R⁷ is halo;
R⁶ is cyclopropyl and R⁷ is halo;
R⁶ is C₁-C₆ alkyl, and R⁷ is C₁-C₆ alkoxy optionally substituted with one or more halo;
R⁶ is C₁-C₆ alkyl, and R⁷ is C₁-C₆ alkoxy;
R⁶ is C₁-C₆ alkyl, and R⁷ is C₁-C₆ alkoxy substituted with one or more halo;
R⁶ is halo, and R⁷ is C₁-C₆ haloalkyl;
R⁶ is halo, and R⁷ is C₁-C₆ haloalkoxy;
R⁶ is C₁-C₆ alkoxy; and R⁷ is halo;
R⁶ is C₁-C₆ alkoxy; and R⁷ is chloro;
R⁷ is C₁-C₆ alkyl, and R⁶ is C₁-C₆ alkyl optionally substituted with one or more halo;
R⁷ is C₁-C₆ alkyl, and R⁶ is C₁-C₆ alkyl substituted with one or more halo;
R⁷ is C₁-C₆ alkyl, and R⁶ is C₃-C₇ cycloalkyl;
R⁷ is C₁-C₆ alkyl, and R⁶ is halo;
R⁷ is C₁-C₆ alkyl and R⁶ is halo;
R⁷ is C₁-C₆ alkyl, and R⁶ is cyano;
R⁷ is C₃-C₇ cycloalkyl, and R⁶ is C₃-C₇ cycloalkyl;
R⁷ is C₃-C₇ cycloalkyl, and R⁶ is halo;
R⁷ is C₃-C₇ cycloalkyl and R⁶ is halo;
R⁷ is C₁-C₆ alkyl, and R⁶ is C₁-C₆ alkoxy optionally substituted with one or more halo;
R⁷ is C₁-C₆ alkyl, and R⁶ is C₁-C₆ alkoxy;
R⁷ is C₁-C₆ alkyl, and R⁶ is C₁-C₆ alkoxy substituted with one or more halo;
R⁷ is halo, and R⁶ is C₁-C₆ haloalkyl;
R⁷ is halo, and R⁶ is C₁-C₆ haloalkoxy;
R⁷ is C₁-C₆ alkoxy; and R⁶ is halo;
R⁷ is C₁-C₆ alkoxy; and R⁶ is chloro;
R⁶ and R⁷ on adjacent atoms taken together with the atoms connecting them form a C₄-C₆ aliphatic carbocyclic ring optionally substituted with one or more hydroxy, oxo, or C₁-C₆ alkyl; or
R⁶ and R⁷ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

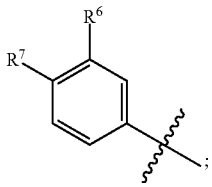

and $R^6$ and $R^7$ are one of the following combinations:
- $R^6$ is isopropyl; and $R^7$ is methyl;
- $R^6$ is isopropyl; and $R^7$ is isopropyl;
- $R^6$ is isopropyl; and $R^7$ is trifluoromethyl;
- $R^6$ is isopropyl; and $R^7$ is cyclopropyl;
- $R^6$ is isopropyl; and $R^7$ is chloro;
- $R^6$ is isopropyl; and $R^7$ is fluoro;
- $R^6$ is ethyl; and $R^7$ is fluoro;
- $R^6$ is isopropyl; and $R^7$ is cyano;
- $R^6$ is cyclopropyl; and $R^7$ is cyclopropyl;
- $R^6$ is cyclopropyl; and $R^7$ is chloro;
- $R^6$ is cyclopropyl; and $R^7$ is fluoro;
- $R^6$ is isopropyl; and $R^7$ is methoxy;
- $R^6$ is isopropyl; and $R^7$ is trifluoromethoxy;
- $R^6$ is chloro; and $R^7$ is trifluoromethyl;
- $R^6$ is chloro; and $R^7$ is trifluoromethoxy;
- $R^7$ is isopropyl; and $R^6$ is methyl;
- $R^7$ is isopropyl; and $R^6$ is trifluoromethyl;
- $R^7$ is isopropyl; and $R^6$ is cyclopropyl;
- $R^7$ is isopropyl; and $R^6$ is chloro;
- $R^7$ is ethyl; and $R^6$ is fluoro;
- $R^7$ is isopropyl; and $R^6$ is cyano;
- $R^7$ is cyclopropyl; and $R^6$ is cyclopropyl;
- $R^7$ is cyclopropyl; and $R^6$ is chloro;
- $R^7$ is cyclopropyl; and $R^6$ is fluoro;
- $R^7$ is isopropyl; and $R^6$ is methoxy;
- $R^7$ is isopropyl; and $R^6$ is trifluoromethoxy;
- $R^7$ is chloro; and $R^6$ is trifluoromethyl;
- $R^7$ is chloro; and $R^6$ is trifluoromethoxy;
- $R^6$ and $R^7$ on adjacent atoms taken together with the atoms connecting them form a $C_4$ aliphatic carbocyclic ring;
- $R^6$ and $R^7$ on adjacent atoms taken together with the atoms connecting them form a $C_5$ aliphatic carbocyclic ring;
- $R^6$ and $R^7$ on adjacent atoms taken together with the atoms connecting them form a $C_6$ aliphatic carbocyclic ring;
- $R^6$ and $R^7$ on adjacent atoms taken together with the atoms connecting them form a 5-membered heterocyclic ring containing 1 heteroatoms independently selected from O, N, and S;
- $R^6$ and $R^7$ on adjacent atoms taken together with the atoms connecting them form a 6-membered heterocyclic ring containing 1 heteroatoms independently selected from O, N, and S; or
- $R^6$ and $R^7$ on adjacent atoms taken together with the atoms connecting them form a $C_5$ aliphatic carbocyclic ring.

In some embodiments, of the compound of formula AA, the substituted ring B is

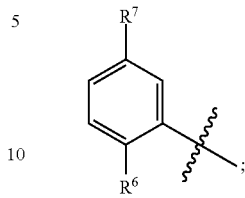

and $R^6$ and $R^7$ are one of the following combinations:
- $R^6$ is isopropyl; and $R^7$ is methyl;
- $R^6$ is isopropyl; and $R^7$ is isopropyl;
- $R^6$ is isopropyl; and $R^7$ is trifluoromethyl;
- $R^6$ is isopropyl; and $R^7$ is cyclopropyl;
- $R^6$ is isopropyl; and $R^7$ is chloro;
- $R^6$ is isopropyl; and $R^7$ is fluoro;
- $R^6$ is ethyl; and $R^7$ is fluoro;
- $R^6$ is isopropyl; and $R^7$ is cyano;
- $R^6$ is cyclopropyl; and $R^7$ is cyclopropyl;
- $R^6$ is cyclopropyl; and $R^7$ is chloro;
- $R^6$ is cyclopropyl; and $R^7$ is fluoro;
- $R^6$ is isopropyl; and $R^7$ is methoxy;
- $R^6$ is isopropyl; and $R^7$ is trifluoromethoxy;
- $R^6$ is chloro; and $R^7$ is trifluoromethyl;
- $R^6$ is chloro; and $R^7$ is trifluoromethoxy;
- $R^7$ is isopropyl; and $R^6$ is methyl;
- $R^7$ is isopropyl; and $R^6$ is trifluoromethyl;
- $R^7$ is isopropyl; and $R^6$ is cyclopropyl;
- $R^7$ is isopropyl; and $R^6$ is chloro;
- $R^7$ is ethyl; and $R^6$ is fluoro;
- $R^7$ is isopropyl; and $R^6$ is cyano;
- $R^7$ is cyclopropyl; and $R^6$ is cyclopropyl;
- $R^7$ is cyclopropyl; and $R^6$ is chloro;
- $R^7$ is cyclopropyl; and $R^6$ is fluoro;
- $R^7$ is isopropyl; and $R^6$ is methoxy;
- $R^7$ is isopropyl; and $R^6$ is trifluoromethoxy;
- $R^7$ is chloro; and $R^6$ is trifluoromethyl; or
- $R^7$ is chloro; and $R^6$ is trifluoromethoxy.

In some embodiments, of the compound of formula AA, the substituted ring B is

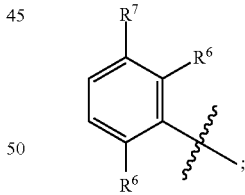

and $R^6$ and $R^7$ are one of the following combinations:
- each $R^6$ is independently $C_1$-$C_6$ alkyl, and $R^7$ is $C_1$-$C_6$ alkyl optionally substituted with one or more halo;
- each $R^6$ is independently $C_1$-$C_6$ alkyl and $R^7$ is $C_1$-$C_6$ alkyl;
- each $R^6$ is independently $C_1$-$C_6$ alkyl, and $R^7$ is $C_1$-$C_6$ alkyl substituted with one or more halo;
- each $R^6$ is independently $C_1$-$C_6$ alkyl, and $R^7$ is $C_3$-$C_7$ cycloalkyl;
- each $R^6$ is independently $C_1$-$C_6$ alkyl, and $R^7$ is halo;
- each $R^6$ is independently $C_1$-$C_6$ alkyl, and $R^7$ is cyano;
- each $R^6$ is independently $C_3$-$C_7$ cycloalkyl, and $R^7$ is $C_3$-$C_7$ cycloalkyl;
- each $R^6$ is independently $C_3$-$C_7$ cycloalkyl, and $R^7$ is halo;
- each $R^6$ is independently cyclopropyl and $R^7$ is halo;

each R⁶ is independently C₁-C₆ alkyl, and R⁷ is C₁-C₆ alkoxy optionally substituted with one or more halo;
each R⁶ is independently C₁-C₆ alkyl, and R⁷ is C₁-C₆ alkoxy;
each R⁶ is independently C₁-C₆ alkyl, and R⁷ is C₁-C₆ alkoxy substituted with one or more halo;
each R⁶ is independently halo, and R⁷ is C₁-C₆ haloalkyl;
each R⁶ is independently halo, and R⁷ is C₁-C₆ haloalkoxy;
each R⁶ is independently C₁-C₆ alkoxy; and R⁷ is halo;
each R⁶ is independently C₁-C₆ alkoxy; and R⁷ is chloro;
R⁷ is C₁-C₆ alkyl, and each R⁶ is independently C₁-C₆ alkyl optionally substituted with one or more halo;
R⁷ is C₁-C₆ alkyl, and each R⁶ is independently C₁-C₆ alkyl substituted with one or more halo;
R⁷ is C₁-C₆ alkyl, and each R⁶ is independently C₃-C₇ cycloalkyl;
R⁷ is C₁-C₆ alkyl, and each R⁶ is independently halo;
R⁷ is C₁-C₆ alkyl and each R⁶ is independently halo;
R⁷ is C₁-C₆ alkyl, and R⁶ is cyano;
R⁷ is C₃-C₇ cycloalkyl, and each R⁶ is independently C₃-C₇ cycloalkyl;
R⁷ is C₃-C₇ cycloalkyl, and each R⁶ is independently halo;
R⁷ is C₃-C₇ cycloalkyl and each R⁶ is independently halo;
R⁷ is C₁-C₆ alkyl, and each R⁶ is independently C₁-C₆ alkoxy optionally substituted with one or more halo;
R⁷ is C₁-C₆ alkyl, and each R⁶ is independently C₁-C₆ alkoxy;
R⁷ is C₁-C₆ alkyl, and each R⁶ is independently C₁-C₆ alkoxy substituted with one or more halo;
R⁷ is halo, and each R⁶ is independently C₁-C₆ haloalkyl;
R⁷ is halo, and each R⁶ is independently C₁-C₆ haloalkoxy;
R⁷ is C₁-C₆ alkoxy; and each R⁶ is independently halo;
R⁷ is C₁-C₆ alkoxy; and R⁶ is chloro;
R⁶ and R⁷ on adjacent atoms taken together with the atoms connecting them form a C₅ aliphatic carbocyclic ring;
R⁶ and R⁷ on adjacent atoms taken together with the atoms connecting them form a C₄-C₆ aliphatic carbocyclic ring optionally substituted with one or more hydroxy, oxo, or C₁-C₆ alkyl; and one R⁶ is halo or cyano; or
R⁶ and R⁷ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or C₁-C₆ alkyl; and one R⁶ is halo or cyano.

In some embodiments, of the compound of formula AA, the substituted ring B is

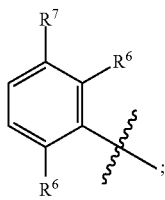

and R⁶ and R⁷ are one of the following combinations:
each R⁶ is isopropyl; and R⁷ is methyl;
each R⁶ is isopropyl; and R⁷ is isopropyl;
each R⁶ is isopropyl; and R⁷ is trifluoromethyl;
each R⁶ is isopropyl; and R⁷ is cyclopropyl;
each R⁶ is isopropyl; and R⁷ is chloro;
each R⁶ is isopropyl; and R⁷ is fluoro;
each R⁶ is ethyl; and R⁷ is fluoro;
each R⁶ is isopropyl; and R⁷ is cyano;
each R⁶ is cyclopropyl; and R⁷ is cyclopropyl;
each R⁶ is cyclopropyl; and R⁷ is chloro;
each R⁶ is cyclopropyl; and R⁷ is fluoro;
each R⁶ is isopropyl; and R⁷ is methoxy;
each R⁶ is isopropyl; and R⁷ is trifluoromethoxy;
each R⁶ is chloro; and R⁷ is trifluoromethyl;
each R⁶ is chloro; and R⁷ is trifluoromethoxy;
R⁷ is isopropyl; and each R⁶ is methyl;
R⁷ is isopropyl; and each R⁶ is trifluoromethyl;
R⁷ is isopropyl; and each R⁶ is cyclopropyl;
R⁷ is isopropyl; and each R⁶ is chloro;
R⁷ is ethyl; and each R⁶ is fluoro;
R⁷ is isopropyl; and each R⁶ is cyano;
R⁷ is cyclopropyl; and each R⁶ is cyclopropyl;
R⁷ is cyclopropyl; and each R⁶ is chloro;
R⁷ is cyclopropyl; and each R⁶ is fluoro;
R⁷ is isopropyl; and each R⁶ is methoxy;
R⁷ is isopropyl; and each R⁶ is trifluoromethoxy;
R⁷ is chloro; and each R⁶ is trifluoromethyl;
R⁷ is chloro; and each R⁶ is trifluoromethoxy;
one R⁶ is isopropyl; the other R⁶ is trifluoromethyl; and R⁷ is chloro;
R⁶ and R⁷ on adjacent atoms taken together with the atoms connecting them form a C₄ aliphatic carbocyclic ring; and one R⁶ is fluoro, chloro, or cyano;
R⁶ and R⁷ on adjacent atoms taken together with the atoms connecting them form a C₅ aliphatic carbocyclic ring; and one R⁶ is fluoro, chloro, or cyano;
R⁶ and R⁷ on adjacent atoms taken together with the atoms connecting them form a C₆ aliphatic carbocyclic ring; and one R⁶ is fluoro, chloro, or cyano;
R⁶ and R⁷ on adjacent atoms taken together with the atoms connecting them form a 5-membered heterocyclic ring containing 1 heteroatoms independently selected from O, N, and S; and one R⁶ is fluoro, chloro, or cyano; or
R⁶ and R⁷ on adjacent atoms taken together with the atoms connecting them form a 6-membered heterocyclic ring containing 1 heteroatoms independently selected from O, N, and S; and one R⁶ is fluoro, chloro, or cyano.

In some embodiments, of the compound of formula AA, the substituted ring B is

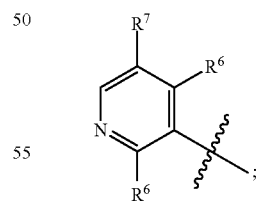

and R⁶ and R⁷ are one of the following combinations:
each R⁶ is independently C₁-C₆ alkyl, and R⁷ is C₁-C₆ alkyl optionally substituted with one or more halo;
each R⁶ is independently C₁-C₆ alkyl and R⁷ is C₁-C₆ alkyl;
each R⁶ is independently C₁-C₆ alkyl, and R⁷ is C₁-C₆ alkyl substituted with one or more halo;
each R⁶ is independently C₁-C₆ alkyl, and R⁷ is C₃-C₇ cycloalkyl;

each $R^6$ is independently $C_1$-$C_6$ alkyl, and $R^7$ is halo;
each $R^6$ is independently $C_1$-$C_6$ alkyl, and $R^7$ is cyano;
each $R^6$ is independently $C_3$-$C_7$ cycloalkyl, and $R^7$ is $C_3$-$C_7$ cycloalkyl;
each $R^6$ is independently $C_3$-$C_7$ cycloalkyl, and $R^7$ is halo;
each $R^6$ is independently cyclopropyl and $R^7$ is halo;
each $R^6$ is independently $C_1$-$C_6$ alkyl, and $R^7$ is $C_1$-$C_6$ alkoxy optionally substituted with one or more halo;
each $R^6$ is independently $C_1$-$C_6$ alkyl, and $R^7$ is $C_1$-$C_6$ alkoxy;
each $R^6$ is independently $C_1$-$C_6$ alkyl, and $R^7$ is $C_1$-$C_6$ alkoxy substituted with one or more halo;
each $R^6$ is independently halo, and $R^7$ is $C_1$-$C_6$ haloalkyl;
each $R^6$ is independently halo, and $R^7$ is $C_1$-$C_6$ haloalkoxy;
each $R^6$ is independently $C_1$-$C_6$ alkoxy; and $R^7$ is halo;
each $R^6$ is independently $C_1$-$C_6$ alkoxy; and $R^7$ is chloro;
$R^7$ is $C_1$-$C_6$ alkyl, and each $R^6$ is independently $C_1$-$C_6$ alkyl optionally substituted with one or more halo;
$R^7$ is $C_1$-$C_6$ alkyl, and each $R^6$ is independently $C_1$-$C_6$ alkyl substituted with one or more halo;
$R^7$ is $C_1$-$C_6$ alkyl, and each $R^6$ is independently $C_3$-$C_7$ cycloalkyl;
$R^7$ is $C_1$-$C_6$ alkyl, and each $R^6$ is independently halo;
$R^7$ is $C_1$-$C_6$ alkyl and each $R^6$ is independently halo;
$R^7$ is $C_1$-$C_6$ alkyl, and $R^6$ is cyano;
$R^7$ is $C_3$-$C_7$ cycloalkyl, and each $R^6$ is independently $C_3$-$C_7$ cycloalkyl;
$R^7$ is $C_3$-$C_7$ cycloalkyl, and each $R^6$ is independently halo;
$R^7$ is $C_3$-$C_7$ cycloalkyl and each $R^6$ is independently halo;
$R^7$ is $C_1$-$C_6$ alkyl, and each $R^6$ is independently $C_1$-$C_6$ alkoxy optionally substituted with one or more halo;
$R^7$ is $C_1$-$C_6$ alkyl, and each $R^6$ is independently $C_1$-$C_6$ alkoxy;
$R^7$ is $C_1$-$C_6$ alkyl, and each $R^6$ is independently $C_1$-$C_6$ alkoxy substituted with one or more halo;
$R^7$ is halo, and each $R^6$ is independently $C_1$-$C_6$ haloalkyl;
$R^7$ is halo, and each $R^6$ is independently $C_1$-$C_6$ haloalkoxy;
$R^7$ is $C_1$-$C_6$ alkoxy; and each $R^6$ is independently halo; or
$R^7$ is $C_1$-$C_6$ alkoxy; and $R^6$ is chloro.

In some embodiments, of the compound of formula AA, the substituted ring B is

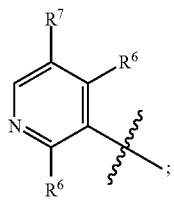

and $R^6$ and $R^7$ are one of the following combinations:
each $R^6$ is isopropyl; and $R^7$ is methyl;
each $R^6$ is isopropyl; and $R^7$ is isopropyl;
each $R^6$ is isopropyl; and $R^7$ is trifluoromethyl;
each $R^6$ is isopropyl; and $R^7$ is cyclopropyl;
each $R^6$ is isopropyl; and $R^7$ is chloro;
each $R^6$ is isopropyl; and $R^7$ is fluoro;
each $R^6$ is ethyl; and $R^7$ is fluoro;
each $R^6$ is isopropyl; and $R^7$ is cyano;
each $R^6$ is cyclopropyl; and $R^7$ is cyclopropyl;
each $R^6$ is cyclopropyl; and $R^7$ is chloro;
each $R^6$ is cyclopropyl; and $R^7$ is fluoro;
each $R^6$ is isopropyl; and $R^7$ is methoxy;
each $R^6$ is isopropyl; and $R^7$ is trifluoromethoxy;
each $R^6$ is chloro; and $R^7$ is trifluoromethyl;
each $R^6$ is chloro; and $R^7$ is trifluoromethoxy;
$R^7$ is isopropyl; and each $R^6$ is methyl;
$R^7$ is isopropyl; and each $R^6$ is trifluoromethyl;
$R^7$ is isopropyl; and each $R^6$ is cyclopropyl;
$R^7$ is isopropyl; and each $R^6$ is chloro;
$R^7$ is ethyl; and each $R^6$ is fluoro;
$R^7$ is isopropyl; and each $R^6$ is cyano;
$R^7$ is cyclopropyl; and each $R^6$ is cyclopropyl;
$R^7$ is cyclopropyl; and each $R^6$ is chloro;
$R^7$ is cyclopropyl; and each $R^6$ is fluoro;
$R^7$ is isopropyl; and each $R^6$ is methoxy;
$R^7$ is isopropyl; and each $R^6$ is trifluoromethoxy;
$R^7$ is chloro; and each $R^6$ is trifluoromethyl;
$R^7$ is chloro; and each $R^6$ is trifluoromethoxy; or one $R^6$ is isopropyl; the other $R^6$ is trifluoromethyl; and $R^7$ is chloro.

In some embodiments, of the compound of formula AA, the substituted ring B is

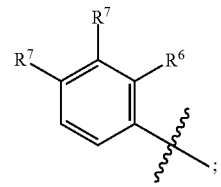

and $R^6$ and $R^7$ are one of the following combinations:
$R^6$ is $C_1$-$C_6$ alkyl, and each $R^7$ is independently $C_1$-$C_6$ alkyl optionally substituted with one or more halo;
$R^6$ is $C_1$-$C_6$ alkyl and each $R^7$ is independently $C_1$-$C_6$ alkyl;
$R^6$ is $C_1$-$C_6$ alkyl, and each $R^7$ is independently $C_1$-$C_6$ alkyl substituted with one or more halo;
$R^6$ is $C_1$-$C_6$ alkyl, and each $R^7$ is independently $C_3$-$C_7$ cycloalkyl;
$R^6$ is $C_1$-$C_6$ alkyl, and each $R^7$ is independently halo;
$R^6$ is $C_1$-$C_6$ alkyl, and $R^7$ is cyano;
$R^6$ is $C_3$-$C_7$ cycloalkyl, and each $R^7$ is independently $C_3$-$C_7$ cycloalkyl;
$R^6$ is $C_3$-$C_7$ cycloalkyl, and each $R^7$ is independently halo;
$R^6$ is cyclopropyl and each $R^7$ is independently halo;
$R^6$ is $C_1$-$C_6$ alkyl, and each $R^7$ is independently $C_1$-$C_6$ alkoxy optionally substituted with one or more halo;
$R^6$ is $C_1$-$C_6$ alkyl, and each $R^7$ is independently $C_1$-$C_6$ alkoxy;
$R^6$ is $C_1$-$C_6$ alkyl, and each $R^7$ is independently $C_1$-$C_6$ alkoxy substituted with one or more halo;
$R^6$ is halo, and each $R^7$ is independently $C_1$-$C_6$ haloalkyl;
$R^6$ is halo, and each $R^7$ is independently $C_1$-$C_6$ haloalkoxy;
$R^6$ is $C_1$-$C_6$ alkoxy; and each $R^7$ is independently halo;
$R^6$ is $C_1$-$C_6$ alkoxy; and $R^7$ is chloro;
each $R^7$ is independently $C_1$-$C_6$ alkyl, and $R^6$ is $C_1$-$C_6$ alkyl optionally substituted with one or more halo;
each $R^7$ is independently $C_1$-$C_6$ alkyl, and $R^6$ is $C_1$-$C_6$ alkyl substituted with one or more halo;
each $R^7$ is independently $C_1$-$C_6$ alkyl, and $R^6$ is $C_3$-$C_7$ cycloalkyl;
each $R^7$ is independently $C_1$-$C_6$ alkyl, and $R^6$ is halo;
each $R^7$ is independently $C_1$-$C_6$ alkyl and $R^6$ is halo;
each $R^7$ is independently $C_1$-$C_6$ alkyl, and $R^6$ is cyano;

each $R^7$ is independently $C_3$-$C_7$ cycloalkyl, and $R^6$ is $C_3$-$C_7$ cycloalkyl.
each $R^7$ is independently $C_3$-$C_7$ cycloalkyl, and $R^6$ is halo;
each $R^7$ is independently $C_3$-$C_7$ cycloalkyl and $R^6$ is halo;
each $R^7$ is independently $C_1$-$C_6$ alkyl, and $R^6$ is $C_1$-$C_6$ alkoxy optionally substituted with one or more halo;
each $R^7$ is independently $C_1$-$C_6$ alkyl, and $R^6$ is $C_1$-$C_6$ alkoxy;
each $R^7$ is independently $C_1$-$C_6$ alkyl, and $R^6$ is $C_1$-$C_6$ alkoxy substituted with one or more halo;
each $R^7$ is independently halo, and $R^6$ is $C_1$-$C_6$ haloalkyl;
each $R^7$ is independently halo, and $R^6$ is $C_1$-$C_6$ haloalkoxy;
each $R^7$ is independently $C_1$-$C_6$ alkoxy; and $R^6$ is halo;
each $R^7$ is independently $C_1$-$C_6$ alkoxy; and $R^6$ is chloro;
$R^6$ and $R^7$ on adjacent atoms taken together with the atoms connecting them form a $C_5$ aliphatic carbocyclic ring;
$R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; or
$R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

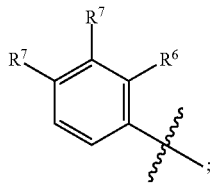

and $R^6$ and $R^7$ are one of the following combinations:
$R^6$ is isopropyl; and each $R^7$ is methyl;
$R^6$ is isopropyl; and each $R^7$ is isopropyl;
$R^6$ is isopropyl; and each $R^7$ is trifluoromethyl;
$R^6$ is isopropyl; and each $R^7$ is cyclopropyl;
$R^6$ is isopropyl; and each $R^7$ is chloro;
$R^6$ is isopropyl; and each $R^7$ is fluoro;
$R^6$ is ethyl; and each $R^7$ is fluoro;
$R^6$ is isopropyl; and each $R^7$ is cyano;
$R^6$ is cyclopropyl; and each $R^7$ is cyclopropyl;
$R^6$ is cyclopropyl; and each $R^7$ is chloro;
$R^6$ is cyclopropyl; and each $R^7$ is fluoro;
$R^6$ is isopropyl; and $R^7$ is methoxy;
$R^6$ is isopropyl; and each $R^7$ is trifluoromethoxy;
$R^6$ is chloro; and each $R^7$ is trifluoromethyl;
$R^6$ is chloro; and each $R^7$ is trifluoromethoxy;
each $R^7$ is isopropyl; and $R^6$ is methyl;
each $R^7$ is isopropyl; and $R^6$ is trifluoromethyl;
each $R^7$ is isopropyl; and $R^6$ is cyclopropyl;
each $R^7$ is isopropyl; and $R^6$ is chloro;
each $R^7$ is ethyl; and $R^6$ is fluoro;
each $R^7$ is isopropyl; and $R^6$ is cyano;
each $R^7$ is cyclopropyl; and $R^6$ is cyclopropyl;
each $R^7$ is cyclopropyl; and $R^6$ is chloro;
each $R^7$ is cyclopropyl; and $R^6$ is fluoro;
each $R^7$ is isopropyl; and $R^6$ is methoxy;
each $R^7$ is isopropyl; and $R^6$ is trifluoromethoxy;
each $R^7$ is chloro; and $R^6$ is trifluoromethyl;
each $R^7$ is chloro; and $R^6$ is trifluoromethoxy;
$R^6$ and $R^7$ on adjacent atoms taken together with the atoms connecting them form a $C_5$ aliphatic carbocyclic ring; and one $R^7$ is fluoro, chloro, or cyano;
$R^6$ and $R^7$ on adjacent atoms taken together with the atoms connecting them form a $C_4$ aliphatic carbocyclic ring; and one $R^7$ is fluoro, chloro, or cyano;
$R^6$ and $R^7$ on adjacent atoms taken together with the atoms connecting them form a $C_6$ aliphatic carbocyclic ring; and one $R^7$ is fluoro, chloro, or cyano;
$R^6$ and $R^7$ on adjacent atoms taken together with the atoms connecting them form a 5-membered heterocyclic ring containing 1 heteroatoms independently selected from O, N, and S; and one $R^7$ is fluoro, chloro, or cyano; or
$R^6$ and $R^7$ on adjacent atoms taken together with the atoms connecting them form a 6-membered heterocyclic ring containing 1 heteroatoms independently selected from O, N, and S; and one $R^7$ is fluoro, chloro, or cyano.

In some embodiments, of the compound of formula AA, the substituted ring B is

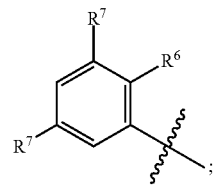

and $R^6$ and $R^7$ are one of the following combinations:
$R^6$ is $C_1$-$C_6$ alkyl, and each $R^7$ is independently $C_1$-$C_6$ alkyl optionally substituted with one or more halo;
$R^6$ is $C_1$-$C_6$ alkyl and each $R^7$ is independently $C_1$-$C_6$ alkyl;
$R^6$ is $C_1$-$C_6$ alkyl, and each $R^7$ is independently $C_1$-$C_6$ alkyl substituted with one or more halo;
$R^6$ is $C_1$-$C_6$ alkyl, and each $R^7$ is independently $C_3$-$C_7$ cycloalkyl;
$R^6$ is $C_1$-$C_6$ alkyl, and each $R^7$ is independently halo;
$R^6$ is $C_1$-$C_6$ alkyl, and $R^7$ is cyano;
$R^6$ is $C_3$-$C_7$ cycloalkyl, and each $R^7$ is independently $C_3$-$C_7$ cycloalkyl;
$R^6$ is $C_3$-$C_7$ cycloalkyl, and each $R^7$ is independently halo;
$R^6$ is cyclopropyl and each $R^7$ is independently halo;
$R^6$ is $C_1$-$C_6$ alkyl, and each $R^7$ is independently $C_1$-$C_6$ alkoxy optionally substituted with one or more halo;
$R^6$ is $C_1$-$C_6$ alkyl, and each $R^7$ is independently $C_1$-$C_6$ alkoxy;
$R^6$ is $C_1$-$C_6$ alkyl, and each $R^7$ is independently $C_1$-$C_6$ alkoxy substituted with one or more halo;
$R^6$ is halo, and each $R^7$ is independently $C_1$-$C_6$ haloalkyl;
$R^6$ is halo, and each $R^7$ is independently $C_1$-$C_6$ haloalkoxy;
$R^6$ is $C_1$-$C_6$ alkoxy; and each $R^7$ is independently halo;
$R^6$ is $C_1$-$C_6$ alkoxy; and $R^7$ is chloro;
each $R^7$ is independently $C_1$-$C_6$ alkyl, and $R^6$ is $C_1$-$C_6$ alkyl optionally substituted with one or more halo;
each $R^7$ is independently $C_1$-$C_6$ alkyl, and $R^6$ is $C_1$-$C_6$ alkyl substituted with one or more halo;
each $R^7$ is independently $C_1$-$C_6$ alkyl, and $R^6$ is $C_3$-$C_7$ cycloalkyl;

each $R^7$ is independently $C_1$-$C_6$ alkyl, and $R^6$ is halo;
each $R^7$ is independently $C_1$-$C_6$ alkyl and $R^6$ is halo;
each $R^7$ is independently $C_1$-$C_6$ alkyl, and $R^6$ is cyano;
each $R^7$ is independently $C_3$-$C_7$ cycloalkyl, and $R^6$ is $C_3$-$C_7$ cycloalkyl;
each $R^7$ is independently $C_3$-$C_7$ cycloalkyl, and $R^6$ is halo;
each $R^7$ is independently $C_3$-$C_7$ cycloalkyl and $R^6$ is halo;
each $R^7$ is independently $C_1$-$C_6$ alkyl, and $R^6$ is $C_1$-$C_6$ alkoxy optionally substituted with one or more halo;
each $R^7$ is independently $C_1$-$C_6$ alkyl, and $R^6$ is $C_1$-$C_6$ alkoxy;
each $R^7$ is independently $C_1$-$C_6$ alkyl, and $R^6$ is $C_1$-$C_6$ alkoxy substituted with one or more halo;
each $R^7$ is independently halo, and $R^6$ is $C_1$-$C_6$ haloalkyl;
each $R^7$ is independently halo, and $R^6$ is $C_1$-$C_6$ haloalkoxy;
each $R^7$ is independently $C_1$-$C_6$ alkoxy; and $R^6$ is halo;
each $R^6$ is independently $C_1$-$C_6$ alkoxy; and $R^6$ is chloro;
$R^6$ and $R^7$ on adjacent atoms taken together with the atoms connecting them form a $C_5$ aliphatic carbocyclic ring;
$R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; or
$R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

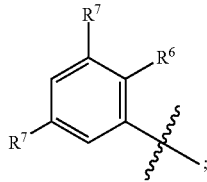

and $R^6$ and $R^7$ are one of the following combinations:
$R^6$ is isopropyl; and each $R^7$ is methyl;
$R^6$ is isopropyl; and each $R^7$ is isopropyl;
$R^6$ is isopropyl; and each $R^7$ is trifluoromethyl;
$R^6$ is isopropyl; and each $R^7$ is cyclopropyl;
$R^6$ is isopropyl; and each $R^7$ is chloro;
$R^6$ is isopropyl; and each $R^7$ is fluoro;
$R^6$ is ethyl; and each $R^7$ is fluoro;
$R^6$ is isopropyl; and each $R^7$ is cyano;
$R^6$ is cyclopropyl; and each $R^7$ is cyclopropyl;
$R^6$ is cyclopropyl; and each $R^7$ is chloro;
$R^6$ is cyclopropyl; and each $R^7$ is fluoro;
$R^6$ is isopropyl; and each $R^7$ is methoxy;
$R^6$ is isopropyl; and each $R^7$ is trifluoromethoxy;
$R^6$ is chloro; and each $R^7$ is trifluoromethyl;
$R^6$ is chloro; and each $R^7$ is trifluoromethoxy;
each $R^7$ is isopropyl; and $R^6$ is methyl;
each $R^7$ is isopropyl; and $R^6$ is trifluoromethyl;
each $R^7$ is isopropyl; and $R^6$ is cyclopropyl;
each $R^7$ is isopropyl; and $R^6$ is chloro;
each $R^7$ is ethyl; and $R^6$ is fluoro;
each $R^7$ is isopropyl; and $R^6$ is cyano;
each $R^7$ is cyclopropyl; and $R^6$ is cyclopropyl;
each $R^7$ is cyclopropyl; and $R^6$ is chloro;
each $R^7$ is cyclopropyl; and $R^6$ is fluoro;
each $R^7$ is isopropyl; and $R^6$ is methoxy;
each $R^7$ is isopropyl; and $R^6$ is trifluoromethoxy;
each $R^7$ is chloro; and $R^6$ is trifluoromethyl;
each $R^7$ is chloro; and $R^6$ is trifluoromethoxy;
$R^6$ and $R^7$ on adjacent atoms taken together with the atoms connecting them form a $C_5$ aliphatic carbocyclic ring; and one $R^7$ is fluoro, chloro, or cyano;
$R^6$ and $R^7$ on adjacent atoms taken together with the atoms connecting them form a $C_4$ aliphatic carbocyclic ring; and one $R^7$ is fluoro, chloro, or cyano;
$R^6$ and $R^7$ on adjacent atoms taken together with the atoms connecting them form a $C_6$ aliphatic carbocyclic ring; and one $R^7$ is fluoro, chloro, or cyano;
$R^6$ and $R^7$ on adjacent atoms taken together with the atoms connecting them form a 5-membered heterocyclic ring containing 1 heteroatoms independently selected from O, N, and S; and one $R^7$ is fluoro, chloro, or cyano; or
$R^6$ and $R^7$ on adjacent atoms taken together with the atoms connecting them form a 6-membered heterocyclic ring containing 1 heteroatoms independently selected from O, N, and S; and one $R^7$ is fluoro, chloro, or cyano.

In some embodiments, of the compound of formula AA, the substituted ring B is

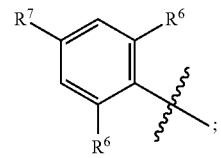

and $R^6$ and $R^7$ are one of the following combinations:
each $R^6$ is independently $C_1$-$C_6$ alkyl, and $R^7$ is $C_1$-$C_6$ alkyl optionally substituted with one or more halo;
each $R^6$ is independently $C_1$-$C_6$ alkyl and $R^7$ is $C_1$-$C_6$ alkyl;
each $R^6$ is independently $C_1$-$C_6$ alkyl, and $R^7$ is $C_1$-$C_6$ alkyl substituted with one or more halo;
each $R^6$ is independently $C_1$-$C_6$ alkyl, and $R^7$ is $C_3$-$C_7$ cycloalkyl;
each $R^6$ is independently $C_1$-$C_6$ alkyl, and $R^7$ is halo;
each $R^6$ is independently $C_1$-$C_6$ alkyl, and $R^7$ is cyano;
each $R^6$ is independently $C_3$-$C_7$ cycloalkyl, and $R^7$ is $C_3$-$C_7$ cycloalkyl;
each $R^6$ is independently $C_3$-$C_7$ cycloalkyl, and $R^7$ is halo;
each $R^6$ is independently cyclopropyl and $R^7$ is halo;
each $R^6$ is independently $C_1$-$C_6$ alkyl, and $R^7$ is $C_1$-$C_6$ alkoxy optionally substituted with one or more halo;
each $R^6$ is independently $C_1$-$C_6$ alkyl, and $R^7$ is $C_1$-$C_6$ alkoxy;
each $R^6$ is independently $C_1$-$C_6$ alkyl, and $R^7$ is $C_1$-$C_6$ alkoxy substituted with one or more halo;
each $R^6$ is independently halo, and $R^7$ is $C_1$-$C_6$ haloalkyl;
each $R^6$ is independently halo, and $R^7$ is $C_1$-$C_6$ haloalkoxy;
each $R^6$ is independently $C_1$-$C_6$ alkoxy; and $R^7$ is halo;
each $R^6$ is independently $C_1$-$C_6$ alkoxy; and $R^7$ is chloro;
$R^7$ is $C_1$-$C_6$ alkyl, and each $R^6$ is independently $C_1$-$C_6$ alkyl optionally substituted with one or more halo;
$R^7$ is $C_1$-$C_6$ alkyl, and each $R^6$ is independently $C_1$-$C_6$ alkyl substituted with one or more halo;

R$^7$ is C$_1$-C$_6$ alkyl, and each R$^6$ is independently C$_3$-C$_7$ cycloalkyl;
R$^7$ is C$_1$-C$_6$ alkyl, and each R$^6$ is independently halo;
R$^7$ is C$_1$-C$_6$ alkyl and each R$^6$ is independently halo;
R$^7$ is C$_1$-C$_6$ alkyl, and R$^6$ is cyano;
R$^7$ is C$_3$-C$_7$ cycloalkyl, and each R$^6$ is independently C$_3$-C$_7$ cycloalkyl;
R$^7$ is C$_3$-C$_7$ cycloalkyl, and each R$^6$ is independently halo;
R$^7$ is C$_3$-C$_7$ cycloalkyl and each R$^6$ is independently halo;
R$^7$ is C$_1$-C$_6$ alkyl, and each R$^6$ is independently C$_1$-C$_6$ alkoxy optionally substituted with one or more halo;
R$^7$ is C$_1$-C$_6$ alkyl, and each R$^6$ is independently C$_1$-C$_6$ alkoxy;
R$^7$ is C$_1$-C$_6$ alkyl, and each R$^6$ is independently C$_1$-C$_6$ alkoxy substituted with one or more halo;
R$^7$ is halo, and each R$^6$ is independently C$_1$-C$_6$ haloalkyl;
R$^7$ is halo, and each R$^6$ is independently C$_1$-C$_6$ haloalkoxy;
R$^7$ is C$_1$-C$_6$ alkoxy; and each R$^6$ is independently halo; or
R$^7$ is C$_1$-C$_6$ alkoxy; and R$^6$ is chloro.

In some embodiments, of the compound of formula AA, the substituted ring B is

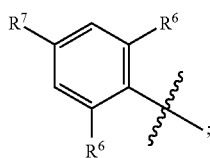
;

and R$^6$ and R$^7$ are one of the following combinations:
each R$^6$ is isopropyl; and R$^7$ is methyl;
each R$^6$ is isopropyl; and R$^7$ is isopropyl;
each R$^6$ is isopropyl; and R$^7$ is trifluoromethyl;
each R$^6$ is isopropyl; and R$^7$ is cyclopropyl;
each R$^6$ is isopropyl; and R$^7$ is chloro;
each R$^6$ is isopropyl; and R$^7$ is fluoro;
each R$^6$ is ethyl; and R$^7$ is fluoro;
each R$^6$ is isopropyl; and R$^7$ is cyano;
each R$^6$ is cyclopropyl; and R$^7$ is cyclopropyl;
each R$^6$ is cyclopropyl; and R$^7$ is chloro;
each R$^6$ is cyclopropyl; and R$^7$ is fluoro;
each R$^6$ is isopropyl; and R$^7$ is methoxy;
each R$^6$ is isopropyl; and R$^7$ is trifluoromethoxy;
each R$^6$ is chloro; and R$^7$ is trifluoromethyl;
each R$^6$ is chloro; and R$^7$ is trifluoromethoxy;
R$^7$ is isopropyl; and each R$^6$ is methyl;
R$^7$ is isopropyl; and each R$^6$ is trifluoromethyl;
R$^7$ is isopropyl; and each R$^6$ is cyclopropyl;
R$^7$ is isopropyl; and each R$^6$ is chloro;
R$^7$ is ethyl; and each R$^6$ is fluoro;
R$^7$ is isopropyl; and each R$^6$ is cyano;
R$^7$ is cyclopropyl; and each R$^6$ is cyclopropyl;
R$^7$ is cyclopropyl; and each R$^6$ is chloro;
R$^7$ is cyclopropyl; and each R$^6$ is fluoro;
R$^7$ is isopropyl; and each R$^6$ is methoxy;
R$^7$ is isopropyl; and each R$^6$ is trifluoromethoxy;
R$^7$ is chloro; and each R$^6$ is trifluoromethyl;
R$^7$ is chloro; and each R$^6$ is trifluoromethoxy; or one R$^6$ is isopropyl; the other R$^6$ is trifluoromethyl; and R$^7$ is chloro.

In some embodiments, of the compound of formula AA, the substituted ring B is

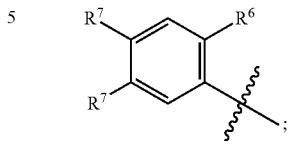
;

and R$^6$ and R$^7$ are one of the following combinations:
R$^6$ is C$_1$-C$_6$ alkyl, and each R$^7$ is independently C$_1$-C$_6$ alkyl optionally substituted with one or more halo;
R$^6$ is C$_1$-C$_6$ alkyl and each R$^7$ is independently C$_1$-C$_6$ alkyl;
R$^6$ is C$_1$-C$_6$ alkyl, and each R$^7$ is independently C$_1$-C$_6$ alkyl substituted with one or more halo;
R$^6$ is C$_1$-C$_6$ alkyl, and each R$^7$ is independently C$_3$-C$_7$ cycloalkyl;
R$^6$ is C$_1$-C$_6$ alkyl, and each R$^7$ is independently halo;
R$^6$ is C$_1$-C$_6$ alkyl, and R$^7$ is cyano;
R$^6$ is C$_3$-C$_7$ cycloalkyl, and each R$^7$ is independently C$_3$-C$_7$ cycloalkyl;
R$^6$ is C$_3$-C$_7$ cycloalkyl, and each R$^7$ is independently halo;
R$^6$ is cyclopropyl and each R$^7$ is independently halo;
R$^6$ is C$_1$-C$_6$ alkyl, and each R$^7$ is independently C$_1$-C$_6$ alkoxy optionally substituted with one or more halo;
R$^6$ is C$_1$-C$_6$ alkyl, and each R$^7$ is independently C$_1$-C$_6$ alkoxy;
R$^6$ is C$_1$-C$_6$ alkyl, and each R$^7$ is independently C$_1$-C$_6$ alkoxy substituted with one or more halo;
R$^6$ is halo, and each R$^7$ is independently C$_1$-C$_6$ haloalkyl;
R$^6$ is halo, and each R$^7$ is independently C$_1$-C$_6$ haloalkoxy;
R$^6$ is C$_1$-C$_6$ alkoxy; and each R$^7$ is independently halo;
R$^6$ is C$_1$-C$_6$ alkoxy; and R$^7$ is chloro;
each R$^7$ is independently C$_1$-C$_6$ alkyl, and R$^6$ is C$_1$-C$_6$ alkyl optionally substituted with one or more halo;
each R$^7$ is independently C$_1$-C$_6$ alkyl, and R$^6$ is C$_1$-C$_6$ alkyl substituted with one or more halo;
each R$^7$ is independently C$_1$-C$_6$ alkyl, and R$^6$ is C$_3$-C$_7$ cycloalkyl;
each R$^7$ is independently C$_1$-C$_6$ alkyl, and R$^6$ is halo;
each R$^7$ is independently C$_1$-C$_6$ alkyl and R$^6$ is halo;
each R$^7$ is independently C$_1$-C$_6$ alkyl, and R$^6$ is cyano;
each R$^7$ is independently C$_3$-C$_7$ cycloalkyl, and R$^6$ is C$_3$-C$_7$ cycloalkyl;
each R$^7$ is independently C$_3$-C$_7$ cycloalkyl, and R$^6$ is halo;
each R$^7$ is independently C$_3$-C$_7$ cycloalkyl and R$^6$ is halo;
each R$^7$ is independently C$_1$-C$_6$ alkyl, and R$^6$ is C$_1$-C$_6$ alkoxy optionally substituted with one or more halo;
each R$^7$ is independently C$_1$-C$_6$ alkyl, and R$^6$ is C$_1$-C$_6$ alkoxy;
each R$^7$ is independently C$_1$-C$_6$ alkyl, and R$^6$ is C$_1$-C$_6$ alkoxy substituted with one or more halo;
each R$^7$ is independently halo, and R$^6$ is C$_1$-C$_6$ haloalkyl;
each R$^7$ is independently halo, and R$^6$ is C$_1$-C$_6$ haloalkoxy;
each R$^7$ is independently C$_1$-C$_6$ alkoxy; and R$^6$ is halo; or
each R$^7$ is independently C$_1$-C$_6$ alkoxy; and R$^6$ is chloro.

In some embodiments, of the compound of formula AA, the substituted ring B is

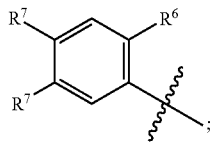

and $R^6$ and $R^7$ are one of the following combinations:
$R^6$ is isopropyl; and each $R^7$ is methyl;
$R^6$ is isopropyl; and each $R^7$ is isopropyl;
$R^6$ is isopropyl; and each $R^7$ is trifluoromethyl;
$R^6$ is isopropyl; and each $R^7$ is cyclopropyl;
$R^6$ is isopropyl; and each $R^7$ is chloro;
$R^6$ is isopropyl; and each $R^7$ is fluoro;
$R^6$ is ethyl; and each $R^7$ is fluoro;
$R^6$ is isopropyl; and each $R^7$ is cyano;
$R^6$ is cyclopropyl; and each $R^7$ is cyclopropyl;
$R^6$ is cyclopropyl; and each $R^7$ is chloro;
$R^6$ is cyclopropyl; and each $R^7$ is fluoro;
$R^6$ is isopropyl; and each $R^7$ is methoxy;
$R^6$ is isopropyl; and each $R^7$ is trifluoromethoxy;
$R^6$ is chloro; and each $R^7$ is trifluoromethyl;
$R^6$ is chloro; and each $R^7$ is trifluoromethoxy;
each $R^7$ is isopropyl; and $R^6$ is methyl;
each $R^7$ is isopropyl; and $R^6$ is trifluoromethyl;
each $R^7$ is isopropyl; and $R^6$ is cyclopropyl;
each $R^7$ is isopropyl; and $R^6$ is chloro;
each $R^7$ is ethyl; and $R^6$ is fluoro;
each $R^7$ is isopropyl; and $R^6$ is cyano;
each $R^7$ is cyclopropyl; and $R^6$ is cyclopropyl;
each $R^7$ is cyclopropyl; and $R^6$ is chloro;
each $R^7$ is cyclopropyl; and $R^6$ is fluoro;
each $R^7$ is isopropyl; and $R^6$ is methoxy;
each $R^7$ is isopropyl; and $R^6$ is trifluoromethoxy;
each $R^7$ is chloro; and $R^6$ is trifluoromethyl; or each $R^7$ is chloro; and $R^6$ is trifluoromethoxy.

In some embodiments, of the compound of formula AA, the substituted ring B is

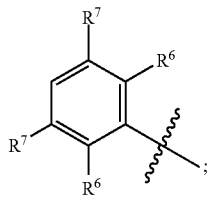

and $R^6$ and $R^7$ are one of the following combinations:
each $R^6$ is independently $C_1$-$C_6$ alkyl, and each $R^7$ is independently $C_1$-$C_6$ alkyl optionally substituted with one or more halo;
each $R^6$ is independently $C_1$-$C_6$ alkyl and each $R^7$ is independently $C_1$-$C_6$ alkyl; each $R^6$ is independently $C_1$-$C_6$ alkyl, and each $R^7$ is independently $C_1$-$C_6$ alkyl substituted with one or more halo;
each $R^6$ is independently $C_1$-$C_6$ alkyl, and each $R^7$ is independently $C_3$-$C_7$ cycloalkyl;
each $R^6$ is independently $C_1$-$C_6$ alkyl, and each $R^7$ is independently halo;
each $R^6$ is independently $C_1$-$C_6$ alkyl, and $R^7$ is cyano;
each $R^6$ is independently $C_3$-$C_7$ cycloalkyl, and each $R^7$ is independently $C_3$-$C_7$ cycloalkyl;
each $R^6$ is independently $C_3$-$C_7$ cycloalkyl, and each $R^7$ is independently halo;
each $R^6$ is independently cyclopropyl and each $R^7$ is independently halo;
each $R^6$ is independently $C_1$-$C_6$ alkyl, and each $R^7$ is independently $C_1$-$C_6$ alkoxy optionally substituted with one or more halo;
each $R^6$ is independently $C_1$-$C_6$ alkyl, and each $R^7$ is independently $C_1$-$C_6$ alkoxy;
each $R^6$ is independently $C_1$-$C_6$ alkyl, and each $R^7$ is independently $C_1$-$C_6$ alkoxy substituted with one or more halo;
each $R^6$ is independently halo, and each $R^7$ is independently $C_1$-$C_6$ haloalkyl;
each $R^6$ is independently halo, and each $R^7$ is independently $C_1$-$C_6$ haloalkoxy;
each $R^6$ is independently $C_1$-$C_6$ alkoxy; and each $R^7$ is independently halo;
each $R^6$ is independently $C_1$-$C_6$ alkoxy; and $R^7$ is chloro;
each $R^7$ is independently $C_1$-$C_6$ alkyl, and each $R^6$ is independently $C_1$-$C_6$ alkyl optionally substituted with one or more halo;
each $R^7$ is independently $C_1$-$C_6$ alkyl, and each $R^6$ is independently $C_1$-$C_6$ alkyl substituted with one or more halo;
each $R^7$ is independently $C_1$-$C_6$ alkyl, and each $R^6$ is independently $C_3$-$C_7$ cycloalkyl;
each $R^7$ is independently $C_1$-$C_6$ alkyl, and each $R^6$ is independently halo;
each $R^7$ is independently $C_1$-$C_6$ alkyl and each $R^6$ is independently halo;
each $R^7$ is independently $C_1$-$C_6$ alkyl, and $R^6$ is cyano;
each $R^7$ is independently $C_3$-$C_7$ cycloalkyl, and each $R^6$ is independently $C_3$-$C_7$ cycloalkyl each $R^7$ is independently $C_3$-$C_7$ cycloalkyl, and each $R^6$ is independently halo;
each $R^7$ is independently $C_3$-$C_7$ cycloalkyl and each $R^6$ is independently halo;
each $R^7$ is independently $C_1$-$C_6$ alkyl, and each $R^6$ is independently $C_1$-$C_6$ alkoxy optionally substituted with one or more halo;
each $R^7$ is independently $C_1$-$C_6$ alkyl, and each $R^6$ is independently $C_1$-$C_6$ alkoxy;
each $R^7$ is independently $C_1$-$C_6$ alkyl, and each $R^6$ is independently $C_1$-$C_6$ alkoxy substituted with one or more halo;
each $R^7$ is independently halo, and each $R^6$ is independently $C_1$-$C_6$ haloalkyl;
each $R^7$ is independently halo, and each $R^6$ is independently $C_1$-$C_6$ haloalkoxy;
each $R^7$ is independently $C_1$-$C_6$ alkoxy; and each $R^6$ is independently halo;
each $R^7$ is independently $C_1$-$C_6$ alkoxy; and $R^6$ is chloro;
two pairs, each of one $R^6$ and one $R^7$, are on adjacent atoms, and each pair of one $R^6$ and one $R^7$ taken together with the atoms connecting them form a $C_4$-$C_5$ aliphatic carbocyclic ring;
two pairs, each of one $R^6$ and one $R^7$, are on adjacent atoms, and each pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl;
two pairs, each of one $R^6$ and one $R^7$, are on adjacent atoms, and one pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl, and the other pair of one $R^6$ and one $R^7$ taken together with the atoms connecting them form a 5-to-6-membered heterocyclic ring containing 1 heteroatom independently selected from O, N, and S, wherein the heterocyclic ring is optionally substituted with one or more hydroxy, oxo, or $C_1$-$C_6$ alkyl;

or two pairs, each of one $R^6$ and one $R^7$, are on adjacent atoms, and each pair of one $R^6$ and one $R^7$ taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

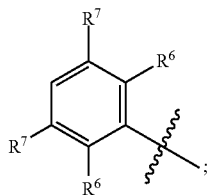

and $R^6$ and $R^7$ are one of the following combinations:
each $R^6$ is isopropyl; and each $R^7$ is methyl;
each $R^6$ is isopropyl; and each $R^7$ is isopropyl;
each $R^6$ is isopropyl; and each $R^7$ is trifluoromethyl;
each $R^6$ is isopropyl; and each $R^7$ is cyclopropyl;
each $R^6$ is isopropyl; and each $R^7$ is chloro;
each $R^6$ is isopropyl; and each $R^7$ is fluoro;
each $R^6$ is ethyl; and each $R^7$ is fluoro;
each $R^6$ is isopropyl; and each $R^7$ is cyano;
each $R^6$ is cyclopropyl; and each $R^7$ is cyclopropyl;
each $R^6$ is cyclopropyl; and each $R^7$ is chloro;
each $R^6$ is cyclopropyl; and each $R^7$ is fluoro;
each $R^6$ is isopropyl; and each $R^7$ is methoxy;
each $R^6$ is isopropyl; and each $R^7$ is trifluoromethoxy;
each $R^6$ is chloro; and each $R^7$ is trifluoromethyl;
each $R^6$ is chloro; and each $R^7$ is trifluoromethoxy;
each $R^7$ is isopropyl; and each $R^6$ is methyl;
each $R^7$ is isopropyl; and each $R^6$ is trifluoromethyl;
each $R^7$ is isopropyl; and each $R^6$ is cyclopropyl;
each $R^7$ is isopropyl; and each $R^6$ is chloro;
each $R^7$ is ethyl; and each $R^6$ is fluoro;
each $R^7$ is isopropyl; and each $R^6$ is cyano;
each $R^7$ is cyclopropyl; and each $R^6$ is cyclopropyl;
each $R^7$ is cyclopropyl; and each $R^6$ is chloro;
each $R^7$ is cyclopropyl; and each $R^6$ is fluoro;
each $R^7$ is isopropyl; and each $R^6$ is methoxy;
each $R^7$ is isopropyl; and each $R^6$ is trifluoromethoxy;
each $R^7$ is chloro; and each $R^6$ is trifluoromethyl;
each $R^7$ is chloro; and each $R^6$ is trifluoromethoxy;
one $R^6$ is isopropyl; the other $R^6$ is trifluoromethyl; and each $R^7$ is chloro;
each $R^6$ is isopropyl; one $R^7$ is fluoro; and the other $R^7$ is cyano;
two pairs, each of one $R^6$ and one $R^7$, are on adjacent atoms, and each pair of one $R^6$ and one $R^7$ taken together with the atoms connecting them form a $C_5$ aliphatic carbocyclic ring;
two pairs, each of one $R^6$ and one $R^7$, are on adjacent atoms, and each pair of one $R^6$ and one $R^7$ taken together with the atoms connecting them form a $C_4$ aliphatic carbocyclic ring optionally substituted with one or more hydroxy, oxo, or methyl;
two pairs, each of one $R^6$ and one $R^7$, are on adjacent atoms, and each pair of one $R^6$ and one $R^7$ taken together with the atoms connecting them form a $C_5$ aliphatic carbocyclic ring optionally substituted with one or more hydroxy, oxo, or methyl;
two pairs, each of one $R^6$ and one $R^7$, are on adjacent atoms, and each pair of one $R^6$ and one $R^7$ taken together with the atoms connecting them form a $C_6$ aliphatic carbocyclic ring optionally substituted with one or more hydroxy, oxo, or methyl;
two pairs, each of one $R^6$ and one $R^7$, are on adjacent atoms, and each pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl;
two pairs, each of one $R^6$ and one $R^7$, are on adjacent atoms, and each pair of one $R^6$ and one $R^7$ taken together with the atoms connecting them form a 6-membered heterocyclic ring containing 1 heteroatom independently selected from O, N, and S, wherein the heterocyclic ring is optionally substituted with one or more hydroxy, oxo, or methyl; or
two pairs, each of one $R^6$ and one $R^7$, are on adjacent atoms, one pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl, and the other pair of one $R^6$ and one $R^7$ taken together with the atoms connecting them form a $C_5$ aliphatic carbocyclic ring optionally substituted with one or more hydroxy, oxo, or methyl.

In some embodiments, of the compound of formula AA, the substituted ring B is

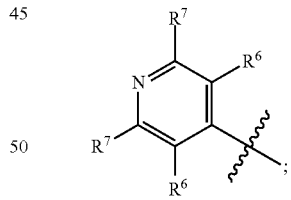

and $R^6$ and $R^7$ are one of the following combinations:
each $R^6$ is independently $C_1$-$C_6$ alkyl, and each $R^7$ is independently $C_1$-$C_6$ alkyl optionally substituted with one or more halo;
each $R^6$ is independently $C_1$-$C_6$ alkyl and each $R^7$ is independently $C_1$-$C_6$ alkyl;
each $R^6$ is independently $C_1$-$C_6$ alkyl, and each $R^7$ is independently $C_1$-$C_6$ alkyl substituted with one or more halo;
each $R^6$ is independently $C_1$-$C_6$ alkyl and $R^7$ is independently $C_3$-$C_7$ cycloalkyl;
each $R^6$ is independently $C_1$-$C_6$ alkyl and each $R^7$ is independently halo;
each $R^6$ is independently $C_1$-$C_6$ alkyl, and $R^7$ is cyano;

each $R^6$ is independently $C_3$-$C_7$ cycloalkyl, and each $R^7$ is independently $C_3$-$C_7$ cycloalkyl;
each $R^6$ is independently $C_3$-$C_7$ cycloalkyl, and each $R^7$ is independently halo;
each $R^6$ is independently cyclopropyl and each $R^7$ is independently halo;
each $R^6$ is independently $C_1$-$C_6$ alkyl, and each $R^7$ is independently $C_1$-$C_6$ alkoxy optionally substituted with one or more halo;
each $R^6$ is independently $C_1$-$C_6$ alkyl, and each $R^7$ is independently $C_1$-$C_6$ alkoxy;
each $R^6$ is independently $C_1$-$C_6$ alkyl, and each $R^7$ is independently $C_1$-$C_6$ alkoxy substituted with one or more halo;
each $R^6$ is independently halo, and each $R^7$ is independently $C_1$-$C_6$ haloalkyl;
each $R^6$ is independently halo, and each $R^7$ is independently $C_1$-$C_6$ haloalkoxy;
each $R^6$ is independently $C_1$-$C_6$ alkoxy; and each $R^7$ is independently halo;
each $R^6$ is independently $C_1$-$C_6$ alkoxy; and $R^7$ is chloro;
each $R^7$ is independently $C_1$-$C_6$ alkyl, and each $R^6$ is independently $C_1$-$C_6$ alkyl optionally substituted with one or more halo;
each $R^7$ is independently $C_1$-$C_6$ alkyl, and each $R^6$ is independently $C_1$-$C_6$ alkyl substituted with one or more halo;
each $R^7$ is independently $C_1$-$C_6$ alkyl, and each $R^6$ is independently $C_3$-$C_7$ cycloalkyl;
each $R^7$ is independently $C_1$-$C_6$ alkyl and each $R^6$ is independently halo;
each $R^7$ is independently $C_1$-$C_6$ alkyl and each $R^6$ is independently halo;
each $R^7$ is independently $C_1$-$C_6$ alkyl, and $R^6$ is cyano;
each $R^7$ is independently $C_3$-$C_7$ cycloalkyl, and each $R^6$ is independently $C_3$-$C_7$ cycloalkyl;
each $R^7$ is independently $C_3$-$C_7$ cycloalkyl, and each $R^6$ is independently halo;
each $R^7$ is independently $C_3$-$C_7$ cycloalkyl and each $R^6$ is independently halo;
each $R^7$ is independently $C_1$-$C_6$ alkyl, and each $R^6$ is independently $C_1$-$C_6$ alkoxy optionally substituted with one or more halo;
each $R^7$ is independently $C_1$-$C_6$ alkyl, and each $R^6$ is independently $C_1$-$C_6$ alkoxy;
each $R^7$ is independently $C_1$-$C_6$ alkyl, and each $R^6$ is independently $C_1$-$C_6$ alkoxy substituted with one or more halo;
each $R^7$ is independently halo, and each $R^6$ is independently $C_1$-$C_6$ haloalkyl;
each $R^7$ is independently halo, and each $R^6$ is independently $C_1$-$C_6$ haloalkoxy;
each $R^7$ is independently $C_1$-$C_6$ alkoxy; and each $R^6$ is independently halo;
each $R^7$ is independently $C_1$-$C_6$ alkoxy; and $R^6$ is chloro;
two pairs, each of one $R^6$ and one $R^7$, are on adjacent atoms, and each pair of one $R^6$ and one $R^7$ taken together with the atoms connecting them form a $C_4$-$C_5$ aliphatic carbocyclic ring;
two pairs, each of one $R^6$ and one $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; or
two pairs, each of one $R^6$ and one $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

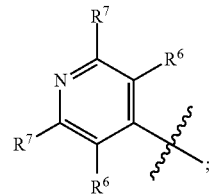

and $R^6$ and $R^7$ are one of the following combinations:
each $R^6$ is isopropyl; and each $R^7$ is methyl;
each $R^6$ is isopropyl; and each $R^7$ is isopropyl;
each $R^6$ is isopropyl; and each $R^7$ is trifluoromethyl;
each $R^6$ is isopropyl; and each $R^7$ is cyclopropyl;
each $R^6$ is isopropyl; and each $R^7$ is chloro;
each $R^6$ is isopropyl; and each $R^7$ is fluoro;
each $R^6$ is ethyl; and each $R^7$ is fluoro;
each $R^6$ is isopropyl; and each $R^7$ is cyano;
each $R^6$ is cyclopropyl; and each $R^7$ is cyclopropyl;
each $R^6$ is cyclopropyl; and each $R^7$ is chloro;
each $R^6$ is cyclopropyl; and each $R^7$ is fluoro;
each $R^6$ is isopropyl; and each $R^7$ is methoxy;
each $R^6$ is isopropyl; and each $R^7$ is trifluoromethoxy;
each $R^6$ is chloro; and each $R^7$ is trifluoromethyl;
each $R^6$ is chloro; and each $R^7$ is trifluoromethoxy;
each $R^7$ is isopropyl; and each $R^6$ is methyl;
each $R^7$ is isopropyl; and each $R^6$ is trifluoromethyl;
each $R^7$ is isopropyl; and each $R^6$ is cyclopropyl;
each $R^7$ is isopropyl; and each $R^6$ is chloro;
each $R^7$ is ethyl; and each $R^6$ is fluoro;
each $R^7$ is isopropyl; and each $R^6$ is cyano;
each $R^7$ is cyclopropyl; and each $R^6$ is cyclopropyl;
each $R^7$ is cyclopropyl; and each $R^6$ is chloro;
each $R^7$ is cyclopropyl; and each $R^6$ is fluoro;
each $R^7$ is isopropyl; and each $R^6$ is methoxy;
each $R^7$ is isopropyl; and each $R^6$ is trifluoromethoxy;
each $R^7$ is chloro; and each $R^6$ is trifluoromethyl;
each $R^7$ is chloro; and each $R^6$ is trifluoromethoxy;
one $R^6$ is isopropyl; the other $R^6$ is trifluoromethyl; and each $R^7$ is chloro;
each $R^6$ is isopropyl; one $R^7$ is fluoro; and the other $R^7$ is cyano; or
two pairs, each of one $R^6$ and one $R^7$ on adjacent atoms taken together with the atoms connecting them form a $C_4$ aliphatic carbocyclic ring optionally substituted with one or more hydroxy, oxo, or methyl;
two pairs, each of one $R^6$ and one $R^7$ on adjacent atoms taken together with the atoms connecting them form a $C_5$ aliphatic carbocyclic ring optionally substituted with one or more hydroxy, oxo, or methyl;
two pairs, each of one $R^6$ and one $R^7$ on adjacent atoms taken together with the atoms connecting them form a $C_6$ aliphatic carbocyclic ring optionally substituted with one or more hydroxy, oxo, or methyl;
two pairs, each of one $R^6$ and one $R^7$ on adjacent atoms taken together with the atoms connecting them form a 5-membered heterocyclic ring containing 1 heteroatom independently selected from O, N, and S, wherein the heterocyclic ring is optionally substituted with one or more hydroxy, oxo, or methyl;

two pairs, each of one $R^6$ and one $R^7$ on adjacent atoms taken together with the atoms connecting them form a 6-membered heterocyclic ring containing 1 heteroatom independently selected from O, N, and S, wherein the heterocyclic ring is optionally substituted with one or more hydroxy, oxo, or methyl; or two pairs, each of one $R^6$ and one $R^7$, are on adjacent atoms, and each pair of one $R^6$ and one $R^7$ taken together with the atoms connecting them form a $C_5$ aliphatic carbocyclic ring.

In some embodiments, of the compound of formula AA, the substituted ring B is

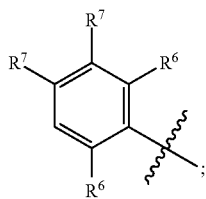

and $R^6$ and $R^7$ are one of the following combinations:
each $R^6$ is independently $C_1$-$C_6$ alkyl, and each $R^7$ is independently $C_1$-$C_6$ alkyl optionally substituted with one or more halo;
each $R^6$ is independently $C_1$-$C_6$ alkyl and each $R^7$ is independently $C_1$-$C_6$ alkyl;
each $R^6$ is independently $C_1$-$C_6$ alkyl, and each $R^7$ is independently $C_1$-$C_6$ alkyl substituted with one or more halo;
each $R^6$ is independently $C_1$-$C_6$ alkyl, and each $R^7$ is independently $C_3$-$C_7$ cycloalkyl;
each $R^6$ is independently $C_1$-$C_6$ alkyl, and each $R^7$ is independently halo;
each $R^6$ is independently $C_1$-$C_6$ alkyl, and $R^7$ is cyano;
each $R^6$ is independently $C_3$-$C_7$ cycloalkyl, and each $R^7$ is independently $C_3$-$C_7$ cycloalkyl;
each $R^6$ is independently $C_3$-$C_7$ cycloalkyl, and each $R^7$ is independently halo;
each $R^6$ is independently cyclopropyl and each $R^7$ is independently halo;
each $R^6$ is independently $C_1$-$C_6$ alkyl, and each $R^7$ is independently $C_1$-$C_6$ alkoxy optionally substituted with one or more halo;
each $R^6$ is independently $C_1$-$C_6$ alkyl, and each $R^7$ is independently $C_1$-$C_6$ alkoxy;
each $R^6$ is independently $C_1$-$C_6$ alkyl, and each $R^7$ is independently $C_1$-$C_6$ alkoxy substituted with one or more halo;
each $R^6$ is independently halo, and each $R^7$ is independently $C_1$-$C_6$ haloalkyl;
each $R^6$ is independently halo, and each $R^7$ is independently $C_1$-$C_6$ haloalkoxy;
each $R^6$ is independently $C_1$-$C_6$ alkoxy; and each $R^7$ is independently halo;
each $R^6$ is independently $C_1$-$C_6$ alkoxy; and $R^7$ is chloro;
each $R^7$ is independently $C_1$-$C_6$ alkyl, and each $R^6$ is independently $C_1$-$C_6$ alkyl optionally substituted with one or more halo;
each $R^7$ is independently $C_1$-$C_6$ alkyl, and each $R^6$ is independently $C_1$-$C_6$ alkyl substituted with one or more halo;
each $R^7$ is independently $C_1$-$C_6$ alkyl, and each $R^6$ is independently $C_3$-$C_7$ cycloalkyl;
each $R^7$ is independently $C_1$-$C_6$ alkyl, and each $R^6$ is independently halo;
each $R^7$ is independently $C_1$-$C_6$ alkyl and each $R^6$ is independently halo;
each $R^7$ is independently $C_1$-$C_6$ alkyl, and $R^6$ is cyano;
each $R^7$ is independently $C_3$-$C_7$ cycloalkyl, and each $R^6$ is independently $C_3$-$C_7$ cycloalkyl;
each $R^7$ is independently $C_3$-$C_7$ cycloalkyl, and each $R^6$ is independently halo;
each $R^7$ is independently $C_3$-$C_7$ cycloalkyl and each $R^6$ is independently halo;
each $R^7$ is independently $C_1$-$C_6$ alkyl, and each $R^6$ is independently $C_1$-$C_6$ alkoxy optionally substituted with one or more halo;
each $R^7$ is independently $C_1$-$C_6$ alkyl, and each $R^6$ is independently $C_1$-$C_6$ alkoxy;
each $R^7$ is independently $C_1$-$C_6$ alkyl, and each $R^6$ is independently $C_1$-$C_6$ alkoxy substituted with one or more halo;
each $R^7$ is independently halo, and each $R^6$ is independently $C_1$-$C_6$ haloalkyl;
each $R^7$ is independently halo, and each $R^6$ is independently $C_1$-$C_6$ haloalkoxy;
each $R^7$ is independently $C_1$-$C_6$ alkoxy; and each $R^6$ is independently halo; or
each $R^7$ is independently $C_1$-$C_6$ alkoxy; and $R^6$ is chloro.

In some embodiments of the compound of formula AA, the substituted ring B is

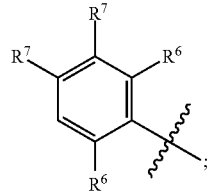

and $R^6$ and $R^7$ are one of the following combinations:
each $R^6$ is isopropyl; and each $R^7$ is methyl;
each $R^6$ is isopropyl; and each $R^7$ is isopropyl;
each $R^6$ is isopropyl; and each $R^7$ is trifluoromethyl;
each $R^6$ is isopropyl; and each $R^7$ is cyclopropyl;
each $R^6$ is isopropyl; and each $R^7$ is chloro;
each $R^6$ is isopropyl; and each $R^7$ is fluoro;
each $R^6$ is ethyl; and each $R^7$ is fluoro;
each $R^6$ is isopropyl; and each $R^7$ is cyano;
each $R^6$ is cyclopropyl; and each $R^7$ is cyclopropyl;
each $R^6$ is cyclopropyl; and each $R^7$ is chloro;
each $R^6$ is cyclopropyl; and each $R^7$ is fluoro;
each $R^6$ is isopropyl; and each $R^7$ is methoxy;
each $R^6$ is isopropyl; and each $R^7$ is trifluoromethoxy;
each $R^6$ is chloro; and each $R^7$ is trifluoromethyl;
each $R^6$ is chloro; and each $R^7$ is trifluoromethoxy;
each $R^7$ is isopropyl; and each $R^6$ is methyl;
each $R^7$ is isopropyl; and each $R^6$ is trifluoromethyl;
each $R^7$ is isopropyl; and each $R^6$ is cyclopropyl;
each $R^7$ is isopropyl; and each $R^6$ is chloro;
each $R^7$ is ethyl; and each $R^6$ is fluoro;
each $R^7$ is isopropyl; and each $R^6$ is cyano;
each $R^7$ is cyclopropyl; and each $R^6$ is cyclopropyl;
each $R^7$ is cyclopropyl; and each $R^6$ is chloro;
each $R^7$ is cyclopropyl; and each $R^6$ is fluoro;
each $R^7$ is isopropyl; and each $R^6$ is methoxy;
each $R^7$ is isopropyl; and each $R^6$ is trifluoromethoxy;
each $R^7$ is chloro; and each $R^6$ is trifluoromethyl;

each $R^7$ is chloro; and each $R^6$ is trifluoromethoxy;
one $R^6$ is isopropyl; the other $R^6$ is trifluoromethyl; and $R^7$ is chloro; or
$R^6$ is isopropyl; one $R^7$ is fluoro; and the other $R^7$ is cyano.

In some embodiments, of the compound of formula AA, the substituted ring B is

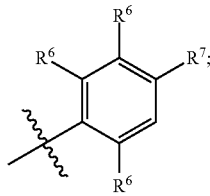

and $R^6$ and $R^7$ are one of the following combinations:
- each $R^6$ is independently $C_1$-$C_6$ alkyl, and each $R^7$ is independently $C_1$-$C_6$ alkyl optionally substituted with one or more halo;
- each $R^6$ is independently $C_1$-$C_6$ alkyl and each $R^7$ is independently $C_1$-$C_6$ alkyl;
- each $R^6$ is independently $C_1$-$C_6$ alkyl, and each $R^7$ is independently $C_1$-$C_6$ alkyl substituted with one or more halo;
- each $R^6$ is independently $C_1$-$C_6$ alkyl, and each $R^7$ is independently $C_3$-$C_7$ cycloalkyl;
- each $R^6$ is independently $C_1$-$C_6$ alkyl, and each $R^7$ is independently halo;
- each $R^6$ is independently $C_1$-$C_6$ alkyl, and each $R^7$ is cyano;
- each $R^6$ is independently $C_3$-$C_7$ cycloalkyl, and each $R^7$ is independently $C_3$-$C_7$ cycloalkyl;
- each $R^6$ is independently $C_3$-$C_7$ cycloalkyl, and each $R^7$ is independently halo;
- each $R^6$ is independently cyclopropyl and each $R^7$ is independently halo;
- each $R^6$ is independently $C_1$-$C_6$ alkyl, and each $R^7$ is independently $C_1$-$C_6$ alkoxy optionally substituted with one or more halo;
- each $R^6$ is independently $C_1$-$C_6$ alkyl, and each $R^7$ is independently $C_1$-$C_6$ alkoxy;
- each $R^6$ is independently $C_1$-$C_6$ alkyl, and each $R^7$ is independently $C_1$-$C_6$ alkoxy substituted with one or more halo;
- each $R^6$ is independently halo, and each $R^7$ is independently $C_1$-$C_6$ haloalkyl;
- each $R^6$ is independently halo, and each $R^7$ is independently $C_1$-$C_6$ haloalkoxy;
- each $R^6$ is independently $C_1$-$C_6$ alkoxy; and each $R^7$ is independently halo;
- each $R^6$ is independently $C_1$-$C_6$ alkoxy; and each $R^7$ is chloro;
- each $R^7$ is independently $C_1$-$C_6$ alkyl, and each $R^6$ is independently $C_1$-$C_6$ alkyl optionally substituted with one or more halo;
- each $R^7$ is independently $C_1$-$C_6$ alkyl, and each $R^6$ is independently $C_1$-$C_6$ alkyl substituted with one or more halo;
- each $R^7$ is independently $C_1$-$C_6$ alkyl, and each $R^6$ is independently $C_3$-$C_7$ cycloalkyl;
- each $R^7$ is independently $C_1$-$C_6$ alkyl and each $R^6$ is independently halo;
- each $R^7$ is independently $C_1$-$C_6$ alkyl, and each $R^6$ is cyano;
- each $R^7$ is independently $C_3$-$C_7$ cycloalkyl, and each $R^6$ is independently $C_3$-$C_7$ cycloalkyl;
- each $R^7$ is independently $C_3$-$C_7$ cycloalkyl, and each $R^6$ is independently halo;
- each $R^7$ is independently $C_3$-$C_7$ cycloalkyl and each $R^6$ is independently halo;
- each $R^7$ is independently $C_1$-$C_6$ alkyl, and each $R^6$ is independently $C_1$-$C_6$ alkoxy optionally substituted with one or more halo;
- each $R^7$ is independently $C_1$-$C_6$ alkyl, and each $R^6$ is independently $C_1$-$C_6$ alkoxy;
- each $R^7$ is independently $C_1$-$C_6$ alkyl, and each $R^6$ is independently $C_1$-$C_6$ alkoxy substituted with one or more halo;
- each $R^7$ is independently halo, and each $R^6$ is independently $C_1$-$C_6$ haloalkyl;
- each $R^7$ is independently halo, and each $R^6$ is independently $C_1$-$C_6$ haloalkoxy;
- each $R^7$ is independently $C_1$-$C_6$ alkoxy; and each $R^6$ is independently halo;
- each $R^7$ is independently $C_1$-$C_6$ alkoxy; and each $R^6$ is chloro;
- $R^6$ and $R^7$ on adjacent atoms taken together with the atoms connecting them form a $C_4$-$C_6$ aliphatic carbocyclic ring optionally substituted with one or more hydroxy, oxo, or $C_1$-$C_6$ alkyl; and one $R^6$ is halo or cyano; or
- $R^6$ and $R^7$ on adjacent atoms taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^6$ is halo or cyano.

In some embodiments, of the compound of formula AA, the substituted ring B is

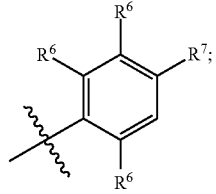

and $R^6$ and $R^7$ are one of the following combinations:
- each $R^6$ is isopropyl; and each $R^7$ is methyl;
- each $R^6$ is isopropyl; and each $R^7$ is isopropyl;
- each $R^6$ is isopropyl; and each $R^7$ is trifluoromethyl;
- each $R^6$ is isopropyl; and each $R^7$ is cyclopropyl;
- each $R^6$ is isopropyl; and each $R^7$ is chloro;
- each $R^6$ is isopropyl; and each $R^7$ is fluoro;
- each $R^6$ is ethyl; and each $R^7$ is fluoro;
- each $R^6$ is isopropyl; and each $R^7$ is cyano;
- each $R^6$ is cyclopropyl; and each $R^7$ is cyclopropyl;
- each $R^6$ is cyclopropyl; and each $R^7$ is chloro;
- each $R^6$ is cyclopropyl; and each $R^7$ is fluoro;
- each $R^6$ is isopropyl; and each $R^7$ is methoxy;
- each $R^6$ is isopropyl; and each $R^7$ is trifluoromethoxy;
- each $R^6$ is chloro; and each $R^7$ is trifluoromethyl;
- each $R^6$ is chloro; and each $R^7$ is trifluoromethoxy;
- each $R^7$ is isopropyl; and each $R^6$ is methyl;
- each $R^7$ is isopropyl; and each $R^6$ is trifluoromethyl;
- each $R^7$ is isopropyl; and each $R^6$ is cyclopropyl;

each $R^7$ is isopropyl; and each $R^6$ is chloro;
each $R^7$ is ethyl; and each $R^6$ is fluoro;
each $R^7$ is isopropyl; and each $R^6$ is cyano;
each $R^7$ is cyclopropyl; and each $R^6$ is cyclopropyl;
each $R^7$ is cyclopropyl; and each $R^6$ is chloro;
each $R^7$ is cyclopropyl; and each $R^6$ is fluoro;
each $R^7$ is isopropyl; and each $R^6$ is methoxy;
each $R^7$ is isopropyl; and each $R^6$ is trifluoromethoxy;
each $R^7$ is chloro; and each $R^6$ is trifluoromethyl;
each $R^7$ is chloro; and each $R^6$ is trifluoromethoxy;
one $R^6$ is isopropyl; the other $R^6$ is trifluoromethyl; and each $R^7$ is chloro;
each $R^6$ is isopropyl; one $R^7$ is fluoro; and the other $R^7$ is cyano;
$R^6$ and $R^7$ on adjacent atoms taken together with the atoms connecting them form a $C_4$ aliphatic carbocyclic ring; and one $R^6$ is chloro, fluoro, or cyano;
$R^6$ and $R^7$ on adjacent atoms taken together with the atoms connecting them form a $C_5$ aliphatic carbocyclic ring; and one $R^6$ is chloro, fluoro, or cyano;
$R^6$ and $R^7$ on adjacent atoms taken together with the atoms connecting them form a $C_6$ aliphatic carbocyclic ring; and one $R^6$ is chloro, fluoro, or cyano;
$R^6$ and $R^7$ on adjacent atoms taken together with the atoms connecting them form a 5-membered heterocyclic ring containing 1 heteroatoms independently selected from O, N, and S; and one $R^6$ is chloro, fluoro, or cyano;
$R^6$ and $R^7$ on adjacent atoms taken together with the atoms connecting them form a 6-membered heterocyclic ring containing 1 heteroatoms independently selected from O, N, and S; and one $R^6$ is chloro, fluoro, or cyano; or
$R^6$ and $R^7$ on adjacent atoms taken together with the atoms connecting them form a $C_5$ aliphatic carbocyclic ring; and one $R^6$ is chloro, fluoro, or cyano.

In some embodiments, of the compound of formula AA, the substituted ring B is

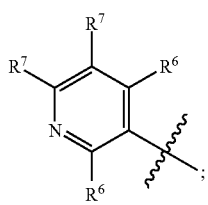

and $R^6$ and $R^7$ are one of the following combinations:
(i) each $R^6$ is independently $C_1$-$C_6$ alkyl, and each $R^7$ is independently $C_1$-$C_6$ alkyl optionally substituted with one or more halo;
(ii) each $R^6$ is independently $C_1$-$C_6$ alkyl and each $R^7$ is independently $C_1$-$C_6$ alkyl;
(iii) each $R^6$ is independently $C_1$-$C_6$ alkyl, and each $R^7$ is independently $C_1$-$C_6$ alkyl substituted with one or more halo;
(iv) each $R^6$ is independently $C_1$-$C_6$ alkyl, and each $R^7$ is independently $C_3$-$C_7$ cycloalkyl;
(v) each $R^6$ is independently $C_1$-$C_6$ alkyl, and each $R^7$ is independently halo;
(vi) each $R^6$ is independently $C_1$-$C_6$ alkyl, and $R^7$ is cyano;
(vii) each $R^6$ is independently $C_3$-$C_7$ cycloalkyl, and each $R^7$ is independently $C_3$-$C_7$ cycloalkyl;
(viii) each $R^6$ is independently $C_3$-$C_7$ cycloalkyl, and each $R^7$ is independently halo;
(ix) each $R^6$ is independently cyclopropyl and each $R^7$ is independently halo;
(x) each $R^6$ is independently $C_1$-$C_6$ alkyl, and each $R^7$ is independently $C_1$-$C_6$ alkoxy optionally substituted with one or more halo;
(xi) each $R^6$ is independently $C_1$-$C_6$ alkyl, and each $R^7$ is independently $C_1$-$C_6$ alkoxy;
(xii) each $R^6$ is independently $C_1$-$C_6$ alkyl, and each $R^7$ is independently $C_1$-$C_6$ alkoxy substituted with one or more halo;
(xiii) each $R^6$ is independently halo, and each $R^7$ is independently $C_1$-$C_6$ haloalkyl;
(xiv) each $R^6$ is independently halo, and each $R^7$ is independently $C_1$-$C_6$ haloalkoxy;
(xv) each $R^6$ is independently $C_1$-$C_6$ alkoxy; and each $R^7$ is independently halo;
(xvi) each $R^6$ is independently $C_1$-$C_6$ alkoxy; and $R^7$ is chloro;
(xvii) each $R^7$ is independently $C_1$-$C_6$ alkyl, and each $R^6$ is independently $C_1$-$C_6$ alkyl optionally substituted with one or more halo;
(xviii) each $R^7$ is independently $C_1$-$C_6$ alkyl, and each $R^6$ is independently $C_1$-$C_6$ alkyl substituted with one or more halo;
(xix) each $R^7$ is independently $C_1$-$C_6$ alkyl, and each $R^6$ is independently $C_3$-$C_7$ cycloalkyl;
(xx) each $R^7$ is independently $C_1$-$C_6$ alkyl, and each $R^6$ is independently halo;
(xxi) each $R^7$ is independently $C_1$-$C_6$ alkyl and each $R^6$ is independently halo;
(xxii) each $R^7$ is independently $C_1$-$C_6$ alkyl, and $R^6$ is cyano;
(xxiii) each $R^7$ is independently $C_3$-$C_7$ cycloalkyl, and each $R^6$ is independently $C_3$-$C_7$ cycloalkyl;
(xxiv) each $R^7$ is independently $C_3$-$C_7$ cycloalkyl, and each $R^6$ is independently halo;
(xxv) each $R^7$ is independently $C_3$-$C_7$ cycloalkyl and each $R^6$ is independently halo;
(xxvi) each $R^7$ is independently $C_1$-$C_6$ alkyl, and each $R^6$ is independently $C_1$-$C_6$ alkoxy optionally substituted with one or more halo;
(xxvii) each $R^7$ is independently $C_1$-$C_6$ alkyl, and each $R^6$ is independently $C_1$-$C_6$ alkoxy;
(xxviii) each $R^7$ is independently $C_1$-$C_6$ alkyl, and each $R^6$ is independently $C_1$-$C_6$ alkoxy substituted with one or more halo;
(xxix) each $R^7$ is independently halo, and each $R^6$ is independently $C_1$-$C_6$ haloalkyl;
(xxx) each $R^7$ is independently halo, and each $R^6$ is independently $C_1$-$C_6$ haloalkoxy;
(xxxi) each $R^7$ is independently $C_1$-$C_6$ alkoxy; and each $R^6$ is independently halo; or
(xxxii) each $R^7$ is independently $C_1$-$C_6$ alkoxy; and $R^6$ is chloro.

In some embodiments, of the compound of formula AA, the substituted ring B is

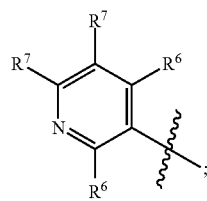

and $R^6$ and $R^7$ are one of the following combinations:
(i) each $R^6$ is isopropyl; and each $R^7$ is methyl;
(ii) each $R^6$ is isopropyl; and each $R^7$ is isopropyl;
(iii) each $R^6$ is isopropyl; and each $R^7$ is trifluoromethyl;
(iv) each $R^6$ is isopropyl; and each $R^7$ is cyclopropyl;
(v) each $R^6$ is isopropyl; and each $R^7$ is chloro;
(vi) each $R^6$ is isopropyl; and each $R^7$ is fluoro;
(vii) each $R^6$ is ethyl; and each $R^7$ is fluoro;
(viii) each $R^6$ is isopropyl; and each $R^7$ is cyano;
(ix) each $R^6$ is cyclopropyl; and each $R^7$ is cyclopropyl;
(x) each $R^6$ is cyclopropyl; and each $R^7$ is chloro;
(xi) each $R^6$ is cyclopropyl; and each $R^7$ is fluoro;
(xii) each $R^6$ is isopropyl; and each $R^7$ is methoxy;
(xiii) each $R^6$ is isopropyl; and each $R^7$ is trifluoromethoxy;
(xiv) each $R^6$ is chloro; and each $R^7$ is trifluoromethyl;
(xv) each $R^6$ is chloro; and each $R^7$ is trifluoromethoxy;
(xvi) each $R^7$ is isopropyl; and each $R^6$ is methyl;
(xvii) each $R^7$ is isopropyl; and each $R^6$ is trifluoromethyl;
(xviii) each $R^7$ is isopropyl; and each $R^6$ is cyclopropyl;
(xix) each $R^7$ is isopropyl; and each $R^6$ is chloro;
(xx) each $R^7$ is ethyl; and each $R^6$ is fluoro;
(xxi) each $R^7$ is isopropyl; and each $R^6$ is cyano;
(xxii) each $R^7$ is cyclopropyl; and each $R^6$ is cyclopropyl;
(xxiii) each $R^7$ is cyclopropyl; and each $R^6$ is chloro;
(xxiv) each $R^7$ is cyclopropyl; and each $R^6$ is fluoro;
(xxv) each $R^7$ is isopropyl; and each $R^6$ is methoxy;
(xxvi) each $R^7$ is isopropyl; and each $R^6$ is trifluoromethoxy;
(xxvii) each $R^7$ is chloro; and each $R^6$ is trifluoromethyl;
(xxviii) each $R^7$ is chloro; and each $R^6$ is trifluoromethoxy;
(xxix) one $R^6$ is isopropyl; the other $R^6$ is trifluoromethyl; and each $R^7$ is chloro; or
(xxx) each $R^6$ is isopropyl; one $R^7$ is fluoro; and the other $R^7$ is cyano.

In some embodiments, of the compound of formula AA, the substituted ring B is

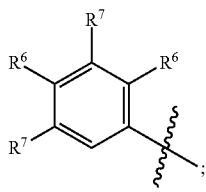

and $R^6$ and $R^7$ are one of the following combinations:
(i) each $R^6$ is independently $C_1$-$C_6$ alkyl, and each $R^7$ is independently $C_1$-$C_6$ alkyl optionally substituted with one or more halo;
(ii) each $R^6$ is independently $C_1$-$C_6$ alkyl and each $R^7$ is independently $C_1$-$C_6$ alkyl;
(iii) each $R^6$ is independently $C_1$-$C_6$ alkyl, and each $R^7$ is independently $C_1$-$C_6$ alkyl substituted with one or more halo;
(iv) each $R^6$ is independently $C_1$-$C_6$ alkyl, and each $R^7$ is independently $C_3$-$C_7$ cycloalkyl;
(v) each $R^6$ is independently $C_1$-$C_6$ alkyl, and each $R^7$ is independently halo;
(vi) each $R^6$ is independently $C_1$-$C_6$ alkyl, and $R^7$ is cyano;
(vii) each $R^6$ is independently $C_3$-$C_7$ cycloalkyl, and each $R^7$ is independently $C_3$-$C_7$ cycloalkyl;
(viii) each $R^6$ is independently $C_3$-$C_7$ cycloalkyl, and each $R^7$ is independently halo;
(ix) each $R^6$ is independently cyclopropyl and each $R^7$ is independently halo;
(x) each $R^6$ is independently $C_1$-$C_6$ alkyl, and each $R^7$ is independently $C_1$-$C_6$ alkoxy optionally substituted with one or more halo;
(xi) each $R^6$ is independently $C_1$-$C_6$ alkyl, and each $R^7$ is independently $C_1$-$C_6$ alkoxy; (xii) each $R^6$ is independently $C_1$-$C_6$ alkyl, and each $R^7$ is independently $C_1$-$C_6$ alkoxy substituted with one or more halo;
(xiii) each $R^6$ is independently halo, and each $R^7$ is independently $C_1$-$C_6$ haloalkyl; (xiv) each $R^6$ is independently halo, and each $R^7$ is independently $C_1$-$C_6$ haloalkoxy; (xv) each $R^6$ is independently $C_1$-$C_6$ alkoxy; and each $R^7$ is independently halo;
(xvi) each $R^6$ is independently $C_1$-$C_6$ alkoxy; and $R^7$ is chloro;
(xvii) each $R^7$ is independently $C_1$-$C_6$ alkyl, and each $R^6$ is independently $C_1$-$C_6$ alkyl optionally substituted with one or more halo;
(xviii) each $R^7$ is independently $C_1$-$C_6$ alkyl, and each $R^6$ is independently $C_1$-$C_6$ alkyl substituted with one or more halo;
(xix) each $R^7$ is independently $C_1$-$C_6$ alkyl, and each $R^6$ is independently $C_3$-$C_7$ cycloalkyl;
(xx) each $R^7$ is independently $C_1$-$C_6$ alkyl, and each $R^6$ is independently halo;
(xxi) each $R^7$ is independently $C_1$-$C_6$ alkyl and each $R^6$ is independently halo;
(xxii) each $R^7$ is independently $C_1$-$C_6$ alkyl, and $R^6$ is cyano;
(xxiii) each $R^7$ is independently $C_3$-$C_7$ cycloalkyl, and each $R^6$ is independently $C_3$-$C_7$ cycloalkyl;
(xxiv) each $R^7$ is independently $C_3$-$C_7$ cycloalkyl, and each $R^6$ is independently halo;
(xxv) each $R^7$ is independently $C_3$-$C_7$ cycloalkyl and each $R^6$ is independently halo;
(xxvi) each $R^7$ is independently $C_1$-$C_6$ alkyl, and each $R^6$ is independently $C_1$-$C_6$ alkoxy optionally substituted with one or more halo;
(xxvii) each $R^7$ is independently $C_1$-$C_6$ alkyl, and each $R^6$ is independently $C_1$-$C_6$ alkoxy;
(xxviii) each $R^7$ is independently $C_1$-$C_6$ alkyl, and each $R^6$ is independently $C_1$-$C_6$ alkoxy substituted with one or more halo;
(xxix) each $R^7$ is independently halo, and each $R^6$ is independently $C_1$-$C_6$ haloalkyl;
(xxx) each $R^7$ is independently halo, and each $R^6$ is independently $C_1$-$C_6$ haloalkoxy;
(xxxi) each $R^7$ is independently $C_1$-$C_6$ alkoxy; and each $R^6$ is independently halo;
(i) each $R^7$ is independently $C_1$-$C_6$ alkoxy; and $R^6$ is chloro;
(ii) two pairs, each of one $R^6$ and one $R^7$, are on adjacent atoms, and each pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl;
(xxxii) two pairs, each of one $R^6$ and one $R^7$, are on adjacent atoms, and each pair of one $R^6$ and one $R^7$ taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl; or (xxxiii) two pairs, each of one $R^6$ and one $R^7$, are on adjacent atoms, one pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl, and the other pair of one $R^6$ and one $R^7$ taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl.

In some embodiments, of the compound of formula AA, the substituted ring B is

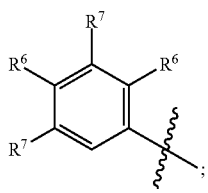

and $R^6$ and $R^7$ are one of the following combinations:
(i) each $R^6$ is isopropyl; and each $R^7$ is methyl;
(ii) each $R^6$ is isopropyl; and each $R^7$ is isopropyl;
(iii) each $R^6$ is isopropyl; and each $R^7$ is trifluoromethyl;
(iv) each $R^6$ is isopropyl; and each $R^7$ is cyclopropyl;
(v) each $R^6$ is isopropyl; and each $R^7$ is chloro;
(vi) each $R^6$ is isopropyl; and each $R^7$ is fluoro;
(vii) each $R^6$ is ethyl; and each $R^7$ is fluoro;
(viii) each $R^6$ is isopropyl; and each $R^7$ is cyano;
(ix) each $R^6$ is cyclopropyl; and each $R^7$ is cyclopropyl;
(x) each $R^6$ is cyclopropyl; and each $R^7$ is chloro;
(xi) each $R^6$ is cyclopropyl; and each $R^7$ is fluoro;
(xii) each $R^6$ is isopropyl; and each $R^7$ is methoxy;
(xiii) each $R^6$ is isopropyl; and each $R^7$ is trifluoromethoxy;
(xiv) each $R^6$ is chloro; and each $R^7$ is trifluoromethyl;
(xv) each $R^6$ is chloro; and each $R^7$ is trifluoromethoxy;
(xvi) each $R^7$ is isopropyl; and each $R^6$ is methyl;
(xvii) each $R^7$ is isopropyl; and each $R^6$ is trifluoromethyl;
(xviii) each $R^7$ is isopropyl; and each $R^6$ is cyclopropyl;
(xix) each $R^7$ is isopropyl; and each $R^6$ is chloro;
(xx) each $R^7$ is ethyl; and each $R^6$ is fluoro;
(xxi) each $R^7$ is isopropyl; and each $R^6$ is cyano;
(xxii) each $R^7$ is cyclopropyl; and each $R^6$ is cyclopropyl;
(xxiii) each $R^7$ is cyclopropyl; and each $R^6$ is chloro;
(xxiv) each $R^7$ is cyclopropyl; and each $R^6$ is fluoro;
(xxv) each $R^7$ is isopropyl; and each $R^6$ is methoxy;
(xxvi) each $R^7$ is isopropyl; and each $R^6$ is trifluoromethoxy;
(xxvii) $R^7$ is chloro; and each $R^6$ is trifluoromethyl;
(xxviii) $R^7$ is chloro; and each $R^6$ is trifluoromethoxy;
(xxix) one $R^6$ is isopropyl; the other $R^6$ is trifluoromethyl; and $R^7$ is chloro;
(xxx) $R^6$ is isopropyl; one $R^7$ is fluoro; and the other $R^7$ is cyano; two pairs, each of one $R^6$ and one $R^7$, are on adjacent atoms, and each pair of one $R^6$ and one $R^7$ taken together with the atoms connecting them form a $C_5$ aliphatic carbocyclic ring;
(xxxi) two pairs, each of one $R^6$ and one $R^7$, are on adjacent atoms, and each pair of one $R^6$ and one $R^7$ taken together with the atoms connecting them form a $C_4$ aliphatic carbocyclic ring optionally substituted with one or more hydroxy, oxo, or methyl;
(xxxii) two pairs, each of one $R^6$ and one $R^7$, are on adjacent atoms, and each pair of one $R^6$ and one $R^7$ taken together with the atoms connecting them form a $C_5$ aliphatic carbocyclic ring optionally substituted with one or more hydroxy, oxo, or methyl;
(xxxiii) two pairs, each of one $R^6$ and one $R^7$, are on adjacent atoms, and each pair of one $R^6$ and one $R^7$ taken together with the atoms connecting them form a $C_6$ aliphatic carbocyclic ring optionally substituted with one or more hydroxy, oxo, or methyl;
(xxxiv) two pairs, each of one $R^6$ and one $R^7$, are on adjacent atoms, and each pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl
(xxxv) two pairs, each of one $R^6$ and one $R^7$, are on adjacent atoms, and each pair of one $R^6$ and one $R^7$ taken together with the atoms connecting them form a 6-membered heterocyclic ring containing 1 heteroatom independently selected from O, N, and S, wherein the heterocyclic ring is optionally substituted with one or more hydroxy, oxo, or methyl; or
(xxxvi) two pairs, each of one $R^6$ and one $R^7$, are on adjacent atoms, one pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl, and the other pair of one $R^6$ and one $R^7$ taken together with the atoms connecting them form a $C_5$ aliphatic carbocyclic ring optionally substituted with one or more hydroxy, oxo, or methyl.

In some embodiments, of the compound of formula AA, the substituted ring B is

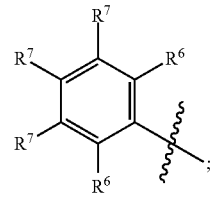

and $R^6$ and $R^7$ are one of the following combinations:
(i) each $R^6$ is independently $C_1$-$C_6$ alkyl, and $R^7$ is $C_1$-$C_6$ alkyl optionally substituted with one or more halo;
(ii) each $R^6$ is independently $C_1$-$C_6$ alkyl and $R^7$ is $C_1$-$C_6$ alkyl;
(iii) each $R^6$ is independently $C_1$-$C_6$ alkyl, and $R^7$ is $C_1$-$C_6$ alkyl substituted with one or more halo;
(iv) each $R^6$ is independently $C_1$-$C_6$ alkyl, and $R^7$ is $C_3$-$C_7$ cycloalkyl;
(v) each $R^6$ is independently $C_1$-$C_6$ alkyl, and $R^7$ is halo;
(vi) each $R^6$ is independently $C_1$-$C_6$ alkyl, and $R^7$ is cyano;
(vii) each $R^6$ is independently $C_3$-$C_7$ cycloalkyl, and $R^7$ is $C_3$-$C_7$ cycloalkyl;
(viii) each $R^6$ is independently $C_3$-$C_7$ cycloalkyl, and $R^7$ is halo;
(ix) each $R^6$ is independently cyclopropyl and $R^7$ is halo;
(x) each $R^6$ is independently $C_1$-$C_6$ alkyl, and $R^7$ is $C_1$-$C_6$ alkoxy optionally substituted with one or more halo;

(xi) each $R^6$ is independently $C_1$-$C_6$ alkyl, and $R^7$ is $C_1$-$C_6$ alkoxy;
(xii) each $R^6$ is independently $C_1$-$C_6$ alkyl, and $R^7$ is $C_1$-$C_6$ alkoxy substituted with one or more halo;
(xiii) each $R^6$ is independently halo, and $R^7$ is $C_1$-$C_6$ haloalkyl;
(xiv) each $R^6$ is independently halo, and $R^7$ is $C_1$-$C_6$ haloalkoxy;
(xv) each $R^6$ is independently $C_1$-$C_6$ alkoxy; and $R^7$ is halo;
(xvi) each $R^6$ is independently $C_1$-$C_6$ alkoxy; and $R^7$ is chloro;
(xvii) $R^7$ is $C_1$-$C_6$ alkyl, and each $R^6$ is independently $C_1$-$C_6$ alkyl optionally substituted with one or more halo;
(xviii) $R^7$ is $C_1$-$C_6$ alkyl, and each $R^6$ is independently $C_1$-$C_6$ alkyl substituted with one or more halo;
(xix) $R^7$ is $C_1$-$C_6$ alkyl, and each $R^6$ is independently $C_3$-$C_7$ cycloalkyl;
(xx) $R^7$ is $C_1$-$C_6$ alkyl, and each $R^6$ is independently halo;
(xxi) $R^7$ is $C_1$-$C_6$ alkyl and each $R^6$ is independently halo;
(xxii) $R^7$ is $C_1$-$C_6$ alkyl, and $R^6$ is cyano;
(xxiii) $R^7$ is $C_3$-$C_7$ cycloalkyl, and each $R^6$ is independently $C_3$-$C_7$ cycloalkyl;
(xxiv) $R^7$ is $C_3$-$C_7$ cycloalkyl, and each $R^6$ is independently halo;
(xxv) $R^7$ is $C_3$-$C_7$ cycloalkyl and each $R^6$ is independently halo;
(xxvi) $R^7$ is $C_1$-$C_6$ alkyl, and each $R^6$ is independently $C_1$-$C_6$ alkoxy optionally substituted with one or more halo;
(xxvii) $R^7$ is $C_1$-$C_6$ alkyl, and each $R^6$ is independently $C_1$-$C_6$ alkoxy;
(xxviii) $R^7$ is $C_1$-$C_6$ alkyl, and each $R^6$ is independently $C_1$-$C_6$ alkoxy substituted with one or more halo;
(xxix) $R^7$ is halo, and each $R^6$ is independently $C_1$-$C_6$ haloalkyl;
(xxx) $R^7$ is halo, and each $R^6$ is independently $C_1$-$C_6$ haloalkoxy;
(xxxi) $R^7$ is $C_1$-$C_6$ alkoxy; and each $R^6$ is independently halo;
(xxxii) $R^7$ is $C_1$-$C_6$ alkoxy; and $R^6$ is chloro;
(xxxiii) two pairs, each of one $R^6$ and one $R^7$, are on adjacent atoms, and each pair of one $R^6$ and one $R^7$ taken together with the atoms connecting them form a $C_4$-$C_5$ aliphatic carbocyclic ring; and one $R^7$ is halo;
(xxxiv) two pairs, each of one $R^6$ and one $R^7$, are on adjacent atoms, and each pair of one $R^6$ and one $R^7$ taken together with the atoms connecting them form a $C_4$-$C_5$ aliphatic carbocyclic ring; and one $R^7$ is cyano;
(xxxv) two pairs, each of one $R^6$ and one $R^7$, are on adjacent atoms, and each pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl; and one $R^7$ is halo or cyano;
(xxxvi) two pairs, each of one $R^6$ and one $R^7$, are on adjacent atoms, and each pair of one $R^6$ and one $R^7$ taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^7$ is halo or cyano; or
(xxxvii) two pairs, each of one $R^6$ and one $R^7$, are on adjacent atoms, one pair of one $R^6$ and one $R^7$ taken together with the atoms connecting them form a $C_4$-$C_6$ aliphatic carbocyclic ring optionally substituted with one or more hydroxy, oxo, or $C_1$-$C_6$ alkyl, and the other pair of one $R^6$ and one $R^7$ taken together with the atoms connecting them form a 5-to-6-membered heterocyclic ring containing 1 heteroatom independently selected from O, N, and S, wherein the heterocyclic ring optionally substituted with one or more hydroxy, oxo, or $C_1$-$C_6$ alkyl; and one $R^7$ is halo or cyano.

In some embodiments, of the compound of formula AA, the substituted ring B is

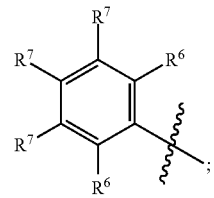

and $R^6$ and $R^7$ are one of the following combinations:
(i) each $R^6$ is isopropyl; and each $R^7$ is methyl;
(ii) each $R^6$ is isopropyl; and each $R^7$ is isopropyl;
(iii) each $R^6$ is isopropyl; and each $R^7$ is trifluoromethyl;
(iv) each $R^6$ is isopropyl; and each $R^7$ is cyclopropyl;
(v) each $R^6$ is isopropyl; and each $R^7$ is chloro;
(vi) each $R^6$ is isopropyl; and each $R^7$ is fluoro;
(vii) each $R^6$ is ethyl; and each $R^7$ is fluoro;
(viii) each $R^6$ is isopropyl; and each $R^7$ is cyano;
(ix) each $R^6$ is cyclopropyl; and each $R^7$ is cyclopropyl;
(x) each $R^6$ is cyclopropyl; and each $R^7$ is chloro;
(xi) each $R^6$ is cyclopropyl; and each $R^7$ is fluoro;
(xii) each $R^6$ is isopropyl; and each $R^7$ is methoxy;
(xiii) each $R^6$ is isopropyl; and each $R^7$ is trifluoromethoxy;
(xiv) each $R^6$ is chloro; and each $R^7$ is trifluoromethyl;
(xv) each $R^6$ is chloro; and each $R^7$ is trifluoromethoxy;
(xvi) each $R^7$ is isopropyl; and each $R^6$ is methyl;
(xvii) each $R^7$ is isopropyl; and each $R^6$ is trifluoromethyl;
(xviii) each $R^7$ is isopropyl; and each $R^6$ is cyclopropyl;
(xix) each $R^7$ is isopropyl; and each $R^6$ is chloro;
(xx) each $R^7$ is ethyl; and each $R^6$ is fluoro;
(xxi) each $R^7$ is isopropyl; and each $R^6$ is cyano;
(xxii) each $R^7$ is cyclopropyl; and each $R^6$ is cyclopropyl;
(xxiii) each $R^7$ is cyclopropyl; and each $R^6$ is chloro;
(xxiv) each $R^7$ is cyclopropyl; and each $R^6$ is fluoro;
(xxv) each $R^7$ is isopropyl; and each $R^6$ is methoxy;
(xxvi) each $R^7$ is isopropyl; and each $R^6$ is trifluoromethoxy;
(xxvii) each $R^7$ is chloro; and each $R^6$ is trifluoromethyl;
(xxviii) each $R^7$ is chloro; and each $R^6$ is trifluoromethoxy;
(xxix) each $R^6$ is isopropyl; two $R^7$ are fluoro; and one $R^7$ is chloro;
(xxx) two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is chloro;
(xxxi) two pairs, each of one $R^6$ and one $R^7$, are on adjacent atoms, and each pair of one $R^6$ and one $R^7$ taken together with the atoms connecting them form a $C_5$ aliphatic carbocyclic ring; and one $R^7$ is fluoro;
(xxxii) two pairs, each of one $R^6$ and one $R^7$, are on adjacent atoms, and each pair of one $R^6$ and one $R^7$ taken together with the atoms connecting them form a $C_4$ aliphatic carbocyclic ring optionally substituted with one or more hydroxy, oxo, or methyl; and one $R^7$ is fluoro or chloro;

(xxxiii) two pairs, each of one $R^6$ and one $R^7$, are on adjacent atoms, and each pair of one $R^6$ and one $R^7$ taken together with the atoms connecting them form a $C_5$ aliphatic carbocyclic ring optionally substituted with one or more hydroxy, oxo, or methyl; and one $R^7$ is fluoro or chloro;

(xxxiv) two pairs, each of one $R^6$ and one $R^7$, are on adjacent atoms, and each pair of one $R^6$ and one $R^7$ taken together with the atoms connecting them form a $C_6$ aliphatic carbocyclic ring optionally substituted with one or more hydroxy, oxo, or methyl; and one $R^7$ is fluoro or chloro;

(xxxv) two pairs, each of one $R^6$ and one $R^7$, are on adjacent atoms, and each pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl; and one $R^7$ is fluoro or chloro;

(xxxvi) two pairs, each of one $R^6$ and one $R^7$, are on adjacent atoms, and each pair of one $R^6$ and one $R^7$ taken together with the atoms connecting them form a 6-membered heterocyclic ring containing 1 heteroatom independently selected from O, N, and S, wherein the heterocyclic ring is optionally substituted with one or more hydroxy, oxo, or methyl; and one $R^7$ is fluoro or chloro; or (xxxvii) two pairs, each of one $R^6$ and one $R^7$, are on adjacent atoms, one pair of one $R^6$ and one $R^7$ taken together with the atoms connecting them form a 5-membered heterocyclic ring containing 1 heteroatom independently selected from O, N, and S, wherein the heterocyclic ring is optionally substituted with one or more hydroxy, oxo, or methyl, and the other pair of one $R^6$ and one $R^7$ taken together with the atoms connecting them form a $C_5$ aliphatic carbocyclic ring optionally substituted with one or more hydroxy, oxo, or methyl; and one $R^7$ is fluoro or chloro.

Non-Limiting Combinations

In some embodiments of the compound of Formula AA the compound has Formula AA-1:

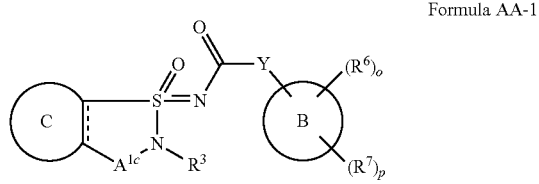

Formula AA-1 wherein:
$A^{1c}$ is C(O) or $CH_2$ (e.g., C(O));
ring C is selected from the group consisting of:
(a) $C_{6-10}$ aryl optionally substituted with from 1-5 independently selected $R^a$; and
(b) heteroaryl including from 5-10 ring atoms, wherein from 1-4 ring atoms are each independently selected from the group consisting of N, $N(R^N)$, O, and S, wherein the heteroaryl is optionally substituted with from 1-3 independently selected $R^a$; and
$R^3$, ring B, Y, $R^6$, $R^7$, o, and p are as defined herein.

In some embodiments of Formula AA-1, $A^{1c}$ is C(O).

In some embodiments of Formula AA-1, ring C is $C_6$ aryl optionally substituted with from 1-2 independently selected $R^a$.

In certain of these embodiments, ring C is $C_6$ aryl which is unsubstituted.

In certain other of these embodiments, ring C is $C_6$ aryl substituted with from 1-2 (e.g., 1) independently selected $R^a$.

In certain embodiments of Formula AA-1, each occurrence of $R^a$ is independently selected from the group consisting of: hydroxy, halo, $C_1$-$C_6$ alkyl, $C_2$-$C_6$ alkenyl, $C_1$-$C_6$ alkoxy, $OC_3$-$C_{10}$ cycloalkyl, $NR^8R^9$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, $OC_6$-$C_{10}$ aryl, 5- to 10-membered heteroaryl, $C_3$-$C_{10}$ cycloalkyl, 3- to 10-membered heterocycloalkyl, $CO_2H$, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents each independently selected from hydroxy, halo, $C_1$-$C_6$ alkyl, $C_{1-4}$ haloalkyl, $C_3$-$C_{10}$ cycloalkyl, 3- to 10-membered heterocycloalkyl, $C_1$-$C_6$ alkoxy, oxo, $NR^8R^9$, $COOC_1$-$C_6$ alkyl, $C_6$-$C_{10}$ aryl, $CO_2H$, and $CONR^8R^9$.

In certain of these embodiments, one or more occurrences of $R^a$ is $C_1$-$C_6$ alkyl which is optionally substituted with one or more substituents each independently selected from hydroxy, halo, $C_3$-$C_{10}$ cycloalkyl, 3- to 10-membered heterocycloalkyl, $C_1$-$C_6$ alkoxy, oxo, $NR^8R^9$, $COOC_1$-$C_6$ alkyl, $C_6$-$C_{10}$ aryl, $CO_2H$, and $CONR^8R^9$.

In certain of these embodiments, one or more occurrences of $R^a$ is $C_1$-$C_6$ alkyl which is optionally substituted with one or more substituents each independently selected from halo, hydroxy and $NR^8R^9$.

In certain embodiments, one or more occurrences of $R^a$ is $OC_6$-$C_{10}$ aryl, $C_2$-$C_6$ alkenyl, 3- to 10-membered heterocycloalkyl, $C_6$-$C_{10}$ aryl, or 5- to 10-membered heteroaryl, each of which is optionally substituted as defined herein.

In certain embodiments, one or more occurrences of $R^a$ is CN, halo, $CO_2H$, $CONR^8R^9$, or $COOC_1$-$C_6$ alkyl.

In some embodiments of the compound of Formula AA, the compound has Formula AA-2:

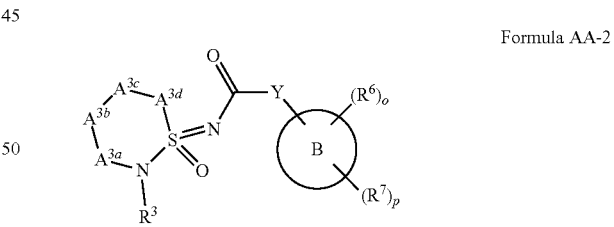

Formula AA-2 wherein:
$A^{3a}$ is C(O) or $CH_2$;
$A^{3b}$ is $CH_2$, $CHR^1$, or $C(R^2)_2$,
$A^{3c}$ is $CH_2$, $CHR^1$, or $C(R^2)_2$,
$A^{3d}$ is a bond or $CH_2$; and
each of $R^3$, Y, ring B, $R^6$, $R^7$, o, and p are as defined herein.

In some embodiments of Formula AA-2, $A^{3a}$ is C(O); and $A^{3d}$ is a bond.

In certain of these embodiments, $A^{3b}$ is $CH_2$; and $A^{3c}$ is $CH_2$.

In certain other of these embodiments, $A^{3A}$ is $C(R^2)_2$; and $A^{3c}$ is $CH_2$.

In certain other embodiments, $A^{3b}$ is $CH_2$; and $A^{3c}$ is $CHR^1$.

In some embodiments of Formula AA-2, $A^{3a}$ is $CH_2$; and $A^{3d}$ is a bond.

In certain of these embodiments, $A^{3b}$ is $CH_2$; and $A^{3c}$ is $CH_2$.

In some embodiments of Formula AA-2, $A^{3a}$ is $C(O)$; and $A^{3d}$ is $CH_2$.

In certain of these embodiments, $A^{3b}$ is $CH_2$; and $A^{3c}$ is $CH_2$.

In some embodiments of Formula AA-1 or Formula AA-2, each $R^1$ is independently selected from the group consisting of: $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_8$ cycloalkyl, $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $CONR^8R^9$, $S(O_2)C_1$-$C_6$ alkyl, $S(O)C_1$-$C_6$ alkyl, $S(O_2)NR^{11}R^{12}$, $C_3$-$C_7$ cycloalkyl, and 3- to 7-membered heterocycloalkyl, wherein the $C_1$-$C_6$ alkyl, $C_6$-$C_{10}$ aryl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein when $R^1$ is $C_3$-$C_7$ cycloalkyl, 3- to 7-membered heterocycloalkyl, $C_6$-$C_{10}$ aryl, or 5- to 10-membered heteroaryl, each $C_1$-$C_6$ alkyl substituent and each $C_1$-$C_6$ alkoxy substituent on $R^1$, when present, is further optionally independently substituted with one to three hydroxy, $C_1$-$C_6$ alkoxy, halo, $NR^8R^9$, or oxo; and wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) substituents on $R^1$ are optionally substituted with one or more substituents independently selected from halo, $C_1$-$C_6$ alkyl, and $OC_1$-$C_6$ alkyl.

In some embodiments of Formula AA-1 or Formula AA-2, B is

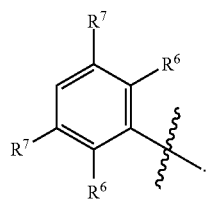

In certain of these embodiments, wherein each $R^6$ and $R^7$ is independently selected from $C_1$-$C_6$ alkyl optionally substituted with hydroxy, $C_3$-$C_7$ cycloalkyl, $C_1$-$C_6$ haloalkyl, and halo;

or at least one pair (e.g., two pairs) of $R^6$ and $R^7$ on adjacent atoms, taken together with the atoms connecting them, independently form a $C_4$-$C_5$ carbocyclic ring or a 5-membered heterocyclic ring containing 1 O, wherein the carbocyclic ring or heterocyclic ring is optionally independently substituted with one or more substituents independently selected from $C_1$-$C_6$ alkyl.

In some embodiments of Formula AA-1 or Formula AA-2, B is

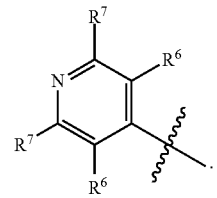

In certain of these embodiments, each $R^6$ and $R^7$ is independently selected from $C_1$-$C_6$ alkyl optionally substituted with hydroxy, $C_3$-$C_7$ cycloalkyl, $C_1$-$C_6$ haloalkyl, and halo;

or at least one pair (e.g., one pair or two pairs) of $R^6$ and $R^7$ on adjacent atoms, taken together with the atoms connecting them, independently form a $C_4$-$C_5$ carbocyclic ring or a 5-membered heterocyclic ring containing 1 O, wherein the carbocyclic ring or heterocyclic ring is optionally independently substituted with one or more substituents independently selected from $C_1$-$C_6$ alkyl.

In some embodiments of Formula AA-1 or Formula AA-2, $R^3$ is H.

In some embodiments of Formula AA-1 or Formula AA-2, Y is NH.

In one embodiment, provided herein is a combination of a compound of any preceding embodiment, for use in the treatment or the prevention of a condition mediated by TNF-α, in a patient in need thereof, wherein the compound is administered to said patient at a therapeutically effective amount. Preferably, the subject is resistant to treatment with an anti-TNFα agent.

Preferably, the condition is a gut disease or disorder.

In one embodiment, provided herein is a pharmaceutical composition of comprising a compound of any preceding embodiment, and an anti-TNFα agent disclosed herein. Preferably wherein the anti-TNFα agent is Infliximab, Etanercept, Certolizumab pegol, Golimumab or Adalimumab, more preferably wherein the anti-TNFα agent is Adalimumab.

In one embodiment, provided herein is a pharmaceutical combination of a compound of any preceding embodiment, and an anti-TNFα agent Preferably wherein the anti-TNFα agent is Infliximab, Etanercept, Certolizumab pegol, Golimumab or Adalimumab, more preferably wherein the anti-TNFα agent is Adalimumab.

In one embodiment, the present invention relates to an NLRP3 antagonist for use in the treatment or the prevention of a condition mediated by TNF-α, in particular a gut disease or disorder, in a patient in need thereof, wherein the NLRP3 antagonist is administered to said patient at a therapeutically effective amount.

In one embodiment, the present invention relates to an NLRP3 antagonist for use in the treatment or the prevention of a condition, in particular a gut disease or disorder, in a patient in need thereof wherein the NLRP3 antagonist is administered to said patient at a therapeutically effective amount.

In one embodiment, the present invention relates to an NLRP3 antagonist for use in the treatment, stabilization or lessening the severity or progression of gut disease or disorder, in a patient in need thereof wherein the NLRP3 antagonist is administered to said patient at a therapeutically effective amount.

In one embodiment, the present invention relates to an NLRP3 antagonist for use in the slowing, arresting, or reducing the development of a gut disease or disorder, in a patient in need thereof wherein the NLRP3 antagonist is administered to said patient at a therapeutically effective amount.

In one embodiment, the present invention relates to an NLRP3 antagonist for use according to above listed embodiments wherein the NLRP3 antagonist is a gut-targeted NLRP3 antagonist.

In one embodiment, the present invention relates ton NLRP3 antagonist for use according to any of the above embodiments, wherein the gut disease is IBD.

In one embodiment, the present invention relates to an NLRP3 antagonist for use according to any of the above embodiments, wherein the gut disease is US or CD.

In one embodiment, the present invention relates to a method for the treatment or the prevention of a condition mediated by TNF-α, in particular a gut disease or disorder, in a patient in need thereof, comprising administering to said patient a therapeutically effective amount of a gut-targeted NLRP3 antagonist.

In one embodiment, the present invention relates to a method for the treatment or the prevention of a condition, in particular a gut disease or disorder, in a patient in need thereof, comprising administering to said patient a therapeutically effective amount of a gut-targeted NLRP3 antagonist.

In one embodiment, the present invention relates to a method for the treatment, stabilization or lessening the severity or progression of gut disease or disorder, in a patient in need thereof comprising administering to said patient a therapeutically effective amount of a gut-targeted NLRP3 antagonist.

In one embodiment, the present invention relates to a method for slowing, arresting, or reducing the development of a gut disease or disorder, in a patient in need thereof comprising administering to said patient a therapeutically effective amount of a gut-targeted NLRP3 antagonist.

In one embodiment, the present invention relates to a method according to any of the above embodiments, wherein the gut disease is IBD.

In one embodiment, the present invention relates to a method according to any of the above embodiments x to xx, wherein the gut disease is UC or CD.

In one embodiment, the present invention relates to a method for the treatment or the prevention of a condition mediated by TNF-α, in particular a gut disease or disorder, in a patient in need thereof, comprising administering to said patient a therapeutically effective amount of a gut-targeted NLRP3 antagonist.

Additional Features of the Embodiments Herein

In some embodiments, provided herein is a compound that is selected from the group consisting of the compounds in Table 1:

TABLE 1

| Cmpd # | Structure |
|--------|-----------|
| 101 | 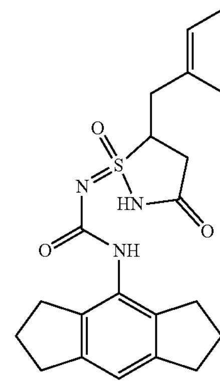 |
| 102 | 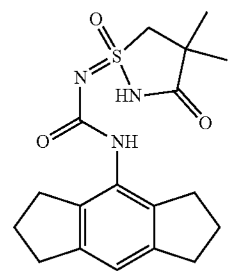 [SMILES: CC1(C)CS(=O)(=NC(=O)Nc2c3c(cc4c2CCC4)CCC3)NC1=O] |
| 103 | 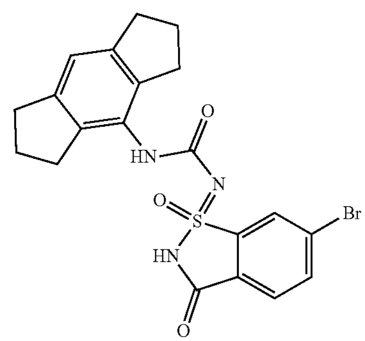 [SMILES: O=C(N=S1(=O)NC(=O)c2ccc(Br)cc21)Nc1c2c(cc3c1CCC3)CCC2] |
| 104 | 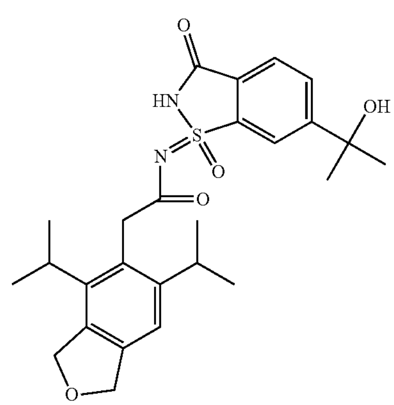 [SMILES: CC(C)c1cc2c(c(C(C)C)c1CC(=O)N=S1(=O)NC(=O)c3ccc(C(C)(C)O)cc31)COC2] |

TABLE 1-continued

| Cmpd # | Structure |
|---|---|
| 105 | 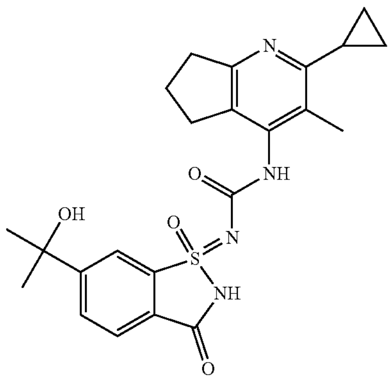 [SMILES: Cc1c(C2CC2)nc2c(c1NC(=O)N=S1(=O)NC(=O)c3ccc(C(C)(C)O)cc31)CCC2] |
| 106 | 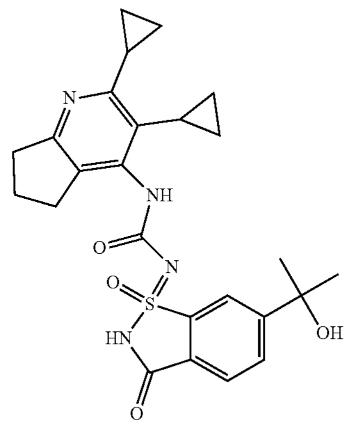 [SMILES: CC(C)(O)c1ccc2c(c1)S(=O)(=NC(=O)Nc1c3c(nc(C4CC4)c1C1CC1)CCC3)NC2=O] |
| 106a | 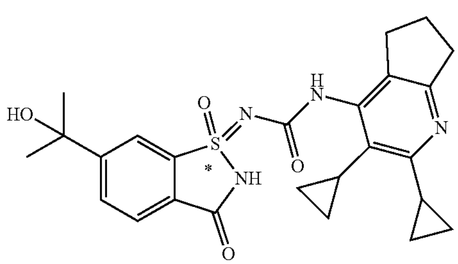 [SMILES: CC(C)(O)c1ccc2c(c1)S(=O)(=NC(=O)Nc1c3c(nc(C4CC4)c1C1CC1)CCC3)NC2=O] |
| 106b | 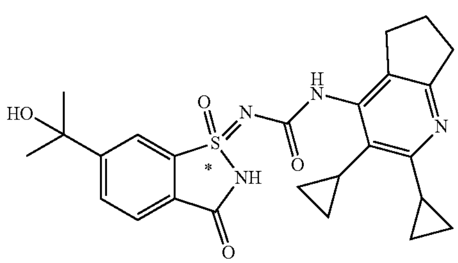 [SMILES: CC(C)(O)c1ccc2c(c1)S(=O)(=NC(=O)Nc1c3c(nc(C4CC4)c1C1CC1)CCC3)NC2=O] |
| 107 | 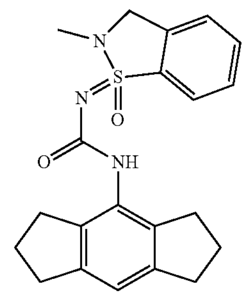 [SMILES: CN1Cc2ccccc2S1(=O)=NC(=O)Nc1c2c(cc3c1CCC3)CCC2] |
| 107a | 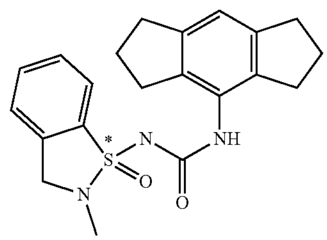 |
| 107b | 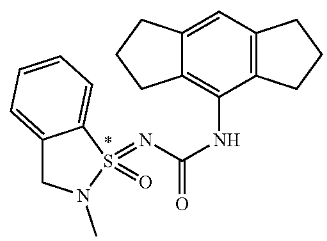 [SMILES: CN1Cc2ccccc2S1(=O)=NC(=O)Nc1c2c(cc3c1CCC3)CCC2] |
| 108 | 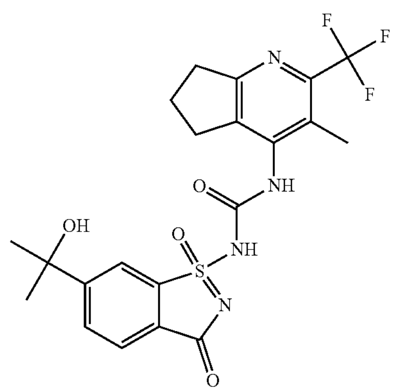 [SMILES: Cc1c(C(F)(F)F)nc2c(c1NC(=O)NS1(=O)=NC(=O)c3ccc(C(C)(C)O)cc31)CCC2] |
| 108a | 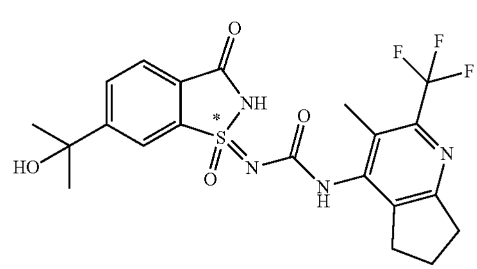 [SMILES: Cc1c(C(F)(F)F)nc2c(c1NC(=O)N=S1(=O)NC(=O)c3ccc(C(C)(C)O)cc31)CCC2] |

TABLE 1-continued

| Cmpd # | Structure |
|---|---|
| 108b | 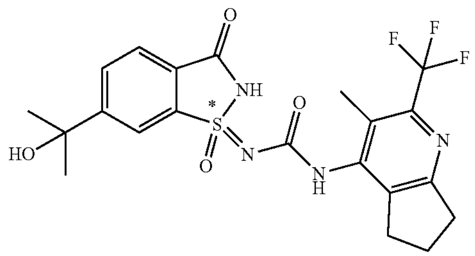 [SMILES: Cc1c(C(F)(F)F)nc2c(c1NC(=O)N=S1(=O)NC(=O)c3ccc(C(C)(C)O)cc31)CCC2] |
| 109 | 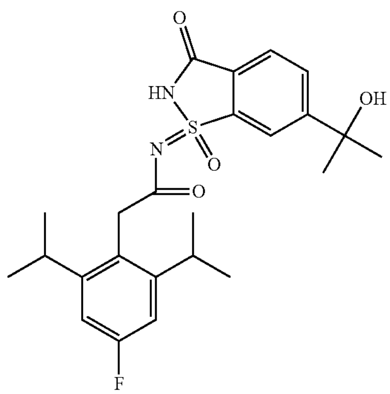 [SMILES: CC(C)c1cc(F)cc(C(C)C)c1CC(=O)N=S1(=O)NC(=O)c2ccc(C(C)(C)O)cc21] |
| 110 | 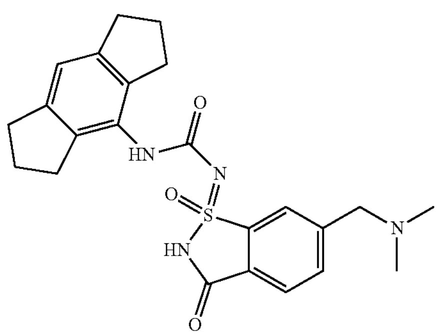 [SMILES: CN(C)Cc1ccc2c(c1)S(=O)(=NC(=O)Nc1c3c(cc4c1CCC4)CCC3)NC2=O] |
| 111 | 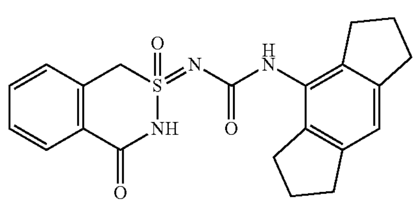 [SMILES: O=C(N=S1(=O)Cc2ccccc2C(=O)N1)Nc1c2c(cc3c1CCC3)CCC2] |
| 112 | 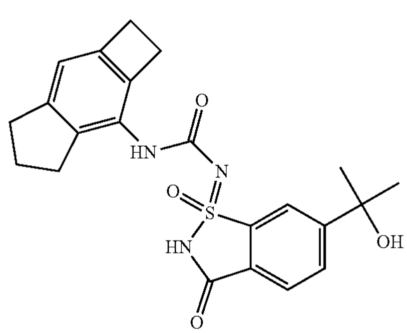 [SMILES: CC(C)(O)c1ccc2c(c1)S(=O)(=NC(=O)Nc1c3c(cc4c1CC4)CCC3)NC2=O] |
| 112a | |
| 112b | |
| 113 | |
| 114 | |
| 115 | |

TABLE 1-continued

| Cmpd # | Structure |
|---|---|
| 116 | 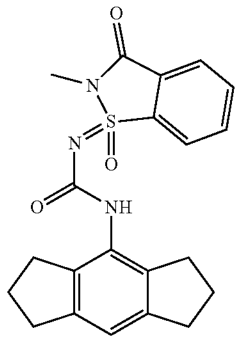 [SMILES: CN1C(=O)c2ccccc2S1(=O)=NC(=O)Nc1c2c(cc3c1CCC3)CCC2] |
| 116a | 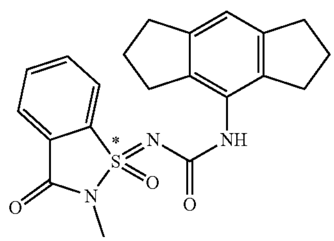 [SMILES: CN1C(=O)c2ccccc2S1(=O)=NC(=O)Nc1c2c(cc3c1CCC3)CCC2] |
| 116b | 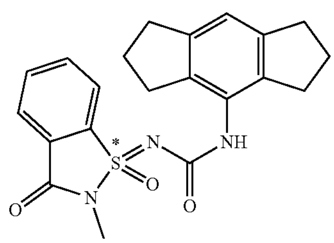 [SMILES: CN1C(=O)c2ccccc2S1(=O)=NC(=O)Nc1c2c(cc3c1CCC3)CCC2] |
| 117 | 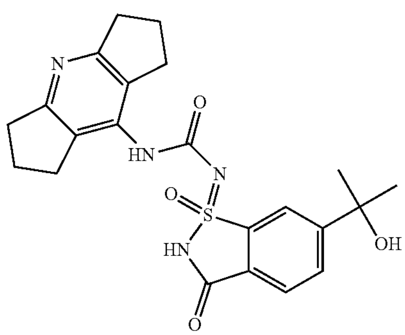 [SMILES: CC(C)(O)c1ccc2c(c1)S(=O)(=NC(=O)Nc1c3c(nc4c1CCC4)CCC3)NC2=O] |
| 118 | 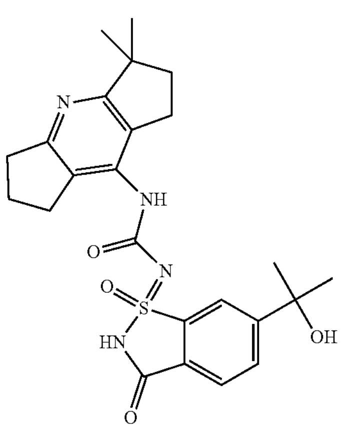 [SMILES: CC(C)(O)c1ccc2c(c1)S(=O)(=NC(=O)Nc1c3c(nc4c1CCC4(C)C)CCC3)NC2=O] |
| 119 | |
| 119a | |
| 119b | |
| 120 | |
| 121 | |

TABLE 1-continued

| Cmpd # | Structure |
|---|---|
| 121a | |
| 121b | |
| 122 | |
| 123 | |
| 123a | 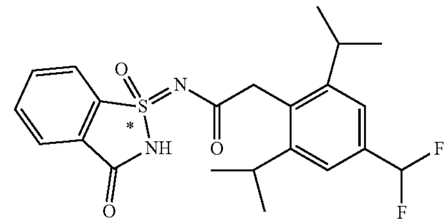 [SMILES: CC(C)c1cc(C(F)F)cc(C(C)C)c1CC(=O)N=S1(=O)NC(=O)c2ccccc21] |
| 123b | 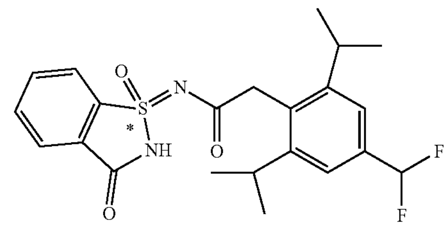 [SMILES: CC(C)c1cc(C(F)F)cc(C(C)C)c1CC(=O)N=S1(=O)NC(=O)c2ccccc21] |
| 124 | 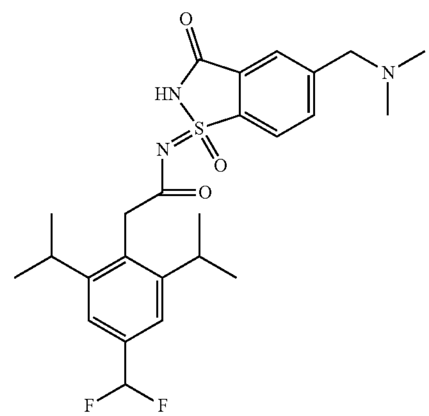 [SMILES: CC(C)c1cc(C(F)F)cc(C(C)C)c1CC(=O)N=S1(=O)NC(=O)c2cc(CN(C)C)ccc21] |
| 124a | 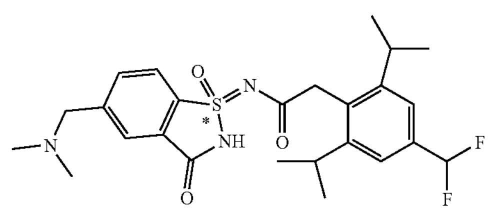 [SMILES: CC(C)c1cc(C(F)F)cc(C(C)C)c1CC(=O)N=S1(=O)NC(=O)c2cc(CN(C)C)ccc21] |
| 124b | 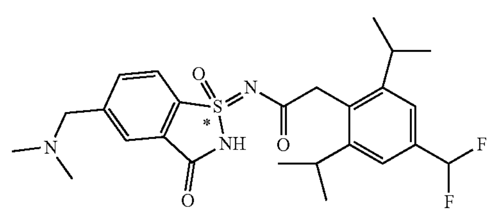 [SMILES: CC(C)c1cc(C(F)F)cc(C(C)C)c1CC(=O)N=S1(=O)NC(=O)c2cc(CN(C)C)ccc21] |

TABLE 1-continued

| Cmpd # | Structure |
|---|---|
| 125 | |
| 126 | |
| 127 | |
| 127a | |
| 127b | |
| 128 | 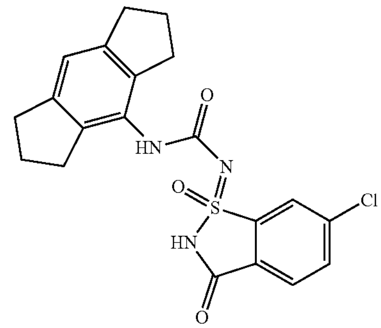 [SMILES: O=C(N=S1(=O)NC(=O)c2ccc(Cl)cc21)Nc1c2c(cc3c1CCC3)CCC2] |
| 129 | 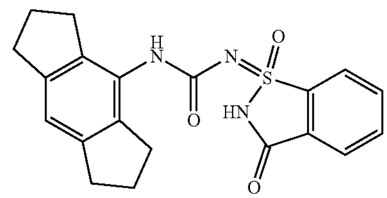 [SMILES: O=C(N=S1(=O)NC(=O)c2ccccc21)Nc1c2c(cc3c1CCC3)CCC2] |
| 129a | 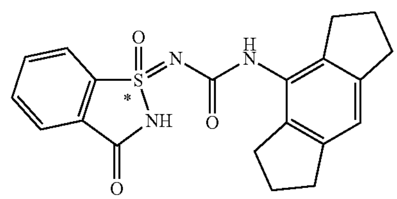 [SMILES: O=C(N=S1(=O)NC(=O)c2ccccc21)Nc1c2c(cc3c1CCC3)CCC2] |
| 129b | 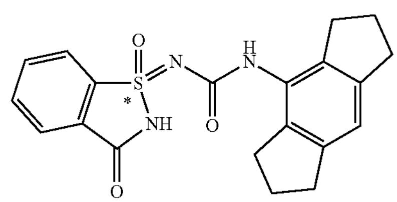 [SMILES: O=C(N=S1(=O)NC(=O)c2ccccc21)Nc1c2c(cc3c1CCC3)CCC2] |
| 130 | 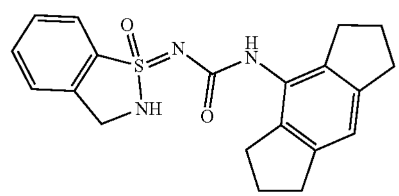 [SMILES: O=C(N=S1(=O)NCc2ccccc21)Nc1c2c(cc3c1CCC3)CCC2] |
| 130a | 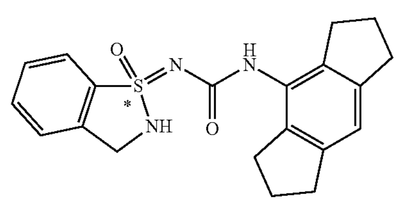 [SMILES: O=C(N=S1(=O)NCc2ccccc21)Nc1c2c(cc3c1CCC3)CCC2] |
| 130b | 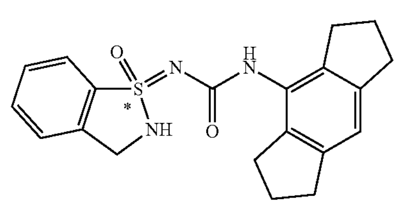 [SMILES: O=C(N=S1(=O)NCc2ccccc21)Nc1c2c(cc3c1CCC3)CCC2] |

TABLE 1-continued
| Cmpd # | Structure |
|---|---|
| 131 | 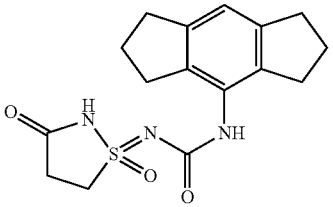 [SMILES: O=C1CCS(=O)(=NC(=O)Nc2c3c(cc4c2CCC4)CCC3)N1] |
| 131a | 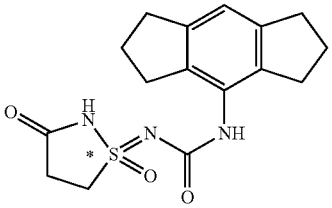 [SMILES: O=C1CCS(=O)(=NC(=O)Nc2c3c(cc4c2CCC4)CCC3)N1] |
| 131b | 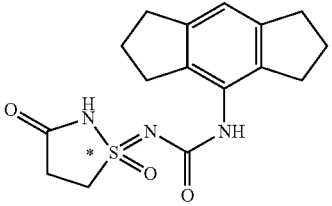 [SMILES: O=C1CCS(=O)(=NC(=O)Nc2c3c(cc4c2CCC4)CCC3)N1] |
and pharmaceutically acceptable salts thereof.
In some embodiments, provided herein is a compound that is selected from the group consisting of the compounds in Table 1a:
TABLE 1a
| Cmpd # | Structure |
|---|---|
| 101 | 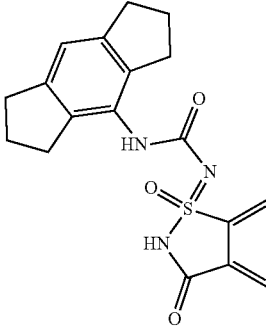 |
| 102 | 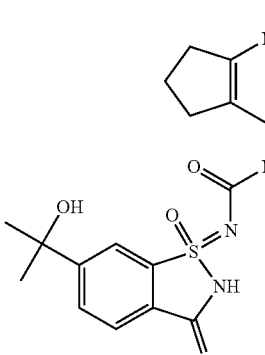 |
TABLE 1a-continued
| Cmpd # | Structure |
|---|---|
| 103 | 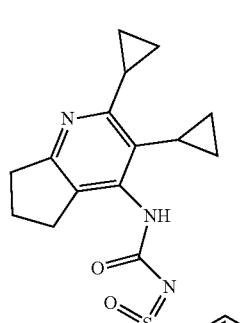 |
| 105 | 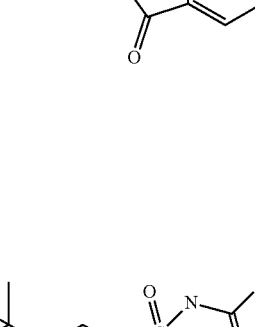 |
| 106 | 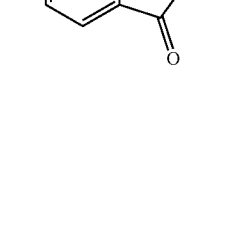 |
| 106a | 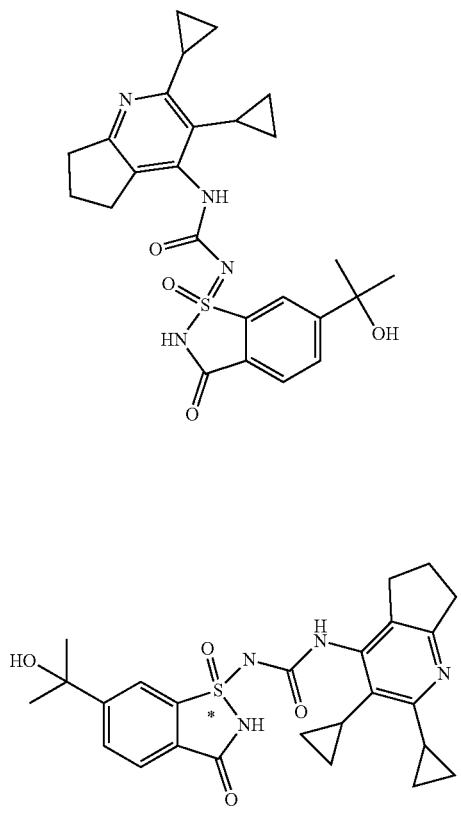 |

TABLE 1a-continued

| Cmpd # | Structure |
|---|---|
| 108 | 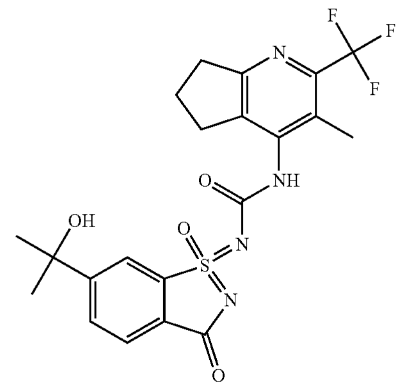 |
| 108a | 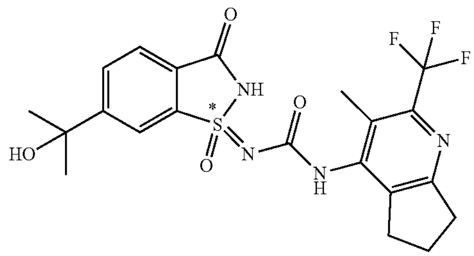 [SMILES: Cc1c(C(F)(F)F)nc2c(c1NC(=O)N=S1(=O)NC(=O)c3ccc(C(C)(C)O)cc31)CCC2] |
| 110 | 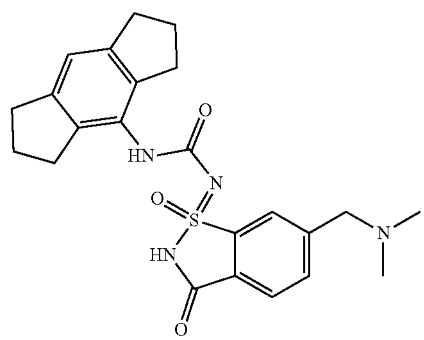 [SMILES: CN(C)Cc1ccc2c(c1)S(=O)(=NC(=O)Nc1c3c(cc4c1CCC4)CCC3)NC2=O] |
| 111 | 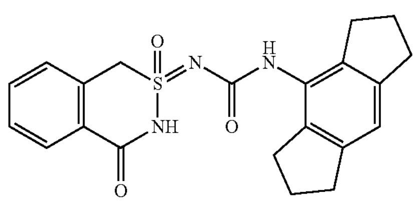 [SMILES: O=C(N=S1(=O)Cc2ccccc2C(=O)N1)Nc1c2c(cc3c1CCC3)CCC2] |
| 112 | 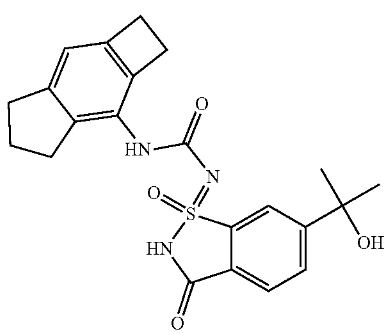 [SMILES: CC(C)(O)c1ccc2c(c1)S(=O)(=NC(=O)Nc1c3c(cc4c1CC4)CCC3)NC2=O] |
| 112a | |
| 112b | |
| 113 | |
| 117 | |

TABLE 1a-continued

| Cmpd # | Structure |
| --- | --- |
| 118 | 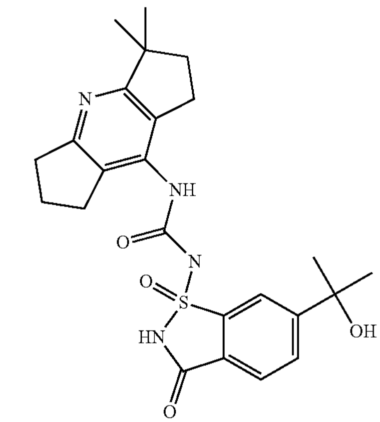 |
| 119 | 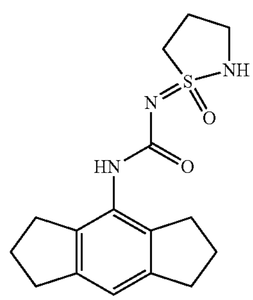 [SMILES: O=C(N=S1(=O)CCCN1)Nc1c2c(cc3c1CCC3)CCC2] |
| 119a | 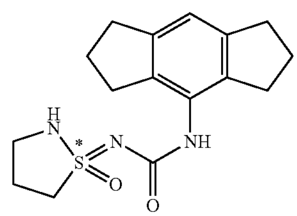 [SMILES: O=C(N=S1(=O)CCCN1)Nc1c2c(cc3c1CCC3)CCC2] |
| 119b | 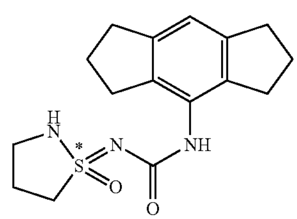 [SMILES: O=C(N=S1(=O)CCCN1)Nc1c2c(cc3c1CCC3)CCC2] |
| 120 | 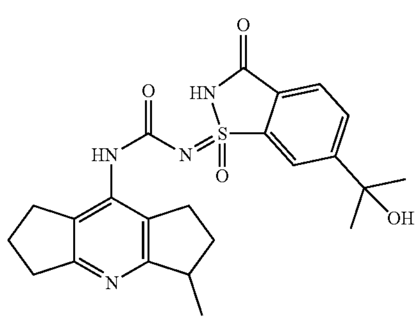 [SMILES: CC1CCc2c1nc1c(c2NC(=O)N=S2(=O)NC(=O)c3ccc(C(C)(C)O)cc32)CCC1] |
| 121 | |
| 121a | |
| 121b | |
| 122 | |

TABLE 1a-continued

| Cmpd # | Structure |
|---|---|
| 125 | |
| 127 | |
| 127a | |
| 127b | |
| 128 | |
| 129 | 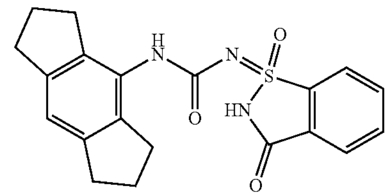 [SMILES: O=C(N=S1(=O)NC(=O)c2ccccc21)Nc1c2c(cc3c1CCC3)CCC2] |
| 129a | 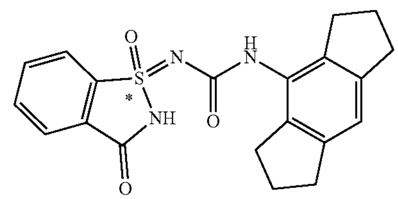 [SMILES: O=C(N=S1(=O)NC(=O)c2ccccc21)Nc1c2c(cc3c1CCC3)CCC2] |
| 129b | 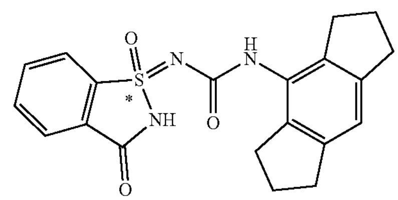 [SMILES: O=C(N=S1(=O)NC(=O)c2ccccc21)Nc1c2c(cc3c1CCC3)CCC2] |
| 130 | 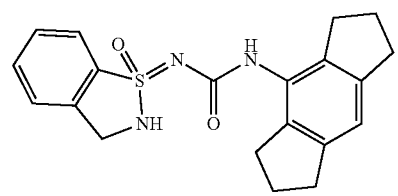 [SMILES: O=C(N=S1(=O)NCc2ccccc21)Nc1c2c(cc3c1CCC3)CCC2] |
| 130b | 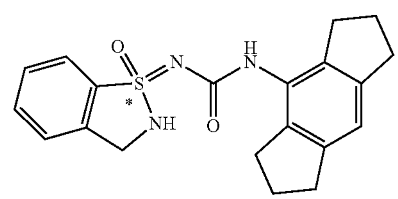 [SMILES: O=C(N=S1(=O)NCc2ccccc21)Nc1c2c(cc3c1CCC3)CCC2] |
| 131 | 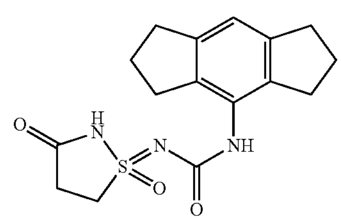 [SMILES: O=C1CCS(=O)(=NC(=O)Nc2c3c(cc4c2CCC4)CCC3)N1] |
| 131a | 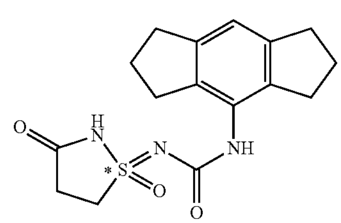 [SMILES: O=C1CCS(=O)(=NC(=O)Nc2c3c(cc4c2CCC4)CCC3)N1] |

TABLE 1a-continued
| Cmpd # | Structure |
|---|---|
| 131b | 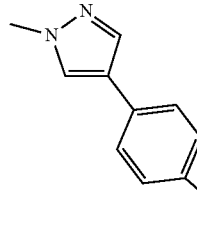 |
and pharmaceutically acceptable salts thereof.
In some embodiments, provided herein is a compound that is selected from the group consisting of the compounds in Table 2:
TABLE 2
| Cmpd # | Structure |
|---|---|
| 201 | 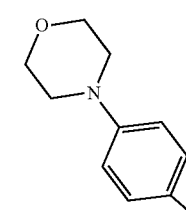 |
| 202 | 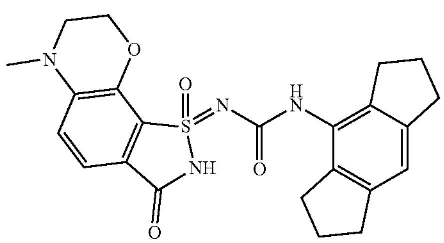 [SMILES: CN1CCOc2c1ccc1c2S(=O)(=NC(=O)Nc2c3c(cc4c2CCC4)CCC3)NC1=O] |
| 203 | 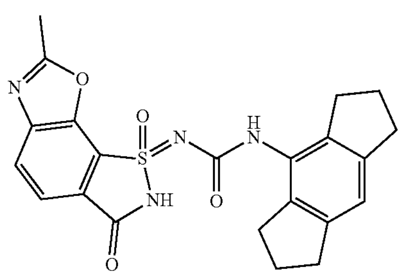 [SMILES: Cc1nc2ccc3c(c2o1)S(=O)(=NC(=O)Nc1c2c(cc4c1CCC4)CCC2)NC3=O] |
| 204 | 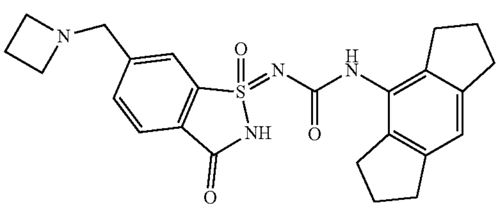 [SMILES: O=C(N=S1(=O)NC(=O)c2ccc(CN3CCC3)cc21)Nc1c2c(cc3c1CCC3)CCC2] |
TABLE 2-continued
| Cmpd # | Structure |
|---|---|
| 205 | 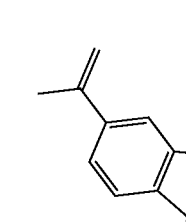 |
| 206 | 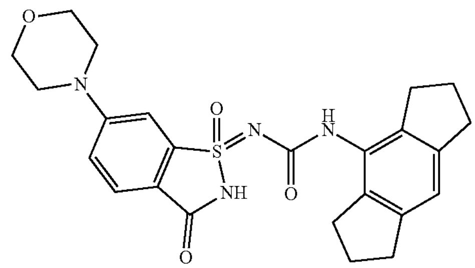 [SMILES: O=C(N=S1(=O)NC(=O)c2ccc(N3CCOCC3)cc21)Nc1c2c(cc3c1CCC3)CCC2] |
| 207 | 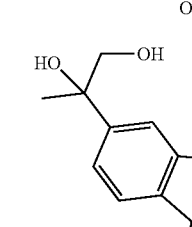 |
| 208 | 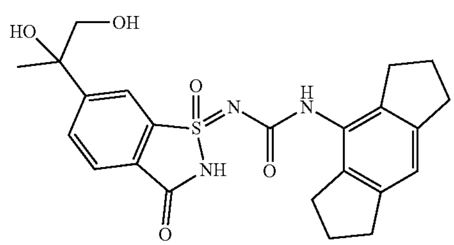 [SMILES: CC(O)(CO)c1ccc2c(c1)S(=O)(=NC(=O)Nc1c3c(cc4c1CCC4)CCC3)NC2=O] |
| 209 | 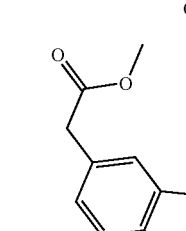 |
| 210 | 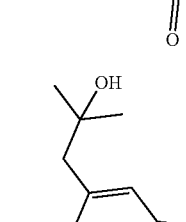 |

TABLE 2-continued
| Cmpd # | Structure |
|---|---|
| 211 | 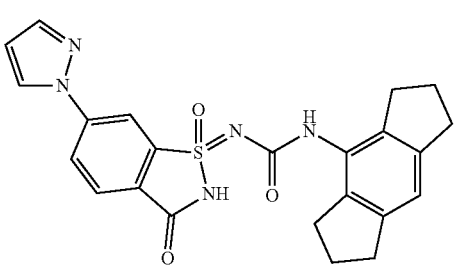 [SMILES: O=C(N=S1(=O)NC(=O)c2ccc(-n3cccn3)cc21)Nc1c2c(cc3c1CCC3)CCC2] |
| 212 | 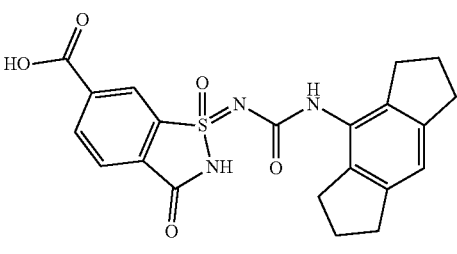 [SMILES: O=C(N=S1(=O)NC(=O)c2ccc(C(=O)O)cc21)Nc1c2c(cc3c1CCC3)CCC2] |
| 213 | 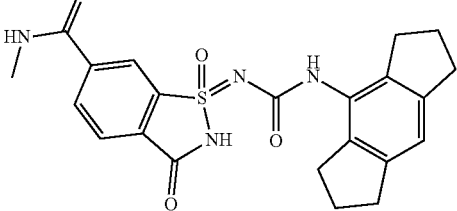 |
| 214 | 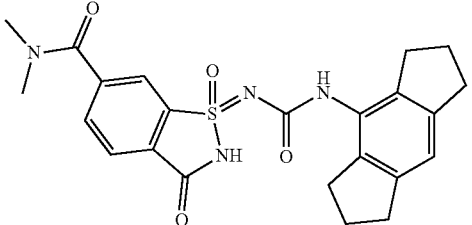 [SMILES: CN(C)C(=O)c1ccc2c(c1)S(=O)(=NC(=O)Nc1c3c(cc4c1CCC4)CCC3)NC2=O] |
| 215 | 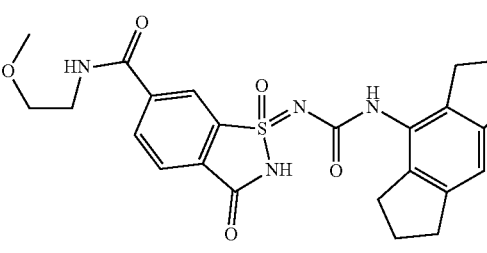 |
| 216 | 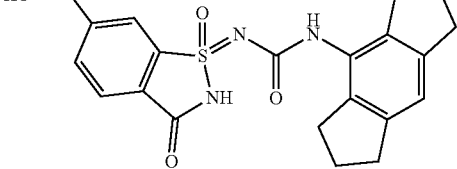 |
| 217 | 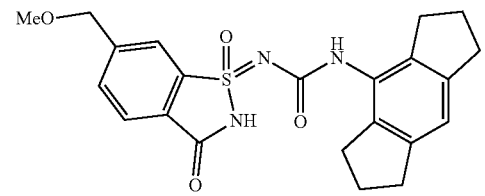 [SMILES: COCc1ccc2c(c1)S(=O)(=NC(=O)Nc1c3c(cc4c1CCC4)CCC3)NC2=O] |
| 218 | 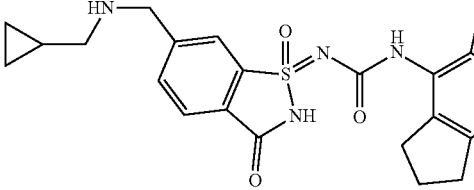 |
| 219 | 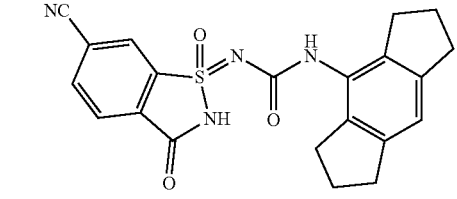 [SMILES: N#Cc1ccc2c(c1)S(=O)(=NC(=O)Nc1c3c(cc4c1CCC4)CCC3)NC2=O] |
| 220 | 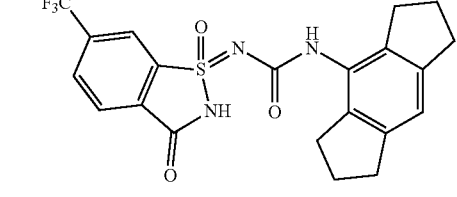 |
| 221 | 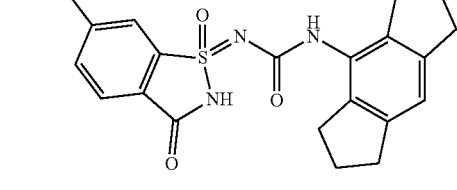 |
| 222 | 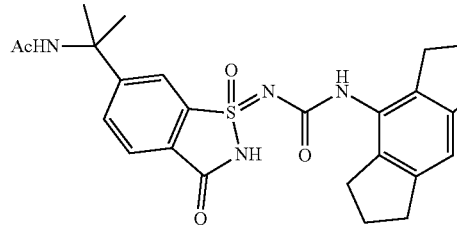 |
| 223 | 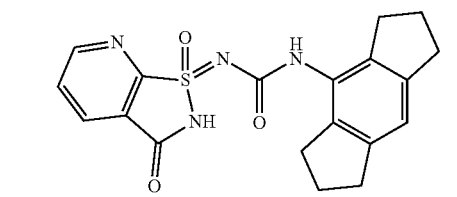 [SMILES: O=C(N=S1(=O)NC(=O)c2cccnc21)Nc1c2c(cc3c1CCC3)CCC2] |

TABLE 2-continued

| Cmpd # | Structure |
|---|---|
| 224 | 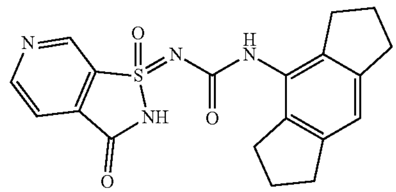 [SMILES: O=C(N=S1(=O)NC(=O)c2ccncc21)Nc1c2c(cc3c1CCC3)CCC2] |
| 225 | 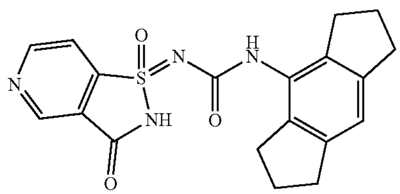 [SMILES: O=C(N=S1(=O)NC(=O)c2cnccc21)Nc1c2c(cc3c1CCC3)CCC2] |
| 226 | 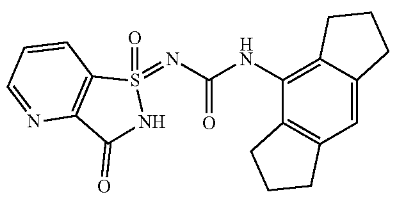 [SMILES: O=C(N=S1(=O)NC(=O)c2ncccc21)Nc1c2c(cc3c1CCC3)CCC2] |
| 227 | 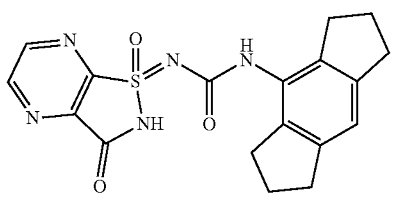 [SMILES: O=C(N=S1(=O)NC(=O)c2nccnc21)Nc1c2c(cc3c1CCC3)CCC2] |
| 228 | 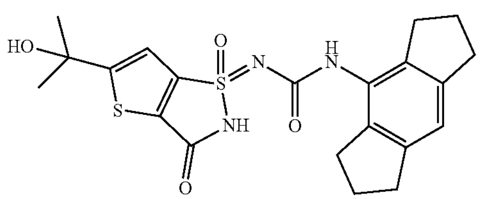 [SMILES: CC(C)(O)c1cc2c(s1)C(=O)NS2(=O)=NC(=O)Nc1c2c(cc3c1CCC3)CCC2] |
| 229 | 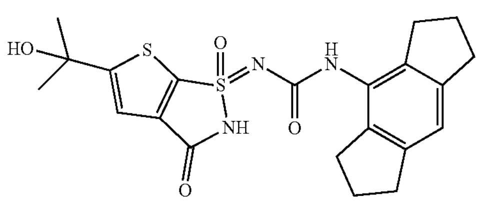 [SMILES: CC(C)(O)c1cc2c(s1)S(=O)(=NC(=O)Nc1c3c(cc4c1CCC4)CCC3)NC2=O] |
| 230 | 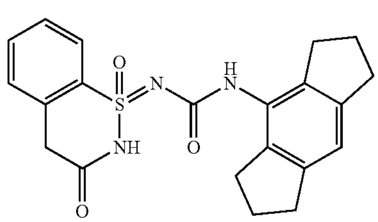 [SMILES: O=C1Cc2ccccc2S(=O)(=NC(=O)Nc2c3c(cc4c2CCC4)CCC3)N1] |
| 231 | |
| 232 | |
| 233 | |
| 234 | |
| 235 | |
| 236 | |
| 237 | |

TABLE 2-continued

| Cmpd # | Structure |
|---|---|
| 238 | 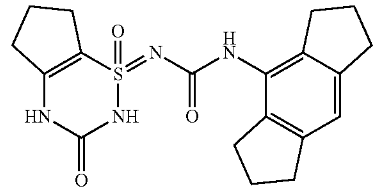 [SMILES: O=C(N=S1(=O)NC(=O)NC2=C1CCC2)Nc1c2c(cc3c1CCC3)CCC2] |
| 239 | 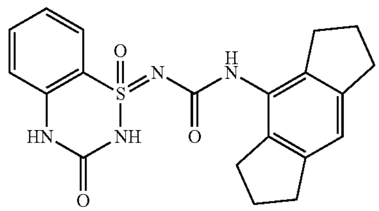 [SMILES: O=C(N=S1(=O)NC(=O)Nc2ccccc21)Nc1c2c(cc3c1CCC3)CCC2] |
| 240 | 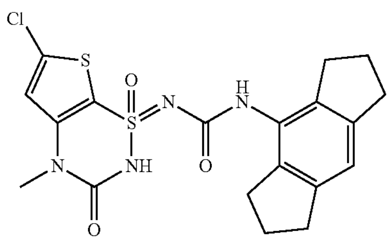 [SMILES: CN1C(=O)NS(=O)(=NC(=O)Nc2c3c(cc4c2CCC4)CCC3)c2sc(Cl)cc21] |
| 241 | 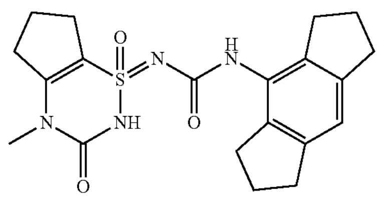 [SMILES: CN1C(=O)NS(=O)(=NC(=O)Nc2c3c(cc4c2CCC4)CCC3)C2=C1CCC2] |
| 242 | 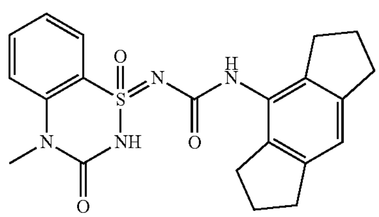 [SMILES: CN1C(=O)NS(=O)(=NC(=O)Nc2c3c(cc4c2CCC4)CCC3)c2ccccc21] |
| 243 | 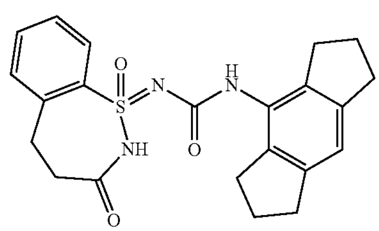 [SMILES: O=C1CCc2ccccc2S(=O)(=NC(=O)Nc2c3c(cc4c2CCC4)CCC3)N1] |
| 244 | 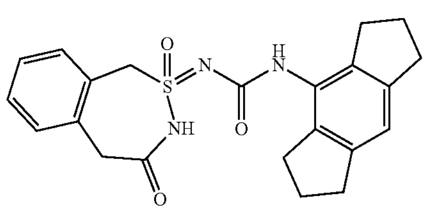 [SMILES: O=C1Cc2ccccc2CS(=O)(=NC(=O)Nc2c3c(cc4c2CCC4)CCC3)N1] |
| 245 | 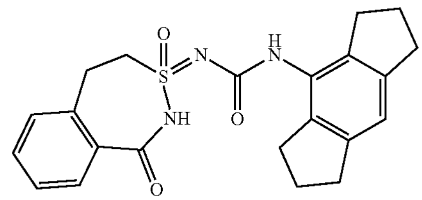 [SMILES: O=C(N=S1(=O)CCc2ccccc2C(=O)N1)Nc1c2c(cc3c1CCC3)CCC2] |
| 246 | 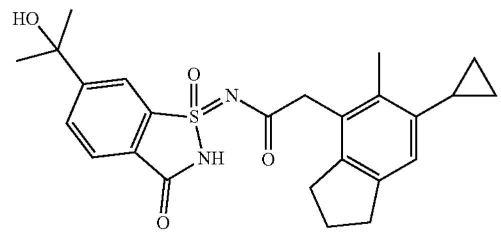 [SMILES: Cc1c(C2CC2)cc2c(c1CC(=O)N=S1(=O)NC(=O)c3ccc(C(C)(C)O)cc31)CCC2] |
| 247 | 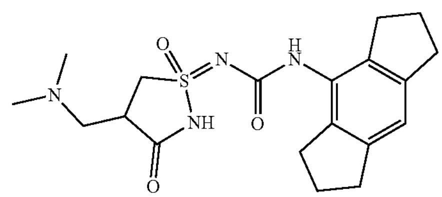 [SMILES: CN(C)CC1CS(=O)(=NC(=O)Nc2c3c(cc4c2CCC4)CCC3)NC1=O] |
| 248 | 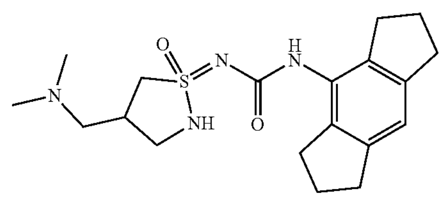 [SMILES: CN(C)CC1CNS(=O)(=NC(=O)Nc2c3c(cc4c2CCC4)CCC3)C1] |
| 249 | 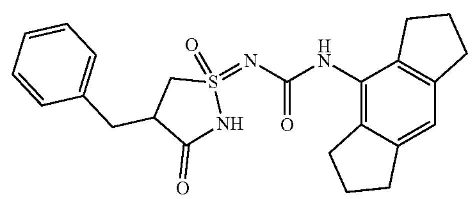 [SMILES: O=C(N=S1(=O)CC(Cc2ccccc2)C(=O)N1)Nc1c2c(cc3c1CCC3)CCC2] |
| 250 | 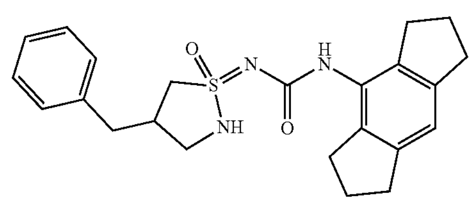 [SMILES: O=C(N=S1(=O)CC(Cc2ccccc2)CN1)Nc1c2c(cc3c1CCC3)CCC2] |
| 251 | 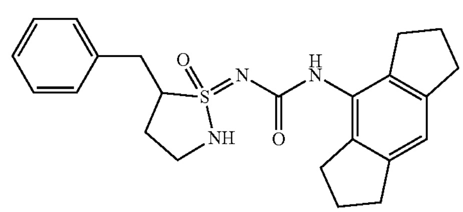 [SMILES: O=C(N=S1(=O)NCCC1Cc1ccccc1)Nc1c2c(cc3c1CCC3)CCC2] |

TABLE 2-continued

| Cmpd # | Structure |
|---|---|
| 252 | 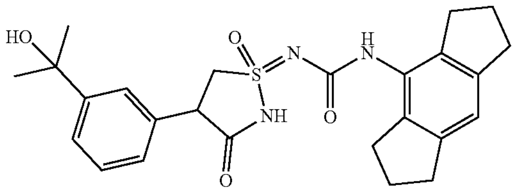 [SMILES: CC(C)(O)c1cccc(C2CS(=O)(=NC(=O)Nc3c4c(cc5c3CCC5)CCC4)NC2=O)c1] |
| 253 | 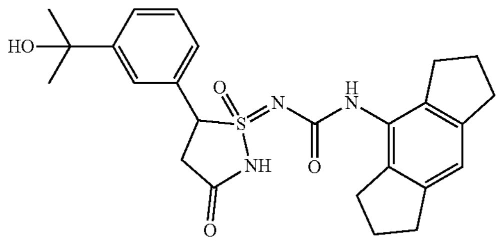 [SMILES: CC(C)(O)c1cccc(C2CC(=O)NS2(=O)=NC(=O)Nc2c3c(cc4c2CCC4)CCC3)c1] |
| 254 | 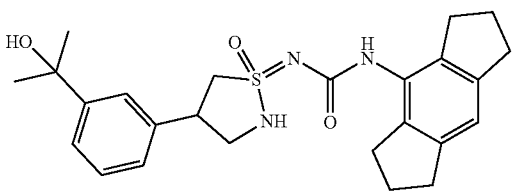 [SMILES: CC(C)(O)c1cccc(C2CNS(=O)(=NC(=O)Nc3c4c(cc5c3CCC5)CCC4)C2)c1] |
| 255 | 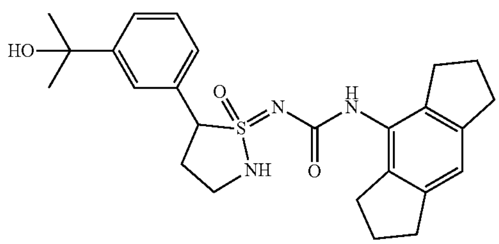 [SMILES: CC(C)(O)c1cccc(C2CCNS2(=O)=NC(=O)Nc2c3c(cc4c2CCC4)CCC3)c1] |
| 256 | 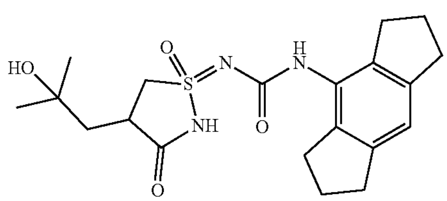 [SMILES: CC(C)(O)CC1CS(=O)(=NC(=O)Nc2c3c(cc4c2CCC4)CCC3)NC1=O] |
| 257 | 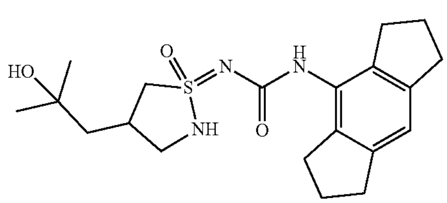 [SMILES: CC(C)(O)CC1CNS(=O)(=NC(=O)Nc2c3c(cc4c2CCC4)CCC3)C1] |
| 258 | 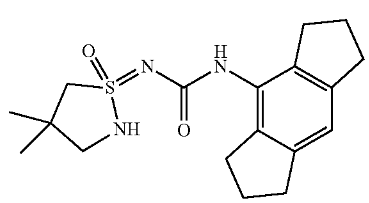 [SMILES: CC1(C)CNS(=O)(=NC(=O)Nc2c3c(cc4c2CCC4)CCC3)C1] |
| 259 | |
| 260 | |
| 261 | |
| 262 | |
| 263 | |
| 264 | |
| 265 | |

TABLE 2-continued

| Cmpd # | Structure |
|---|---|
| 266 | 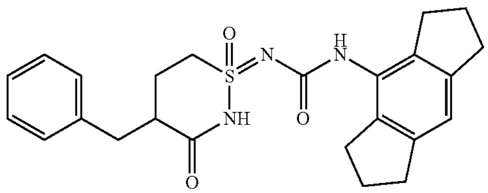 [SMILES: O=C(N=S1(=O)CCC(Cc2ccccc2)C(=O)N1)Nc1c2c(cc3c1CCC3)CCC2] |
| 267 | 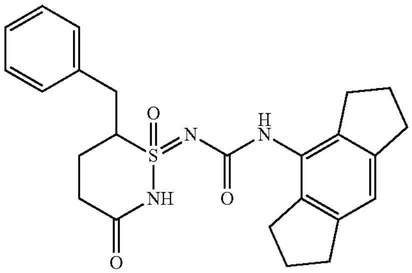 [SMILES: O=C1CCC(Cc2ccccc2)S(=O)(=NC(=O)Nc2c3c(cc4c2CCC4)CCC3)N1] |
| 268 | 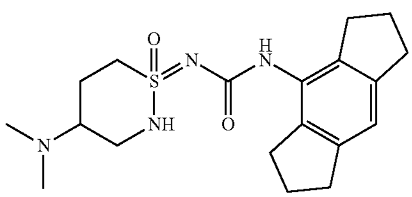 [SMILES: CN(C)C1CCS(=O)(=NC(=O)Nc2c3c(cc4c2CCC4)CCC3)NC1] |
| 269 | 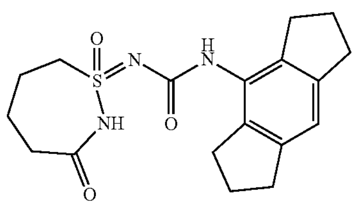 [SMILES: O=C1CCCCS(=O)(=NC(=O)Nc2c3c(cc4c2CCC4)CCC3)N1] |
| 270 | 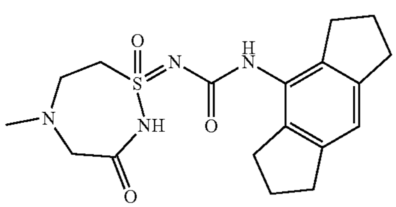 [SMILES: CN1CCS(=O)(=NC(=O)Nc2c3c(cc4c2CCC4)CCC3)NC(=O)C1] |
| 271 | 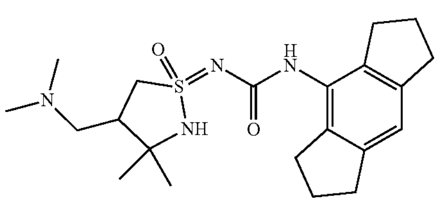 [SMILES: CN(C)CC1CS(=O)(=NC(=O)Nc2c3c(cc4c2CCC4)CCC3)NC1(C)C] |
| 272 | 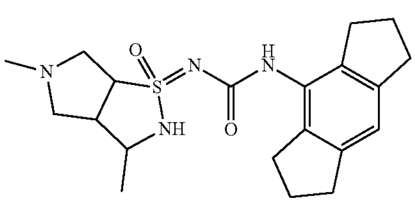 [SMILES: CC1NS(=O)(=NC(=O)Nc2c3c(cc4c2CCC4)CCC3)C2CN(C)CC12] |
| 273 | 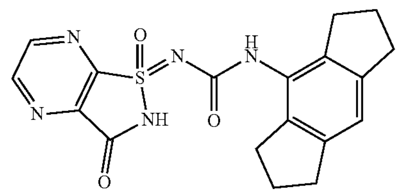 [SMILES: O=C(N=S1(=O)NC(=O)c2nccnc21)Nc1c2c(cc3c1CCC3)CCC2] |
| 274 | 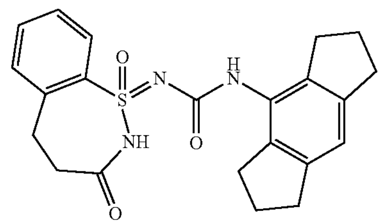 [SMILES: O=C1CCc2ccccc2S(=O)(=NC(=O)Nc2c3c(cc4c2CCC4)CCC3)N1] |
| 275 | 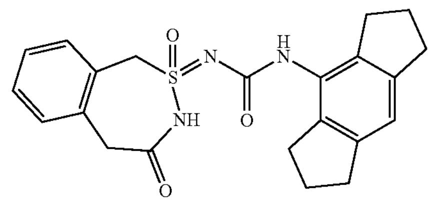 [SMILES: O=C1Cc2ccccc2CS(=O)(=NC(=O)Nc2c3c(cc4c2CCC4)CCC3)N1] |
| 276 | 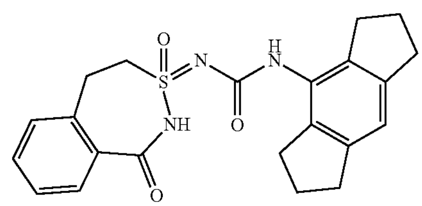 [SMILES: O=C(N=S1(=O)CCc2ccccc2C(=O)N1)Nc1c2c(cc3c1CCC3)CCC2] |
| 277 | 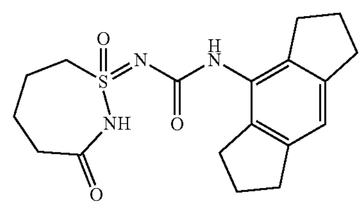 [SMILES: O=C1CCCCS(=O)(=NC(=O)Nc2c3c(cc4c2CCC4)CCC3)N1] |
| 278 | 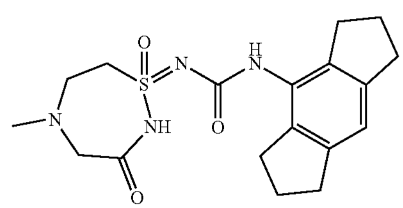 [SMILES: CN1CCS(=O)(=NC(=O)Nc2c3c(cc4c2CCC4)CCC3)NC(=O)C1] |
| 279 | 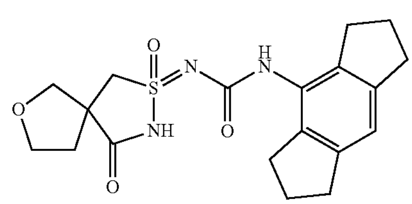 [SMILES: O=C(N=S1(=O)CC2(CCOC2)C(=O)N1)Nc1c2c(cc3c1CCC3)CCC2] |

TABLE 2-continued

| Cmpd # | Structure |
|---|---|
| 280 | (structure) |
| 281 | (structure) |
| 282 | (structure) |
| 283 | (structure) |
| 284 | (structure) |
| 285 | (structure) |
| 286 | (structure) | and pharmaceutically acceptable salts thereof.

In some embodiments, provided herein is a compound that is selected from the group consisting of the compounds in Table 3:

TABLE 3

| Cmpd # | Structure |
|---|---|
| 102a | (structure) |
| 102b | (structure) |
| 103a | (structure) |
| 103b | (structure) |
| 104a | (structure) |
| 113a | (structure) |
| 115a | (structure) |

TABLE 3-continued

| Cmpd # | Structure |
|---|---|
| 132 | 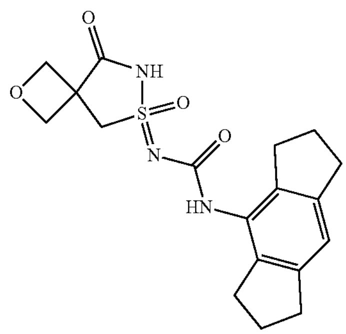 [SMILES: O=C(N=S1(=O)CC2(COC2)C(=O)N1)Nc1c2c(cc3c1CCC3)CCC2] |
| 132a | 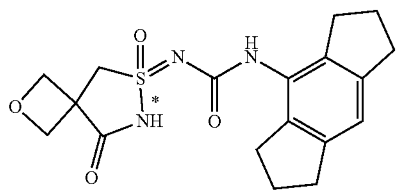 [SMILES: O=C(N=S1(=O)CC2(COC2)C(=O)N1)Nc1c2c(cc3c1CCC3)CCC2] |
| 132b | 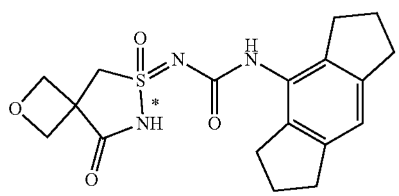 [SMILES: O=C(N=S1(=O)CC2(COC2)C(=O)N1)Nc1c2c(cc3c1CCC3)CCC2] |
| 133 | 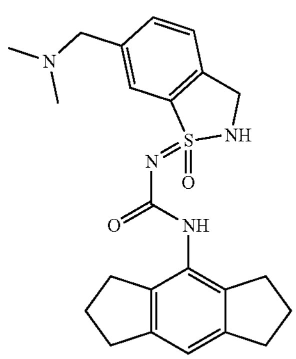 [SMILES: CN(C)Cc1ccc2c(c1)S(=O)(=NC(=O)Nc1c3c(cc4c1CCC4)CCC3)NC2] |
| 133a | 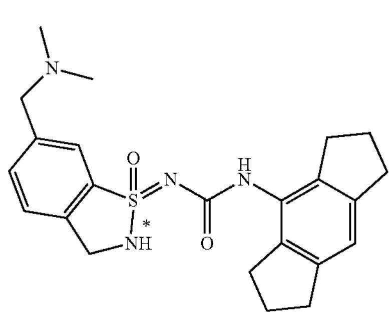 [SMILES: CN(C)Cc1ccc2c(c1)S(=O)(=NC(=O)Nc1c3c(cc4c1CCC4)CCC3)NC2] |
| 133b | |
| 134 | |
| 134a | |
| 134b | |
| 135 | |

TABLE 3-continued
| Cmpd # | Structure |
|---|---|
| 136 | 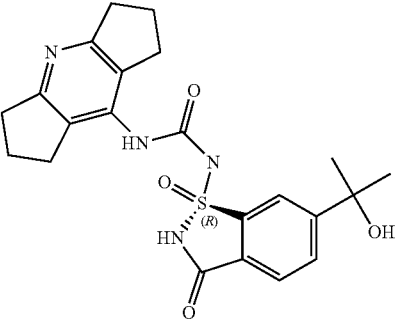 |
| 137 | 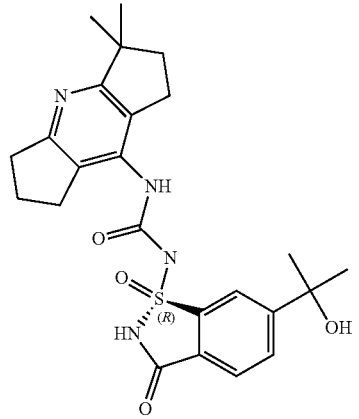 |
| 138 | 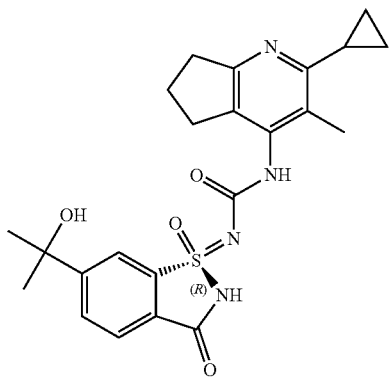 |
| 139a | 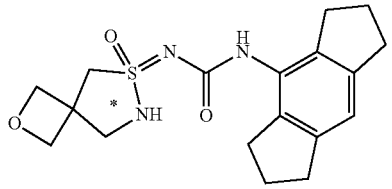 [SMILES: O=C(N=S1(=O)CC2(CN1)COC2)Nc1c2c(cc3c1CCC3)CCC2] |
| 139b | 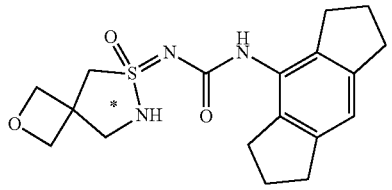 [SMILES: O=C(N=S1(=O)CC2(CN1)COC2)Nc1c2c(cc3c1CCC3)CCC2] |
| 204 | 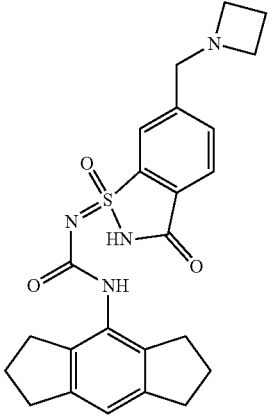 [SMILES: O=C(N=S1(=O)NC(=O)c2ccc(CN3CCC3)cc21)Nc1c2c(cc3c1CCC3)CCC2] |
| 207 | 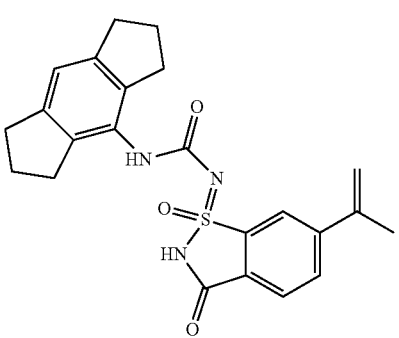 [SMILES: C=C(C)c1ccc2c(c1)S(=O)(=NC(=O)Nc1c3c(cc4c1CCC4)CCC3)NC2=O] |
| 208 | 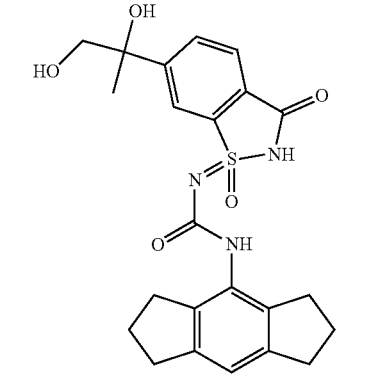 [SMILES: CC(O)(CO)c1ccc2c(c1)S(=O)(=NC(=O)Nc1c3c(cc4c1CCC4)CCC3)NC2=O] |
| 208a | 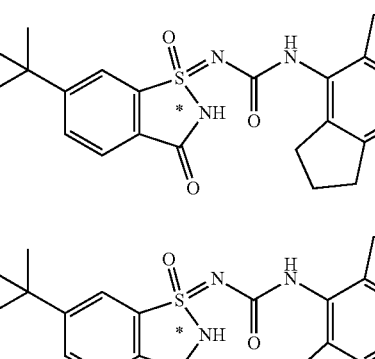 |
| 208b | 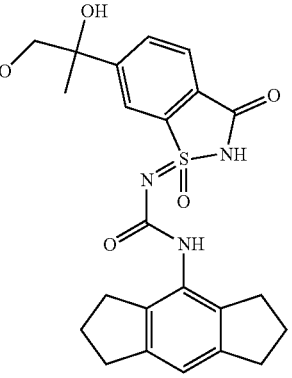 |

TABLE 3-continued

| Cmpd # | Structure |
|---|---|
| 209 | 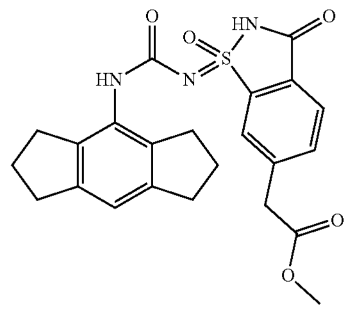 [SMILES: COC(=O)Cc1ccc2c(c1)S(=O)(=NC(=O)Nc1c3c(cc4c1CCC4)CCC3)NC2=O] |
| 211 | 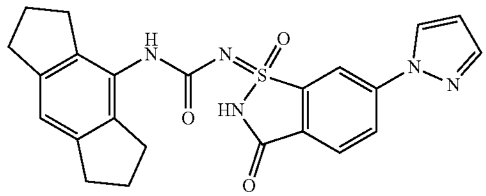 [SMILES: O=C(N=S1(=O)NC(=O)c2ccc(-n3cccn3)cc21)Nc1c2c(cc3c1CCC3)CCC2] |
| 211a | 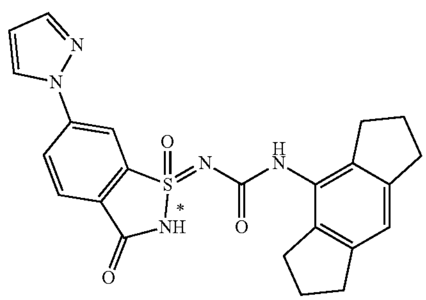 [SMILES: O=C(N=S1(=O)NC(=O)c2ccc(-n3cccn3)cc21)Nc1c2c(cc3c1CCC3)CCC2] |
| 211b | 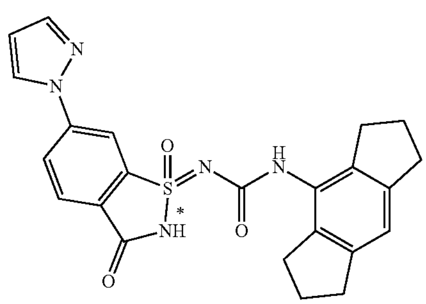 [SMILES: O=C(N=S1(=O)NC(=O)c2ccc(-n3cccn3)cc21)Nc1c2c(cc3c1CCC3)CCC2] |
| 213 | 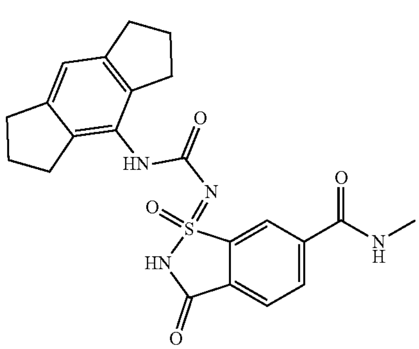 [SMILES: CNC(=O)c1ccc2c(c1)S(=O)(=NC(=O)Nc1c3c(cc4c1CCC4)CCC3)NC2=O] |
| 214 | |
| 216 | |
| 217 | |
| 218 | |

TABLE 3-continued

| Cmpd # | Structure |
|---|---|
| 223 | |
| 223a | |
| 223b | |
| 229 | |
| 249a | | and pharmaceutically acceptable salts thereof.

In one embodiment, provided herein is a pharmaceutical composition comprising any NLRP3 antagonist species defined here (for example, any one of compounds listed in Table 1, 1A, 2 or 3, or referred to in Table BA), and an anti-TNFα agent disclosed herein. Preferably wherein the anti-TNFα agent is Infliximab, Etanercept, Certolizumab pegol, Golimumab or Adalimumab, more preferably wherein the anti-TNFα agent is Adalimumab.

In one embodiment, provided herein is a pharmaceutical combination of a compound of any NLRP3 antagonist species defined here (for example, any one of compounds listed in Table 1, 1A, 2 or 3, or referred to in Table BA), and an anti-TNFα agent Preferably wherein the anti-TNFα agent is Infliximab, Etanercept, Certolizumab pegol, Golimumab or Adalimumab, more preferably wherein the anti-TNFα agent is Adalimumab.

Pharmaceutical Compositions and Administration

General

In some embodiments, a chemical entity (e.g., a compound that modulates (e.g., antagonizes) NLRP3, or a pharmaceutically acceptable salt, and/or hydrate, and/or cocrystal, and/or drug combination thereof) is administered as a pharmaceutical composition that includes the chemical entity and one or more pharmaceutically acceptable excipients, and optionally one or more additional therapeutic agents as described herein.

In some embodiments, the chemical entities can be administered in combination with one or more conventional pharmaceutical excipients. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a chemical entity as described herein in the range of 0.005% to 100% with the balance made up from non-toxic excipient may be prepared. The contemplated compositions may contain 0.001%-100% of a chemical entity provided herein, in one embodiment 0.1-95%, in another embodiment 75-85%, in a further embodiment 20-80%. Actual methods of preparing such dosage forms are known, or will be apparent, to those skilled in this art; for example, see Remington: The Science and Practice of Pharmacy, 22$^{nd}$ Edition (Pharmaceutical Press, London, U K. 2012).

In some embodiments, an NLRP3 antagonist and/or an anti-TNFα agent disclosed herein is administered as a pharmaceutical composition that includes the NLRP3 antagonist and/or anti-TNFα agent and one or more pharmaceutically acceptable excipients, and optionally one or more additional therapeutic agents as described herein. Preferably the pharmaceutical composition that includes an NLRP3 antagonist and an anti-TNFα agent.

Preferably the above pharmaceutical composition embodiments comprise an NLRP3 antagonist disclosed herein. More preferably the above pharmaceutical composition embodiments comprise an NLRP3 antagonist and an anti-TNFα agent disclosed herein.

Routes of Administration and Composition Components

In some embodiments, the chemical entities described herein or a pharmaceutical composition thereof can be administered to subject in need thereof by any accepted route of administration. Acceptable routes of administration include, but are not limited to, buccal, cutaneous, endocervical, endosinusial, endotracheal, enteral, epidural, interstitial, intra-abdominal, intra-arterial, intrabronchial, intraburpal, intracerebral, intracisternal, intracoronary, intradermal, intraductal, intraduodenal, intradural, intraepidermal, intraesophageal, intragastric, intragingival, intraileal, intralymphatic, intramedullary, intrameningeal, intramuscular, intraovarian, intraperitoneal, intraprostatic, intrapulmonary, intrasinal, intraspinal, intrasynovial, intratesticular, intrathecal, intratubular, intratumoral, intrauterine, intravascular, intravenous, nasal, nasogastric, oral, parenteral, percutaneous, peridural, rectal, respiratory (inhalation), subcutaneous, sublingual, submucosal, topical, transdermal, transmucosal, transtracheal, ureteral, urethral and vaginal. In certain embodiments, a preferred route of administration is parenteral (e.g., intratumoral).

Compositions can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and the preparations can also be emulsified. The preparation of such formulations will be known to those of skill in the art in light of the present disclosure.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Intratumoral injections are discussed, e.g., in Lammers, et al., "*Effect of Intratumoral Injection on the Biodistribution and the Therapeutic Potential of HPMA Copolymer-Based Drug Delivery Systems*" Neoplasia. 2006, 10, 788-795.

In certain embodiments, the chemical entities described herein or a pharmaceutical composition thereof are suitable for local, topical administration to the digestive or GI tract, e.g., rectal administration. Rectal compositions include, without limitation, enemas, rectal gels, rectal foams, rectal aerosols, suppositories, jelly suppositories, and enemas (e.g., retention enemas).

Pharmacologically acceptable excipients usable in the rectal composition as a gel, cream, enema, or rectal suppository, include, without limitation, any one or more of cocoa butter glycerides, synthetic polymers such as polyvinylpyrrolidone, PEG (like PEG ointments), glycerine, glycerinated gelatin, hydrogenated vegetable oils, poloxamers, mixtures of polyethylene glycols of various molecular weights and fatty acid esters of polyethylene glycol Vaseline, anhydrous lanolin, shark liver oil, sodium saccharinate, menthol, sweet almond oil, sorbitol, sodium benzoate, anoxid SBN, vanilla essential oil, aerosol, parabens in phenoxyethanol, sodium methyl p-oxybenzoate, sodium propyl p-oxybenzoate, diethylamine, carbomers, carbopol, methyloxybenzoate, macrogol cetostearyl ether, cocoyl caprylocaprate, isopropyl alcohol, propylene glycol, liquid paraffin, xanthan gum, carboxy-metabisulfite, sodium edetate, sodium benzoate, potassium metabisulfite, grapefruit seed extract, methyl sulfonyl methane (MSM), lactic acid, glycine, vitamins, such as vitamin A and E and potassium acetate.

In certain embodiments, suppositories can be prepared by mixing the chemical entities described herein with suitable non-irritating excipients or carriers such as cocoa butter, polyethylene glycol or a suppository wax which are solid at ambient temperature but liquid at body temperature and therefore melt in the rectum and release the active compound. In other embodiments, compositions for rectal administration are in the form of an enema.

In other embodiments, the compounds described herein or a pharmaceutical composition thereof are suitable for local delivery to the digestive or GI tract by way of oral administration (e.g., solid or liquid dosage forms.).

Solid dosage forms for oral administration include capsules, tablets, pills, powders, and granules. In such solid dosage forms, the chemical entity is mixed with one or more pharmaceutically acceptable excipients, such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

In one embodiment, the compositions will take the form of a unit dosage form such as a pill or tablet and thus the composition may contain, along with a chemical entity provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more chemical entities provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Other physiologically acceptable compounds include wetting agents, emulsifying agents, dispersing agents or preservatives that are particularly useful for preventing the growth or action of microorganisms. Various preservatives are well known and include, for example, phenol and ascorbic acid.

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

In certain embodiments, solid oral dosage forms can further include one or more components that chemically and/or structurally predispose the composition for delivery of the chemical entity to the stomach or the lower GI; e.g., the ascending colon and/or transverse colon and/or distal colon and/or small bowel. Exemplary formulation techniques are described in, e.g., Filipski, K. J., et al., *Current Topics in Medicinal Chemistry*, 2013, 13, 776-802, which is incorporated herein by reference in its entirety.

Examples include upper-GI targeting techniques, e.g., Accordion Pill (Intec Pharma), floating capsules, and materials capable of adhering to mucosal walls.

Other examples include lower-GI targeting techniques. For targeting various regions in the intestinal tract, several enteric/pH-responsive coatings and excipients are available. These materials are typically polymers that are designed to dissolve or erode at specific pH ranges, selected based upon the GI region of desired drug release. These materials also function to protect acid labile drugs from gastric fluid or limit exposure in cases where the active ingredient may be irritating to the upper GI (e.g., hydroxypropyl methylcellulose phthalate series, Coateric (polyvinyl acetate phthalate), cellulose acetate phthalate, hydroxypropyl methylcellulose acetate succinate, Eudragit series (methacrylic acid-methyl methacrylate copolymers), and Marcoat). Other techniques include dosage forms that respond to local flora in the GI tract, Pressure-controlled colon delivery capsule, and Pulsincap.

Ocular compositions can include, without limitation, one or more of any of the following: viscogens (e.g., Carboxymethylcellulose, Glycerin, Polyvinylpyrrolidone, Polyethylene glycol); Stabilizers (e.g., Pluronic (triblock copolymers), Cyclodextrins); Preservatives (e.g., Benzalkonium chloride, ETDA, SofZia (boric acid, propylene glycol, sorbitol, and zinc chloride; Alcon Laboratories, Inc.), Purite (stabilized oxychloro complex; Allergan, Inc.)).

Topical compositions can include ointments and creams. Ointments are semisolid preparations that are typically based on petrolatum or other petroleum derivatives. Creams containing the selected active agent are typically viscous liquid or semisolid emulsions, often either oil-in-water or water-in-oil. Cream bases are typically water-washable, and contain an oil phase, an emulsifier and an aqueous phase. The oil phase, also sometimes called the "internal" phase, is generally comprised of petrolatum and a fatty alcohol such as cetyl or stearyl alcohol; the aqueous phase usually, although not necessarily, exceeds the oil phase in volume, and generally contains a humectant. The emulsifier in a cream formulation is generally a nonionic, anionic, cationic or amphoteric surfactant. As with other carriers or vehicles, an ointment base should be inert, stable, nonirritating and non-sensitizing.

In any of the foregoing embodiments, pharmaceutical compositions described herein can include one or more one or more of the following: lipids, interbilayer crosslinked multilamellar vesicles, biodegradable poly(D,L-lactic-co-glycolic acid) [PLGA]-based or poly anhydride-based nanoparticles or microparticles, and nanoporous particle-supported lipid bilayers.

Enema Formulations

In some embodiments, enema formulations containing the chemical entities described herein are provided in "ready-to-use" form.

In some embodiments, enema formulations containing the chemical entities described herein are provided in one or more kits or packs. In certain embodiments, the kit or pack includes two or more separately contained/packaged components, e.g. two components, which when mixed together, provide the desired formulation (e.g., as a suspension). In certain of these embodiments, the two component system includes a first component and a second component, in which: (i) the first component (e.g., contained in a sachet) includes the chemical entity (as described anywhere herein) and optionally one or more pharmaceutically acceptable excipients (e.g., together formulated as a solid preparation, e.g., together formulated as a wet granulated solid preparation); and (ii) the second component (e.g., contained in a vial or bottle) includes one or more liquids and optionally one or more other pharmaceutically acceptable excipients together forming a liquid carrier. Prior to use (e.g., immediately prior to use), the contents of (i) and (ii) are combined to form the desired enema formulation, e.g., as a suspension. In other embodiments, each of component (i) and (ii) is provided in its own separate kit or pack.

In some embodiments, each of the one or more liquids is water, or a physiologically acceptable solvent, or a mixture of water and one or more physiologically acceptable solvents. Typical such solvents include, without limitation, glycerol, ethylene glycol, propylene glycol, polyethylene glycol and polypropylene glycol. In certain embodiments, each of the one or more liquids is water. In other embodiments, each of the one or more liquids is an oil, e.g. natural and/or synthetic oils that are commonly used in pharmaceutical preparations.

Further pharmaceutical excipients and carriers that may be used in the pharmaceutical products herein described are listed in various handbooks (e.g. D. E. Bugay and W. P. Findlay (Eds) Pharmaceutical excipients (Marcel Dekker, New York, 1999), E-M Hoepfner, A. Reng and P. C. Schmidt (Eds) Fiedler Encyclopedia of Excipients for Pharmaceuticals, Cosmetics and Related Areas (Edition Cantor, Munich, 2002) and H. P. Fielder (Ed) Lexikon der Hilfsstoffe für Pharmazie, Kosmetik and angrenzende Gebiete (Edition Cantor Aulendorf, 1989)).

In some embodiments, each of the one or more pharmaceutically acceptable excipients can be independently selected from thickeners, viscosity enhancing agents, bulking agents, mucoadhesive agents, penetration enhancers, buffers, preservatives, diluents, binders, lubricants, glidants, disintegrants, fillers, solubilizing agents, pH modifying agents, preservatives, stabilizing agents, anti-oxidants, wetting or emulsifying agents, suspending agents, pigments, colorants, isotonic agents, chelating agents, emulsifiers, and diagnostic agents.

In certain embodiments, each of the one or more pharmaceutically acceptable excipients can be independently selected from thickeners, viscosity enhancing agents, mucoadhesive agents, buffers, preservatives, diluents, binders, lubricants, glidants, disintegrants, and fillers.

In certain embodiments, each of the one or more pharmaceutically acceptable excipients can be independently selected from thickeners, viscosity enhancing agents, bulking agents, mucoadhesive agents, buffers, preservatives, and fillers.

In certain embodiments, each of the one or more pharmaceutically acceptable excipients can be independently selected from diluents, binders, lubricants, glidants, and disintegrants.

Examples of thickeners, viscosity enhancing agents, and mucoadhesive agents include without limitation: gums, e.g. xanthan gum, guar gum, locust bean gum, tragacanth gums, karaya gum, ghatti gum, cholla gum, *psyllium* seed gum and gum arabic; poly(carboxylic acid-containing) based polymers, such as poly (acrylic, maleic, itaconic, citraconic, hydroxyethyl methacrylic or methacrylic) acid which have strong hydrogen-bonding groups, or derivatives thereof such as salts and esters; cellulose derivatives, such as methyl cellulose, ethyl cellulose, methylethyl cellulose, hydroxymethyl cellulose, hydroxyethyl cellulose, hydroxypropyl cellulose, hydroxyethyl ethyl cellulose, carboxymethyl cellulose, hydroxypropylmethyl cellulose or cellulose esters or ethers or derivatives or salts thereof; clays such as manomorillonite clays, e.g. Veegun, attapulgite clay; polysaccharides such as dextran, pectin, amylopectin, agar, mannan or polygalactonic acid or starches such as hydroxypropyl starch or carboxymethyl starch; polypeptides such as casein, gluten, gelatin, fibrin glue; chitosan, e.g. lactate or glutamate or carboxymethyl chitin; glycosaminoglycans such as hyaluronic acid; metals or water soluble salts of alginic acid such as sodium alginate or magnesium alginate; schleroglucan; adhesives containing bismuth oxide or aluminium oxide; atherocollagen; polyvinyl polymers such as carboxyvinyl polymers; polyvinylpyrrolidone (povidone); polyvinyl alcohol; polyvinyl acetates, polyvinylmethyl ethers, polyvinyl chlorides, polyvinylidenes, and/or the like; polycarboxylated vinyl polymers such as polyacrylic acid as mentioned above; polysiloxanes; polyethers; polyethylene oxides and glycols; polyalkoxys and polyacrylamides and derivatives and salts thereof. Preferred examples can include cellulose derivatives, such as methyl cellulose, ethyl cellulose, methylethyl cellulose, hydroxymethyl cellulose, hydroxyethyl cellulose, hydroxypropyl cellulose, hydroxyethyl ethyl cellulose, carboxymethyl cellulose, hydroxypropylmethyl cellulose or cellulose esters or ethers or derivatives or salts thereof (e.g., methyl cellulose); and polyvinyl polymers such as polyvinylpyrrolidone (povidone).

Examples of preservatives include without limitation: benzalkonium chloride, benzoxonium chloride, benzethonium chloride, cetrimide, sepazonium chloride, cetylpyridinium chloride, domiphen bromide (Bradosol®), thiomersal, phenylmercuric nitrate, phenylmercuric acetate, phenylmercuric borate, methylparaben, propylparaben, chlorobutanol, benzyl alcohol, phenyl ethyl alcohol, chlorohexidine, polyhexamethylene biguanide, sodium perborate, imidazolidinyl urea, sorbic acid, Purite®), Polyquart®), and sodium perborate tetrahydrate and the like.

In certain embodiments, the preservative is a paraben, or a pharmaceutically acceptable salt thereof. In some embodiments, the paraben is an alkyl substituted 4-hydroxybenzoate, or a pharmaceutically acceptable salt or ester thereof. In certain embodiments, the alkyl is a C1-C4 alkyl. In certain embodiments, the preservative is methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof.

Examples of buffers include without limitation: phosphate buffer system (sodium dihydrogen phosphate dehydrate, disodium phosphate dodecahydrate, bibasic sodium phosphate, anhydrous monobasic sodium phosphate), bicarbonate buffer system, and bisulfate buffer system.

Examples of disintegrants include, without limitation: carmellose calcium, low substituted hydroxypropyl cellulose (L-HPC), carmellose, croscarmellose sodium, partially pregelatinized starch, dry starch, carboxymethyl starch sodium, crospovidone, polysorbate 80 (polyoxyethylenesorbitan oleate), starch, sodium starch glycolate, hydroxypropyl cellulose pregelatinized starch, clays, cellulose, alginine, gums or cross linked polymers, such as cross-linked PVP (Polyplasdone XL from GAF Chemical Corp). In certain embodiments, the disintegrant is crospovidone.

Examples of glidants and lubricants (aggregation inhibitors) include without limitation: talc, magnesium stearate, calcium stearate, colloidal silica, stearic acid, aqueous silicon dioxide, synthetic magnesium silicate, fine granulated silicon oxide, starch, sodium laurylsulfate, boric acid, magnesium oxide, waxes, hydrogenated oil, polyethylene glycol, sodium benzoate, stearic acid glycerol behenate, polyethylene glycol, and mineral oil. In certain embodiments, the glidant/lubricant is magnesium stearate, talc, and/or colloidal silica; e.g., magnesium stearate and/or talc.

Examples of diluents, also referred to as "fillers" or "bulking agents" include without limitation: dicalcium phosphate dihydrate, calcium sulfate, lactose (e.g., lactose monohydrate), sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. In certain embodiments, the diluent is lactose (e.g., lactose monohydrate).

Examples of binders include without limitation: starch, pregelatinized starch, gelatin, sugars (including sucrose, glucose, dextrose, lactose and sorbitol), polyethylene glycol, waxes, natural and synthetic gums such as acacia tragacanth, sodium alginate cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone (povidone). In certain embodiments, the binder is polyvinylpyrrolidone (povidone).

In some embodiments, enema formulations containing the chemical entities described herein include water and one or more (e.g., all) of the following excipients:

One or more (e.g., one, two, or three) thickeners, viscosity enhancing agents, binders, and/or mucoadhesive agents (e.g., cellulose or cellulose esters or ethers or derivatives or salts thereof (e.g., methyl cellulose); and polyvinyl polymers such as polyvinylpyrrolidone (povidone);

One or more (e.g., one or two; e.g., two) preservatives, such as a paraben, e.g., methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof;

One or more (e.g., one or two; e.g., two) buffers, such as phosphate buffer system (e.g., sodium dihydrogen phosphate dehydrate, disodium phosphate dodecahydrate);

One or more (e.g., one or two, e.g., two) glidants and/or lubricants, such as magnesium stearate and/or talc;

One or more (e.g., one or two; e.g., one) disintegrants, such as crospovidone; and One or more (e.g., one or two; e.g., one) diluents, such as lactose (e.g., lactose monohydrate).

In certain of these embodiments, the chemical entity is a compound of Formula AA, or a pharmaceutically acceptable salt and/or hydrate and/or cocrystal thereof.

In certain embodiments, enema formulations containing the chemical entities described herein include water, methyl cellulose, povidone, methylparaben, propylparaben, sodium dihydrogen phosphate dehydrate, disodium phosphate dodecahydrate, crospovidone, lactose monohydrate, magnesium stearate, and talc. In certain of these embodiments, the chemical entity is a compound of Formula AA, or a pharmaceutically acceptable salt and/or hydrate and/or cocrystal thereof.

In certain embodiments, enema formulations containing the chemical entities described herein are provided in one or more kits or packs. In certain embodiments, the kit or pack includes two separately contained/packaged components, which when mixed together, provide the desired formulation (e.g., as a suspension). In certain of these embodiments, the two component system includes a first component and a second component, in which: (i) the first component (e.g., contained in a sachet) includes the chemical entity (as described anywhere herein) and one or more pharmaceutically acceptable excipients (e.g., together formulated as a solid preparation, e.g., together formulated as a wet granulated solid preparation); and (ii) the second component (e.g., contained in a vial or bottle) includes one or more liquids and one or more other pharmaceutically acceptable excipients together forming a liquid carrier. In other embodiments, each of component (i) and (ii) is provided in its own separate kit or pack.

In certain of these embodiments, component (i) includes the chemical entity (e.g., a compound of Formula AA, or a pharmaceutically acceptable salt and/or hydrate and/or cocrystal thereof; e.g., a compound of Formula AA) and one or more (e.g., all) of the following excipients:

(a) One or more (e.g., one) binders (e.g., a polyvinyl polymer, such as polyvinylpyrrolidone (povidone));

(b) One or more (e.g., one or two, e.g., two) glidants and/or lubricants, such as magnesium stearate and/or talc;

(c) One or more (e.g., one or two; e.g., one) disintegrants, such as crospovidone; and (d) One or more (e.g., one or two; e.g., one) diluents, such as lactose (e.g., lactose monohydrate).

In certain embodiments, component (i) includes from about 40 weight percent to about 80 weight percent (e.g., from about 50 weight percent to about 70 weight percent, from about 55 weight percent to about 70 weight percent; from about 60 weight percent to about 65 weight percent; e.g., about 62.1 weight percent) of the chemical entity (e.g., a compound of Formula AA, or a pharmaceutically acceptable salt and/or hydrate and/or cocrystal thereof).

In certain embodiments, component (i) includes from about 0.5 weight percent to about 5 weight percent (e.g., from about 1.5 weight percent to about 4.5 weight percent, from about 2 weight percent to about 3.5 weight percent; e.g., about 2.76 weight percent) of the binder (e.g., povidone).

In certain embodiments, component (i) includes from about 0.5 weight percent to about 5 weight percent (e.g., from about 0.5 weight percent to about 3 weight percent, from about 1 weight percent to about 3 weight percent; about 2 weight percent e.g., about 1.9 weight percent) of the disintegrant (e.g., crospovidone).

In certain embodiments, component (i) includes from about 10 weight percent to about 50 weight percent (e.g., from about 20 weight percent to about 40 weight percent, from about 25 weight percent to about 35 weight percent; e.g., about 31.03 weight percent) of the diluent (e.g., lactose, e.g., lactose monohydrate).

In certain embodiments, component (i) includes from about 0.05 weight percent to about 5 weight percent (e.g., from about 0.05 weight percent to about 3 weight percent) of the glidants and/or lubricants.

In certain embodiments (e.g., when component (i) includes one or more lubricants, such as magnesium stearate), component (i) includes from about 0.05 weight percent to about 1 weight percent (e.g., from about 0.05 weight percent to about 1 weight percent; from about 0.1 weight percent to about 1 weight percent; from about 0.1 weight percent to about 0.5 weight percent; e.g., about 0.27 weight percent) of the lubricant (e.g., magnesium stearate).

In certain embodiments (when component (i) includes one or more lubricants, such as talc), component (i) includes from about 0.5 weight percent to about 5 weight percent (e.g., from about 0.5 weight percent to about 3 weight percent, from about 1 weight percent to about 3 weight percent; from about 1.5 weight percent to about 2.5 weight percent; from about 1.8 weight percent to about 2.2 weight percent; about 1.93 weight percent) of the lubricant (e.g., talc).

In certain of these embodiments, each of (a), (b), (c), and (d) above is present.

In certain embodiments, component (i) includes the ingredients and amounts as shown in Table A.

TABLE A

| Ingredient | Weight Percent |
|---|---|
| A compound of Formula AA | 40 weight percent to about 80 weight percent (e.g., from about 50 weight percent to about 70 weight percent, from about 55 weight percent to about 70 weight percent; from about 60 weight percent to about 65 weight percent; e.g., about 62.1 weight percent) |
| Crospovidone (Kollidon CL) | 0.5 weight percent to about 5 weight percent (e.g., from about 0.5 weight percent to about 3 weight percent, from about 1 weight percent to about 3 weight percent; about 1.93 weight percent |
| lactose monohydrate (Pharmatose 200M) | about 10 weight percent to about 50 weight percent (e.g., from about 20 weight percent to about 40 weight percent, from about 25 weight percent to about 35 weight percent; e.g., about 31.03 weight percent |

TABLE A-continued

| Ingredient | Weight Percent |
| --- | --- |
| Povidone (Kollidon K30) | about 0.5 weight percent to about 5 weight percent (e.g., from about 1.5 weight percent to about 4.5 weight percent, from about 2 weight percent to about 3.5 weight percent; e.g., about 2.76 weight percent |
| talc | 0.5 weight percent to about 5 weight percent (e.g., from about 0.5 weight percent to about 3 weight percent, from about 1 weight percent to about 3 weight percent; from about 1.5 weight percent to about 2.5 weight percent; from about 1.8 weight percent to about 2.2 weight percent; e.g., about 1.93 weight percent |
| Magnesium stearate | about 0.05 weight percent to about 1 weight percent (e.g., from about 0.05 weight percent to about 1 weight percent; from about 0.1 weight percent to about 1 weight percent; from about 0.1 weight percent to about 0.5 weight percent; e.g., about 0.27 weight percent |

In certain embodiments, component (i) includes the ingredients and amounts as shown in Table B.

TABLE B

| Ingredient | Weight Percent |
| --- | --- |
| A compound of Formula AA | About 62.1 weight percent) |
| Crospovidone (Kollidon CL) | About 1.93 weight percent |
| lactose monohydrate (Pharmatose 200M) | About 31.03 weight percent |
| Povidone (Kollidon K30) | About 2.76 weight percent |
| talc | About 1.93 weight percent |
| Magnesium stearate | About 0.27 weight percent |

In certain embodiments, component (i) is formulated as a wet granulated solid preparation. In certain of these embodiments an internal phase of ingredients (the chemical entity, disintegrant, and diluent) are combined and mixed in a high-shear granulator. A binder (e.g., povidone) is dissolved in water to form a granulating solution. This solution is added to the Inner Phase mixture resulting in the development of granules. While not wishing to be bound by theory, granule development is believed to be facilitated by the interaction of the polymeric binder with the materials of the internal phase. Once the granulation is formed and dried, an external phase (e.g., one or more lubricants—not an intrinsic component of the dried granulation), is added to the dry granulation. It is believed that lubrication of the granulation is important to the flowability of the granulation, in particular for packaging.

In certain of the foregoing embodiments, component (ii) includes water and one or more (e.g., all) of the following excipients:
(a') One or more (e.g., one, two; e.g., two) thickeners, viscosity enhancing agents, binders, and/or mucoadhesive agents (e.g., cellulose or cellulose esters or ethers or derivatives or salts thereof (e.g., methyl cellulose); and polyvinyl polymers such as polyvinylpyrrolidone (povidone);
(b') One or more (e.g., one or two; e.g., two) preservatives, such as a paraben, e.g., methyl 4-hydroxybenzoate (methylparaben), or a pharmaceutically acceptable salt or ester thereof, propyl 4-hydroxybenzoate (propylparaben), or a pharmaceutically acceptable salt or ester thereof, or a combination thereof, and
(c') One or more (e.g., one or two; e.g., two) buffers, such as phosphate buffer system (e.g., sodium dihydrogen phosphate dihydrate, disodium phosphate dodecahydrate);

In certain of the foregoing embodiments, component (ii) includes water and one or more (e.g., all) of the following excipients:
(a") a first thickener, viscosity enhancing agent, binder, and/or mucoadhesive agent (e.g., a cellulose or cellulose ester or ether or derivative or salt thereof (e.g., methyl cellulose));
(a'") a second thickener, viscosity enhancing agent, binder, and/or mucoadhesive agent (e.g., a polyvinyl polymer, such as polyvinylpyrrolidone (povidone));
(b") a first preservative, such as a paraben, e.g., propyl 4-hydroxybenzoate (propylparaben), or a pharmaceutically acceptable salt or ester thereof;
(b'") a second preservative, such as a paraben, e.g., methyl 4-hydroxybenzoate (methylparaben), or a pharmaceutically acceptable salt or ester thereof,
(c") a first buffer, such as phosphate buffer system (e.g., disodium phosphate dodecahydrate);
(c'") a second buffer, such as phosphate buffer system (e.g., sodium dihydrogen phosphate dehydrate), In certain embodiments, component (ii) includes from about 0.05 weight percent to about 5 weight percent (e.g., from about 0.05 weight percent to about 3 weight percent, from about 0.1 weight percent to about 3 weight percent; e.g., about 1.4 weight percent) of (a").

In certain embodiments, component (ii) includes from about 0.05 weight percent to about 5 weight percent (e.g., from about 0.05 weight percent to about 3 weight percent, from about 0.1 weight percent to about 2 weight percent; e.g., about 1.0 weight percent) of (a'").

In certain embodiments, component (ii) includes from about 0.005 weight percent to about 0.1 weight percent (e.g., from about 0.005 weight percent to about 0.05 weight percent; e.g., about 0.02 weight percent) of (b").

In certain embodiments, component (ii) includes from about 0.05 weight percent to about 1 weight percent (e.g., from about 0.05 weight percent to about 0.5 weight percent; e.g., about 0.20 weight percent) of (b'").

In certain embodiments, component (ii) includes from about 0.05 weight percent to about 1 weight percent (e.g., from about 0.05 weight percent to about 0.5 weight percent; e.g., about 0.15 weight percent) of (c").

In certain embodiments, component (ii) includes from about 0.005 weight percent to about 0.5 weight percent (e.g., from about 0.005 weight percent to about 0.3 weight percent; e.g., about 0.15 weight percent) of (c'").

In certain of these embodiments, each of (a")-(c'") is present.

In certain embodiments, component (ii) includes water (up to 1000) and the ingredients and amounts as shown in Table C.

TABLE C

| Ingredient | Weight Percent |
| --- | --- |
| methyl cellulose (Methocel A15C premium) | 0.05 weight percent to about 5 weight percent (e.g., from about 0.05 weight percent to about 3 weight percent, from about 0.1 weight percent to about 3 weight percent; e.g., about 1.4 weight percent |

TABLE C-continued

| Ingredient | Weight Percent |
|---|---|
| Povidone (Kollidon K30) | 0.05 weight percent to about 5 weight percent (e.g., from about 0.05 weight percent to about 3 weight percent, from about 0.1 weight percent to about 2 weight percent; e.g., about 1.0 weight percent |
| propyl 4-hydroxybenzoate | about 0.005 weight percent to about 0.1 weight percent (e.g., from about 0.005 weight percent to about 0.05 weight percent; e.g., about 0.02 weight percent) |
| methyl 4-hydroxybenzoate | about 0.05 weight percent to about 1 weight percent (e.g., from about 0.05 weight percent to about 0.5 weight percent; e.g., about 0.20 weight percent) |
| disodium phosphate dodecahydrate | about 0.05 weight percent to about 1 weight percent (e.g., from about 0.05 weight percent to about 0.5 weight percent; e.g., about 0.15 weight percent) |
| sodium dihydrogen phospahate dihydrate | about 0.005 weight percent to about 0.5 weight percent (e.g., from about 0.005 weight percent to about 0.3 weight percent; e.g., about 0.15 weight percent) |

In certain embodiments, component (ii) includes water (up to 100%) and the ingredients and amounts as shown in Table D.

TABLE D

| Ingredient | Weight Percent |
|---|---|
| methyl cellulose (Methocel A15C premium) | about 1.4 weight percent |
| Povidone (Kollidon K30) | about 1.0 weight percent |
| propyl 4-hydroxybenzoate | about 0.02 weight percent |
| methyl 4-hydroxybenzoate | about 0.20 weight percent |
| disodium phosphate dodecahydrate | about 0.15 weight percent |
| sodium dihydrogen phospahate dihydrate | about 0.15 weight percent |

Ready-to-use" enemas are generally be provided in a "single-use" sealed disposable container of plastic or glass. Those formed of a polymeric material preferably have sufficient flexibility for ease of use by an unassisted patient. Typical plastic containers can be made of polyethylene. These containers may comprise a tip for direct introduction into the rectum. Such containers may also comprise a tube between the container and the tip. The tip is preferably provided with a protective shield which is removed before use. Optionally the tip has a lubricant to improve patient compliance.

In some embodiments, the enema formulation (e.g., suspension) is poured into a bottle for delivery after it has been prepared in a separate container. In certain embodiments, the bottle is a plastic bottle (e.g., flexible to allow for delivery by squeezing the bottle), which can be a polyethylene bottle (e.g., white in color). In some embodiments, the bottle is a single chamber bottle, which contains the suspension or solution. In other embodiments, the bottle is a multichamber bottle, where each chamber contains a separate mixture or solution. In still other embodiments, the bottle can further include a tip or rectal cannula for direct introduction into the rectum.

Dosages

The dosages may be varied depending on the requirement of the patient, the severity of the condition being treating and the particular compound being employed. Determination of the proper dosage for a particular situation can be determined by one skilled in the medical arts. The total daily dosage may be divided and administered in portions throughout the day or by means providing continuous delivery.

In some embodiments, the compounds described herein are administered at a dosage of from about 0.001 mg/Kg to about 500 mg/Kg (e.g., from about 0.001 mg/Kg to about 200 mg/Kg; from about 0.01 mg/Kg to about 200 mg/Kg; from about 0.01 mg/Kg to about 150 mg/Kg; from about 0.01 mg/Kg to about 100 mg/Kg; from about 0.01 mg/Kg to about 50 mg/Kg; from about 0.01 mg/Kg to about 10 mg/Kg; from about 0.01 mg/Kg to about 5 mg/Kg; from about 0.01 mg/Kg to about 1 mg/Kg; from about 0.01 mg/Kg to about 0.5 mg/Kg; from about 0.01 mg/Kg to about 0.1 mg/Kg; from about 0.1 mg/Kg to about 200 mg/Kg; from about 0.1 mg/Kg to about 150 mg/Kg; from about 0.1 mg/Kg to about 100 mg/Kg; from about 0.1 mg/Kg to about 50 mg/Kg; from about 0.1 mg/Kg to about 10 mg/Kg; from about 0.1 mg/Kg to about 5 mg/Kg; from about 0.1 mg/Kg to about 1 mg/Kg; from about 0.1 mg/Kg to about 0.5 mg/Kg).

In some embodiments, enema formulations include from about 0.5 mg to about 2500 mg (e.g., from about 0.5 mg to about 2000 mg, from about 0.5 mg to about 1000 mg, from about 0.5 mg to about 750 mg, from about 0.5 mg to about 600 mg, from about 0.5 mg to about 500 mg, from about 0.5 mg to about 400 mg, from about 0.5 mg to about 300 mg, from about 0.5 mg to about 200 mg; e.g., from about 5 mg to about 2500 mg, from about 5 mg to about 2000 mg, from about 5 mg to about 1000 mg; from about 5 mg to about 750 mg; from about 5 mg to about 600 mg; from about 5 mg to about 500 mg; from about 5 mg to about 400 mg; from about 5 mg to about 300 mg; from about 5 mg to about 200 mg; e.g., from about 50 mg to about 2000 mg, from about 50 mg to about 1000 mg, from about 50 mg to about 750 mg, from about 50 mg to about 600 mg, from about 50 mg to about 500 mg, from about 50 mg to about 400 mg, from about 50 mg to about 300 mg, from about 50 mg to about 200 mg; e.g., from about 100 mg to about 2500 mg, from about 100 mg to about 2000 mg, from about 100 mg to about 1000 mg, from about 100 mg to about 750 mg, from about 100 mg to about 700 mg, from about 100 mg to about 600 mg, from about 100 mg to about 500 mg, from about 100 mg to about 400 mg, from about 100 mg to about 300 mg, from about 100 mg to about 200 mg; e.g., from about 150 mg to about 2500 mg, from about 150 mg to about 2000 mg, from about 150 mg to about 1000 mg, from about 150 mg to about 750 mg, from about 150 mg to about 700 mg, from about 150 mg to about 600 mg, from about 150 mg to about 500 mg, from about 150 mg to about 400 mg, from about 150 mg to about 300 mg, from about 150 mg to about 200 mg; e.g., from about 150 mg to about 500 mg; e.g., from about 300 mg to about 2500 mg, from about 300 mg to about 2000 mg, from about 300 mg to about 1000 mg, from about 300 mg to about 750 mg, from about 300 mg to about 700 mg, from about 300 mg to about 600 mg; e.g., from about 400 mg to about 2500 mg, from about 400 mg to about 2000 mg, from about 400 mg to about 1000 mg, from about 400 mg to about 750 mg, from about 400 mg to about 700 mg, from about 400 mg to about 600 from about 400 mg to about 500 mg; e.g., 150 mg or 450 mg) of the chemical entity in from about 1 mL to about 3000 mL (e.g., from about 1 mL to about 2000 mL, from about 1 mL to about 1000 mL, from about 1 mL to about 500 mL, from about 1 mL to about 250 mL, from about 1 mL to about 100 mL, from about 1 mL to about 1000 mL, from about 10 mL to about 500 mL, from about 10 mL to about 250 mL, from about 10 mL to about 100 mL, from about 30 mL to about 90 mL, from about 40 mL to about 80 mL; from about 50 mL to about 70 mL; e.g., about 1 mL, about 5 mL, about 10 mL, about 15 mL, about 20 mL, about 25 mL, about 30 mL, about 35 mL, about 40 mL, about 45 mL, about 50 mL, about 55 mL, about 60 mL, about 65 mL, about 70 mL, about 75 mL, about 100 mL, about 250 mL, or about 500 mL, or about 1000 mL, or about 2000 mL, or about 3000 mL; e.g., 60 mL) of liquid carrier.

In certain embodiments, enema formulations include from about 50 mg to about 250 mg (e.g., from about 100 mg to about 200; e.g., about 150 mg) of the chemical entity in from about 10 mL to about 100 mL (e.g., from about 20 mL to about 100 mL, from about 30 mL to about 90 mL, from about 40 mL to about 80 mL; from about 50 mL to about 70 mL) of liquid carrier. In certain embodiments, enema formulations include about 150 mg of the chemical entity in about 60 mL of the liquid carrier. In certain of these embodiments, the chemical entity is a compound of Formula AA, or a pharmaceutically acceptable salt and/or hydrate and/or cocrystal thereof. For example, enema formulations can include about 150 mg of a compound of Formula AA in about 60 mL of the liquid carrier.

In certain embodiments, enema formulations include from about 350 mg to about 550 mg (e.g., from about 400 mg to about 500; e.g., about 450 mg) of the chemical entity in from about 10 mL to about 100 mL (e.g., from about 20 mL to about 100 mL, from about 30 mL to about 90 mL, from about 40 mL to about 80 mL; from about 50 mL to about 70 mL) of liquid carrier. In certain embodiments, enema formulations include about 450 mg of the chemical entity in about 60 mL of the liquid carrier. In certain of these embodiments, the chemical entity is a compound of Formula AA, or a pharmaceutically acceptable salt and/or hydrate and/or cocrystal thereof. For example, enema formulations can include about 450 mg of a compound of Formula AA in about 60 mL of the liquid carrier.

In some embodiments, enema formulations include from about from about 0.01 mg/mL to about 50 mg/mL (e.g., from about 0.01 mg/mL to about 25 mg/mL; from about 0.01 mg/mL to about 10 mg/mL; from about 0.01 mg/mL to about 5 mg/mL; from about 0.1 mg/mL to about 50 mg/mL; from about 0.01 mg/mL to about 25 mg/mL; from about 0.1 mg/mL to about 10 mg/mL; from about 0.1 mg/mL to about 5 mg/mL; from about 1 mg/mL to about 10 mg/mL; from about 1 mg/mL to about 5 mg/mL; from about 5 mg/mL to about 10 mg/mL; e.g., about 2.5 mg/mL or about 7.5 mg/mL) of the chemical entity in liquid carrier. In certain of these embodiments, the chemical entity is a compound of Formula AA, or a pharmaceutically acceptable salt and/or hydrate and/or cocrystal thereof. For example, enema formulations can include about 2.5 mg/mL or about 7.5 mg/mL of a compound of Formula AA in liquid carrier.

Regimens

The foregoing dosages can be administered on a daily basis (e.g., as a single dose or as two or more divided doses) or non-daily basis (e.g., every other day, every two days, every three days, once weekly, twice weeks, once every two weeks, once a month).

In some embodiments, the period of administration of a compound described herein is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In an embodiment, a therapeutic compound is administered to an individual for a period of time followed by a separate period of time. In another embodiment, a therapeutic compound is administered for a first period and a second period following the first period, with administration stopped during the second period, followed by a third period where administration of the therapeutic compound is started and then a fourth period following the third period where administration is stopped. In an aspect of this embodiment, the period of administration of a therapeutic compound followed by a period where administration is stopped is repeated for a determined or undetermined period of time. In a further embodiment, a period of administration is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In a further embodiment, a period of during which administration is stopped is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

Methods of Treatment

In some embodiments, methods for treating a subject having condition, disease or disorder in which a decrease or increase in NLRP3 activity (e.g., an increase, e.g., NLRP3 signaling) contributes to the pathology and/or symptoms and/or progression of the condition, disease or disorder are provided, comprising administering to a subject an effective amount of a chemical entity described herein (e.g., a compound described generically or specifically herein or a pharmaceutically acceptable salt thereof or compositions containing the same).

Indications

In some embodiments, the condition, disease or disorder is selected from: inappropriate host responses to infectious diseases where active infection exists at any body site, such as septic shock, disseminated intravascular coagulation, and/or adult respiratory distress syndrome; acute or chronic inflammation due to antigen, antibody and/or complement deposition; inflammatory conditions including arthritis, cholangitis, colitis, encephalitis, endocarditis, glomerulonephritis, hepatitis, myocarditis, pancreatitis, pericarditis, reperfusion injury and vasculitis, immune-based diseases such as acute and delayed hypersensitivity, graft rejection, and graft-versus-host disease; auto-immune diseases including Type 1 diabetes mellitus and multiple sclerosis. For example, the condition, disease or disorder may be an inflammatory disorder such as rheumatoid arthritis, osteoarthritis, septic shock, COPD and periodontal disease.

In some embodiments, the condition, disease or disorder is an autoimmune diseases. Non-limiting examples include rheumatoid arthritis, systemic lupus erythematosus, multiple sclerosis, inflammatory bowel diseases (IBDs) comprising Crohn disease (CD) and ulcerative colitis (UC), which are chronic inflammatory conditions with polygenic susceptibility. In certain embodiments, the condition is an inflammatory bowel disease. In certain embodiments, the condition is Crohn's disease, autoimmune colitis, iatrogenic autoimmune colitis, ulcerative colitis, colitis induced by one or more chemotherapeutic agents, colitis induced by treatment with adoptive cell therapy, colitis associated by one or more alloimmune diseases (such as graft-vs-host disease, e.g., acute graft vs. host disease and chronic graft vs. host disease), radiation enteritis, collagenous colitis, lymphocytic colitis, microscopic colitis, and radiation enteritis. In certain of these embodiments, the condition is alloimmune disease (such as graft-vs-host disease, e.g., acute graft vs. host disease and chronic graft vs. host disease), celiac disease, irritable bowel syndrome, rheumatoid arthritis, lupus, scleroderma, psoriasis, cutaneous T-cell lymphoma, uveitis, and mucositis (e.g., oral mucositis, esophageal mucositis or intestinal mucositis).

In some embodiments, the condition, disease or disorder is selected from major adverse cardiovascular events such as cardiovascular death, non-fatal myocardial infarction and non-fatal stroke in patients with a prior hear attack and inflammatory atherosclerosis (see for example, NCT01327846).

In some embodiments, the condition, disease or disorder is selected from metabolic disorders such as type 2 diabetes, atherosclerosis, obesity and gout, as well as diseases of the central nervous system, such as Alzheimer's disease and multiple sclerosis and Amyotrophic Lateral Sclerosis and Parkinson disease, lung disease, such as asthma and COPD and pulmonary idiopathic fibrosis, liver disease, such as NASH syndrome, viral hepatitis and cirrhosis, pancreatic disease, such as acute and chronic pancreatitis, kidney disease, such as acute and chronic kidney injury, intestinal disease such as Crohn's disease and Ulcerative Colitis, skin disease such as psoriasis, musculoskeletal disease such as scleroderma, vessel disorders, such as giant cell arteritis, disorders of the bones, such as Osteoarthritis, osteoporosis and osteopetrosis disorders eye disease, such as glaucoma and macular degeneration, diseased caused by viral infection such as HIV and AIDS, autoimmune disease such as Rheumatoid Arthritis, Systemic Lupus Erythematosus, Autoimmune Thyroiditis, Addison's disease, pernicious anemia, cancer and aging.

In some embodiments, the condition, disease or disorder is a cardiovascular indication. In some embodiments, the condition, disease or disorder is myocardial infraction. In some embodiments, the condition, disease or disorder is stroke.

In some embodiments, the condition, disease or disorder is obesity.

In some embodiments, the condition, disease or disorder is Type 2 Diabetes.

In some embodiments, the condition, disease or disorder is NASH.

In some embodiments, the condition, disease or disorder is Alzheimer's disease.

In some embodiments, the condition, disease or disorder is gout.

In some embodiments, the condition, disease or disorder is SLE.

In some embodiments, the condition, disease or disorder is rheumatoid arthritis.

In some embodiments, the condition, disease or disorder is IBD.

In some embodiments, the condition, disease or disorder is multiple sclerosis.

In some embodiments, the condition, disease or disorder is COPD.

In some embodiments, the condition, disease or disorder is asthma.

In some embodiments, the condition, disease or disorder is scleroderma.

In some embodiments, the condition, disease or disorder is pulmonary fibrosis.

In some embodiments, the condition, disease or disorder is age related macular degeneration (AMD).

In some embodiments, the condition, disease or disorder is cystic fibrosis.

In some embodiments, the condition, disease or disorder is Muckle Wells syndrome.

In some embodiments, the condition, disease or disorder is familial cold autoinflammatory syndrome (FCAS).

In some embodiments, the condition, disease or disorder is chronic neurologic cutaneous and articular syndrome.

In some embodiments, the condition, disease or disorder is selected from: myelodysplastic syndromes (MDS); non-small cell lung cancer, such as non-small cell lung cancer in patients carrying mutation or overexpression of NLRP3; acute lymphoblastic leukemia (ALL), such as ALL in patients resistant to glucocorticoids treatment; Langerhan's cell histiocytosis (LCH); multiple myeloma; promyelocytic leukemia; acute myeloid leukemia (AML) chronic myeloid leukemia (CML); gastric cancer; and lung cancer metastasis.

In some embodiments, the condition, disease or disorder is selected from: myelodysplastic syndromes (MDS); non-small cell lung cancer, such as non-small cell lung cancer in patients carrying mutation or overexpression of NLRP3; acute lymphoblastic leukemia (ALL), such as ALL in patients resistant to glucocorticoids treatment; Langerhan's cell histiocytosis (LCH); multiple myeloma; promyelocytic leukemia; gastric cancer; and lung cancer metastasis.

In some embodiments, the indication is MDS.

In some embodiments, the indication is non-small lung cancer in patients carrying mutation or overexpression of NLRP3.

In some embodiments, the indication is ALL in patients resistant to glucocorticoids treatment.

In some embodiments, the indication is LCH.

In some embodiments, the indication is multiple myeloma.

In some embodiments, the indication is promyelocytic leukemia.

In some embodiments, the indication is gastric cancer.

In some embodiments, the indication is lung cancer metastasis.

Combination Therapy

This disclosure contemplates both monotherapy regimens as well as combination therapy regimens.

In some embodiments, the methods described herein can further include administering one or more additional therapies (e.g., one or more additional therapeutic agents and/or one or more therapeutic regimens) in combination with administration of the compounds described herein.

In certain embodiments, the second therapeutic agent or regimen is administered to the subject prior to contacting with or administering the chemical entity (e.g., about one hour prior, or about 6 hours prior, or about 12 hours prior, or about 24 hours prior, or about 48 hours prior, or about 1 week prior, or about 1 month prior).

In other embodiments, the second therapeutic agent or regimen is administered to the subject at about the same time as contacting with or administering the chemical entity. By way of example, the second therapeutic agent or regimen and the chemical entity are provided to the subject simultaneously in the same dosage form. As another example, the second therapeutic agent or regimen and the chemical entity are provided to the subject concurrently in separate dosage forms.

In still other embodiments, the second therapeutic agent or regimen is administered to the subject after contacting with or administering the chemical entity (e.g., about one hour after, or about 6 hours after, or about 12 hours after, or about 24 hours after, or about 48 hours after, or about 1 week after, or about 1 month after).

Patient Selection

In some embodiments, the methods described herein further include the step of identifying a subject (e.g., a patient) in need of treatment for an indication related to NLRP3 activity, such as an indication related to NLRP3 polymorphism.

In some embodiments, the methods described herein further include the step of identifying a subject (e.g., a patient) in need of treatment for an indication related to NLRP3 activity, such as an indication related to NLRP3 where polymorphism is a gain of function In some embodiments, the methods described herein further include the step of identifying a subject (e.g., a patient) in need of treatment for an indication related to NLRP3 activity, such as an indication related to NLRP3 polymorphism found in CAPS syndromes.

In some embodiments, the methods described herein further include the step of identifying a subject (e.g., a patient) in need of treatment for an indication related to NLRP3 activity, such as an indication related NLRP3 polymorphism where the polymorphism is VAR_014104 (R262W)

In some embodiments, the methods described herein further include the step of identifying a subject (e.g., a patient) in need of treatment for an indication related to NLRP3 activity, such as an indication related NLRP3 polymorphism where the polymorphism is a natural variant reported in http.//www.uniprot.org/uniprot/Q96P20.

In some embodiments, the methods described herein further include the step of identifying a subject (e.g., a patient) in need of treatment for an indication related to NLRP3 activity, such as an indication related to point mutation of NLRP3 signaling.

Anti-TNFα Agents

The term "anti-TNFα agent" refers to an agent which directly or indirectly blocks, down-regulates, impairs, inhibits, impairs, or reduces TNFα activity and/or expression. In some embodiments, an anti-TNFα agent is an antibody or an antigen-binding fragment thereof, a fusion protein, a soluble TNFα receptor (a soluble tumor necrosis factor receptor superfamily member 1A (TNFR1) or a soluble tumor necrosis factor receptor superfamily 1B (TNFR2)), an inhibitory nucleic acid, or a small molecule TNFα antagonist. In some embodiments, the inhibitory nucleic acid is a ribozyme, small hairpin RNA, a small interfering RNA, an antisense nucleic acid, or an aptamer.

Exemplary anti-TNFα agents that directly block, down-regulate, impair, inhibit, or reduce TNFα activity and/or expression can, e.g., inhibit or decrease the expression level of TNFα or a receptor of TNFα (TNFR1 or TNFR2) in a cell (e.g., a cell obtained from a subject, a mammalian cell), or inhibit or reduce binding of TNFα to its receptor (TNFR1 and/or TNFR2) and/or. Non-limiting examples of anti-TNFα agents that directly block, down-regulate, impair, inhibit, or reduce TNFα activity and/or expression include an antibody or fragment thereof, a fusion protein, a soluble TNFα receptor (e.g., a soluble TNFR1 or soluble TNFR2), inhibitory nucleic acids (e.g., any of the examples of inhibitory nucleic acids described herein), and a small molecule TNFα antagonist.

Exemplary anti-TNFα agents that can indirectly block, down-regulate, impair, inhibit reduce TNFα activity and/or expression can, e.g., inhibit or decrease the level of downstream signaling of a TNFα receptor (e.g., TNFR1 or TNFR2) in a mammalian cell (e.g., decrease the level and/or activity of one or more of the following signaling proteins: AP-1, mitogen-activated protein kinase kinase kinase 5 (ASK1), inhibitor of nuclear factor kappa B (IKK), mitogen-activated protein kinase 8 (JNK), mitogen-activated protein kinase (MAPK), MEKK 1/4, MEKK 4/7, MEKK 3/6, nuclear factor kappa B (NF-κB), mitogen-activated protein kinase kinase kinase 14 (NIK), receptor interacting serine/threonine kinase 1 (RIP), TNFRSF1A associated via death domain (TRADD), and TNF receptor associated factor 2 (TRAF2), in a cell), and/or decrease the level of TNFα-induced gene expression in a mammalian cell (e.g., decrease the transcription of genes regulated by, e.g., one or more transcription factors selected from the group of activating transcription factor 2 (ATF2), c-Jun, and NF-κB). A description of downstream signaling of a TNFα receptor is provided in Wajant et al., *Cell Death Differentiation* 10:45-65, 2003 (incorporated herein by reference). For example, such indirect anti-TNFα agents can be an inhibitory nucleic acid that targets (decreases the expression) a signaling component downstream of a TNFα-induced gene (e.g., any TNFα-induced gene known in the art), a TNFα receptor (e.g., any one or more of the signaling components downstream of a TNFα receptor described herein or known in the art), or a transcription factor selected from the group of NF-κB, c-Jun, and ATF2.

In other examples, such indirect anti-TNFα agents can be a small molecule inhibitor of a protein encoded by a TNFα-induced gene (e.g., any protein encoded by a TNFα-induced gene known in the art), a small molecule inhibitor of a signaling component downstream of a TNFα receptor (e.g., any of the signaling components downstream of a TNFα receptor described herein or known in the art), and a small molecule inhibitor of a transcription factor selected from the group of ATF2, c-Jun, and NF-κB.

In other embodiments, anti-TNFα agents that can indirectly block, down-regulate, impair, or reduce one or more components in a cell (e.g., a cell obtained from a subject, a mammalian cell) that are involved in the signaling pathway that results in TNFα mRNA transcription, TNFα mRNA stabilization, and TNFα mRNA translation (e.g., one or more components selected from the group of CD14, c-Jun, ERK1/2, IKK, IκB, interleukin 1 receptor associated kinase 1 (IRAK), JNK, lipopolysaccharide binding protein (LBP), MEK1/2, MEK3/6, MEK4/7, MK2, MyD88, NF-κB, NIK, PKR, p38, AKT serine/threonine kinase 1 (rac), raf kinase (raf), ras, TRAF6, TTP). For example, such indirect anti-TNFα agents can be an inhibitory nucleic acid that targets (decreases the expression) of a component in a mammalian cell that is involved in the signaling pathway that results in TNFα mRNA transcription, TNFα mRNA stabilization, and TNFα mRNA translation (e.g., a component selected from the group of CD14, c-Jun, ERK1/2, IKK, IκB, IRAK, JNK, LBP, MEK1/2, MEK3/6, MEK4/7, MK2, MyD88, NF-1B, NIK, IRAK, lipopolysaccharide binding protein (LBP), PKR, p38, rac, raf, ras, TRAF6, TTP). In other examples, an indirect anti-TNFα agents is a small molecule inhibitor of a component in a mammalian cell that is involved in the signaling pathway that results in TNFα mRNA transcription, TNFα mRNA stabilization, and TNFα mRNA translation (e.g., a component selected from the group of CD14, c-Jun, ERK1/2, IKK, IκB, IRAK, JNK, lipopolysaccharide binding protein (LBP), MEK1/2, MEK3/6, MEK4/7, MK2, MyD88, NF-κB, NIK, IRAK, lipopolysaccharide binding protein (LBP), PKR, p38, rac, raf, ras, TRAF6, TTP).

Antibodies

In some embodiments, the anti-TNFα agent is an antibody or an antigen-binding fragment thereof (e.g., a Fab or a scFv). In some embodiments, an antibody or antigen-binding fragment of an antibody described herein can bind specifically to TNFα. In some embodiments, an antibody or antigen-binding fragment described herein binds specifically to any one of TNFα, TNFR1, or TNFR2. In some embodiments, an antibody or antigen-binding fragment of an antibody described herein can bind specifically to a TNFα receptor (TNFR1 or TNFR2).

In some embodiments, the antibody can be a humanized antibody, a chimeric antibody, a multivalent antibody, or a fragment thereof. In some embodiments, an antibody can be a scFv-Fc, a VHH domain, a VNAR domain, a (scFv)2, a minibody, or a BiTE.

In some embodiments, an antibody can be a crossmab, a diabody, a scDiabody, a scDiabody-CH$_3$, a Diabody-CH$_3$, a DutaMab, a DT-IgG, a diabody-Fc, a scDiabody-HAS, a charge pair antibody, a Fab-arm exchange antibody, a SEEDbody, a Triomab, a LUZ-Y, a Fcab, a kλ-body, an orthogonal Fab, a DVD-IgG, an IgG(H)-scFv, a scFv-(H) IgG, an IgG(L)-scFv, a scFv-(L)-IgG, an IgG (L,H)-Fc, an IgG(H)-V, a V(H)—IgG, an IgG(L)-V, a V(L)-IgG, an KIH IgG-scFab, a 2scFv-IgG, an IgG-2scFv, a scFv4-Ig, a Zybody, a DVI-IgG, a nanobody, a nanobody-HSA, a DVD-Ig, a dual-affinity re-targeting antibody (DART), a triomab, a kih IgG with a common LC, an ortho-Fab IgG, a 2-in-1-IgG, IgG-ScFv, scFv2-Fc, a bi-nanobody, tanden antibody, a DART-Fc, a scFv-HAS-scFv, a DAF (two-in-one or four-in-one), a DNL-Fab3, knobs-in-holes common LC, knobs-in-holes assembly, a TandAb, a Triple Body, a miniantibody, a minibody, a TriBi minibody, a scFv-CH3 KIH, a Fab-scFv, a scFv-CH-CL-scFv, a F(ab')2-scFV2, a scFv-KIH, a Fab-scFv-Fc, a tetravalent HCAb, a scDiabody-Fc, a tandem scFv-Fc, an intrabody, a dock and lock bispecific antibody, an ImmTAC, a HSAbody, a tandem scFv, an IgG-IgG, a Cov-X-Body, and a scFv1-PEG-scFv2.

Non-limiting examples of an antigen-binding fragment of an antibody include an Fv fragment, a Fab fragment, a F(ab')2 fragment, and a Fab' fragment. Additional examples of an antigen-binding fragment of an antibody is an antigen-binding fragment of an antigen-binding fragment of an IgA (e.g., an antigen-binding fragment of IgA1 or IgA2) (e.g., an antigen-binding fragment of a human or humanized IgA, e.g., a human or humanized IgA1 or IgA2); an antigen-binding fragment of an IgD (e.g., an antigen-binding fragment of a human or humanized IgD); an antigen-binding fragment of an IgE (e.g., an antigen-binding fragment of a human or humanized IgE); an IgG (e.g., an antigen-binding fragment of IgG1, IgG2, IgG3, or IgG4) (e.g., an antigen-binding fragment of a human or humanized IgG, e.g., human or humanized IgG1, IgG2, IgG3, or IgG4); or an antigen-binding fragment of an IgM (e.g., an antigen-binding fragment of a human or humanized IgM).

Non-limiting examples of anti-TNFα agents that are antibodies that specifically bind to TNFα are described in Ben-Horin et al., *Autoimmunity Rev.* 13(1):24-30, 2014; Bongartz et al., *JAMA* 295(19):2275-2285, 2006; Butler et al., *Eur. Cytokine Network* 6(4):225-230, 1994; Cohen et al., *Canadian J. Gastroenterol. Hepatol.* 15(6):376-384, 2001; Elliott et al., *Lancet* 1994; 344: 1125-1127, 1994; Feldmann et al., *Ann. Rev. Immunol.* 19(1):163-196, 2001; Rankin et al., *Br. J. Rheumatol.* 2:334-342, 1995; Knight et al., *Molecular Immunol.* 30(16):1443-1453, 1993; Lorenz et al., *J. Immunol.* 156(4):1646-1653, 1996; Hinshaw et al., *Circulatory Shock* 30(3):279-292, 1990; Ordas et al., *Clin. Pharmacol. Therapeutics* 91(4):635-646, 2012; Feldman, *Nature Reviews Immunol.* 2(5):364-371, 2002; Taylor et al., *Nature Reviews Rheumatol.* 5(10):578-582, 2009; Garces et al., *Annals Rheumatic Dis.* 72(12):1947-1955, 2013; Palladino et al., *Nature Rev. Drug Discovery* 2(9):736-746, 2003; Sandborn et al., *Inflammatory Bowel Diseases* 5(2):119-133, 1999; Atzeni et al., *Autoimmunity Reviews* 12(7):703-708, 2013; Maini et al., *Immunol. Rev.* 144(1):195-223, 1995; Wanner et al., *Shock* 11(6):391-395, 1999; and U.S. Pat. Nos. 6,090,382; 6,258,562; and 6,509,015).

In certain embodiments, the anti-TNFα agent can include or is golimumab (Golimumab™), adalimumab (Humira™), infliximab (Remicade™), CDP571, CDP 870, or certolizumab pegol (Cimzia™). In certain embodiments, the anti-TNFα agent can be a TNFα inhibitor biosimilar. Examples of approved and late-phase TNFα inhibitor biosimilars include, but are not limited to, infliximab biosimilars such as Flixabi™ (SB2) from Samsung Bioepis, Inflectra® (CT-P13) from Celltrion/Pfizer, GS071 from Aprogen, Remsima™, PF-06438179 from Pfizer/Sandoz, NI-071 from Nichi-Iko Pharmaceutical Co., and ABP 710 from Amgen; adalimumab biosimilars such as Amgevita® (ABP 501) from Amgen and Exemptia™ from Zydus Cadila, BMO-2 or MYL-1401-A from Biocon/Mylan, CHS-1420 from Coherus, FKB327 from Kyowa Kirin, and BI 695501 from Boehringer Ingelheim; Solymbic®, SB5 from Samsung Bioepis, GP-2017 from Sandoz, ONS-3010 from Oncobiologics, M923 from Momenta, PF-06410293 from Pfizer, and etanercept biosimilars such as Erelzi™ from Sandoz/Novartis, Brenzys™ (SB4) from Samsung Bioepis, GP2015 from Sandoz, TuNEX® from Mycenax, LBEC0101 from LG Life, and CHS-0214 from Coherus.

In some embodiments of any of the methods described herein, the anti-TNFα agent is selected from the group consisting of: adalimumab, certolizumab, etanercept, golimumab, infliximabm, CDP571, and CDP 870.

In some embodiments, any of the antibodies or antigen-binding fragments described herein has a dissociation constant ($K_D$) of less than $1\times10^{-5}$ M (e.g., less than $0.5\times10^{-5}$ M, less than $1\times10^{-6}$ M, less than $0.5\times10^{-6}$ M, less than $1\times10^{-7}$ M, less than $0.5\times10^{-7}$ M, less than $1\times10^{-8}$ M, less than $0.5\times10^{-9}$ M, less than $1\times10^{-9}$ M, less than $0.5\times10^{-9}$ M, less than $1\times10^{-10}$ M, less than $0.5\times10^{-10}$ M, less than $1\times10^{-11}$ M, less than $0.5\times10^{-11}$ M, or less than $1\times10^{-12}$ M), e.g., as measured in phosphate buffered saline using surface plasmon resonance (SPR).

In some embodiments, any of the antibodies or antigen-binding fragments described herein has a $K_D$ of about $1\times10^{-12}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, about $1\times10^{-8}$ M, about $0.5\times10^{-8}$ M, about $1\times10^{-9}$ M, about $0.5\times10^{-9}$ M, about $1\times10^{-10}$ M, about $0.5\times10^{-10}$ M, about $1\times10^{-11}$ M, or about $0.5\times10^{-11}$ M (inclusive); about $0.5\times10^{-11}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, about $1\times10^{-8}$ M, about $0.5\times10^{-8}$ M, about $1\times10^{-9}$ M, about $0.5\times10^{-9}$ M, about $1\times10^{10}$ M, about $0.5\times10^{-10}$ M, or about $1\times10^{-11}$ M (inclusive); about $1\times10^{-11}$ M to about $1\times10^{-5}$ M, about $0.5\times10^{-5}$ M, about $1\times10^{-6}$ M, about $0.5\times10^{-6}$ M, about $1\times10^{-7}$ M, about $0.5\times10^{-7}$ M, about $1\times10^{-8}$ M, about $0.5\times10^{-8}$ M, about $1\times10^{-9}$ M, about $0.5\times10^{-9}$ M, about $1\times10^{-10}$ M, or about $0.5\times10^{-10}$ M (inclusive); about $0.5 \times 10^{-10}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-9}$ M, about $1 \times 10^{-9}$ M, about $0.5 \times 10^{-9}$ M, or about $1 \times 10^{-10}$ M (inclusive); about $1 \times 10^{-10}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, about $0.5 \times 10^{-8}$ M, about $1 \times 10^{-9}$M, or about $0.5 \times 10^{-9}$ M (inclusive); about $0.5 \times 10^{-9}$M to about $1 \times 10^{-5}$ M, about $0.5 \times 10^{-5}$ M, about $1 \times 10^{-6}$ M, about $0.5 \times 10^{-6}$ M, about $1 \times 10^{-7}$M, about $0.5 \times 10^{-7}$ M, about $1 \times 10^{-8}$ M, about $0.5 \times 10^{-8}$ M, or about $1 \times 10^{-9}$ M (inclusive); about $1 \times 10^{-9}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, about $1 \times 10^{-8}$ M, or about $0.5 \times 10^{-8}$ M (inclusive); about $0.5 \times 10^{-8}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, about $0.5 \times 10^{-7}$ M, or about $1 \times 10^{-8}$ M (inclusive); about $1 \times 10^{-8}$ M to about $1 \times 10^{-5}$ M, about $0.5 \times 10^{-5}$ M, about $1 \times 10^{-6}$ M, about $0.5 \times 10^{-6}$ M, about $1 \times 10^{-7}$ M, or about $0.5 \times 10^{-7}$ M (inclusive); about $0.5 \times 10^{-7}$ M to about $1 \times 10^{-5}$ M, about $0.5 \times 10^{-5}$ M, about $1 \times 10^{-6}$ M, about $0.5 \times 10^{-6}$ M, or about $1 \times 10^{-7}$ M (inclusive); about $1 \times 10^{-7}$ M to about $1 \times 10^{-5}$ M, about $0.5 \times 10^{-5}$ M, about $1 \times 10^{-6}$ M, or about $0.5 \times 10^{-6}$ M (inclusive); about $0.5 \times 10^{-6}$ M to about $1 \times 10^{-5}$ M, about $0.5 \times 10^{-5}$ M, or about $1 \times 10^{-6}$ M (inclusive); about $1 \times 10^{-6}$ M to about $1 \times 10^{-5}$ M or about $0.5 \times 10^{-5}$ M (inclusive); or about $0.5 \times 10^{-5}$ M to about $1 \times 10^{-5}$ M (inclusive), e.g., as measured in phosphate buffered saline using surface plasmon resonance (SPR).

In some embodiments, any of the antibodies or antigen-binding fragments described herein has a $K_{off}$ of about $1 \times 10^{-6}$ s$^{-1}$ to about $1 \times 10^{-3}$ s$^{-1}$, about $0.5 \times 10^{-3}$ s$^{-1}$, about $1 \times 10^{-4}$ s$^{-1}$, about $0.5 \times 10^{-4}$ s$^{-1}$, about $1 \times 10^{-5}$ s$^{-1}$, or about $0.5 \times 10^{-5}$ s$^{-1}$ (inclusive); about $0.5 \times 10^{-5}$ s$^{-1}$ to about $1 \times 10^{-3}$ s$^{-1}$, about $0.5 \times 10^{-3}$ s$^{-1}$, about $1 \times 10^{-4}$ s$^{-1}$, about $0.5 \times 10^{-4}$ s$^{-1}$, or about $1 \times 10^{-5}$ s$^{-1}$ (inclusive); about $1 \times 10^{-5}$ s$^{-1}$ to about $1 \times 10^{-3}$ s$^{-1}$, about $0.5 \times 10^{-3}$ s$^{-1}$, about $1 \times 10^{-4}$ s$^{-1}$, or about $0.5 \times 10^{-4}$ s$^{-1}$ (inclusive); about $0.5 \times 10^{-4}$ s$^{-1}$ to about $1 \times 10^{-3}$ s$^{-1}$, about $0.5 \times 10^{-3}$ s$^{-1}$, or about $1 \times 10^{-4}$ s$^{-1}$ (inclusive); about $1 \times 10^{-4}$ s$^{-1}$ to about $1 \times 10^{-3}$ s$^{-1}$, or about $0.5 \times 10^{-3}$ s$^{-1}$ (inclusive); or about $0.5 \times 10^{-5}$ s$^{-1}$ to about $1 \times 10^{-3}$ s$^{-1}$ (inclusive), e.g., as measured in phosphate buffered saline using surface plasmon resonance (SPR).

In some embodiments, any of the antibodies or antigen-binding fragments described herein has a $K_{on}$ of about $1 \times 10^{2}$ M$^{-1}$ s$^{-1}$ to about $1 \times 10^{6}$ M$^{-1}$ s$^{-1}$, about $0.5 \times 10^{6}$ M$^{-1}$ s$^{-1}$, about $1 \times 10^{5}$ M$^{-1}$ s$^{-1}$, about $0.5 \times 10^{-5}$ M$^{-1}$ s$^{-1}$, about $1 \times 10^{4}$ M$^{-1}$ s$^{-1}$, about $0.5 \times 10^{4}$ M$^{-1}$ s$^{-1}$, about $1 \times 10^{3}$ M$^{-1}$ s$^{-1}$, or about $0.5 \times 10^{3}$ M$^{-1}$ s$^{-1}$ (inclusive); about $0.5 \times 10^{3}$ M$^{-1}$ s$^{-1}$ to about $1 \times 10^{6}$ M$^{-1}$ s$^{-1}$, about $0.5 \times 10^{6}$ M$^{-1}$ s$^{-1}$, about $1 \times 10^{-5}$ M$^{-1}$ s$^{-1}$, about $0.5 \times 10^{-5}$ M$^{-1}$ s$^{-1}$, about $1 \times 10^{-4}$ M$^{-1}$ s$^{-1}$, about $0.5 \times 10^{-4}$ M$^{-1}$ s$^{-1}$, or about $1 \times 10^{3}$ M$^{-1}$ s$^{-1}$ (inclusive); about $1 \times 10^{3}$ M$^{-1}$ s$^{-1}$ to about $1 \times 10^{6}$ M$^{-1}$ s$^{-1}$, about $0.5 \times 10^{6}$ M$^{-1}$ s$^{-1}$, about $1 \times 10^{5}$ M$^{-1}$ s$^{-1}$, about $0.5 \times 10^{-5}$ M$^{-1}$ s$^{-1}$, about $1 \times 10^{4}$ M$^{-1}$ s$^{-1}$, or about $0.5 \times 10^{4}$ M$^{-1}$ s$^{-1}$ (inclusive); about $0.5 \times 10^{4}$ M$^{-1}$ s$^{-1}$ to about $1 \times 10^{6}$ M$^{-1}$ s$^{-1}$, about $0.5 \times 10^{6}$ M$^{-1}$ s$^{-1}$, about $1 \times 10^{5}$ M$^{-1}$ s$^{-1}$, about $0.5 \times 10^{5}$ M$^{-1}$ s$^{-1}$, or about $1 \times 10^{4}$ M$^{-1}$ s$^{1}$ (inclusive); about $1 \times 10^{-4}$ M$^{-1}$ s$^{-1}$ to about $1 \times 10^{6}$ M$^{-1}$ s$^{-1}$, about $0.5 \times 10^{6}$ M$^{-1}$ s$^{-1}$, about $1 \times 10^{5}$ M$^{-1}$ s$^{-1}$, or about $0.5 \times 10^{-5}$ M$^{-1}$ s$^{-1}$ (inclusive); about $0.5 \times 10^{5}$ M$^{-1}$ s$^{-1}$ to about $1 \times 10^{6}$ M$^{-1}$ s$^{-1}$, about $0.5 \times 10^{6}$ M$^{-1}$ s$^{-1}$, or about $1 \times 10^{-5}$ M$^{-1}$ s$^{-1}$ (inclusive); about $1 \times 10^{5}$ M$^{-1}$ s$^{-1}$ to about $1 \times 10^{6}$ M$^{-1}$ s$^{-1}$, or about $0.5 \times 10^{6}$ M$^{-1}$ s$^{-1}$ (inclusive); or about $0.5 \times 10^{6}$ M$^{-1}$ s$^{-1}$ to about $1 \times 10^{6}$ M$^{-1}$ s$^{-1}$ (inclusive), e.g., as measured in phosphate buffered saline using surface plasmon resonance (SPR).

Fusion Proteins

In some embodiments, the anti-TNFα agent is a fusion protein (e.g., an extracellular domain of a TNFR fused to a partner peptide, e.g., an Fc region of an immunoglobulin, e.g., human IgG) (see, e.g., Deeg et al., *Leukemia* 16(2):162, 2002; Peppel et al., *J. Exp. Med.* 174(6):1483-1489, 1991) or a soluble TNFR (e.g., TNFR1 or TNFR2) that binds specifically to TNFα. In some embodiments, the anti-TNFα agent includes or is a soluble TNFα receptor (e.g., Bjornberg et al., *Lymphokine Cytokine Res.* 13(3):203-211, 1994; Kozak et al., *Am. J. Physiol. Reg. Integrative Comparative Physiol.* 269(1):R23-R29, 1995; Tsao et al., *Eur Respir J.* 14(3):490-495, 1999; Watt et al., *J Leukoc Biol.* 66(6):1005-1013, 1999; Mohler et al., *J. Immunol.* 151(3):1548-1561, 1993; Nophar et al., *EMBO J.* 9(10):3269, 1990; Piguet et al., *Eur. Respiratory J.* 7(3):515-518, 1994; and Gray et al., *Proc. Natd. Acad. Sci. U.S.A.* 87(19):7380-7384, 1990). In some embodiments, the anti-TNFα agent includes or is etanercept (Enbrel™) (see, e.g., WO 91/03553 and WO 09/406,476, incorporated by reference herein). In some embodiments, the anti-TNFα agent inhibitor includes or is r-TBP-I (e.g., Gradstein et al., *J. Acquir. Immune Defic. Syndr.* 26(2): 111-117, 2001).

Inhibitory Nucleic Acids

Inhibitory nucleic acids that can decrease the expression of AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA expression in a mammalian cell include antisense nucleic acid molecules, i.e., nucleic acid molecules whose nucleotide sequence is fully or partially complementary to all or part of a AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA (e.g., fully or partially complementary to all or a part of any one of the sequences presented in Table E).

TABLE E

| Human gene | mRNA GenBank accession number(s) |
|---|---|
| Tumor necrosis factor (TNF, a.k.a. TNF-alpha) | NM_000594 |
| TNF receptor superfamily member 1A (TNFRSF1A) (a.k.a. TNFR1) | NM_001065 |
| | NM_001346091 |
| | NM_001346092 |
| TNF receptor superfamily member 1B (TNFRSF1B) (a.k.a. TNFR2) | NM_001066 |
| | XM_011542060 |
| | XM_011542063 |
| | XM_017002214 |
| | XM_017002215 |
| | XM_017002211 |
| TNFRSF1A associated via death domain (TRADD) | NM_003789 |
| | NM_001323552 |
| | XM_005256213 |
| | XM_017023815 |
| TNF receptor associated factor 2 (TRAF2) | NM_021138 |
| | XM_011518976 |
| | XM_011518977 |
| | XM_011518974 |
| JunD proto-oncogene, AP-1 transcription factor subunit (JUND) | NM_001286968 |
| | NM_005354 |
| Mitogen-activated protein kinase kinase kinase 5 (MAP3K5) (a.k.a. ASK1) | NM_005923 |
| | XM_017010875 |
| | XM_017010872 |
| | XM_017010873 |
| | XM_017010877 |
| | XM_017010874 |
| | XM_017010871 |

TABLE E-continued

| Human gene | mRNA GenBank accession number(s) |
|---|---|
| | XM_017010870 |
| | XM_017010876 |
| | XM_011535839 |
| CD14 | NM_000591 |
| | NM_001040021 |
| | NM_001174104 |
| | NM_001174105 |
| Mitogen-activated protein kinase 3 (MAPK3) (a.k.a. ERK1) | NM_001040056 |
| | NM_001109891 |
| | NM_002746 |
| Mitogen-activated protein kinase 1 (MAPK1) (a.k.a. ERK2) | NM_002745 |
| | NM_138957 |
| Inhibitor of nuclear factor kappa B kinase subunit beta (IKBKB) | NM_001190720 |
| | NM_001242778 |
| | NM_001556 |
| | XM_005273491 |
| | XM_005273496 |
| | XM_005273493 |
| | XM_005273498 |
| | XM_011544518 |
| | XM_005273492 |
| | XM_005273490 |
| | XM_005273494 |
| | 12XM_017013396 |
| | XM_011544521 |
| | XM_011544522 |
| | XM_005273495 |
| | XM_011544517 |
| | XM_011544520 |
| | XM_011544519 |
| NFKB inhibitor alpha (NFKBIA) | NM_020529 |
| Interleukin 1 receptor associated kinase 1 (IRAK1) | NM_001025242 |
| | NM_001025243 |
| | NM_001569 |
| | XM_005274668 |
| Mitogen-activated protein kinase 8 (MAPK8) (a.k.a. JNK) | NM_001278547 |
| | NM_001278548 |
| | NM_001323302 |
| | NM_001323320 |
| | NM_001323321 |
| | NM_001323322 |
| | NM_001323323 |
| | NM_001323324 |
| | NM_001323325 |
| | NM_001323326 |
| | NM_001323327 |
| | NM_001323328 |
| | NM_001323329 |
| | NM_001323330 |
| | NM_001323331 |
| | NM_139046 |
| | NM_139049 |
| | XM_024448079 |
| | XM_024448080 |
| Lipopolysaccharide binding protein (LBP) | NM_004139 |
| Mitogen-activated protein kinase kinase 1 (MAP2K1) (a.k.a. MEK1) | NM_002755 |
| | XM_017022411 |
| | XM_011521783 |
| | XM_017022412 |
| | XM_017022413 |
| Mitogen-activated protein kinase kinase 2 (MAP2K2) (a.k.a. MEK2) | NM_030662 |
| | XM_006722799 |
| | XM_017026990 |
| | XM_017026989 |
| | XM_017026991 |
| Mitogen-activated protein kinase kinase 3 (MAP2K3) (a.k.a. MEK3) | NM_001316332 |
| | NM_002756 |
| | NM_145109 |
| | XM_017024859 |
| | XM_005256723 |
| | XM_017024857 |
| | XM_011523959 |
| | XM_017024858 |
| | XM_011523958 |
| Mitogen-activated protein kinase kinase 6 (MAP2K6) (a.k.a. MEK6) | NM_001330450 |
| | NM_002758 |
| | XM_005257516 |

TABLE E-continued

| Human gene | mRNA GenBank accession number(s) |
|---|---|
| | XM_011525027 |
| | XM_011525026 |
| | XM_006721975 |
| Mitogen-activated protein kinase kinase kinase 1 (MAP3K1) (a.k.a. MEKK1) | NM_005921 |
| | XM_017009485 |
| | XM_017009484 |
| Mitogen-activated protein kinase kinase kinase 3 (MAP3K3) (a.k.a. MEKK3) | NM_001330431 |
| | NM_001363768 |
| | NM_002401 |
| | NM_203351 |
| | XM_005257378 |
| Mitogen-activated protein kinase kinase kinase 4 (MAP3K4) (a.k.a. MEKK4) | NM_001291958 |
| | NM_001301072 |
| | NM_001363582 |
| | NM_005922 |
| | NM_006724 |
| | XM_017010869 |
| Mitogen-activated protein kinase kinase kinase 6 (MAP3K6) (a.k.a. MEKK6) | NM_001297609 |
| | NM_004672 |
| | XM_017002771 |
| | XM_017002772 |
| Mitogen-activated protein kinase kinase kinase 7 (MAP3K7) (a.k.a. MEKK7) | NM_003188 |
| | NM_145331 |
| | NM_145332 |
| | NM_145333 |
| | XM_006715553 |
| | XM_017011226 |
| MAPK activated protein kinase 2 (MAPKAPK2) (a.k.a. MK2) | NM_004759 |
| | NM_032960 |
| | XM_005273353 |
| | XM_017002810 |
| MYD88, innate immune signal transduction adaptor (MYD88) | NM_001172566 |
| | NM_001172567 |
| | NM_001172568 |
| | NM_001172569 |
| | NM_001365876 |
| | NM_001365877 |
| | NM_002468 |
| Nuclear factor kappa B subunit 1 (NFKB1) | NM_001165412 |
| | NM_001319226 |
| | NM_003998 |
| | XM_024454069 |
| | XM_024454067 |
| | XM_011532006 |
| | XM_024454068 |
| Mitogen-activated protein kinase kinase kinase 14 (MAP3K14) (a.k.a. NIK) | NM_003954 |
| | XM_011525441 |
| Mitogen-activated protein kinase 14 (MAPK14) (a.k.a. p38) | NM_001315 |
| | NM_139012 |
| | NM_139013 |
| | NM_139014 |
| | XM_011514310 |
| | XM_017010300 |
| | XM_017010299 |
| | XM_017010301 |
| | XM_017010304 |
| | XM_017010303 |
| | XM_017010302 |
| | XM_006714998 |
| Eukaryotic translation initiation factor 2 alpha kinase 2 (EIF2AK2) (a.k.a. PKR) | NM_001135651 |
| | NM_001135652 |
| | NM_002759 |
| | XM_011532987 |
| | XM_017004503 |
| AKT serine/threonine kinase 1 (AKT1) (a.k.a. RAC) | NM_001014431 |
| | NM_001014432 |
| | NM_005163 |
| Zinc fingers and homeoboxes 2 (ZHX2) (a.k.a. RAF) | NM_001362797 |
| | NM_014943 |
| | XM_011516932 |
| | XM_005250836 |
| KRAS proto-oncogene, GTPase (KRAS) | NM_001369786 |
| | NM_001369787 |
| | NM_004985 |
| | NM_033360 |

TABLE E-continued

| Human gene | mRNA GenBank accession number(s) |
| --- | --- |
| NRAS proto-oncogene, GTPase (NRAS) | NM_002524 |
| Receptor interacting serine/threonine kinase 1 (RIPK1) (a.k.a. RIP) | NM_001317061 |
| | NM_001354930 |
| | NM_001354931 |
| | NM_001354932 |
| | NM_001354933 |
| | NM_001354934 |
| | NM_003804 |
| | XM_017011405 |
| | XM_006715237 |
| | XM_017011403 |
| | XM_017011404 |
| TNF receptor associated factor 6 (TRAF6) | NM_004620 |
| | NM_145803 |
| | XM_017018220 |
| ZFP36 ring finger protein (ZFP36) (a.k.a. TTP) | NM_003407 |

An antisense nucleic acid molecule can be fully or partially complementary to all or part of a non-coding region of the coding strand of a nucleotide sequence encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP protein. Non-coding regions (5' and 3' untranslated regions) are the 5' and 3' sequences that flank the coding region in a gene and are not translated into amino acids.

Based upon the sequences disclosed herein, one of skill in the art can easily choose and synthesize any of a number of appropriate antisense nucleic acids to target a nucleic acid encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP protein described herein. Antisense nucleic acids targeting a nucleic acid encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP protein can be designed using the software available at the Integrated DNA Technologies website.

An antisense nucleic acid can be, for example, about 5, 10, 15, 18, 20, 22, 24, 25, 26, 28, 30, 32, 35, 36, 38, 40, 42, 44, 45, 46, 48, or 50 nucleotides or more in length. An antisense oligonucleotide can be constructed using enzymatic ligation reactions and chemical synthesis using procedures known in the art. For example, an antisense nucleic acid can be chemically synthesized using variously modified nucleotides or naturally occurring nucleotides designed to increase the physical stability of the duplex formed between the antisense and sense nucleic acids, e.g., phosphorothioate derivatives and acridine substituted nucleotides or to increase the biological stability of the molecules.

Examples of modified nucleotides which can be used to generate an antisense nucleic acid include 1-methylguanine, 1-methylinosine, 2,2-dimethylguanine, 2-methyladenine, 2-methylguanine, 3-methylcytosine, 2-methylthio-N6-isopentenyladenine, uracil-5-oxyacetic acid (v), wybutoxosine, pseudouracil, queosine, 2-thiocytosine, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules described herein can be prepared in vitro and administered to a subject, e.g., a human subject. Alternatively, they can be generated in situ such that they hybridize with or bind to cellular mRNA and/or genomic DNA encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP protein to thereby inhibit expression, e.g., by inhibiting transcription and/or translation. The hybridization can be by conventional nucleotide complementarities to form a stable duplex, or, for example, in the case of an antisense nucleic acid molecule that binds to DNA duplexes, through specific interactions in the major groove of the double helix. The antisense nucleic acid molecules can be delivered to a mammalian cell using a vector (e.g., an adenovirus vector, a lentivirus, or a retrovirus).

An antisense nucleic acid can be an α-anomeric nucleic acid molecule. An α-anomeric nucleic acid molecule forms specific double-stranded hybrids with complementary RNA in which, contrary to the usual, β-units, the strands run parallel to each other (Gaultier et al., Nucleic Acids Res. 15:6625-6641, 1987). The antisense nucleic acid can also comprise a chimeric RNA-DNA analog (Inoue et al., FEBS Lett. 215:327-330, 1987) or a 2'-O-methylribonucleotide (Inoue et al., Nucleic Acids Res. 15:6131-6148, 1987).

Another example of an inhibitory nucleic acid is a ribozyme that has specificity for a nucleic acid encoding an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA, e.g., specificity for any one of the sequences presented in Table E). Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach, Nature 334:585-591, 1988)) can be used to catalytically cleave mRNA transcripts to thereby inhibit translation of the protein encoded by the mRNA. An AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA can be used to select a catalytic RNA having a specific ribonuclease activity from a pool of RNA molecules. See, e.g., Bartel et al., Science 261:1411-1418, 1993.

Alternatively, a ribozyme having specificity for an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA can be designed based upon the nucleotide sequence of any of the AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA sequences disclosed herein (e.g., in Table E). For example, a derivative of a Tetrahymena L-19 IVS RNA can be constructed in which the nucleotide sequence of the active site is complementary to the nucleotide sequence to be cleaved in an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP mRNA (see, e.g., U.S. Pat. Nos. 4,987,071 and 5,116,742).

An inhibitory nucleic acid can also be a nucleic acid molecule that forms triple helical structures. For example, expression of an AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP polypeptide can be inhibited by targeting nucleotide sequences complementary to the regulatory region of the gene encoding the AP-1, ASK1, CD14, c-jun, ERK1/2, IκB, IKK, IRAK, JNK, LBP, MAPK, MEK1/2, MEKK1/4, MEKK4/7, MEKK 3/6, MK2, MyD88, NF-κB, NIK, p38, PKR, rac, ras, raf, RIP, TNFα, TNFR1, TNFR2, TRADD, TRAF2, TRAF6, or TTP polypeptide (e.g., the promoter and/or enhancer, e.g., a sequence that is at least 1 kb, 2 kb, 3 kb, 4 kb, or 5 kb upstream of the transcription initiation start state) to form triple helical structures that prevent transcription of the gene in target cells. See generally Maher, *Bioassays* 14(12):807-15, 1992; Helene, *Anticancer Drug Des.* 6(6):569-84, 1991; and Helene, *Ann. N.Y. Acad. Sci.* 660:27-36, 1992.

In various embodiments, inhibitory nucleic acids can be modified at the sugar moiety, the base moiety, or phosphate backbone to improve, e.g., the solubility, stability, or hybridization, of the molecule. For example, the deoxyribose phosphate backbone of the nucleic acids can be modified to generate peptide nucleic acids (see, e.g., Hyrup et al., *Bioorganic Medicinal Chem.* 4(1):5-23, 1996). Peptide nucleic acids (PNAs) are nucleic acid mimics, e.g., DNA mimics, in which the deoxyribose phosphate backbone is replaced by a pseudopeptide backbone and only the four natural nucleobases are retained. The neutral backbone of PNAs allows for specific hybridization to RNA and DNA under conditions of low ionic strength. PNA oligomers can be synthesized using standard solid phase peptide synthesis protocols (see, e.g., Perry-O'Keefe et al., *Proc. Natl. Acad. Sci. U.S.A.* 93:14670-675, 1996). PNAs can be used as antisense or antigene agents for sequence-specific modulation of gene expression by, e.g., inducing transcription or translation arrest or inhibiting replication.

Small Molecules

In some embodiments, the anti-TNFα agent is a small molecule. In some embodiments, the small molecule is a tumor necrosis factor-converting enzyme (TACE) inhibitor (e.g., Moss et al., *Nature Clinical Practice Rheumatology* 4: 300-309, 2008). In some embodiments, the anti-TNFα agent is C87 (Ma et al., *J. Biol. Chem.* 289(18):12457-66, 2014). In some embodiments, the small molecule is LMP-420 (e.g., Haraguchi et al., *AIDS Res. Ther.* 3:8, 2006). In some embodiments, the TACE inhibitor is TMI-005 and BMS-561392. Additional examples of small molecule inhibitors are described in, e.g., He et al., *Science* 310(5750):1022-1025, 2005.

In some examples, the anti-TNFα agent is a small molecule that inhibits the activity of one of AP-1, ASK1, IKK, JNK, MAPK, MEKK 1/4, MEKK4/7, MEKK 3/6, NIK, TRADD, RIP, NF-κB, and TRADD in a cell (e.g., in a cell obtained from a subject, a mammalian cell).

In some examples, the anti-TNFα agent is a small molecule that inhibits the activity of one of CD14, MyD88 (see, e.g., Olson et al., *Scientific Reports* 5:14246, 2015), ras (e.g., Baker et al., *Nature* 497:577-578, 2013), raf (e.g., vemurafenib (PLX4032, RG7204), sorafenib tosylate, PLX-4720, dabrafenib (GSK2118436), GDC-0879, RAF265 (CHIR-265), AZ 628, NVP-BHG712, SB590885, ZM 336372, sorafenib, GW5074, TAK-632, CEP-32496, encorafenib (LGX818), CCT196969, LY3009120, RO5126766 (CH5126766), PLX7904, and MLN2480).

In some examples, the anti-TNFα agent TNFα inhibitor is a small molecule that inhibits the activity of one of MK2 (PF 3644022 and PHA 767491), INK (e.g., AEG 3482, BI 78D3, CEP 1347, c-JUN peptide, IQ 1S, JIP-1 (153-163), SP600125, SU 3327, and TCS JNK60), c-jun (e.g., AEG 3482, BI 78D3, CEP 1347, c-JUN peptide, IQ 1S, JIP-1 (153-163), SP600125, SU 3327, and TCS JNK60), MEK3/6 (e.g., Akinleye et al., *J. Hematol. Oncol.* 6:27, 2013), p38 (e.g., AL 8697, AMG 548, BIRB 796, CMPD-1, DBM 1285 dihydrochloride, EO 1428, JX 401, ML 3403, Org 48762-0, PH 797804, RWJ 67657, SB 202190, SB 203580, SB 239063, SB 706504, SCIO 469, SKF 86002, SX 011, TA 01, TA 02, TAK 715, VX 702, and VX 745), PKR (e.g., 2-aminopurine or CAS 608512-97-6), TTP (e.g., CAS 329907-28-0), MEK1/2 (e.g., Facciorusso et al., *Expert Review Gastroentrol. Hepatol.* 9:993-1003, 2015), ERK1/2 (e.g., Mandal et al., *Oncogene* 35:2547-2561, 2016), NIK (e.g., Mortier et al., *Bioorg. Med. Chem. Lett.* 20:4515-4520, 2010), IKK (e.g., Reilly et al., *Nature Med.* 19:313-321, 2013), IκB (e.g., Suzuki et al., *Expert. Opin. Invest. Drugs* 20:395-405, 2011), NF-κB (e.g., Gupta et al., *Biochim. Biophys. Acta* 1799(10-12):775-787, 2010), rac (e.g., U.S. Pat. No. 9,278,956), MEK4/7, IRAK (Chaudhary et al., *J. Med. Chem.* 58(1):96-110, 2015), LBP (see, e.g., U.S. Pat. No. 5,705,398), and TRAF6 (e.g., 3-[(2,5-Dimethylphenyl) amino]-1-phenyl-2-propen-1-one).

In some embodiments of any of the methods described herein, the inhibitory nucleic acid can be about 10 nucleotides to about 50 nucleotides (e.g., about 10 nucleotides to about 45 nucleotides, about 10 nucleotides to about 40 nucleotides, about 10 nucleotides to about 35 nucleotides, about 10 nucleotides to about 30 nucleotides, about 10 nucleotides to about 28 nucleotides, about 10 nucleotides to about 26 nucleotides, about 10 nucleotides to about 25 nucleotides, about 10 nucleotides to about 24 nucleotides, about 10 nucleotides to about 22 nucleotides, about 10 nucleotides to about 20 nucleotides, about 10 nucleotides to about 18 nucleotides, about 10 nucleotides to about 16 nucleotides, about 10 nucleotides to about 14 nucleotides, about 10 nucleotides to about 12 nucleotides, about 12 nucleotides to about 50 nucleotides, about 12 nucleotides to about 45 nucleotides, about 12 nucleotides to about 40 nucleotides, about 12 nucleotides to about 35 nucleotides, about 12 nucleotides to about 30 nucleotides, about 12 nucleotides to about 28 nucleotides, about 12 nucleotides to about 26 nucleotides, about 12 nucleotides to about 25 nucleotides, about 12 nucleotides to about 24 nucleotides, about 12 nucleotides to about 22 nucleotides, about 12 nucleotides to about 20 nucleotides, about 12 nucleotides to about 18 nucleotides, about 12 nucleotides to about 16 nucleotides, about 12 nucleotides to about 14 nucleotides, about 15 nucleotides to about 50 nucleotides, about 15 nucleotides to about 45 nucleotides, about 15 nucleotides to about 40 nucleotides, about 15 nucleotides to about 35 nucleotides, about 15 nucleotides to about 30 nucleotides, about 15 nucleotides to about 28 nucleotides, about 15 nucleotides to about 26 nucleotides, about 15 nucleotides to about 25 nucleotides, about 15 nucleotides to about 24 nucleotides, about 15 nucleotides to about 22 nucleotides, about 15 nucleotides to about 20 nucleotides, about 15 nucleotides to about 18 nucleotides, about 15 nucleotides to about 16 nucleotides, about 16 nucleotides to about 50 nucleotides, about 16 nucleotides to about 45 nucleotides, about 16 nucleotides to about 40 nucleotides, about 16 nucleotides to about 35 nucleotides, about 16 nucleotides to about 30 nucleotides, about 16 nucleotides to about 28 nucleotides, about 16 nucleotides to about 26 nucleotides, about 16 nucleotides to about 25 nucleotides, about 16 nucleotides to about 24 nucleotides, about 16 nucleotides to about 22 nucleotides, about 16 nucleotides to about 20 nucleotides, about 16 nucleotides to about 18 nucleotides, about 18 nucleotides to about 20 nucleotides, about 20 nucleotides to about 50 nucleotides, about 20 nucleotides to about 45 nucleotides, about 20 nucleotides to about 40 nucleotides, about 20 nucleotides to about 35 nucleotides, about 20 nucleotides to about 30 nucleotides, about 20 nucleotides to about 28 nucleotides, about 20 nucleotides to about 26 nucleotides, about 20 nucleotides to about 25 nucleotides, about 20 nucleotides to about 24 nucleotides, about 20 nucleotides to about 22 nucleotides, about 24 nucleotides to about 50 nucleotides, about 24 nucleotides to about 45 nucleotides, about 24 nucleotides to about 40 nucleotides, about 24 nucleotides to about 35 nucleotides, about 24 nucleotides to about 30 nucleotides, about 24 nucleotides to about 28 nucleotides, about 24 nucleotides to about 26 nucleotides, about 24 nucleotides to about 25 nucleotides, about 26 nucleotides to about 50 nucleotides, about 26 nucleotides to about 45 nucleotides, about 26 nucleotides to about 40 nucleotides, about 26 nucleotides to about 35 nucleotides, about 26 nucleotides to about 30 nucleotides, about 26 nucleotides to about 28 nucleotides, about 28 nucleotides to about 50 nucleotides, about 28 nucleotides to about 45 nucleotides, about 28 nucleotides to about 40 nucleotides, about 28 nucleotides to about 35 nucleotides, about 28 nucleotides to about 30 nucleotides, about 30 nucleotides to about 50 nucleotides, about 30 nucleotides to about 45 nucleotides, about 30 nucleotides to about 40 nucleotides, about 30 nucleotides to about 38 nucleotides, about 30 nucleotides to about 36 nucleotides, about 30 nucleotides to about 34 nucleotides, about 30 nucleotides to about 32 nucleotides, about 32 nucleotides to about 50 nucleotides, about 32 nucleotides to about 45 nucleotides, about 32 nucleotides to about 40 nucleotides, about 32 nucleotides to about 35 nucleotides, about 35 nucleotides to about 50 nucleotides, about 35 nucleotides to about 45 nucleotides, about 35 nucleotides to about 40 nucleotides, about 40 nucleotides to about 50 nucleotides, about 40 nucleotides to about 45 nucleotides, about 42 nucleotides to about 50 nucleotides, about 42 nucleotides to about 45 nucleotides, or about 45 nucleotides to about 50 nucleotides) in length. One skilled in the art will appreciate that inhibitory nucleic acids may comprises at least one modified nucleic acid at either the 5' or 3' end of DNA or RNA.

In some embodiments, the inhibitory nucleic acid can be formulated in a liposome, a micelle (e.g., a mixed micelle), a nanoemulsion, or a microemulsion, a solid nanoparticle, or a nanoparticle (e.g., a nanoparticle including one or more synthetic polymers). Additional exemplary structural features of inhibitory nucleic acids and formulations of inhibitory nucleic acids are described in US 2016/0090598.

In some embodiments, the inhibitory nucleic acid (e.g., any of the inhibitory nucleic acid described herein) can include a sterile saline solution (e.g., phosphate-buffered saline (PBS)). In some embodiments, the inhibitory nucleic acid (e.g., any of the inhibitory nucleic acid described herein) can include a tissue-specific delivery molecule (e.g., a tissue-specific antibody).

Compound Preparation and Biological Assays

As can be appreciated by the skilled artisan, methods of synthesizing the compounds of the formulae herein will be evident to those of ordinary skill in the art. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and R G M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

PREPARATIVE EXAMPLES

The following abbreviations have the indicated meaning
ACN=acetonitrile
AIBN=azodiisobutyronitrile
BTC=trichloromethyl chloroformate
Bu=butyl
DAST=Diethylaminosulfurtrifluoride
DCM=dichloromethane
DEA=diethylamine
DMF=N,N-dimethylformamide
DMSO=dimethyl sulfoxide
DIEA=N,N-diisopropylethylamine
DPPF=1,1'-Ferrocenediyl-bis(diphenylphosphine)
Dba=1,1'-Ferrocenediyl-bis(diphenylphosphine)
EtOH=ethanol
HPLC=high performance liquid chromatography
IPA=isopropanol
LC-MS=liquid chromatography-mass spectrometry
M=mol/L
Me=methyl
MeOH=methanol
NMR=nuclear magnetic resonance
Pd(dppf)$Cl_2$=dichloro[1,1'-bis(diphenylphosphino)ferrocene]palladium
Ph=phenyl
PPh$_3$Cl$_2$=dichlorotriphenylphosphorane
RT=room temperature
Rt=Retention time
Rf=Retardation factor
TEDA=Triethylenediamine
TBS=tert-butyldimethylsilyl
TBSCl=tert-butyldimethylsilyl chloride
TEA=triethylamine
TFA=trifluoroacetic acid
THF=tetrahydrofuran
TMEDA=N,N,N',N'-tetramethyl-ethane-1,2-diamine
TLC=thin layer chromatography
UV=ultraviolet General The progress of reactions was monitored by TLC or LC-MS. The identity of the products was confirmed by LC-MS. The LC-MS was recorded using one of the following methods:

Method A: Shim-pack XR-ODS, C18, 3×50 mm, 2.5 μm column, 1.0 μL injection, 1.5 mL/min flow rate, 90-900 amu scan range, 190-400 nm UV range, 5-100% (1.1 min), 100% (0.6 min) gradient with ACN (0.05% TFA) and water (0.05% TFA), 2 minute total run time.

Method B: Kinetex EVO, C18, 3×50 mm, 2.2 m column, 1.0 μL injection, 1.5 mL/min flow rate, 90-900 amu scan range, 190-400 nm UV range, 10-95% (1.1 min), 95% (0.6 min) gradient with ACN and water (0.5% NH4HCO3), 2 minute total run time.

Method C: Shim-pack XR-ODS, C18, 3×50 mm, 2.5 μm column, 1.0 μL injection, 1.5 mL/min flow rate, 90-900 amu scan range, 190-400 nm UV range, 5-100% (2.1 min), 100% (0.6 min) gradient with ACN (0.05% TFA) and water (0.05% TFA), 3 minute total run time.

Method D: Kinetex EVO, C18, 3×50 mm, 2.2 μm column, 1.0 μL injection, 1.5 mL/min flow rate, 90-900 amu scan range, 190-400 nm UV range, 10-95% (2.1 min), 95% (0.6 min) gradient with ACN and water (0.5% NH4HCO3), 3 minute total run time.

Method F: Phenomenex, CHO-7644, Onyx Monolithic C18, 50×4.6 mm, 10.0 μL injection, 1.5 mL/min flow rate, 100-1500 amu scan range, 220 and 254 nm UV detection, 5% with ACN (0.1% TFA) to 100% water (0.1% TFA) over 9.5 min, with a stay at 100% (ACN, 0.1% TFA) for 1 min, then equilibration to 5% (ACN, 0.1% TFA) over 1.5 min.

The final targets were purified by Prep-HPLC. The Prep-HPLC was carried out using the following method.

Method E: Prep-HPLC: Column, XBridge Shield RP18 OBD (19×250 mm, 10 μm); mobile phase, Water (10 mmol/L NH4HCO3) and ACN, UV detection 254/210 nm.

Method G: Prep-HPLC: Higgins Analytical Proto 200, C18 Column, 250×20 mm, 10 μm; mobile phase, Water (0.1% TFA) and ACN (0.1% TFA), UV detection 254/210 nm.

NMR was recorded on BRUKER NMR 300.03 MHz, DUL-C-H, ULTRASHIELD™ 300, AVANCE II 300 B-ACS™ 120 or BRUKER NMR 400.13 MHz, BBFO, ULTRA-SHIELD™ 400, AVANCE III 400, B-ACS™ 120

Scheme for the Preparation of Key Intermediates:

Scheme 1

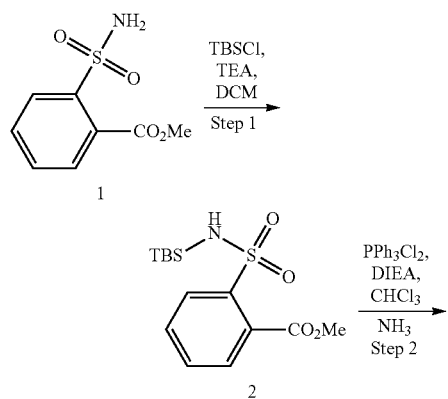

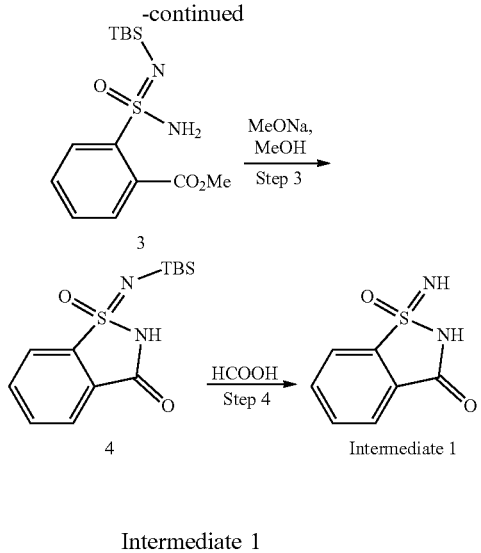

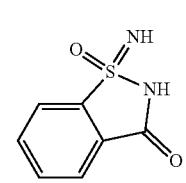 [SMILES: N=S1(=O)NC(=O)c2ccccc21]

1-Imino-1,2-dihydro-3H-1$^{\lambda 4}$-benzo[d]isothiazol-3-one 1-oxide

Step 1: Methyl 2-(N-(tert-butyldimethylsilyl)sulfamoyl)benzoate

Into a 50 mL round-bottom flask, was placed methyl 2-sulfamoylbenzoate (1.50 g, 6.7 mmol) in DCM (20 mL). To the stirred solution was added TEA (2.12 g, 21.0 mmol) and TBSCl (1.58 g, 10.0 mmol) in portions at 0° C. The resulting solution was stirred for overnight at ambient temperature. The reaction was then quenched by the addition of 20 mL of water and extracted with DCM. The organic layers were combined, dried over anhydrous sodium sulfate, and concentrated under vacuum. This resulted in 2.0 g (85%) of the title compound as a yellow solid. MS-ESI. 330.1 (M+1).

Step 2: Methyl 2-(N'-(tert-butyldimethylsilyl)sulfamidimidoyl)benzoate

Into a 50 mL 3-necked round-bottom flask purged and maintained with an inert atmosphere of nitrogen, was placed fresh prepared PPh$_3$Cl$_2$ (25 mL, 0.5 M in CHCl$_3$, 12.5 mmol, 2.5 equiv.) in CHCl$_3$ (50 mL). This was followed by the addition of DIEA (3.24 g, 25.0 mmol) dropwise at 0° C. with stirring in 10 min. The resulting solution was stirred for 10 min at ambient temperature and the reaction system was cooled to 0° C. To the mixture was added methyl 2-(N-(tert-butyldimethylsilyl)sulfamoyl) benzoate (1.65 g, 5.0 mmol) in CHCl3 (10 mL) dropwise at 0° C. with stirring. NH$_3$(g) was bubbled at 0° C. for 30 min. The resulting solution was stirred overnight at ambient temperature. The resulting solution was extracted with ethyl acetate. The organic layers were combined, dried over anhydrous sodium sulfate, and concentrated. The residue was purified by silica gel column with ethyl acetate/petroleum ether (40%) to give 400 mg (24%) of the title compound as a solid. MS-ESI. 329.1 (M+1).

Step 3: 1-((Tert-butyldimethylsilyl)imino)-1,2-dihydro-3H-1$^\lambda$4-benzo[d]isothiazol-3-one 1-oxide Into a 50 mL round-bottom flask, was placed methyl 2-(N'-(tert-butyldimethylsilyl)sulfamidimidoyl)benzoate (400 mg, 1.22 mmol) in MeOH (10 mL). To this was added MeONa (197 mg, 3.65 mmol) in portions at 0° C. The resulting solution was stirred for 4 h at ambient temperature. The resulting solution was extracted with ethyl acetate and then dried over anhydrous sodium sulfate. Filtration and concentration in vacuo delivered 300 mg (83%) of the title compound as a solid. MS-ESI: 297.2 (M+1).

Step 4: 1-Imino-1,2-dihydro-3H-1$^\lambda$4-benzo[d]isothiazol-3-one 1-oxide

Into a 50 mL round-bottom flask, was placed 1-((tert-butyldimethylsilyl)imino)-1,2-dihydro-3H-1$^\lambda$4-benzo[d]isothiazol-3-one 1-oxide (300 mg, 1.01 mmol), HCOOH (233 mg, 5.06 mmol). The resulting solution was stirred for 3 h at ambient temperature in an ice bath. The resulting solution was extracted with ethyl acetate dried over anhydrous sodium sulfate. Filtration and concentration in vacuo delivered 100 mg (65%) of the title compound as a solid. MS-ESI. 183.0 (M+1).

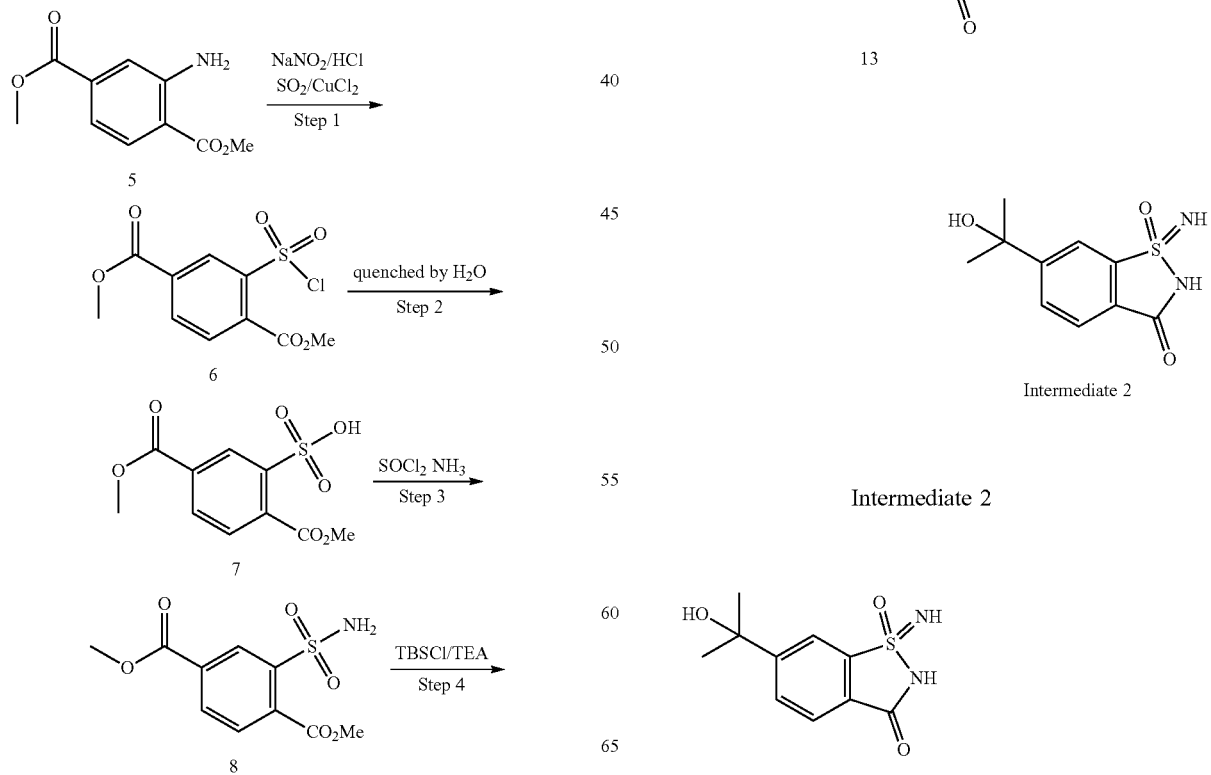

Scheme 2

Intermediate 2

6-(2-hydroxypropan-2-yl)-1-imino-2,3-dihydro-1-$^\lambda$-6,2-benzothiazole-1,3-dione Steps 1 and 2: 2,5-bis(methoxycarbonyl)benzene-1-sulfonic Acid Into a 100 mL round-bottom flask, was placed 1,4-dimethyl 2-aminobenzene-1,4-dicarboxylate (10.00 g, 47.80 mmol, 1.00 equiv.) in HCl (6M) (15 mL), and then NaNO$_2$ (3.96 g, 57.4 mmol, 1.20 equiv.) in water (30 ml) was added dropwise at −10° C. The resulting solution was stirred for 0.5 h at −10° C., then SO$_2$ in CH$_3$COOH (20 mL, 10% w/w) was added dropwise, then followed CuCl$_2$.2H$_2$O (9.78 g, 57.4 mmol, 1.20 equiv.) was added. The resulting solution was stirred for 0.5 h at −10° C. The resulting solution was quenched by water (20 ml). The resulting solution was extracted with ethyl acetate, then the organic layer was combined and, dried over anhydrous sodium sulfate and concentrated. The residue was purified by flash column chromatography on silica gel (1/7 DCM/hexanes) to give 7.0 g (53.4%) of 2,5-bis(methoxycarbonyl)benzene-1-sulfonic acid as a yellow solid. MS-ESI: 275.0 (M+1). $^1$H NMR: (400 MHz, DMSO-d6) δ 14.44 (brs, 1H), 8.31 (d, 1H), 7.94 (dd, 1H), 7.44 (d, 1H), 3.87 (s, 3H), 3.74 (s, 3H).

Step 3: 1,4-dimethyl 2-sulfamoylbenzene-1,4-dicarboxylate

Into a 100 mL round-bottom flask, was placed 2,5-bis(methoxycarbonyl)benzene-1-sulfonic acid (7.00 g, 25.55 mmol, 1 equiv.) in SOCl$_2$ (15 mL). The resulting solution was stirred for 1 h at 80° C. The resulting mixture was concentrated and the residue dissolved in DCM (20 mL). To the above, NH$_3$ $_{(g)}$ was bubbled for 10 min at 0° C. The resulting mixture was concentrated. The residue was purified by flash column chromatography on silica gel (1/2 ethyl acetate/petroleum ether) to give 5.0 g (71.7%) of 1,4-dimethyl 2-sulfamoylbenzene-1,4-dicarboxylate as a yellow solid. MS-ESI: 274.0 (M+1).

Step 4: 1,4-dimethyl 2-[(tert-butyldimethylsilyl)sulfamoyl]benzene-1,4-dicarboxylate Into a 100 mL round-bottom flask, was placed a solution of 1,4-dimethyl 2-sulfamoylbenzene-1,4-dicarboxylate (5.00 g, 18.31 mmol, 1 equiv.), TBSCl (4.15 g, 27.47 mmol, 1.5 equiv.) and TEA (5.55 g, 54.95 mmol, 3.00 equiv.) in DCM (35 mL). The resulting solution was stirred for 8 h at 25° C. The resulting mixture was concentrated to give 5.05 g of 1,4-dimethyl 2-[(tert-butyldimethylsilyl)sulfamoyl]benzene-1,4-dicarboxylate as an off-white solid that was used without further purification. MS-ESI: 388.1 (M+1).

Steps 5 and 6: 1,4-dimethyl 2-[(tert-butyldimethylsilyl)-S-aminosulfonimidoyl]benzene-1,4-dicarboxylate Into a 250 mL round-bottom flask purged and maintained with an inert atmosphere of nitrogen, was placed 1,4-dimethyl 2-[(tert-butyldimethylsilyl)sulfamoyl]benzene-1,4-dicarboxylate (5.05 g, 13.01 mmol, 1 equiv.) and DIEA (15.11 g, 117.14 mmol, 9 equiv.) in CHCl3 (30 mL), then a solution of PPh$_3$Cl$_2$ (78 mL, 39.05 mmol, 0.5 M in CHCl$_3$) in CHCl3 (30 ml) was added dropwise at 0° C. The resulting solution was stirred for 2 h at 0° C. under N2 atmosphere. To the above NH$_3$ $_{(g)}$ was bubbled for 10 min at 0° C. The residue was purified by flash column chromatography on silica gel (1/2 ethyl acetate/petroleum ether) to give 2.0 g (39.7%) of 1,4-dimethyl 2-[(tert-butyldimethylsilyl)-S-aminosulfonimidoyl]benzene-1,4-dicarboxylate as a yellow solid. MS-ESI: 387.1 (M+1).

Step 7: Methyl 1-[(tert-butyldimethylsilyl)imino]-1,3-dioxo-2,3-dihydro-1-$^\lambda$-6,2-benzothiazole-6-carboxylate Into a 100 mL round-bottom flask, was placed 1,4-dimethyl 2-[(tert-butyldimethylsilyl)-S-aminosulfonimidoyl]benzene-1,4-dicarboxylate (1.9 g, 4.9 mmol, 1 equiv.) and THF (20 mL). NaH (0.98 g, 60%, 24.6 mmol, 5 equiv.) was added to the mixture at 0° C. in portions over 30 min. The resulting solution was stirred for 2 h at 25° C. The reaction was then quenched by the addition of 10 mL of MeOH. The resulting mixture was concentrated. This resulted in 1.47 g of methyl 1-[(tert-butyldimethylsilyl)imino]-1,3-dioxo-2,3-dihydro-1-$^\lambda$-6,2-benzothiazole-6-carboxylate as a yellow solid that was used without further purification. MS-ESI: 355.2 (M+1).

Step 8: Methyl 1-imino-1,3-dioxo-2,3-dihydro-1-$^\lambda$-6,2-benzothiazole-6-carboxylate Into a 100 mL round-bottom flask, was placed methyl 1-[(tert-butyldimethylsilyl)imino]-1,3-dioxo-2,3-dihydro-1-$^\lambda$-6,2-benzothiazole-6-carboxylate (1.45 g, 4.1 mmol, 1 equiv.) in THF (20 mL). To the solution was added HF-Pyridine solution (0.1 mL). The resulting solution was stirred for 4 h at 25° C. The resulting mixture was concentrated. This resulted in 0.92 g of methyl 1-imino-1,3-dioxo-2,3-dihydro-1-$^\lambda$-6,2-benzothiazole-6-carboxylate as a yellow solid. MS-ESI: 241.0 (M+1).

Step 9: 6-(2-hydroxypropan-2-yl)-1-imino-2,3-dihydro-1-$^\lambda$-6,2-benzothiazole-1,3-dione Into a 100 mL round-bottom flask purged and maintained with an inert atmosphere of nitrogen, was placed methyl 1-imino-1,3-dioxo-2,3-dihydro-1-$^\lambda$-6,2-benzothiazole-6-carboxylate (900 mg, 3.75 mmol, 1 equiv.) in THF (15 mL). To the solution was added methyl magnesium bromide (6.3 mL, 18.8 mmol, 5.0 equiv, 3M in Et$_2$O) at 0° C. The resulting solution was stirred for overnight at 25° C. The reaction was then quenched by the addition of NH$_4$Cl (aq.). The resulting solution was extracted with ethyl acetate and the organic layers were combined and concentrated. The crude was purified by reverse phase with HP-flash with the following conditions: A:Water (10 mM NH$_4$HCO$_3$), Mobile Phase B: ACN; Flow rate: 100 mL/min; Gradient: 2% B to 50% B in 30 min. This resulted in 250 mg (28%) of 6-(2-hydroxypropan-2-yl)-1-imino-2,3-dihydro-1-$^\lambda$-2-benzothiazole-1,3-dione as a yellow solid. MS-ESI: 241.1 (M+1). $^1$H NMR (300 MHz, Methanol-d$_4$) δ 8.41 (s, 1H), 8.31 (d, 1H), 7.09-7.01 (m, 1H), 3.31 (s, 6H).

Scheme 3

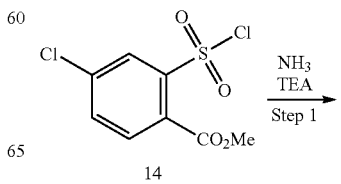

14

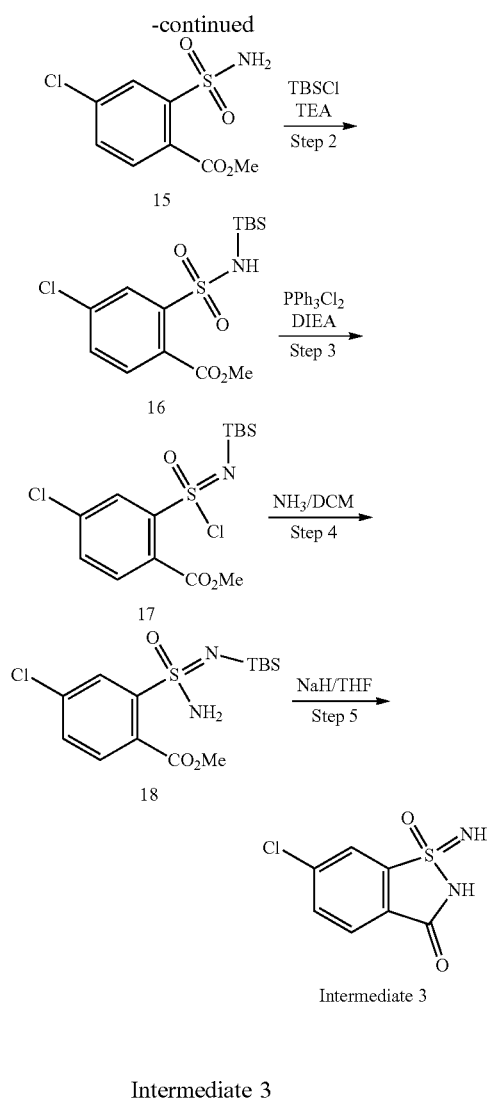

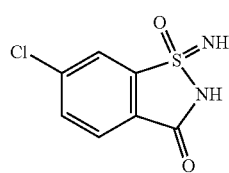 [SMILES: N=S1(=O)NC(=O)c2ccc(Cl)cc21]

6-chloro-1-imino-1,2-dihydro-3H-1$^\lambda$4-benzo[d]iso-
thiazol-3-one 1-oxide

Step 1: Methyl 4-chloro-2-sulfamoylbenzoate

Into a 250 mL round-bottom flask, was placed methyl 4-chloro-2-(chlorosulfonyl)benzoate (2.7 g, 10.03 mmol, 1 equiv.), TEA (3.05 g, 30.10 mmol, 3 equiv.) in DCM (30 mL). To the above NH$_3$ $_{(g)}$ was introduced in at 25° C. The resulting solution was stirred for additional 15 min at 25° C. The resulting mixture was concentrated. The residue was purified by flash column chromatography on silica gel (1/1 ethyl acetate/petroleum ether) to give 1.1 g (43.9%) of methyl 4-chloro-2-sulfamoylbenzoate as a yellow solid.

MS-ESI: 250.0 (M+1). $^1$H NMR (400 MHz, DMSO-d$_6$) δ 7.99 (d, 1H), 7.81 (d, 1H), 7.72 (d, 1H), 7.53 (s, 2H), 3.84 (s, 3H)

Step 2: Methyl 2-[(tert-butyldimethylsilyl)sulfa-
moyl]-4-chlorobenzoate

Into a 100 mL round-bottom flask, was placed methyl 4-chloro-2-sulfamoylbenzoate (900 mg, 3.6 mmol, 1 equiv.) in DCM (20 mL). To the solution were added TEA (2189 mg, 21.63 mmol, 6.00 equiv.) and TBSCl (1090 mg, 7.21 mmol, 2 equiv.). The resulting solution was stirred for 3 h at 25° C. The resulting mixture was concentrated. The residue was purified by flash column chromatography on silica gel (1/10 ethyl acetate/petroleum ether) to give 1.1 g of methyl 2-[(tert-butyldimethylsilyl)sulfamoyl]-4-chlorobenzoate as a yellow solid. MS-ESI: 364.1 (M+1).

Steps 3 and 4: Methyl 2-[(tert-butyldimethylsilyl)-
S-aminosulfonimidoyl]-4-chlorobenzoate Into a 100 mL round-bottom flask purged and maintained with an inert atmosphere of nitrogen, was placed methyl 2-[(tert-butyldimethylsilyl)sulfamoyl]-4-chlorobenzoate (940 mg, 2.6 mmol, 1 equiv.) and DIEA (2.0 g, 15.5 mmol, 6 equiv.) in CH$_3$Cl$_3$ (15 ml). Then a solution of PPh$_3$Cl$_2$ (15 mL, 0.5 M in CHCl$_3$, 7.5 mmol, 3 equiv.) in CH$_3$Cl$_3$ (15 mL) was added dropwise at 0° C. The resulting solution was stirred for 1 h at 0° C. To the above, NH$_3$ $_{(g)}$ was bubbled for 10 min at 0° C. The resulting solution was stirred for additional 2 h at 0° C. The resulting mixture was concentrated. The residue was purified by flash column chromatography on silica gel (1/5 ethyl acetate/petroleum ether) to give 200 mg (21.3%) of methyl 2-[(tert-butyldimethylsilyl)-S-aminosulfonimidoyl]-4-chlorobenzoate as a yellow solid. MS-ESI: 363.0 (M+1). $^1$H NMR (400 MHz, DMSO-d$_6$) δ 8.00 (d, 1H), 7.72 (d, 1H), 7.65 (d, 1H), 6.68 (s, 2H), 3.84 (s, 3H), 0.85 (s, 9H).

Step 5: 6-chloro-1-imino-1,2-dihydro-3H-1$^\lambda$4-benzo
[d]isothiazol-3-one 1-oxide Into a 50 mL round-bottom flask, was placed methyl 2-[(tert-butyldimethylsilyl)-S-aminosulfonimidoyl]-4-chlorobenzoate (200 mg, 0.6 mmol, 1 equiv.) in DCM (10 mL). To the solution was added NaH (66.1 mg, 60%, 1.65 mmol, 3 equiv.). The resulting solution was stirred for 3 h at 25° C. The reaction was then quenched by the addition of 5 mL of CH$_3$OH. The resulting mixture was concentrated. The residue was purified by flash column chromatography on silica gel (20/1 DCM/methanol) to give 112 mg (61.4%) of 6-chloro-1-imino-1,2-dihydro-3H-1l4-benzo[d]isothiazol-3-one 1-oxide as a yellow solid. MS-ESI: 217.1 (M+1).

Scheme 4

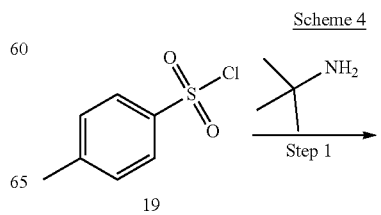

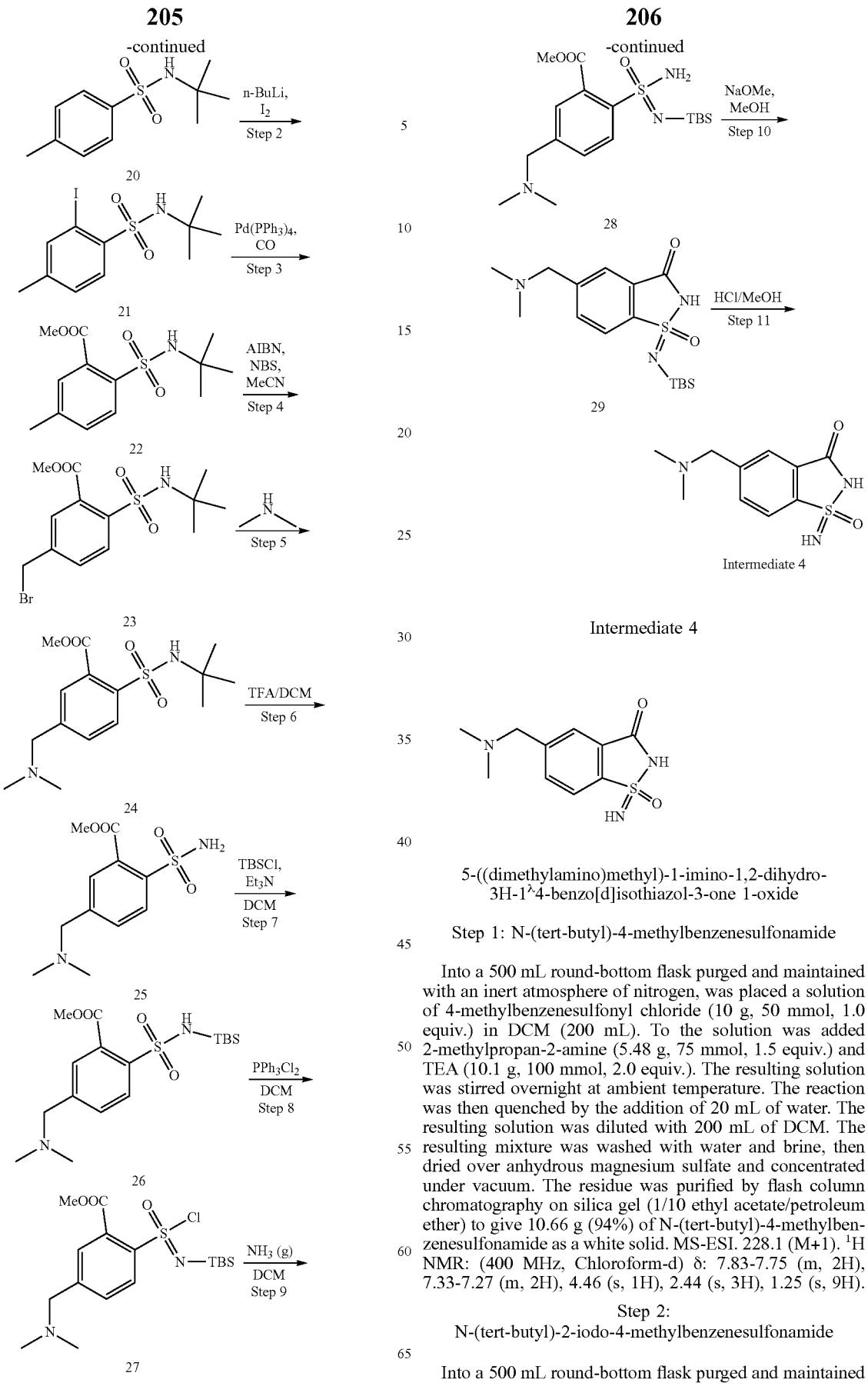

5-((dimethylamino)methyl)-1-imino-1,2-dihydro-
3H-1$^\lambda{}^4$-benzo[d]isothiazol-3-one 1-oxide Step 1: N-(tert-butyl)-4-methylbenzenesulfonamide Into a 500 mL round-bottom flask purged and maintained with an inert atmosphere of nitrogen, was placed a solution of 4-methylbenzenesulfonyl chloride (10 g, 50 mmol, 1.0 equiv.) in DCM (200 mL). To the solution was added 2-methylpropan-2-amine (5.48 g, 75 mmol, 1.5 equiv.) and TEA (10.1 g, 100 mmol, 2.0 equiv.). The resulting solution was stirred overnight at ambient temperature. The reaction was then quenched by the addition of 20 mL of water. The resulting solution was diluted with 200 mL of DCM. The resulting mixture was washed with water and brine, then dried over anhydrous magnesium sulfate and concentrated under vacuum. The residue was purified by flash column chromatography on silica gel (1/10 ethyl acetate/petroleum ether) to give 10.66 g (94%) of N-(tert-butyl)-4-methylbenzenesulfonamide as a white solid. MS-ESI. 228.1 (M+1). $^1$H NMR: (400 MHz, Chloroform-d) δ: 7.83-7.75 (m, 2H), 7.33-7.27 (m, 2H), 4.46 (s, 1H), 2.44 (s, 3H), 1.25 (s, 9H).

Step 2: N-(tert-butyl)-2-iodo-4-methylbenzenesulfonamide

Into a 500 mL round-bottom flask purged and maintained with an inert atmosphere of nitrogen, was placed a solution of N-(tert-butyl)-4-methylbenzenesulfonamide (20 g, 88.1 mmol, 1.0 equiv.) and TMEDA (22.48 g, 193.8 mmol, 2.2 equiv.) in THF (200 mL). To the solution were added n-BuLi (77 mL, 193.8 mmol, 2.2 equiv, 2.5 M in hexane) dropwise at −78° C. The resulting solution was stirred at −78° C. for 1 h. Then I2 (33.6 g, 132.2 mmol, 1.5 equiv.) in THF (50 mL) was added dropwise at −78° C. The resulting solution was stirred for 3 h at −78° C. The reaction was then quenched by the addition of 20 mL of water. The resulting solution was diluted with 200 mL of EtOAc. The resulting mixture was washed with water and brine, then dried over anhydrous magnesium sulfate and concentrated under vacuum. The residue was purified by flash column chromatography on silica gel (1/10 ethyl acetate/petroleum ether) to give 28.5 g (92%) of N-(tert-butyl)-2-iodo-4-methylbenzenesulfonamide as a white solid. MS-ESI: 354.0 (M+1). 1H NMR: (300 MHz, Chloroform-d) δ: 8.10 (d, 1H), 7.89 (dd, 1H), 7.33-7.25 (m, 1H), 5.16 (s, 1H), 2.39 (s, 3H), 1.24 (s, 9H).

Step 3: Methyl 2-(N-(tert-butyl)sulfamoyl)-5-methylbenzoate

Into a 250 mL high pressure reactor was placed a solution of N-(tert-butyl)-2-iodo-4-methylbenzenesulfonamide (5 g, 19.8 mmol, 1.0 equiv.) and Pd(PPh$_3$)$_4$ (4 g, 40 mmol, 2.0 equiv.) in MeOH (100 mL). The reactor was charged with CO$_{(g)}$ (10 atm) and stirred at 80° C. overnight. The mixture was concentrated and the residue was purified by flash column chromatography on silica gel (1/5 ethyl acetate/petroleum ether) to give 2.58 g (46%) of methyl 2-(N-(tert-butyl)sulfamoyl)-5-methylbenzoate as a yellow solid. MS-ESI: 286.1 (M+1). 1H NMR: (300 MHz, Chloroform-d) δ: 8.01 (d, 1H), 7.64-7.57 (m, 1H), 7.40 (d, 1H), 5.99 (s, 1H), 3.96 (s, 3H), 2.44 (s, 3H), 1.26 (s, 9H).

Step 4: Ethyl 5-(bromomethyl)-2-(N-(tert-butyl)sulfamoyl)benzoate

Into a 50 mL round-bottom flask purged and maintained with an inert atmosphere of nitrogen, was placed a solution of 2-(N-(tert-butyl)sulfamoyl)-5-methylbenzoate (2 g, 7.0 mmol, 1.0 equiv.), AIBN (115 mg, 0.7 mmol, 0.1 equiv.) and NBS (1.37 g, 7.7 mmol, 1.1 equiv.) in MeCN (50 mL). The resulting solution was stirred at 80° C. for 2 h. The mixture was then concentrated to give the methyl 5-(bromomethyl)-2-(N-(tert-butyl)sulfamoyl)benzoate as a yellow oil, which was used to next step without further purification. MS-ESI: 364.0 (M+1).

Step 5: Methyl 2-(N-(tert-butyl)sulfamoyl)-5-((dimethylamino)methyl)benzoate

Into a 250 mL round-bottom flask purged and maintained with an inert atmosphere of nitrogen, was placed a solution of methyl 5-(bromomethyl)-2-(N-(tert-butyl)sulfamoyl)benzoate (17.54 mmol, 1.0 equiv.) in THF (50 mL). To the solution were added dimethylamine solution (18 mL, 35 mmol, 2.0 equiv, 2 M in THF.) dropwise at 0° C. The resulting solution was stirred at ambient temperature overnight. The reaction was then quenched by the addition of 100 mL of water. The resulting solution was diluted with 200 mL of EtOAc. The resulting mixture was washed with water and brine, then dried over anhydrous magnesium sulfate and concentrated under vacuum. The residue was purified by flash column chromatography on silica gel (1/3 ethyl acetate/petroleum ether) to give 5.2 g (90%) of methyl 2-(N-(tert-butyl)sulfamoyl)-5-((dimethylamino)methyl)benzoate as a yellow oil. MS-ESI: 329.1 (M+1).

Step 6: Methyl 5-((dimethylamino)methyl)-2-sulfamoylbenzoate

Into a 50 mL round-bottom flask purged and maintained with an inert atmosphere of nitrogen, was placed a solution of methyl 2-(N-(tert-butyl)sulfamoyl)-5-((dimethylamino)methyl)benzoate (1 g, 3.05 mmol, 1.0 equiv.) in THF (20 mL) at at 0° C. TFA (1 mL) was added and the solution was stirred at ambient temperature overnight. The reaction was then concentrated. The residue was purified by flash column chromatography on silica gel (1/20 MeOH/DCM) to give 700 mg (84%) of methyl 5-((dimethylamino)methyl)-2-sulfamoylbenzoate as a yellow oil. MS-ESI: 273.1 (M+1).

Step 7: Methyl 2-(N-(tert-butyldimethylsilyl)sulfamoyl)-5-((dimethylamino)methyl)benzoate Into a 100 mL round-bottom flask purged and maintained with an inert atmosphere of nitrogen, was placed a solution of methyl 5-((dimethylamino)methyl)-2-sulfamoylbenzoate (1 g, 3.68 mmol, 1.0 equiv.) and Et$_3$N (740 mg, 7.36 mmol, 2.0 equiv.) in DCM (20 mL). To the solution were added TBSCl (834 mg, 5.52 mmol, 2.0 equiv.). The resulting solution was stirred at ambient temperature for 4 h. The reaction was then quenched by the addition of 10 mL of water. The resulting solution was diluted with 50 mL of EtOAc. The resulting mixture was washed with water and brine, then dried over anhydrous magnesium sulfate and concentrated under vacuum. This resulted in methyl 2-(N-(tert-butyldimethylsilyl)sulfamoyl)-5-((dimethylamino)methyl)benzoate as a yellow oil which was used in the next step without purification. MS-ESI. 387.2 (M+1).

Step 8: Methyl 2-(N-(tert-butyldimethylsilyl)-S-chlorosulfonimidoyl)-5-((dimethylamino)methyl)benzoate Into a 100 mL round-bottom flask purged and maintained with an inert atmosphere of nitrogen, was placed a solution of PPh$_3$Cl$_2$ (7.36 mmol) in DCM (20 mL), and then DIEA (950 mg, 7.36 mmol, 2.0 equiv.) was added, followed by methyl 2-(N-(tert-butyldimethylsilyl)sulfamoyl)-5-((dimethylamino)methyl)benzoate (3.68 mmol, 1.0 equiv.) in DCM (5 mL). The resulting solution was stirred at ambient temperature for 2 h. This resulted in methyl 2-(N-(tert-butyldimethylsilyl)-S-chlorosulfonimidoyl)-5-((dimethylamino)methyl)benzoate which was used in the next step without purification.

Step 9: Methyl 2-(N'-(tert-butyldimethylsilyl)sulfamidimidoyl)-5-((dimethylamino)methyl)benzoate Into a 100 mL round-bottom flask purged and maintained with an inert atmosphere of nitrogen, was placed a solution of methyl 2-(N-(tert-butyldimethylsilyl)-S-chlorosulfonimidoyl)-5-((dimethylamino)methyl)benzoate (3.68 mmol, 1.0 equiv.) in DCM (50 mL). NH$_3$(g) was bubbled for 30 min. The resulting solution was stirred at ambient temperature overnight. The resulting solution was diluted with 50 mL of DCM. The resulting mixture was washed with 1×100 mL of water and 1×100 mL of brine. The mixture was dried over anhydrous magnesium sulfate and concentrated under vacuum. This resulted in 460 mg methyl 2-(N'-(tert-butyldimethylsilyl)sulfamidimidoyl)-5-((dimethylamino)methyl) benzoate as a yellow oil. MS-ESI. 386.2 (M+1).

Step 10: 1-((tert-butyldimethylsilyl)imino)-5-((dimethylamino)methyl)-1,2-dihydro-3H-1$^{\lambda}$4-benzo[d] isothiazol-3-one 1-oxide A 50 mL round bottom flask was placed under an atmosphere of nitrogen, was placed a solution of methyl 2-(N'-(tert-butyldimethylsilyl)sulfamidimidoyl)-5-((dimethylamino)methyl)benzoate (460 mg, 1.19 mmol, 1.0 equiv.) in MeOH (20 mL). To the solution was added NaOMe (129 mg, 2.38 mmol, 2.0 equiv.). The resulting solution was stirred at ambient temperature overnight. The reaction was then concentrated. The residue was purified by flash column chromatography on silica gel (1/5 MeOH/DCM) to give 320 mg (76%) 1-((tert-butyldimethylsilyl)imino)-5-((dimethylamino)methyl)-1,2-dihydro-3H-1$^{\lambda}$4-benzo[d]isothiazol-3-one 1-oxide as a yellow oil. MS-ESI: 354.2 (M+1).

Step 11: 5-((dimethylamino)methyl)-1-imino-1,2-dihydro-3H-1$^{\lambda}$4-benzo[d]isothiazol-3-one 1-oxide Into a 50 mL round-bottom flask purged and maintained with an inert atmosphere of nitrogen, was placed a solution of 1-((tert-butyldimethylsilyl)imino)-5-((dimethylamino) methyl)-1,2-dihydro-3H-1$^{\lambda}$4-benzo[d]isothiazol-3-one 1-oxide (320 mg, 0.9 mmol, 1.0 equiv.) in MeOH (20 mL). To the solution was added HCl in MeOH (2 M, 5 mL, 10 mmol, 11.1 equiv.). The resulting solution was stirred at ambient temperature for 3 h. The reaction was then filtered, and the filter cake was washed by MeOH. The combined organic layers were concentrated under vacuum. This resulted in 120 mg (39%) 5-((dimethylamino)methyl)-1-imino-1,2-dihydro-3H-1l4-benzo[d]isothiazol-3-one 1-oxide as a yellow oil. MS-ESI: 340.1 (M+1).

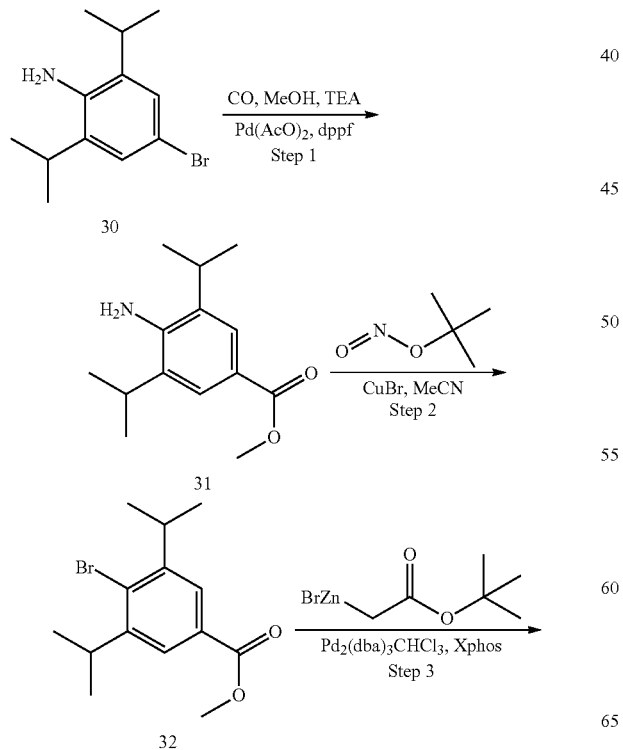

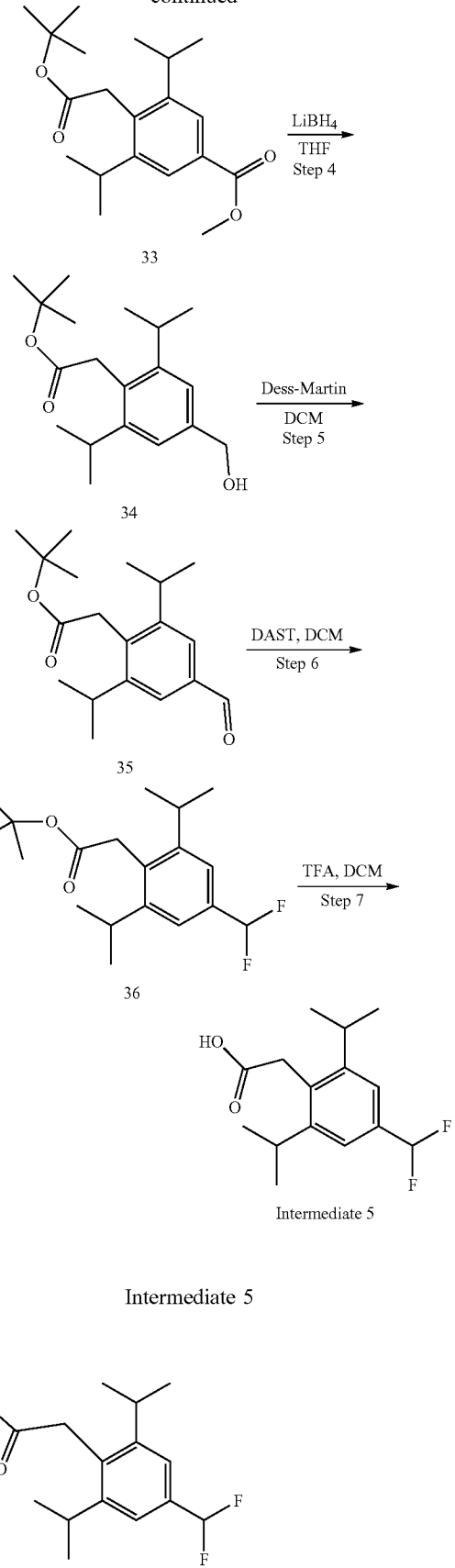

2-(4-(difluoromethyl)-2,6-diisopropylphenyl)acetic acid

Step 1: Methyl 4-amino-3,5-diisopropylbenzoate

Into a 1-L autoclave was placed a solution of 4-bromo-2,6-diisopropylbenzenamine (10 g, 39.0 mmol, 1 equiv.) in MeOH (300 mL). To the solution were added Pd(OAc)$_2$ (1.75 g, 7.8 mmol, 0.2 equiv.), dppf (4.3 g, 7.8 mmol, 0.2 equiv.), and TEA (20 g, 197.6 mmol, 5.1 equiv). After sealed the autoclave, the gas was exchanged with CO for 3 times. The reaction was stirred at 120° C. for overnight. After cooling the reaction mixture, the reaction was concentrated and diluted with water (300 mL). The resulting solution was extracted with EtOAc and the combined organic layers were dried over anhydrous Na$_2$SO$_4$ and concentrated. The residue was purified by flash column chromatography on silica gel (1/5, ethyl acetate/petroleum ether) to give 5.6 g (62%) of the title compound as a brown oil. MS-ESI. 236.2 (M+1).

Step 2: Methyl 4-bromo-3,5-bis(propan-2-yl)benzoate

Into a 250-mL round-bottom flask, was placed a solution of methyl 4-amino-3,5-bis(propan-2-yl)benzoate (5 g, 21.2 mmol, 1.0 equiv.) in ACN (80 mL). To the solution was added tert-butyl nitrite (4.39 g, 42.6 mmol, 2.0 equiv.), and then CuBr (6.08 g, 42.4 mmol, 2.0 equiv). The resulting solution was stirred for 3 h at 60° C. in an oil bath. The resulting mixture was concentrated under vacuum. The residue was purified by flash column chromatography on silica gel (1/10, ethyl acetate/petroleum ether) to give 3.37 g (53%) of methyl 4-bromo-3,5-bis(propan-2-yl)benzoate as an orange solid.

Step 3: Methyl 4-amino-3,5-diisopropylbenzoate

Into a 250-mL round-bottom flask, was placed a solution of methyl 4-bromo-3,5-bis(propan-2-yl)benzoate (3.38 g, 11.28 mmol, 1.0 equiv.) in THF (80 mL). To the solution was added Pd$_2$(dba)$_3$CHCl$_3$ (586.0 mg, 2.22 mmol, 0.2 equiv.), XPhos (540.0 mg, 2.23 mmol, 0.2 equiv) and tert-butyl 2-(zincio-^2-bromanyl)acetate (5.85 g, 22.5 mmol, 2.0 equiv.) under nitrogen. The resulting solution was stirred for 3 h at 65° C. in an oil bath. The resulting mixture was concentrated under vacuum. The residue was purified by flash column chromatography on silica gel (1/10, ethyl acetate/petroleum ether) to give 2.1 g (56%) of methyl 4-[2-(tert-butoxy)-2-oxoethyl]-3,5-bis(propan-2-yl)benzoate as yellow oil.

Step 4: Tert-butyl 2-(4-(hydroxymethyl)-2,6-diisopropylphenyl)acetate

Into a 100 mL round bottom flask was placed a solution of methyl 4-(2-tert-butoxy-2-oxoethyl)-3,5-diisopropylbenzoate (2 g, 6.0 mmol, 1.0 equiv.) in THF (25 mL). LiBH$_4$ (264 mg, 12.0 mmol, 2.0 equiv.) was added to the mixture at 0° C. in portions over 10 mins. The mixture was stirred at 0° C. for 1 h. The reaction was quenched with ice-water (20 mL). The solution was extracted with EtOAc and the combined organic layers were dried over anhydrous Na$_2$SO$_4$ and concentrated under vacuum. The residue was purified by flash column chromatography on silica gel (1/5-1/2, ethyl acetate/petroleum ether) to give 1.1 g (60%) of tert-butyl 2-(4-(hydroxymethyl)-2,6-diisopropylphenyl)acetate as a white solid. MS-ESI: 307.2 (M+1).

Step 5: Tert-butyl 2-(4-formyl-2,6-diisopropylphenyl)acetate

Into a 100 mL round bottom flask was placed a solution of tert-butyl 2-(4-(hydroxymethyl)-2,6-diisopropylphenyl)acetate (1.1 g, 3.6 mmol, 1.0 equiv.) in DCM (20 mL). Dess-Martin Periodinane (2.29 g, 5.4 mmol, 1.5 equiv.) was added to the mixture at 0° C. in portions over 10 mins. The mixture was stirred at ambient temperature overnight and quenched with ice-water (20 mL). The solution was extracted with DCM and the combined organic layers were dried over anhydrous Na$_2$SO$_4$ and concentrated under vacuum. The residue was purified by flash column chromatography on silica gel (1/20-1/10, ethyl acetate/petroleum ether) to give 0.98 g (90%) of tert-butyl 2-(4-formyl-2,6-diisopropylphenyl)acetate as a yellow solid. MS-ESI: 305.2 (M+1).

Step 6: Tert-butyl 2-(4-(difluoromethyl)-2,6-diisopropylphenyl)acetate

Into a 100 mL round bottom flask was placed a solution of tert-butyl 2-(4-formyl-2,6-diisopropylphenyl)acetate (912 mg, 3.0 mmol, 1.0 equiv.) in DCM (15 mL). DAST (2.41 g, 15 mmol, 5.0 equiv.) was added to the mixture at 0° C. The mixture was stirred at ambient temperature overnight. The mixture was quenched with water (10 mL) and the solution was extracted with DCM. The combined organic layers were dried over Na$_2$SO$_4$ and concentrated under vacuum. The residue was purified by flash column chromatography on silica gel (1/20-1/15, ethyl acetate/petroleum ether) to give 586 mg (60%) of tert-butyl 2-[4-(difluoromethyl)-2,6-bis(propan-2-yl)phenyl]acetate as a yellow solid. MS-ESI: 327.2 (M+1).

Step 7: 2-(4-(difluoromethyl)-2,6-diisopropylphenyl)acetic Acid

Into a 15-mL round-bottom flask, was placed a solution of tert-butyl 2-[4-(difluoromethyl)-2,6-bis(propan-2-yl)phenyl]acetate (586 mg, 1.79 mmol, 1.0 equiv.) in dichloromethane (2 mL) and trifluoroacetic acid (0.4 mL). The resulting solution was stirred for 2 h at ambient temperature. The resulting solution was concentrated under vacuum. This resulted in 480 mg of 2-[4-(difluoromethyl)-2,6-bis(propan-2-yl)phenyl]acetic acid as a yellow solid which was used without additional purification. MS-ESI: 269.1 (M−1).

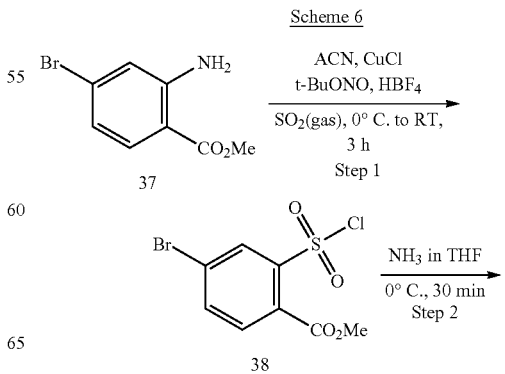

Scheme 6

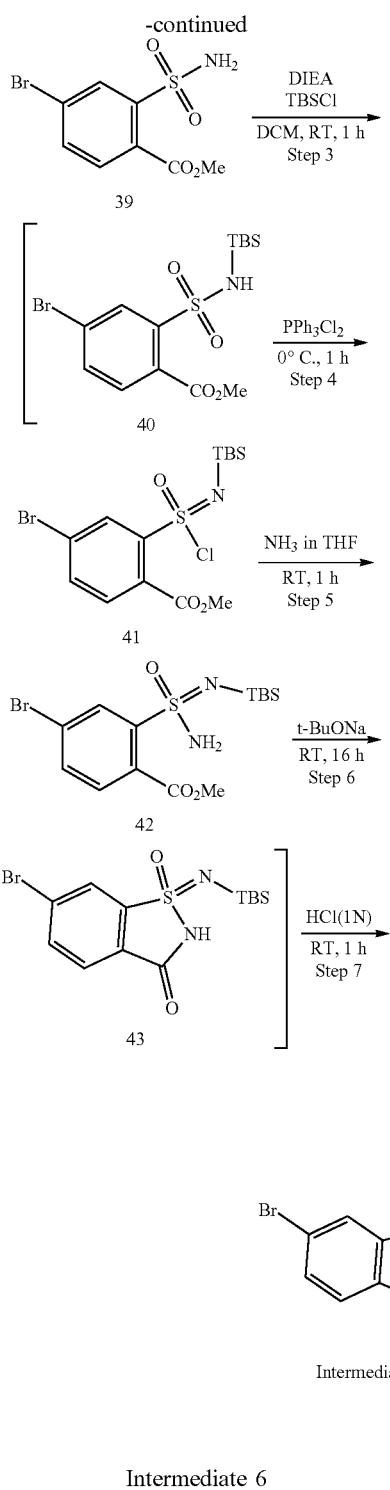

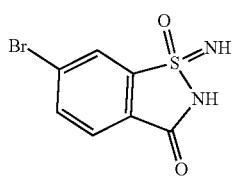 [SMILES: N=S1(=O)NC(=O)c2ccc(Br)cc21]

Intermediate 6

6-bromo-1-imino-1,2-dihydro-3H-1λ4-benzo[d]iso-thiazol-3-one 1-oxide

Step 1: Methyl 4-bromo-2-(chlorosulfonyl)benzoate

Solution A: A 1 L 4-neck flask was charged with a solution of CuCl (12.7 g, 131 mmol, 3.0 equiv.) in ACN (200 mL). To the solution, $SO_{2(g)}$ was bubbled for 3 hours at 0° C. give a saturated solution (bubbles observed in the outgas bubbler, assuming it was saturated).

Solution B: A 250 ml 4-neck flask was charged with a solution of methyl 2-amino-4-bromobenzoate (10 g, 34.6 mmol, 1.0 equiv.) in ACN (100 mL) and cooled to 0° C. $HBF_4$ (40% in water, 14.4 g, 65.5 mmol, 1.5 equiv.) was added dropwise, maintaining the internal temperature at 0° C. The resulting solution was stirred for 15 min at 0° C., and then t-BuONO (6.7 g, 65.5 mmol, 1.5 equiv.) was added by dropwise at 0° C. The resulting solution was stirred for 1 h at 0° C.

Solution B was introduced to Solution A at 0° C. via cannula under N2. The resulting solution was kept stirring for an additional 3 h at room temperature (25° C.). The reaction was quenched by pouring into water/ice at 0° C. The resulting mixture was extracted with methyl tert-butyl ether (3×300 mL). The combined organic layers were washed with water (2×300 mL), dried over by anhydrous $MgSO_4$ and concentrated under reduced pressure at ambient temperature to afford methyl 4-bromo-2-(chlorosulfonyl) benzoate as a light yellow solid (12.5 g).

Step 2: Methyl 4-bromo-2-sulfamoylbenzoate

To a 2 L 4-neck flask placed a solution of methyl 4-bromo-2-(chlorosulfonyl) benzoate (12 g, 38.6 mmol, 1.0 equiv.) in THF (120 mL) was added $NH_3$ (1M in THF) (115 ml, 115 mmol, 3.0 equiv.) dropwise at 0° C. The resulting solution was kept stirring for 30 min at ambient temperature.

The resulting mixture was diluted with water (50 mL) and extracted with ethyl acetate (3×500 mL). The combined organic layers were washed with brine (2×500 mL). The organic layer was dried over by anhydrous $Na_2SO_4$. After filtration, the filtrate was concentrated under reduced pressure. The crude product was re-crystallized from petroleum ether/ethyl acetate (10:1, 70 mL) to afford methyl 4-bromo-2-sulfamoylbenzoate as a light-yellow solid (10.6 g). MS-ESI: 294.1 (M+1).

Step 3: Methyl 4-bromo-2-(N-(tert-butyldimethylsi-lyl)sulfamoyl)benzoate

To a 1 L flask was placed a solution of methyl 4-bromo-2-sulfamoylbenzoate (40.9 g, 139 mmol, 1.0 equiv.) in DCM (410 mL). DIEA (147.9 mL, 836 mmol, 6.0 equiv.) was then added. The resulting solution was cooled to 0° C., and TBSCl (42.2 g, 280.0 mmol, 2.0 equiv.) was added to the solution in several portions at 0° C. The resulting solution was kept stirring for 1 h at ambient temperature and then used to next step directly. MS-ESI: 408.2 (M+1).

Step 4: Methyl 4-bromo-2-(N-(tert-butyldimethylsi-lyl)-S-chlorosulfonimidoyl)benzoate The above solution of methyl 4-bromo-2-(N-(tert-butyldi-methylsilyl)sulfamoyl)benzoate in DCM from step 3 was cooled to 0° C. $PPh_3Cl_2$ (834.4 mL, 25 mL, 0.5 M in $CHCl_3$, 417.2 mmol, 3.0 equiv.) was added to the solution in several portions at 0° C. The resulting solution was kept stirring for additional 1 h at 0° C. The reaction was monitored by quenching aliquots with THF/NH₃ solution (0.5 M), until no methyl 4-bromo-2-(N-(tert-butyldimethylsilyl)sulfamoyl)benzoate was observed in the LCMS trace. Then the solution was used to next step directly.

Step 5: Methyl 4-bromo-2-(N'-(tert-butyldimethylsilyl)sulfamimidoyl)benzoate

To a 5 L 4-neck flask was charged with NH₃ (1.1M in THF) (2 L, 2.2 mol, 15.8 equiv.) and the solution was cooled to 0° C. The reaction solution of step 4 (methyl 4-bromo-2-(N-(tert-butyldimethylsilyl)-S-chlorosulfonimidoyl)benzoate in DCM) was introduced to this solution via cannula at 0° C. The resulting solution was kept stirring for 1 h at ambient temperature, until no methyl 4-bromo-2-(N-(tert-butyldimethylsilyl)-S-chlorosulfonimidoyl)benzoate was observed from LC or LCMS.

Step 6: 6-bromo-1-((tert-butyldimethylsilyl)imino)-1,2-dihydro-3H-1λ4-benzo[d]isothiazol-3-one 1-oxide t-BuONa (40.0 g, 417 mmol, 3.0 equiv.) was added to the above solution (methyl 4-bromo-2-(N'-(tert-butyldimethylsilyl)sulfamimidoyl)benzoate in DCM) from step 5 at ambient temperature. The resulting mixture was kept stirring for an additional overnight at ambient temperature.

Step 7: 6-bromo-1-imino-1,2-dihydro-3H-1λ4-benzo[d]isothiazol-3-one 1-oxide

The reaction mixture of 6-bromo-1-((tert-butyldimethylsilyl)imino)-1,2-dihydro-3H-1λ4-benzo[d]isothiazol-3-one 1-oxide from step 6 was acidified to pH 2 with HCl (1M) at 0° C. and kept stirring for 1 h. The resulting solution was extracted with ethyl acetate (3×5 L). The combined organic layers were adjusted to pH 8 with NaOH (aq, 2N) and exacted with 2×5 L of water. The aqueous phases was combined, cooled to 0° C. and then adjusted to pH 2 with conc. HCl. The aqueous phases were extracted with ethyl acetate (3×5 L) and dried over anhydrous Na₂SO₄. After filtration, the filtrate was concentrated under reduced pressure to afford 6-bromo-1-imino-1,2-dihydro-3H-1λ4-benzo[d]isothiazol-3-one 1-oxide as a white solid (28.9 g). MS-ESI: 261.0/263.0 (M+1). ¹HNMR: (300 MHz, DMSO-d₆): δ 8.25 (s, 2H), 8.17 (d, 1H), 8.04-8.07 (m, 1H), 7.78 (d, 1H).

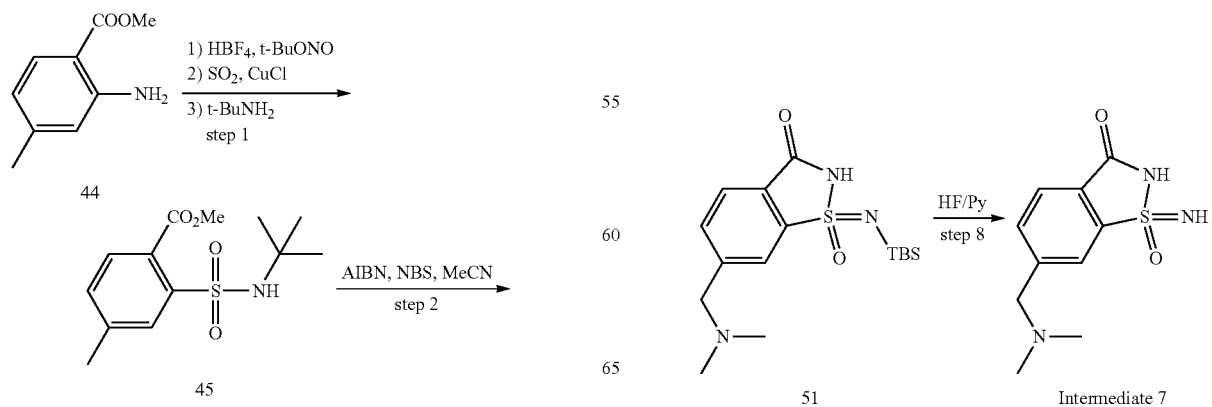

Intermediate 7

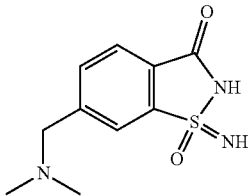 [SMILES: CN(C)Cc1ccc2c(c1)S(=N)(=O)NC2=O]

6-((dimethylamino)methyl)-1-imino-1,2-dihydro-3H-114-benzo[d]isothiazol-3-one 1-oxide

Step 1: Methyl 2-(N-tert-butylsulfamoyl)-4-methylbenzoate

Into a 500 mL round-bottom flask was placed 100 mL of CH₃COOH. To the solution was bubbled SO₂ for ~3 hours at 0° C. to give a saturated solution (bubbles observed in the outgas bubbler, assuming it was saturated).

Into a 500 mL round-bottom flask purged and maintained with an inert atmosphere of nitrogen, was placed a solution of methyl 2-amino-4-methylbenzoate (2.00 g, 12.1 mmol, 1.0 equiv.) in ACN (200 mL) and the solution was cooled to 0° C. HBF₄ (1.61 g, 18.2 mmol, 1.5 equiv.) and tert-butyl nitrite (1.87 g, 18.2 mmol, 1.5 equiv.). After stirring for 0.5 h at 0° C., the above SO₂/CH₃COOH solution (20 mL, saturated) was added dropwise, followed by the addition of CuCl₂.2H₂O (24.00 g, 242.1 mmol, 20.0 equiv.). The resulting solution was stirred for additional 3 h at ambient temperature and then quenched by the addition of ice-water at 0° C. The solution was extracted with methyl tert-butyl ether. The combined organic layers were washed with brine, dried over anhydrous Mg₂SO₄, and concentrated under vacuum to afford crude methyl 2-(chlorosulfonyl)-4-methylbenzoate as a light-yellow solid. The solid was dissolved in DCM (5 mL) and the solution was added to a solution of t-BuNH₂ (3.50 g, 47.9 mmol, 4.0 equiv.) in DCM (20 mL) at 0° C. The mixture was stirred at ambient temperature overnight. The mixture was concentrated, and the residue was purified by flash column chromatography on silica gel (ethyl acetate/hexane=1:2) to give 1.54 g of methyl 2-(N-tert-butylsulfamoyl)-4-methylbenzoate as a yellow solid. MS-ESI: 286.1 (M+1). ¹H NMR: (400 MHz, CDCl₃) δ: 7.83-7.75 (m, 2H), 7.33-7.27 (m, 2H), 4.46 (s, 1H), 2.44 (s, 3H), 1.25 (s, 9H).

Step 2: Methyl 5-(bromomethyl)-2-(N-(tert-butyl)sulfamoyl)benzoate

Into a 50-mL round-bottom flask purged and maintained with an inert atmosphere of nitrogen, was placed a solution of 2-(N-(tert-butyl)sulfamoyl)-5-methylbenzoate (1.50 g, 5.3 mmol, 1.0 equiv.), AIBN (115 mg, 0.7 mmol, 0.1 equiv.) and NBS (1.40 g, 7.7 mmol, 1.1 equiv.) in MeCN (50 mL). The resulting solution was stirred at 80° C. for 2 h. The mixture was then cooled to ambient temperature, concentrated and the residue was purified by flash column chromatography on silica gel column (ethyl acetate/hexane=1:5) to give crude methyl 5-(bromomethyl)-2-(N-(tert-butyl)sulfamoyl)benzoate as a yellow oil, which was used directly without further purification.

Step 3: Methyl 2-(N-tert-butylsulfamoyl)-4-((dimethylamino)methyl)benzoate

Into a 250 mL round-bottom flask purged and maintained with an inert atmosphere of nitrogen, was placed a solution of methyl 5-(bromomethyl)-2-(N-(tert-butyl)sulfamoyl)benzoate (1.00 g, 2.7 mmol, 1.0 equiv.) in DCM (50.0 mL).To the solution was added dimethylamine (2.43 g, 54.0 mmol, 20.0 equiv.). The resulting solution was stirred overnight at ambient temperature. The resulting mixture was concentrated and the residue was purified by flash column chromatography on silica gel (ethyl acetate/hexane=1:1) to give 600 mg of methyl 2-(N-tert-butylsulfamoyl)-4-((dimethylamino)methyl)benzoate as yellow oil. MS-ESI: 329.1 (M+1).

Step 4: Methyl 4-[(dimethylamino)methyl]-2-sulfamoylbenzoate

Into a 100-mL round-bottom flask was placed a solution of methyl 2-(N-tert-butylsulfamoyl)-4-((dimethylamino)methyl)benzoate (600 mg, 6.3 mmol, 1.0 equiv.) in DCM (20.0 mL) and TFA (20.0 mL). The resulting solution was stirred for overnight at ambient temperature. The resulting mixture was concentrated, and the residue was purified by flash column chromatography on silica gel (10:1 DCM/methanol) to give 450 mg of methyl 4-[(dimethylamino)methyl]-2-sulfamoylbenzoate as a yellow solid. MS-ESI: 273.1 (M+1).

Step 5: Methyl 2-[(tert-butyldimethylsilyl)sulfamoyl]-4-[(dimethylamino)methyl]benzoate Into a 50 mL round-bottom flask, was placed a solution of methyl 4-[(dimethylamino)methyl]-2-sulfamoylbenzoate (300 mg, 1.1 mmol, 1.0 equiv.) and DIEA (0.46 mL, 3.3 mmol, 3.0 equiv.) in DCM (10.0 mL). To the solution was added TBSCl (332 mg, 2.2 mmol, 2.0 equiv.). The resulting solution was stirred for 3 h at ambient temperature. The reaction was then quenched by the addition of 20 mL of water. The resulting solution was extracted with dichloromethane, and the organic layers were combined and concentrated. This resulted in 380 mg of methyl 2-[(tert-butyldimethylsilyl)sulfamoyl]-4-[(dimethylamino)methyl]benzoate as yellow oil. MS-ESI: 387.2 (M+1).

Step 6: Methyl 2-[(tert-butyldimethylsilyl)-S-aminosulfonimidoyl]-4-[(dimethylamino)methyl]benzoate Into a 100 mL round-bottom flask purged and maintained with an inert atmosphere of nitrogen, was placed a solution of PPh₃Cl₂ (6 mL, 0.5 M in CHCl₃, 3.0 mmol, 3.0 equiv.) in DCM (5 mL). Then DIEA (0.5 mL, 2.9 mmol, 3.0 equiv.) was added, followed by the addition of a solution of methyl 2-[(tert-butyldimethylsilyl)sulfamoyl]-4-[(dimethylamino)methyl]benzoate (370 mg, 1.0 mmol, 1.0 equiv.) in DCM (5 mL). The resulting solution was stirred at ambient temperature for 2 h, after which NH₃ (g) was bubbled through the reaction mixture for 10 min at 0° C. The resulting solution was stirred for overnight at room temperature. The reaction was then quenched by the addition of 50 mL of water. The resulting solution was extracted with ethyl acetate and the combined organic layers were concentrated. The residue was purified by flash column chromatography on silica gel (ethyl acetate/hexane=1:1) to give 180 mg of methyl 2-[(tert-butyldimethylsilyl)-S-aminosulfonimidoyl]-4-[(dimethyl-amino)methyl]benzoate as a yellow solid. MS-ESI: 386.2 (M+1).

Step 7: 1-((tert-butyldimethylsilyl)imino)-6-((dim-ethylamino)methyl)-1,2-dihydro-3H-1λ4-benzo[d]isothiazol-3-one 1-oxide A 25 mL round-bottom flask was charged with a solution of methyl 2-[(tert-butyldimethylsilyl)-S-aminosulfonimi-doyl]-4-[(dimethylamino)methyl]benzoate (200 mg, 0.5 mmol, 1.0 equiv.) in MeOH (5.0 mL). NaOMe (84 mg, 1.6 mmol, 3.2 equiv.) was added and the resulting solution was stirred overnight at ambient temperature. The resulting mixture was concentrated and the residue was purified by flash column chromatography on silica gel (ethyl acetate/hexane=1:1) to give 100 mg of 1-((tert-butyldimethylsilyl)imino)-6-((dimethylamino)methyl)-1,2-dihydro-3H-1λ4-benzo[d]isothiazol-3-one 1-oxide as a yellow oil. MS-ESI: 354.2 (M+1).

Step 8: 6-((dimethylamino)methyl)-1-imino-1,2-dihydro-3H-1λ4-benzo[d]isothiazol-3-one 1-oxide A 25 mL round-bottom flask was charged with a solution of 1-((tert-butyldimethylsilyl)imino)-6-((dimethylamino)methyl)-1,2-dihydro-3H-1λ4-benzo[d]isothiazol-3-one 1-oxide (100 mg, 0.3 mmol, 1.0 equiv.) in THF (2 mL) and HF-Pyridine (140 mg, 1.4 mmol, 5 equiv.). The resulting solution was stirred for 6 h at ambient temperature and then quenched by the addition of water. The resulting solution was extracted with ethyl acetate and the combined organic layers were concentrated. The residue was purified by flash column chromatography on silica gel (ethyl acetate/hexane=1:1) to give 50 mg of 6-((dimethylamino)methyl)-1-imino-1,2-dihydro-3H-1λ4-benzo[d]isothiazol-3-one 1-oxide as a yellow oil. MS-ESI: 240.1 (M+1).

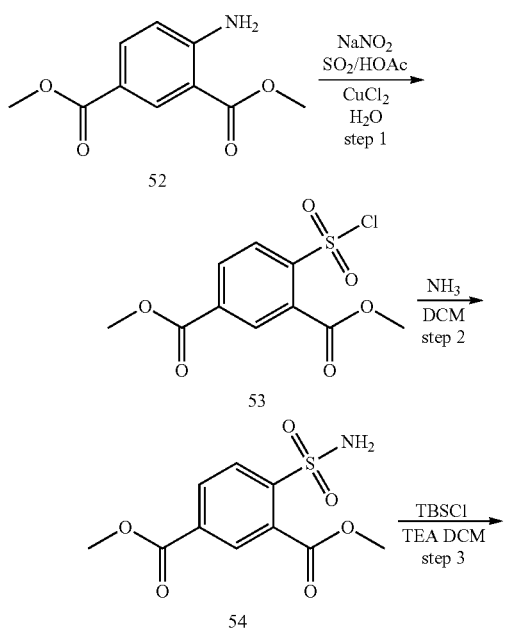

Scheme 8

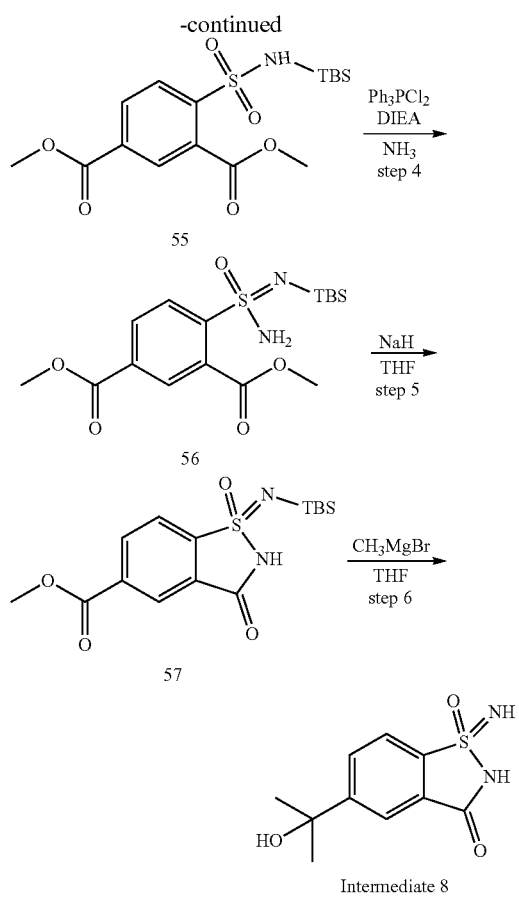

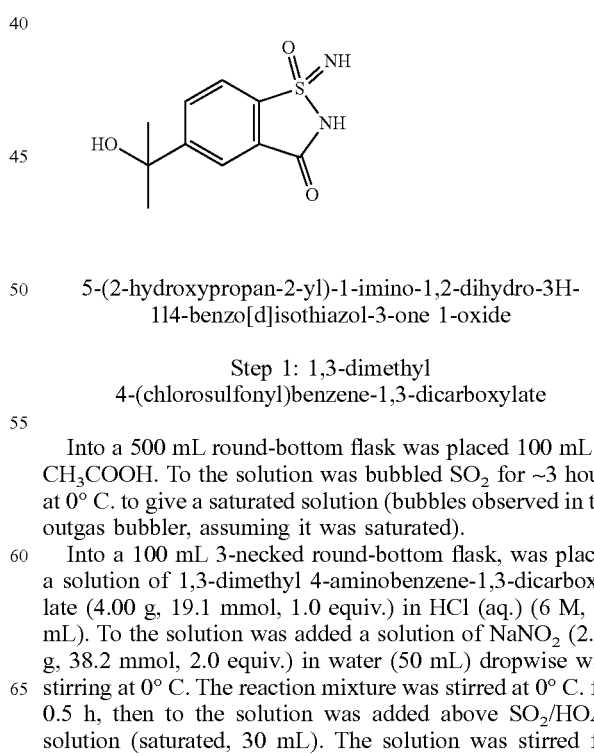

Intermediate 8

5-(2-hydroxypropan-2-yl)-1-imino-1,2-dihydro-3H-1λ4-benzo[d]isothiazol-3-one 1-oxide Step 1: 1,3-dimethyl 4-(chlorosulfonyl)benzene-1,3-dicarboxylate Into a 500 mL round-bottom flask was placed 100 mL of CH₃COOH. To the solution was bubbled SO₂ for ~3 hours at 0° C. to give a saturated solution (bubbles observed in the outgas bubbler, assuming it was saturated).

Into a 100 mL 3-necked round-bottom flask, was placed a solution of 1,3-dimethyl 4-aminobenzene-1,3-dicarboxy-late (4.00 g, 19.1 mmol, 1.0 equiv.) in HCl (aq.) (6 M, 15 mL). To the solution was added a solution of NaNO₂ (2.60 g, 38.2 mmol, 2.0 equiv.) in water (50 mL) dropwise with stirring at 0° C. The reaction mixture was stirred at 0° C. for 0.5 h, then to the solution was added above SO₂/HOAc solution (saturated, 30 mL). The solution was stirred for additional 0.5 h at 0° C. and followed by addition of CuCl$_2$ (5.10 g, 38.2 mmol, 2.0 equiv.). The resulting solution was stirred at 0° C. for another 0.5 h in a water/ice bath. The resulting solution was extracted with dichloromethane and the combined organic layers were dried over anhydrous sodium sulfate and concentrated. This resulted in 6.0 g of 1,3-dimethyl 4-(chlorosulfonyl)benzene-1,3-dicarboxylate as a brown oil, which was used directly in the next step without additional purification.

Step 2: 1,3-dimethyl 4-sulfamoylbenzene-1,3-dicarboxylate

Into a 250 mL round-bottom flask, was placed a solution of 1,3-dimethyl 4-(chlorosulfonyl)benzene-1,3-dicarboxylate (6.00 g, 20.5 mmol, 1.0 equiv.) in DCM (100 mL). Then to the solution, NH$_{3\,(g)}$ was bubbled for 10 min at 0° C. The resulting solution was stirred for 1 h at 0° C. The resulting mixture was concentrated. The residue was applied onto a silica gel column with ethyl acetate/petroleum ether (1:3) to give 1.5 g of 1,3-dimethyl 4-sulfamoylbenzene-1,3-dicarboxylate as a yellow solid. MS-ESI: 274.0 (M+1).

Step 3: 1,4-dimethyl 2-[(tert-butyldimethylsilyl)sulfamoyl]benzene-1,4-dicarboxylate Into a 250 mL round-bottom flask, was placed a solution of 1,3-dimethyl 4-sulfamoylbenzene-1,3-dicarboxylate (1.40 g, 5.1 mmol, 1.0 equiv.) and TEA (3.70 mL, 27.0 mmol, 5.0 equiv.) in DCM (50 mL). To the solution was added tert-butyl(chloro)dimethylsilane (1.20 g, 8.1 mmol, 1.5 equiv.). The resulting solution was stirred for 16 h at ambient temperature. The resulting mixture was concentrated. This resulted in 5 g of crude 1,4-dimethyl 2-[(tert-butyldimethylsilyl)sulfamoyl]benzene-1,4-dicarboxylate as a brown solid, which was used to next step without purification. MS-ESI: 274.0 (M+1).

Step 4: 1,3-dimethyl 4-[(tert-butyldimethylsilyl)-S-aminosulfonimidoyl]benzene-1,3-dicarboxylate A 250 mL 3-necked round-bottom flask was charged with a solution of PPh$_3$Cl$_2$ (78 mL, 0.5 M in CHCl$_3$, 39.0 mmol, 3.0 equiv.) in DCM (50 mL) and then DIEA (11.35 mL, 64.5 mmol, 5.0 equiv.) was added dropwise at 0° C. The reaction mixture was stirred for 0.5 h at 0° C. This was followed by the addition of a solution of 1,3-dimethyl 4-[(tert-butyldimethylsilyl)sulfamoyl]benzene-1,3-dicarboxylate (5.00 g, 12.9 mmol, 1.0 equiv.) in DCM (20 ml) dropwise with stirring at 0° C. The reaction mixture was stirred for an additional 0.5 h, and then NH$_{3(g)}$ was bubbled into the reaction mixture for 10 min at 0° C. and then allowed to stir for an additional 1.0 h. The resulting mixture was concentrated and the residue was purified via flash column chromatography on silica gel, eluting with ethyl acetate/petroleum ether (1:3) to give 350 mg of 1,3-dimethyl 4-[(tert-butyldimethylsilyl)-S-aminosulfonimidoyl]benzene-1,3-dicarboxylate as a yellow solid. MS-ESI: 274.0 (M+1).

Step 5: Methyl 1-((tert-butyldimethylsilyl)imino)-3-oxo-2,3-dihydro-1H-1l4-benzo[d]isothiazole-5-carboxylate 1-oxide Into a 100 mL round-bottom flask, was placed a solution of 1,3-dimethyl 4-[(tert-butyldimethylsilyl)-S-aminosulfonimidoyl]benzene-1,3-dicarboxylate (300 mg, 0.8 mmol, 1.0 equiv) in THF (5 ml). To the solution was added NaH (60% wt in mineral oil, 62 mg, 0.9 mmol, 1.2 equiv). The resulting solution was stirred for 3 h at ambient temperature and then quenched by the addition of 5 mL of MeOH. The resulting mixture was concentrated and the residue was purified via flash column chromatography on silica gel with ethyl acetate/petroleum ether (1:2) to give 200 mg of methyl 1-((tert-butyldimethylsilyl)imino)-3-oxo-2,3-dihydro-1H-1l4-benzo[d]isothiazole-5-carboxylate 1-oxide as an off-white solid. MS-ESI: 355.1 (M+1).

Step 6: 5-(2-hydroxypropan-2-yl)-1-imino-1,2-dihydro-3H-1l4-benzo[d]isothiazol-3-one 1-oxide Into a 100 mL round-bottom flask, was placed a solution of methyl 1-((tert-butyldimethylsilyl)imino)-3-oxo-2,3-dihydro-1H-1l4-benzo[d]isothiazole-5-carboxylate 1-oxide (200 mg, 0.6 mmol, 1.0 equiv.) in THF (15 mL), then to the solution was added CH$_3$MgBr (3M in hexane, 1.0 mL, 3.0 mmol, 5.0 equiv.). The resulting solution was stirred for 16 h at ambient temperature. The reaction was then quenched by the addition of 10 mL of MeOH. The resulting mixture was concentrated to give 500 mg (crude) of 5-(2-hydroxypropan-2-yl)-1-imino-1,2-dihydro-3H-1l4-benzo[d]isothiazol-3-one 1-oxide as an off-white solid, which was used directly in the next step without additional purification. MS-ESI: 241.0 (M+1).

Scheme 9

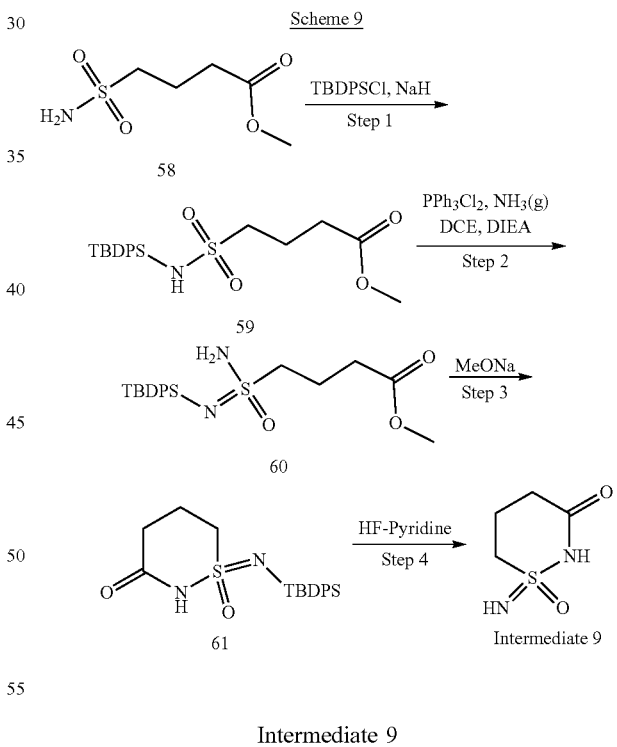

Intermediate 9

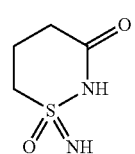

1-imino-1l6,2-thiazinan-3-one 1-oxide

Step 1: Methyl 4-(N-(tert-butyldiphenylsilyl)sulfamoyl)butanoate

Into a 50 mL 3-necked round-bottom flask purged and maintained with an inert atmosphere of nitrogen, was placed a solution of methyl 4-sulfamoylbutanoate (3.00 g, 17.9 mmol, 1.0 equiv.) in THE (30 mL). This was followed by the addition of NaH (60% wt in mineral oil, 1.08 g, 27.0 mmol, 1.5 equiv.) at 0° C. To this was added tert-butyl(chloro)diphenylsilane (5.90 g, 21.6 mmol, 1.2 equiv.) at 0° C. The resulting solution was stirred overnight at ambient temperature and then quenched by the addition of 0.5 mL MeOH. The resulting mixture was concentrated under vacuum. The residue was purified by flash column chromatography on silica gel, eluting with ethyl acetate/petroleum ether (1:8) to give 1.5 g of methyl 4-(N-(tert-butyldiphenylsilyl)sulfamoyl)butanoate as a white solid. MS-ESI: 420.2 (M+1).

Step 2: Methyl 4-(N'-(tert-butyldiphenylsilyl)sulfamidimidoyl)butanoate

Into a 500 mL 3-necked round-bottom flask purged and maintained with an inert atmosphere of nitrogen, was placed a solution of PPh$_3$Cl$_2$ (45 mL, 0.5 M in CHCl$_3$, 22.5 mmol, 3.0 equiv.) in DCE (30 mL) and then DIEA (3.92 mL, 22.4 mmol, 3.0 equiv.) was added dropwise at 0° C. The reaction mixture was stirred for 0.5 h at 0° C., followed by the addition of a solution 4-(N-(tert-butyldiphenylsilyl)sulfamoyl)butanoate (2.50 g, 7.5 mmol, 2.0 equiv.) in DCE (10 mL) dropwise with stirring at 0° C. The resulting solution was stirred for additional 1 h at 0° C., then NH$_{3(g)}$ was bubbled into the reaction mixture for 10 min at 0° C. The resulting solution was stirred for overnight at ambient temperature and then quenched by the addition of 80 mL of water. The resulting solution was extracted with dichloromethane and the combined organic layers were dried over anhydrous sodium sulfate and concentrated under vacuum. The residue was purified by flash column chromatography on silica gel, eluting with ethyl acetate/petroleum ether (1:9) to give 0.51 g of methyl 4-(N'-(tert-butyldiphenylsilyl)sulfamidimidoyl)butanoate as yellow oil. MS-ESI: 419.2 (M+1).

Step 3: 1-((tert-butyldiphenylsilyl)imino)-1l6,2-thiazinan-3-one 1-oxide

Into a 100 mL round-bottom flask purged and maintained with an inert atmosphere of nitrogen, was placed a solution of methyl 4-(N'-(tert-butyldiphenylsilyl)sulfamidimidoyl)butanoate (100 mg, 0.3 mmol, 1.0 equiv.) in methanol (30 mL). To the solution was added MeONa (40 mg, 0.7 mmol, 3.0 equiv.). The resulting solution was stirred for overnight at ambient temperature. The resulting mixture was concentrated under vacuum and the residue was purified by flash column chromatography on silica gel, eluting with ethyl acetate/petroleum ether (1:3) to give 50 mg of 1-((tert-butyldiphenylsilyl)imino)-1l6,2-thiazinan-3-one 1-oxide as a light yellow solid. MS-ESI: 387.2 (M+1).

Step 4: 1-imino-1l6,2-thiazinan-3-one 1-oxide

Into a 250 mL round-bottom flask was placed a solution of 1-((tert-butyldiphenylsilyl)imino)-1l6,2-thiazinan-3-one 1-oxide (350 mg, 0.9 mmol, 1.0 equiv.) in THF (20 mL). To the solution was added HF-Pyridine (0.1 mL, w/t 70%, 5.5 mmol, 6.1 equiv.). The resulting solution was stirred for 3 h at ambient temperature. The reaction was then quenched by the addition of 2.8 mL of saturated aqueous ammonium bicarbonate. The resulting mixture was concentrated under vacuum. The resulting solid was washed with dichloromethane and petroleum ether and then dissolved in 15 mL of methanol. The solids were removed by filtration and the filtrate was concentrated under vacuum. This resulted in 82 mg of 1-imino-1l6,2-thiazinan-3-one 1-oxide as a light-yellow solid, which was used in subsequent steps without additional purification. MS-ESI: 149.0 (M+1).

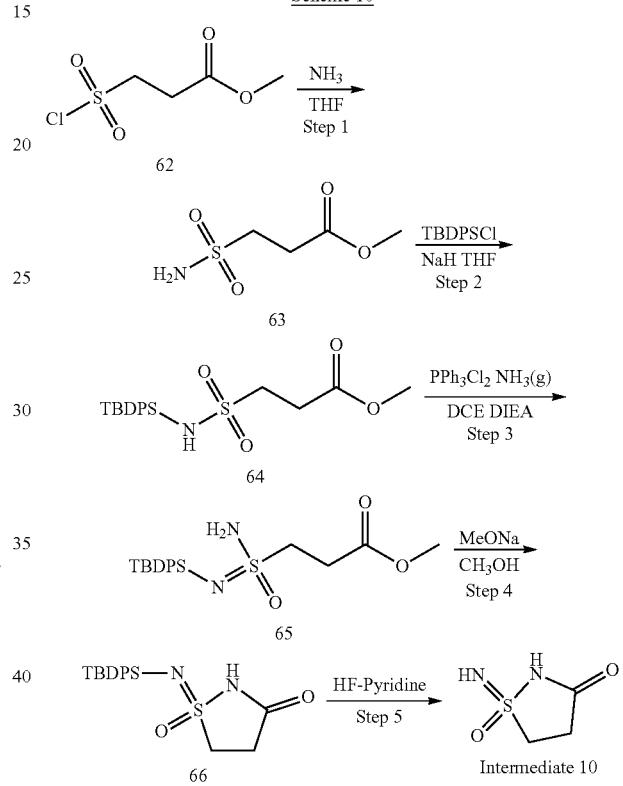

Scheme 10

Intermediate 10

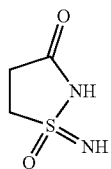

1-imino-1l6-isothiazolidin-3-one 1-oxide

Step 1: Methyl 3-sulfamoylpropanoate

Into a 100 mL round-bottom flask, was placed a solution of methyl 3-(chlorosulfonyl)propanoate (5.00 g, 26.8 mmol, 1.0 equiv.) in THF (30 mL), then NH$_{3(g)}$ was bubbled into the reaction mixture for 10 min at ~5° C. The resulting solution was stirred for 0.5 h at 5° C. The solids were removed via filtration and the filtrate was concentrated under vacuum. This resulted in 3.5 g of methyl 3-sulfamoylpropanoate as a white solid that was used without additional purification. MS-ESI: 168.0 (M+1).

Step 2: Methyl 3-[(tert-butyldiphenylsilyl)sulfamoyl]propanoate

Into a 100 mL 3-necked round-bottom flask purged and maintained under an inert atmosphere of nitrogen, was placed a solution of methyl 3-sulfamoylpropanoate (3.00 g, 17.9 mmol, 1.0 equiv.) in THF (30 mL). This was followed by the addition of NaH (60% wt in mineral oil, 1.10 g, 27.0 mmol, 1.5 equiv.) at 0° C. To this was added TBDPSCl (5.90 g, 21.6 mmol, 1.2 equiv.) at 5° C. The resulting solution was stirred overnight at ambient temperature. The reaction was then quenched by the addition of 0.5 mL of MeOH. The resulting mixture was concentrated under vacuum and the residue was purified by flash column chromatography on silica gel, eluting with ethyl acetate/petroleum ether (1:8) to give 1.5 g of methyl 3-[(tert-butyldiphenylsilyl)sulfamoyl]propanoate as a white solid. MS-ESI: 406.2 (M+1).

Step 3: Methyl 3-[(tert-butyldiphenylsilyl)-S-aminosulfonimidoyl]propanoate

Into a 250 mL 3-necked round-bottom flask purged and maintained under an inert atmosphere of nitrogen, was placed a solution of PPh$_3$Cl$_2$ (22.2 mL, 0.5 M in CHCl$_3$, 11.1 mmol, 3.0 equiv.) in DCE (70 mL) and then DIEA (3.92 mL, 22.4 mmol, 6.0 equiv.) was added dropwise at 0° C. The reaction mixture was stirred for 0.5 h at 0° C. This was followed by the addition of a solution methyl 3-[(tert-butyldiphenylsilyl)sulfamoyl]propanoate (1.50 g, 3.7 mmol, 1.0 equiv.) in DCE (20 mL). The resulting solution was stirred for 1 h at 0° C., then NH$_{3(g)}$ was bubbled through the reaction mixture for 10 min at 0° C. The resulting solution was stirred overnight at room temperature. The reaction was then quenched by the addition of 80 mL of water. The resulting solution was extracted with dichloromethane and the combined organic layers were dried over anhydrous sodium sulfate and concentrated under vacuum. The residue was purified by flash column chromatography on silica gel, eluting with ethyl acetate/petroleum ether (1:9) to give 0.51 g of methyl 3-[(tert-butyldiphenylsilyl)-S-aminosulfonimidoyl]propanoate as yellow oil. MS-ESI: 405.2 (M+1).

Step 4: 1-((tert-butyldiphenylsilyl)imino)-1l6-isothiazolidin-3-one 1-oxide

Into a 100 mL round-bottom flask purged and maintained with an inert atmosphere of nitrogen, was placed a solution of methyl 3-[(tert-butyldiphenylsilyl)-S-aminosulfonimidoyl]propanoate (100 mg, 0.25 mmol, 1.0 equiv.) in MeOH (30 mL). To the solution was added NaOMe (40 mg, 0.7 mmol, 3.0 equiv.). The resulting solution was stirred overnight at ambient temperature, and then concentrated under vacuum. The resulting residue was purified by flash column chromatography on silica gel, eluting with ethyl acetate/petroleum ether (1:3) to give 50 mg of 1-((tert-butyldiphenylsilyl)imino)-1l6-isothiazolidin-3-one 1-oxide as a light yellow solid. MS-ESI: 373.1 (M+1).

Step 5: 1-imino-1l6-isothiazolidin-3-one 1-oxide

Into a 250 mL round-bottom flask was placed a solution of 1-((tert-butyldiphenylsilyl)imino)-1l6-isothiazolidin-3-one 1-oxide (350 mg, 0.9 mmol, 1.0 equiv.) in THF (20 mL). To the solution was added HF-Pyridine (0.1 mL, w/t 70%, 5.5 mmol, 6.1 equiv.). The resulting solution was stirred for 3 h at ambient temperature. The reaction was then quenched by the addition of 3 mL of saturated aqueous ammonium bicarbonate. The resulting mixture was concentrated under vacuum. The residue was washed with dichloromethane and petroleum ether then dissolved in 15 mL of MeOH. The solids were removed by filtration and the filtrate was concentrated under vacuum to give 82 mg of 1-imino-1l6-isothiazolidin-3-one 1-oxide as light yellow solid. MS-ESI: 135.0 (M+1).

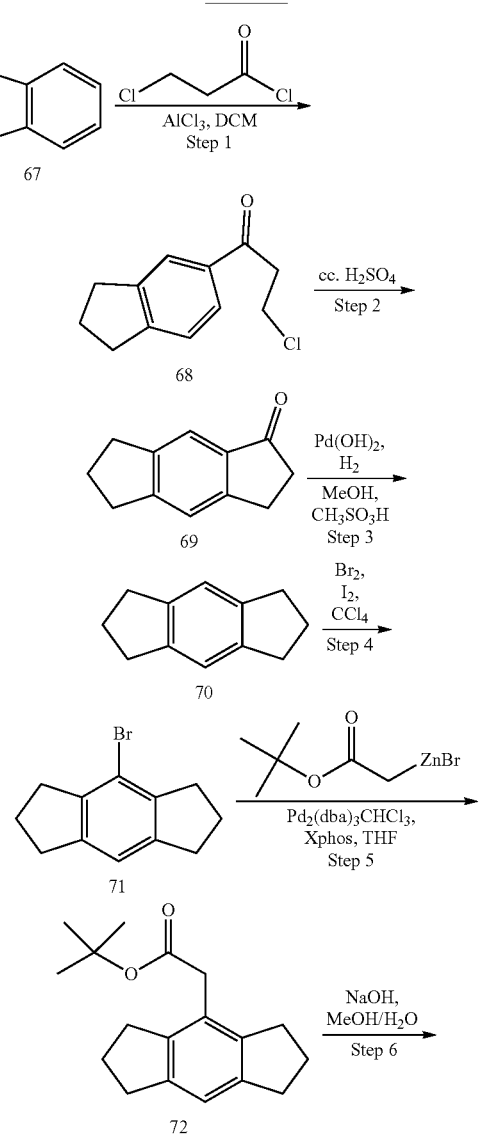

-continued

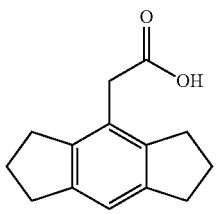

Intermediate 11

Intermediate 11

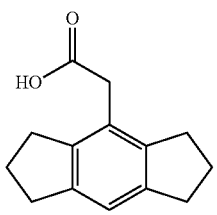 [SMILES: O=C(O)Cc1c2c(cc3c1CCC3)CCC2]

2-(1,2,3,5,6,7-hexahydros-indacen-4-yl)acetic acid

Step 1: 3-Chloro-1-(2,3-dihydro-1H-inden-5-yl)propan-1-one

Into a 1000 mL round-bottom flask was placed a solution of AlCl$_3$ (37.00 g, 277.5 mmol, 1.1 equiv.) in DCM (400 mL). This was followed by the addition of a solution of 2,3-dihydro-1H-indene (30.00 g, 253.8 mmol, 1.0 equiv.) and 3-chloropropanoyl chloride (32.10 g, 252.8 mmol, 1.0 equiv.) in DCM (100 mL) dropwise with stirring at −10° C. over 30 min. The resulting solution was stirred for 16 h at ambient temperature. Then the reaction mixture was added dropwise to cold HCl (aq) (3 N, 400 mL, 1.2 mol, 4.7 equiv.) over 45 min at −10° C. The resulting solution was extracted with DCM and the combined organic layers were dried over anhydrous Na$_2$SO$_4$ and concentrated under vacuum to give 53.5 g of 3-chloro-1-(2,3-dihydro-1H-inden-5-yl)propan-1-one as a yellow solid, which was used in the next step without purification.

Step 2: 1,2,3,5,6,7-Hexahydro-s-indacen-1-one

Into a 1,000 mL round-bottom flask was placed a solution of 3-chloro-1-(2,3-dihydro-1H-inden-5-yl)propan-1-one (53.50 g, 253.0 mmol, 1.0 equiv.) in conc. H$_2$SO$_4$ (300 mL). The resulting solution was stirred for 16 h at 55° C. and then was quenched by adding the reaction mixture carefully to 1,500 mL of water/ice. The solids were collected by filtration and then dried under an infrared lamp for 24 h. This resulted in 37.4 g (85%) of 1,2,3,5,6,7-Hexahydro-s-indacen-1-one as a yellow solid.

Step 3: 1,2,3,5,6,7-Hexahydro-s-indacene

Into a 1000 mL round-bottom flask was placed a solution of 1,2,3,5,6,7-hexahydros-indacen-1-one (37.20 g, 216.0 mmol, 1.0 equiv.) and CH$_3$SO$_3$H (42.00 g, 437.5 mmol, 2.0 equiv.) in MeOH (300 mL). Then Pd(OH)$_2$/C (20% wt., 8 g) was added. The flask was evacuated and flushed three times with hydrogen. The resulting solution was stirred for 16 h at ambient temperature under an atmosphere of hydrogen. The solids were removed by filtration and the filtrate was concentrated under vacuum. The residue was purified by flash column chromatography on silica gel column, eluting with ethyl acetate/petroleum ether (1:150 to 1:100) to give 27.1 g of 1,2,3,5,6,7-Hexahydro-s-indacene as a white solid.

Step 4: 4-Bromo-1,2,3,5,6,7-hexahydro-s-indacene

Into a 500 mL 3-necked round-bottom flask purged with and maintained under nitrogen was placed a solution of 1,2,3,5,6,7-hexahydro-s-indacene (15.00 g, 94.8 mmol, 1.0 equiv.) in CCl$_4$ (200 mL). Then 12 (1.21 g, 4.7 mmol, 0.05 equiv.) was added. This was followed by the addition of a solution of Br$_2$ (16 g, 100.0 mmol, 1.1 equiv.) in CCl$_4$ (50 mL) dropwise with stirring at 0° C. over 10 min. The resulting solution was stirred for 2 h at 0° C. The reaction was then quenched by the addition of 150 mL of saturated aqueous NH$_4$Cl. The resulting solution was extracted with DCM and the combined organic layers were dried over anhydrous Na$_2$SO$_4$ and concentrated under vacuum. The residue was purified by flash column chromatography on silica gel column, eluting with ethyl acetate:petroleum ether (1:10) to give 18.0 g of 4-Bromo-1,2,3,5,6,7-hexahydro-s-indacene as yellow oil. $^1$H NMR (300 MHz, DMSO-d$_6$) δ 7.02 (s, 1H), 2.95-2.75 (m, 8H), 2.03-2.01 (m, 4H).

Step 5: Tert-butyl 2-(1,2,3,5,6,7-hexahydro-s-indacen-4-yl)acetate

Into a 100 mL round-bottom flask purged with and maintained under nitrogen was placed a solution of 4-bromo-1,2,3,5,6,7-hexahydro-s-indacene (1.00 g, 4.2 mmol, 1.0 equiv.) in THF (20 mL). Then X-Phos (200 mg, 0.4 mmol, 0.1 equiv.) and Pd$_2$(dba)$_3$CHCl$_3$ (220 mg, 0.2 mmol, 0.05 equiv.) were added. The resulting solution was stirred for 10 min at room temperature. This was followed by the addition of tert-butyl 2-(bromozincio)acetate (2.20 g, 8.5 mmol, 2.0 equiv.). The resulting solution was stirred for 4 h at 80° C. and then quenched by the addition of 50 mL of NH$_4$Cl (sat.). The resulting solution was extracted with DCM. The combined organic layers were dried over anhydrous Na$_2$SO$_4$ and concentrated under vacuum to give 1.4 g of tert-butyl 2-(1,2,3,5,6,7-hexahydro-s-indacen-4-yl)acetate as brown oil. $^1$H NMR (400 MHz, DMSO-d$_6$) δ 6.96 (s, 1H), 3.47 (s, 2H), 2.80-2.78 (m, 8H), 2.01-1.99 (m, 4H), 1.39 (s, 9H).

Step 6: 2-(1,2,3,5,6,7-hexahydro-s-indacen-4-yl)acetic Acid

Into a 40 mL sealed tube was placed a solution of tert-butyl 2-(1,2,3,5,6,7-hexahydro-s-indacen-4-yl)acetate (1.41 g, 5.1 mmol, 1.0 equiv.) in 6 M NaOH (aq.)/MeOH (4/6 mL). The resulting solution was stirred for 16 h at 100° C. The reaction was then quenched by the addition of 20 mL of water. The resulting solution was washed with DCM and the aqueous layers combined. The solution was adjusted to pH 2 with aqueous hydrogen chloride (1 N). The resulting solution was extracted with ethyl acetate and the combined organic layers were dried over anhydrous Na$_2$SO$_4$, then concentrated under vacuum to give 180 mg of 2-(1,2,3,5,6,7-hexahydro-s-indacen-4-yl)acetic acid as a yellow solid. MS-ESI. 215.1 (M−1).

Scheme 12

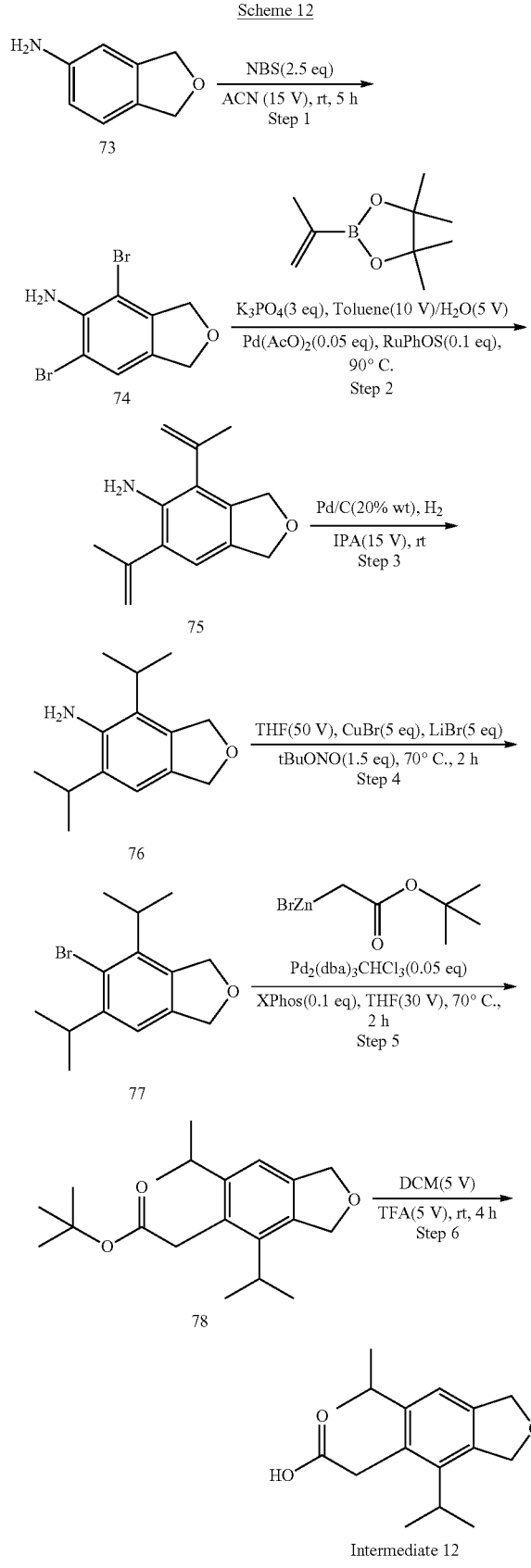

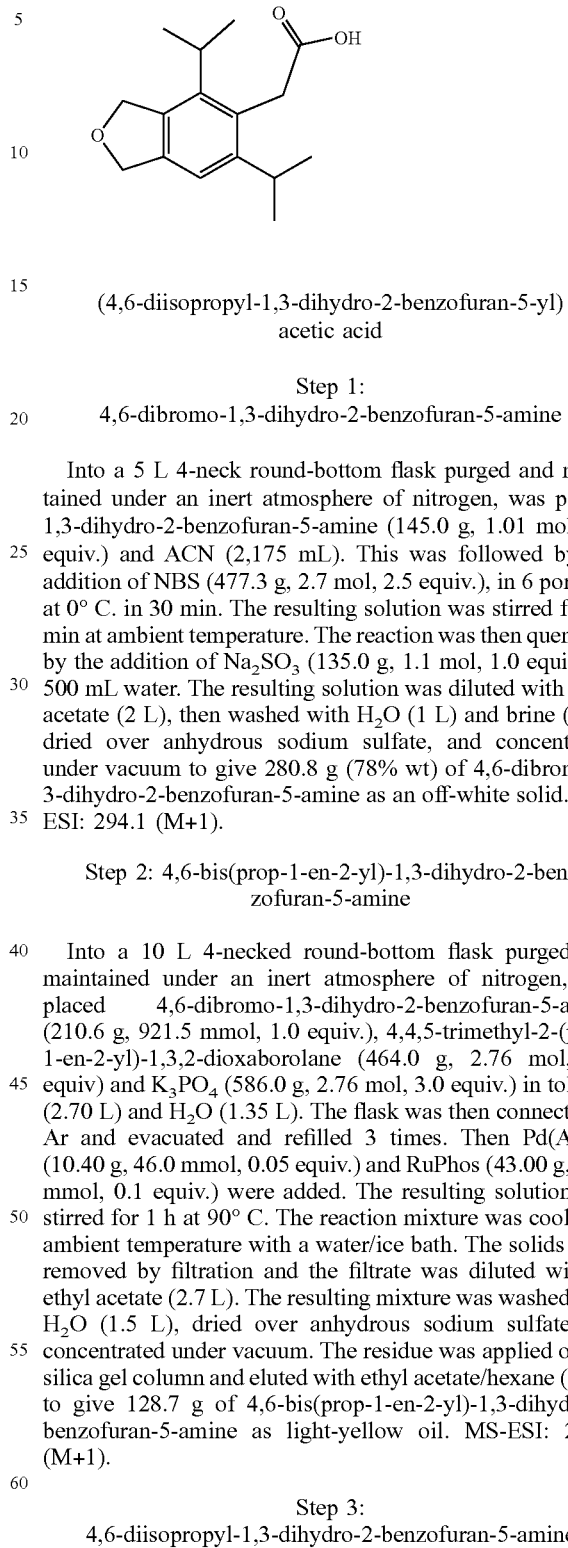

Intermediate 12

(4,6-diisopropyl-1,3-dihydro-2-benzofuran-5-yl) acetic acid

Step 1: 4,6-dibromo-1,3-dihydro-2-benzofuran-5-amine

Into a 5 L 4-neck round-bottom flask purged and maintained under an inert atmosphere of nitrogen, was placed 1,3-dihydro-2-benzofuran-5-amine (145.0 g, 1.01 mol, 1.0 equiv.) and ACN (2,175 mL). This was followed by the addition of NBS (477.3 g, 2.7 mol, 2.5 equiv.), in 6 portions at 0° C. in 30 min. The resulting solution was stirred for 30 min at ambient temperature. The reaction was then quenched by the addition of $Na_2SO_3$ (135.0 g, 1.1 mol, 1.0 equiv.) in 500 mL water. The resulting solution was diluted with ethyl acetate (2 L), then washed with $H_2O$ (1 L) and brine (1 L), dried over anhydrous sodium sulfate, and concentrated under vacuum to give 280.8 g (78% wt) of 4,6-dibromo-1,3-dihydro-2-benzofuran-5-amine as an off-white solid. MS-ESI: 294.1 (M+1).

Step 2: 4,6-bis(prop-1-en-2-yl)-1,3-dihydro-2-benzofuran-5-amine

Into a 10 L 4-necked round-bottom flask purged and maintained under an inert atmosphere of nitrogen, was placed 4,6-dibromo-1,3-dihydro-2-benzofuran-5-amine (210.6 g, 921.5 mmol, 1.0 equiv.), 4,4,5-trimethyl-2-(prop-1-en-2-yl)-1,3,2-dioxaborolane (464.0 g, 2.76 mol, 3.0 equiv) and $K_3PO_4$ (586.0 g, 2.76 mol, 3.0 equiv.) in toluene (2.70 L) and $H_2O$ (1.35 L). The flask was then connected to Ar and evacuated and refilled 3 times. Then $Pd(AcO)_2$ (10.40 g, 46.0 mmol, 0.05 equiv.) and RuPhos (43.00 g, 92.1 mmol, 0.1 equiv.) were added. The resulting solution was stirred for 1 h at 90° C. The reaction mixture was cooled to ambient temperature with a water/ice bath. The solids were removed by filtration and the filtrate was diluted with of ethyl acetate (2.7 L). The resulting mixture was washed with $H_2O$ (1.5 L), dried over anhydrous sodium sulfate and concentrated under vacuum. The residue was applied onto a silica gel column and eluted with ethyl acetate/hexane (1:50) to give 128.7 g of 4,6-bis(prop-1-en-2-yl)-1,3-dihydro-2-benzofuran-5-amine as light-yellow oil. MS-ESI: 215.1 (M+1).

Step 3: 4,6-diisopropyl-1,3-dihydro-2-benzofuran-5-amine

Into a 5 L round-bottom flask, was placed 4,6-bis(prop-1-en-2-yl)-1,3-dihydro-2-benzofuran-5-amine (120.5 g, 683.7 mmol, 1.0 equiv.) in IPA (2.20 L). Pd/C (29.40 g, 20% wt) was added to the flask, then the flask was connected to hydrogen and evacuated and refilled 3 times. The flask was then fitted with a hydrogen balloon and the reaction mixture was stirred overnight at 30° C. The Pd/C was removed by filtration and the filtrate was concentrated under vacuum. The residue was dissolved in DCM and dried over anhydrous sodium sulfate. Filtration and concentration gave 130 g of 4,6-diisopropyl-1,3-dihydro-2-benzofuran-5-amine as a light-yellow oil. MS-ESI: 219.1 (M+1). $^1$H-NMR: (400 MHz, DMSO-d$_6$) δ 6.82 (s, 1H), 5.00 (t, 2H), 4.81 (td, 2H), 4.46 (s, 2H), 3.15 (h, 1H), 3.00 (hept, 1H), 1.15 (dd, 12H).

Step 4:
5-bromo-4,6-diisopropyl-1,3-dihydroisobenzofuran

Into a 2 L 4-necked round-bottom flask purged and maintained with an inert atmosphere of nitrogen, was placed a solution of 4,6-diisopropyl-1,3-dihydroisobenzofuran-5-amine (20.00 g, 91.3 mmol, 1.0 equiv.) in tetrahydrofuran (800 mL), then 4A molecular sieve (20 g, powder), CuBr (60.00 g, 457.1 mmol, 5.0 equiv.), LiBr (40.00 g, 460.6 mmol, 5.0 equiv.) was added in sequence at ambient temperature. The solution was warmed to 70° C., and this was followed by the addition of a solution of tBuONO (14.00 g, 135.8 mmol, 1.5 equiv.) in THF (200 mL) dropwise at 70° C. in 15 min. The resulting solution was stirred for an additional 2 h at 70° C. The reaction organic solution was washed with brine, dried over anhydrous sodium sulfate and concentrated under vacuum. The residue was applied onto a silica gel column and eluted with petroleum ether to give 12.1 g of 5-bromo-4,6-diisopropyl-1,3-dihydroisobenzofuran as a light-yellow oil. $^1$H-NMR: (300 MHz, DMSO-d$_6$) δ7.18 (s, 1H), 5.12 (t, 2H), 4.89 (d, 2H), 3.40 (h, 1H), 1.18 (dd, 12H).

Step 5: tert-butyl 2-(4,6-diisopropyl-1,3-dihydro-2-benzofuran-5-yl)acetate

Into a 5 L 4-necked round-bottom flask purged and maintained with an inert atmosphere of nitrogen, was placed 5-bromo-4,6-diisopropyl-1,3-dihydro-2-benzofuran (63.65 g, 335.7 mmol, 1.0 equiv.) and THF (2.85 L). The flask was then connected to Ar and evacuated and refilled 3 times, then Pd$_2$(dba)$_3$·CHCl$_3$ (17.40 g, 16.8 mmol, 0.05 equiv.), X-Phos (16.00 g, 33.6 mmol, 0.1 equiv.) and tert-butyl-2-(bromozincio)acetate (436.02 g, 1.7 mol, 5.0 equiv.) was rapidly added. The resulting solution was stirred for 2 h at 70° C. The reaction mixture was cooled to room temperature with a water/ice bath. The resulting solution was diluted with petroleum ether. The solids were removed by filtration and the filtrate was dried over anhydrous sodium sulfate and concentrated under vacuum to give 69.9 g of tert-butyl 2-(4,6-diisopropyl-1,3-dihydro-2-benzofuran-5-yl)acetate as brown oil. $^1$H-NMR: (400 MHz, DMSO-d$_6$) δ 7.10 (s, 1H), 5.08 (t, 2H), 4.90 (s, 2H), 3.69 (s, 1H), 3.25-3.21 (m, 1H), 3.15-3.11 (m, 1H), 1.39 (s, 9H), 1.14 (t, 12H).

Step 6: (4,6-diisopropyl-1,3-dihydro-2-benzofuran-5-yl)acetic Acid

Into a 2 L 3 neck round-bottom flask was placed tert-butyl 2-(4,6-diisopropyl-1,3-dihydro-2-benzofuran-5-yl)acetate (69.9 g, 1.22 mmol, 1.0 equiv.), DCM (700 mL), then TFA (700 mL) was added. The resulting solution was stirred for 4 h at ambient temperature. The resulting mixture was concentrated and the residue was dissolved in 2 L of 2 M NaOH aq. The mixture was extracted with methyl tert-butyl ether and the aqueous layers collected. The aqueous layers were adjusted to pH 2 with aqueous HCl (4 M). The resulting solution was extracted with dichloromethane and the combined organic layers were concentrated. The crude product was re-crystallized from 2:1 petroleum ether:ethyl acetate to give 38 g of the title compound. The mother liquor was concentrated, and the residue was purified by flash column chromatography on silica gel, eluting with ethyl acetate/hexanes (1:30) to give 12 g of title compound. This resulted in a total of 50 g of (4,6-diisopropyl-1,3-dihydro-2-benzofuran-5-yl)acetic acid as an off-white solid. MS-ESI: 261.1 (M−1). $^1$H-NMR: (300 MHz, DMSO-d$_6$) δ 12.27 (s, 1H), 7.09 (s, 1H), 5.08 (d, 2H), 4.89 (s, 2H), 3.23-3.21 (m, 1H), 3.12-3.09 (m, 1H), 1.14 (dd, 12H).

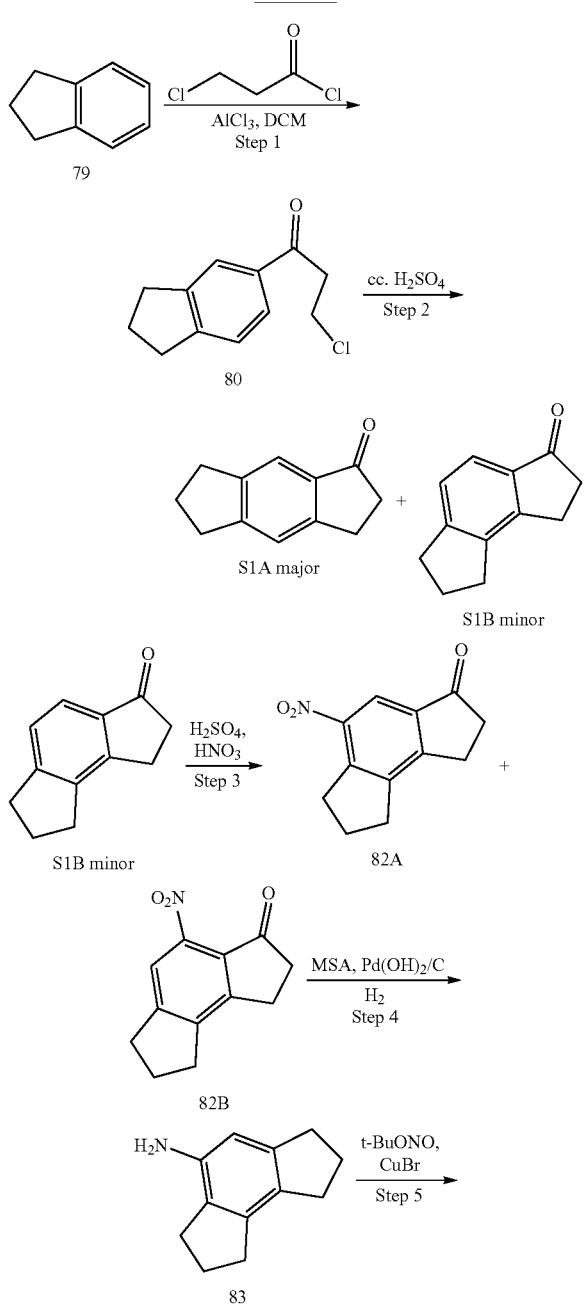

Scheme 13

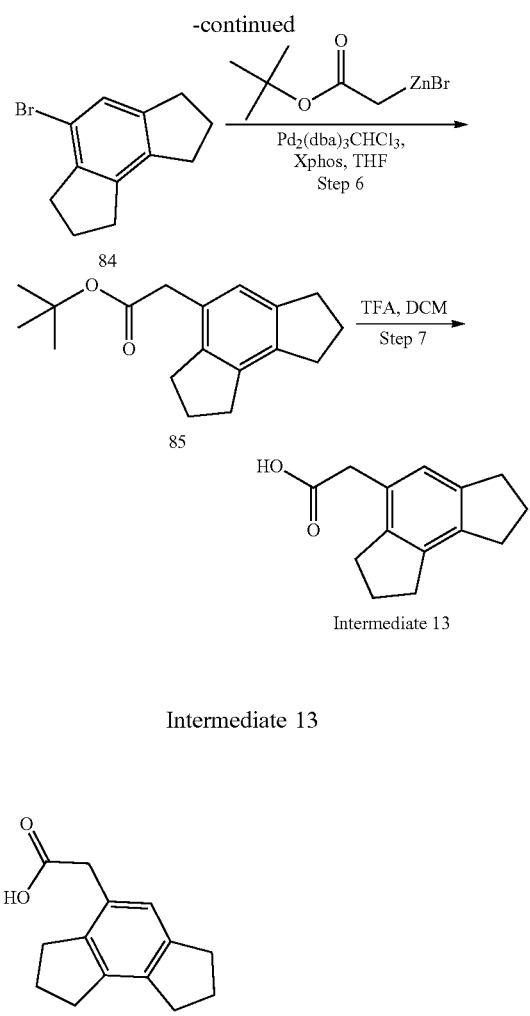

Intermediate 13

2-(1,2,3,6,7,8-hexahydroas-indacen-4-yl)acetic acid

Step 1: 3-Chloro-1-(2,3-dihydro-1H-inden-5-yl)propan-1-one

Into a 1,000 mL round-bottom flask was placed a solution of AlCl$_3$ (37.00 g, 277.5 mmol, 1.1 equiv.) in DCM (400 mL). This was followed by the addition of a solution of 2,3-dihydro-1H-indene (30.00 g, 253.8 mmol, 1.0 equiv.) and 3-chloropropanoyl chloride (32.10 g, 252.8 mmol, 1.0 equiv.) in DCM (100 mL) dropwise with stirring at −10° C. over 30 min. The resulting solution was stirred for 16 h at ambient temperature. Then the reaction mixture was added dropwise to cold HCl aqueous (3 N, 400 mL) over 45 min at −10° C. The resulting solution was extracted with DCM and the combined organic layers were dried over anhydrous Na$_2$SO$_4$ and concentrated under vacuum to give 53.5 g of 3-Chloro-1-(2,3-dihydro-1H-inden-5-yl)propan-1-one as a yellow solid, which was used in the next step without additional purification.

Step 2: 3,5,6,7-tetrahydro-s-indacen-1(2H)-one and 1,6,7,8-tetrahydro-as-indacen-3(2H)-one Into a 1,000 mL round-bottom flask was placed a solution of 3-chloro-1-(2,3-dihydro-1H-inden-5-yl)propan-1-one (160.50 g, 759.0 mmol, 1.0 equiv.) in conc. H$_2$SO$_4$ (900 mL). The resulting solution was stirred for 16 h at 55° C. and then was quenched by adding the reaction mixture carefully to 4,500 mL of water/ice. The solids were collected by filtration and dried under an infrared lamp for 24 h. The solids were purified by flash column chromatography, eluting with ethyl acetate/petroleum ether (1:100) to give 112.2 g of 3,5,6,7-tetrahydro-s-indacen-1(2H)-one and 10 g of 1,6,7,8-tetrahydro-as-indacen-3(2H)-one as a yellow solid. Major: $^1$H NMR (400 MHz, DMSO-d$_6$) δ 7.44 (s, 1H), 7.39 (s, 1H), 3.13-2.79 (m, 6H), 2.70-2.55 (m, 2H), 2.20-1.90 (m, 2H).
Minor: $^1$H NMR (400 MHz, DMSO-d$_6$) δ 7.49 (d, 1H), 7.31 (d, 1H), 3.19-2.98 (m, 4H), 2.93-2.80 (m, 2H), 2.68-2.54 (m, 2H), 2.15-1.95 (m, 2H).

Step 3: 5-nitro-1,6,7,8-tetrahydro-as-indacen-3(2H)-one and 4-nitro-1,6,7,8-tetrahydro-as-indacen-3(2H)-one Into a 1,000 mL round-bottom flask was placed a solution of 1,6,7,8-tetrahydro-as-indacen-3(2H)-one (9.80 g, 46.5 mmol, 1.0 equiv.) in H$_2$SO$_4$ (50 mL). Then HNO$_3$ (5.85 g, 92.9 mmol, 2.0 equiv.) was added dropwise over 10 min at 0° C. The resulting solution was stirred for 1 h at 0° C. The reaction mixture was slowly added to a mixture of water/ice (100 mL) and DCM (50 mL) with ice bath cooling. The organic layer was collected, dried over Na$_2$SO$_4$ and concentrated under vacuum to give 11 g of a mixture of 5-nitro-1,6,7,8-tetrahydro-as-indacen-3(2H)-one and 4-nitro-1,6,7,8-tetrahydro-as-indacen-3(2H)-one as a yellow solid.

Step 4: 1,2,3,6,7,8-Hexahydro-as-indacen-4-amine

Into a 100 mL round-bottom flask was placed a solution of the mixture of 5-nitro-1,6,7,8-tetrahydro-as-indacen-3(2H)-one and 4-nitro-1,6,7,8-tetrahydro-as-indacen-3(2H)-one (10.85 g, 50.0 mmol, 1.0 equiv.) in MeOH (150 mL). To the solution was added MSA (5.75 g, 60.0 mmol, 1.2 equiv.). Then Pd(OH)$_2$/C (20% wt., 2.5 g, 3.6 mmol, 0.07 equiv.) was added. The flask was evacuated and filled three times with hydrogen. The resulting mixture was stirred for 16 h at ambient temperature under hydrogen (50 psi). The solids were filtered out and washed with MeOH. The MeOH filtrate was diluted with water (250 mL) and the pH was adjusted to 10.6 with aqueous 2 N NaOH. The solid was collected by filtration and then recrystallized from MeOH/water (9:1) with heating. This resulted in 6.9 g of 1,2,3,6,7,8-hexahydro-as-indacen-4-amine as an off-white solid. MS-ESI: 174 (M+1).

Step 5: 4-bromo-1,2,3,6,7,8-hexahydro-as-indacene

Into a 500 mL round-bottom flask purged with and maintained under nitrogen was placed a solution of 1,2,3,6,7,8-hexahydroas-indacen-4-amine (6.20 g, 35.9 mmol, 1.0 equiv.) and CuBr (7.70 g, 53.9 mmol, 1.5 equiv.) in ACN (300 mL). This was followed by the addition of tert-butyl nitrite (5.60 g, 54.3 mmol, 1.5 equiv.) dropwise with stirring at 0° C. The resulting solution was stirred for additional 3 h at 60° C. and then concentrated under vacuum. The residue was purified via flash column chromatography on silica gel, eluting with petroleum ether to give 2.9 g of 4-bromo-1,2,3,6,7,8-hexahydro-as-indacene as a yellow oil.

Step 6: tert-butyl 2-(1,2,3,6,7,8-hexahydro-as-indacen-4-yl)acetate

Into a 50 mL round-bottom flask, was placed a solution of 4-bromo-1,2,3,6,7,8-hexahydro-as-indacene (400 mg, 1.7 mmol, 1.0 equiv.) in THF (30 mL). To this was added X-Phos (80 mg, 0.2 mmol, 0.1 equiv.), Pd$_2$(dba)$_3$CHCl$_3$ (174 mg, 0.2 mmol, 0.1 equiv.), tert-butyl-2-(bromozincio)acetate (1.32 g, 5.1 mmol, 3.0 equiv.) under nitrogen atmosphere. The resulting solution was stirred for 2 h at 60° C. in an oil bath. The mixture was concentrated. The residue was purified via flash column chromatography on silica, eluting with ethyl acetate/petroleum ether (1:50) to give 350 mg of tert-butyl 2-(1,2,3,6,7,8-hexahydro-as-indacen-4-yl)acetate as a yellow solid.

Step 7: 2-(1,2,3,6,7,8-hexahydro-as-indacen-4-yl)acetic Acid

Into a 25 mL round-bottom flask, was placed tert-butyl 2-(1,2,3,6,7,8-hexahydro-as-indacen-4-yl)acetate (350 mg, 1.3 mmol) in DCM (5 mL) and TFA (5 mL). The resulting solution was stirred for 5 h at ambient temperature. The resulting mixture was concentrated to give 300 mg of 2-(1,2,3,6,7,8-hexahydro-as-indacen-4-yl)acetic acid as a yellow solid. MS-ESI: 215.1 (M−1).

Scheme 14

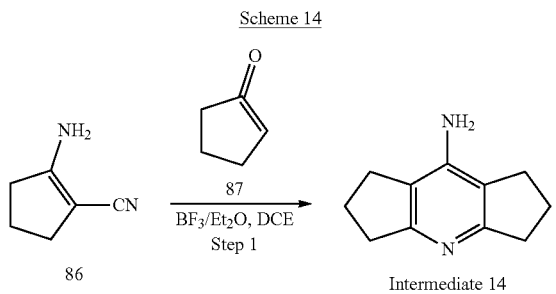

Intermediate 14

Intermediate 14

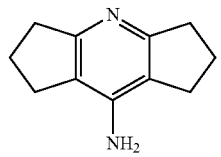 [SMILES: Nc1c2c(nc3c1CCC3)CCC2]

1,2,3,5,6,7-Hexahydrodicyclopenta[b,e]pyridin-8-amine

Step 1: 1,2,3,5,6,7-Hexahydrodicyclopenta[b,e]pyridin-8-amine

Into a 250 mL 3-necked round-bottom flask purged and maintained with an inert atmosphere of nitrogen, was placed a mixture of 2-aminocyclopent-1-enecarbonitrile (5.40 g, 50.0 mmol, 1.0 equiv.) in DCE (125 mL). To this solution was added cyclopentanone (8.40 g, 100.0 mmol, 2.0 equiv.). Then BF$_3$·Et$_2$O (46.5% wt., 14.5 g, 45.6 mmol, 0.9 equiv.) was added to this solution at 0° C. in an ice bath. The reaction was heat to 75° C. for 6 h and then quenched by the addition of 100 mL of water/ice. The solution was washed with DCM. The aqueous phase was collected, and the pH adjusted to 14 with NaOH (6 M) until a solid precipitated. The solids were collected by filtration. The filter cake was washed with water (150 mL) then dried under an infra-red lamp to give 7.0 g of 1,2,3,5,6,7-Hexahydrodicyclopenta[b,e]pyridin-8-amine as a white solid. MS-ESI. 175 (M+1).

TABLE E1

The Intermediates in the following Table were prepared using the similar procedures for converting compound 86 to Intermediate 14 shown in Scheme 14 from appropriated starting materials.

| Intermediate # | Structure | Ketone | IUPAC Name | Exact Mass [M + H]$^+$ |
| --- | --- | --- | --- | --- |
| Intermediate 15 | 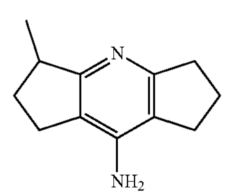 | | 3-Methyl-1,2,3,5,6,7-hexahydrodicyclopenta[b,e]pyridin-8-amine | 189.1 |
| Intermediate 16 | 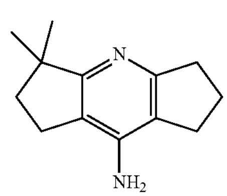 | | 3,3-Dimethyl-1,2,3,5,6,7-hexahydrodicyclopenta[b,e]pyridin-8-amine | 203.1 |

TABLE E1-continued

The Intermediates in the following Table were prepared using the similar procedures for converting compound 86 to Intermediate 14 shown in Scheme 14 from appropriated starting materials.

| Intermediate # | Structure | Ketone | IUPAC Name | Exact Mass [M + H]+ |
|---|---|---|---|---|
| Intermediate 17 | 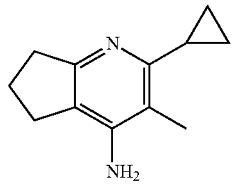 | | 2-Cyclopropyl-3-methyl-6,7-dihydro-5H-cyclopenta[b]pyridin-4-amine | 189.1 |
| Intermediate 18 | 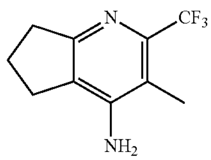 | | 3-Methyl-2-(trifluoromethyl)-6,7-dihydro-5H-cyclopenta[b]pyridin-4-amine | 217.1 |

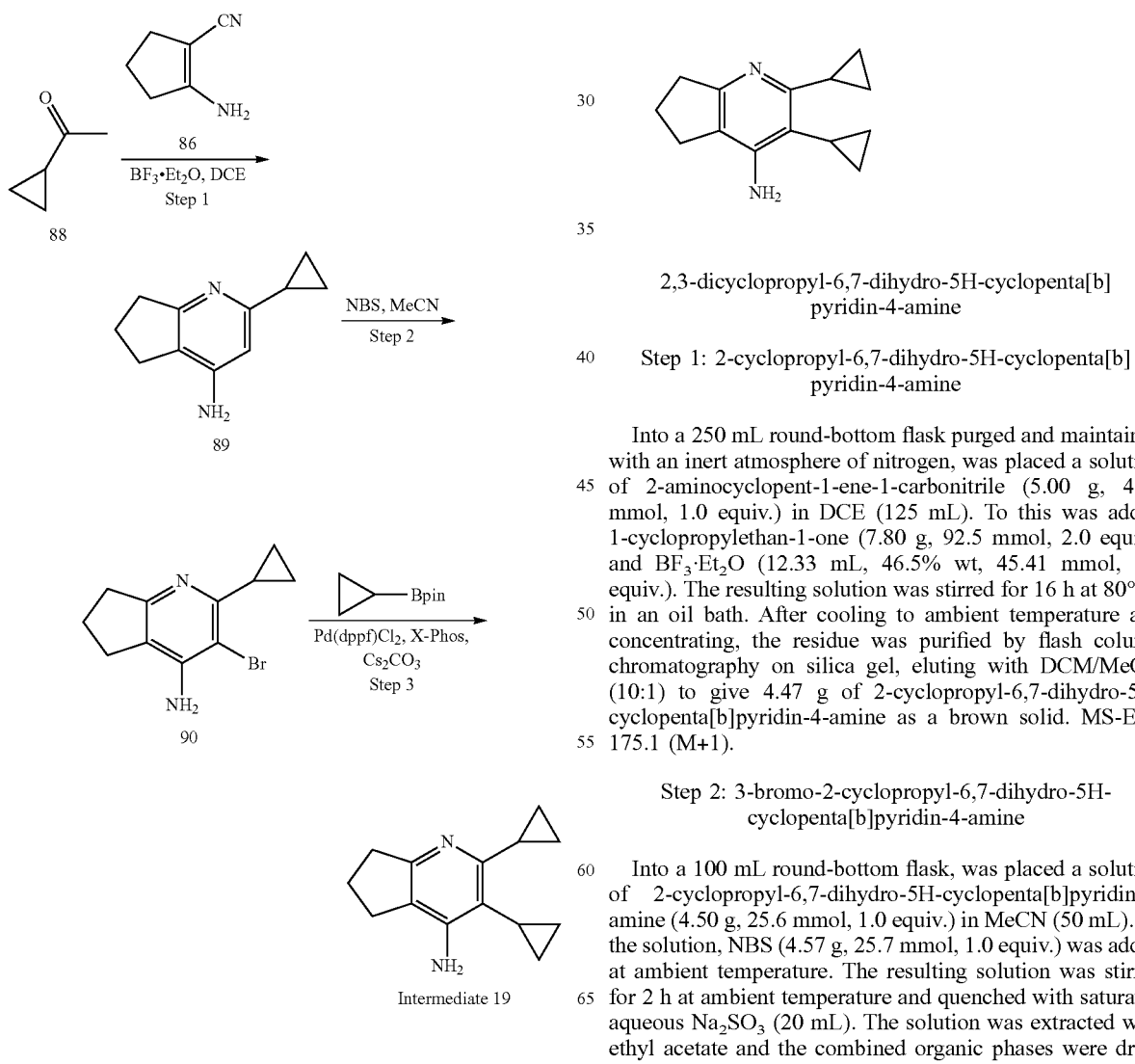

Intermediate 19

2,3-dicyclopropyl-6,7-dihydro-5H-cyclopenta[b]pyridin-4-amine

Step 1: 2-cyclopropyl-6,7-dihydro-5H-cyclopenta[b]pyridin-4-amine

Into a 250 mL round-bottom flask purged and maintained with an inert atmosphere of nitrogen, was placed a solution of 2-aminocyclopent-1-ene-1-carbonitrile (5.00 g, 46.2 mmol, 1.0 equiv.) in DCE (125 mL). To this was added 1-cyclopropylethan-1-one (7.80 g, 92.5 mmol, 2.0 equiv.) and BF$_3$·Et$_2$O (12.33 mL, 46.5% wt, 45.41 mmol, 1.0 equiv.). The resulting solution was stirred for 16 h at 80° C. in an oil bath. After cooling to ambient temperature and concentrating, the residue was purified by flash column chromatography on silica gel, eluting with DCM/MeOH (10:1) to give 4.47 g of 2-cyclopropyl-6,7-dihydro-5H-cyclopenta[b]pyridin-4-amine as a brown solid. MS-ESI: 175.1 (M+1).

Step 2: 3-bromo-2-cyclopropyl-6,7-dihydro-5H-cyclopenta[b]pyridin-4-amine

Into a 100 mL round-bottom flask, was placed a solution of 2-cyclopropyl-6,7-dihydro-5H-cyclopenta[b]pyridin-4-amine (4.50 g, 25.6 mmol, 1.0 equiv.) in MeCN (50 mL). To the solution, NBS (4.57 g, 25.7 mmol, 1.0 equiv.) was added at ambient temperature. The resulting solution was stirred for 2 h at ambient temperature and quenched with saturated aqueous Na$_2$SO$_3$ (20 mL). The solution was extracted with ethyl acetate and the combined organic phases were dried over Na₂SO₄ and concentrated. The residue was purified by flash column chromatography on silica gel, eluting with ethyl acetate/petroleum ether (1:5) to give 1.93 g of 3-bromo-2-cyclopropyl-6,7-dihydro-5H-cyclopenta[b]pyridin-4-amine as a light-yellow solid. MS-ESI: 253.0/255.0 (M+1).

Step 3: 2,3-dicyclopropyl-6,7-dihydro-5H-cyclopenta[b]pyridin-4-amine

Into a 50 mL 3-necked round-bottom flask purged and maintained with an inert atmosphere of nitrogen, was placed a solution of 3-bromo-2-cyclopropyl-6,7-dihydro-5H-cyclopenta[b]pyridin-4-amine (500 mg, 2.0 mmol, 1.0 equiv.) in dioxane (15 mL) and water (2 mL). To this was added 2-cyclopropyl-4,4,5,5-tetramethyl-1,3,2-dioxaborolane (497 mg, 3.0 mmol, 1.5 equiv.), Pd(dppf)Cl₂ (144 mg, 0.2 mmol, 0.1 equiv.), X-Phos (188 mg, 0.4 mmol, 0.2 equiv.), and Cs₂CO₃ (3.96 g, 11.9 mmol, 6.0 equiv.). The resulting solution was stirred for 4 h at 100° C. The resulting mixture was concentrated, and the residue was purified by flash column chromatography on silica gel, eluting with ethyl acetate/petroleum ether (1:2) to give 300 mg of 2,3-dicyclopropyl-6,7-dihydro-5H-cyclopenta[b]pyridin-4-amine as a brown solid. MS-ESI: 215.1 (M+1).

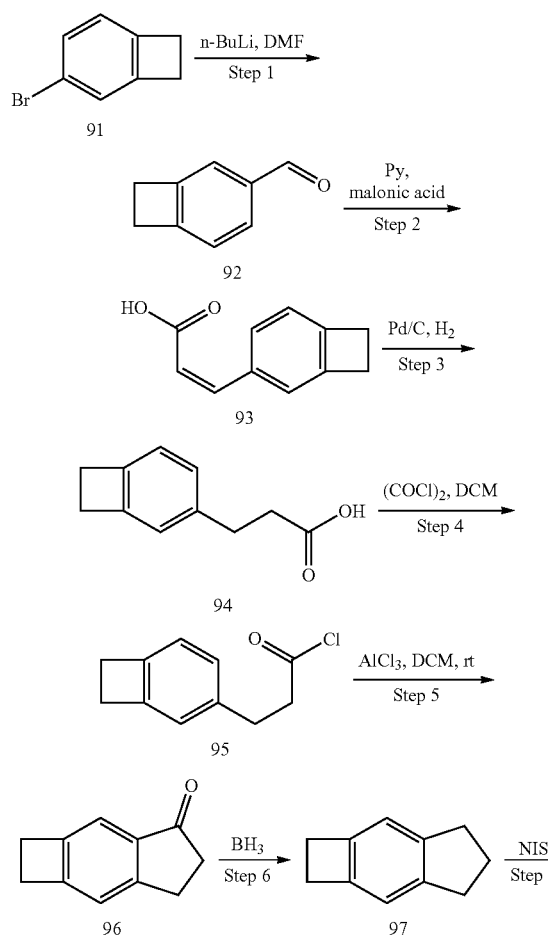

Scheme 16

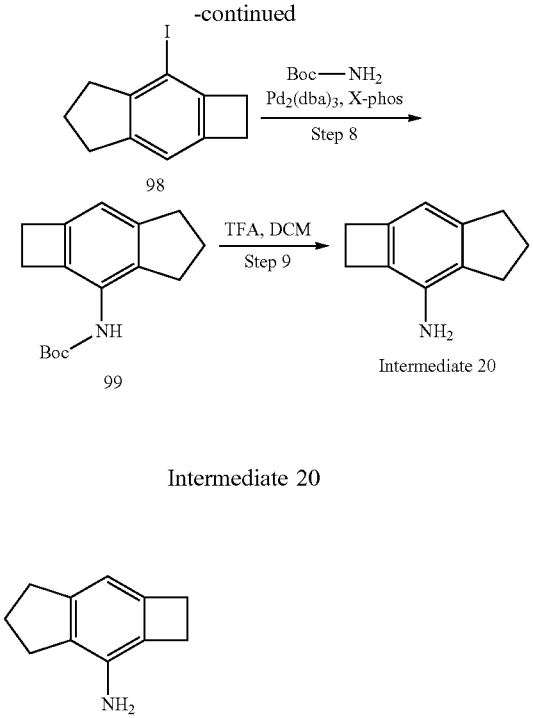

Intermediate 20

2,4,5,6-Tetrahydro-1H-cyclobuta[f]inden-3-amine

Step 1: Bicyclo[4.2.0]octa-1(6),2,4-triene-3-carbaldehyde

Into a 500 mL round-bottom flask purged and maintained with an inert atmosphere of nitrogen, was placed 3-bromo-bicyclo[4.2.0]octa-1(6),2,4-triene (70.00 g, 382.4 mmol, 1.0 equiv.) in THF (300 mL). This was followed by the addition of n-BuLi (2.5 M in hexane, 184 mL, 458.9 mmol, 1.5 equiv.) dropwise with stirring, maintaining an internal temperature<−70° C. The reaction mixture was stirred for 30 min at −70° C. To this solution was added DMF (38.4 mL, 497.1 mmol, 1.5 equiv.) dropwise with stirring at −70° C. The resulting solution was stirred for additional 30 min at −70° C. The reaction was slowly warmed to ambient temperature and then quenched by the addition of 100 mL of water. The resulting solution was extracted with DCM and the organic layer was dried over anhydrous Na₂SO₄ and concentrated to give 50 g of bicyclo[4.2.0]octa-1(6),2,4-triene-3-carbaldehyde as light yellow oil. MS-ESI: 133 (M+1).

Step 2: (Z/E)-3-(bicyclo[4.2.0]octa-1(6),2,4-trien-3-yl)acrylic Acid

Into a 250 mL round-bottom flask purged and maintained with an inert atmosphere of nitrogen, was placed bicyclo[4.2.0]octa-1(6),2,4-triene-3-carbaldehyde (1.70 g, 12.9 mmol, 1.0 equiv.) in pyridine (20 mL). To the solution were added propanedioic acid (2.00 g, 19.2 mmol, 1.5 equiv) and piperidine (0.2 mL, 1.3 mmol, 0.1 equiv.). The resulting solution was stirred for overnight at 90° C. in an oil bath. The resulting mixture was concentrated to give 2.1 g of Z/E-3-[bicyclo[4.2.0]octa-1(6),2,4-trien-3-yl]prop-2-enoic acid as a solid. MS-ESI: 173 (M−1).

Step 3: 3-(Bicyclo[4.2.0]octa-1(6),2,4-trien-3-yl) propanoic Acid

Into a 250 mL round-bottom flask, was placed Z/E-3-[bicyclo[4.2.0]octa-1(6),2,4-trien-3-yl]prop-2-enoic acid (2.10 g, 12.1 mmol, 1.0 equiv.) in MeOH (20 mL). To the solution was added Pd/C (10% wt., 200 mg). The flask was evacuated and flushed three times with hydrogen. The resulting solution was stirred for 12 h at ambient temperature under an atmosphere of hydrogen (balloon). The Pd/C catalyst was filtered out by filtration, and the filtrate was concentrated to give 2.1 g of 3-[bicyclo[4.2.0]octa-1(6),2,4-trien-3-yl]propanoic acid as a solid. MS-ESI: 175 (M−1).

Step 4: 3-(Bicyclo[4.2.0]octa-1(6),2,4-trien-3-yl) propanoyl chloride

Into a 250 mL round-bottom flask purged and maintained with an inert atmosphere of nitrogen, was placed 3-[bicyclo[4.2.0]octa-1(6),2,4-trien-3-yl]propanoic acid (10.00 g, 56.7 mmol, 1.0 equiv.) in DCM (100 mL). This was followed by the addition of oxalyl chloride (4.8 mL, 56.8 mmol, 1.0 equiv.) dropwise with stirring at 0° C. The resulting solution was stirred for 2 h at 0° C. in a water/ice bath and then concentrated to give 10 g of 3-[bicyclo[4.2.0]octa-1(6),2,4-trien-3-yl]propanoyl chloride as light yellow oil, which was used directly without additional purification.

Step 5: 1,2,5,6-Tetrahydro-4H-cyclobuta[f]inden-4-one

Into a 100 mL round-bottom flask, was placed 3-[bicyclo[4.2.0]octa-1(6),2,4-trien-3-yl]propanoyl chloride (5.00 g, 25.7 mmol, 1.0 equiv.) in DCM (50 mL) and the reaction mixture was cooled to 0° C. This was followed by the addition of AlCl₃ (3.40 g, 25.7 mmol, 1.0 equiv.) in portions over 10 min, maintaining the temperature below 0° C. The resulting solution was stirred for additional 1 h at 0° C. and then quenched by the addition of 100 mL of water. The resulting solution was extracted with DCM and the combined organic layers were dried over anhydrous $Na_2SO_4$ and concentrated. The residue was purified by flash column chromatography on silica gel, eluting with ethyl acetate/petroleum ether (1:20 to 1:15) to give 3.5 g of 1,2,5,6-tetrahydrocyclobuta[f]inden-4-one as a white solid. $^1$H NMR (300 MHz, CDCl₃) δ 7.45 (s, 1H), 7.17 (s, 1H), 3.22 (s, 4H), 3.18-3.00 (m, 2H), 2.73-2.63 (m, 2H).

Step 6: 2,4,5,6-Tetrahydro-1H-cyclobuta[f]indene

Into a 500 mL round-bottom flask purged and maintained with an inert atmosphere of nitrogen, was placed 1,2,5,6-tetrahydrocyclobuta[f]inden-4-one (20.00 g, 126.4 mmol, 1.0 equiv.) in THF (200 mL), and the reaction mixture was cooled to 0° C. This was followed by the addition of BH₃·SMe₂ (25.3 mL, 252.9 mmol, 10 M, 2.0 equiv.) dropwise, maintaining the internal temperature at 0° C. The resulting solution was stirred for 14 h at 70° C. The reaction was then quenched by the addition of 20 mL of MeOH. The resulting mixture was concentrated, and the residue was purified by flash column chromatography on silica gel, eluting with ethyl acetate/petroleum ether (1:100 to 1:50) to give 15 g of 2,4,5,6-tetrahydro-1H-cyclobuta [f]indene as colorless oil. $^1$H NMR (300 MHz, CDCl₃) δ 6.95 (s, 2H), 3.10 (s, 4H), 2.88 (t, 4H), 2.04-2.02 (m, 2H).

Step 7: 3-Iodo-2,4,5,6-tetrahydro-1H-cyclobuta[f] indene

Into a 500 mL round-bottom flask, was placed 2,4,5,6-tetrahydro-1H-cyclobuta[f]indene (15.00 g, 104.0 mmol, 1.0 equiv.) in acetic acid (100 mL). To the solution was added N-Iodosuccinimide (35.11 g, 156.0 mmol, 1.5 equiv.). The resulting solution was stirred for 3 h at 50° C. in an oil bath. The resulting solution was diluted with 200 mL of water. The mixture was extracted with dichloromethane. The combined organic layers were dried over anhydrous $Na_2SO_4$ and concentrated. The residue was purified by flash column chromatography on silica gel, eluting with ethyl acetate/petroleum ether (1:100 to 1:80) to give 5 g of 3-iodo-2,4,5,6-tetrahydro-1H-cyclobuta[f]indene as yellow oil.

Step 8: Tert-butyl (2,4,5,6-tetrahydro-1H-cyclobuta [f]inden-3-yl)carbamate

Into a 250 mL round-bottom flask purged and maintained with an inert atmosphere of nitrogen, was placed 3-iodo-2,4,5,6-tetrahydro-1H-cyclobuta[f]indene (5.00 g, 18.5 mmol, 1.0 equiv.) in toluene (100 mL). To the solution were added tert-butyl carbamate (6.5 g, 55.5 mmol, 3.0 equiv.), X-Phos (0.91 g, 1.9 mmol, 0.1 equiv.), Pd₂(dba)₃ (0.80 g, 0.9 mmol, 0.05 equiv.) and t-BuOK (6.21 g, 55.5 mmol, 3.0 equiv.). The resulting solution was stirred for 14 h at 100° C. in an oil bath. The resulting mixture was concentrated and the residue was purified by flash column chromatography on silica gel, eluting with ethyl acetate/petroleum ether (1:50 to 1:20) to give 3 g of tert-butyl (2,4,5,6-tetrahydro-1H-cyclobuta[f]inden-3-yl)carbamate as a white solid. MS-ESI: 260 (M+1).
$^1$H NMR (300 MHz, CDCl₃) δ 6.72 (s, 1H), 6.13 (br, 1H), 3.26 (d, 2H), 3.01 (d, 2H), 2.90 (t, 2H), 2.75 (t, 2H), 2.07-2.05 (m, 2H), 1.52 (s, 9H).

Step 9: 2,4,5,6-Tetrahydro-1H-cyclobuta[f]inden-3-amine

Into a 100 mL round-bottom flask, was placed tert-butyl (2,4,5,6-tetrahydro-1H-cyclobuta[f]inden-3-yl)carbamate (3.00 g, 11.6 mmol, 1.0 equiv.) in DCM (20 mL) and TFA (5 mL). The resulting solution was stirred for 2 h at ambient temperature. The resulting solution was diluted with 50 mL of water. The pH value of the solution was adjusted to 10 with sat. aqueous $Na_2CO_3$. The resulting solution was extracted with DCM. The combined organic layers were dried over anhydrous $Na_2SO_4$ and concentrated to give 1.5 g of 2,4,5,6-Tetrahydro-1H-cyclobuta[f]inden-3-amine as a yellow solid. MS-ESI: 160 (M+1).

Scheme 17

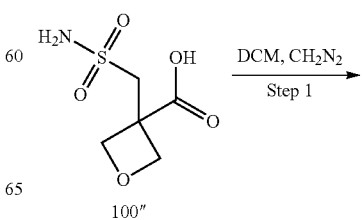

100″

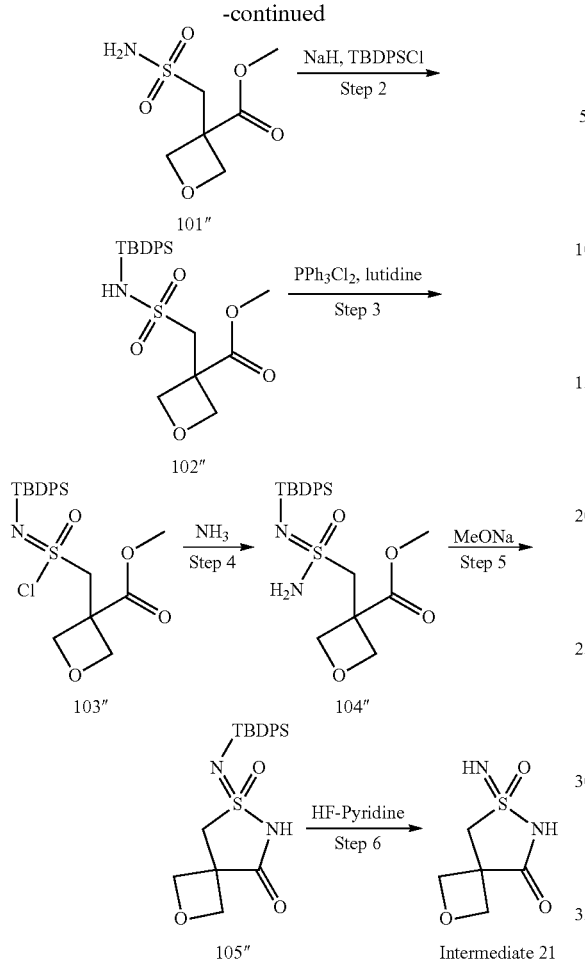

7-imino-2-oxa-7l6-thia-6-azaspiro[3.4]octan-5-one 7-oxide

Intermediate 21

Step 1: Methyl 3-(sulfamoylmethyl)oxetane-3-carboxylate

Into a 100 mL round-bottom flask purged and maintained with an inert atmosphere of nitrogen, was placed a solution of 3-(sulfamoylmethyl)oxetane-3-carboxylic acid (1.0 g, 5.1 mmol, 1.0 equiv.) in DCM (10 mL). This was followed by the addition of diazomethane (0.43 g, 10.2 mmol, 2.0 equiv.). The resulting solution was stirred for 2 h at 0° C. and then quenched by the addition of 2 mL of TFA and concentrated under vacuum to give 800 mg of methyl 3-(sulfamoylmethyl)oxetane-3-carboxylate as yellow oil. MS-ESI: 210.0 (M+1).

Step 2 to Step 6

Intermediate 21 was prepared from 101", using procedures similar to those used for converting 58 to Intermediate 9. MS-ESI: 177.0 (M+1).

Scheme 18

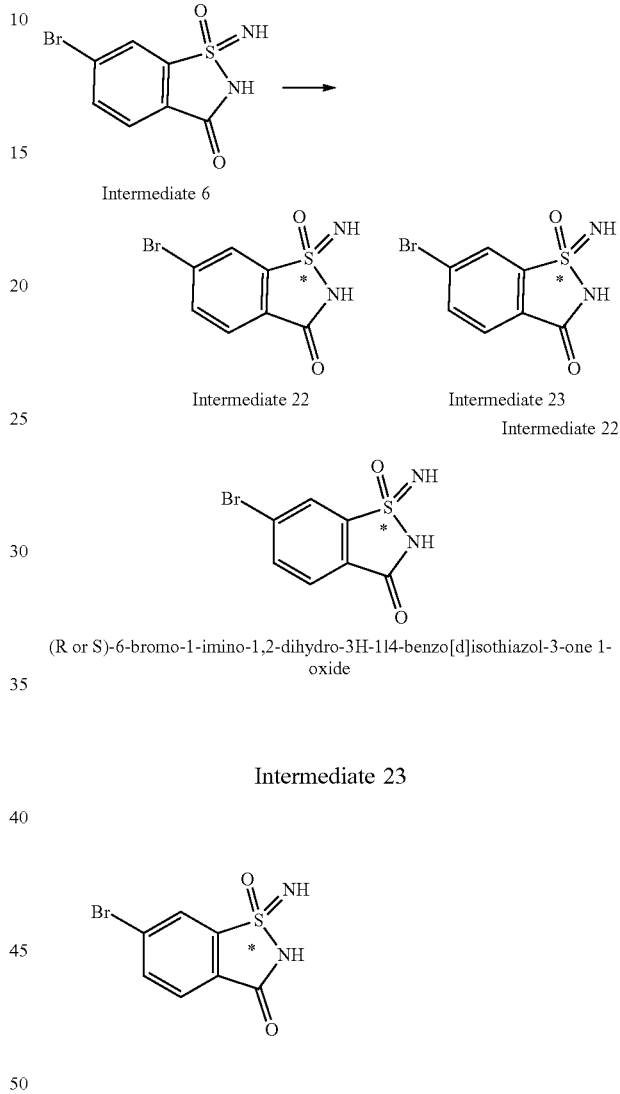

Intermediate 23

(S or R)-6-bromo-1-imino-1,2-dihydro-3H-1l4-benzo[d]isothiazol-3-one 1-oxide

The racemic 6-bromo-1-imino-1,2-dihydro-3H-1l4-benzo[d]isothiazol-3-one 1-oxide Intermediate 6, 500 mg) was resolved by Prep-Chiral-HPLC with the following conditions: Column: CHIRALPAK IG, 3*25 cm, 5 μm; Mobile Phase A: Hex (0.1% FA)—HPLC, Mobile Phase B: EtOH—HPLC; Flow rate: 20 mL/min; Gradient: 30 B to 30 B in 15 min; 254/220 nm; RT1: 5.75; RT2: 8.58. This resulted in 150 mg of (R or S)-6-bromo-1-imino-1,2-dihydro-3H-1l4-benzo[d]isothiazol-3-one 1-oxide (front peak, intermediate 22) as a white solid and 137 mg of (S or R)-6-bromo-1-imino-1,2-dihydro-3H-1l4-benzo[d]isothiazol-3-one 1-oxide (second peak, intermediate 23) as a white solid. MS-ESI: 261.1 (M+1).

TABLE E1'

The Intermediates in the following Table were prepared using the similar procedures for converting Intermediate 6 to Intermediate 22 and Intermediate 23, as shown in Scheme 18, from appropriate starting materials.

| Int. # | Structure | Precursor | IUPAC Name | Exact Mass [M + H]⁺ |
|---|---|---|---|---|
| Int. 24 (front peak) | 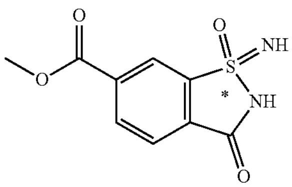 [SMILES: COC(=O)c1ccc2c(c1)S(=N)(=O)NC2=O] | | methyl (R or S)-1-imino-3-oxo-2,3-dihydro-1H-1λ4-benzo[d]isothiazole-6-carboxylate 1-oxide | 241.0 |
| Int. 25 (second peak) | 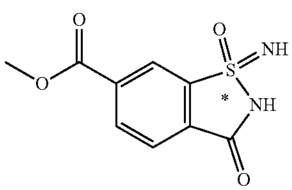 [SMILES: COC(=O)c1ccc2c(c1)S(=N)(=O)NC2=O] | | methyl (S or R)-1-imino-3-oxo-2,3-dihydro-1H-1λ4-benzo[d]isothiazole-6-carbovlate 1-oxide | 241.0 |
| Int. 26 (front peak) | 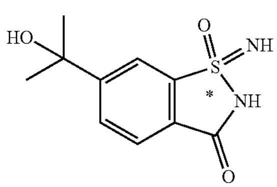 [SMILES: CC(C)(O)c1ccc2c(c1)S(=N)(=O)NC2=O] | Intermediate 2 | (R or S)-6-(2-hydroxypropan-2-yl)-1-imino-1,2-dihydro-3H-1λ4-benzo[d]isothiazol-3-one 1-oxide | 241.1 |
| Int. 27 (second Peak) | 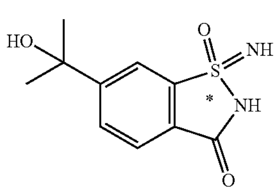 [SMILES: CC(C)(O)c1ccc2c(c1)S(=N)(=O)NC2=O] | Intermediate 2 | (S or R)-6-(2-hydroxypropan-2-yl)-1-imino-1,2-dihydro-3H-1λ4-benzo[d]isothiazol-3-one 1-oxide | 241.1 |

Scheme 19

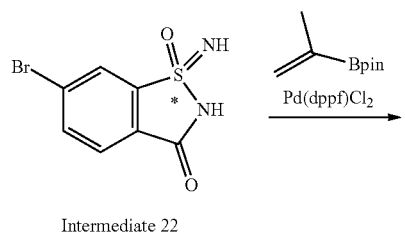

Intermediate 22

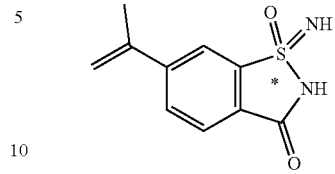

Intermediate 28

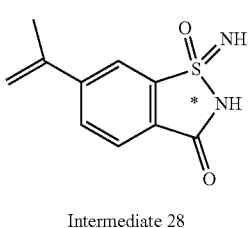

Intermediate 28

Intermediate 28

(R or S)-1-imino-6-(prop-1-en-2-yl)-1,2-dihydro-3H-1λ4-benzo[d]isothiazol-3-one 1-oxide Into a 40-mL vial purged and maintained with an inert atmosphere of nitrogen, was placed a solution of (R)-6-bromo-1-imino-1,2-dihydro-3H-1λ4-benzo[d]isothiazol-3-one 1-oxide (150 mg, 0.6 mmol, 1.0 equiv.) and 4,4,5,5-tetramethyl-2-(prop-1-en-2-yl)-1,3,2-dioxaborolane (116 mg, 0.7 mmol, 1.2 equiv.) in dioxane/water (5 mL/0.5 mL). This was followed by the addition of Pd(dppf)Cl$_2$ (42 mg, 0.06 mmol, 0.1 equiv.), X-Phos (55 mg, 0.12 mmol, 0.2 equiv.), Cs$_2$CO$_3$ (562 mg, 1.7 mmol, 3.0 equiv.). The resulting solution was stirred for 2 h at 100° C. and concentrated under vacuum. The residue was purified by flash column chromatography on silica gel, eluting with dichloromethane/methanol (10:1), to give 140 mg of (R or S)-1-imino-6-(prop-1-en-2-yl)-1,2-dihydro-3H-1λ4-benzo[d]isothiazol-3-one 1-oxide as a white solid. MS-ESI: 223.0 (M+1).

TABLE E1"

The Intermediates in the following Table were prepared using the similar procedures for converting Intermediate 22 to Intermediate 28, as shown in Scheme 19, from the appropriate starting materials.

| Int. # | Structure | Precursor | IUPAC Name | Exact Mass [M + H]$^+$ |
|---|---|---|---|---|
| Int. 29 | (structure shown) | (structure shown) Intermediate 23 | (S or R)-1-imino-6-(prop-1-en-2-yl)-1,2-dihydro-3H-1λ4-benzo[d]isothiazol-3-one 1-oxide | 223.0 |
| Int. 30 | (structure shown) | (structure shown) Intermediate 6 | 1-imino-6-(prop-1-en-2-yl)-1,2-dihydro-3H-1λ4-benzo[d]isothiazol-3-one 1-oxide | 223.0 |

Scheme 20

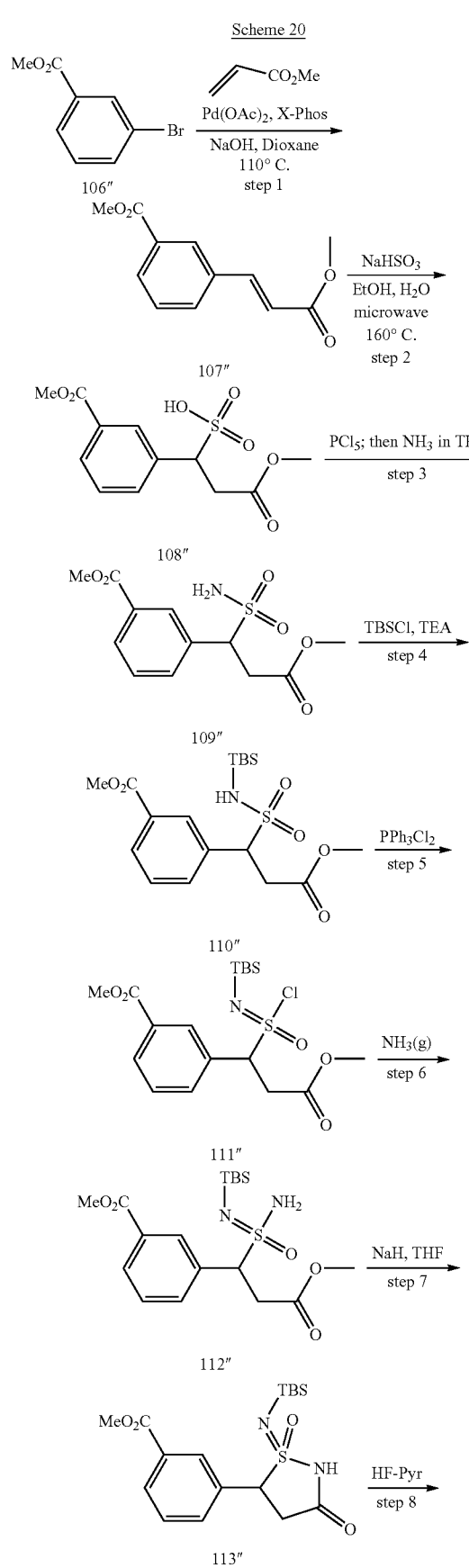

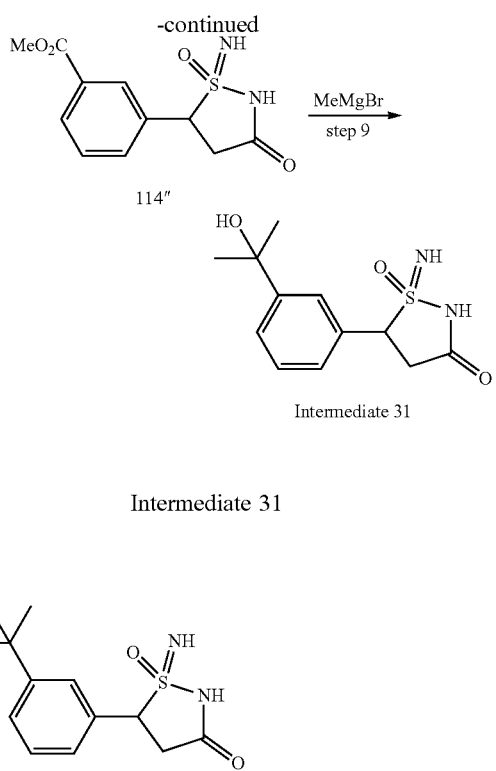

Intermediate 31

5-(3-(2-hydroxypropan-2-yl)phenyl)-1-imino-1λ6-isothiazolidin-3-one 1-oxide

Step 1: methyl (E)-3-(3-methoxy-3-oxoprop-1-en-1-yl)benzoate

To a solution of methyl 3-bromobenzoate (10.0 g, 46.5 mmol, 1.0 equiv.) in dioxane (80 mL), were added Pd(OAc)$_2$ (2.1 g, 9.3 mmol, 0.2 equiv.), NaOH (4.7 g, 116.3 mmol, 2.5 equiv.), X-Phos (1.6 g, 18.6 mmol, 0.4 equiv.) and methyl acrylate (6.0 g, 69.7 mmol, 1.5 equiv.) under nitrogen. The resulting solution was stirred for overnight at 110° C. and concentrated under vacuum. The residue was purified by silica gel column chromatography, eluting with ethyl acetate/petroleum ether (3:10) to give 9.7 g of methyl (E)-3-(3-methoxy-3-oxoprop-1-en-1-yl)benzoate as a yellow solid. MS-ESI: 221.1 (M+1).

Step 2: 3-methoxy-1-(3-(methoxycarbonyl)phenyl)-3-oxopropane-1-sulfonic Acid NaHSO$_3$ (2.4 g, 22.7 mmol, 2.0 equiv.) was added into a 20-mL pressure tank reactor containing a solution of methyl (E)-3-(3-methoxy-3-oxoprop-1-en-1-yl)benzoate (2.5 g, 11.3 mmol, 1.0 equiv.) in EtOH/water (5 mL/5 mL). The reaction mixture was irradiated with microwave radiation for 3 h at 140° C. Concentration of the mixture gave 3.5 g of crude 3-methoxy-1-(3-(methoxycarbonyl)phenyl)-3-oxopropane-1-sulfonic acid as a yellow solid. MS-ESI: 301.1 (M−1).

Step 3: Methyl 3-(3-methoxy-3-oxo-1-sulfamoylpropyl)benzoate

To a solution of 3-methoxy-1-(3-(methoxycarbonyl)phenyl)-3-oxopropane-1-sulfonic acid (10.0 g, 33.1 mmol, 1.0 equiv.) in DCM (100 mL), was added PCl₅ (34.4 g, 165.4 mmol, 5.0 equiv.). The resulting solution was stirred for overnight at ambient temperature. This was followed by the addition of NH₄OH (70.0 mL, 1798 mmol, 54.3 equiv.) dropwise and then the reaction mixture was stirred for an additional 15 minutes at ambient temperature. The reaction mixture was quenched by the addition of 50 mL of water, then extracted with ethyl acetate and the combined organic layers were washed with brine, dried over anhydrous sodium sulfate and concentrated under vacuum. The residue was purified by flash column chromatography on silica gel, eluting with ethyl acetate/petroleum ether (7:10) to give 842 mg of methyl 3-(3-methoxy-3-oxo-1-sulfamoylpropyl)benzoate as a white solid. MS-ESI: 302.1 (M−1).

Step 4 to step 8

Steps 4-8 used similar procedures for converting compound 58 to Intermediate 9, to afford compound 114 from compound 109. MS-ESI: 269.1 (M+1).

Step 9: 5-(3-(2-hydroxypropan-2-yl)phenyl)-1-imino-1l6-isothiazolidin-3-one 1-oxide To a solution of methyl 3-(1-imino-1-oxido-3-oxo-1l6-isothiazolidin-5-yl)benzoate (81 mg, 0.2 mmol, 1.0 equiv.) in THF (8 mL), was added MeMgBr (1M in THF, 1.1 mL, 1.1 mmol, 5.5 equiv.) dropwise at ambient temperature. The resulting solution was stirred for 30 min at ambient temperature and then quenched by the addition of 10 mL of saturated aqueous NH₄Cl. The resulting mixture was extracted with ethyl acetate and the combined organic layers were concentrated under vacuum. The residue was purified by flash column chromatography on silica gel, eluting with dichloromethane/methanol (5:1) to give 39 mg of 5-(3-(2-hydroxypropan-2-yl)phenyl)-1-imino-1l6-isothiazolidin-3-one 1-oxide as a white solid. MS-ESI: 269.1 (M+1).

Intermediate 32

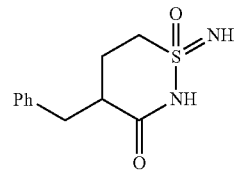

4-benzyl-1-imino-1l6,2-thiazinan-3-one 1-oxide

Step 1: 4-benzyl-1-((tert-butyldiphenylsilyl)imino)-1l6,2-thiazinan-3-one 1-oxide To a −78° C. solution of 1-((tert-butyldiphenylsilyl)imino)-1l6,2-thiazinan-3-one 1-oxide (200 mg, 0.52 mmol, 1.0 equiv.) in THF (5 mL) was added LDA (2M in THF, 0.5 mL, 1.0 mmol, 2.0 equiv.) dropwise over 5 min. The resulting mixture was stirred for additional 30 min at −78° C. This was followed by the addition of benzyl bromide (0.15 mL, 1.3 mmol, 2.4 equiv.) dropwise, maintaining the internal temperature at −78° C. The resulting mixture was stirred for an additional 2 h at ambient temperature, then the reaction mixture was concentrated under vacuum. The residue was purified by flash column chromatography on silica gel, eluting with ethyl acetate/petroleum ether (1:5) to give 80 mg of 4-benzyl-1-((tert-butyldiphenylsilyl)imino)-1l6,2-thiazinan-3-one 1-oxide as a yellow oil. MS-ESI: 477.2 (M+1).

Step 2: 4-benzyl-1-imino-1l6,2-thiazinan-3-one 1-oxide

To a solution of 4-benzyl-1-((tert-butyldiphenylsilyl)imino)-1l6,2-thiazinan-3-one 1-oxide (200 mg, 0.4 mmol, 1.0 equiv.) in THF (5 mL), was added HCl in 1,4-dioxane (4M, 5 mL). The resulting mixture was stirred for 2 h at ambient temperature and then concentrated under vacuum to afford 70 mg of 4-benzyl-1-imino-1l6,2-thiazinan-3-one 1-oxide as a yellow oil. MS-ESI: 239.1 (M+1).

Scheme 21

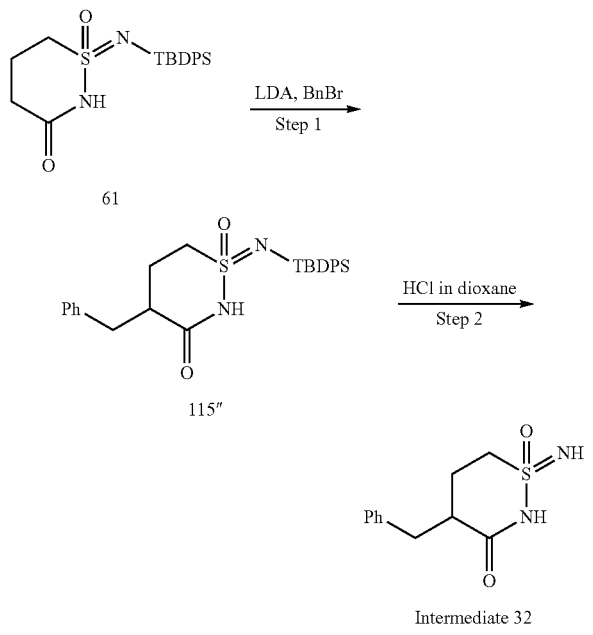

Scheme 22

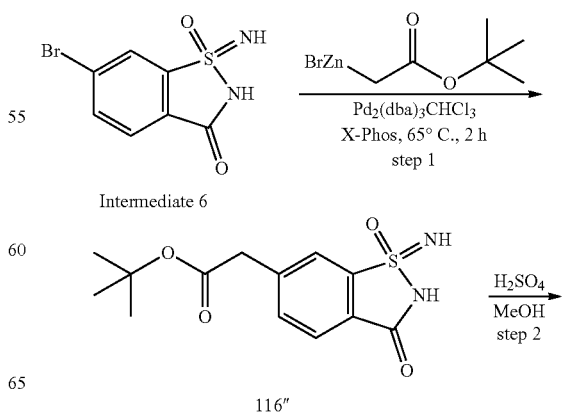

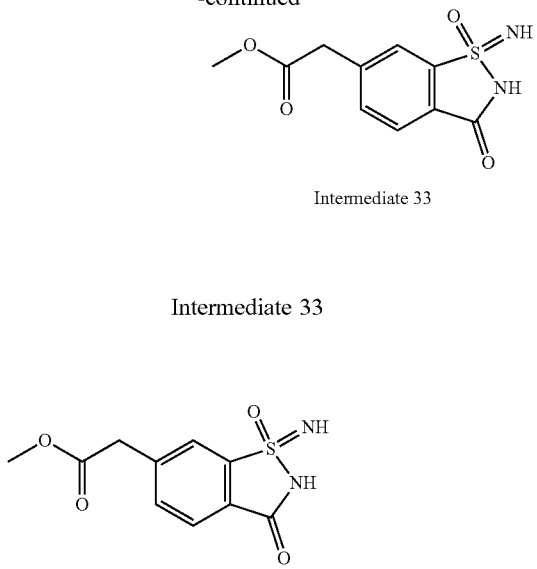

Intermediate 33

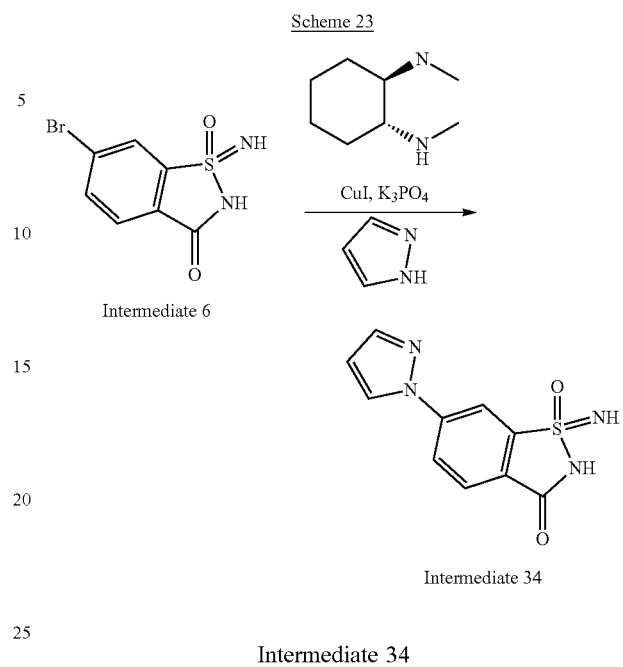

Intermediate 34 methyl 2-(1-imino-1-oxido-3-oxo-2,3-dihydro-1H-1l4-benzo[d]isothiazol-6-yl)acetate Step 1: tert-butyl 2-(1-imino-1-oxido-3-oxo-2,3-dihydro-1H-1l4-benzo[d]isothiazol-6-yl)acetate To a solution of 6 6-bromo-1-imino-1,2-dihydro-3H-1l4-benzo[d]isothiazol-3-one 1-oxide (50 mg, 0.2 mmol, 1.0 equiv.) and (2-(tert-butoxy)-2-oxoethyl)zinc(II) bromide (500 mg, 1.9 mmol, 10.0 equiv.) in THF (5 mL), were added Pd$_2$(dba)$_3$CHCl$_3$ (10 mg, 0.01 mmol, 0.05 equiv.) and X-Phos (9.0 mg, 0.02 mmol, 0.1 equiv.) under nitrogen. The resulting solution was stirred for 2 h at 65° C. and then concentrated under vacuum. The residue was purified by flash column chromatography on silica gel, eluting with dichloromethane/methanol (5:1), to give 34 mg of tert-butyl 2-(1-imino-1-oxido-3-oxo-2,3-dihydro-1H-1l4-benzo[d]isothiazol-6-yl)acetate as a white solid. MS-ESI. 297.1 (M+1).

Step 2: Methyl 2-(1-imino-1-oxido-3-oxo-2,3-dihydro-1H-1l4-benzo[d]isothiazol-6-yl)acetate To a solution of tert-butyl 2-(1-imino-1-oxido-3-oxo-2,3-dihydro-1H-1l4-benzo[d]isothiazol-6-yl)acetate (150 mg, 0.5 mmol, 1.0 equiv.) in MeOH (10 mL), was added conc. sulfuric acid (0.10 mL). The resulting solution was stirred for 1 h at ambient temperature. The solution was adjusted to pH 7 with aqueous NaHCO$_3$(3 M). After filtration and concentration, the residue was purified by flash column chromatography on silica gel, eluting with dichloromethane/methanol (5:1), to give 50 mg of methyl 2-(1-imino-1-oxido-3-oxo-2,3-dihydro-1H-1l4-benzo[d]isothiazol-6-yl)acetate as a white solid. MS-ESI: 255.0 (M+1).

Scheme 23

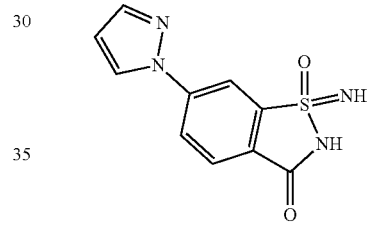

Intermediate 34

1-imino-6-(1H-pyrazol-1-yl)-1,2-dihydro-3H-1l4-benzo[d]isothiazol-3-one 1-oxide

To a solution of 6-bromo-1-imino-1,2-dihydro-3H-1l4-benzo[d]isothiazol-3-one 1-oxide (500 mg, 1.9 mmol, 1.0 equiv.) in dioxane (20 mL), were added pyrazole (150 mg, 2.2 mmol, 1.2 equiv.), (1R,2R)—N1,N2-dimethylcyclohexane-1,2-diamine (150 mg, 1.05 mmol, 0.6 equiv.), CuI (150 mg, 0.8 mmol, 0.4 equiv.), and K$_3$PO$_4$ (1.50 g, 7.1 mmol, 3.7 equiv.) under nitrogen. The resulting solution was stirred for 2 h at ambient temperature and then concentrated under vacuum. The residue was purified by flash column chromatography on silica gel, eluting with ethyl acetate/petroleum ether (1/1), to give 100 mg of 1-imino-6-(1H-pyrazol-1-yl)-1,2-dihydro-3H-1l4-benzo[d]isothiazol-3-one 1-oxide as a yellow solid. MS-ESI: 249.0 (M+1).

Scheme 24

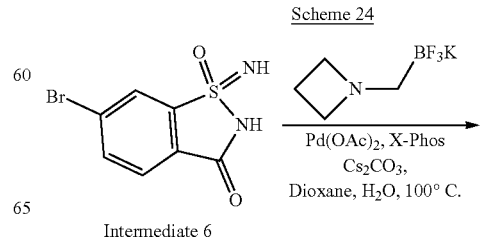

Intermediate 6

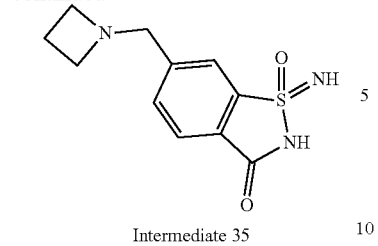

Intermediate 35

Intermediate 35

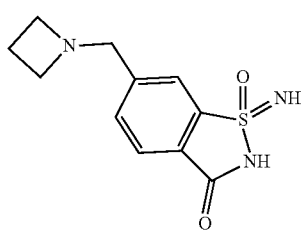 [SMILES: N=S1(=O)NC(=O)c2ccc(CN3CCC3)cc21]

6-(azetidin-1-ylmethyl)-1-imino-1,2-dihydro-3H-1l4-benzo[d]isothiazol-3-one 1-oxide To a solution of 6-bromo-1-imino-1,2-dihydro-3H-1l4-benzo[d]isothiazol-3-one 1-oxide (50 mg, 0.2 mmol, 1.0 equiv.) in dioxane/water (5 mL/0.5 mL), were added Pd(OAc)$_2$ (9 mg, 0.04 mmol, 0.2 equiv.), X-Phos (18 mg, 0.04 mmol, 0.2 equiv.) and Cs$_2$CO$_3$ (187 mg, 0.6 mmol, 3.0 equiv.) under nitrogen. This was followed by the addition of 1-((trifluoro-14-boraneyl)methyl)azetidine, potassium salt (34 mg, 0.2 mmol, 1.0 equiv.). The resulting solution was stirred for 2 h at 100° C. and then concentrated under vacuum. The residue was purified by flash column chromatography on silica gel, eluting with dichloromethane/methanol (5:1) to give 27 mg of 6-(azetidin-1-ylmethyl)-1-imino-1,2-dihydro-3H-1l4-benzo[d]isothiazol-3-one 1-oxide as a white solid. MS-ESI. 252.1 (M+1).

Scheme 25

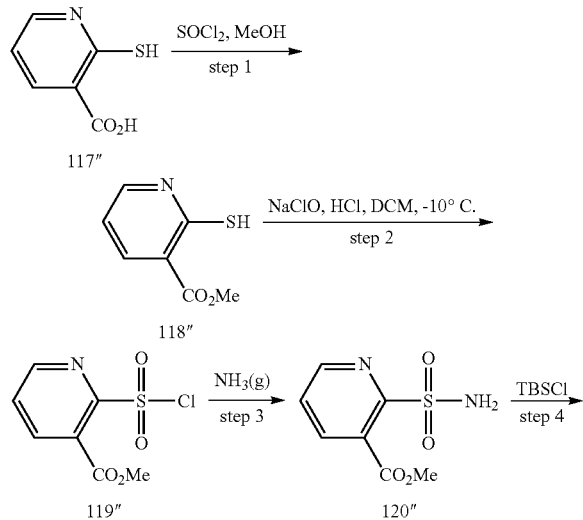

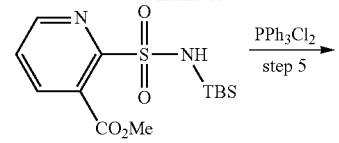

121″

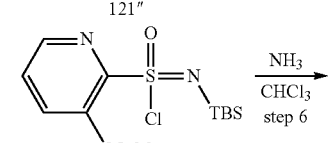

122″

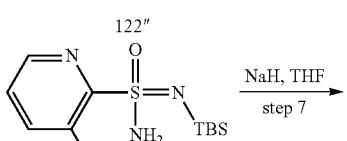

123″

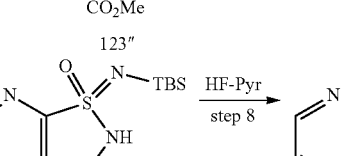

124″                    Intermediate 36

Intermediate 36

1-imino-1,2-dihydro-3H-1l4-isothiazolo[5,4-b]pyridin-3-one 1-oxide

Step 1: Methyl 2-mercaptonicotinate

To a stirred solution of SOCl$_2$ (4.2 g, 35.4 mmol, 1.1 equiv.) in MeOH (50 mL), was added 2-sulfanylpyridine-3-carboxylic acid (5.0 g, 32.2 mmol, 1.0 equiv.) in portions at 0° C. The resulting mixture was stirred for 1 h at ambient temperature and then concentrated under reduced pressure. The residue was purified by reverse flash chromatography with the following conditions: column, C18 silica gel; mobile phase, A: MeOH, B: water, 10% B to 50% B in 10 min; detector, UV 254 nm. This resulted in 2 g of methyl 2-mercaptonicotinate as a yellow solid. MS-ESI: 170.0 (M+1).

Step 2 and Step 3: Methyl 2-sulfamoylnicotinate

To a stirred solution of methyl 2-mercaptonicotinate (2.5 g, 14.8 mmol, 1.0 equiv.) in DCM (20 mL), was added aq. HCl (1 N, 20 mL) dropwise at −10° C. under nitrogen atmosphere. The resulting solution was stirred for 30 min at this temperature, was followed by the addition of sodium hypochlorite (8% in water, 20 mL, 21.5 mmol, 71.6 equiv.) dropwise at −10° C. The resulting mixture was stirred for an additional 30 min at 0° C. The resulting mixture was extracted with DCM and the combined organic layers were washed with brine, dried over anhydrous $Na_2SO_4$ and concentrated under vacuum. The residue was re-dissolved into DCM (80 mL), then $NH_4OH$ (29 mL, 740.0 mmol, 50.0 equiv.) was added dropwise at 0° C. The resulting mixture was stirred for 30 min at 0° C. and concentrated under vacuum. The residue was purified by reverse phase flash chromatography with the following conditions: column, C18 silica gel; mobile phase, MeOH in water, 10% to 50% in 10 min; detector, UV 254 nm. This resulted in 1.1 g of methyl 2-sulfamoylpyridine-3-carboxylate as a light yellow solid. MS-ESI: 217.0 (M+1).

Step 4 to Step 8

Intermediate 36 was prepared from 120″, using procedures similar to those used for converting 58 to Intermediate 9. MS-ESI: 184.0 (M+1).

Intermediate 37

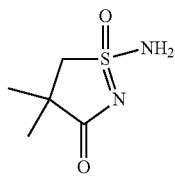

1-amino-4,4-dimethyl-4,5-dihydro-3H-1λ6-isothi-azol-3-one 1-oxide

Step 1 to step 5

Intermediate 37 was prepared from 125″, using procedures similar to those used for converting 58 to Intermediate 9. MS-ESI. 163.0 (M+1).

Scheme 26

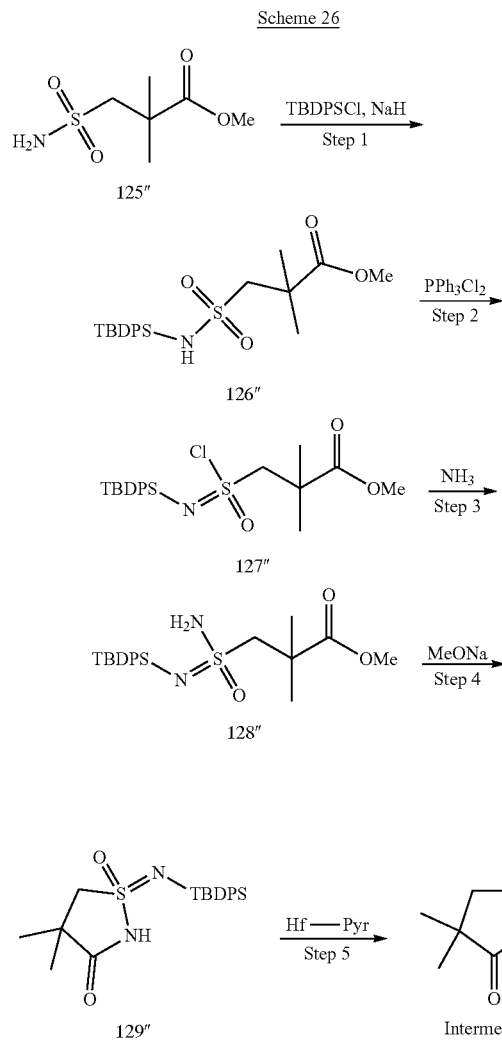

Scheme 27

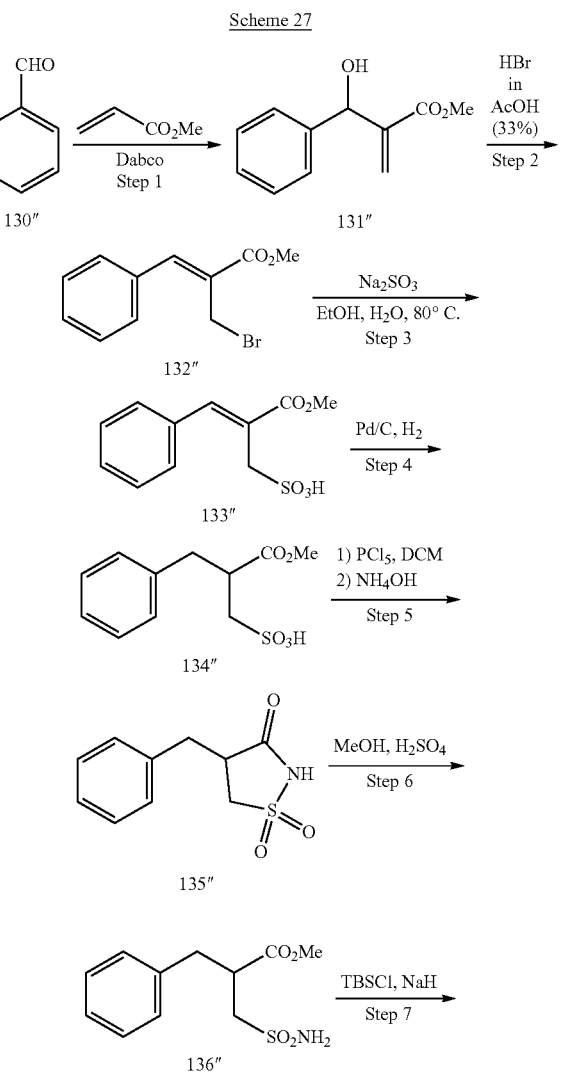

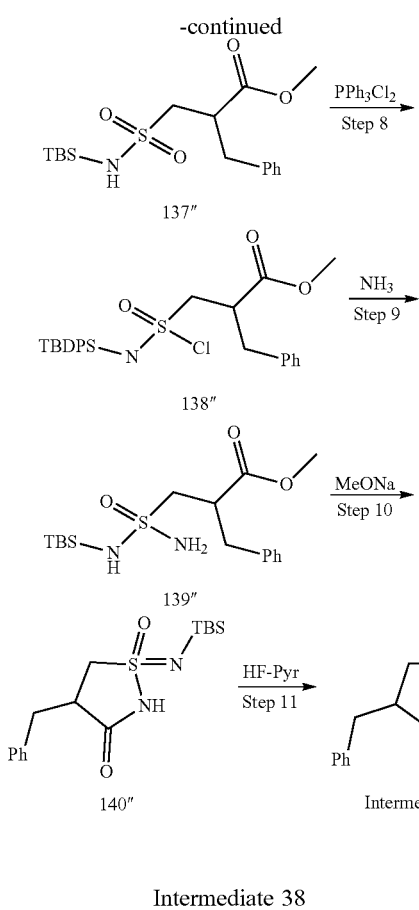

Intermediate 38

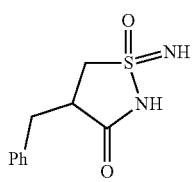

4-benzyl-1-imino-1l6-isothiazolidin-3-one 1-oxide

Step 1: Methyl 2-(hydroxy(phenyl)methyl)acrylate

To a solution of benzaldehyde (30 g, 282.7 mmol, 1.0 equiv.) in dioxane/water (150 mL/150 mL), were added TEDA (47 g, 424.0 mmol, 1.5 equiv.) and methyl prop-2-enoate (36 g, 424.0 mmol, 1.5 equiv.). The resulting solution was stirred for 120 h at 80° C. in an oil bath. The resulting solution was extracted with ethyl acetate and the combined organic layers were dried over anhydrous sodium sulfate and concentrated under vacuum. The residue was purified by flash column chromatography on silica gel column, eluting with ethyl acetate/petroleum ether (1/10) to give 15 g of methyl 2-(hydroxy(phenyl)methyl)acrylate as a yellow oil.

Step 2: methyl (Z)-2-(bromomethyl)-3-phenylacrylate

Methyl 2-(hydroxy(phenyl)methyl)acrylate (300 mg, 1.6 mmol, 1.0 equiv.) was dissolved in a solution of HBr in AcOH (3M, 15 mL). After 1.5 h at ambient temperature, the reaction mixture was diluted with 30 mL of water. The resulting mixture was extracted with ethyl acetate and the combined organic layers were dried over anhydrous sodium sulfate and concentrated under vacuum to give 250 mg of methyl (Z)-2-(bromomethyl)-3-phenylacrylate as brown yellow oil. $^1$H NMR (400 MHz, CDCl$_3$): 7.86 (s, 1H), 7.62-7.59 (m, 2H), 7.52-7.44 (m, 3H), 4.42 (s, 2H), 3.91 (s, 3H).

Step 3: (Z)-2-(methoxycarbonyl)-3-phenylprop-2-ene-1-sulfonic Acid

To a solution of methyl (Z)-2-(bromomethyl)-3-phenylacrylate (200 mg, 0.8 mmol, 1.0 equiv.) in EtOH/water (15 mL/10 mL), was added Na$_2$SO$_3$ (99 mg, 0.8 mmol, 1.0 equiv.). The resulting solution was heated to 80° C. and stirred for 16 h at this temperature, then concentrated to give 250 mg of (Z)-2-(methoxycarbonyl)-3-phenylprop-2-ene-1-sulfonic acid as a yellow solid that was used without additional purification. MS-ESI: 255.0 (M−1).

Step 4: 2-benzyl-3-methoxy-3-oxopropane-1-sulfonic Acid

To a solution of (Z)-2-(methoxycarbonyl)-3-phenylprop-2-ene-1-sulfonic acid (250 mg, 1.1 mmol, 1.0 equiv.) in MeOH (20 mL), was added Pd/C (10% wt., 25 mg, 0.02 mmol, 0.02 equiv.). The pressure vessel was evacuated and flushed three times with hydrogen and then stirred for 16 h at ambient temperature under a hydrogen atmosphere (10 atm.). The reaction mixture was filtered through Celite, then the filtrate was concentrated to give 250 mg of 2-benzyl-3-methoxy-3-oxopropane-1-sulfonic acid as a yellow solid that was used without additional purification. MS-ESI: 257.1 (M−1).

Step 5: 4-benzylisothiazolidin-3-one 1,1-dioxide

To a 0° C. solution of 2-benzyl-3-methoxy-3-oxopropane-1-sulfonic acid (2.00 g, 7.136 mmol, 1.00 equiv.) in DCM (50 mL), was added PCl$_5$ (3.0 g, 14.3 mmol, 2.0 equiv.). The reaction mixture was warmed to ambient temperature and stirred for 16 h, then the reaction mixture was cooled to 0° C. and NH$_4$OH (50 mL) was added dropwise. The resulting mixture was stirred for 1 h at ambient temperature and then concentrated under vacuum to give 3 g of 4-benzylisothiazolidin-3-one 1,1-dioxide as a white solid that was used without additional purification. MS-ESI: 226.1 (M+1).

Step 6: Methyl 2-benzyl-3-sulfamoylpropanoate

To a solution of 4-benzylisothiazolidin-3-one 1,1-dioxide (3.0 g, 13.3 mmol, 1.0 equiv.) in MeOH (50 mL), was added conc. sulfuric acid (3 mL). The resulting solution was heated to 80° C. and stirred for 2 h, then diluted with 50 mL of water. The resulting mixture was extracted with ethyl acetate and the combined organic layers were dried over anhydrous sodium sulfate and concentrated under vacuum. The residue was purified by flash column chromatography on silica gel, eluting with ethyl acetate/petroleum ether (1/5) to give 400 mg of methyl 2-benzyl-3-sulfamoylpropanoate as yellow oil. MS-ESI: 258.1 (M+1).

Step 7 to Step 11

Intermediate 38 was prepared from 134″, using procedures similar to those used for converting 58 to Intermediate 9. MS-ESI: 225.1 (M+1).

Scheme 28

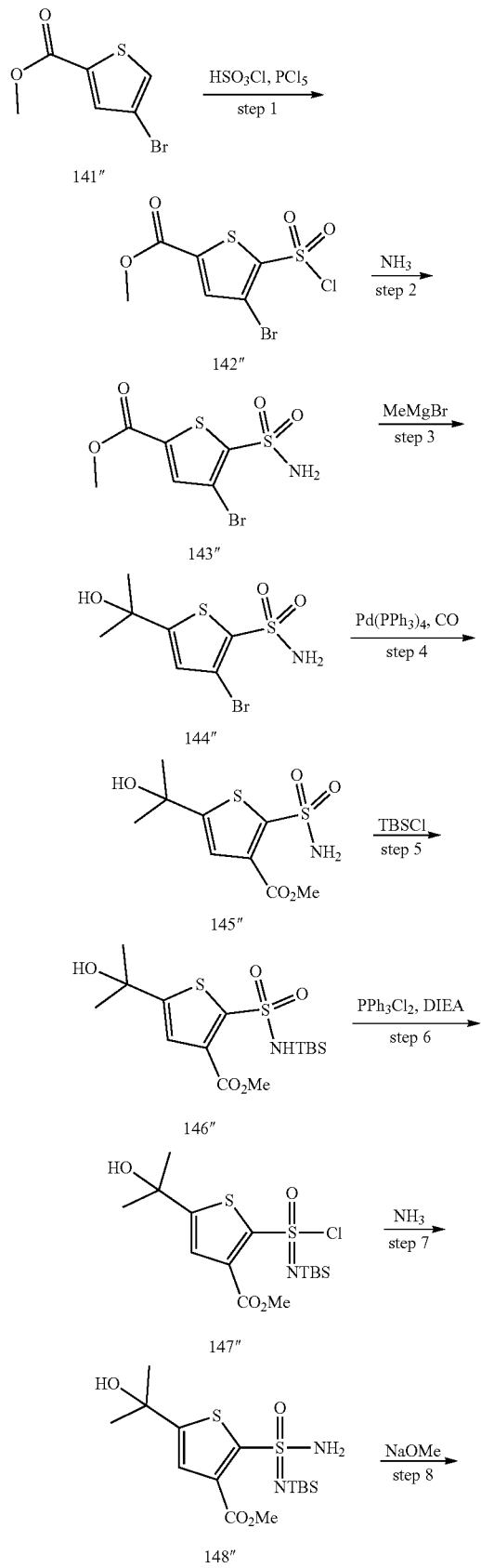

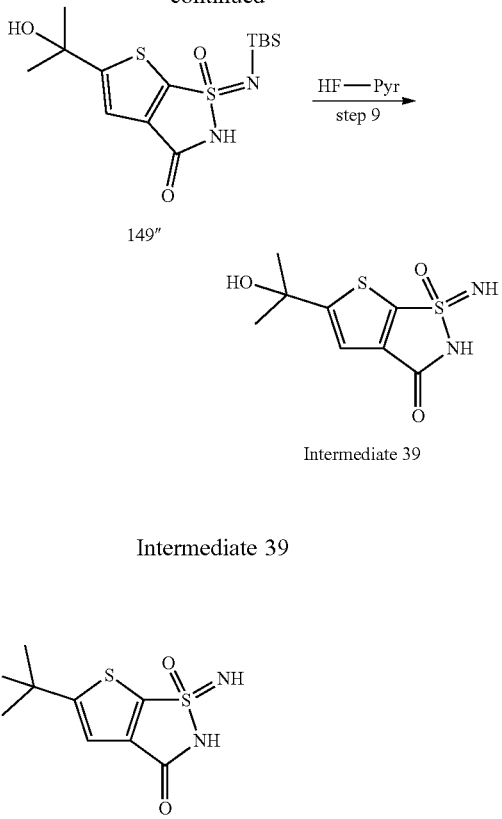

Intermediate 39

5-(2-hydroxypropan-2-yl)-1-imino-1,2-dihydro-3H-1λ4-thieno[3,2-d]isothiazol-3-one 1-oxide Step 1 and Step 2: Methyl 4-bromo-5-sulfamoylthiophene-2-carboxylate To a solution of methyl 4-bromothiophene-2-carboxylate (10.0 g, 45.2 mmol, 1.0 equiv.) in DCM (100 mL), was added $HSO_3Cl$ (6.0 mL, 90.5 mmol, 2.00 equiv.) and the mixture was stirred for 16 h at ambient temperature. Then to the reaction solution was added $PCl_5$ (34.4 g, 165.4 mmol, 3.7 equiv.) batchwise at 0° C. The resulting solution was stirred for additional 5 h at ambient temperature. This was followed by the addition of $NH_4OH$ (70.0 mL, 1797.6 mmol, 39.8 equiv.) dropwise and the resulting solution was stirred for an additional 15 min at ambient temperature. The resulting mixture was quenched by the addition of 50 mL of water, then extracted with ethyl acetate and the combined organic layers were washed with brine, dried over anhydrous sodium sulfate and concentrated under vacuum to give 12 g of methyl 4-bromo-5-sulfamoylthiophene-2-carboxylate as a yellow solid that was used without additional purification. MS-ESI. 300.1 (M+1).

Step 3: 3-bromo-5-(2-hydroxypropan-2-yl)thiophene-2-sulfonamide

MeMgBr (10 mL, 3M in THF, 30.0 mmol, 2.2 equiv.) was added dropwise to 0° C. a solution of methyl 4-bromo-5-sulfamoylthiophene-2-carboxylate (4 g, 13.3 mmol, 1.0 equiv.) in THF (100 mL). The resulting solution was stirred for 16 h at ambient temperature and then concentrated under vacuum. The residue was purified by flash column chromatography on silica gel, eluting with ethyl acetate/petroleum ether (2/1) to give 1.4 g of 3-bromo-5-(2-hydroxypropan-2-yl)thiophene-2-sulfonamide as an off-white solid. MS-ESI. 300.2 (M+1).

Step 4: Methyl 5-(2-hydroxypropan-2-yl)-2-sulfamoylthiophene-3-carboxylate

To a solution of 3-bromo-5-(2-hydroxypropan-2-yl)thiophene-2-sulfonamide (1.0 g, 3.3 mmol, 1.0 equiv.) in MeOH (15 mL), were added Pd(PPh$_3$)$_4$ (1.0 g, 0.8 mmol, 0.25 equiv.), TEA (1.4 mL, 10.0 mmol, 3.00 equiv) and Pd(dppf)Cl$_2$ (609 mg, 0.8 mmol, 0.25 equiv.). The resulting solution was heated to 100° C. and stirred for 16 h at 100° C. under an atmosphere of CO (50 atm). After concentration, the residue was dissolved into 100 mL of water, then the resulting solution was extracted with ethyl acetate and the combined organic layers were dried over anhydrous sodium sulfate and concentrated under vacuum. The residue was purified by flash column chromatography on silica gel column, eluting with ethyl acetate/petroleum ether (1/3) to give 200 mg of methyl 5-(2-hydroxypropan-2-yl)-2-sulfamoylthiophene-3-carboxylate as a yellow solid. MS-ESI: 280.0 (M+1).

Step 5 to Step 9

Intermediate 39 was prepared from 145", using procedures similar to those used for converting 58 to Intermediate 9. MS-ESI: 247.0 (M+1).

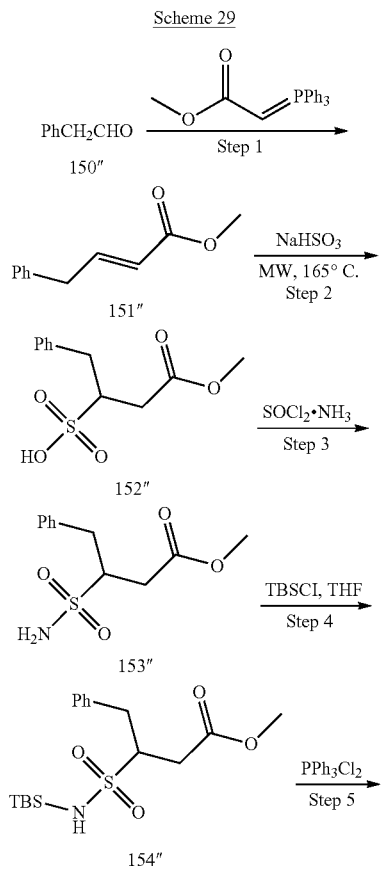

Scheme 29

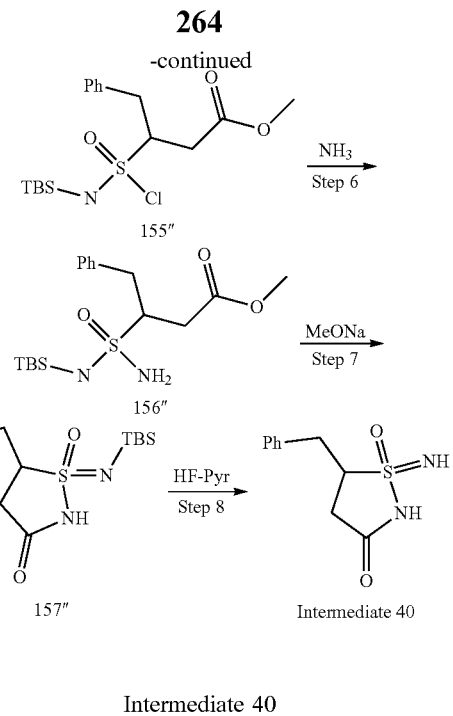

Intermediate 40

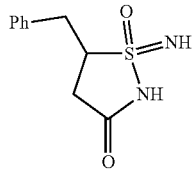

5-benzyl-1-imino-1l6-isothiazolidin-3-one 1-oxide

Step 1: methyl (E)-4-phenylbut-2-enoate

Into a 100-mL 3-necked round-bottom flask under an atmosphere of nitrogen, was placed a solution of methyl 2-(triphenyl-15-phosphaneylidene)acetate (2.0 g, 6.0 mmol, 1.0 equiv.) in THF (50 mL). Then 2-phenylacetaldehyde (3.6 g, 30.0 mmol, 5.0 equiv.) and NaOMe (2.0 g, 37.7 mmol, 6.3 equiv.) were added. The resulting solution was stirred for 6 h at ambient temperature and then concentrated under vacuum. The residue was purified by flash column chromatography on silica gel column, eluting with ethyl acetate/petroleum ether (1:50) to afford 1.5 g of methyl (E)-4-phenylbut-2-enoate as a white solid. MS-ESI: 177.1 (M+1).

Step 2: 4-methoxy-4-oxo-1-phenylbutane-2-sulfonic Acid

Into a 20-mL sealed tube under an atmosphere of argon, was placed a solution of methyl (2E)-4-phenylbut-2-enoate (1.0 g, 0.06 mmol, 1.0 equiv.) and NaHSO$_3$ (1.2 g, 0.14 mmol, 2.4 equiv.) in DMF (8 mL). The reaction mixture was irradiated with microwave radiation for 2 h at 165° C. The solution was adjusted to pH 3 with aqueous HCl (1 M). After concentration, the residue was purified by flash column chromatography on silica gel column, eluting with ethyl acetate/petroleum ether (1:10) to afford 0.6 g of 4-methoxy-4-oxo-1-phenylbutane-2-sulfonic acid as a white solid. MS-ESI: 257.1 (M−1).

Step 3: Methyl 4-phenyl-3-sulfamoylbutanoate

To a solution of 4-methoxy-4-oxo-1-phenylbutane-2-sulfonic acid (1.0 g, 3.9 mmol, 1.0 equiv.) in DCM (20 mL) was added SOCl₂ (10 mL, 137.9 mmol, 35.6 equiv.). The resulting solution was stirred overnight at ambient temperature. This was followed by the dropwise addition of NH₄OH (10.0 mL, 352.3 mmol, 91.0 equiv.) and then the reaction mixture was stirred for an additional 3 h at ambient temperature. The reaction was quenched by the addition of 50 mL of water, then extracted with ethyl acetate, and the combined organic layers were washed with brine, dried over anhydrous sodium sulfate and concentrated under vacuum. The residue was purified by flash column chromatography on silica gel column, eluting with ethyl acetate/petroleum ether (1:12) to afford 0.4 g of methyl 4-phenyl-3-sulfamoylbutanoate as a white solid. MS-ESI: 258.1 (M−1).

Step 4 to Step 8

Intermediate 40 was prepared from 153″, using procedures similar to those used for converting 58 to Intermediate 9. MS-ESI. 225.1 (M+1).

Scheme 30

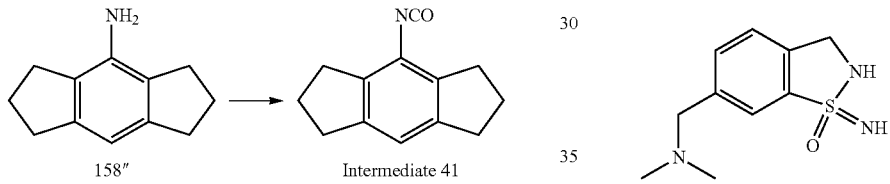

158″      Intermediate 41

Intermediate 41

4-isocyanato-1,2,3,5,6,7-hexahydro-s-indacene

Into a 500 mL round-bottom flask, was placed a solution of 1,2,3,5,6,7-hexahydro-s-indacen-4-amine (20.0 g, 115.4 mmol, 1.0 equiv.) in THF (250 mL). This was followed by the portionwise addition of ditrichloromethyl carbonate (13.7 g, 46.2 mmol, 0.4 equiv.). The resulting solution was stirred for 3 h at 70° C. and concentrated under vacuum to give 22.5 g of 4-isocyanato-1,2,3,5,6,7-hexahydro-s-indacene as a yellow solid, which was used directly in the next step without additional purification. The reaction progress was monitored by quenching aliquots with MeOH, and monitoring for the corresponding signal of methyl (1,2,3,5,6,7-hexahydro-s-indacen-4-yl)carbamate (MW=231.3) via LCMS analysis. MS-ESI. 232.2 (M+1).

Scheme 31

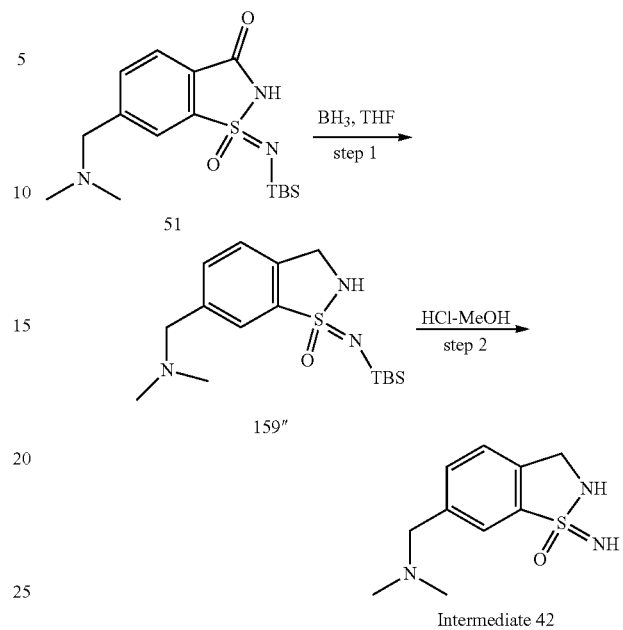

6-((dimethylamino)methyl)-1-imino-2,3-dihydro-1H-1λ4-benzo[d]isothiazole 1-oxide

Step 1: 1-((tert-butyldimethylsilyl)imino)-6-((dimethylamino)methyl)-2,3-dihydro-1H-1λ4-benzo[d]isothiazole 1-oxide To a solution of methyl 2-[(tert-butyldimethylsilyl)-S-aminosulfonimidoyl]-4-[(dimethylamino)methyl]benzoate (500 mg, 1.3 mmol, 1.0 equiv.) in THF (10 mL), was added BH₃-THF (1M, 2.5 mL, 2.5 mmol, 2.0 equiv.) at 0° C. The resulting mixture was stirred overnight at ambient temperature and then the reaction was quenched by the addition of MeOH (20 mL) at 0° C. and concentrated under vacuum to give 200 mg of 1-((tert-butyldimethylsilyl)imino)-6-((dimethylamino)methyl)-2,3-dihydro-1H-1λ4-benzo[d]isothiazole 1-oxide as a yellow oil. MS-ESI: 340.2 (M+1).

Step 2: 6-((dimethylamino)methyl)-1-imino-2,3-dihydro-1H-1λ4-benzo[d]isothiazole 1-oxide A solution of HCl(g) in MeOH (2.5 mL) was added to a solution of 1-((tert-butyldimethylsilyl)imino)-6-((dimethylamino)methyl)-2,3-dihydro-1H-1λ4-benzo[d]isothiazole 1-oxide (500 mg, 1.5 mmol, 1.0 equiv.) in MeOH (7.5 mL). The reaction mixture was stirred for 2 h and then concentrated under vacuum to give 100 mg of 6-((dimethylamino)methyl)-1-imino-2,3-dihydro-1H-1λ4-benzo[d]isothiazole 1-oxide as a yellow oil, which was used in the next step directly without additional purification. MS-ESI: 226.1 (M+1).

Scheme 32

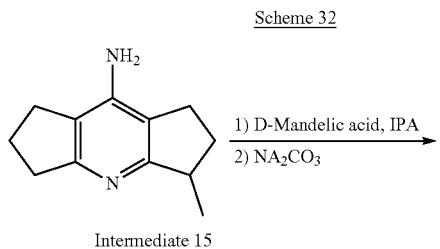

Intermediate 15

Intermediate 43

Intermediate 43

(R)-3-methyl-1,2,3,5,6,7-hexahydrodicyclopenta[b,e]pyridin-8-amine

A solution of 3-methyl-1,2,3,5,6,7-hexahydrodicyclopenta[b,e]pyridin-8-amine (47 g, 250 mmol, 1.0 equiv.) in isopropyl alcohol (423 mL) was heated to 80° C. and stirred for 0.5 h. After cooling to 50° C., the solution was filtered at that temperature though a Buchner funnel to remove insoluble impurities. The solid was washed with isopropyl alcohol (3×10 mL). The combined filtrate was concentrated to around 380 mL, then it was heated 80° C. and a solution of (R)-(−)-Mandelic acid (38 g, 250 mmol, 1.0 equiv.) in isopropyl alcohol (188 mL) was added dropwise at that temperature. The resulting mixture was stirred for 5 min at 80° C. and cooled in 5° C. steps and a small amount of the seed crystals of the product was added. If the seed dissolved, above operation was repeated. When the system was cooled to 65° C., the seed was undissolved and crystals started to grow, the system turned to cloudy slowly. The solution was stirred for 30 minutes at this temperature. From then on, the solution was stirred and maintained for 30 minutes, while the temperature was cooled in 5° C. steps until the system temperature was 40° C. Then the heating switch of oil bath was turned off and the mixture was allowed to slowly cool to 28° C. After 16 h, the ee value of solid was monitored (96% ee). The solid was collected by filtration. The resulting solid was slurried in isopropyl alcohol (180 mL) for 1 h and filtered again. The filtrate was decanted, and the precipitate was washed with HPLC grade isopropyl alcohol (30 mL) to give 35 g of the (R)-(−)-Mandelic acid salt of the title compound. The resulting solid was dissolved in water (420 mL) and concentrated to afford 29.2 g white solid (KF=5.1%), which was free-based by dissolving in aqueous $Na_2CO_3$ (4 M, 500 mL). Then the mixture was extracted with ethyl acetate and the combined organic layers were washed with brine, dried over anhydrous $Na_2SO_4$ and concentrated under vacuum to give 14.3 g of (R)-3-methyl-1,2,3,5,6,7-hexahydrodicyclopenta[b,e]pyridin-8-amine. MS-ESI 189.1 (M+1).

Example 1 Synthesis of Compound 129, 129b, and 129a

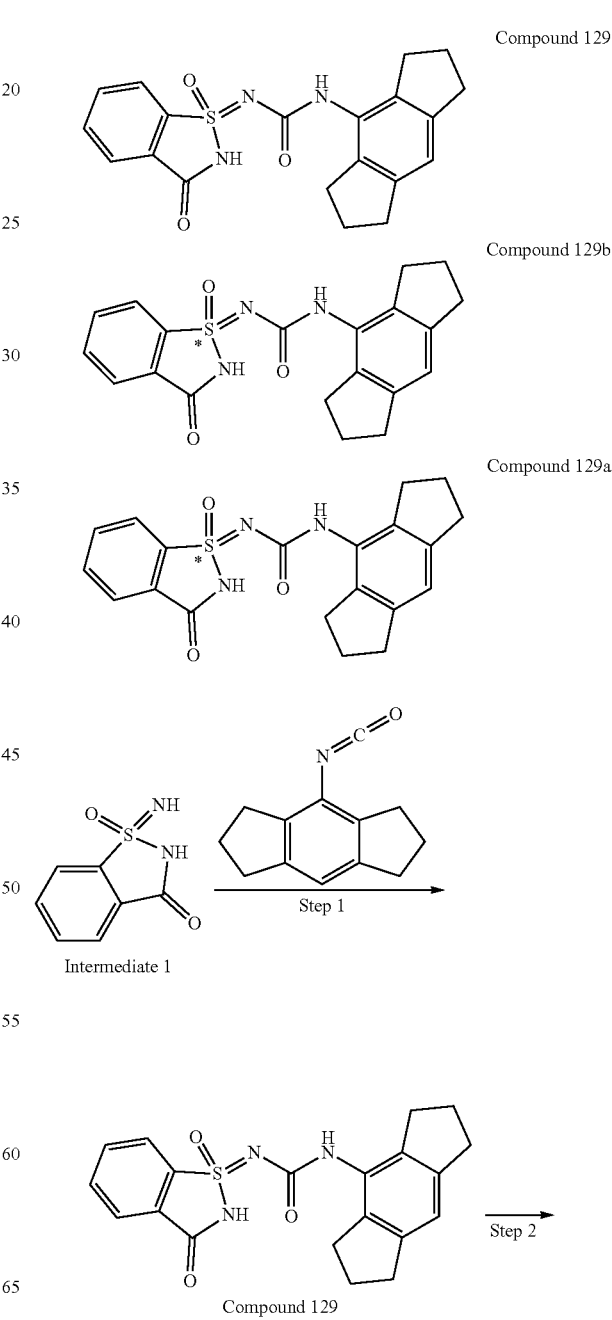

-continued

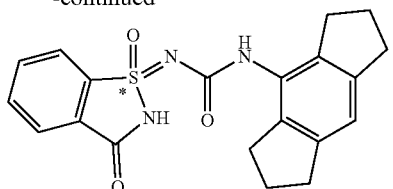

Compound 129b

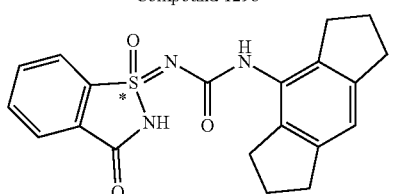

Compound 129a

Step 1: N-(1,3-dioxo-2,3-dihydro-1-$^\lambda$-6,2-benzothiazol-1-ylidene)-1-[(1,2,3,5,6,7-hexahydro-S-indacen-4-yl)imino]formamide Into a 50 mL round-bottom flask purged and maintained with an inert atmosphere of nitrogen, was placed 1-imino-2,3-dihydro-1-, -6,2-benzothiazole-1,3-dione (100 mg, 0.55 mmol, 1 equiv.) in THE (10 mL). To this was added NaH (26.34 mg, 1.10 mmol, 2 equiv.) with stirring at 0° C. To the mixture was added 4-isocyanato-1,2,3,5,6,7-hexahydro-s-indacene (164 mg, 0.82 mmol, 1.50 equiv.), batchwise within 10 mins at 0° C. The resulting solution was stirred overnight at ambient temperature. The reaction was quenched by the addition of water. The resulting solution was extracted with ethyl acetate and the organic layers combined, dried over anhydrous sodium sulfate and concentrated under vacuum. The residue was purified with Flash-Prep-HPLC with the following conditions (IntelFlash-1): Column, C18 silica gel; mobile phase, MeCN/H$_2$O=10/90 increasing to MeCN/H$_2$O=90/10 within 1 h; Detector, UV254. This resulted in 94 mg of N-(1,3-dioxo-2,3-dihydro-1-$^\lambda$-6,2-benzothiazol-1-ylidene)-1-[(1,2,3,5,6,7-hexahydro-s-indacen-4-yl)imino]formamide as a solid. MS-ESI: 382.0 (M+1). 1HNMR: (300 MHz, Methanol-d4) δ: 8.17-8.16 (m, 1H), 7.81-7.80 (m, 1H), 7.71-7.67 (m, 2H), 6.88 (s, 1H), 2.89-2.83 (m, 4H), 2.83-2.77 (m, 4H), 2.03-1.95 (m, 4H).

Step 2: 3-[(1S or 1R)-1,3-dioxo-2,3-dihydro-1-$^\lambda$-6,2-benzothiazol-1-ylidene]-1-(1,2,3,5,6,7-hexahydro-s-indacen-4-yl)urea (front peak, Compound 129b) and 3-[(1R or 1S)-1,3-dioxo-2,3-dihydro-1-$^\lambda$-6,2-benzothiazol-1-ylidene]-1-(1,2,3,5,6,7-hexahydro-s-indacen-4-yl)urea (second peak, Compound 129a)

The racemic 3-(1,3-dioxo-2,3-dihydro-1-$^\lambda$-6,2-benzothiazol-1-ylidene)-1-(1,2,3,5,6,7-hexahydro-s-indacen-4-yl)urea (80 mg) was purified by Prep-Chiral-HPLC with the following conditions Column: chiralpak AS-H, 2*25 cm (Sum); Mobile Phase A:CO2:80, Mobile Phase B: MEOH (2 mM NH$_4$OH-MEOH):20; Flow rate: 50 mL/min; 220 nm; RT1:4.38; RT2:6.5. This resulted in 19 mg of 3-[(1S or 1R)-1,3-dioxo-2,3-dihydro-1-$^\lambda$-6,2-benzothiazol-1-ylidene]-1-(1,2,3,5,6,7-hexahydro-s-indacen-4-yl)urea (front peak, 129b) as a white solid and 16 mg of 3-[(1R or 1S)-1,3-dioxo-2,3-dihydro-1-$^\lambda$-6,2-benzothiazol-1-ylidene]-1-(1,2,3,5,6,7-hexahydro-s-indacen-4-yl)urea (second peak, 129a) as a white solid.

Compound 129b: MS-ESI: 382.0 (M+1). 1H NMR: (300 MHz, DMSO-d$_6$) δ: 8.08-8.06 (m, 2H), 7.84-7.63 (m, 2H), 7.83-7.62 (br s, 1H), 6.82 (s, 1H), 2.78-2.73 (m, 4H), 2.68-2.63 (m, 4H), 1.95-1.90 (m, 4H).

Compound 129a: MS-ESI 382.0 (M+1). 1H NMR: (300 MHz, DMSO-d$_6$) δ: 8.08-8.05 (m, 2H), 7.60-7.58 (m, 2H), 7.60-7.58 (br s, 1H), 6.81 (s, 1H), 2.78-2.76 (m, 4H), 2.68-2.64 (m, 4H), 1.97-1.88 (m, 4H).

Example 2 Synthesis of Compounds 130, 130b, and 130a

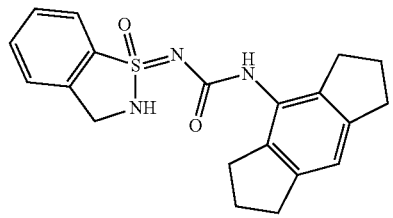

Compound 130

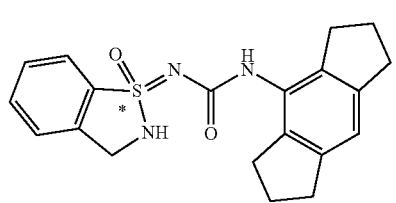

Compound 130a

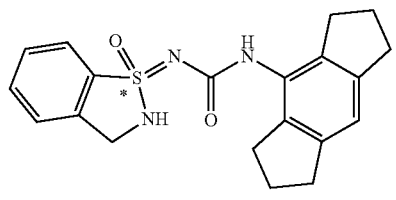

Compound 130b

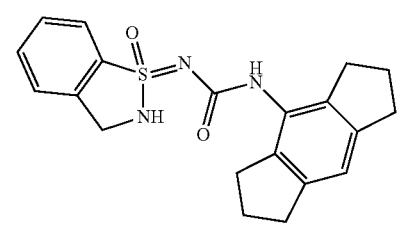

Compound 129

Step 1 →

Compound 130

Step 2 →

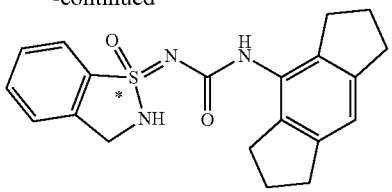

Compound 130a

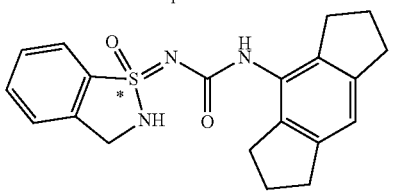

Compound 130b

Step 1: 1-(1,2,3,5,6,7-hexahydro-s-indacen-4-yl)-3-(1-oxo-2,3-dihydro-1-$\lambda$-6,2-benzothiazol-1-ylidene) urea Into a 50 mL round-bottom flask, was placed 3-(1,3-dioxo-2,3-dihydro-1-$\lambda$-6,2-benzothiazol-1-ylidene)-1-(1,2,3,5,6,7-hexahydro-s-indacen-4-yl)urea (100 mg, 0.262 mmol, 1 equiv) in THF (2 mL). $BH_3$-THF (112.65 mg, 1.311 mmol, 5 equiv) was added. The resulting solution was stirred for overnight at ambient temperature. The reaction was then quenched by the addition of water. The resulting solution was extracted with ethyl acetate and the organic layers combined, dried over anhydrous sodium sulfate and concentrated under vacuum. The crude product was purified by Prep-HPLC with the following conditions: Column: XBridge Prep OBD C18 Column Sum; Mobile Phase A: Water (10 MMOL/L $NH_4HCO_3$), Mobile Phase B: ACN; Flow rate: 60 mL/min; Gradient: 15% B to 70% B in 7.5 min; 210/254 nm; Rt: 7.15 min. This resulted in 5 mg (5.19%) of 1-(1,2,3,5,6,7-hexahydro-s-indacen-4-yl)-3-(1-oxo-2,3-dihydro-1-$\lambda$-6,2-benzothiazol-1-ylidene)urea as a white solid. MS-ESI: 368.0 (M+1). 1H NMR: (300 MHz, Methanol-d4) δ: 7.94 (d, 1H), 7.70-7.52 (m, 3H), 6.88 (s, 1H), 4.71-4.60 (m, 2H), 2.83-2.68 (m, 9H), 2.03-1.95 (m, 4H).

Step 2: 1-(1,2,3,5,6,7-hexahydro-s-indacen-4-yl)-3-[(1S or 1R)-1-oxo-2,3-dihydro-1-$\lambda$-6,2-benzothiazol-1-ylidene]urea (front peak, 130a) and 1-(1,2,3,5,6,7-hexahydro-s-indacen-4-yl)-3-[(1R or 1S)-1-oxo-2,3-dihydro-1-$\lambda$-6,2-benzothiazol-1-ylidene]urea (second peak, 130b)

The racemic 1-(1,2,3,5,6,7-hexahydro-s-indacen-4-yl)-3-(1-oxo-2,3-dihydro-1-$\lambda$-6,2-benzothiazol-1-ylidene)urea (100 mg) was purified by Prep-Chiral-HPLC with the following conditions: Column: CHIRALPAK IA, 2*25 cm, 5 um; Mobile Phase A: Hex (8 mmol/L $NH_3$·MeOH)—HPLC, Mobile Phase B: EtOH—HPLC; Flow rate: 20 mL/min; Gradient: 30 B to 30 B in 15 min; 254/220 nm; RT1:9.365; RT2:11.63. This resulted in 50 mg of 1-(1,2,3,5,6,7-hexahydro-s-indacen-4-yl)-3-[(1S or 1R)-1-oxo-2,3-dihydro-1-$\lambda$-6,2-benzothiazol-1-ylidene]urea (front peak, 130a) as a white solid and 48 mg of 1-(1,2,3,5,6,7-hexahydro-s-indacen-4-yl)-3-[(1R or 1S)-1-oxo-2,3-dihydro-1-$\lambda$-6,2-benzothiazol-1-ylidene]urea (second peak, 130b) as a white solid.

Compound 130a: MS-ESI 368.1 (M+1). 1HNMR: (300 MHz, DMSO-$d_6$) δ: 8.51 (br s, 1H), 8.19 (s, 1H), 7.88 (d, 1H), 7.69-7.67 (m, 1H), 7.61-7.55 (m, 2H), 6.84 (s, 1H), 4.54-4.52 (m, 2H), 2.77-2.75 (m, 4H), 2.61-2.59 (m, 4H), 1.92-1.87 (m, 4H)

Compound 130b: MS-ESI 382.0 (M+1). 1H NMR: (300 MHz, DMSO-$d_6$) δ: 8.45 (br s, 1H), 8.17 (s, 1H), 7.86 (d, 1H), 7.69-7.64 (m, 1H), 7.58-7.53 (m, 2H), 6.82 (s, 1H), 4.53-4.51 (m, 2H), 2.73-2.71 (m, 4H), 2.59-2.57 (m, 4H), 1.89-1.85 (m, 4H)

Example 3 Synthesis of Compounds 127, 127b and 127a

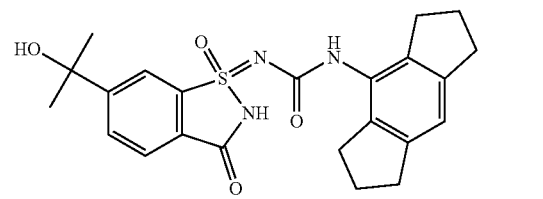

Compound 127

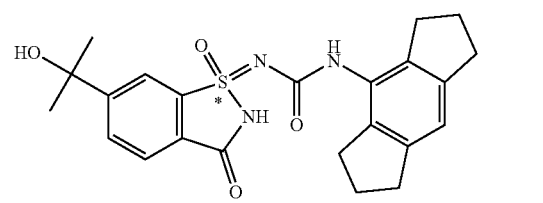

Compound 127b

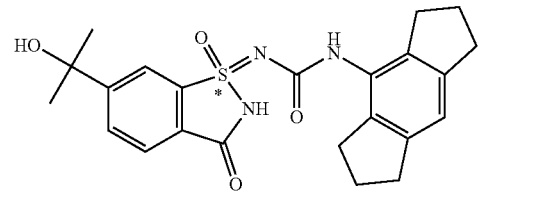

Compound 127a

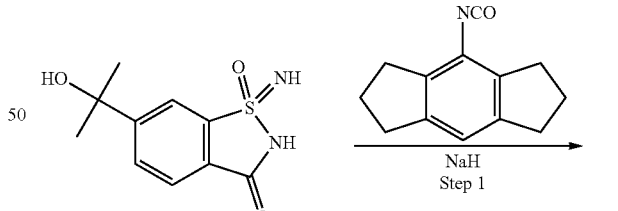

Intermediate 2

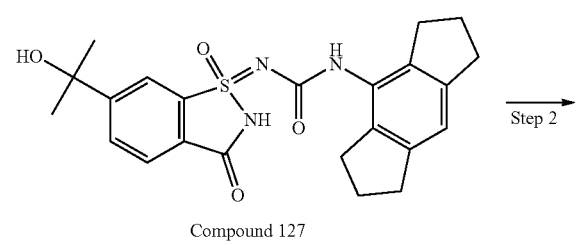

Compound 127

-continued

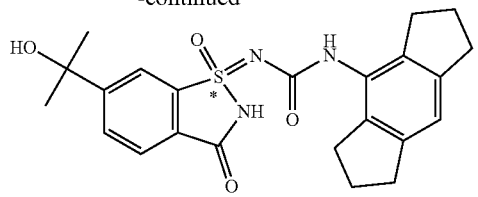

Compound 127b

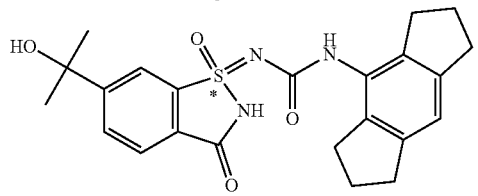

Compound 127a

Step 1: 1-(1,2,3,5,6,7-hexahydro-s-indacen-4-yl)-3-[6-(2-hydroxypropan-2-yl)-1,3-dioxo-2,3-dihydro-1-$^\lambda$-6,2-benzothiazol-1-ylidene]urea Into a 50 mL round-bottom flask, was placed 6-(2-hydroxypropan-2-yl)-1-imino-2,3-dihydro-1-$^\lambda$-6,2-benzothiazole-1,3-dione (250 mg, 1.0 mmol, 1 equiv) and NaH (125 mg, 60%, 3.1 mmol, 3.00 equiv.) in THF (10 mL). To the solution was added 4-isocyanato-1,2,3,5,6,7-hexahydro-s-indacene (249 mg, 1.3 mmol, 1.2 equiv.). The resulting solution was stirred for 2 h at 25° C. The reaction was then quenched by the addition of 3 mL of MeOH. The resulting mixture was concentrated under vacuum. The crude product was purified by Prep-HPLC with the following conditions: Column: XBridge Prep OBD C18 Column 30×150 mm Sum; Mobile Phase A:Water (10 MMOL/L NH4HCO3), Mobile Phase B: ACN; Flow rate: 60 mL/min; Gradient: 14% B to 45% B in 7 min; 254/210 nm; Rt: 6.05 min. This resulted in 7 mg (1.5%) of 1-(1,2,3,5,6,7-hexahydro-s-indacen-4-yl)-3-[6-(2-hydroxypropan-2-yl)-1,3-dioxo-2,3-dihydro-1-$^\lambda$-6,2-benzothiazol-1-ylidene]urea as a white solid. MS-ESI: 440.2 (M+1). 1H NMR: (400 MHz, Methanol-d4) δ: 8.28 (s, 1H), 7.90 (d, 1H), 7.78 (d, 1H), 6.89 (s, 1H), 2.84-2.71 (m, 8H), 2.03-1.96 (m, 4H), 1.57 (s, 6H).

Step 2: (S or R)-1-(1,2,3,5,6,7-hexahydro-s-indacen-4-yl)-3-(6-(2-hydroxypropan-2-yl)-1-oxido-3-oxo-2,3-dihydro-1l4-benzo[d]isothiazol-1-ylidene)urea and (R or S)-1-(1,2,3,5,6,7-hexahydro-s-indacen-4-yl)-3-(6-(2-hydroxypropan-2-yl)-1-oxido-3-oxo-2,3-dihydro-1l4-benzo[d]isothiazol-1-ylidene)urea The racemate was purified by Chiral-Prep-HPLC with the following conditions: Column: CHIRALPAK IC, 2*25 cm, 5 um; Mobile Phase A:MTBE (0.2% IPA)—HPLC, Mobile Phase B: MeOH—HPLC; Flow rate: 20 mL/min; Gradient: 20 B to 20 B in 15 min; 220/254 nm; RT 1:7.086; RT2: 10.527. This resulted in 6 mg of (S or R)-1-(1,2,3,5,6,7-hexahydro-s-indacen-4-yl)-3-(6-(2-hydroxypropan-2-yl)-1-oxido-3-oxo-2,3-dihydro-1l4-benzo[d]isothiazol-1-ylidene)urea (front peak, Compound 127b) as a white solid and 6 mg of (R or S)-1-(1,2,3,5,6,7-hexahydro-s-indacen-4-yl)-3-(6-(2-hydroxypropan-2-yl)-1-oxido-3-oxo-2,3-dihydro-1l4-benzo[d]isothiazol-1-ylidene)urea (second peak, Compound 127a) as a white solid.

Compound 127b: MS-ESI: 440.2 (M+1). 1H NMR: (400 MHz, Methanol-d4) δ: 8.29 (s, 1H), 7.86 (d, 1H), 7.74 (d, 1H), 6.88 (s, 1H), 2.84-2.70 (m, 8H), 2.03-1.96 (m, 4H), 1.57 (s, 6H).

Compound 127a: MS-ESI: 440.2 (M+1). 1H NMR: (400 MHz, Methanol-d4) δ: 8.29 (s, 1H), 7.86 (d, 1H), 7.74 (d, 1H), 6.88 (s, 1H), 2.84-2.70 (m, 8H), 2.03-1.96 (m, 4H), 1.57 (s, 6H).

Example 4 Synthesis of Compound 126

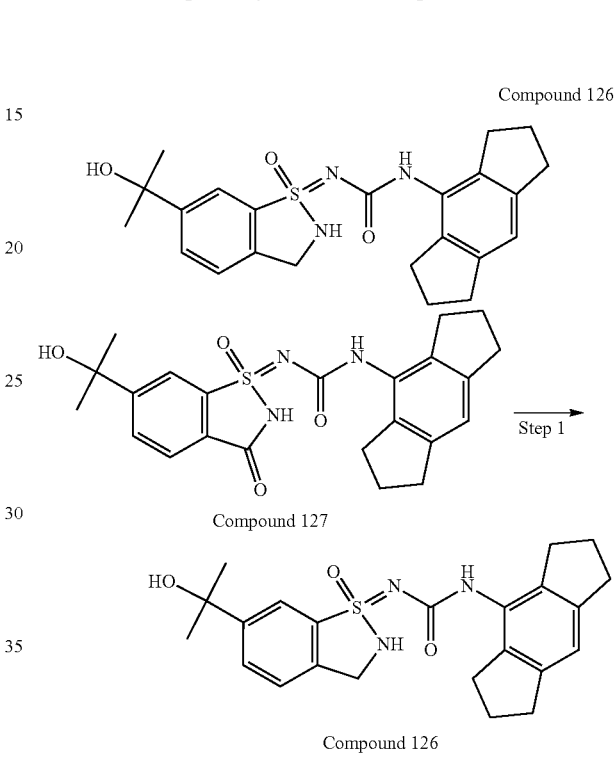

Compound 126

Step 1: 1-(1,2,3,5,6,7-hexahydro-s-indacen-4-yl)-3-[6-(2-hydroxypropan-2-yl)-1-oxo-2,3-dihydro-1-$^\lambda$-6,2-benzothiazol-1-ylidene]urea Into a 50 mL round-bottom flask purged and maintained with an inert atmosphere of nitrogen, was placed 1-(1,2,3,5,6,7-hexahydro-s-indacen-4-yl)-3-[6-(2-hydroxypropan-2-yl)-1,3-dioxo-2,3-dihydro-1-$^\lambda$-6,2-benzothiazol-1-ylidene]urea (5 mg, 0.01 mmol, 1 equiv.) in THE (3 mL). To the solution was added BH$_3$-THF (0.11 mL, 1M, 0.11 mmol, 10 equiv.). The resulting solution was stirred for 2 h at 50° C. The reaction was then quenched by the addition of 3 mL of conc. HCl. The resulting mixture was concentrated. The crude product was purified by Prep-HPLC with the following conditions: Column: XBridge Prep OBD C18 Column 30×150 mm Sum; Mobile Phase A:Water (10 mMol NH$_4$HCO$_3$), Mobile Phase B: ACN; Flow rate: 60 mL/min; Gradient: 10% B to 65% B in 7.5 min; 254/210 nm; Rt: 7.13 min. This resulted in 2.9 mg (56.91%) of 1-(1,2,3,5,6,7-hexahydro-s-indacen-4-yl)-3-[6-(2-hydroxypropan-2-yl)-1-oxo-2,3-dihydro-1-$^\lambda$-6,2-benzothiazol-1-ylidene]urea as a white solid. MS-ESI: 426.2 (M+1). 1H NMR: (400 MHz, Methanol-d4) δ: 8.28 (s, 1H), 7.89 (d, 1H), 7.78 (d, 1H), 6.89 (s, 1H), 2.84-2.69 (m, 8H), 2.03-1.96 (m, 4H), 1.57 (s, 6H).

Example 5 Synthesis of Compound 128

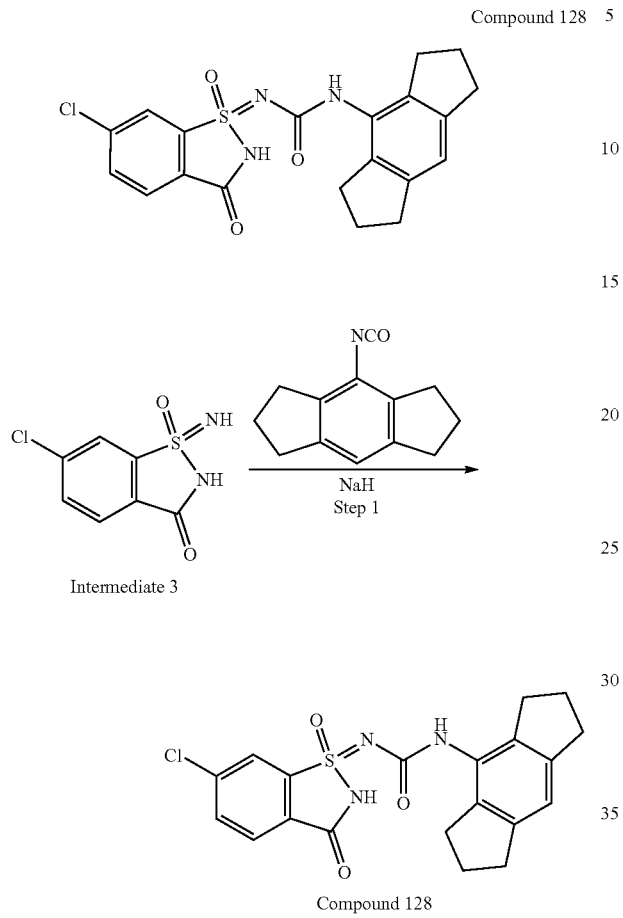

Step 1: 3-(6-chloro-1,3-dioxo-2,3-dihydro-1-$^\lambda$-6,2-benzothiazol-1-ylidene)-1-(1,2,3,5,6,7-hexahydro-s-indacen-4-yl)urea Into a 50 mL round-bottom flask, was placed 6-chloro-1-imino-1,2-dihydro-3H-1$^\lambda$4-benzo[d]isothiazol-3-one 1-oxide (44 mg, 0.20 mmol, 1 equiv.) in THF (7 mL). To the solution was added NaH (24 mg, 60%, 0.61 mmol, 3.00 equiv.), after stilled for 0.5 h, 4-isocyanato-1,2,3,5,6,7-hexahydro-s-indacene (48.56 mg, 0.24 mmol, 1.20 equiv.) was added. The resulting solution was stirred for 2 h at 25° C. The reaction was then quenched by the addition of 5 mL of CH$_3$OH. The resulting mixture was concentrated. The crude product was purified by Prep-HPLC with the following conditions: Column: XBridge Prep C18 OBD Column 19×150 mm Sum; Mobile Phase A: Water (10 MMOL/L NH$_4$HCO$_3$+0.1% NH$_3$.H$_2$O), Mobile Phase B: ACN; Flow rate: 25 mL/min; Gradient: 23% B to 42% B in 8 min 254/210 nm; Rt: 7.83 min. This resulted in 1.7 mg (2.01%) of 3-(6-chloro-1,3-dioxo-2,3-dihydro-1-1-6,2-benzothiazol-1-ylidene)-1-(1,2,3,5,6,7-hexahydro-s-indacen-4-yl)urea as a white solid. MS-ESI: 416.1 (M+1). 1H NMR: (400 MHz, Methanol-d4) δ: 8.19 (s, 1H), 7.77-7.68 (m, 2H), 6.891 (s, 1H), 2.85-2.72 (m, 8H), 2.05-1.98 (m, 4H).

Example 6 Synthesis of Compound 125

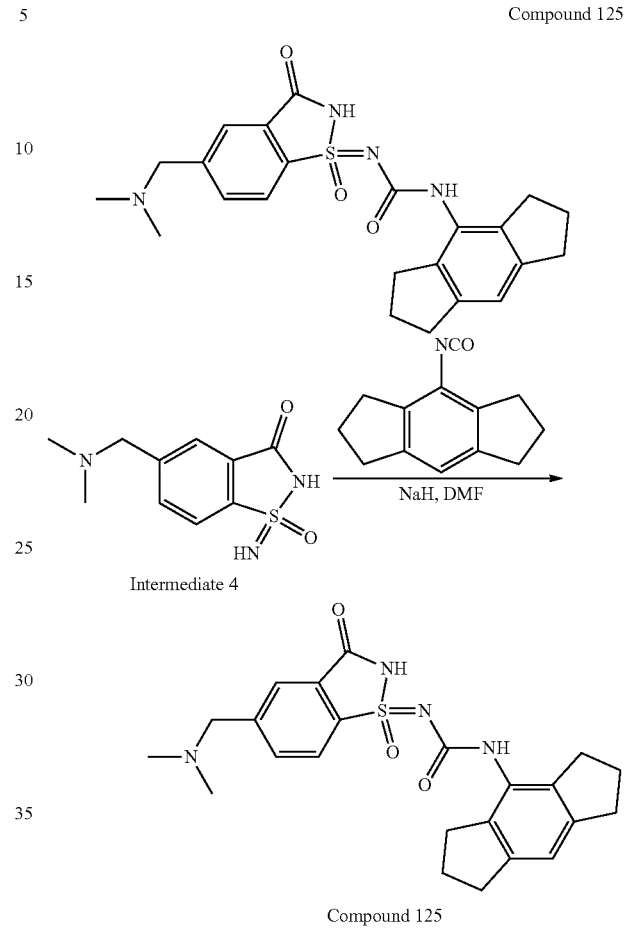

Step 1: 1-{5-[(dimethylamino)methyl]-1,3-dioxo-2,3-dihydro-1$16,2-benzothiazol-1-ylidene}-3-(1,2,3,5,6,7-hexahydro-s-indacen-4-yl)urea Into a 50 mL round-bottom flask purged and maintained with an inert atmosphere of nitrogen, was placed a solution of 5-((dimethylamino)methyl)-1-imino-1,2-dihydro-3H-1l4-benzo[d]isothiazol-3-one 1-oxide (200 mg, 0.91 mmol, 1.0 equiv.) in DMF (10 mL). To the solution was added NaH (44 mg, 1.82 mmol, 2.0 equiv.). The resulting solution was stirred at ambient temperature for 0.5 h. To the solution was added 4-isocyanato-1,2,3,5,6,7-hexahydro-s-indacene (360 mg, 1.82 mmol, 2.0 equiv.). The resulting solution was stirred at ambient temperature overnight. The reaction was then quenched by the addition of 20 mL of water. The reaction was then concentrated and the crude product was purified by prep-HPLC with the following conditions (PREP_HPLC_MC4): Column: XBridge Prep C18 OBD Column 19×150 mm Sum; Mobile Phase A:Water (10 MMOL/L NH$_4$HCO$_3$+0.1% NH$_4$OH), Mobile Phase B: ACN; Flow rate: 25 mL/min; Gradient: 18% B to 40% B in 7 min; 254/210 nm; Rt: 5.53 min. That resulted in 22 mg of 1-{5-[(dimethylamino)methyl]-1,3-dioxo-2,3-dihydro-1$16, 2-benzothiazol-1-ylidene}-3-(1,2,3,5,6,7-hexahydro-s-indacen-4-yl)urea as a white solid. MS-ESI: 438.2 (M+1). 1H NMR: (300 MHz, Methanol-d4) δ: 8.15 (d, 1H), 8.12 (s, 1H), 7.82 (s, 1H), 7.68 (d, 1H), 6.84 (s, 1H), 4.33 (s, 2H), 2.78 (t, 4H), 2.71-2.61 (m, 10H), 1.97-1.90 (m, 4H).

Example 7 Synthesis of Compound 122

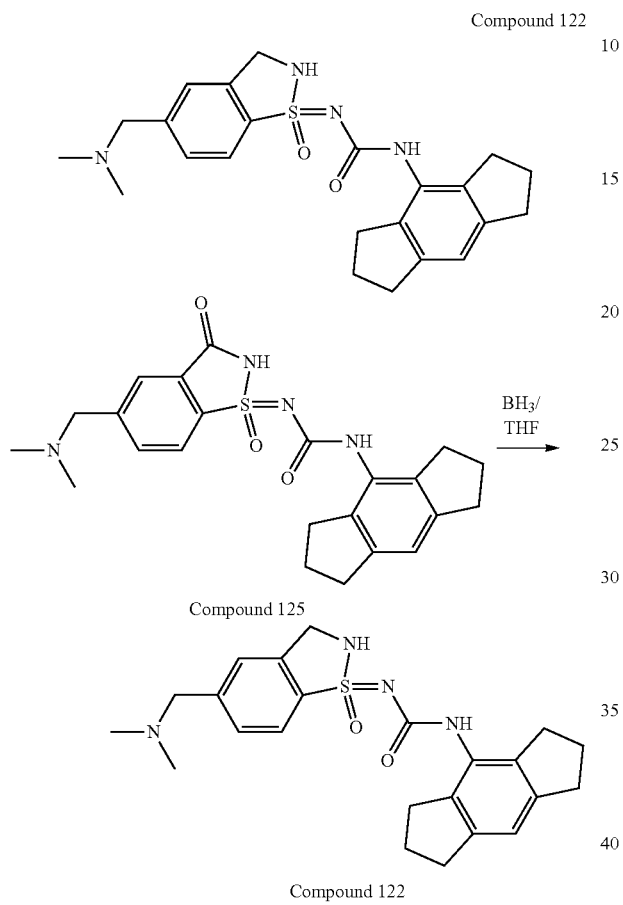

Step 1: 1-{5-[(dimethylamino)methyl]-1-oxo-2,3-dihydro-1$l6,2-benzothiazol-1-ylidene}-3-(1,2,3,5,6,7-hexahydro-s-indacen-4-yl)urea Into a 50 mL round-bottom flask purged and maintained with an inert atmosphere of nitrogen, was placed a solution of 1-(5-((dimethylamino)methyl)-1-oxido-3-oxo-2,3-dihydro-1l4-benzo[d]isothiazol-1-ylidene)-3-(1,2,3,5,6,7-hexahydro-s-indacen-4-yl)urea (100 mg, 0.23 mmol, 1.0 equiv.) in THF (1 mL). To the solution was added 2 M BH$_3$/THF (5 mL, 10 mmol, 43.7 equiv.). The resulting solution was stirred at 0° C. overnight. The reaction was then quenched by the addition of 1 mL of MeOH. The reaction was then concentrated and subjected to prep-HPLC. The crude product was purified by prep-HPLC with the following conditions (PREP_HPLC_MC4): Column: XBridge Prep C18 OBD Column 19×150 mm 5um; Mobile Phase A:Water (10 MMOL/L NH$_4$HCO$_3$+0.1% NH$_4$OH), Mobile Phase B: ACN; Flow rate: 25 mL/min; Gradient: 32% B to 60% B in 7 min; 254/210 nm; Rt: 7.02 min. That resulted in 5 mg of 1-{5-[(dimethylamino)methyl]-1-oxo-2,3-dihydro-1$l6,2-benzothiazol-1-ylidene}-3-(1,2,3,5,6,7-hexahydro-s- indacen-4-yl)urea. MS-ESI: 424.0 (M+1). 1H NMR: (300 MHz, DMSO-d$_6$) δ 8.57 (br s, 1H), 8.29 (s, 1H), 7.93 (d, 1H), 7.72-7.67 (m, 2H), 6.86 (s, 1H), 4.52 (d, 2H), 4.04 (s, 2H), 2.82-2.72 (m, 4H), 2.63-2.55 (m, 4H), 2.47 (s, 6H), 1.93-1.82 (m, 4H).

Example 8 Synthesis of Compound 124

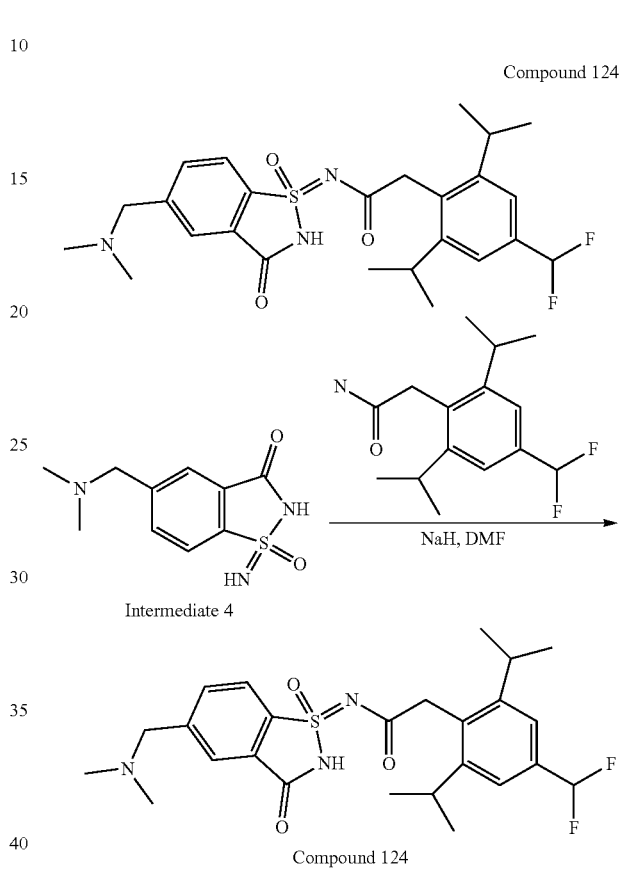

Step 1: 2-[4-(difluoromethyl)-2,6-bis(propan-2-yl)phenyl]-N-{5-[(dimethylamino)methyl]-1,3-dioxo-2,3-dihydro-1$l6,2-benzothiazol-1-ylidene}acetamide Into a 50 mL round-bottom flask purged and maintained with an inert atmosphere of nitrogen, was placed a solution of 5-((dimethylamino)methyl)-1-imino-1,2-dihydro-3H-1l4-benzo[d]isothiazol-3-one 1-oxide (200 mg, 0.84 mmol, 1.0 equiv.) in THF (5 mL). To the solution was added NaH (40 mg, 1.68 mmol, 2.0 equiv.). The resulting solution was stirred at ambient temperature for 0.5 h. To the solution was added 2-(4-(difluoromethyl)-2,6-diisopropylphenyl)acetyl chloride (0.84 mmol, 1.0 equiv.). The resulting solution was stirred at ambient temperature overnight. The reaction was then quenched by the addition of 1 mL of MeOH. The reaction was then concentrated and the crude product was purified by prep-HPLC with the following conditions (PREP_HPLC_MC4): Column: XBridge Prep C18 OBD Column 19×150 mm 5um; Mobile Phase A:Water (10 MMOL/L NH$_4$HCO$_3$+0.1% NH$_4$OH), Mobile Phase B: ACN; Flow rate: 25 mL/min; Gradient: 32% B to 60% B in 7 min; 254/210 nm; Rt: 7.02 min. That resulted in 30 mg of 2-[4-(difluoromethyl)-2,6-bis(propan-2-yl)phenyl]-N-{5-[(dimethylamino)methyl]-1,3-dioxo-2,3-dihydro-1$l6,2- benzothiazol-1-ylidene}acetamide. MS-ESI: 492.2 (M+1). 1H NMR: (400 MHz, DMSO-$d_6$) δ 9.68 (br s, 1H), 7.99 (d, 1H), 7.82 (s, 1H), 7.64 (d, 1H), 7.22 (s, 2H), 6.93 (t, 1H), 4.31 (s, 2H), 3.64-3.63 (m, 2H), 3.16 (p, 2H), 2.67 (s, 6H), 1.08-1.04 (m, 12H).

Example 9 Synthesis of Compound 123

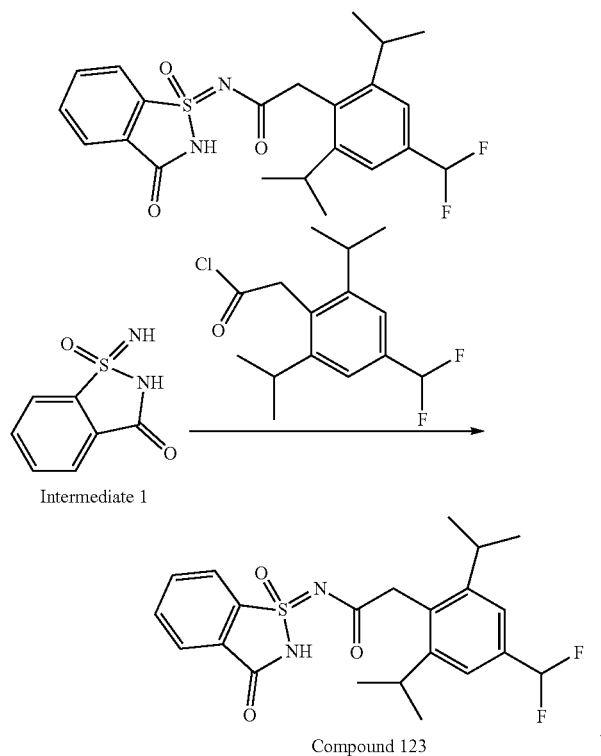

Compound 123

Step 1: 2-[4-(difluoromethyl)-2,6-bis(propan-2-yl)phenyl]-N-(1,3-dioxo-2,3-dihydro-1-$\lambda$-6,2-benzothiazol-1-ylidene)acetamide Into a 25 mL round-bottom flask, was placed 1-imino-2,3-dihydro-1-$\lambda$-6,2-benzothiazole-1,3-dione (100 mg, 0.55 mmol, 1 equiv), NaH (4.39 mg, 60%, 0.11 mmol, 0.2 equiv) in THF (15 mL), 2-(4-(difluoromethyl)-2,6-diisopropylphenyl)acetyl chloride (0.659 mmol, 1.2 equiv). The resulting solution was stirred for 2 h at 25° C. The resulting solution was extracted with 3×20 mL of ethyl acetate and the organic combined layers were concentrated under vacuum. The crude product was purified by Flash-Prep-HPLC with the following conditions (IntelFlash-1): Column, C18 silica gel; mobile phase, ACN/$H_2O$=0 increasing to ACN/$H_2O$=90 within 60 min; Detector, 254. This resulted in 120 mg (50.32%) of 2-[4-(difluoromethyl)-2,6-bis(propan-2-yl)phenyl]-N-(1,3-dioxo-2,3-dihydro-1-$\lambda$-6,2-benzothiazol-1-ylidene)acetamide as a white solid. MS-ESI: 435.0 (M+1). 1H NMR: (300 MHz, DMSO-$d_6$): 7.91 (d, 1H), 7.63-7.56 (m, 2H), 7.26-7.21 (m, 2H), 6.92 (s, 1H), 3.69 (s, 2H), 3.18-3.11 (m, 2H), 1.08-1.05 (m, 12H).

Example 10 Synthesis of Compound 115

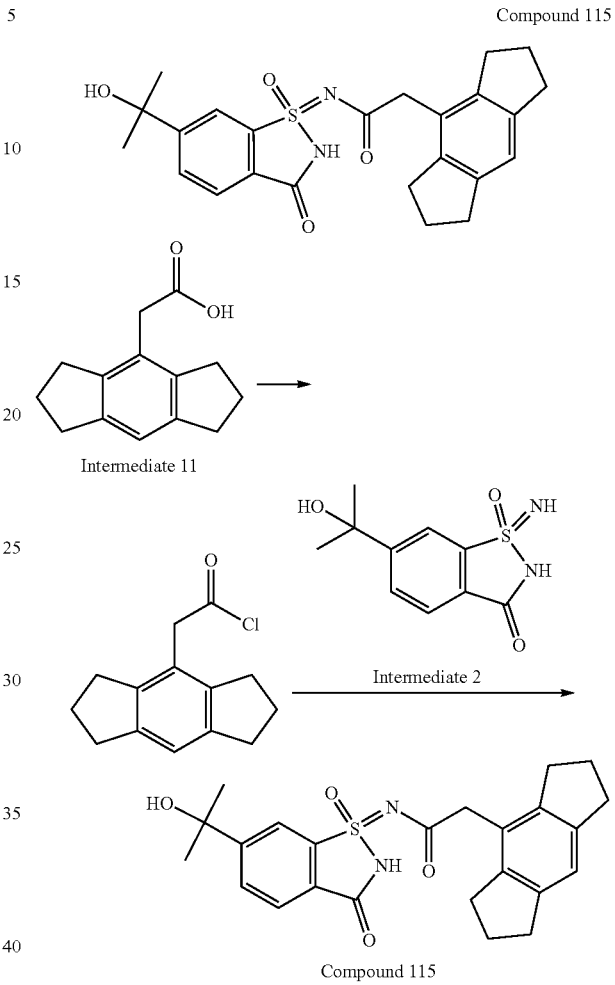

Compound 115

Step 1: 2-(1,2,3,5,6,7-hexahydro-s-indacen-4-yl)acetyl chloride

Into a 100 mL round-bottom flask, was placed a solution of 2-(1,2,3,5,6,7-hexahydro-s-indacen-4-yl)acetic acid (50 mg, 0.3 mmol, 1.0 equiv.) in DCM (5 mL). To the solution were added oxalyl dichloride (1.0 mL) and DMF (0.01 mL, cat.). The resulting solution was stirred for 2 h at ambient temperature. The resulting mixture was concentrated under vacuum and the resulting 2-(1,2,3,5,6,7-hexahydro-s-indacen-4-yl)acetyl chloride was used in the next step without further purification.

Step 2: 2-(1,2,3,5,6,7-hexahydro-s-indacen-4-yl)-N-(6-(2-hydroxypropan-2-yl)-1-oxido-3-oxo-2,3-dihydro-1l4-benzo[d]isothiazol-1-ylidene)acetamide Into a 100 mL round-bottom flask, was placed a solution of 6-(2-hydroxypropan-2-yl)-1-imino-1,2-dihydro-3H-14-benzo[d]isothiazol-3-one 1-oxide (50 mg, 0.2 mmol, 1.0 equiv.) and NaOH (25 mg, 0.6 mmol, 3.0 equiv.) in THF (5.0 mL). To the solution was added a solution of 2-(1,2,3,5,6, 7-hexahydro-s-indacen-4-yl)acetyl chloride (0.23 mmol, 1.1 equiv.) in THF (1.0 mL) at 0° C. The resulting solution was stirred for 2 h at ambient temperature. The resulting mixture was concentrated under vacuum. The resulting residue was purified by prep-HPLC with the following conditions (PRE-P_HPLC_MC4): Column: XBridge Prep C18 OBD Column 19×150 mm 5 um; Mobile Phase A:Water (10 mmol/L NH$_4$HCO$_3$+0.1% NH$_4$OH), Mobile Phase B: ACN; Flow rate: 25 mL/min; Gradient: 32% B to 60% B in 7 min; 254/210 nm; Rt: 7.02 min. This resulted in 5 mg of 2-(1,2,3,5,6,7-hexahydro-s-indacen-4-yl)-N-(6-(2-hydroxypropan-2-yl)-1-oxido-3-oxo-2,3-dihydro-1l4-benzo[d]isothiazol-1-ylidene)acetamide as a solid. MS-ESI: 439.2 (M+1); $^1$H NMR (400 MHz, Methanol-d4): 8.18 (d, 1H), 7.88 (dd, 1H), 7.77 (d, 1H), 6.89 (s, 1H), 3.64-3.50 (m, 2H), 3.32 (s, 2H), 2.79 (dt, 8H), 2.06-2.00 (m, 4H), 1.56 (s, 6H).

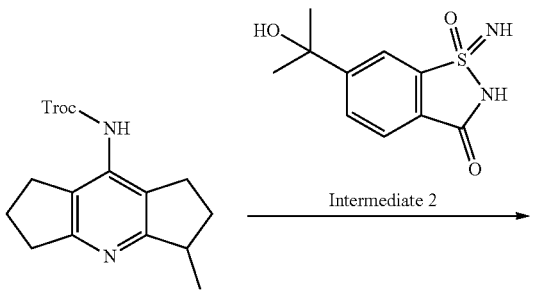

Intermediate 2

TABLE E2

Examples in the following table were prepared using similar conditions as described in Example 10 through the coupling of Intermediate 2 with respective coupling partner as noted in Table E2.

| Ex. # | Final Target # | Coupling Partner | Structure | IUPAC Name | Exact Mass [M + H]⁺ |
|---|---|---|---|---|---|
| 11 | 114 | Intermediate 13 | 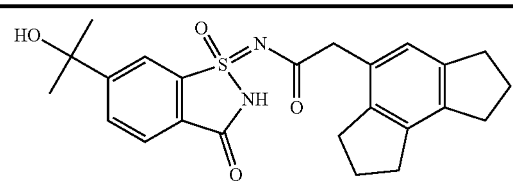 | 2-(1,2,3,6,7,8-hexahydro-as-indacen-4-yl)-N-(6-(2-hydroxypropan-2-yl)-1-oxido-3-oxo-2,3-dihydro-1l4-benzo[d]isothiazol-1-ylidene)acetamide | 439.2 |
| 12 | 104 | Intermediate 12 | 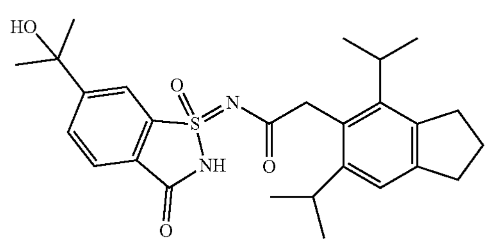 [SMILES: CC(C)c1cc2c(c(C(C)C)c1CC(=O)N=S1(=O)NC(=O)c3ccc(C(C)(C)O)cc31)CCC2] | 2-(4,6-diisopropyl-1,3-dihydroisobenzofuran-5-yl)-N-(6-(2-hydroxypropan-2-yl)-1-oxido-3-oxo-2,3-dihydro-1l4-benzo[d]isothiazol-1-ylidene)acetamide | 485.2 |

Example 13 Synthesis of Compound 120

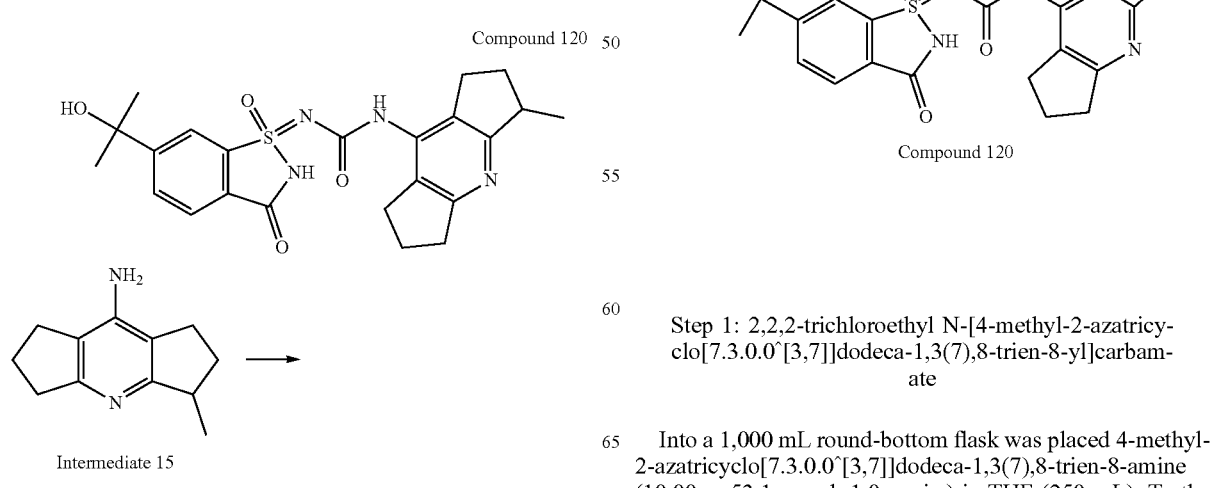

Step 1: 2,2,2-trichloroethyl N-[4-methyl-2-azatricyclo[7.3.0.0ˆ[3,7]]dodeca-1,3(7),8-trien-8-yl]carbamate Into a 1,000 mL round-bottom flask was placed 4-methyl-2-azatricyclo[7.3.0.0ˆ[3,7]]dodeca-1,3(7),8-trien-8-amine (10.00 g, 53.1 mmol, 1.0 equiv.) in THF (250 mL). To the solution were added DIEA (18.5 mL, 106.2 mmol, 2.0 equiv.) and 2,2,2-trichloroethyl carbonochloridate (22.5 g, 106.3 mmol, 2.0 equiv.). The resulting solution was stirred for 16 h at ambient temperature. The reaction was then quenched by the addition of 250 mL of water. The resulting solution was extracted with ethyl acetate, and the organic layer was dried over anhydrous sodium sulfate and concentrated. The residue was purified by silica gel chromatography, eluting with ethyl acetate/petroleum ether (1:5) to give 6.25 g of 2,2,2-trichloroethyl N-[4-methyl-2-azatricyclo[7.3.0.0^[3,7]]dodeca-1,3(7),8-trien-8-yl]carbamate as a yellow solid. MS-ESI: 349.1/351.1 (M+1).

Step 2: 1-(6-(2-hydroxypropan-2-yl)-1-oxido-3-oxo-2,3-dihydro-1l4-benzo[d]isothiazol-1-ylidene)-3-(3-methyl-1,2,3,5,6,7-hexahydrodicyclopenta[b,e]pyridin-8-yl)urea Into a 50 mL round-bottom flask, was placed 6-(2-hydroxypropan-2-yl)-1-imino-1,2-dihydro-3H-1l4-benzo[d]isothiazol-3-one 1-oxide (50 mg, 0.2 mmol, 1.0 equiv.) and NaH (60% wt in mineral oil, 25 mg, 0.6 mmol, 3.0 equiv.) in THF (5.0 mL). To the solution was added 2,2,2-trichloroethyl N-[4-methyl-2-azatricyclo[7.3.0.0^[3,7]]dodeca-1,3(7),8-trien-8-yl]carbamate (76 mg, 0.2 mmol, 1.0 equiv.). The resulting solution was stirred for 5 h at ambient temperature. The reaction was then quenched by the addition of MeOH. The resulting mixture was concentrated and the crude product was purified by Prep-HPLC with the following conditions: Column XBridge Shield RP18 OBD Column 19*250 mm, 10 um; Mobile Phase A: Water (10 mmol/L, NH$_4$HCO$_3$), Mobile Phase B: ACN; Flow rate: 25 mL/min; Gradient: 170% B to 24% B in 7 min; 210/254 nm; Rt: 5.95 min. This resulted in 7.5 mg (7.90%) of 1-(6-(2-hydroxypropan-2-yl)-1-oxido-3-oxo-2,3-dihydro-1l4-benzo[d]isothiazol-1-ylidene)-3-(3-methyl-1,2,3,5,6,7-hexahydrodicyclopenta[b,e]pyridin-8-yl)urea as a white solid. MS-ESI: 455.6 (M1); $^1$H NMR (400 MHz, Methanol-d4): 8.31 (s, 1H), 7.87 (d, 1H), 7.76 (d, 1H), 2.71-3.04 (m, 6H), 2.35-2.40 (m, 1H), 2.14-2.16 (m, 2H), 1.72-1.75 (m, 1H), 1.58 (s, 6H), 1.29-1.37 (m, 4H).

TABLE E3

Examples in the following table were prepared using similar conditions as described in Example 13 through the coupling of Intermediate 2 with respective coupling partner as noted in Table E3.

| Example # | Final Target Number | RHS | Structure | IUPAC Name | Exact Mass [M + H]$^+$ |
|---|---|---|---|---|---|
| 14 | 118 | Intermediate 16 | 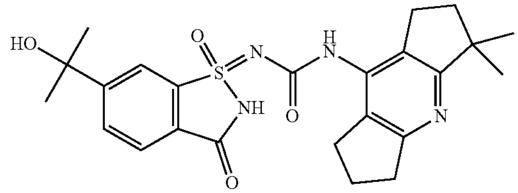 [SMILES: CC(C)(O)c1ccc2c(c1)S(=O)(=NC(=O)Nc1c3c(nc4c1CCC4(C)C)CCC3)NC2=O] | 1-(3,3-dimethyl-1,2,3,5,6,7-hexahydrodicyclopenta[b,e]pyridin-8-yl)-3-(6-(2-hydroxypropan-2-yl)-1-oxido-3-oxo-2,3-dihydro-1l4-benzo[d]isothiazol-1-ylidene)urea | 469.6 |
| 15 | 117 | Intermediate 14 | 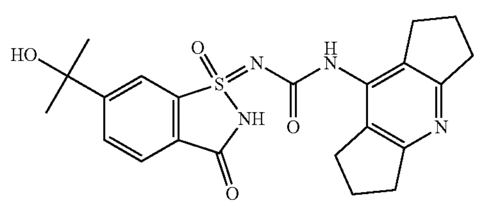 [SMILES: CC(C)(O)c1ccc2c(c1)S(=O)(=NC(=O)Nc1c3c(nc4c1CCC4)CCC3)NC2=O] | 1,2,3,5,6,7-hexahydrodicyclopenta[b,e]pyridin-8-yl)-3-(6-(2-hydroxypropan-2-yl)-1-oxido-3-oxo-2,3-dihydro-1l4-benzo[d]isothiazol-1-ylidene)urea | 441.2 |
| 16 | 112 | Intermediate 20 | 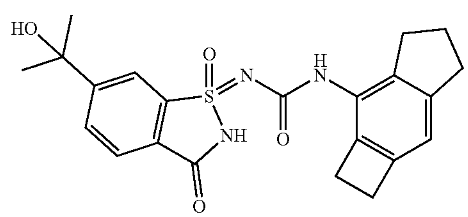 [SMILES: CC(C)(O)c1ccc2c(c1)S(=O)(=NC(=O)Nc1c3c(cc4c1CC4)CCC3)NC2=O] | 1-(6-(2-hydroxypropan-2-yl)-1-oxido-3-oxo-2,3-dihydro-1l4-benzo[d]isothiazol-1-ylidene)-3-(2,4,5,6-tetrahydro-1H-cyclobuta[f]inden-3-yl)urea | 426.1 |
| 17 | 108 | Intermediate 18 | 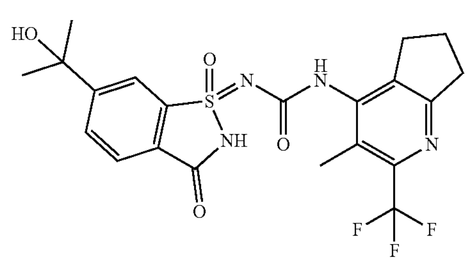 [SMILES: Cc1c(C(F)(F)F)nc2c(c1NC(=O)N=S1(=O)NC(=O)c3ccc(C(C)(C)O)cc31)CCC2] | 1-(6-(2-hydroxypropan-2-yl)-1-oxido-3-oxo-2,3-dihydro-1l4-benzo[d]isothiazol-1-ylidene)-3-(3-methyl-2-(trifluoromethyl)-6,7-dihydro-5H-cyclopenta[b]pyridin-4-yl)urea | 483.1 |

TABLE E3-continued

Examples in the following table were prepared using similar conditions as described in Example 13 through the coupling of Intermediate 2 with respective coupling partner as noted in Table E3.

| Example # | Final Target Number | RHS | Structure | IUPAC Name | Exact Mass [M + H]+ |
|---|---|---|---|---|---|
| 18 | 106 | Intermediate 19 | 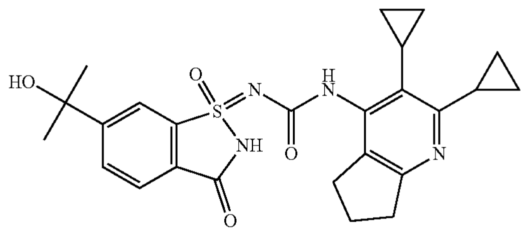 [SMILES: CC(C)(O)c1ccc2c(c1)S(=O)(=NC(=O)Nc1c3c(nc(C4CC4)c1C1CC1)CCC3)NC2=O] | 1-(2,3-dicyclopropyl-6,7-dihydro-5H-cyclopenta[b]pyridin-4-yl)-3-(6-(2-hydroxypropan-2-yl)-1-oxido-3-oxo-2,3-dihydro-1λ4-benzo[d]isothiazol-1-ylidene)urea | 481.6 |
| 19 | 105 | Intermediate 17 | 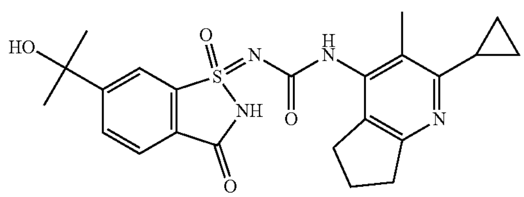 [SMILES: Cc1c(C2CC2)nc2c(c1NC(=O)N=S1(=O)NC(=O)c3ccc(C(C)(C)O)cc31)CCC2] | 1-(2-cyclopropyl-3-methyl-6,7-dihydro-5H-cyclopenta[b]pyridin-4-yl)-3-(6-(2-hydroxypropan-2-yl)-1-oxido-3-oxo-2,3-dihydro-1λ4-benzo[d]isothiazol-1-ylidene)urea | 455.2 |

Example 20 Synthesis of Compound 103

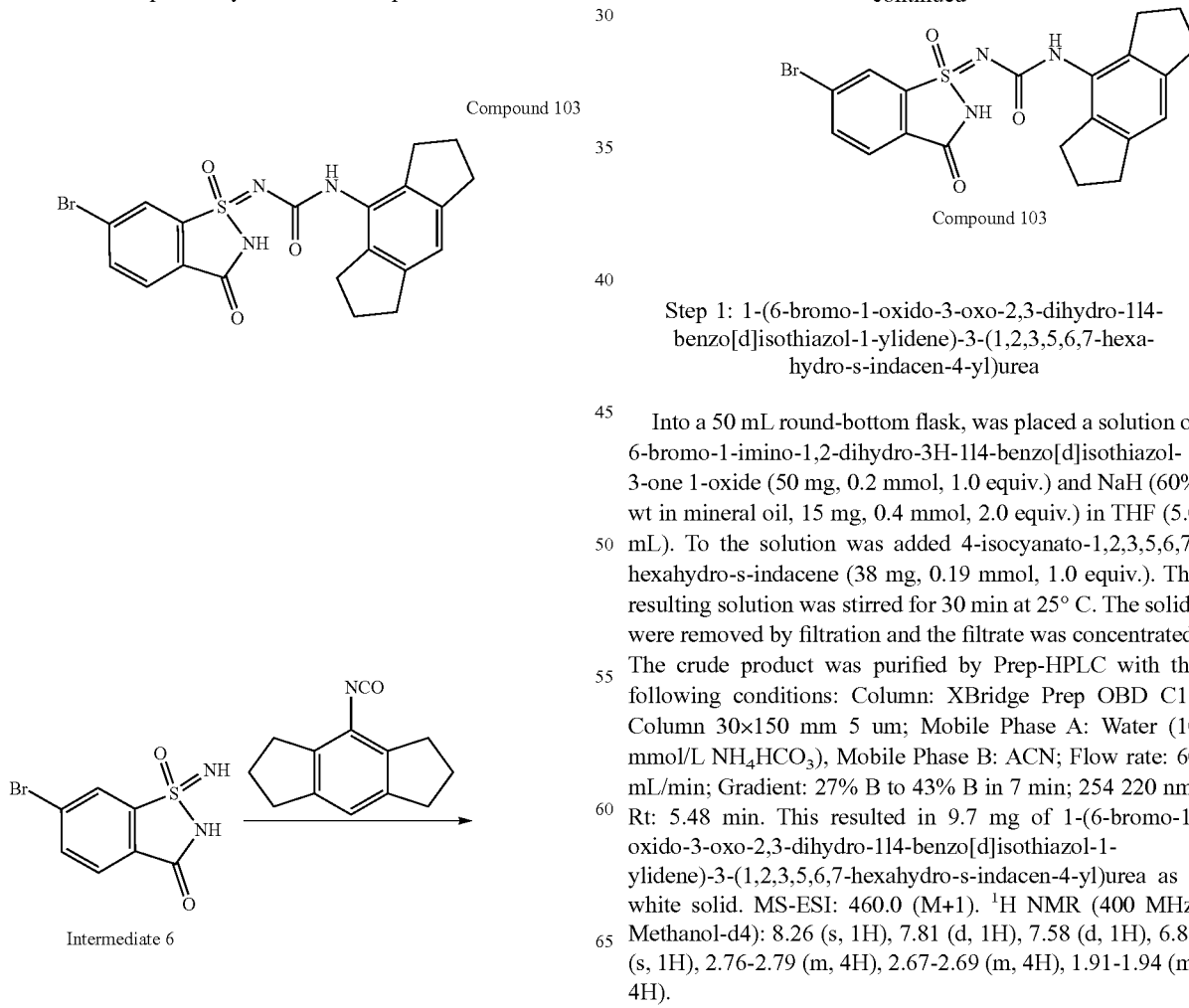

Step 1: 1-(6-bromo-1-oxido-3-oxo-2,3-dihydro-1λ4-benzo[d]isothiazol-1-ylidene)-3-(1,2,3,5,6,7-hexahydro-s-indacen-4-yl)urea Into a 50 mL round-bottom flask, was placed a solution of 6-bromo-1-imino-1,2-dihydro-3H-1λ4-benzo[d]isothiazol-3-one 1-oxide (50 mg, 0.2 mmol, 1.0 equiv.) and NaH (60% wt in mineral oil, 15 mg, 0.4 mmol, 2.0 equiv.) in THF (5.0 mL). To the solution was added 4-isocyanato-1,2,3,5,6,7-hexahydro-s-indacene (38 mg, 0.19 mmol, 1.0 equiv.). The resulting solution was stirred for 30 min at 25° C. The solids were removed by filtration and the filtrate was concentrated. The crude product was purified by Prep-HPLC with the following conditions: Column: XBridge Prep OBD C18 Column 30×150 mm 5 um; Mobile Phase A: Water (10 mmol/L NH$_4$HCO$_3$), Mobile Phase B: ACN; Flow rate: 60 mL/min; Gradient: 27% B to 43% B in 7 min; 254 220 nm; Rt: 5.48 min. This resulted in 9.7 mg of 1-(6-bromo-1-oxido-3-oxo-2,3-dihydro-1λ4-benzo[d]isothiazol-1-ylidene)-3-(1,2,3,5,6,7-hexahydro-s-indacen-4-yl)urea as a white solid. MS-ESI: 460.0 (M+1). $^1$H NMR (400 MHz, Methanol-d4): 8.26 (s, 1H), 7.81 (d, 1H), 7.58 (d, 1H), 6.85 (s, 1H), 2.76-2.79 (m, 4H), 2.67-2.69 (m, 4H), 1.91-1.94 (m, 4H).

Example 21 Synthesis of Compound 110

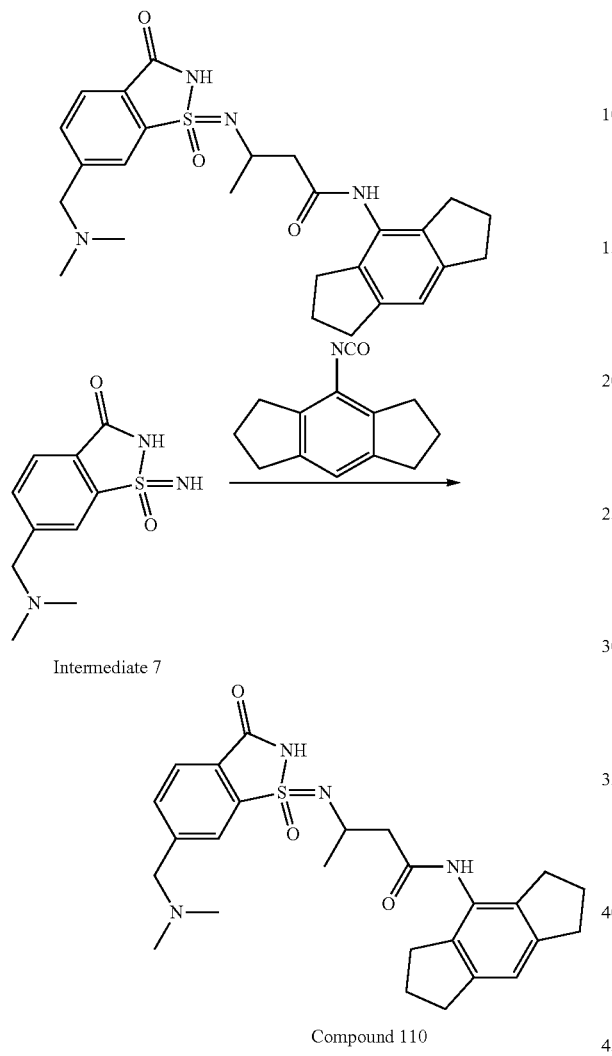

Step 1: 1-(6-((dimethylamino)methyl)-1-oxido-3-oxo-2,3-dihydro-1l4-benzo[d]isothiazol-1-ylidene)-3-(1,2,3,5,6,7-hexahydro-s-indacen-4-yl)urea Into a 50 mL round-bottom flask, was placed 6-((dimethylamino)methyl)-1-imino-1,2-dihydro-3H-1l4-benzo[d]isothiazol-3-one 1-oxide (100 mg, 0.4 mmol, 1.0 equiv.) in THF (5.0 mL). To the solution wad added NaH (60% wt in mineral oil, 50 mg, 1.25 mmol, 3.0 equiv.). This was followed by the addition of 4-isocyanato-1,2,3,5,6,7-hexahydro-s-indacene (83 mg, 0.4 mmol, 1.0 equiv.). The resulting solution was stirred for 4 h at ambient temperature and then quenched by the addition of 0.5 mL of water. The resulting mixture was concentrated and the residue was purified by Prep-HPLC with the following conditions: Column: XBridge Prep C18 OBD Column 19×150 mm Sum; Mobile Phase A: Water (10 MMOL/L NH$_4$HCO$_3$+0.1% NH$_4$OH), Mobile Phase B: ACN; Flow rate: 25 mL/min; Gradient: 16% B to 43% B in 7 min; 254/210 nm; Rt: 6.60 min. This resulted in 30 mg of 1-(6-((dimethylamino)methyl)-1-oxido-3-oxo-2,3-dihydro-1l4-benzo[d]isothiazol-1-ylidene)-3-(1,2,3,5,6,7-hexahydro-s-indacen-4-yl)urea as a white solid. MS-ESI: 439.2 (M+1).

$^1$H NMR (400 MHz, Methanol-d4): 9.73 (s, 1H), 8.28 (s, 1H), 8.14 (s, 1H), 7.71 (s, 2H), 6.82 (s, 1H), 4.40-4.45 (m, 2H), 2.78 (d, 2H), 2.75-2.78 (m, 6H), 2.66-2.69 (m, 8H), 1.88-1.92 (m, 4H).

Example 22 Synthesis of Compound 113

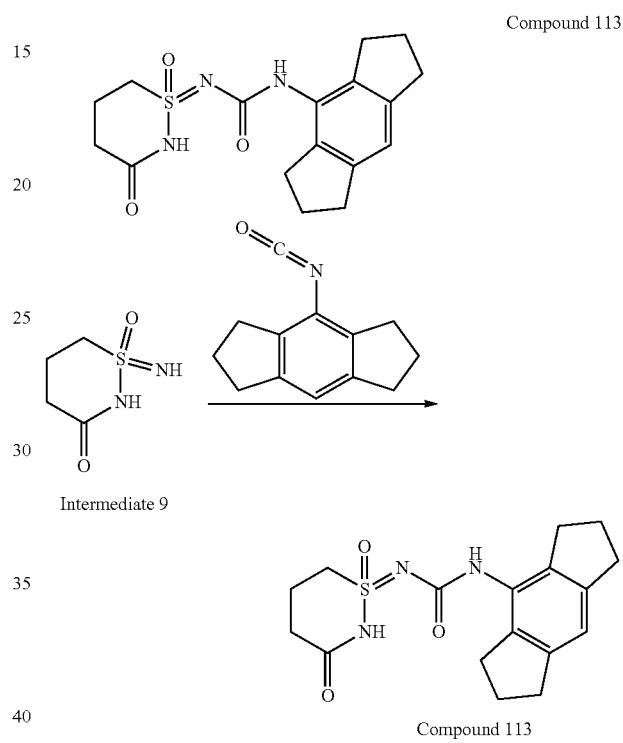

Step 1: 1-(1,2,3,5,6,7-hexahydro-s-indacen-4-yl)-3-(1-oxido-3-oxo-1l6,2-thiazinan-1-ylidene)urea Into a 50 mL round-bottom flask purged and maintained with an inert atmosphere of nitrogen, was placed 1-imino-1l6,2-thiazinan-3-one 1-oxide (63 mg, 0.5 mmol, 1.0 equiv.) and NaH (60% wt in mineral oil, 30 mg, 0.8 mmol, 1.6 equiv.) in THE (8 mL). To the solution was added 4-isocyanato-1,2,3,5,6,7-hexahydro-s-indacene (98 mg, 0.5 mmol, 1.1 equiv.). The resulting solution was stirred for 3 h at ambient temperature and then quenched by the addition of 0.2 mL of water. The resulting mixture was concentrated under vacuum and the residue was purified by Prep-HPLC with the following conditions: Column: XBridge Shield RP18 OBD Column 19*250 mm, 10 um; Mobile Phase A:Water (10 mmol/L NH$_4$HCO$_3$), Mobile Phase B: ACN; Flow rate: 25 mL/min; Gradient: 10% B to 25% B in 10 min; 210/254 nm; Rt: 10.33 min. This resulted in 5 mg of 1-(1,2,3,5,6,7-hexahydro-s-indacen-4-yl)-3-(1-oxido-3-oxo-1l6,2-thiazinan-1-ylidene)urea as a white solid. MS-ESI: 347.1 (M+1).

$^1$H NMR (400 MHz, Methanol-d4): 6.80 (s, 1H), 2.65-2.80 (m, 2H), 2.68-2.77 (m, 9H), 2.30 (s, 1H), 2.1 (t, 2H), 1.88-1.96 (t, 6H).

289

Example 23 Synthesis of Compound 131, 131b, and 131a

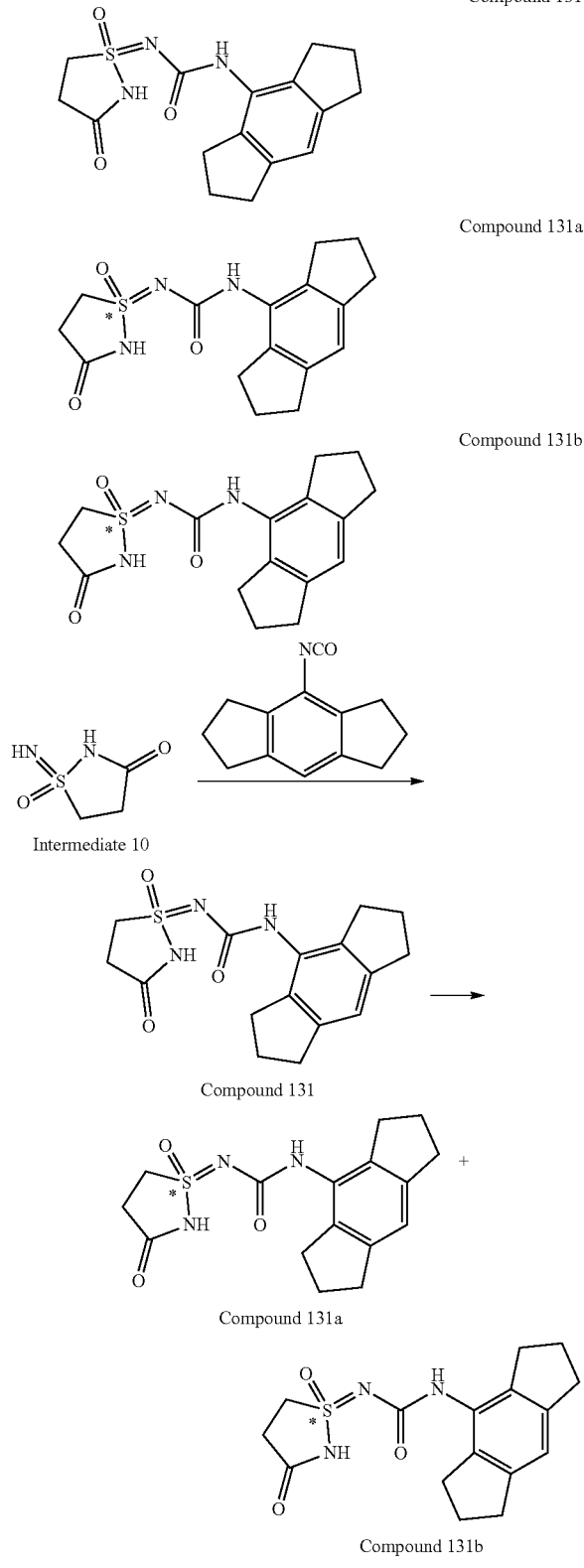

Compound 131

Compound 131a

Compound 131b

Intermediate 10

Compound 131

Compound 131a

Compound 131b

290

Step 1: 1-(1,2,3,5,6,7-hexahydro-s-indacen-4-yl)-3-(1-oxido-3-oxo-1l6-isothiazolidin-1-ylidene)urea Into a 50 mL round-bottom flask purged and maintained with an inert atmosphere of nitrogen, was placed 1-imino-1l6-isothiazolidin-3-one 1-oxide (63 mg, 0.5 mmol, 1.0 equiv.) and NaH (60% wt in mineral oil, 30 mg, 0.8 mmol, 1.6 equiv.) in THF (8 mL). To the solution was added 4-isocyanato-1,2,3,5,6,7-hexahydro-s-indacene (98 mg, 0.5 mmol, 1.1 equiv.). The resulting solution was stirred for 3 h at ambient temperature and then quenched by the addition of 0.2 mL of water.

The resulting mixture was concentrated under vacuum and the residue was purified by Prep-HPLC with the following conditions: Column: XBridge Shield RP18 OBD Column 19*250 mm, 10 um; Mobile Phase A:Water (10 mmol/L NH$_4$HCO$_3$), Mobile Phase B: ACN; Flow rate: 25 mL/min; Gradient: 10% B to 25% B in 10 min; 210/254 nm; Rt: 10.33 min. This resulted in 14 mg of 1-(1,2,3,5,6,7-hexahydro-s-indacen-4-yl)-3-(1-oxido-3-oxo-1l6-isothiazolidin-1-ylidene)urea as a white solid. MS-ESI: 334.2.

Step 2: (S or R)-1-(1,2,3,5,6,7-hexahydro-s-indacen-4-yl)-3-(1-oxido-3-oxo-1l6-isothiazolidin-1-ylidene)urea and (R or S)-1-(1,2,3,5,6,7-hexahydro-s-indacen-4-yl)-3-(1-oxido-3-oxo-1l6-isothiazolidin-1-ylidene)urea 1-(1,2,3,5,6,7-hexahydro-s-indacen-4-yl)-3-(1-oxido-3-oxo-1l6-isothiazolidin-1-ylidene)urea (130 mg, 0.4 mmol, 1.0 equiv.) was separated by Prep-SFC with the following conditions: Column name: CHIRALPAK AD-3 3*100 mm, 3 um; Co-Solvent: MeOH (0.1% DEA); Gradient (B %): 10% to 50% in 4.0 min, hold 2.0 min at 50%; Back Pressure (psi): 1500.000; Flow (ml/min): 2; Temperature: 35; Detector: 220 nm. This resulted in 30 mg of (S or R)-1-(1,2,3,5,6,7-hexahydro-s-indacen-4-yl)-3-(1-oxido-3-oxo-1l6-isothiazolidin-1-ylidene)urea as a white solid and 32 mg of (R or S)-1-(1,2,3,5,6,7-hexahydro-s-indacen-4-yl)-3-(1-oxido-3-oxo-1l6-isothiazolidin-1-ylidene)urea as a white solid.

(S or R)-1-(1,2,3,5,6,7-hexahydro-s-indacen-4-yl)-3-(1-oxido-3-oxo-1l6-isothiazolidin-1-ylidene)urea: MS-ESI: 334.2 (M+1). $^1$H NMR: (300 MHz, MeOH-d4) δ: 6.90 (s, 1H), 3.95-3.87 (m, 1H), 3.42 (s, 1H), 3.11-2.93 (m, 2H), 2.87-2.79 (m, 8H), 2.08-1.99 (m, 4H).

(R or S)-1-(1,2,3,5,6,7-hexahydro-s-indacen-4-yl)-3-(1-oxido-3-oxo-1l6-isothiazolidin-1-ylidene)urea: MS-ESI: 334.2 (M+1). $^1$H NMR: (300 MHz, MeOH-d4) δ: 6.90 (s, 1H), 3.96-3.86 (m, 1H), 3.44 (s, 1H), 3.13-2.93 (m, 2H), 2.87-2.79 (m, 8H), 2.08-2.00 (m, 4H).

Example 24 Synthesis of Compound 119, 119b, and 119a

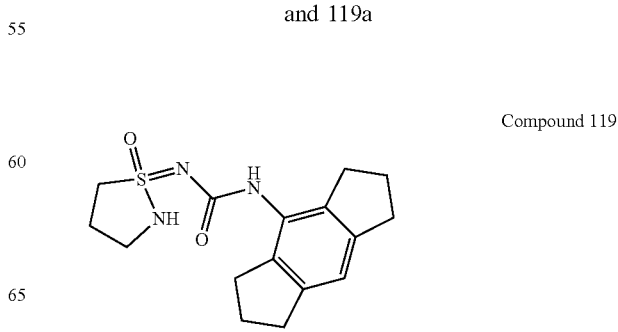

Compound 119

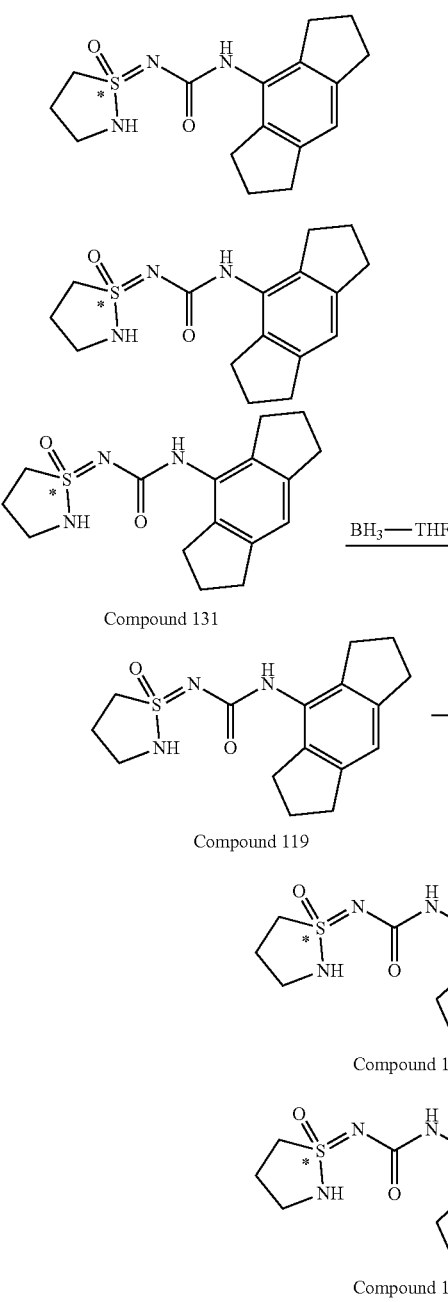

47% in 7 min); Detector, UV 254 nm. This resulted in 102 mg of 1-(1,2,3,5,6,7-hexahydro-s-indacen-4-yl)-3-(1-oxido-1l6-isothiazolidin-1-ylidene)urea as a white solid. MS-ESI: 319.2.

Step 2: (S or R)-1-(1,2,3,5,6,7-hexahydro-s-indacen-4-yl)-3-(1-oxido-1l6-isothiazolidin-1-ylidene)urea and (R or S)-1-(1,2,3,5,6,7-hexahydro-s-indacen-4-yl)-3-(1-oxido-1l6-isothiazolidin-1-ylidene)urea The racemate (90 mg) was separated by Chiral-Prep-HPLC with the following conditions (Prep-HPLC-009): Column, CHIRALPAK IE, 2*25 cm, 5 um; mobile phase, Hex (8 mmol/L $NH_3 \cdot MeOH$)—and EtOH—(hold 50% EtOH—in 21 min); Detector, UV: 254 nm. This resulted in 25.4 mg of (S or R)-1-(1,2,3,5,6,7-hexahydro-s-indacen-4-yl)-3-(1-oxido-1l6-isothiazolidin-1-ylidene)urea as a white solid and 27.4 mg of (R or S)-1-(1,2,3,5,6,7-hexahydro-s-indacen-4-yl)-3-(1-oxido-1l6-isothiazolidin-1-ylidene)urea as a white solid.

(S or R)-1-(1,2,3,5,6,7-hexahydro-s-indacen-4-yl)-3-(1-oxido-1l6-isothiazolidin-1-ylidene)urea: MS-ESI: 319.2 (M+1). $^1$H NMR: (400 MHz, DMSO-$d_6$) δ: 8.42 (s, 1H), 7.23 (t, 1H), 6.88 (s, 1H), 3.51-3.55 (m, 1H), 3.18-3.32 (m, 3H), 2.79 (t, 4H), 2.73 (t, 4H), 2.20-2.45 (m, 2H), 1.91-1.97 (m, 3H).

(R or S)-1-(1,2,3,5,6,7-hexahydro-s-indacen-4-yl)-3-(1-oxido-1l6-isothiazolidin-1-ylidene)urea: MS-ESI: 319.2 (M+1). $^1$H NMR: (400 MHz, DMSO-$d_6$) δ: 8.42 (s, 1H), 7.23 (t, 1H), 6.88 (s, 1H), 3.51-3.55 (m, 1H), 3.18-3.32 (m, 3H), 2.79 (t, 4H), 2.73 (t, 4H), 2.20-2.45 (m, 2H), 1.92-1.98 (m, 3H).

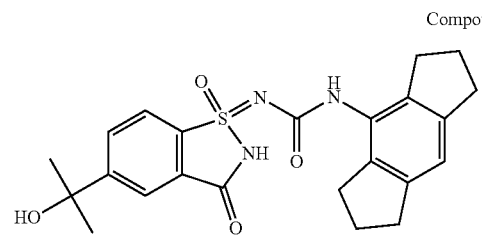

Compound 121

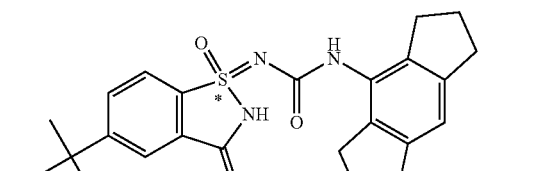

Compound 121b

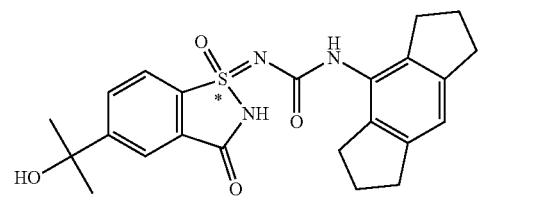

Compound 121a

Step 1: 1-(1,2,3,5,6,7-hexahydro-s-indacen-4-yl)-3-(1-oxido-1l6-isothiazolidin-1-ylidene)urea Into a 25 mL round-bottom flask purged and maintained with an inert atmosphere of nitrogen, was placed 1-(1,2,3,5,6,7-hexahydro-s-indacen-4-yl)-3-(1-oxido-3-oxo-1l6-isothiazolidin-1-ylidene)urea (200 mg, 0.6 mmol, 1.0 equiv.) in THF (5.0 mL). To the solution was added $BH_3$-THF (5.00 mL). The resulting solution was stirred for 2 h at ambient temperature. The resulting mixture was concentrated and the residue was purified by Prep-HPLC with the following conditions (2# SHIMADZU (HPLC-01)): Column, XBridge Prep OBD C18 Column, 30*150 mm Sum; mobile phase, Water (10 mmol/L $NH_4HCO_3$) and ACN (26% PhaseB up to -continued

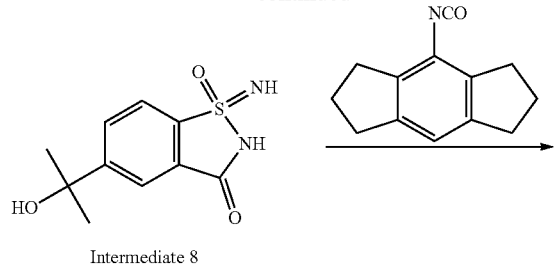

Intermediate 8

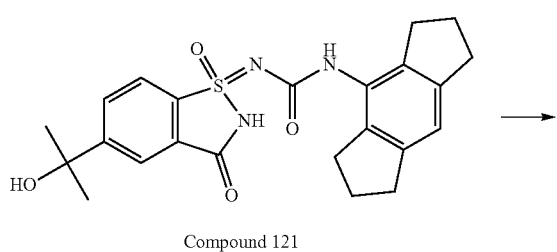

Compound 121

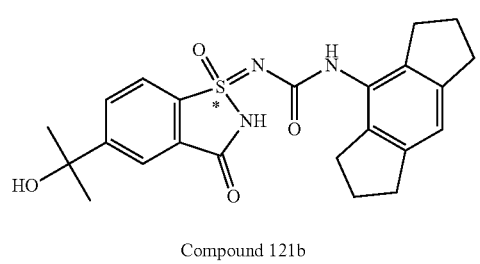

Compound 121b

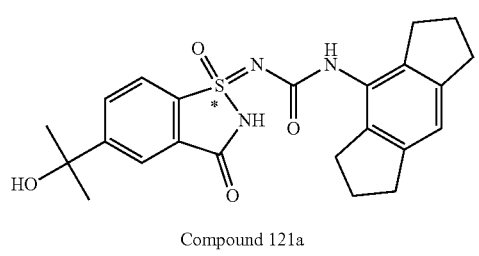

Compound 121a

Example 25 Synthesis of Compound 121, 121b, and 121a

Step 1: 1-(1,2,3,5,6,7-hexahydro-s-indacen-4-yl)-3-(5-(2-hydroxypropan-2-yl)-1-oxido-3-oxo-2,3-dihydro-1λ4-benzo[d]isothiazol-1-ylidene)urea Into a 50 mL round-bottom flask, was placed 5-(2-hydroxypropan-2-yl)-1-imino-1,2-dihydro-3H-1λ4-benzo[d]isothiazol-3-one 1-oxide (150 mg, 0.6 mmol, 1.0 equiv.) and NaH (60% wt in mineral oil, 50 mg, 1.3 mmol, 2.0 equiv.) in THF (15 mL). To the solution was added 4-isocyanato-1,2,3,5,6,7-hexahydro-s-indacene (186.6 mg, 0.9 mmol, 1.5 equiv.). The resulting solution was stirred for 2 h at ambient temperature and then quenched by the addition of 3 mL of MeOH. The resulting mixture was concentrated. The crude product was purified by Prep-HPLC with the following conditions: Column: XSelect CSH Prep C18 OBD Column, 19×150 mm 5um; Mobile Phase A: Water (10 mmol/L NH₄HCO₃+0.1% NH₄OH), Mobile Phase B: ACN; Flow rate: 25 mL/min; Gradient: 24% B to 34% B in 7 min; 254 nm; Rt:6.10 min. This resulted in 4.1 mg of 1-(1,2,3,5,6,7-hexahydro-s-indacen-4-yl)-3-(5-(2-hydroxypropan-2-yl)-1-oxido-3-oxo-2,3-dihydro-1λ4-benzo[d]isothiazol-1-ylidene)urea as a white solid. MS-ESI: 440.2.

Step 2: (S)-1-(1,2,3,5,6,7-hexahydro-s-indacen-4-yl)-3-(5-(2-hydroxypropan-2-yl)-1-oxido-3-oxo-2,3-dihydro-1λ4-benzo[d]isothiazol-1-ylidene)urea and (R)-1-(1,2,3,5,6,7-hexahydro-s-indacen-4-yl)-3-(5-(2-hydroxypropan-2-yl)-1-oxido-3-oxo-2,3-dihydro-1λ4-benzo[d]isothiazol-1-ylidene)urea The racemic 1-(1,2,3,5,6,7-hexahydro-s-indacen-4-yl)-3-(5-(2-hydroxypropan-2-yl)-1-oxido-3-oxo-2,3-dihydro-1λ4-benzo[d]isothiazol-1-ylidene)urea was separated by Chiral-Prep-HPLC with the following conditions (Prep-HPLC-009): Column: Chiralpak AD-H, 2*25 cm (5 um); Mobile Phase A: CO₂: 75, Mobile Phase B: MeOH (2 mM NH₃-MeOH): 25; Flow rate: 40 mL/min; 220 nm; Rt1:4.88; Rt2:6.98. This resulted in 4.3 mg of (S or R)-1-(1,2,3,5,6,7-hexahydro-s-indacen-4-yl)-3-(5-(2-hydroxypropan-2-yl)-1-oxido-3-oxo-2,3-dihydro-1λ4-benzo[d]isothiazol-1-ylidene)urea as a white solid and 3.7 mg of (R or S)-1-(1,2,3,5,6,7-hexahydro-s-indacen-4-yl)-3-(5-(2-hydroxypropan-2-yl)-1-oxido-3-oxo-2,3-dihydro-1λ4-benzo[d]isothiazol-1-ylidene)urea as a white solid.

(S or R)-1-(1,2,3,5,6,7-hexahydro-s-indacen-4-yl)-3-(5-(2-hydroxypropan-2-yl)-1-oxido-3-oxo-2,3-dihydro-1λ4-benzo[d]isothiazol-1-ylidene)urea: MS-ESI: 440.2 (M+1). ¹H NMR: (400 MHz, MeOH-d4) δ: 8.08 (s, 1H), 7.98 (s, 1H), 7.87 (d, 1H), 6.90 (s, 1H), 2.80-2.85 (m, 8H), 1.97-2.09 (m, 4H), 1.58 (s, 6H).

(R or S)-1-(1,2,3,5,6,7-hexahydro-s-indacen-4-yl)-3-(5-(2-hydroxypropan-2-yl)-1-oxido-3-oxo-2,3-dihydro-1λ4-benzo[d]isothiazol-1-ylidene)urea: MS-ESI: 319.2 (M+1). ¹H NMR: (400 MHz, MeOH-d4) δ: 8.05 (s, 1H), 7.98 (s, 1H), 7.87 (d, 1H), 6.91 (s, 1H), 2.80-2.85 (m, 8H), 1.96-2.04 (m, 4H), 1.58 (s, 6H).

Example 26 Synthesis of Compound 111 and 232

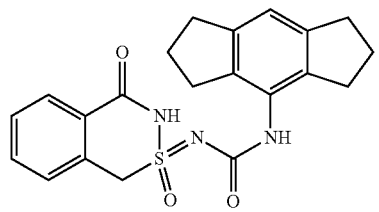

Compound 111

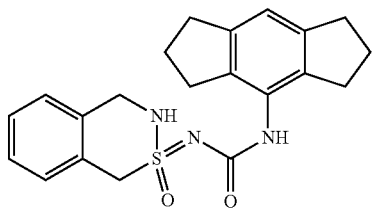

Compound 232

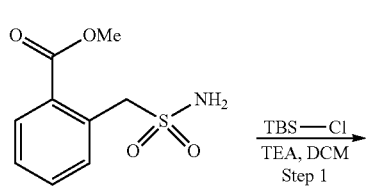 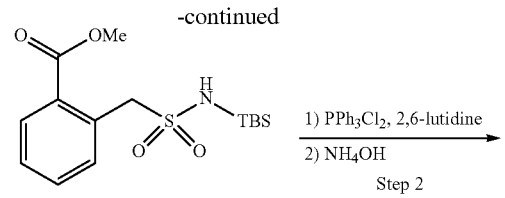 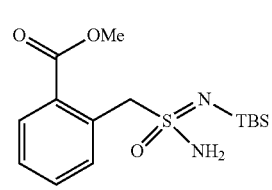

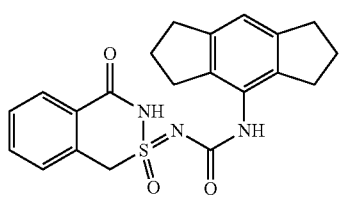 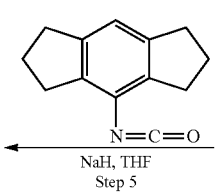 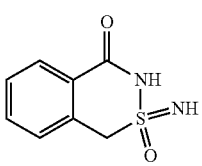 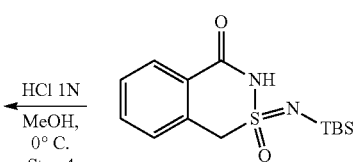

Compound 111

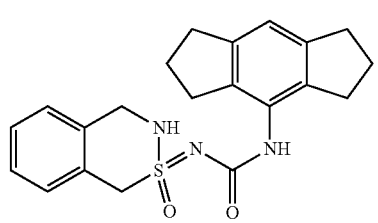

Compound 232

Preparation of 1-(1,2,3,5,6,7-hexahydro-s-indacen-4-yl)-3-(2-oxido-4-oxo-3,4-dihydro-1H-2λ⁴-benzo[d][1,2]thiazin-2-ylidene)urea (Compound 111)

Step 1: Methyl 2-((N-(tert-butyldimethylsilyl)sulfamoyl)methyl)benzoate

TBSCl (1.62 g, 10.75 mmol, 1.2 eq) was added to a solution of o-carbomethoxybenzyl sulfonamide (2 g, 8.72 mmol) and TEA (3.8 mL, 27.2 mmol, 3.1 eq) in dry DCM (25 mL) and the resulting mixture was stirred at ambient temperature for 24 h. Then, a saturated solution of aqueous NH₄Cl (10 mL) was added, the layers were separated, and the aqueous layer was extracted with EtOAc (2×20 mL). The combined organic layers were washed with brine (10 mL), dried over Na₂SO₄, filtered and concentrated under reduced pressure, resulting in isolation of 3.00 g of the title compound (100%) as a white solid.

Step 2: Methyl 2-((N'-(tert-butyldimethylsilyl)sulfamidimidoyl)methyl)benzoate

A suspension of freshly prepared PPh₃Cl₂ (1.34 g, 4.02 mmol, 1.2 eq) solution in CHCl₃ (10 mL) was cooled to 0° C. This solution was cannulated into a solution of methyl 2-((N-(tert-butyldimethylsilyl)sulfamoyl)methyl)benzoate (1.14 g, 3.32 mmol) and 2,6-lutidine (0.5 mL, 4.29 mmol, 1.29 eq) in dry DCM (12 mL) at 0° C. under an argon atmosphere. The reaction was stirred at r.t. overnight. Afterwards, the mixture was cooled to 0° C. and a saturated solution of NH₄OH (4 mL) was added dropwise. The resulting mixture was vigorously stirred at the same temperature for 1 h. Then the layers were separated and the organic layer was washed with aqueous HCl 1 N (2×10 mL), a saturated solution of aqueous NaHCO₃ (10 mL), water (10 mL) and brine (10 mL), dried over Na₂SO₄, filtered and concentrated under reduced pressure. The residue was suspended in Et₂O (20 mL) and the mixture was filtered in order to remove Ph₃PO. The residual clear solution was concentrated again, and the product was purified by flash column chromatography eluting with a gradient of 0-50% EtOAc in hexane to afford 550 mg of the title compound (48%) as a pale yellow solid. MS-ESI: 229.1 (M-TBS+1).

Step 3: 2-((tert-butyldimethylsilyl)imino)-2,3-dihydro-2λ⁴-benzo[d][1,2]thiazin-4(1H)-one 2-oxide Sodium methoxide (10 mL, 25% in MeOH) was added dropwise to a solution of methyl 2-((N-(tert-butyldimethylsilyl)sulfamidimidoyl)methyl)benzoate (410 mg, 1.20 mmol) in dry MeOH (10 mL) at 0° C. under an argon atmosphere and the mixture was stirred at the same temperature for 1 h. Then, a saturated solution of NH₄Cl (15 mL) was added, the organic solvent was removed under reduced pressure and the aqueous residue was extracted with EtOAc (2×20 mL). The combined organic layers were dried over Na₂SO₄, filtered and concentrated under reduced pressure, resulting in isolation of 310 mg of the title compound (83%) as a white solid. MS-ESI: 311.1 (M+1).

Step 4: 2-imino-2,3-dihydro-2$\lambda^4$-benzo[d][1,2]thiazin-4(1H)-one 2-oxide

HCl 1 N aqueous (1 mL) was added dropwise to a solution of 2-((tert-butyldimethylsilyl)imino)-2,3-dihydro-2$\lambda^4$-benzo[d][1,2]thiazin-4(1H)-one 2-oxide (49 mg, 0.16 mmol) in MeOH (1 mL) at 0° C. and the resulting milky white mixture was vigorously stirred at the same temperature for 20 min. The mixture was concentrated under reduced pressure at room temperature and the residue was washed with DCM to afford 31 mg of the title compound (100%) as a white solid. MS-ESI: 197.1 (M+1).

Step 5: 1-(1,2,3,5,6,7-hexahydro-s-indacen-4-yl)-3-(2-oxido-4-oxo-3,4-dihydro-1H-2$\lambda^4$-benzo[d][1,2]thiazin-2-ylidene)urea NaH (14 mg, 60% in mineral oil, 0.35 mmol, 2.2 eq) was added to a suspension of 2-imino-2,3-dihydro-2$\lambda^4$-benzo[d][1,2]thiazin-4(1H)-one 2-oxide (31 mg, 0.16 mmol) in dry THF (10 mL) at 0° C. under an argon atmosphere and the mixture was stirred at the same temperature for 1 h. Then, 4-isocyanato-1,2,3,5,6,7-hexahydro-s-indacene (39 mg, 0.20 mmol, 1.25 eq) was added and the reaction was stirred at room temperature for 2 h. Afterwards, the reaction was cooled to 0° C. and quenched by adding one drop of formic acid. The mixture was diluted with EtOAc (20 mL) and washed with water (5 mL) and brine (5 mL). The organic layer was dried over Na$_2$SO$_4$, filtered and concentrated under reduced pressure. The residue was purified by reverse phase flash chromatography using a gradient of 10-100% CH$_3$CN in H$_2$O (ammonium carbonate 0.1%) to afford 26 mg of the title compound (42%) as a white powder. MS-ESI: 396.1 (M+1). $^1$H-NMR (400 MHz, CD$_3$OD) δ: 8.07 (d, 1H), 7.57 (t, 1H), 7.50 (t, 1H), 7.40 (d, 1H), 6.89 (s, 1H), 5.12 (d, 1H), 4.72 (d, 1H), 2.83 (t, 4H), 2.75-2.71 (m, 4H), 2.04-1.99 (m, 4H) ppm.

Preparation of 1-(1,2,3,5,6,7-hexahydro-s-indacen-4-yl)-3-(2-oxido-3,4-dihydro-1H-2l4-benzo[d][1,2]thiazin-2-ylidene)urea (Compound 232)

Step 6: 2-imino-1,2,3,4-tetrahydro-2$\lambda^4$-benzo[d][1,2]thiazine 2-oxide

Triflic anhydride (0.030 mL, 0.18 mmol, 1.1 eq) was added dropwise to a suspension of 2-((tert-butyldimethylsilyl)imino)-2,3-dihydro-2$\lambda^4$-benzo[d][1,2]thiazin-4(1H)-one 2-oxide (50 mg, 0.16 mmol) in dry DCM (2 mL) at 0° C. under an argon atmosphere and the mixture was stirred at the same temperature for 30 min. Afterwards, NaBH$_4$ (9 mg, 0.24 mmol, 1.5 eq) was added in one portion and dry THF (1 mL) was added dropwise and the mixture was stirred at room temperature for 1 h. Then, the reaction was cooled to 0° C. and a saturated aqueous solution of NaHCO$_3$ (2 mL) was added. The mixture was extracted with EtOAc (3×10 mL) and the combined organic layers were washed with brine (2 mL), dried over Na$_2$SO$_4$, filtered and concentrated under reduced pressure. The residue was purified by reverse phase flash chromatography using a gradient of 10-100% CH$_3$CN in H$_2$O (ammonium carbonate 0.1%) to afford 14 mg of the title compound (48%) as a white solid. MS-ESI: 183.1 (M+1).

Step 7: 1-(1,2,3,5,6,7-hexahydro-s-indacen-4-yl)-3-(2-oxido-3,4-dihydro-1H-2$\lambda^4$-benzo[d][1,2]thiazin-2-ylidene)urea, NC-26

NaH (7 mg, 60% in mineral oil, 0.17 mmol, 2.2 eq) was added to a solution of 2-imino-2,3-dihydro-2l4-benzo[d][1,2]thiazin-4(1H)-one 2-oxide (14 mg, 0.077 mmol) in dry THF (3 mL) at 0° C. under an argon atmosphere and the mixture was stirred at the same temperature for 30 min. Then, 4-isocyanato-1,2,3,5,6,7-hexahydro-s-indacene (18 mg, 0.09 mmol, 1.1 eq) was added and the reaction was stirred at room temperature for 1 h. Afterwards, the reaction was cooled to 0° C. and quenched by adding one drop of formic acid. The mixture was concentrated under reduced pressure and the residue was triturated in MeOH to afford 19 mg of the title compound (65%) as a white solid. MS-ESI: 382.2 (M+1). $^1$H-NMR (400 MHz, DMSO-d$_6$) δ: 8.46 (br. s, 1H), 7.54 (br. s, 1H), 7.33-7.26 (m, 2H), 7.23 (d, 1H), 7.19 (d, 1H), 6.87 (s, 1H), 4.93 (d, 1H), 4.53 (d, 1H), 4.43 (br. s, 2H), 2.77 (t, 4H), 2.66-2.59 (m, 4H), 1.95-1.87 (m, 4H) ppm.

Example 27: Preparation of Compounds 113a and 113b

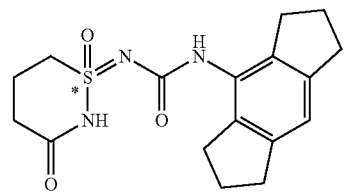

Compound 113a (S or R)-1-(1,2,3,5,6,7-hexahydro-s-indacen-4-yl)-3-(1-oxido-3-oxo-1l6,2-thiazinan-1-ylidene)urea

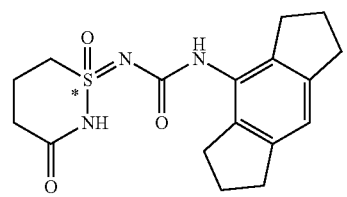

Compound 113b (R or S)-1-(1,2,3,5,6,7-hexahydro-s-indacen-4-yl)-3-(1-oxido-3-oxo-1l6,2-thiazinan-1-ylidene)urea 1-(1,2,3,5,6,7-hexahydro-s-indacen-4-yl)-3-(1-oxido-3-oxo-1l6,2-thiazinan-1-ylidene)urea (Compound 113, 100 mg) was separated by Prep-SFC with the following conditions: Column: CHIRALPAK AD-H-TC001 SFC, 2*25 cm, 5 µm; Mobile Phase A: CO$_2$, Mobile Phase B: MeOH (2 mM NH$_3$); Flow rate: 40 mL/min; Gradient: hold 45% B for 15 min; 220 nm; RT1: 2.81; RT2: 8.41. This resulted in 20 mg of Compound 113a, (S or R)-1-(1,2,3,5,6,7-hexahydro-s-indacen-4-yl)-3-(1-oxido-3-oxo-1l6,2-thiazinan-1-ylidene) urea (isomer 1) as a white solid and 21 mg of Compound 113b, (R or S)-1-(1,2,3,5,6,7-hexahydro-s-indacen-4-yl)-3-(1-oxido-3-oxo-1l6,2-thiazinan-1-ylidene)urea (isomer 2) as a white solid.

MS-ESI: 348.1 (M+1) $^1$H NMR: (400 MHz, DMSO-d$_6$) δ: 7.82 (br s, 1H), 7.11 (br s, 1H), 6.82 (s, 1H), 3.75-3.70 (m, 1H), 3.05-2.99 (m, 1H), 2.79-2.70 (m, 8H), 2.20-2.13 (m, 2H), 1.99-1.92 (m, 6H).

TABLE E4

Examples in the following table were prepared using similar conditions as described in Example 25, with the respective coupling partner as noted in Table E4.

| Ex. # | Final Target # | LHS | Structure | IUPAC Name | Exact Mass [M + H]⁺ |
|---|---|---|---|---|---|
| 28 | Compound 132 | 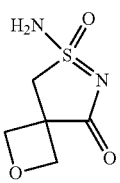<br>Intermediate 21 | 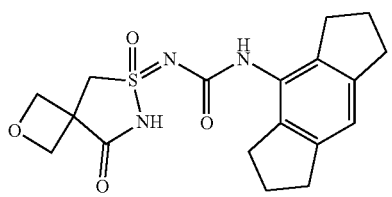 [SMILES: O=C(N=S1(=O)CC2(COC2)C(=O)N1)Nc1c2c(cc3c1CCC3)CCC2] | 1-(1,2,3,5,6,7-hexahydro-s-indacen-4-yl)-3-(6-oxido-8-oxo-2-oxa-6λ6-thia-7-azaspiro[3.4]octan-6-ylidene)urea | 376.2 |
| 29 | Compound 132a | 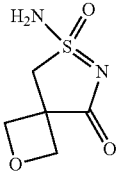<br>Intermediate 21 | 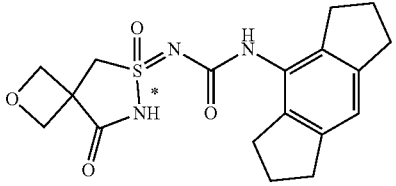 [SMILES: O=C(N=S1(=O)CC2(COC2)C(=O)N1)Nc1c2c(cc3c1CCC3)CCC2] | (S or R)-1-(1,2,3,5,6,7-hexahydro-s-indacen-4-yl)-3-(6-oxido-8-oxo-2-oxa-6λ6-thia-7-azaspiro[3.4]octan-6-ylidene)urea Isomer 1 | 376.1 |
| 30 | Compound 132b | 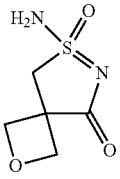<br>Intermediate 21 | 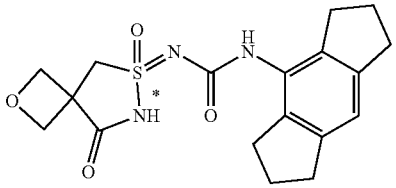 [SMILES: O=C(N=S1(=O)CC2(COC2)C(=O)N1)Nc1c2c(cc3c1CCC3)CCC2] | (R or S)-1-(1,2,3,5,6,7-hexahydro-s-indacen-4-yl)-3-(6-oxido-8-oxo-2-oxa-6λ6-thia-7-azaspiro[3.4]octan-6-ylidene)urea Isomer 2 | 376.2 |
| 31 | Compound 211 | 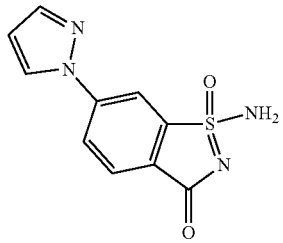<br>Intermediate 34 | 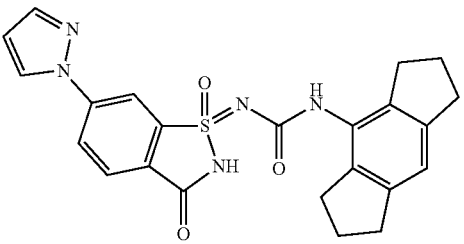 [SMILES: O=C(N=S1(=O)NC(=O)c2ccc(-n3cccn3)cc21)Nc1c2c(cc3c1CCC3)CCC2] | 1-(1,2,3,5,6,7-hexahydro-s-indacen-4-yl)-3-(1-oxido-3-oxo-6-(1H-pyrazol-1-yl)-2,3-dihydro-1λ4-benzo[d]isothiazol-1-ylidene)urea | 448.1 |
| 32 | Compound 211a | 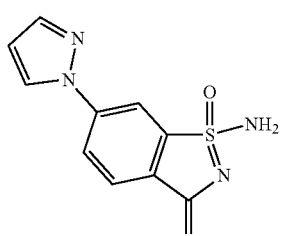<br>Intermediate 34 | 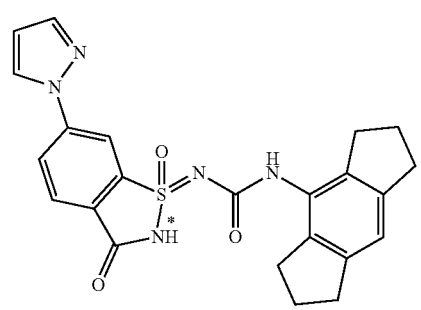 [SMILES: O=C(N=S1(=O)NC(=O)c2ccc(-n3cccn3)cc21)Nc1c2c(cc3c1CCC3)CCC2] | (S or R)-1-(1,2,3,5,6,7-hexahydro-s-indacen-4-yl)-3-(1-oxido-3-oxo-6-(1H-pyrazol-1-yl)-2,3-dihydro-1λ4-benzo[d]isothiazol-1-ylidene)urea Isomer 1 | 448.1 |

TABLE E4-continued

Examples in the following table were prepared using similar conditions as described in Example 25, with the respective coupling partner as noted in Table E4.

| Ex. # | Final Target # | LHS | Structure | IUPAC Name | Exact Mass [M + H]+ |
|---|---|---|---|---|---|
| 33 | Compound 211b | Intermediate 34 | 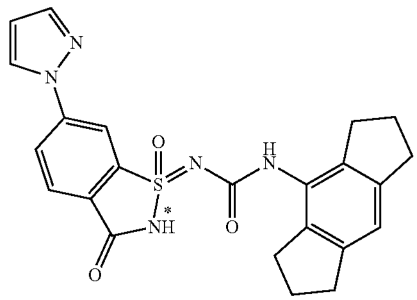 [SMILES: O=C(N=S1(=O)NC(=O)c2ccc(-n3cccn3)cc21)Nc1c2c(cc3c1CCC3)CCC2] | (R or S)-1-(1,2,3,5,6,7-hexahydro-s-indacen-4-yl)-3-(1-oxido-3-oxo-6-(1H-pyrazol-1-yl)-2,3-dihydro-1λ4-benzo[d]isothiazol-1-ylidene)urea | 448.1 |
| 34 | Compound 223 | Intermediate 36 | 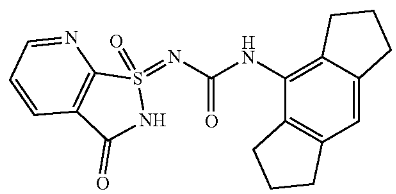 [SMILES: O=C(N=S1(=O)NC(=O)c2cccnc21)Nc1c2c(cc3c1CCC3)CCC2] | 1-(1,2,3,5,6,7-hexahydro-s-indacen-4-yl)-3-(1-oxido-3-oxo-2,3-dihydro-1λ4-isothiazolo[5,4-b]pyridin-1-ylidene)urea | 383.1 |
| 35 | Compound 223a | Intermediate 36 | 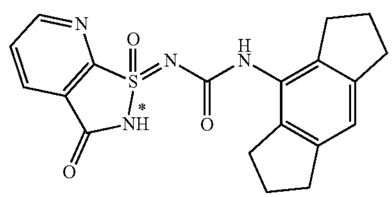 [SMILES: O=C(N=S1(=O)NC(=O)c2cccnc21)Nc1c2c(cc3c1CCC3)CCC2] | (S or S)-1-(1,2,3,5,6,7-hexahydro-s-indacen-4-yl)-3-(1-oxido-3-oxo-2,3-dihydro-1λ4-isothiazolo[5,4-b]pyridin-1-ylidene)urea Isomer 1 | 383.2 |
| 36 | Compound 223b | Intermediate 36 | 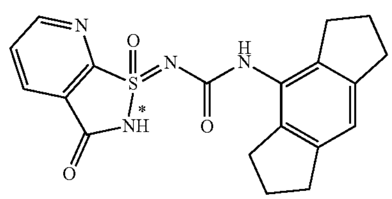 [SMILES: O=C(N=S1(=O)NC(=O)c2cccnc21)Nc1c2c(cc3c1CCC3)CCC2] | (R or S)-1-(1,2,3,5,6,7-hexahydro-s-indacen-4-yl)-3-(1-oxido-3-oxo-2,3-dihydro-1λ4-isothiazolo[5,4-b]pyridin-1-ylidene)urea Isomer 2 | 383.1 |
| 37 | Compound 102 | Intermediate 37 | 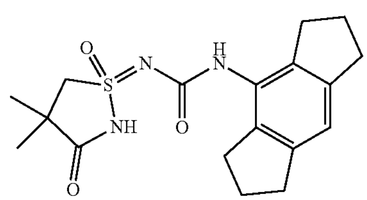 [SMILES: CC1(C)CS(=O)(=NC(=O)Nc2c3c(cc4c2CCC4)CCC3)NC1=O] | 1-(4,4-dimethyl-1-oxido-3-oxo-1λ6-isothiazolidin-1-ylidene)-3-(1,2,3,5,6,7-hexahydro-s-indacen-4-yl)urea | 362.2 |
| 38 | Compound 102a | Intermediate 37 | 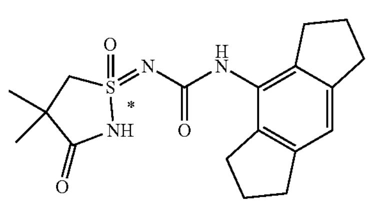 [SMILES: CC1(C)CS(=O)(=NC(=O)Nc2c3c(cc4c2CCC4)CCC3)NC1=O] | (S or R)-1-(4,4-dimethyl-1-oxido-3-oxo-1λ6-isothiazolidin-1-ylidene)-3-(1,2,3,5,6,7-hexahydro-s-indacen-4-yl)urea Isomer 1 | 362.0 |

TABLE E4-continued

Examples in the following table were prepared using similar conditions as described in Example 25, with the respective coupling partner as noted in Table E4.

| Ex. # | Final Target # | LHS | Structure | IUPAC Name | Exact Mass [M + H]+ |
|---|---|---|---|---|---|
| 39 | Compound 102b | Intermediate 37 | 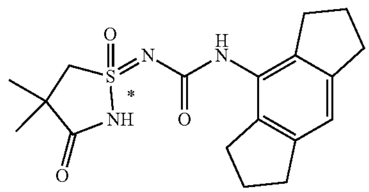 [SMILES: CC1(C)CS(=O)(=NC(=O)Nc2c3c(cc4c2CCC4)CCC3)NC1=O] | (R or S)-1-(4,4-dimethyl-1-oxido-3-oxo-1l6-isothiazolidin-1-ylidene)-3-(1,2,3,5,6,7-hexahydro-s-indacen-4-yl)urea Isomer 2 | 362.1 |
| 40 | Compound 133 | Intermediate 42 | 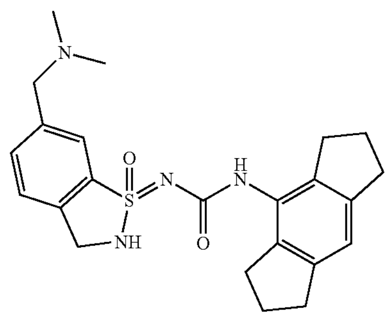 [SMILES: CN(C)Cc1ccc2c(c1)S(=O)(=NC(=O)Nc1c3c(cc4c1CCC4)CCC3)NC2] | 1-(6-((dimethylamino)methyl)-1-oxido-2,3-dihydro-1l4-benzo[d]isothiazol-1-ylidene)-3-(1,2,3,5,6,7-hexahydro-s-indacen-4-yl)urea | 425.2 |
| 41 | Compound 133a | Intermediate 42 | 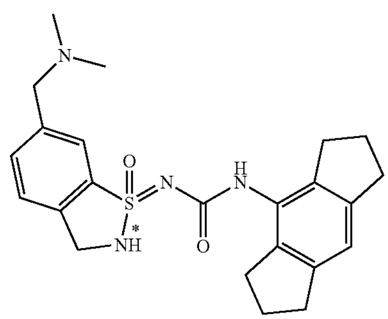 [SMILES: CN(C)Cc1ccc2c(c1)S(=O)(=NC(=O)Nc1c3c(cc4c1CCC4)CCC3)NC2] | (R or S)-1-(6-((dimethylamino)methyl)-1-oxido-2,3-dihydro-1l4-benzo[d]isothiazol-1-ylidene)-3-(1,2,3,5,6,7-hexahydro-s-indacen-4-yl)urea Isomer 1 | 425.2 |
| 42 | Compound 133b | Intermediate 42 | 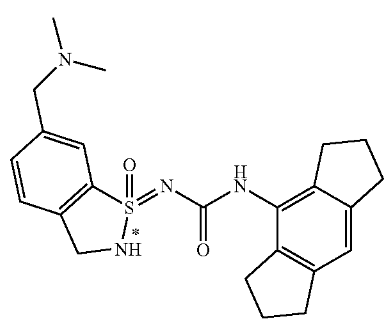 [SMILES: CN(C)Cc1ccc2c(c1)S(=O)(=NC(=O)Nc1c3c(cc4c1CCC4)CCC3)NC2] | (S or R)-1-(6-((dimethylamino)methyl)-1-oxido-2,3-dihydro-1l4-benzo[d]isothiazol-1-ylidene)-3-(1,2,3,5,6,7-hexahydro-s-indacen-4-yl)urea Isomer 2 | 425.1 |

Example 43: Synthesis of Compound 253

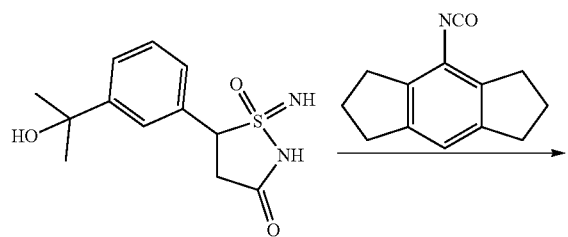

Intermediate 31

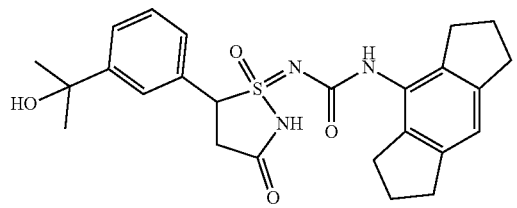

Compound 253

1-(1,2,3,5,6,7-hexahydro-s-indacen-4-yl)-3-(5-(3-(2-hydroxypropan-2-yl)phenyl)-1-oxido-3-oxo-1l6-isothiazolidin-1-ylidene)urea 4-isocyanato-1,2,3,5,6,7-hexahydro-s-indacene (29.0 mg, 0.15 mmol, 1.0 equiv.) was added to a 100 mL round-bottom flask containing 5-[3-(2-hydroxypropan-2-yl)phenyl]-1-imino-1lambda6,2-thiazolidine-1,3-dione (39 mg, 0.15 mmol, 1.0 equiv.) and DBU (0.04 mL, 0.29 mmol, 2.0 equiv.) in THF (2 mL). The resulting solution was stirred overnight at ambient temperature, then concentrated under vacuum. The residue was purified by Prep-HPLC with the following conditions: Column, XBridge Prep OBD C18 Column, 30*150 mm 54 m; mobile phase, Water (10 mM $NH_4HCO_3$+0.1% $NH_4OH$) and ACN (13% Phase B up to 43% in 7 min); Detector, UV 210/254 nm. This resulted in 2.2 mg of 1-(1,2,3,5,6,7-hexahydro-s-indacen-4-yl)-3-(5-(3-(2-hydroxypropan-2-yl)phenyl)-1-oxido-3-oxo-1l6-isothiazolidin-1-ylidene)urea as a white solid. MS-ESI: 468.3. $^1$H NMR: (400 MHz, MeOH-$d_4$) δ: 7.61 (s, 1H), 7.49-7.46 (m, 1H) 7.38-7.29 (m, 2H), 6.93-6.84 (d, 1H), 5.51 (t, 05H), 5.02 (t, 0.5H), 3.50-3.44 (m, 1H), 3.15-3.10 (m, 1H), 2.89-2.85 (m, 4H), 2.80 (t, 2H), 2.51 (t, 2H), 2.10-2.03 (m, 2H), 2.00-1.93 (m, 2H), 1.55-1.50 (m, 6H).

TABLE E5

Examples in the following table were prepared using similar conditions as described in Example 43, with the respective coupling partner as noted in Table E5.

| Ex. # | Final Target # | Coupling Partner | Structure | IUPAC Name | Exact Mass [M + H]$^+$ |
|---|---|---|---|---|---|
| 44 | Compound 266 | Intermediate 32 | 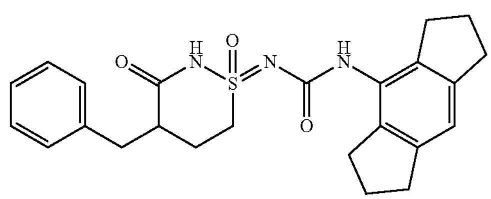 [SMILES: O=C(N=S1(=O)CCC(Cc2ccccc2)C(=O)N1)Nc1c2c(cc3c1CCC3)CCC2] | 1-(4-benzyl-1-oxido-3-oxo-1l6,2-thiazinan-1-ylidene)-3-(1,2,3,5,6,7-hexahydro-s-indacen-4-yl)urea | 438.3 |
| 45 | Compound 209 | Intermediate 33 | 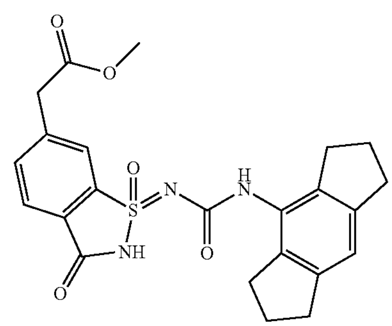 [SMILES: COC(=O)Cc1ccc2c(c1)S(=O)(=NC(=O)Nc1c3c(cc4c1CCC4)CCC3)NC2=O] | methyl 2-(1-(((1,2,3,5,6,7-hexahydro-s-indacen-4-yl)carbamoyl)imino)-1-oxido-3-oxo-2,3-dihydro-1H-1l4-benzo[d]isothiazol-6-yl)acetate | 454.2 |

TABLE E5-continued

Examples in the following table were prepared using similar conditions as described in Example 43, with the respective coupling partner as noted in Table E5.

| Ex. # | Final Target # | Coupling Partner | Structure | IUPAC Name | Exact Mass [M + H]+ |
|---|---|---|---|---|---|
| 46 | Compound 204 | 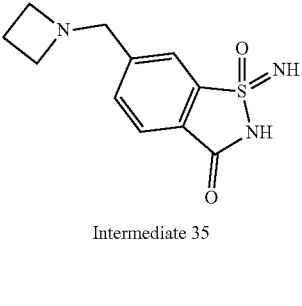 [SMILES: N=S1(=O)NC(=O)c2ccc(CN3CCC3)cc21]<br>Intermediate 35 | 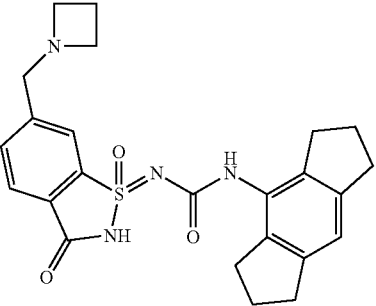 [SMILES: O=C(N=S1(=O)NC(=O)c2ccc(CN3CCC3)cc21)Nc1c2c(cc3c1CCC3)CCC2] | 1-(6-(azetidin-1-ylmethyl)-1-oxido-3-oxo-2,3-dihydro-1λ4-benzo[d]isothiazol-1-ylidene)-3-(1,2,3,5,6,7-hexahydro-s-indacen-4-yl)urea | 376.2 |
| 47 | Compound 134 | 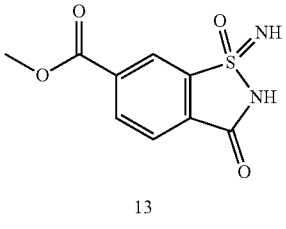 [SMILES: COC(=O)c1ccc2c(c1)S(=N)(=O)NC2=O]<br>13 | 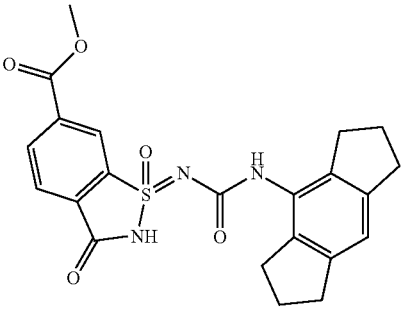 [SMILES: COC(=O)c1ccc2c(c1)S(=O)(=NC(=O)Nc1c3c(cc4c1CCC4)CCC3)NC2=O] | methyl 1-(((1,2,3,5,6,7-hexahydro-s-indacen-4-yl)carbamoyl)imino)-3-oxo-2,3-dihydro-1H-1λ4-benzo[d]isothiazole-6-carboxylate 1-oxide | 440.1 |
| 48 | Compound 134a | 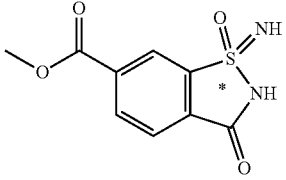<br>Intermediate 24 | 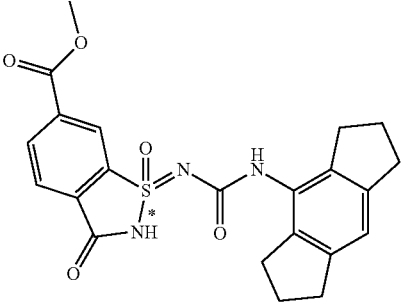 [SMILES: COC(=O)c1ccc2c(c1)S(=O)(=NC(=O)Nc1c3c(cc4c1CCC4)CCC3)NC2=O] | methyl (R or S)-1-(((1,2,3,5,6,7-hexahydro-s-indacen-4-yl)carbamoyl)imino)-3-oxo-2,3-dihydro-1H-1λ4-benzo[d]isothiazole-6-carboxylate 1-oxide | 440.2 |
| 49 | Compound 134b | 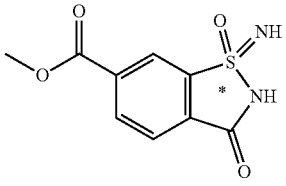<br>Intermediate 25 | 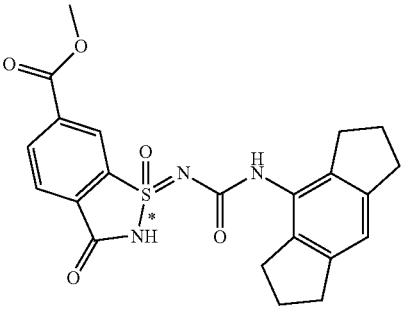 [SMILES: COC(=O)c1ccc2c(c1)S(=O)(=NC(=O)Nc1c3c(cc4c1CCC4)CCC3)NC2=O] | methyl (S or R)-1-(((1,2,3,5,6,7-hexahydro-s-indacen-4-yl)carbamoyl)imino)-3-oxo-2,3-dihydro-1H-1λ4-benzo[d]isothiazole-6-carboxylate 1-oxide | 440.2 |

TABLE E5-continued

Examples in the following table were prepared using similar conditions as described in Example 43, with the respective coupling partner as noted in Table E5.

| Ex. # | Final Target # | Coupling Partner | Structure | IUPAC Name | Exact Mass [M + H]+ |
|---|---|---|---|---|---|
| 50 | Compound 103a | Intermediate 22 | 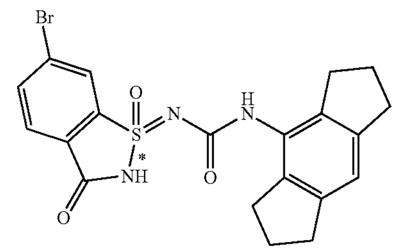 [SMILES: O=C(N=S1(=O)NC(=O)c2ccc(Br)cc21)Nc1c2c(cc3c1CCC3)CCC2] | (R or S)-1-(6-bromo-1-oxido-3-oxo-2,3-dihydro-1l4-benzo[d]isothiazol-1-ylidene)-3-(1,2,3,5,6,7-hexahydro-s-indacen-4-yl)urea | 462.0 |
| 51 | Compound 103b | Intermediate 23 | 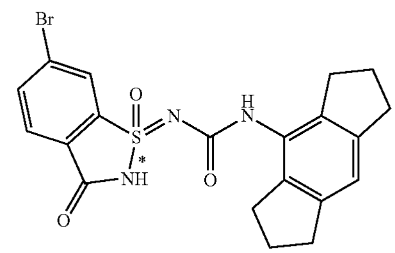 [SMILES: O=C(N=S1(=O)NC(=O)c2ccc(Br)cc21)Nc1c2c(cc3c1CCC3)CCC2] | (S or R)-1-(6-bromo-1-oxido-3-oxo-2,3-dihydro-1l4-benzo[d]isothiazol-1-ylidene)-3-(1,2,3,5,6,7-hexahydro-s-indacen-4-yl)urea | 462.0 |
| 52 | Compound 207 | Intermediate 34 | | 1-(1,2,3,5,6,7-hexahydro-s-indacen-4-yl)-3-(1-oxido-3-oxo-6-(prop-1-en-2-yl)-2,3-dihydro-1l4-benzo[d]isothiazol-1-ylidene)urea | 422.2 |
| 52 | Compound 229 | Intermediate 39 | | 1-(1,2,3,5,6,7-hexahydro-s-indacen-4-yl)-3-(5-(2-hydroxypropan-2-yl)-1-oxido-3-oxo-2,3-dihydro-1l4-thieno[3,2-d]isothiazol-1-ylidene)urea | 446.2 |
| 53 | Compound 101 | Intermediate 40 | 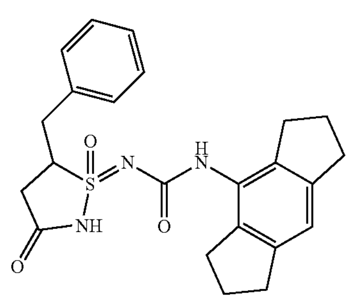 [SMILES: O=C1CC(Cc2ccccc2)S(=O)(=NC(=O)Nc2c3c(cc4c2CCC4)CCC3)N1] | 1-(5-benzyl-1-oxido-3-oxo-1l6-isothiazolidin-1-ylidene)-3-(1,2,3,5,6,7-hexahydro-s-indacen-4-yl)urea | 424.2 |

Example 54: Synthesis of Compound 135

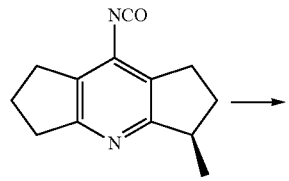

Intermediate 43

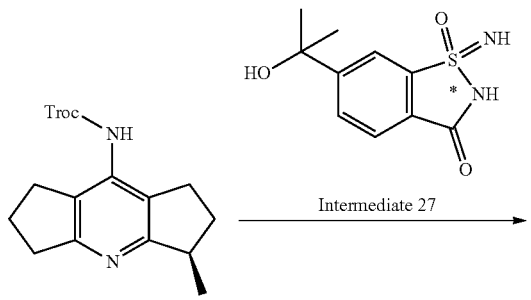

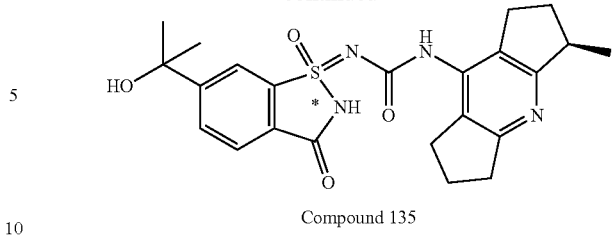

Compound 135

Compound 135 was prepared from Intermediate 43, using procedures similar to those to prepare Compound 120, as described in Example 13. MS-ESI: 455.2 (M+1). $^1$HNMR: (400 MHz, MeOH-d$_4$) δ: 8.33 (s, 1H), 7.49 (s, 1H), 7.92-7.89 (m, 1H), 7.80 (d, 1H), 3.55-3.51 (m, 1H), 3.20-3.16 (m, 2H), 3.07-3.03 (m, 1H), 2.95-2.87 (m, 3H), 2.52-2.47 (m, 1H), 2.30-2.23 (m, 2H), 1.85-1.80 (m, 1H), 1.61 (s, 3H), 1.60 (s, 3H), 1.40 (d, 3H).

TABLE E6

Examples in the following table were prepared using similar conditions as described in Example 54 from common Intermediate 27, with the respective coupling partner as noted in Table E6

| Ex. # | Final Target # | RHS | Structure | IUPAC Name | Exact Mass [M + H]$^+$ |
|---|---|---|---|---|---|
| 55 | Compound 136 | Intermediate 14 | 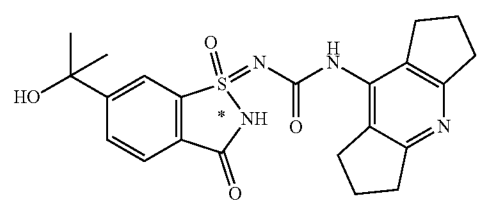 [SMILES: CC(C)(O)c1ccc2c(c1)S(=O)(=NC(=O)Nc1c3c(nc4c1CCC4)CCC3)NC2=O] | (S or R)-1-(1,2,3,5,6,7-hexahydrodicyclopenta[b,e]pyridin-8-yl)-3-(6-(2-hydroxypropan-2-yl)-1-oxido-3-oxo-2,3-dihydro-1l4-benzo[d]isothiazol-1-ylidene)urea | 441.2 |
| 56 | Compound 137 | Intermediate 16 | 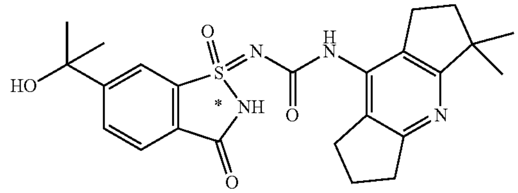 [SMILES: CC(C)(O)c1ccc2c(c1)S(=O)(=NC(=O)Nc1c3c(nc4c1CCC4(C)C)CCC3)NC2=O] | (S or R)-1-(3,3-dimethyl-1,2,3,5,6,7-hexahydrodicyclopenta[b,e]pyridin-8-yl)-3-(6-(2-hydroxypropan-2-yl)-1-oxido-3-oxo-2,3-dihydro-1l4-benzo[d]isothiazol-1-ylidene)urea | 469.2 |
| 57 | Compound 138 | Intermediate 17 | 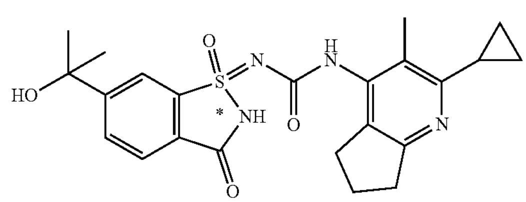 [SMILES: Cc1c(C2CC2)nc2c(c1NC(=O)N=S1(=O)NC(=O)c3ccc(C(C)(C)O)cc31)CCC2] | (S or R)-1-(2-cyclopropyl-3-methyl-6,7-dihydro-5H-cyclopenta[b]pyridin-4-yl)-3-(6-(2-hydroxypropan-2-yl)-1-oxido-3-oxo-2,3-dihydro-1l4-benzo[d]isothiazol-1-ylidene)urea | 455.3 |

Example 58: Preparation of Compounds 106a and 106b

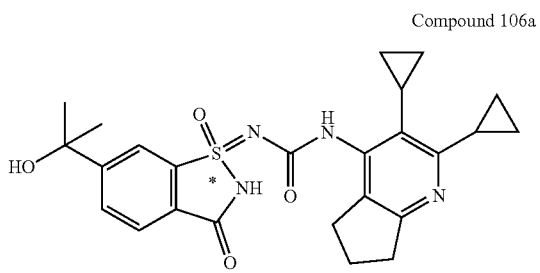 [SMILES: CC(C)(O)c1ccc2c(c1)S(=O)(=NC(=O)Nc1c3c(nc(C4CC4)c1C1CC1)CCC3)NC2=O]

Compound 106a

1(R or S)-1-(2,3-dicyclopropyl-6,7-dihydro-5H-cyclopenta[b]pyridin-4-yl)-3-(6-(2-hydroxypropan-2-yl)-1-oxido-3-oxo-2,3-dihydro-1l4-benzo[d]isothiazol-1-ylidene)urea

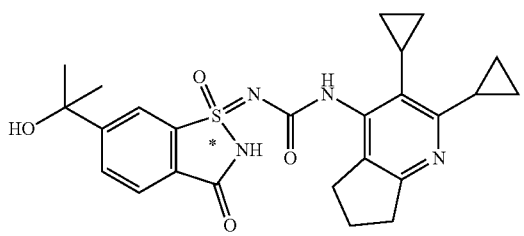

Compound 106b

1(S or R)-1-(2,3-dicyclopropyl-6,7-dihydro-5H-cyclopenta[b]pyridin-4-yl)-3-(6-(2-hydroxypropan-2-yl)-1-oxido-3-oxo-2,3-dihydro-1l4-benzo[d]isothiazol-1-ylidene)urea The racemic 1-[2,3-dicyclopropyl-5H,6H,7H-cyclopenta[b]pyridin-4-yl]-3-[6-(2-hydroxypropan-2-yl)-1,3-dioxo-2H-1lambda6,2-benzothiazol-1-ylidene]urea (80 mg) was resolved by Chiral-Prep-HPLC with the following conditions: Column: CHIRALPAK IC, 2*25 cm, 5 µm; Mobile Phase A Hex (8 mM $NH_3$·MeOH)—HPLC, Mobile Phase B: EtOH—HPLC; Flow rate: 18 mL/min; Gradient: 50% B to 50% B in 15 min; 220/254 nm; RT1: 7.516 min, RT2: 9.245 min. This resulted in 31.9 mg of Compound 106a, 1(R or S)-1-(2,3-dicyclopropyl-6,7-dihydro-5H-cyclopenta[b]pyridin-4-yl)-3-(6-(2-hydroxypropan-2-yl)-1-oxido-3-oxo-2,3-dihydro-1l4-benzo[d]isothiazol-1-ylidene)urea (isomer 1) as a white solid and 28.2 mg of Compound 106b, 1(S or R)-1-(2,3-dicyclopropyl-6,7-dihydro-5H-cyclopenta[b]pyridin-4-yl)-3-(6-(2-hydroxypropan-2-yl)-1-oxido-3-oxo-2,3-dihydro-1l4-benzo[d]isothiazol-1-ylidene)urea (isomer 2) as a white solid.

MS-ESI: 481.2 (M+1). $^1$H NMR: (400 MHz, MeOH-d4) δ: 8.28 (s, 1H), 7.89-7.86 (m, 1H), 7.77 (d, 1H), 3.10-3.06 (m, 2H), 2.99-2.93 (m, 1H), 2.88-2.82 (m, 1H), 2.63-2.59 (m, 1H), 2.17-2.13 (m, 2H), 1.83 (t, 1H), 1.56 (s, 3H), 1.55 (s, 3H), 1.27-1.23 (m, 2H), 1.11-1.04 (m, 4H), 0.57-0.53 (m, 2H)

TABLE E7

Examples in the following table were prepared using similar conditions as described in Example 58, from the appropriate racemate precursor noted in Table E7.

| Ex. # | Final Target # | Racemate Precursor | Structure | IUPAC Name | Exact Mass [M + H]$^+$ |
|---|---|---|---|---|---|
| 59 | Compound 112a | Compound 112 | 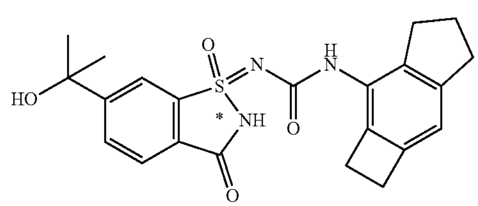 [SMILES: CC(C)(O)c1ccc2c(c1)S(=O)(=NC(=O)Nc1c3c(cc4c1CC4)CCC3)NC2=O] | (R or S)-1-(6-(2-hydroxypropan-2-yl)-1-oxido-3-oxo-2,3-dihydro-1l4-benzo[d]isothiazol-1-ylidene)-3-(2,4,5,6-tetrahydro-1H-cyclobuta[f]inden-3-yl)urea | 426.2 |
| 60 | Compound 112b | Compound 112 | 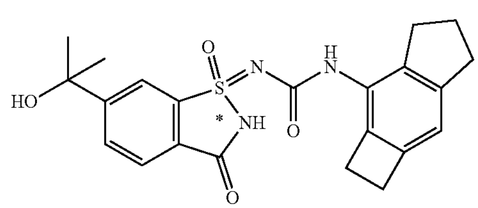 [SMILES: CC(C)(O)c1ccc2c(c1)S(=O)(=NC(=O)Nc1c3c(cc4c1CC4)CCC3)NC2=O] | (S or R)-1-(6-(2-hydroxypropan-2-yl)-1-oxido-3-oxo-2,3-dihydro-1l4-benzo[d]isothiazol-1-ylidene)-3-(2,4,5,6-tetrahydro-1H-cyclobuta[f]inden-3-yl)urea | 426.2 |

TABLE E7-continued

Examples in the following table were prepared using similar conditions as described in Example 58, from the appropriate racemate precursor noted in Table E7.

| Ex. # | Final Target # | Racemate Precursor | Structure | IUPAC Name | Exact Mass [M + H]+ |
|---|---|---|---|---|---|
| 61 | Compound 108a | Compound 108 | 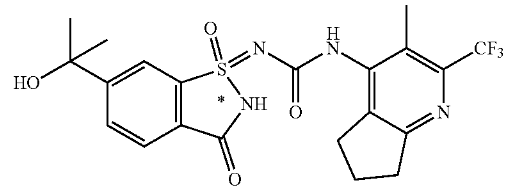 [SMILES: Cc1c(C(F)(F)F)nc2c(c1NC(=O)N=S1(=O)NC(=O)c3ccc(C(C)(C)O)cc31)CCC2] | (R or S)-1-(6-(2-hydroxypropan-2-yl)-1-oxido-3-oxo-2,3-dihydro-1l4-benzo[d]isothiazol-1-ylidene)-3-(3-methyl-2-(trifluoromethyl)-6,7-dihydro-5H-cyclopenta[b]pyridin-4-yl)urea | 483.2 |
| 62 | Compound 108b | Compound 108 | 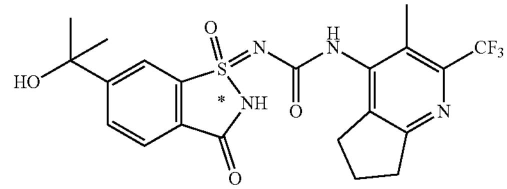 [SMILES: Cc1c(C(F)(F)F)nc2c(c1NC(=O)N=S1(=O)NC(=O)c3ccc(C(C)(C)O)cc31)CCC2] | (S or R)-1-(6-(2-hydroxypropan-2-yl)-1-oxido-3-oxo-2,3-dihydro-1l4-benzo[d]isothiazol-1-ylidene)-3-(3-methyl-2-(trifluoromethyl)-6,7-dihydro-5H-cyclopenta[b]pyridin-4-yl)urea | 483.2 |

Example 63: Synthesis of Compound 207 and Compound 208

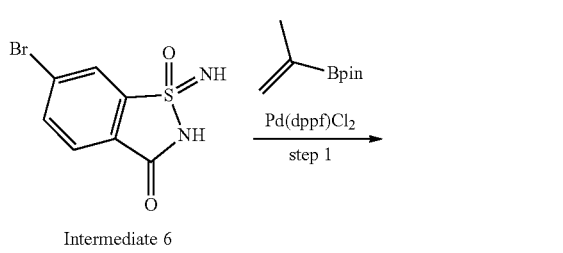

Compound 208

Step 1: 1-imino-6-(prop-1-en-2-yl)-1,2-dihydro-3H-1l4-benzo[d]isothiazol-3-one 1-oxide To a solution of 6-bromo-1-imino-1,2-dihydro-3H-1l4-benzo[d]isothiazol-3-one 1-oxide (100 mg, 0.4 mmol, 1.0 equiv.) and 4,4,5,5-tetramethyl-2-(prop-1-en-2-yl)-1,3,2-dioxaborolane (77 mg, 0.5 mmol, 1.2 equiv.) in dioxane/water (5 mL/0.5 mL), were added Pd(dppf)Cl$_2$ (28 mg, 0.04 mmol, 0.1 equiv.), X-Phos (36 mg, 0.08 mmol, 0.2 equiv.), and Cs$_2$CO$_3$ (374 mg, 1.1 mmol, 3.0 equiv.) under nitrogen. The resulting solution was stirred for 1 h at 100° C. and then concentrated under vacuum. The residue was purified by flash column chromatography on silica gel column, eluting with dichloromethane/methanol (9:1) to give 118 mg of 1-imino-6-(prop-1-en-2-yl)-1,2-dihydro-3H-1l4-benzo[d]isothiazol-3-one 1-oxide as a white solid. MS-ESI: 223.1 (M+1).

Step 2: 1-(1,2,3,5,6,7-hexahydro-s-indacen-4-yl)-3-(1-oxido-3-oxo-6-(prop-1-en-2-yl)-2,3-dihydro-1l4-benzo[d]isothiazol-1-ylidene)urea 4-isocyanato-1,2,3,5,6,7-hexahydro-s-indacene (106 mg, 0.5 mmol, 1.0 equiv.) was added to a 0° C. solution of 1-imino-6-(prop-1-en-2-yl)-1,2-dihydro-3H-1l4-benzo[d]isothiazol-3-one 1-oxide (118 mg, 0.5 mmol, 1.0 equiv.) and NaH (60% wt in mineral oil, 108 mg, 2.7 mmol, 2.0 equiv.) in THF (5 mL). The reaction mixture was stirred for 1 h at ambient temperature then concentrated under vacuum. The residue was purified by flash column chromatography on silica gel column, eluting with dichloromethane/methanol (8:1) to give 144 mg of Compound 207, 1-(1,2,3,5,6,7-hexahydro-s-indacen-4-yl)-3-(1-oxido-3-oxo-6-(prop-1-en-2-yl)-2,3-dihydro-1l4-benzo[d]isothiazol-1-ylidene)urea as a white solid. MS-ESI: 422.2 (M+1).

Step 3: 1-(6-(1,2-dihydroxypropan-2-yl)-1-oxido-3-oxo-2,3-dihydro-1l4-benzo[d]isothiazol-1-ylidene)-3-(1,2,3,5,6,7-hexahydro-s-indacen-4-yl)urea A 250-mL 3-necked round-bottom flask was placed under and atmosphere of nitrogen, then charged with a solution of 1-(1,2,3,5,6,7-hexahydro-s-indacen-4-yl)-3-(1-oxido-3-oxo-6-(prop-1-en-2-yl)-2,3-dihydro-1l4-benzo[d]isothiazol-1-ylidene)urea (144 mg, 0.3 mmol, 1.0 equiv.) in t-BuOH/acetone/water (1/1/1.5 ratio, 17.5 mL total volume). This was followed by the addition of N-Methylmorpholine-N-oxide (80 mg, 0.68 mmol, 2.3 equiv.) in one portion. Then $OSO_4$ (500 mg, 2.0 mmol, 6.7 equiv.) was added and the reaction mixture stirred for 10 h at ambient temperature. The reaction was quenched by the addition of 700 mg of $Na_2S_2O_3$, filtered, and the filtrate was concentrated in vacuo. The residue was purified by Prep-HPLC with the following conditions: Column, X Bridge Prep OBD C18 Column, 30*150 mm 5 μm; mobile phase, Water (10 mM $NH_4HCO_3$+ 0.1% $NH_4OH$) and ACN (8% Phase B up to 38% in 7 min); Detector, UV 254 nm. This resulted in 58 mg of Compound 208, 1-(6-(1,2-dihydroxypropan-2-yl)-1-oxido-3-oxo-2,3-dihydro-1l4-benzo[d]isothiazol-1-ylidene)-3-(1,2,3,5,6,7-hexahydro-s-indacen-4-yl)urea as a white solid. MS-ESI: 456.2 (M+1). $^1$H NMR: (400 MHz, MeOH-d4) δ: 8.30 (d, 1H), 7.90-7.87 (m, 1H), 7.78 (d, 1H), 6.90 (s, 1H), 3.70-3.62 (m, 2H), 2.87-2.74 (m, 8H), 2.06-1.99 (m, 4H), 1.56 (s, 2H).

TABLE E8

Examples in the following table were prepared using similar conditions as described in Example 63, from the appropriate enantiopure bromide, as noted in Table E8.

| Ex. # | Final Target # | Bromide | Structure | IUPAC Name | Exact Mass [M + H]$^+$ |
|---|---|---|---|---|---|
| 64 | Compound 208a | Intermediate 22 | 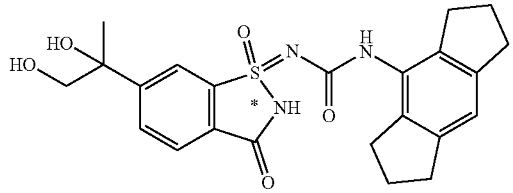 [SMILES: CC(O)(CO)c1ccc2c(c1)S(=O)(=NC(=O)Nc1c3c(cc4c1CCC4)CCC3)NC2=O] | 1-((1R or S)-6-(1,2-dihydroxypropan-2-yl)-1-oxido-3-oxo-2,3-dihydro-1l4-benzo[d]isothiazol-1-ylidene)-3-(1,2,3,5,6,7-hexahydro-s-indacen-4-yl)urea | 456.2 |
| 65 | Compound 208b | Intermediate 23 | 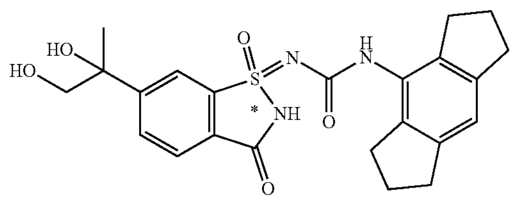 [SMILES: CC(O)(CO)c1ccc2c(c1)S(=O)(=NC(=O)Nc1c3c(cc4c1CCC4)CCC3)NC2=O] | 1-((1S or R)-6-(1,2-dihydroxypropan-2-yl)-1-oxido-3-oxo-2,3-dihydro-1l4-benzo[d]isothiazol-1-ylidene)-3-(1,2,3,5,6,7-hexahydro-s-iadacen-4-yl)urea | 456.2 |

TABLE E9

Examples in the following table were prepared using similar conditions as described in Example 10, through the coupling of Intermediate 27 with a respective coupling partner, as noted in Table E9

| Ex. # | Final Target # | Coupling Partner | Structure | IUPAC Name | Exact Mass [M + H]$^+$ |
|---|---|---|---|---|---|
| 66 | Compound 115a | Intermediate 11 | 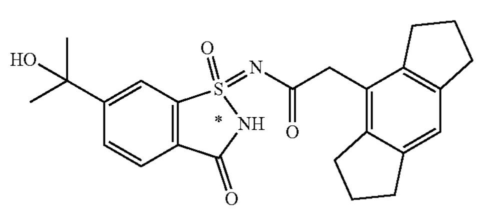 [SMILES: CC(C)(O)c1ccc2c(c1)S(=O)(=NC(=O)Cc1c3c(cc4c1CCC4)CCC3)NC2=O] | (S or R)-2-(1,2,3,5,6,7-hexahydro-s-indacen-4-yl)-N-(6-(2-hydroxypropan-2-yl)-1-oxido-3-oxo-2,3-dihydro-1l4-benzo[d]isothiazol-1-ylidene)acetamide | 439.2 |

TABLE E9-continued

Examples in the following table were prepared using similar conditions as described in Example 10, through the coupling of Intermediate 27 with a respective coupling partner, as noted in Table E9

| Ex. # | Final Target # | Coupling Partner | Structure | IUPAC Name | Exact Mass [M + H]+ |
|---|---|---|---|---|---|
| 67 | Compound 104a | Intermediate 12 | 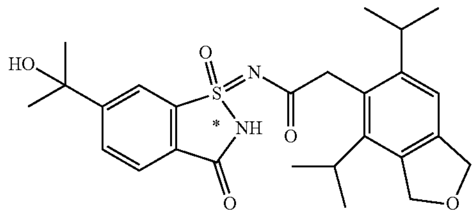 [SMILES: CC(C)c1cc2c(c(C(C)C)c1CC(=O)N=S1(=O)NC(=O)c3ccc(C(C)(C)O)cc31)COC2] | (S or R)-2-(4,6-diisopropyl-1,3-dihydroisobenzofuran-5-yl)-N-(6-(2-hydroxypropan-2-yl)-1-oxido-3-oxo-2,3-dihydro-1l4-benzo[d]isothiazol-1-ylidene)acetamide | 485.2 |

Example 68: Synthesis of Compound 139

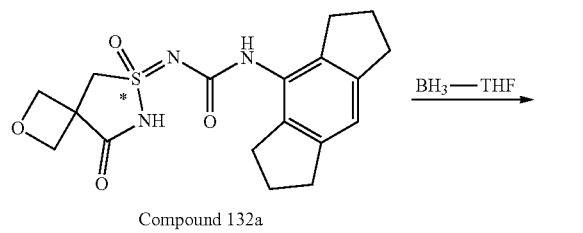

Compound 132a

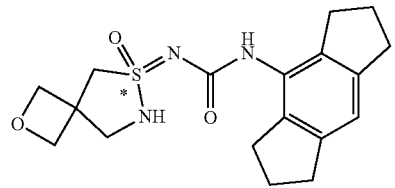

Compound 139a

Step 1: (S or R)-1-(1,2,3,5,6,7-hexahydro-s-indacen-4-yl)-3-(6-oxido-2-oxa-6l6-thia-7-azaspiro[3.4]octan-6-ylidene)urea To a solution of Compound 132a, (S or R)-1-(1,2,3,5,6,7-hexahydro-s-indacen-4-yl)-3-(6-oxido-8-oxo-2-oxa-6l6-thia-7-azaspiro[3.4]octan-6-ylidene)urea (5 mg, 0.01 mmol, 1.0 equiv.) in THF (3 mL) was added BH$_3$ (1M in THF, 0.1 mL, 0.1 mmol, 10.0 equiv.) at 0° C. The resulting solution was stirred for 5 h at 50° C. and then quenched by the addition of 0.5 mL of MeOH and concentrated under vacuum. The residue was purified by Prep-HPLC with the following conditions: Column: XSelect CSH Prep C18 OBD Column, 5 μm, 19*150 mm; Mobile Phase A: Water (10 mM NH$_4$HCO$_3$+0.1% NH$_4$OH), Mobile Phase B:ACN; Flow rate:25 mL/min; Gradient: 28% B to 43% B in 7 min; 254/210 nm. This resulted in 6.5 mg of (S or R)-1-(1,2,3,5,6,7-hexahydro-s-indacen-4-yl)-3-(6-oxido-2-oxa-6l6-thia-7-azaspiro[3.4]octan-6-ylidene)urea as a white solid. MS-ESI: 362.1 (M+1); $^1$H NMR (400 MHz, DMSO-d$_6$): 8.42 (s, 1H), 7.45 (s, 1H), 6.87 (s, 1H), 4.65 (t, 2H), 4.52-4.49 (m, 2H), 3.88-3.85 (m, 1H), 3.69-3.51 (m, 3H), 2.80-2.73 (m, 4H), 2.72-2.67 (m, 4H), 1.98-1.90 (m, 4H).

TABLE E10

Examples in the following table were prepared using similar conditions as described in Example 68.

| Ex. # | Final Target # | Precursor | Structure | IUPAC Name | Exact Mass [M + H]+ |
|---|---|---|---|---|---|
| 69 | Compound 139b | Compound 132b | 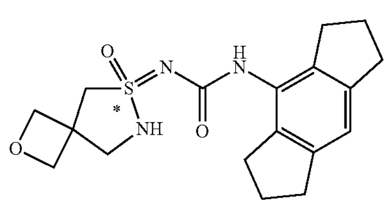 [SMILES: O=C(N=S1(=O)CC2(CN1)COC2)Nc1c2c(cc3c1CCC3)CCC2] | (R or S)-1-(1,2,3,5,6,7-hexahydro-s-indacen-4-yl)-3-(6-oxido-2-oxa-6l6-thiaspiro[3.4]octan-6-ylidene)urea | 362.1 |

Example 70: Synthesis of Compound 216

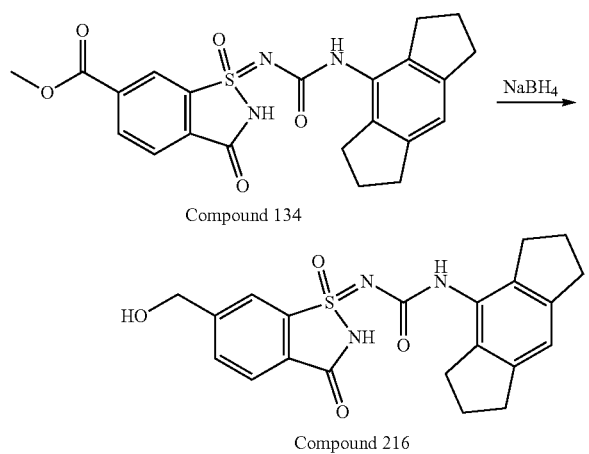

Compound 134

Compound 216

1-(1,2,3,5,6,7-hexahydro-s-indacen-4-yl)-3-(6-(hydroxymethyl)-1-oxido-3-oxo-2,3-dihydro-1l4-benzo[d]isothiazol-1-ylidene)urea To a solution of Compound 134, methyl 1-(((1,2,3,5,6,7-hexahydro-s-indacen-4-yl)carbamoyl)imino)-3-oxo-2,3-dihydro-1H-1l4-benzo[d]isothiazole-6-carboxylate 1-oxide (100 mg, 0.2 mmol, 1.0 equiv.) in THF, was added NaBH₄ (11 mg, 0.27 mmol, 1.2 equiv.). The resulting solution was stirred for 24 h at ambient temperature and then concentrated under vacuum. The residue was purified by Prep-HPLC with the following conditions: Column: XSelect CSH Prep C18 OBD Column, 5 μm, 19*150 mm; Mobile Phase A: Water (10 mM NH₄HCO₃+0.1% NH₄OH), Mobile Phase B. ACN; Flow rate-25 mL/min, Gradient: 10% B to 30% B in 10 min; 210/254 nm. This resulted in 17.5 mg of 1-(1,2,3,5,6,7-hexahydro-s-indacen-4-yl)-3-(6-(hydroxymethyl)-1-oxido-3-oxo-2,3-dihydro-1l4-benzo[d]isothiazol-1-ylidene)urea as a white solid. MS-ESI: 412.2 (M+1); ¹H NMR (400 MHz, MeOD-d₄): δ 8.16 (s, 1H), 7.80 (d, 1H), 7.72 (d, 1H), 6.91 (s, 1H), 4.88 (s, 2H), 2.84 (dt, 8H), 2.06-2.04 (m, 4H)

Example 71: Synthesis of Compound 217

Step 1: (1-(((1,2,3,5,6,7-hexahydro-s-indacen-4-yl)carbamoyl)imino)-1-oxido-3-oxo-2,3-dihydro-1H-1l4-benzo[d]isothiazol-6-yl)methyl methanesulfonate To a solution of 1-(1,2,3,5,6,7-hexahydro-s-indacen-4-yl)-3-(6-(hydroxymethyl)-1-oxido-3-oxo-2,3-dihydro-1l4-benzo[d]isothiazol-1-ylidene)urea (50 mg, 0.1 mmol, 1.0 equiv.) and TEA (0.05 mL, 0.35 mmol, 3.5 equiv.) in THF (5 mL), was added MsCl (20 mg, 0.15 mmol, 1.3 equiv.). The resulting solution was stirred for 1 h at ambient temperature and then concentrated under vacuum to give 60 mg of (1-(((1,2,3,5,6,7-hexahydro-s-indacen-4-yl)carbamoyl)imino)-1-oxido-3-oxo-2,3-dihydro-1H-1l4-benzo[d]isothiazol-6-yl)methyl methanesulfonate as a yellow solid. MS-ESI: 490.1 (M+1).

Step 2: 1-(1,2,3,5,6,7-hexahydro-s-indacen-4-yl)-3-(6-(methoxymethyl)-1-oxido-3-oxo-2,3-dihydro-1l4-benzo[d]isothiazol-1-ylidene)urea To a solution of (1-(((1,2,3,5,6,7-hexahydro-s-indacen-4-yl)carbamoyl)imino)-1-oxido-3-oxo-2,3-dihydro-1H-1l4-benzo[d]isothiazol-6-yl)methyl methanesulfonate (58 mg, 0.12 mmol, 1.0 equiv.) in MeOH (5 mL), was added NaOMe (8 mg, 0.14 mmol, 1.2 equiv.). The resulting solution was stirred overnight at ambient temperature and then quenched by the addition of 5 mL of saturate aqueous NH₄Cl. The resulting mixture was concentrated under vacuum and the crude product was purified by Prep-HPLC with the following conditions: Column: XSelect CSH Prep C18 OBD Column, 5 μm, 19*150 mm; Mobile Phase A: Water (10 mM NH₄HCO₃+0.1% NH₄OH), Mobile Phase 13: ACN; Flow rate. 25 mL/min, Gradient. 20% B to 35% B in 7 min, 210/254 nm. This resulted in 7.4 mg of 1-(1,2,3,5,6,7-hexahydro-s-indacen-4-yl)-3-(6-(methoxymethyl)-1-oxido-3-oxo-2,3-dihydro-1l4-benzo[d]isothiazol-1-ylidene)urea as a white solid. MS-ESI: 426.2 (M+1); ¹H NMR (400 MHz, MeOD-d4): δ 8.20 (s, 1H). 7.79 (d, 1H), 7.68 (d, 1H), 6.91 (s, 1H), 4.63 (s, 2H), 3.46 (s, 3H), 2.87-2.74 (m, 8H), 2.06-2.02 (m, 4H).

Example 72: Synthesis of Compound 218

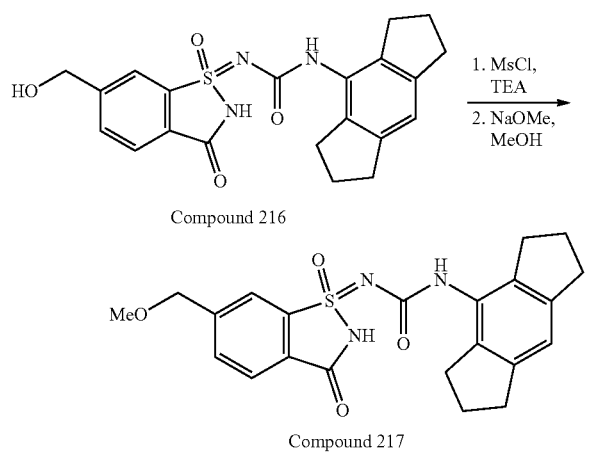

Compound 216

Compound 217

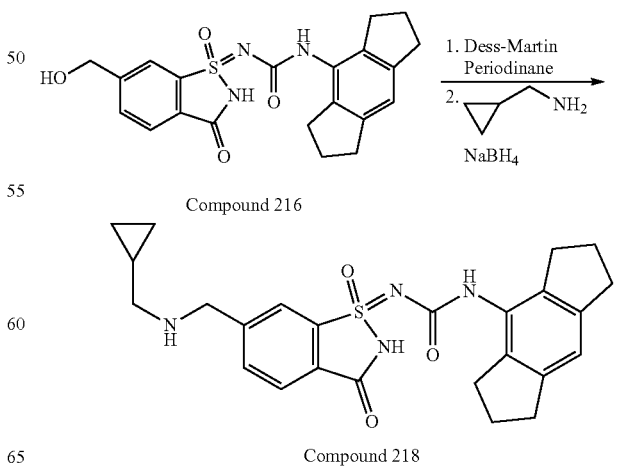

Compound 216

Compound 218

Step 1: 1-(6-formyl-1-oxido-3-oxo-2,3-dihydro-1λ4-benzo[d]isothiazol-1-ylidene)-3-(1,2,3,5,6,7-hexahydro-s-indacen-4-yl)urea To solution of 1-(1,2,3,5,6,7-hexahydro-s-indacen-4-yl)-3-(6-(hydroxymethyl)-1-oxido-3-oxo-2,3-dihydro-1λ4-benzo[d]isothiazol-1-ylidene)urea (200 mg, 0.49 mmol, 1.0 equiv.) in DCM (5 mL), was added Dess-Martin Periodinane (310 mg, 0.75 mmol, 1.5 equiv.). The resulting solution was stirred for 30 min at ambient temperature and concentrated under vacuum. The residue was purified by Prep-HPLC with the following conditions: Column: XBridge Prep C18 OBD Column, 19*150 mm 5 µm; Mobile Phase A: Water (10 mM NH$_4$HCO$_3$+0.1% NH$_4$OH), Mobile Phase B: ACN; Flow rate: 25 mL/min; Gradient: 21% B to 37% B in 7 min; 210/254 nm. This resulted in 14 mg of 1-(6-formyl-1-oxido-3-oxo-2,3-dihydro-1λ4-benzo[d]isothiazol-1-ylidene)-3-(1,2,3,5,6,7-hexahydro-s-indacen-4-yl)urea as a yellow solid. MS-ESI. 410.1 (M+1).

Step 2: 1-(6-(((cyclopropylmethyl)amino)methyl)-1-oxido-3-oxo-2,3-dihydro-1λ4-benzo[d]isothiazol-1-ylidene)-3-(1,2,3,5,6,7-hexahydro-s-indacen-4-yl)urea To a solution of 1-(6-formyl-1-oxido-3-oxo-2,3-dihydro-1λ4-benzo[d]isothiazol-1-ylidene)-3-(1,2,3,5,6,7-hexahydro-s-indacen-4-yl)urea (10 mg, 0.02 mmol, 1.0 equiv.) in MeOH (5 mL), was added 1-cyclopropylmethanamine (10 mg, 0.14 mmol, 0.7 equiv.). The resulting solution was stirred for overnight at ambient temperature, then NaBH$_4$ (4 mg, 0.1 mmol, 5.0 equiv.) was added. The reaction mixture was stirred for an additional 1 h and then concentrated under vacuum. The residue was purified by Prep-HPLC with the following conditions: Column: XSelect CSH Prep C18 OBD Column, 5 µm; 19*150 mm; Mobile Phase A: Water (10 mM NH$_4$HCO$_3$+0.1% NH$_4$OH), Mobile Phase B: ACN; Flow rate: 25 mL/min; Gradient: 2 0% B to 44% B in 7 min; 210/254 nm. This resulted in 3 mg of 1-(6-(((cyclopropylmethyl)amino)methyl)-1-oxido-3-oxo-2,3-dihydro-1λ4-benzo[d]isothiazol-1-ylidene)-3-(1,2,3,5,6,7-hexahydro-s-indacen-4-yl)urea as a white solid. MS-ESI 464.2 (M+1); $^1$H NMR (400 MHz, MeOD-d4). δ 8.25 (s, 1H), 7.83 (d, 1H), 7.74 (d, 1H), 6.92 (s, 1H), 4.19-4.11 (m, 2H), 2.90-2.71 (m, 10H), 2.07-2.00 (m, 4H), 1.07-1.02 (m, 1H), 0.62-0.60 (m, 2H), 0.30-0.27 (m, 2H).

Example 73: Synthesis of Compound 212 and Compound 214

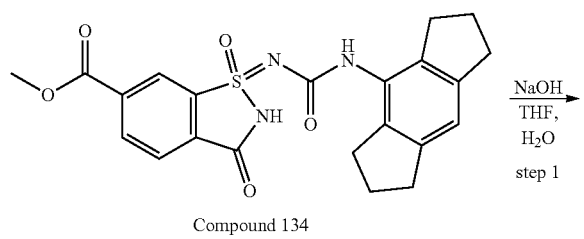

Compound 134

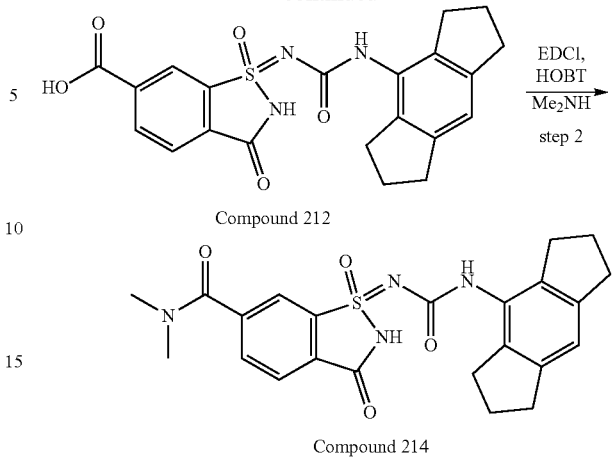

Compound 212

Compound 214

Step 1: 1-(((1,2,3,5,6,7-hexahydro-s-indacen-4-yl)carbamoyl)imino)-3-oxo-2,3-dihydro-1H-1λ4-benzo[d]isothiazole-6-carboxylic acid 1-oxide To a solution of methyl 1-(((1,2,3,5,6,7-hexahydro-s-indacen-4-yl)carbamoyl)imino)-3-oxo-2,3-dihydro-1H-1λ4-benzo[d]isothiazole-6-carboxylate 1-oxide (500 mg, 1.1 mmol, 1.00 equiv.) in THF/water (20 mL/5 mL), was added NaOH (230 mg, 5.7 mmol, 5.0 equiv.) The resulting solution was stirred for 16 h at ambient temperature. The reaction was concentrated to remove THF and then diluted with 30 mL of water. The mixture was washed with ethyl acetate and the aqueous layer was adjusted to pH 1 via the addition of 6N aqueous. HCl, then extracted with DCM and the combined organic layers were concentrated under vacuum to give 310 mg of Compound 212, 1-(((1,2,3,5,6,7-hexahydro-s-indacen-4-yl)carbamoyl)imino)-3-oxo-2,3-dihydro-1H-1λ4-benzo[d]isothiazole-6-carboxylic acid 1-oxide as a white syrup MS-ESI: 426.2 (M+1)

Step 2: 1-(((1,2,3,5,6,7-hexahydro-s-indacen-4-yl)carbamoyl)imino)-N,N-dimethyl-3-oxo-2,3-dihydro-1H-1λ4-benzo[d]isothiazole-6-carboxamide 1-oxide To a solution of 1-(((1,2,3,5,6,7-hexahydro-s-indacen-4-yl)carbamoyl)imino)-3-oxo-2,3-dihydro-1H-1λ4-benzo[d]isothiazole-6-carboxylic acid 1-oxide (50 mg, 0.12 mmol, 1.0 equiv.) in DCM (15), were added EDCI (34 mg, 0.18 mmol, 1.5 equiv.), HOBT (24 mg, 0.18 mmol, 1.5 equiv.), and dimethylamine hydrochloride (15 mg, 0.18 mmol, 1.5 equiv.). The resulting solution was stirred for 14 h at ambient temperature and then concentrated under vacuum. The crude product was purified by Prep-HPLC with the following conditions: Column: XSelect CSH Prep C18 OBD Column, 5 µm, 19*150 mm; Mobile Phase A: Water (10 mM NH$_4$HCO$_3$+0.1% NH$_4$OH), Mobile Phase B:ACN; Flow rate: 25 mL/min; Gradient: 17% B to 47% B in 7 min; 254/210 nm. This resulted in 10 mg of Compound ʃ, 1-(((1,2,3,5,6,7-hexahydro-s-indacen-4-yl)carbamoyl)imino)-N,N-dimethyl-3-oxo-2,3-dihydro-1H-1λ4-benzo[d]isothiazole-6-carboxamide 1-oxide as a white solid. MS-ESI: 453.2 (M+1), $^1$H NMR (400 MHz, MeOD-d$_4$): δ 8.24 (s, 1H), 7.92 (d, 1H), 7.77 (d, 1H), 6.92 (s, 1H), 3.16 (s, 3H), 3.06 (s, 3H), 2.90-2.73 (m, 8H), 2.06-1.98 (m, 4H).

TABLE E11

Examples in the following table were prepared using similar conditions as described in Example 73, through the coupling of Compound 212 with a respective amine, as noted in Table E11.

| Ex. # | Final Target # | amine | Structure | IUPAC Name | Exact Mass [M + H]⁺ |
|---|---|---|---|---|---|
| 74 | Compound 213 | 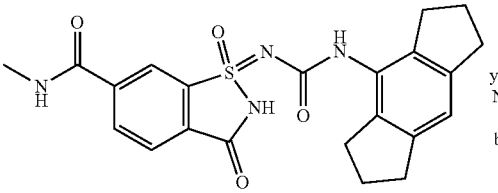 | 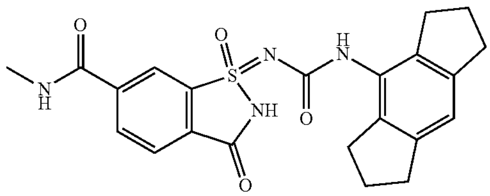 [SMILES: CNC(=O)c1ccc2c(c1)S(=O)(=NC(=O)Nc1c3c(cc4c1CCC4)CCC3)NC2=O] | 1-(((1,2,3,5,6,7-hexahydro-s-indacen-4-yl)carbamoyl)imino)-N-methyl-3-oxo-2,3-dihydro-1H-1λ4-benzo[d]isothiazole-6-carboxamide 1-oxide | 439.0 |

Example 75: Synthesis of Compound 249a and Compound 249b

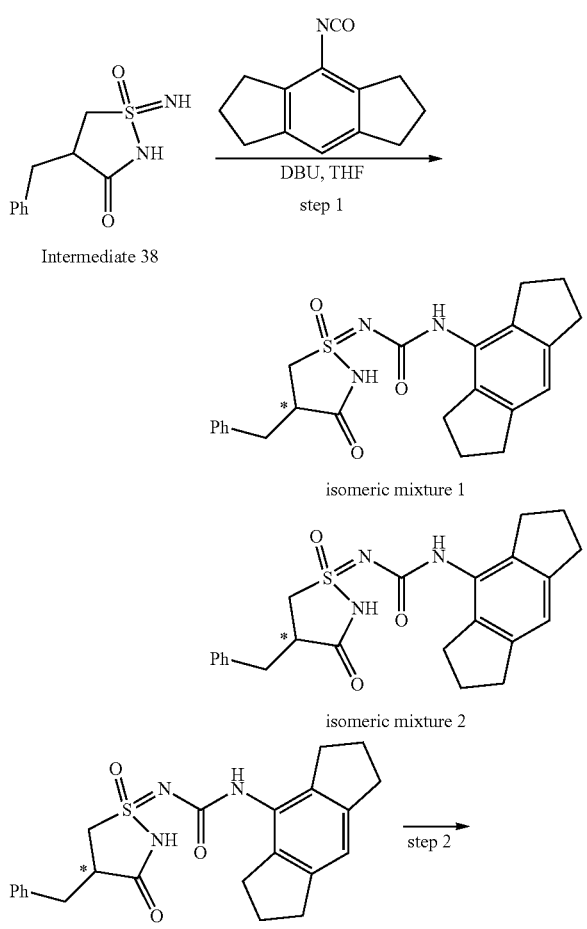

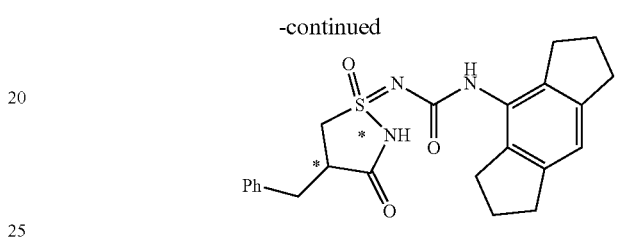

Compound 249b

Step 1: Isomer 2

To a solution of 4-benzyl-1-imino-1λ6-isothiazolidin-3-one 1-oxide (100 mg, 0.45 mmol, 1.0 equiv.), 4-isocyanato-1,2,3,5,6,7-hexahydro-s-indacene (105 mg, 0.55 mmol, 1.2 equiv) in THF (10 mL), was added DBU (110 mg, 0.45 mmol, 1.0 equiv.). The resulting solution was stirred for 1 h at ambient temperature and then concentrated. The residue was purified by Prep-HPLC with the following conditions: Column: XBridge Prep OBD C18 Column, 30×150 mm, 5 μm; Mobile Phase A: Water (10 mM NH₄HCO₃+0.1% NH₄OH), Mobile Phase B: ACN; Flow rate: 60 mL/min; Gradient: 20% B to 50% B in 7 min; 254/210 nm. This resulted in 25.1 mg of isomeric mixture 1 (front peak, mixture of two diastereomers) as a white solid and 25.2 mg of isomeric mixture 2 (second peak, mixture of two diastereomers) as a white solid. MS-ESI: 424.2 (M+1).

Step 2: Isomer 2A

The isomeric mixture 2 (25 mg) was resolved by Prep-SFC with the following conditions: Column: CHIRALPAK AD-H-TC001 SFC, 2*25 cm, 5 μm; Mobile Phase A: CO₂, Mobile Phase B: MeOH (8 mM NH₃); Flow rate: 40 mL/min; 220 nm; RT1: 7.45 min; RT2: 10.54 min. This resulted in 3.9 mg of 1-((1R,4S or 4R)-4-benzyl-1-oxido-3-oxo-1λ6-isothiazolidin-1-ylidene)-3-(1,2,3,5,6,7-hexahydro-s-indacen-4-yl)urea (Compound 249a) as an off-white solid and 4.4 mg of 1-[(1S,4S or 4R)-4-benzyl-1-oxido-3-oxo-1λ6-isothiazolidin-1-ylidene]-3-(1,2,3,5,6,7-hexahydro-s-indacen-4-yl)urea (Compound 249b) as an off-white solid. Compound 249a: MS-ESI: 424.2 (M+1); ¹H NMR (400 MHz, MeOD-d4): δ 7.30-7.18 (m, 5H), 6.92 (s, 1H), 3.69 (br s, 1H), 3.48-3.45 (m, 2H), 3.34-3.31 (m, 1H), 2.95-2.91 (m, 1H), 2.89-2.79 (m, 8H), 2.08-2.04 (m, 4H).

The following protocol is suitable for testing the activity of the compounds disclosed herein.

Procedure 1: IL-1β Production in PMA-Differentiated THP-1 Cells Stimulated with Gramicidin.

THP-1 cells were purchased from the American Type Culture Collection and sub-cultured according to instructions from the supplier. Cells were cultured in complete RPMI 1640 (containing 10% heat inactivated FBS, penicillin (100 units/ml) and streptomycin (100 μg/ml)), and maintained in log phase prior to experimental setup. Prior to the experiment, compounds were dissolved in dimethyl sulfoxide (DMSO) to generate a 30 mM stock. The compound stock was first pre-diluted in DMSO to 3, 0.34, 0.042 and 0.0083 mM intermediate concentrations and subsequently spotted using Echo550 liquid handler into an empty 384-well assay plate to achieve desired final concentration (e.g. 100, 33, 11, 3.7, 1.2, 0.41, 0.14, 0.046, 0.015, 0.0051, 0.0017 μM). DMSO was backfilled in the plate to achieve a final DMSO assay concentration of 0.37%. The plate was then sealed and stored at room temperature until required.

THP-1 cells were treated with PMA (Phorbol 12-myristate 13-acetate) (20 ng/ml) for 16-18 hours. On the day of the experiment the media was removed and adherent cells were detached with trypsin for 5 minutes. Cells were then harvested, washed with complete RPMI 1640, spun down, and resuspended in RPMI 1640 (containing 2% heat inactivated FBS, penicillin (100 units/ml) and streptomycin (100 μg/ml). The cells were plated in the 384-well assay plate containing the spotted compounds at a density of 50,000 cells/well (final assay volume 50 μl). Cells were incubated with compounds for 1 hour and then stimulated with gramicidin (5 μM) (Enzo) for 2 hours. Plates were then centrifuged at 340 g for 5 min. Cell free supernatant (40 μL) was collected using a 96-channel PlateMaster (Gilson) and the production of IL-1β was evaluated by HTRF (cisbio). The plates were incubated for 18 h at 4° C. and read using the preset HTRF program (donor emission at 620 nm, acceptor emission at 668 nm) of the SpectraMax i3x spectrophotometer (Molecular Devices, software SoftMax 6). A vehicle only control and a dose titration of CRID3 (100-0.0017 μM) were run concurrently with each experiment. Data was normalized to vehicle-treated samples (equivalent to 0% inhibition) and CRID3 at 100 μM (equivalent to 100% inhibition). Compounds exhibited a concentration-dependent inhibition of IL-1β production in PMA-differentiated THP-1 cells.

Procedure 2: IL-1β Production in PMA-Differentiated THP-1 Cells Stimulated with Gramicidin.

THP-1 cells were purchased from the American Type Culture Collection and sub-cultured according to instructions from the supplier. Prior to experiments, cells were cultured in complete RPMI 1640 (containing 10% heat inactivated FBS, penicillin (100 units/ml) and streptomycin (100 μg/ml)), and maintained in log phase prior to experimental setup. Prior to the experiment THP-1 were treated with PMA (Phorbol 12-myristate 13-acetate) (20 ng/ml) for 16-18 hours. Compounds were dissolved in dimethyl sulfoxide (DMSO) to generate a 30 mM stock. On the day of the experiment the media was removed and adherent cells were detached with trypsin for 5 minutes. Cells were then harvested, washed with complete RPMI 1640, spun down, resuspended in RPMI 1640 (containing 2% heat inactivated FBS, penicillin (100 units/ml) and streptomycin (100 μg/ml). The cells were plated in a 384-well plate at a density of 50,000 cells/well (final assay volume 50 μl). Compounds were first dissolved in assay medium to obtain a 5× top concentration of 500 μM. 10 step dilutions (1:3) were then undertaken in assay medium containing 1.67% DMSO. 5× compound solutions were added to the culture medium to achieve desired final concentration (e.g. 100, 33, 11, 3.7, 1.2, 0.41, 0.14, 0.046, 0.015, 0.0051, 0.0017 μM). Final DMSO concentration was at 0.37%. Cells were incubated with compounds for 1 hour and then stimulated with gramicidin (5 μM) (Enzo) for 2 hours. Plates were then centrifuged at 340 g for 5 min. Cell free supernatant (40 μL) was collected using a 96-channel PlateMaster (Gilson) and the production of IL-1β was evaluated by HTRF (cisbio). A vehicle only control and a dose titration of CRID3 (100-0.0017 μM) were run concurrently with each experiment. Data was normalized to vehicle-treated samples (equivalent to 0% inhibition) and CRID3 at 100 μM (equivalent to 100% inhibition). Compounds exhibited a concentration-dependent inhibition of IL-1β production in PMA-differentiated THP-1 cells.

Procedure 3

1. Experimental procedure 1.1 Cell Culture
1) Culture THP-1 cells in the complete RPMI-1640 medium with 10% FBS at 37° C., 5% $CO_2$.
2) Passage the cells every 3 days by inoculating $3\times10^5$ cells per ml.

Figure 5:
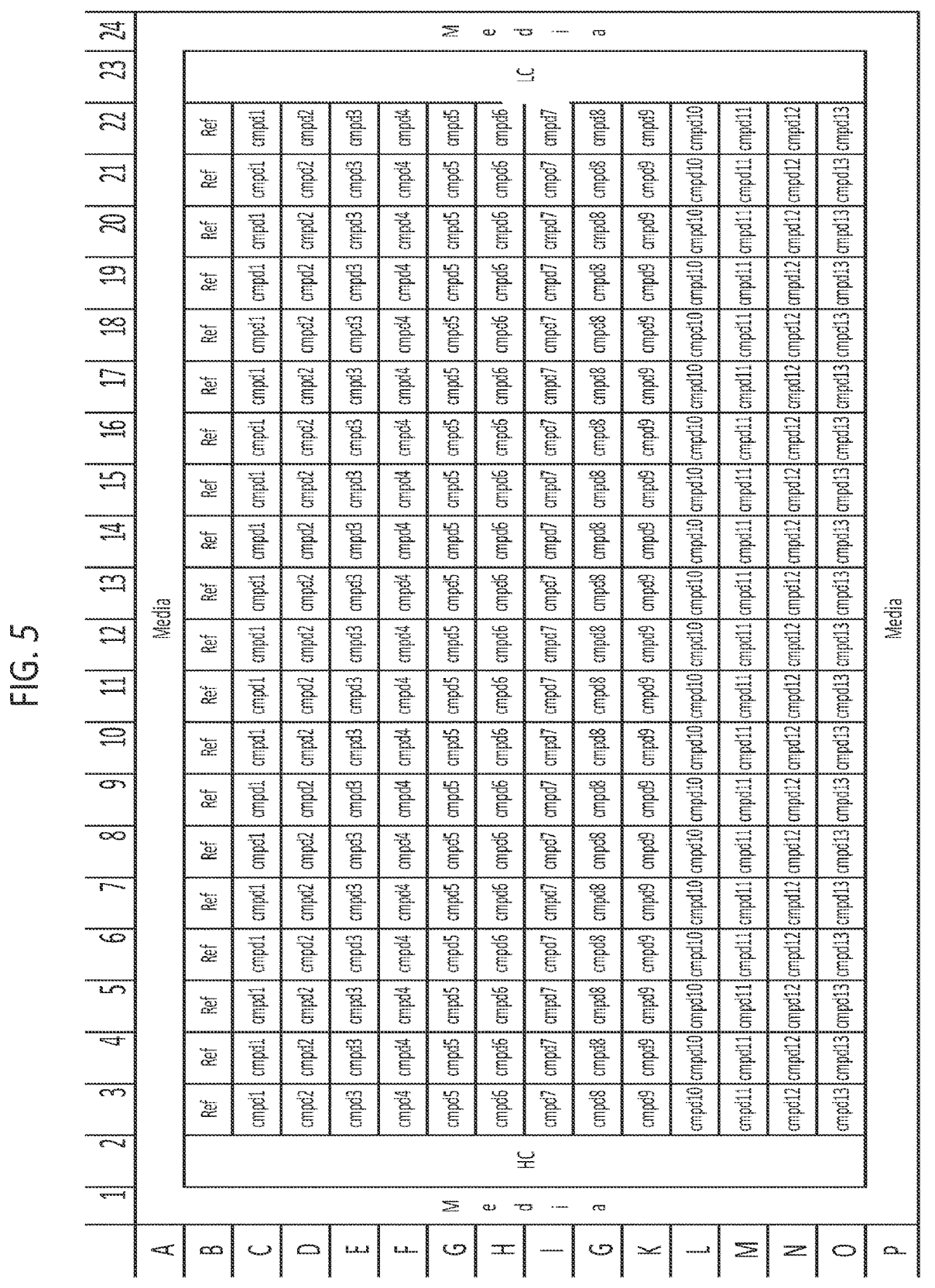

1.2 Compound Preparation
Prepare the 3-fold serial dilution of the compounds with DMSO in a 384-well LDV Microplate using TECAN EVO system to generate the compound source plate with 10 concentrations. Top concentration is 30 mM. FIG. 5 depicts the layout of the microplate.

1.3 Cell Preparation
1) Centrifuge THP-1 cells at 350 g for 5 min.
2) Re-suspend cells with complete RMPI-1640 medium, and count cells.
3) Seed cells in T225 flask, about $2.5\times10^7$ per flask, treat cells with 20 ng/ml PMA (final DMSO concentration<1%).
4) Incubate overnight.

1.4 THP-1 Stimulation
1) Wash adherent THP-1 cells with PBS, and detach cells with 4 ml trypsin for T225 flask.
2) Centrifuge cells at 350 g for 5 min, re-suspend cells with RPMI-1640 containing 2% FBS and count cells with trypan blue.
3) Transfer 50 nl/well the serial dilution of test compound to 384-well plate by Echo; For the high control and first point of CRID3 (MCC950), transfer 165 nl, then back-fill to make the DMSO concentration is consistent in all wells, the plate layout is as below.
4) Seed 50 k cells in 40 ul RPMI-1640 with 2% FBS per well in 384-well plate.
5) Incubate for 1 h at 37° C., 5% $CO_2$.
6) Prepare 5× gramicidin, add 10 μl per well, the final concentration is 5 μM, incubate for 2 hrs at 37° C., 5% $CO_2$.
7) Centrifuge at 350 g for 1 min.
8) Pipet 16 μl supernatant by apricot, and transfer into white 384 proxiplate. FIG. 5 depicts the layout of the plates: HC: 100 μM CRID3 (MCC950)+5 μM gramicidin LC: 5 μM Gramicidin.

1.5 IL-1β Detection
1) Homogenize the 5× diluent #5 with a vortex and add 1 volume of stock solution in 4 volumes of distilled water.
2) Thaw 20× stock solution of anti-IL1β-Cryptate-antibody and anti-IL1β XL-antibody. Dilute these two antibodies to 1× with detection buffer #3.

3) Pre-mix the two ready-to-use antibody solutions just prior to use.
4) Dispense 4 ul of pre-mixed Anti-IL1β antibodies working solution into all wells.
5) Seal the plate and incubate overnight at 4° C.
6) Read the cell plate using EnVison and plot Readout vs. the test compound concentration to calculate the $IC_{50}$.

2. Data Analysis:
   1. $IC_{50}$ of compounds can be calculated using the following formulas
   Formula for $IC_{50}$ % inhibition=$100-100\times[HC_{ave}-\text{Readout}/(HC_{ave}-LC_{ave})]$ 2. Fit the normalized data in a dose-response manner using XLfit, and calculate the compound concentration. Table BA shows the biological activity of compounds in hTHP-1 assay containing 2% fetal bovine serum: <0.008 μM="++++++"; ≥0.008 and <0.04 μM="+++++"; ≥0.04 and <0.2 μM="++++"; ≥0.2 and <1 μM="+++"; ≥1 and <5 μM="++"; ≥5 and <30 μM="+".

TABLE BA

Average $IC_{50}$ of compounds in hTHP-1 assay

| Compound No. | NLRP3 Antagonist, hNLRP3 (THP-1, IL-1b) Normalized: GeoMean IC50 (uM) | Compound No. | NLRP3 Antagonist, hNLRP3 (THP-1, IL-1b) Normalized: GeoMean IC50 (uM) |
|---|---|---|---|
| 101 | ++ | 102a | +++ |
| 102 | +++ | 102b | + |
| 103 | ++ | 103a | >30 |
| 104 | >30 | 103b | + |
| 105 | +++ | 104a | >30 |
| 106 | ++ | 106a | ++ |
| 107 | >30 | 106b | >30 |
| 108 | ++ | 107a | >30 |
| 109 | >30 | 107b | >30 |
| 110 | ++ | 108a | +++ |
| 112 | +++ | 108b | >30 |
| 113 | ++ | 112a | ++++ |
| 114 | >30 | 112b | ++ |
| 115 | >30 | 113a | +++ |
| 116 | >30 | 115a | + |
| 117 | ++ | 116a | >30 |
| 118 | ++ | 116b | >30 |
| 119 | + | 119a | + |
| 120 | +++ | 121a | +++ |
| 121 | +++ | 121b | + |
| 122 | + | 123a | >30 |
| 123 | >30 | 123b | >30 |
| 124 | >30 | 124a | >30 |
| 125 | + | 124b | >30 |
| 126 | >30 | 127a | ++++ |
| 127 | +++ | 127b | + |
| 128 | + | 129a | +++ |
| 129 | ++ | 129b | + |
| 132 | ++ | 130a | >30 |
| 133 | + | 131a | ++ |
| 134 | + | 132a | ++ |
| 135 | ++++ | 132b | + |
| 136 | +++ | 133a | + |
| 137 | +++ | 133b | >30 |
| 138 | +++ | 134a | >30 |
| 204 | +++ | 134b | + |
| 207 | + | 139a | >30 |
| 208 | ++++ | 139b | >30 |
| 209 | + | 208a | ++ |
| 211 | >30 | 208b | ++++ |
| 213 | ++ | 211a | + |
| 214 | + | 211b | >30 |
| 216 | +++ | 223a | ++ |
| 217 | +++ | 223b | + |
| 218 | +++ | 249a | +++ |
| 223 | + | | |

TABLE BA-continued

Average $IC_{50}$ of compounds in hTHP-1 assay

| Compound No. | NLRP3 Antagonist, hNLRP3 (THP-1, IL-1b) Normalized: GeoMean IC50 (uM) | Compound No. | NLRP3 Antagonist, hNLRP3 (THP-1, IL-1b) Normalized: GeoMean IC50 (uM) |
|---|---|---|---|
| 229 | + | | |
| 253 | +++ | | |
| 266 | + | | |

Study Example 1

The CARD8 gene is located within the inflammatory bowel disease (IBD) 6 linkage region on chromosome 19. CARD8 interacts with NLRP3, and Apoptosis-associated Speck-like protein to form a caspase-1 activating complex termed the NLRP3 inflammasome. The NLRP3 inflammasome mediates the production and secretion of interleukin-1β, by processing pro-IL-1β into mature secreted IL-1β. In addition to its role in the inflammasome, CARD8 is also a potent inhibitor of nuclear factor NF-κB. NF-κB activation is essential for the production of pro-IL-1. Since overproduction of IL-1β and dyregulation of NF-κB are hallmarks of Crohn's disease, CARD8 is herein considered to be a risk gene for inflammatory bowel disease. A significant association of CARD8 with Crohn's disease was detected in two British studies with a risk effect for the minor allele of the non-synonymous single-nucleotide polymorphism (SNP) of a C allele at rs2043211. This SNP introduces a premature stop codon, resulting in the expression of a severely truncated protein. This variant CARD8 protein is unable to suppress NF-κB activity, leading to constitutive production of pro-IL-1β, which is a substrate for the NLRP3 inflammasome. It is believed that a gain-of-function mutation in an NLRP3 gene (e.g., any of the gain-of-function mutations described herein, e.g., any of the gain-of-function mutations in an NLRP3 gene described herein) combined with a loss-of-function mutation in a CARD8 gene (e.g., a C allele at rs2043211) results in the development of diseases related to increased NLRP3 inflammasome expression and/or activity. Patients having, e.g., a gain-of-function mutation in an NLRP3 gene and/or a loss-of-function mutation in a CARD8 gene are predicted to show improved therapeutic response to treatment with an NLRP3 antagonist.

A study is designed to determine: whether NLRP3 antagonists inhibit inflammasome function and inflammatory activity in cells and biopsy specimens from patients with Crohn's disease or ulcerative colitis; and whether the specific genetic variants identify patients with Crohn's disease or ulcerative colitis who are most likely to respond to treatment with an NLRP3 antagonist.

The secondary objectives of this study are to: determine if an NLRP3 antagonist reduces inflammasome activity in Crohn's disease and ulcerative biopsy samples (comparing Crohn's disease and ulcerative colitis results with control patient results); determine if an NLRP3 antagonist reduced inflammatory cytokine RNA and protein expression in Crohn's disease and ulcerative colitis samples; determine if baseline (no ex vivo treatment) RNA levels of NLRP3, ASC, and IL-1β are greater in biopsy samples from patients with anti-TNFα agent resistance status; and stratify the results according to presence of specific genetic mutations in genes encoding ATG16L1, NLRP3, and CARD8 (e.g., any of the mutations in the ATG16L1 gene, NLRP3 gene, and CARD8 gene described herein).

Methods
　Evaluation of baseline expression of NLRP3 RNA and quantify inhibition of inflammasome activity by an NLRP3 antagonist in biopsies of disease tissue from patients with Crohn's disease and ulcerative colitis.
　Determine if NLRP3 antagonist treatment reduces the inflammatory response in biopsies of disease from patients with Crohn's disease based on decreased expression of inflammatory gene RNA measured with Nanostring.
　Sequence patient DNA to detect specific genetic mutations in the ATG16L1 gene, NLRP3 gene, and CARD8 gene (e.g., any of the exemplary mutations in these genes described herein) and then stratify the results of functional assays according to the presence of these genetic mutations.
Experimental Design
　Human subjects and tissue:
　　Endoscopic or surgical biopsies from areas of disease in patients with Crohn's disease and ulcerative colitis who are either anti-TNFα treatment naïve or resistant to anti-TNFα treatment; additionally biopsies from control patients (surveillance colonoscopy or inflammation-free areas from patients with colorectal cancer) are studied.
　Ex vivo Treatment Model:
　　Organ or LPMC culture as determined appropriate
　Endpoints to be measured:
　　Before ex vivo treatment—NLRP3 RNA level
　　After ex vivo treatment—inflammasome activity (either processed IL-1β, processed caspase-1, or secreted IL-1β); RNA for inflammatory cytokines (Nanostring); viable T cell number and/or T cell apoptosis.
　Data Analysis Plan:
　　Determine if NLRP3 antagonist treatment decreases processed IL-1β, processed caspase-1 or secreted IL-1β, and inflammatory cytokine RNA levels.
　　Stratify response data according to treatment status at biopsy and the presence of genetic mutations in the NLRP3 gene, CARD8 gene, and ATG16L1 gene (e.g., any of the exemplary genetic mutations of these genes described herein).

Figure 2:
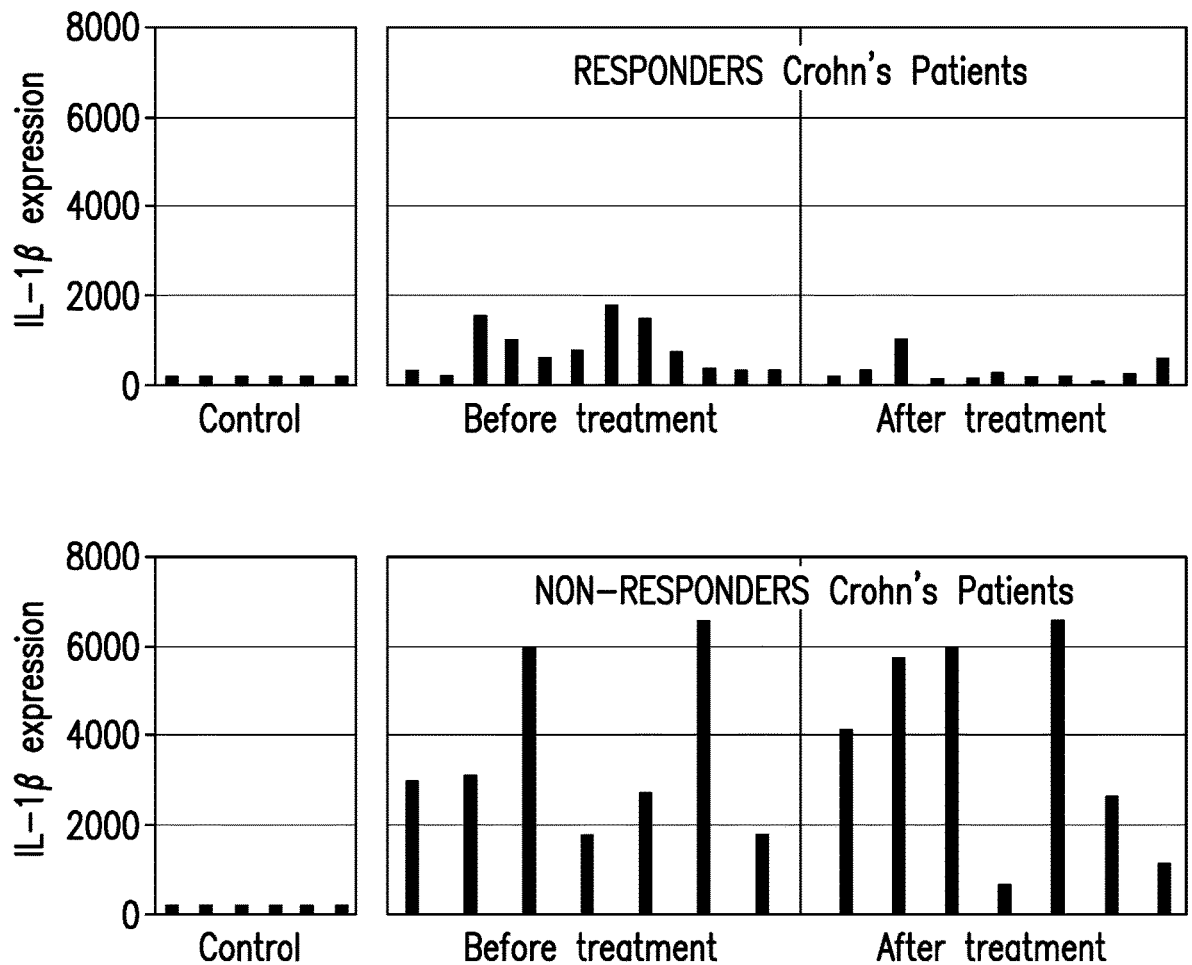
FIG. 2: Expression levels of RNA encoding IL-1β in Crohn's Disease patients who are responsive and non-responsive to infliximab.
Figure 3:
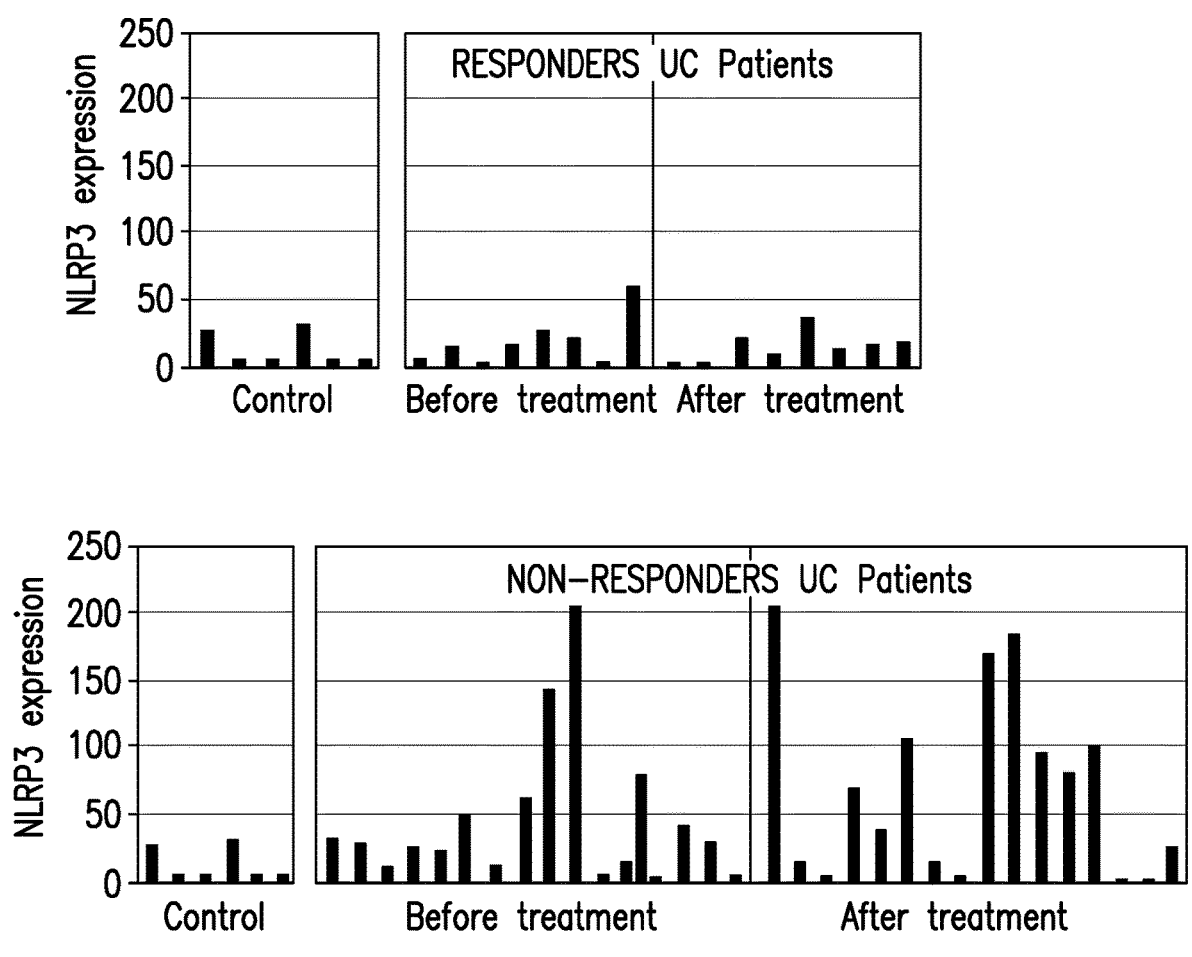
FIG. 3: Expression levels of RNA encoding NLRP3 in Ulcerative Colitis (UC) patients who are responsive and non-responsive to infliximab.
Figure 4:
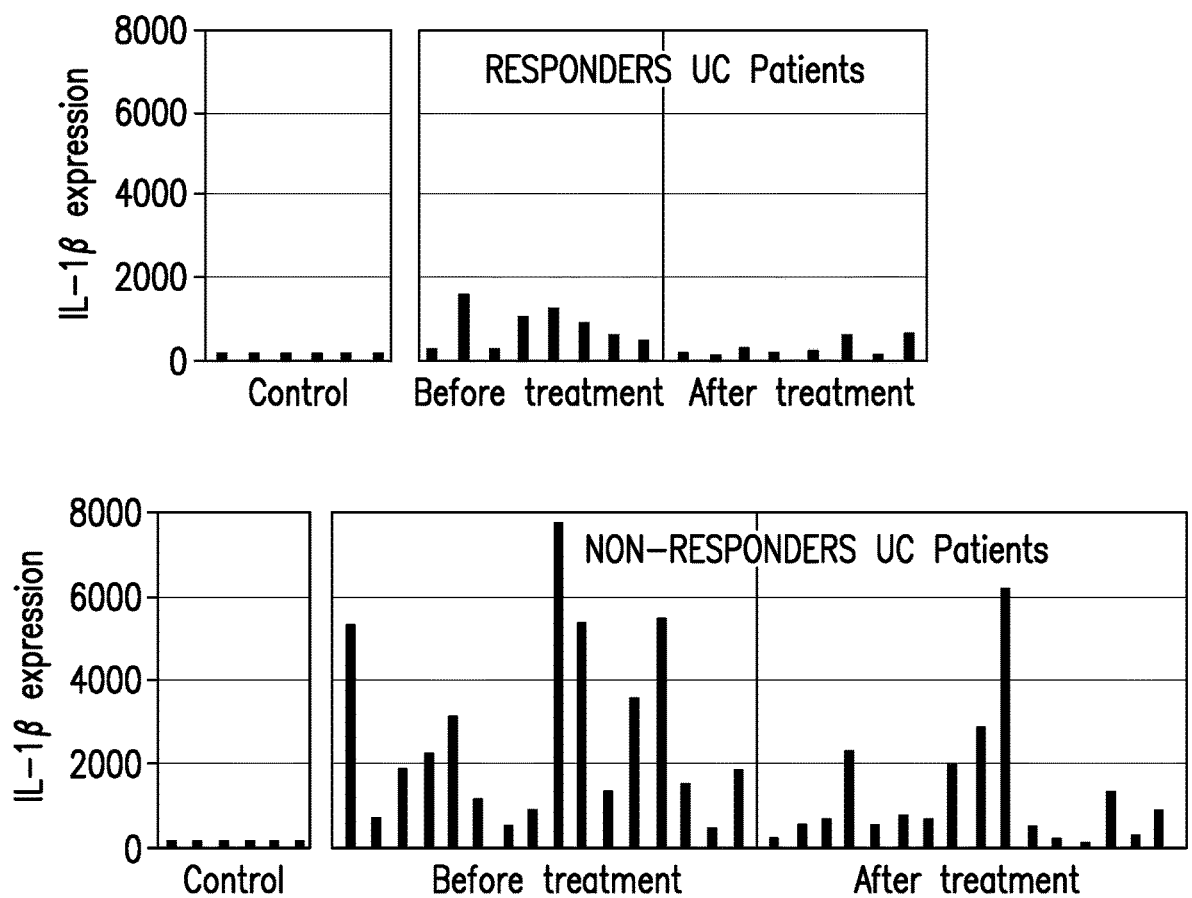
FIG. 4: Expression levels of RNA encoding IL-1β in Ulcerative Colitis (UC) patients who are responsive and non-responsive to infliximab.

Study Example 2. Treatment of Anti-TNFα Resistant Patients with NLRP3 Antagonists PLoS One 2009 Nov. 24; 4(11):e7984, describes that mucosal biopsies were obtained at endoscopy in actively inflamed mucosa from patients with Ulcerative Colitis, refractory to corticosteroids and/or immunosuppression, before and 4-6 weeks after their first infliximab (an anti-TNFα agent) infusion and in normal mucosa from control patients. The patients in this study were classified for response to infliximab based on endoscopic and histologic findings at 4-6 weeks after first infliximab treatment as responder or non-responder. Transcriptomic RNA expression levels of these biopsies were accessed by the inventors of the invention disclosed herein from GSE 16879, the publically available Gene Expression Omnibus (https://www.ncbi.nlm.nih.gov/geo/geo2r/?acc=GSE16879). Expression levels of RNA encoding NLRP3 and IL-1β were determined using GEO2R (a tool available on the same website), based on probe sets 207075_at and 205067_at, respectively. It was surprisingly found that in Crohn's disease patients that are non-responsive to the infliximab (an anti-TNFα agent) have higher expression of NLRP3 and IL-1β RNA than responsive patients (FIGS. 1 and 2). Similar surprising results of higher expression of NLRP3 and IL-1β RNA in UC patients that are non-responsive to infliximab (an anti-TNFα agent) compared to infliximab (an anti-TNFα agent) responsive patients (FIGS. 3 and 4) were found.

Said higher levels of NLRP3 and IL-1β RNA expression levels in anti-TNFα agent non-responders, is hypothesised herein to lead to NLRP3 activation which in turns leads to release of IL-1β that induces IL-23 production, leading to said resistance to anti-TNFα agents. Therefore, treatment of Crohn's and UC anti-TNFα non-responders with an NLRP3 antagonist would prevent this cascade, and thus prevent development of non-responsiveness to anti-TNFα agents. Indeed, resistance to anti-TNFα agents is common in other inflammatory or autoimmune diseases. Therefore, use of an NLRP3 antagonist for the treatment of inflammatory or autoimmune diseases will block the mechanism leading to non-responsiveness to anti-TNFα☐agents. Consequently, use of NLRP3 antagonists will increase the sensitivity of patients with inflammatory or autoimmune diseases to anti-TNFα agents, resulting in a reduced dose of anti-TNFα agents for the treatment of these diseases. Therefore, a combination of an NLRP3 antagonist and an anti-TNFα agent can be used in the treatment of diseases wherein TNFα is overexpressed, such as inflammatory or autoimmune diseases, to avoid such non-responsive development of patients to anti-TNFα agents. Preferably, this combination treatment can be used in the treatment of IBD, for example Crohn's disease and UC.

Further, use of NLRP3 antagonists offers an alternative to anti-TNFα agents for the treatment of diseases wherein TNFα is overexpressed. Therefore, NLRP3 antagonists offers an alternative to anti-TNFα agents inflammatory or autoimmune diseases, such as IBD (e.g. Crohn's disease and UC).

Systematic anti-TNFα agents are also known to increase the risk of infection. Gut restricted NLRP3 antagonists, however, offers a gut targeted treatment (i.e. non-systemic treatment), preventing such infections. Therefore, treatment of TNFα gut diseases, such as IBD (i.e. Crohn's disease and UC), with gut restricted NLRP3 antagonists has the additional advantage of reducing the risk of infection compared to anti-TNFα agents.

Proposed Experiment:
　Determine the expression of NLRP3 and caspase-1 in LPMCs and epithelial cells in patients with non-active disease, in patients with active disease, in patients with active disease resistant to corticosteroids, patients with active disease resistant to TNF-blocking agents. The expression of NLRP3 and caspase-1 in LPMCs and epithelial cells will be analyzed by RNAScope technology. The expression of active NLRP3 signature genes will be analyzed by Nanostring technology. A pilot analysis to determine feasibility will be performed with 5 samples from control, 5 samples from active CD lesions, and 5 samples from active UC lesions.

Study Example 3

It is presented that NLRP3 antagonists reverse resistance to anti-TNF induced T cell depletion/apoptosis in biopsy samples from IBD patients whose disease is clinically considered resistant or unresponsive to anti-TNF therapy.

A study is designed to determine: whether NLRP3 antagonists inhibit inflammasome function and inflammatory activity in cells and biopsy specimens from patients with Crohn's disease or ulcerative colitis; and whether an NLRP3 antagonist will synergize with anti-TNFα therapy in patients with Crohn's disease or ulcerative colitis.

The secondary objectives of this study are to: determine if an NLRP3 antagonist reduces inflammasome activity in Crohn's disease and ulcerative biopsy samples (comparing Crohn's disease and ulcerative colitis results with control patient results); determine if an NLRP3 antagonist reduced inflammatory cytokine RNA and protein expression in Crohn's disease and ulcerative colitis samples; determine if an NLRP3 antagonist in the absence of co-treatment with anti-TNFα antibody induces T cell depletion in Crohn's disease and ulcerative colitis biopsy samples; and determine if baseline (no ex vivo treatment) RNA levels of NLRP3, ASC, and IL-1β are greater in biopsy samples from patients with anti-TNFα agent resistance status.

Methods

Evaluation of baseline expression of NLRP3 RNA and quantify inhibition of inflammasome activity by an NLRP3 antagonist in biopsies of disease tissue from patients with Crohn's disease and ulcerative colitis.

Determine if there is synergy between an NLRP3 antagonist and anti-TNF antibody with respect to effects on T cell depletion/apoptosis in biopsies of disease from patients with Crohn's disease and ulcerative colitis.

Determine if NLRP3 antagonist treatment reduces the inflammatory response in biopsies of disease from patients with Crohn's disease based on decreased expression of inflammatory gene RNA measured with Nanostring.

Experimental Design

Human subjects and tissue:
    Endoscopic or surgical biopsies from areas of disease in patients with Crohn's disease and ulcerative colitis who are either anti-TNFα treatment naïve or resistant to anti-TNFα treatment; additionally biopsies from control patients (surveillance colonoscopy or inflammation-free areas from patients with colorectal cancer) are studied.
Ex vivo Treatment Model:
    Organ or LPMC culture as determined appropriate
Ex vivo Treatments:
    NLRP3 antagonist (2 concentrations), negative control (vehicle), positive control (caspase-1 inhibitor) each in the presence or absence of anti-TNF antibody at a concentration appropriate to distinguish differences in the T cell apoptotic between biopsies from anti-TNF resistant and anti-TNF-sensitive Crohn's disease patients. Each treatment condition is evaluated in a minimum in duplicate samples.
Endpoints to be measured:
    Before ex vivo treatment—NLRP3 RNA level
    After ex vivo treatment—inflammasome activity (either processed IL-1β, processed caspase-1, or secreted IL-1β); RNA for inflammatory cytokines (Nanostring); viable T cell number and/or T cell apoptosis.
Data Analysis Plan:
    Determine if NLRP3 antagonist co-treatment increases T cell apoptosis/deletion in response to anti-TNF.
    Determine if the level of NLRP3 RNA expression is greater in TNF-resistant Crohn's disease and ulcerative colitis samples compared to anti-TNF treatment-naïve samples.
    Determine if NLRP3 antagonist treatment decreases processed IL-1β, processed caspase-1 or secreted IL-1, and inflammatory cytokine RNA levels.

Biological Assay—Nigericin-stimulated IL-1β secretion assay in THP-1 cells

Monocytic THP-1 cells (ATCC: TIB-202) were maintained according to providers' instructions in RPMI media (RPMI/Hepes+10% fetal bovine serum+Sodium Pyruvate+ 0.05 mM Beta-mercaptoethanol (1000× stock)+Pen-Strep). Cells were differentiated in bulk with 0.5 μM phorbol 12-myristate 13-acetate (PMA; Sigma #P8139) for 3 hours, media was exchanged, and cells were plated at 50,000 cells per well in a 384-well flat-bottom cell culture plates (Greiner, #781986), and allowed to differentiate overnight. Compound in a 1:3.16 serial dilution series in DMSO was added 1:100 to the cells and incubated for 1 hour. The NLRP3 inflammasome was activated with the addition of 15 μM (final concentration) Nigericin (Enzo Life Sciences, #BML-CA421-0005), and cells were incubated for 3 hours. 10 μL supernatant was removed, and IL-1β levels were monitored using an HTRF assay (CisBio, #62IL1PEC) according to manufacturers' instructions. Viability and pyroptosis was monitored with the addition of PrestoBlue cell viability reagent (Life Technologies, #A13261) directly to the cell culture plate.

A number of embodiments of the invention have been described. Nevertheless, it will be understood that various modifications may be made without departing from the spirit and scope of the invention. Accordingly, other embodiments are within the scope of the following claims.

What is claimed is:

1. A compound of Formula AA

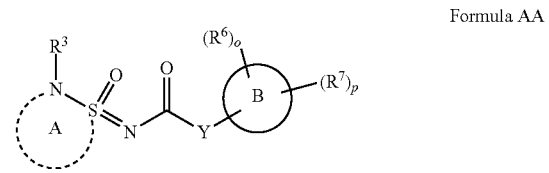

Formula AA wherein
o=1 or 2;
p=0, 1, 2, or 3;
Y is —CR$^{15}$R$^{15}$— or —NR$^{16}$—;
ring A is:
    (i) a saturated or unsaturated monocyclic ring that includes from 5-8 ring atoms (inclusive of N—R$^3$ and S(O)); or
    (ii) a saturated or unsaturated bicyclic or tricyclic ring that includes from 8-20 ring atoms (inclusive of N—R$^3$ and S(O)),
    wherein the dotted, circular line connecting N—R$^3$ and S is a divalent group that includes from 3-6 ring atoms; wherein:
        (a) from 0-2 of the divalent group's ring atoms are ring heteroatoms, which are each independently selected from the group consisting of O, N, NH, NR$^{13}$, S, S(O), and S(O)$_2$; and
        (b) from 1-6 of the divalent group's ring atoms are ring carbon atoms, which are each independently selected from the group consisting of C, CH, CH$_2$, C(O), CR$^1$, C(R$^1$)$_2$, and CHR$^1$;
    wherein:
        (1) when ring A is a monocyclic ring, then each of the divalent group's 1-6 ring carbon atoms is independently selected from the group consisting of CH, $CH_2$, C(O), $CR^1$, $C(R^1)_2$, and $CHR^1$; and (2) when ring A is a bicyclic or tricyclic ring, then (A) or (B) applies:

(A) two or three adjacent ring carbon atoms of the divalent group are each independently selected from the group consisting of C, CH, and $CR^1$, and are fused to a second ring that is selected from the group consisting of:

(a) $C_{6-10}$ aryl optionally substituted with from 1-5 independently selected $R^a$;

(b) heteroaryl including from 5-10 ring atoms, wherein from 1-4 ring atoms are each independently selected from the group consisting of N, $N(R^N)$, O, and S, wherein the heteroaryl is optionally substituted with from 1-3 independently selected $R^a$;

(c) $C_{3-10}$ cycloalkyl optionally substituted with from 1-4 independently selected $R^b$;

(d) heterocycloalkyl including from 3-10 ring atoms, wherein from 1-3 ring atoms are each independently selected from the group consisting of $N(R^N)$, O, and S, wherein the heterocycloalkyl is optionally substituted with from 1-4 independently selected $R^b$; or (B) one of the divalent group's ring carbon atoms is C and is spiro-fused to a second ring that is selected from the group consisting of:

(a) $C_{3-10}$ cycloalkyl optionally substituted with from 1-4 independently selected $R^b$;

(b) heterocycloalkyl including from 3-10 ring atoms, wherein from 1-3 ring atoms are each independently selected from the group consisting of $N(R^N)$, O, and S, wherein the heterocycloalkyl is optionally substituted with from 1-4 independently selected $R^b$;

each $R^1$ is independently selected from the group consisting of: $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, CO—$C_6$-$C_{10}$ aryl, CO(5- to 10-membered heteroaryl), $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5-to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $NHCOOC_1$-$C_6$ alkyl, NH—(C=$NR^{13}$)$NR^{11}R^{12}$, $CONR^8R^9$, $SF_5$, $SC_1$-$C_6$ alkyl, $S(O_2)C_1$-$C_6$ alkyl, $S(O)C_1$-$C_6$ alkyl, $S(O_2)NR^{11}R^{12}$, $C_3$-$C_7$ cycloalkyl, and 3- to 7-membered heterocycloalkyl, wherein the $C_1$-$C_6$ alkyl, $C_6$-$C_{10}$ aryl, 5- to 10-membered heteroaryl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5-to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;

wherein when $R^1$ is $C_3$-$C_7$ cycloalkyl, 3- to 7-membered heterocycloalkyl, $C_6$-$C_{10}$ aryl, or 5- to 10-membered heteroaryl, each $C_1$-$C_6$ alkyl substituent and each $C_1$-$C_6$ alkoxy substituent on $R^1$, when present, is further optionally independently substituted with one to three hydroxy, $C_1$-$C_6$ alkoxy, halo, $NR^8R^9$, or oxo;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) substituents on $R^1$ are optionally substituted with one or more substituents independently selected from halo, $C_1$-$C_6$ alkyl, and $OC_1$-$C_6$ alkyl;

each $R^a$ is independently selected from hydroxy, halo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, =$NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, $OC_6$-$C_{10}$ aryl, 5- to 10-membered heteroaryl, $C_3$-$C_{10}$ cycloalkyl, 3-to 10-membered heterocycloalkyl, $CO_2H$, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents each independently selected from hydroxy, halo, $C_1$-$C_6$ alkyl, $C_{1-4}$ haloalkyl, $C_2$-$C_6$ alkenyl, $C_2$-$C_6$ alkynyl, $C_3$-$C_{10}$ cycloalkyl, 3- to 10-membered heterocycloalkyl, $C_1$-$C_6$ alkoxy, oxo, $NR^8R^9$, =$NR^{10}$, $COOC_1$-$C_6$ alkyl, $C_6$-$C_{10}$ aryl, $CO_2H$, and $CONR^8R^9$, each $R^b$ is independently selected from hydroxy, halo, oxo, $C_1$-$C_6$ alkyl, $C_2$-$C_6$ alkenyl, $C_2$-$C_6$ alkynyl, $C_1$-$C_6$ alkoxy, $OC_3$-$C_{10}$ cycloalkyl, $NR^8R^9$, =$NR^{10}$, CN, $COOC_1$-$C_6$ alkyl, $OS(O_2)C_6$-$C_{10}$ aryl, $S(O_2)C_6$-$C_{10}$ aryl, $C_6$-$C_{10}$ aryl, $OC_6$-$C_{10}$ aryl, 5- to 10-membered heteroaryl, $C_3$-$C_{10}$ cycloalkyl, 3- to 10-membered heterocycloalkyl, $CO_2H$, and $CONR^8R^9$, wherein the $C_1$-$C_6$ alkyl, $C_1$-$C_6$ alkoxy, $S(O_2)C_6$-$C_{10}$ aryl, $C_6$-$C_{10}$ aryl, 5- to 10-membered heteroaryl, $C_3$-$C_{10}$ cycloalkyl, and 3- to 10-membered heterocycloalkyl are optionally substituted with one or more substituents each independently selected from hydroxy, halo, $C_1$-$C_6$ alkyl, $C_2$-$C_6$ alkenyl, $C_2$-$C_6$ alkynyl, $C_3$-$C_{10}$ cycloalkyl, $C_1$-$C_6$ alkoxy, oxo, $NR^8R^9$, =$NR^{10}$, $COOC_1$-$C_6$ alkyl, $C_6$-$C_{10}$ aryl, $CO_2H$, and $CONR^8R^9$;

each $R^N$ is independently selected from hydrogen, $C_1$-$C_6$ alkyl, (C=$NR^{13}$)$NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$;

wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl, or 3- to 7-membered heterocycloalkyl;

ring B is a 5-10-membered heteroaryl or a $C_6$-$C_{10}$ aryl;

$R^6$ and $R^7$ are each independently selected from $C_1$-$C_6$ alkyl, $C_1$-$C_6$ haloalkyl, $C_1$-$C_6$ alkoxy, $C_1$-$C_6$ haloalkoxy, halo, CN, $NO_2$, $COC_1$-$C_6$ alkyl, $CO_2C_1$-$C_6$ alkyl, $CO_2C_3$-$C_8$ cycloalkyl, $OCOC_1$-$C_6$ alkyl, $OCOC_6$-$C_{10}$ aryl, OCO(5- to 10-membered heteroaryl), OCO(3- to 7-membered heterocycloalkyl), $C_6$-$C_{10}$ aryl, 5- to 10-membered heteroaryl, $NH_2$, $NHC_1$-$C_6$ alkyl, $N(C_1$-$C_6$ alkyl$)_2$, $CONR^8R^9$, $SF_5$, $S(O_2)C_1$-$C_6$ alkyl, $C_3$-$C_{10}$ cycloalkyl and 3- to 10-membered heterocycloalkyl, and a $C_2$-$C_6$ alkenyl, wherein $R^6$ and $R^7$ are each optionally substituted with one or more substituents independently selected from hydroxy, halo, CN, oxo, $C_1$-$C_6$ alkyl, $C_1$-$C_6$ alkoxy, $NR^8R^9$, =$NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO (5- to 10-membered heteroaryl), NHCO(3- to 7-membered heterocycloalkyl), $NHCOC_2$-$C_6$ alkynyl, $C_6$-$C_{10}$ aryloxy, and $S(O_2)C_1$-$C_6$ alkyl; and wherein the $C_1$-$C_6$ alkyl or $C_1$-$C_6$ alkoxy that $R^6$ or $R^7$ is substituted with is optionally substituted with one or more hydroxyl, $C_6$-$C_{10}$ aryl or $NR^8R^9$;

wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) are optionally substituted with one or more substituents independently selected from halo, $C_1$-$C_6$ alkyl, and $OC_1$-$C_6$ alkyl;

OR at least one pair of $R^6$ and $R^7$ on adjacent carbon atoms taken together with the carbon atoms to which each is attached form a $C_4$-$C_8$ carbocyclic ring or a 5- to 8-membered heterocyclic ring containing 1-3 heteroatoms and/or heteroatomic groups independently selected from O, N, NH, $NR^{13}$, S, S(O), and $S(O)_2$, wherein the carbocyclic ring or heterocyclic ring is optionally substituted with one or more substituents independently selected from hydroxy, hydroxymethyl, halo, oxo, $C_1$-$C_6$ alkyl, $C_1$-$C_6$ alkoxy, $NR^8R^9$, $CH_2NR^8R^9$, =$NR^{10}$, $COOC_1$-$C_6$ alkyl, $C_6$-$C_{10}$ aryl, and $CONR^8R^9$, each occurrence of $R^8$ and $R^9$ is independently selected from hydrogen, $C_1$-$C_6$ alkyl, (C=$NR^{13}$)$NR^{11}R^{12}$, $S(O_2)C_1$-$C_6$ alkyl, $S(O_2)NR^{11}R^{12}$, $COR^{13}$, $CO_2R^{13}$ and $CONR^{11}R^{12}$;

wherein the $C_1$-$C_6$ alkyl is optionally substituted with one or more hydroxy, halo, $C_1$-$C_6$ alkoxy, $C_6$-$C_{10}$ aryl, 5- to 10-membered heteroaryl, $C_3$-$C_7$ cycloalkyl, or 3- to 7-membered heterocycloalkyl; or $R^8$ and $R^9$ taken together with the nitrogen atom to which each is attached form a 3- to 7-membered ring optionally containing one or more additional heteroatoms;

$R^{10}$ is $C_1$-$C_6$ alkyl;
$R^{13}$ is $C_1$-$C_6$ alkyl, $C_6$-$C_{10}$ aryl, or 5- to 10-membered heteroaryl;
each of $R^{11}$ and $R^{12}$ at each occurrence is independently selected from hydrogen and $C_1$-$C_6$ alkyl;
$R^3$ is selected from hydrogen, cyano, hydroxy, $C_1$-$C_6$ alkoxy, $C_1$-$C_6$ alkyl, and

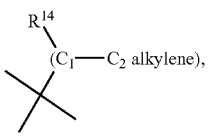

wherein the $C_1$-$C_2$ alkylene group is optionally substituted by oxo;

$R^{14}$ is hydrogen, $C_1$-$C_6$ alkyl, 5- to 10-membered monocyclic or bicyclic heteroaryl or $C_6$-$C_{10}$ monocyclic or bicyclic aryl, wherein each $C_1$-$C_6$ alkyl, aryl, or heteroaryl is optionally independently substituted with 1 or 2 $R^6$;

each occurrence of $R^{15}$ is independently selected from hydrogen and $C_1$-$C_6$ alkyl; and
$R^{16}$ is selected from hydrogen and $C_1$-$C_6$ alkyl;
or a pharmaceutically acceptable salt thereof.

2. The compound of claim 1, wherein ring A has Formula (A1):

wherein:

// represents a single bond or a double bond;
ring C is selected from the group consisting of:
(a) $C_{6-10}$ aryl optionally substituted with from 1-5 independently selected $R^a$;
(b) heteroaryl including from 5-10 ring atoms, wherein from 1-4 ring atoms are each independently selected from the group consisting of N, $N(R^N)$, O, and S, wherein the heteroaryl is optionally substituted with from 1-3 independently selected $R^a$;
(c) $C_{3-10}$ cycloalkyl optionally substituted with from 1-4 independently selected $R^b$; and
(d) heterocycloalkyl including from 3-10 ring atoms, wherein from 1-3 ring atoms are each independently selected from the group consisting of $N(R^N)$, O, and S, wherein the heterocycloalkyl is optionally substituted with from 1-4 independently selected $R^b$; and
each of $A^{1a}$ and $A^{1c}$ is independently selected from: a bond, $CH_2$, $CHR^1$, $C(R^1)_2$, C(O), N, NH, $NR^{13}$, O, $S(O)_2$, and $A^{1d}$-$A^{1e}$-$A^{1f}$;
provided that one or more of $A^{1a}$ and $A^{1c}$ is other than a bond;
wherein each of $A^{1d}$, $A^{1e}$, and $A^{1f}$ is independently a bond, $CH_2$, $CHR^1$, $C(R^1)_2$, C(O), $S(O)_2$, NH, $NR^{13}$, and O, provided that from 2-3 of $A^{1d}$, $A^{1e}$, and $A^{1f}$ are other than a bond,
and provided that $A^{1d}$ and $A^{1e}$ are not both O or not both $S(O)_2$, and $A^{1e}$ and $A^{1f}$ are not both O or not both $S(O)_2$.

3. The compound of claim 2, wherein ring A is selected from:

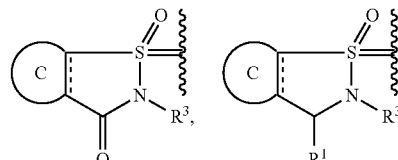

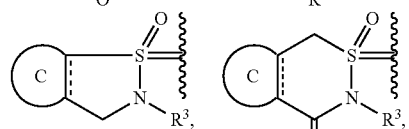

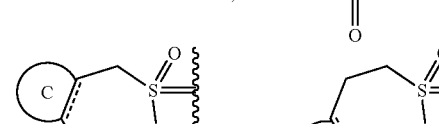

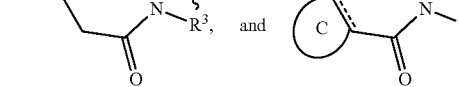

4. The compound of claim 2, wherein each $R^1$ when present is independently selected from the group consisting of: $C_1$-$C_6$ alkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $C_3$-$C_7$ cycloalkyl, and 3- to 7-membered heterocycloalkyl.

5. The compound of claim 2, wherein ring C is selected from the group consisting of:
- $C_6$ aryl optionally substituted with from 1-3 independently selected $R^a$;
- heteroaryl including from 5-10 ring atoms, wherein from 1-4 ring atoms are each independently selected from the group consisting of N, $N(R^N)$, O, and S, wherein the heteroaryl is optionally substituted with from 1-3 independently selected $R^a$;
- thiophenyl optionally substituted with from 1-2 independently selected $R^a$;
- heteroaryl including from 8-10 ring atoms, wherein from 1-3 ring atoms are each independently selected from the group consisting of N, $N(R^N)$, O, and S, wherein the heteroaryl is optionally substituted with from 1-2 independently selected $R^a$;
- $C_{3-10}$ cycloalkyl optionally substituted with from 1-4 independently selected $R^b$; and
- heterocycloalkyl including from 3-10 ring atoms, wherein from 1-3 ring atoms are each independently selected from the group consisting of $N(R^N)$, O, and S, wherein the heterocycloalkyl is optionally substituted with from 1-4 independently selected $R^b$.

6. The compound of claim 1, wherein ring A has Formula (A2):

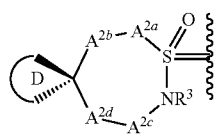

wherein ring D is selected from the group consisting of:
(a) $C_{3-10}$ cycloalkyl optionally substituted with from 1-4 independently selected $R^b$; and
(b) heterocycloalkyl including from 3-10 ring atoms, wherein from 1-3 ring atoms are each independently selected from the group consisting of $N(R^N)$, O, and S, wherein the heterocycloalkyl is optionally substituted with from 1-4 independently selected $R^b$; and each of $A^{2a}$, $A^{2b}$, $A^{2c}$, and $A^{2d}$ is independently selected from: a bond, NH, $NR^{13}$, O, $CH_2$, $CH(R^1)$, $C(R^1)_2$, C(O), and $S(O)_2$; provided that one or more of $A^{2a}$, $A^{2b}$, $A^{2c}$, and $A^{2d}$ are other than a bond, and provided that $A^{2c}$ and $A^{2d}$ are not both O or not both $S(O)_2$; and $A^{2a}$ and $A^{2b}$ are not both O or not both $S(O)_2$.

7. The compound of claim 1, wherein ring A is selected from the group consisting of

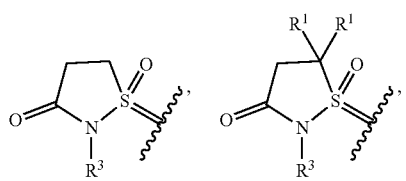

-continued

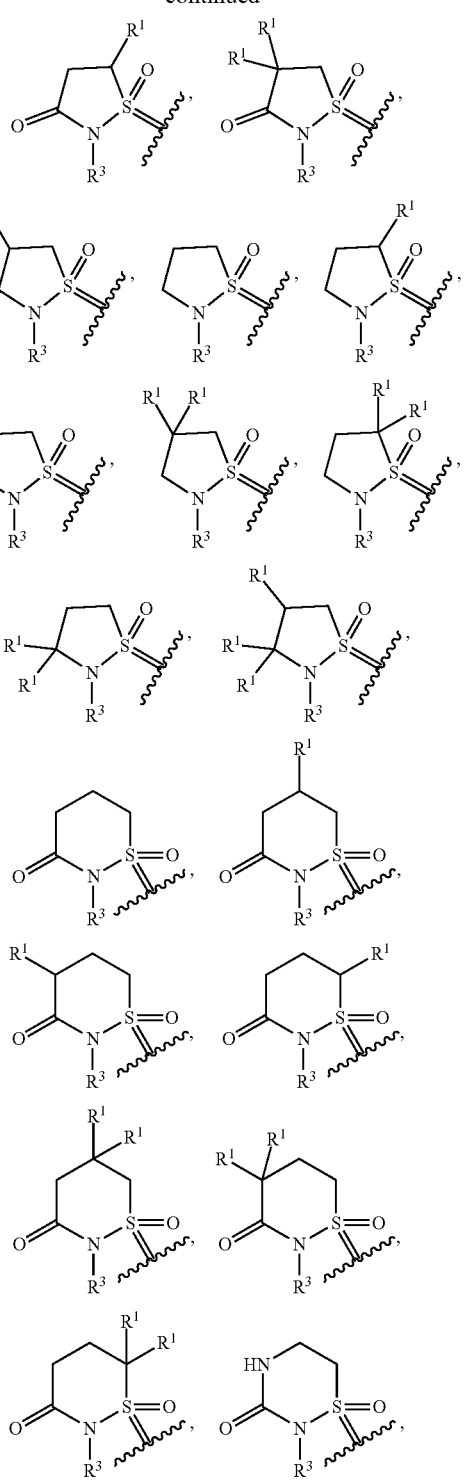

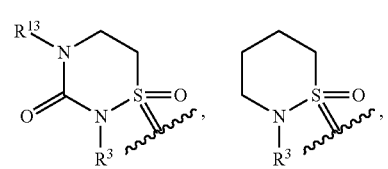

-continued

[chemical structures]

8. The compound of claim 7, wherein each $R^1$ is independently selected from the group consisting of: $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_8$ cycloalkyl, $C_6$-$C_{10}$ aryl, 5- to 10-membered heteroaryl, $NH_2$, $NHC_1$-$C_6$ alkyl, $N(C_1$-$C_6$ alkyl$)_2$, $NHCOC_1$-$C_6$ alkyl, $NHCOC_6$-$C_{10}$ aryl, NHCO(5- to 10-membered heteroaryl), NHCO(3- to 7-membered heterocycloalkyl), $NHCOC_2$-$C_6$ alkynyl, $CONR^8R^9$, $S(O_2)C_1$-$C_6$ alkyl, $S(O)C_1$-$C_6$ alkyl, $S(O_2)NR^{11}R^{12}$, $C_3$-$C_7$ cycloalkyl, and 3- to 7-membered heterocycloalkyl, wherein the $C_1$-$C_6$ alkyl, $C_6$-$C_{10}$ aryl, $C_1$-$C_6$ haloalkyl, $C_3$-$C_7$ cycloalkyl, and 3- to 7-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, $=NR^{10}$, $COOC_1$-$C_6$ alkyl, $CONR^8R^9$, 3- to 7-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(3- to 7-membered heterocycloalkyl), $NHCOC_1$-$C_6$ alkyl, $NHCOC_6$-$C_{10}$ aryl, NHCO(5- to 10-membered heteroaryl), NHCO(3- to 7-membered heterocycloalkyl), and $NHCOC_2$-$C_6$ alkynyl;
wherein when $R^1$ is $C_3$-$C_7$ cycloalkyl, 3- to 7-membered heterocycloalkyl, $C_6$-$C_{10}$ aryl, or 5- to 10-membered heteroaryl, each $C_1$-$C_6$ alkyl substituent and each $C_1$-$C_6$ alkoxy substituent on $R^1$, when present, is further optionally independently substituted with one to three hydroxy, $C_1$-$C_6$ alkoxy, halo, $NR^8R^9$, or oxo; and
wherein the 3- to 7-membered heterocycloalkyl, $C_6$-$C_{10}$ aryl, 5- to 10-membered heteroaryl, $NHCOC_6$-$C_{10}$ aryl, NHCO(5- to 10-membered heteroaryl) and NHCO(3- to 7-membered heterocycloalkyl) substituents on $R^1$ are optionally substituted with one or more substituents independently selected from halo, $C_1$-$C_6$ alkyl, and $OC_1$-$C_6$ alkyl.

9. The compound of claim 1, wherein Bis

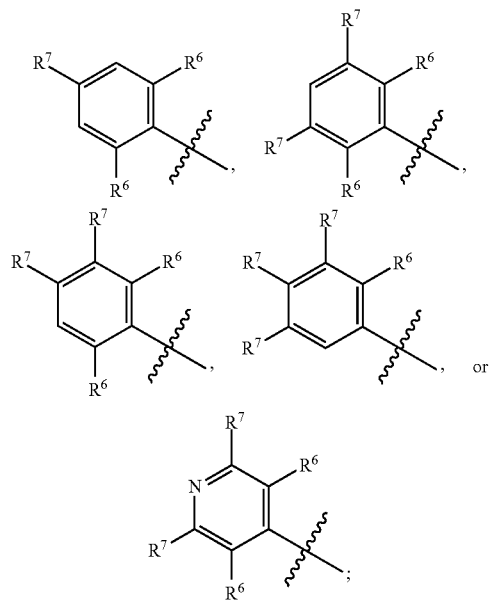

and
wherein each $R^6$ is independently selected from $C_1$-$C_6$ alkyl,
$C_3$-$C_7$ cycloalkyl, $C_1$-$C_6$ haloalkyl, $C_1$-$C_6$ alkoxy, $C_1$-$C_6$ haloalkoxy, halo, CN, $C_6$-$C_{10}$ aryl, 5- to 10-membered heteroaryl, CO—$C_1$-$C_6$ alkyl; $CONR^8R^9$, and 4- to 6-membered heterocycloalkyl,
wherein the $C_1$-$C_6$ alkyl, $C_1$-$C_6$ haloalkyl, $C_3$-$C_7$ cycloalkyl and 4- to 6-membered heterocycloalkyl is optionally substituted with one or more substituents each independently selected from hydroxy, halo, CN, oxo, $C_1$-$C_6$ alkyl, $C_1$-$C_6$ alkoxy, $NR^8R^9$, —$NR^{10}$, $COOC_1$-$C_6$ alkyl, $CONR^8R^9$, 4- to 6-membered heterocycloalkyl, $C_6$-$C_{10}$ aryl, 5- to 10-membered heteroaryl, $OCOC_1$-$C_6$ alkyl, $OCOC_6$-$C_{10}$ aryl, OCO(5- to 10-membered heteroaryl), OCO(4- to 6-membered heterocycloalkyl), $NHCOC_1$-$C_6$ alkyl, $NHCOC_6$-$C_{10}$ aryl, NHCO(5- to 10-membered heteroaryl), NHCO(4- to 6-membered heterocycloalkyl), and $NHCOC_2$-$C_6$ alkynyl;
wherein $R^7$ is independently selected from $C_1$-$C_6$ alkyl, $C_1$-$C_6$ haloalkyl, $C_1$-$C_6$ alkoxy, $C_1$-$C_6$ haloalkoxy, halo, CN, $COC_1$-$C_6$ alkyl, $CO_2C_1$-$C_6$ alkyl, $CO_2C_3$-$C_6$ cycloalkyl, $OCOC_1$-$C_6$ alkyl, $OCOC_6$-$C_{10}$ aryl, OCO (5- to 10-membered heteroaryl), OCO(3- to 7-membered heterocycloalkyl), $C_6$-$C_{10}$ aryl, 5- to 10-membered heteroaryl, $CONR^8R^9$, $SF_5$, $S(O_2)C_1$-$C_6$ alkyl, $C_3$-$C_7$ cycloalkyl and 4- to 6-membered heterocycloalkyl, wherein the $C_1$-$C_6$ alkyl is optionally substituted with one to two $C_1$-$C_6$ alkoxy.

10. The compound of claim 1, wherein $R_3$ is hydrogen, and Y is —$CR^{15}R^{15}$ or $NR^{16}$.

11. The compound of claim 1, wherein the compound has Formula AA-1:

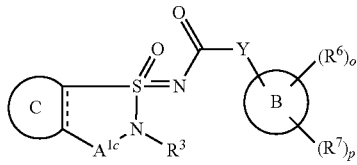

Formula AA-1 wherein:
$A^{1c}$ is C(O) or $CH_2$;
ring C is selected from the group consisting of:
(a) $C_{6-10}$ aryl optionally substituted with from 1-5 independently selected $R^a$; and
(b) heteroaryl including from 5-10 ring atoms, wherein from 1-4 ring atoms are each independently selected from the group consisting of N, $N(R^N)$, O, and S, wherein the heteroaryl is optionally substituted with from 1-3 independently selected $R^a$; and
$R^3$, ring B, Y, $R^6$, $R^7$, o, and p are as defined in claim 1.

12. The compound of claim 11, wherein $A^{1c}$ is C(O) and ring C is $C_6$ aryl optionally substituted with from 1-2 independently selected $R^a$.

13. The compound of claim 1, wherein the compound has Formula AA-2:

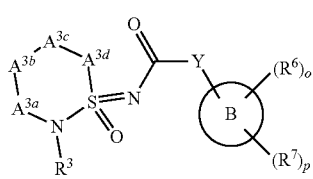

Formula AA-2 wherein:
$A^{3a}$ is C(O) or $CH_2$;
$A^{3b}$ is $CH_2$, $CHR^1$, or $C(R^2)_2$;
$A^{3c}$ is $CH_2$, $CHR^1$, or $C(R^2)_2$;
$A^{3d}$ is a bond or $CH_2$; and
each of $R^3$, Y, ring B, $R^6$, $R^7$, o, and p are as defined in claim 1.

14. The compound of claim 13, wherein B is

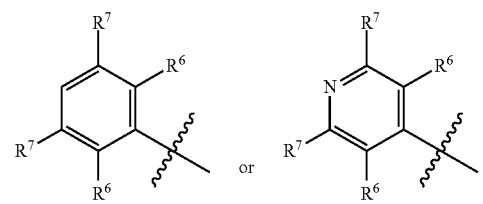

and wherein each $R^6$ and $R^7$ is independently selected from $C_1$-$C_6$ alkyl optionally substituted with hydroxy, $C_3$-$C_7$ cycloalkyl, $C_1$-$C_6$ haloalkyl, and halo;
or at least one pair of $R^6$ and $R^7$ on adjacent atoms, taken together with the atoms connecting them, independently form a $C_4$-$C_8$ carbocyclic ring or a 5-membered heterocyclic ring containing 1 O, wherein the carbocyclic ring or heterocyclic ring is optionally independently substituted with one or more substituents independently selected from $C_1$-$C_6$ alkyl.

15. The compound of claim 14, wherein $R^3$ is H and Y is NH.

16. A compound selected from the group consisting of the compounds in Tables below or pharmaceutically acceptable salts thereof:

| Cmpd # | Structure |
|---|---|
| 101 | 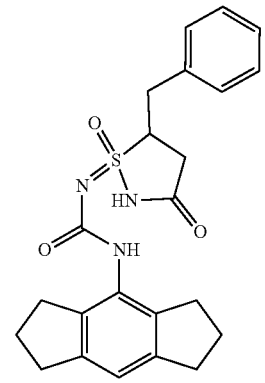 [SMILES: O=C1CC(Cc2ccccc2)S(=O)(=NC(=O)Nc2c3c(cc4c2CCC4)CCC3)N1] |
| 102 | 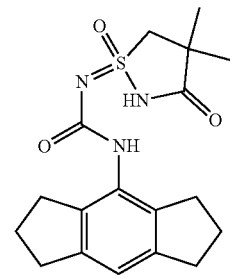 [SMILES: CC1(C)CS(=O)(=NC(=O)Nc2c3c(cc4c2CCC4)CCC3)NC1=O] |
| 103 | 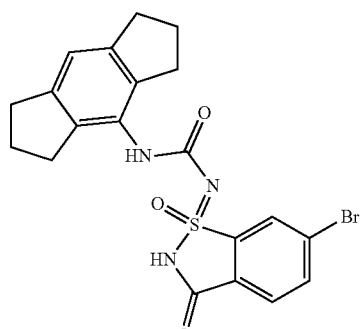 |
| 104 | 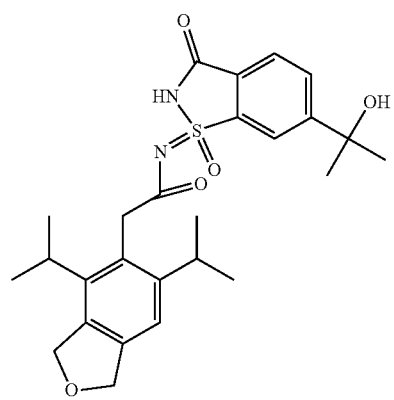 [SMILES: CC(C)c1cc2c(c(C(C)C)c1CC(=O)N=S1(=O)NC(=O)c3ccc(C(C)(C)O)cc31)COC2] |

TABLE 345-continued
| Cmpd # | Structure |
|---|---|
| 105 | 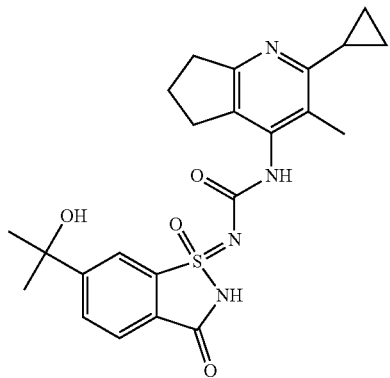 [SMILES: Cc1c(C2CC2)nc2c(c1NC(=O)N=S1(=O)NC(=O)c3ccc(C(C)(C)O)cc31)CCC2] |
| 106 | 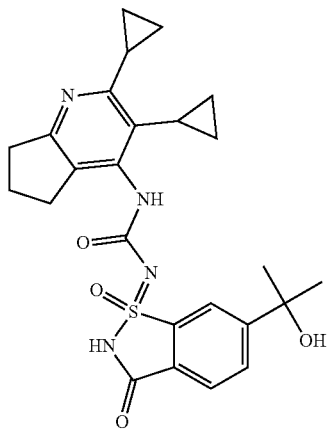 [SMILES: CC(C)(O)c1ccc2c(c1)S(=O)(=NC(=O)Nc1c3c(nc(C4CC4)c1C1CC1)CCC3)NC2=O] |
| 106a | 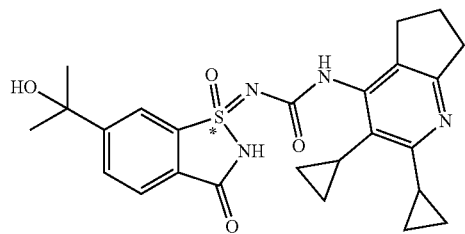 [SMILES: CC(C)(O)c1ccc2c(c1)S(=O)(=NC(=O)Nc1c3c(nc(C4CC4)c1C1CC1)CCC3)NC2=O] |
| 106b | 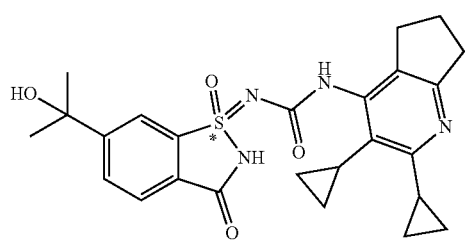 [SMILES: CC(C)(O)c1ccc2c(c1)S(=O)(=NC(=O)Nc1c3c(nc(C4CC4)c1C1CC1)CCC3)NC2=O] |
TABLE 346-continued
| Cmpd # | Structure |
|---|---|
| 107 | 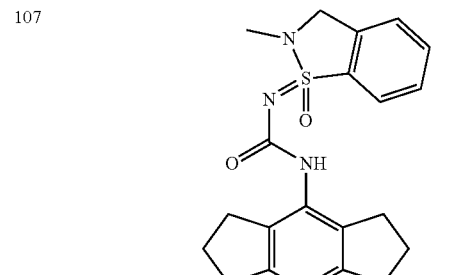 |
| 107a | 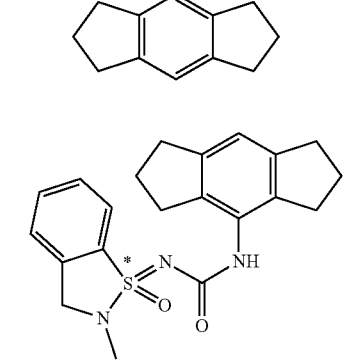 |
| 107b | 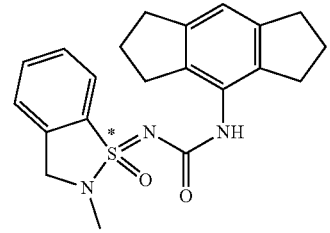 |
| 108 | 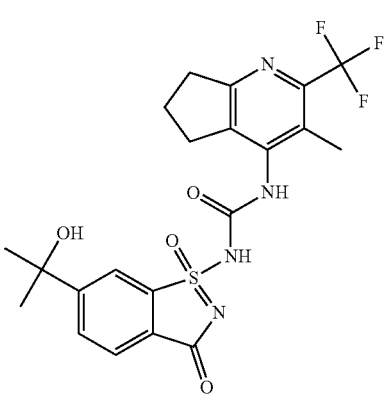 [SMILES: Cc1c(C(F)(F)F)nc2c(c1NC(=O)NS1(=O)=NC(=O)c3ccc(C(C)(C)O)cc31)CCC2] |
| 108a | 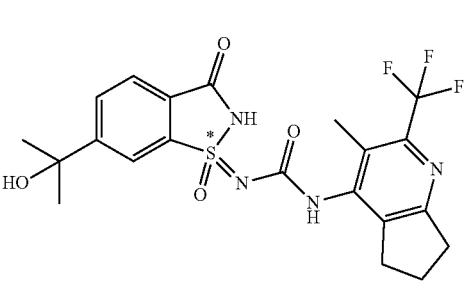 [SMILES: Cc1c(C(F)(F)F)nc2c(c1NC(=O)N=S1(=O)NC(=O)c3ccc(C(C)(C)O)cc31)CCC2] |

| Cmpd # | Structure |
|---|---|
| 108b | 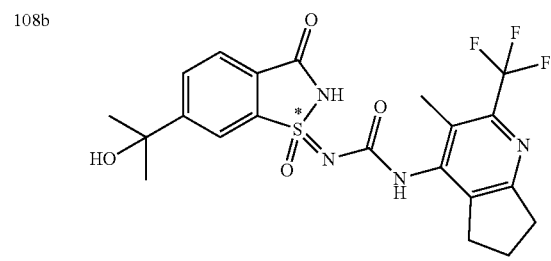 |
| 109 | 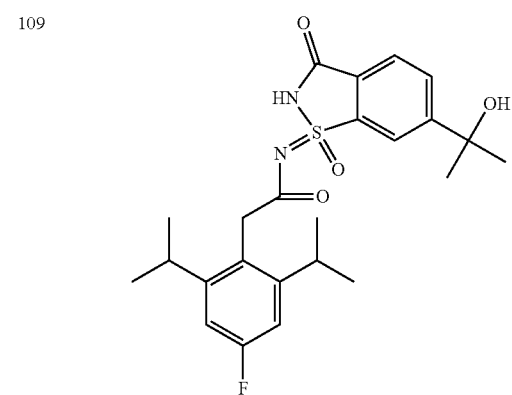 |
| 110 | 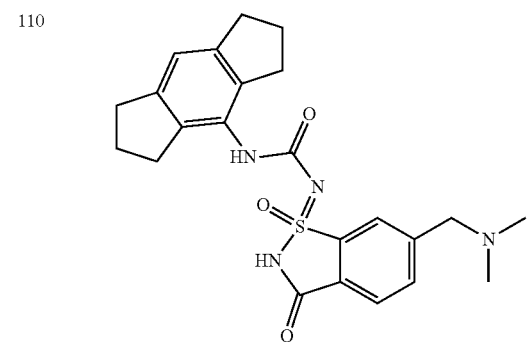 |
| 111 | 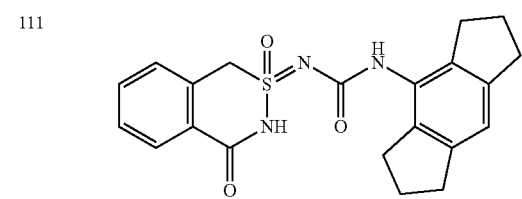 |
| 112 | 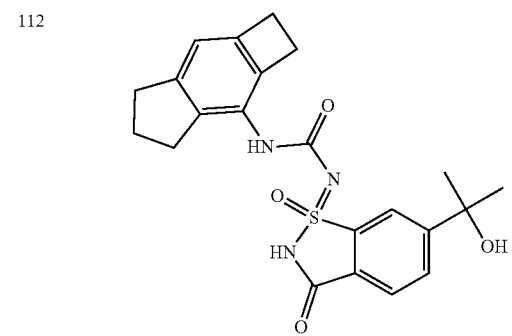 |
| Cmpd # | Structure |
|---|---|
| 112a | 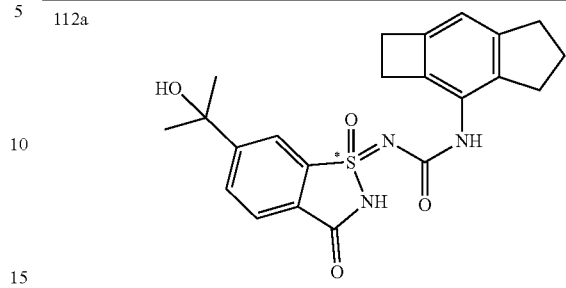 |
| 112b | 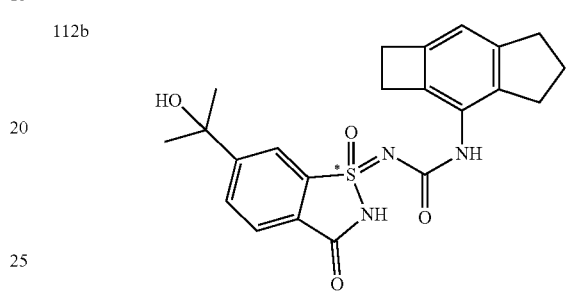 |
| 113 | 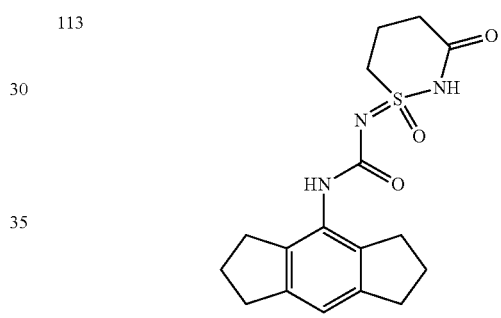 |
| 114 | 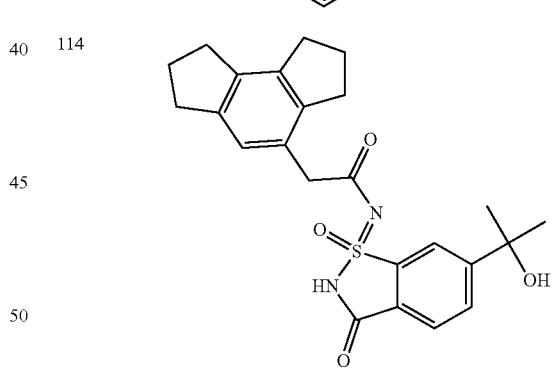 |
| 115 | 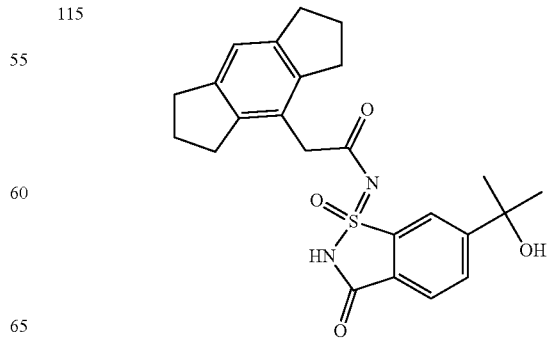 |

-continued
| Cmpd # | Structure |
|---|---|
| 116 | 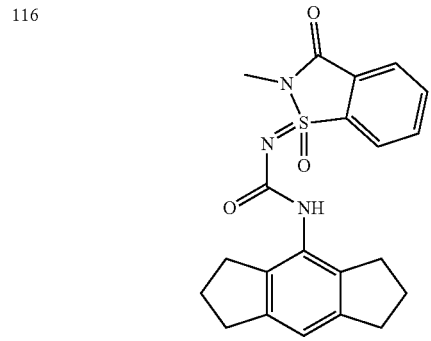 |
| 116a | 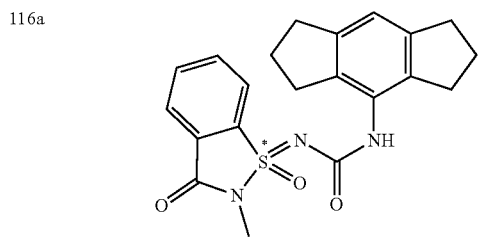 |
| 116b | 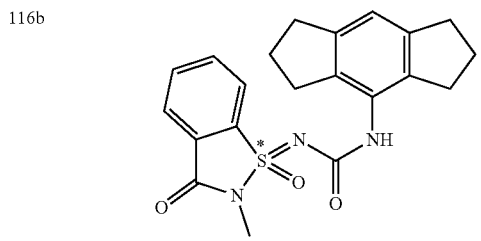 |
| 117 | 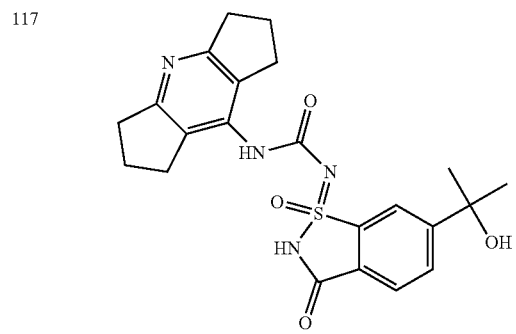 |
| 118 | 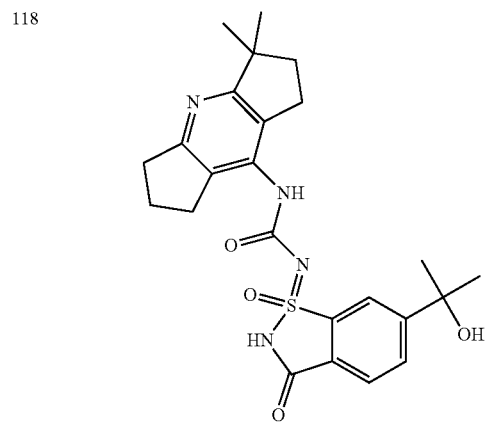 |
-continued
| Cmpd # | Structure |
|---|---|
| 119 | 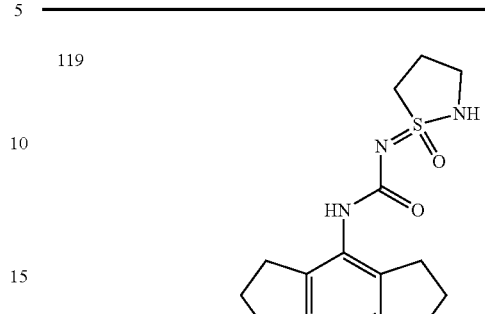 |
| 119a | 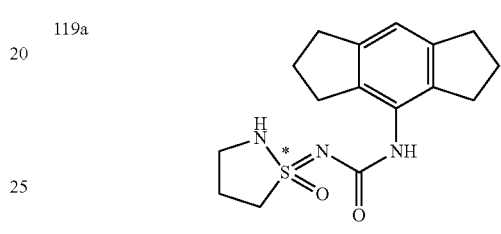 |
| 119b | 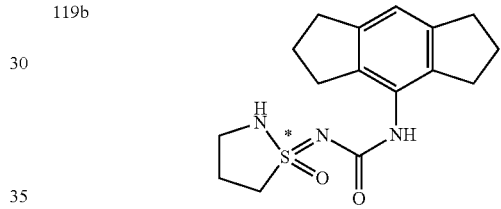 |
| 120 | 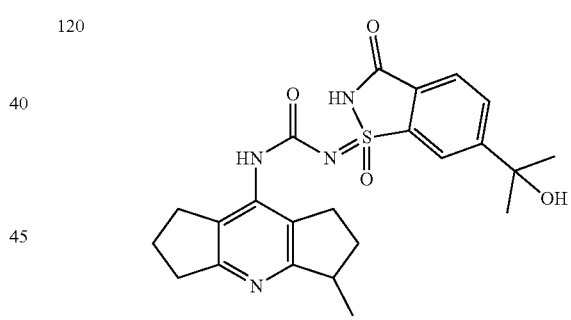 |
| 121 | 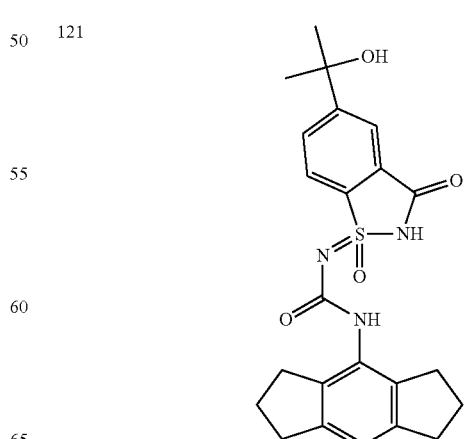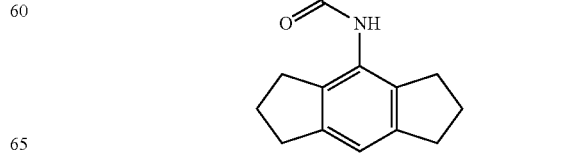 |

| Cmpd # | Structure |
|---|---|
| 121a | 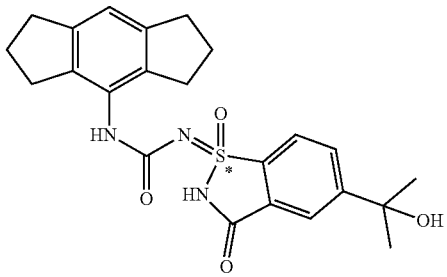 [SMILES: CC(C)(O)c1ccc2c(c1)C(=O)NS2(=O)=NC(=O)Nc1c2c(cc3c1CCC3)CCC2] |
| 121b | 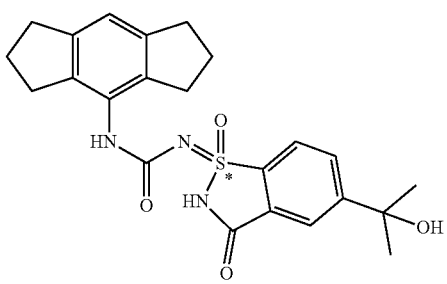 [SMILES: CC(C)(O)c1ccc2c(c1)C(=O)NS2(=O)=NC(=O)Nc1c2c(cc3c1CCC3)CCC2] |
| 122 | 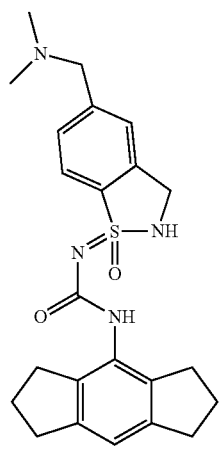 [SMILES: CN(C)Cc1ccc2c(c1)CNS2(=O)=NC(=O)Nc1c2c(cc3c1CCC3)CCC2] |
| 123 | 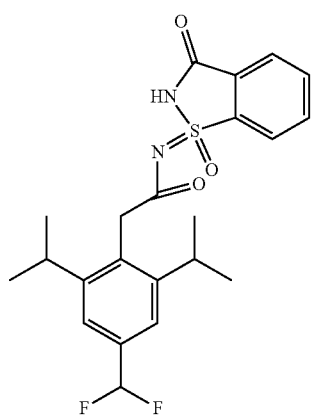 [SMILES: CC(C)c1cc(C(F)F)cc(C(C)C)c1CC(=O)N=S1(=O)NC(=O)c2ccccc21] |
| Cmpd # | Structure |
|---|---|
| 123a | 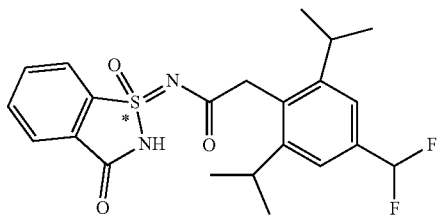 [SMILES: CC(C)c1cc(C(F)F)cc(C(C)C)c1CC(=O)N=S1(=O)NC(=O)c2ccccc21] |
| 123b | 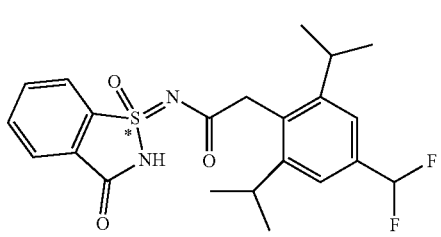 [SMILES: CC(C)c1cc(C(F)F)cc(C(C)C)c1CC(=O)N=S1(=O)NC(=O)c2ccccc21] |
| 124 | 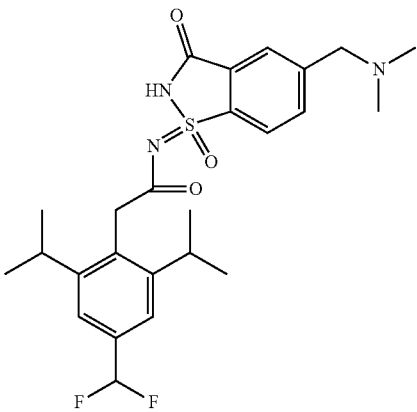 [SMILES: CC(C)c1cc(C(F)F)cc(C(C)C)c1CC(=O)N=S1(=O)NC(=O)c2cc(CN(C)C)ccc21] |
| 124a | 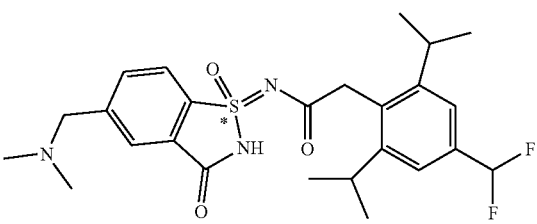 [SMILES: CC(C)c1cc(C(F)F)cc(C(C)C)c1CC(=O)N=S1(=O)NC(=O)c2cc(CN(C)C)ccc21] |
| 124b | 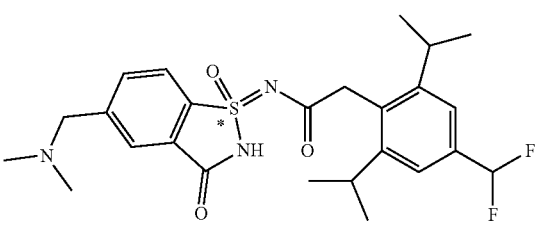 [SMILES: CC(C)c1cc(C(F)F)cc(C(C)C)c1CC(=O)N=S1(=O)NC(=O)c2cc(CN(C)C)ccc21] |

-continued
| Cmpd # | Structure |
|---|---|
| 125 | 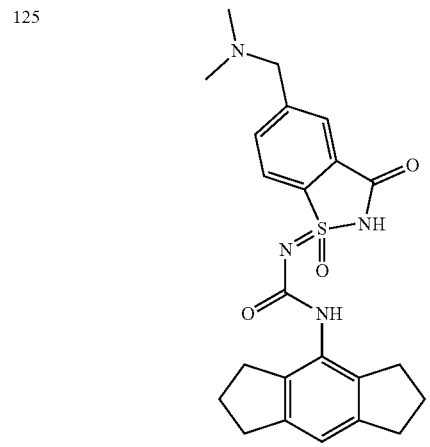 |
| 126 | 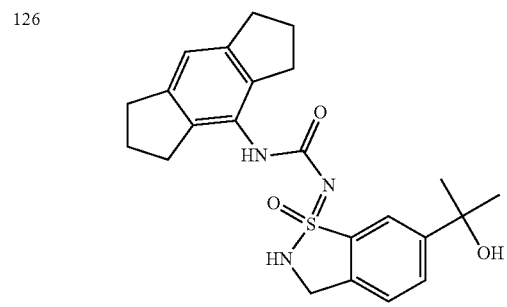 |
| 127 | 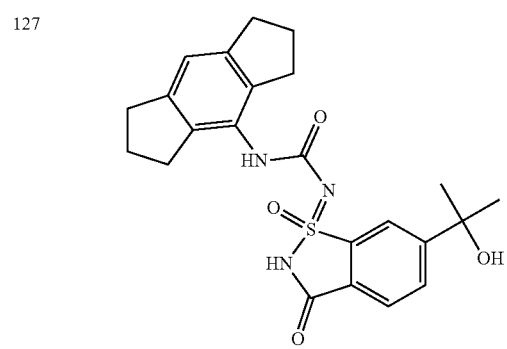 |
| 127a | 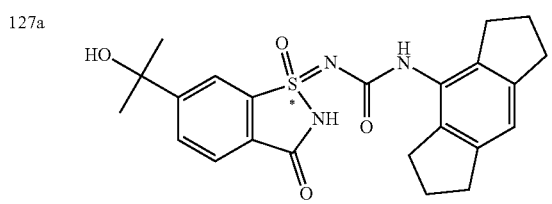 |
| 127b | 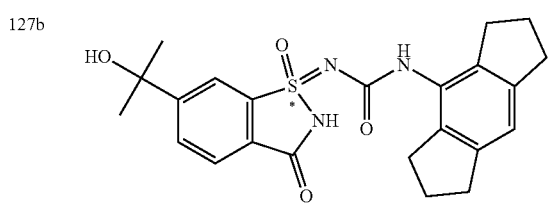 |
-continued
| Cmpd # | Structure |
|---|---|
| 128 | 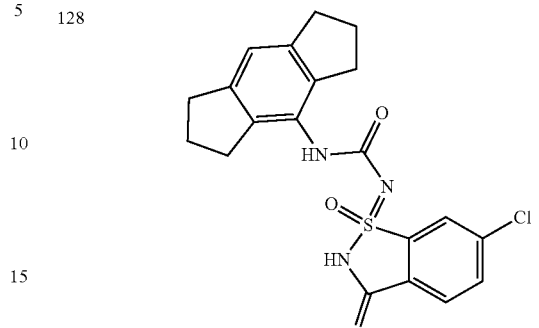 |
| 129 | 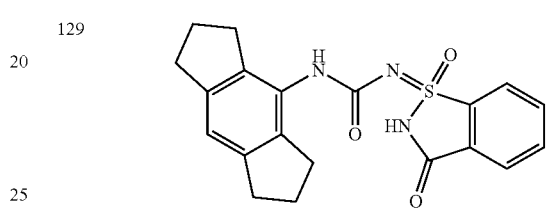 |
| 129a | 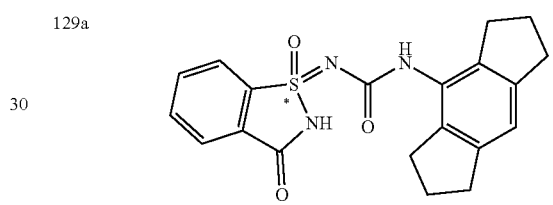 |
| 129b | 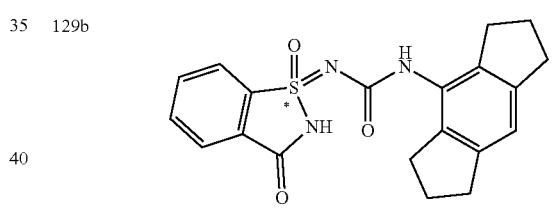 |
| 130 | 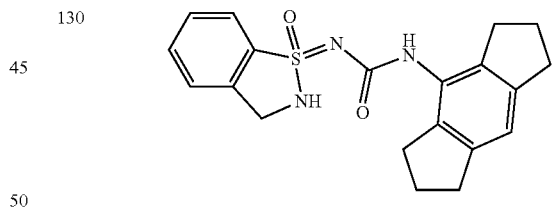 |
| 130a | 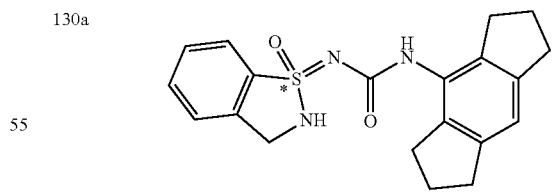 |
| 130b | 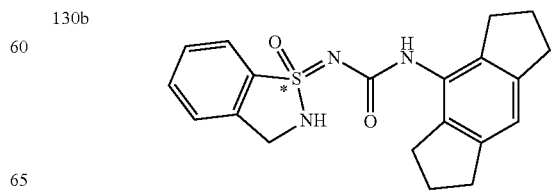 |

| Cmpd # | Structure |
|---|---|
| 131 | |
| 131a | |
| 131b | |
| 201 | |
| 202 | |
| 203 | |
| 204 | 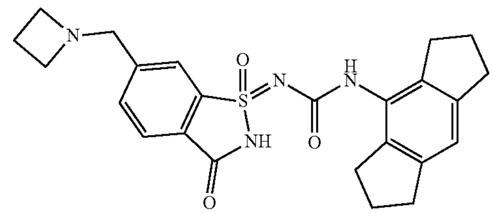 [SMILES: O=C(N=S1(=O)NC(=O)c2ccc(CN3CCC3)cc21)Nc1c2c(cc3c1CCC3)CCC2] |
| 205 | 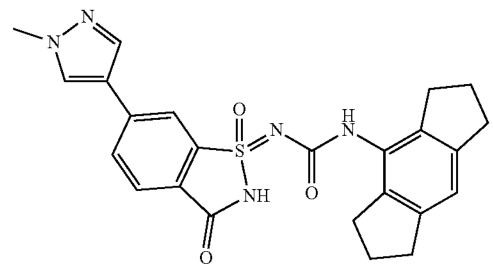 [SMILES: Cn1cc(-c2ccc3c(c2)S(=O)(=NC(=O)Nc2c4c(cc5c2CCC5)CCC4)NC3=O)cn1] |
| 206 | 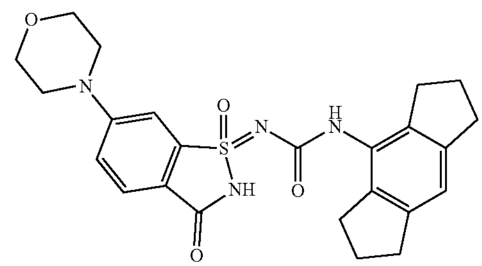 [SMILES: O=C(N=S1(=O)NC(=O)c2ccc(N3CCOCC3)cc21)Nc1c2c(cc3c1CCC3)CCC2] |
| 207 | 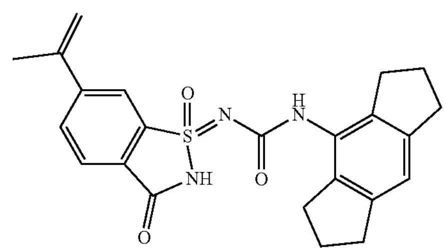 [SMILES: C=C(C)c1ccc2c(c1)S(=O)(=NC(=O)Nc1c3c(cc4c1CCC4)CCC3)NC2=O] |
| 208 | 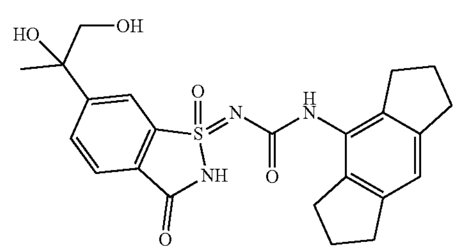 [SMILES: CC(O)(CO)c1ccc2c(c1)S(=O)(=NC(=O)Nc1c3c(cc4c1CCC4)CCC3)NC2=O] |
| 209 | 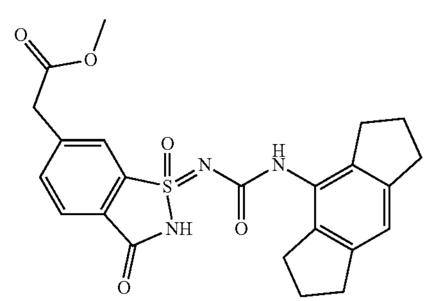 [SMILES: COC(=O)Cc1ccc2c(c1)S(=O)(=NC(=O)Nc1c3c(cc4c1CCC4)CCC3)NC2=O] |

TABLE-continued

| Cmpd # | Structure |
|---|---|
| 210 | (structure) |
| 211 | (structure) |
| 212 | (structure) |
| 213 | (structure) |
| 214 | (structure) |
| 215 | (structure) |
| 216 | (structure) |
| 217 | (structure) |
| 218 | (structure) |
| 219 | (structure) |
| 220 | (structure) |
| 221 | (structure) |
| 222 | (structure) |

| Cmpd # | Structure |
|---|---|
| 223 | 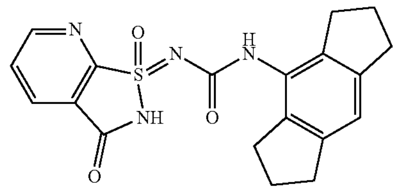 [SMILES: O=C(N=S1(=O)NC(=O)c2cccnc21)Nc1c2c(cc3c1CCC3)CCC2] |
| 224 | 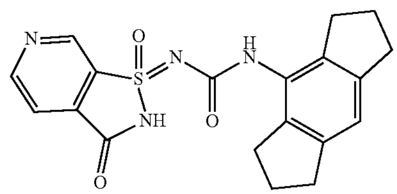 [SMILES: O=C(N=S1(=O)NC(=O)c2ccncc21)Nc1c2c(cc3c1CCC3)CCC2] |
| 225 | 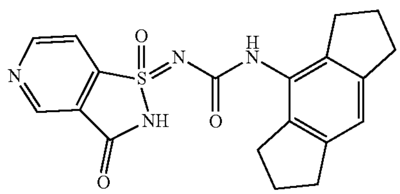 [SMILES: O=C(N=S1(=O)NC(=O)c2cnccc21)Nc1c2c(cc3c1CCC3)CCC2] |
| 226 | 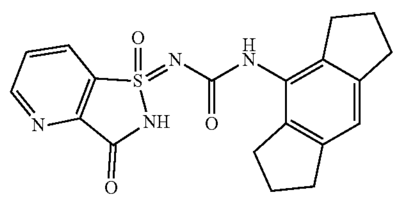 [SMILES: O=C(N=S1(=O)NC(=O)c2ncccc21)Nc1c2c(cc3c1CCC3)CCC2] |
| 227 | 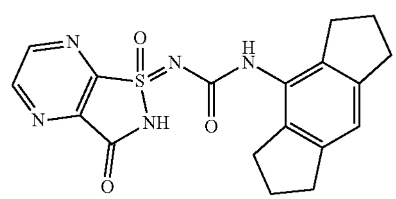 [SMILES: O=C(N=S1(=O)NC(=O)c2nccnc21)Nc1c2c(cc3c1CCC3)CCC2] |
| 228 | 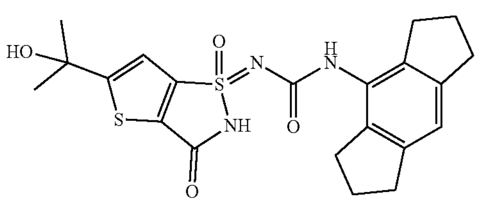 [SMILES: CC(C)(O)c1cc2c(s1)C(=O)NS2(=O)=NC(=O)Nc1c2c(cc3c1CCC3)CCC2] |
| 229 | 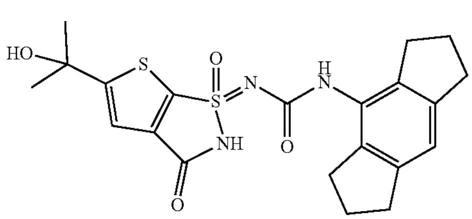 [SMILES: CC(C)(O)c1cc2c(s1)S(=O)(=NC(=O)Nc1c3c(cc4c1CCC4)CCC3)NC2=O] |
| 230 | |
| 231 | |
| 232 | |
| 233 | |
| 234 | |
| 235 | |
| 236 | |

| Cmpd # | Structure |
|---|---|
| 237 | 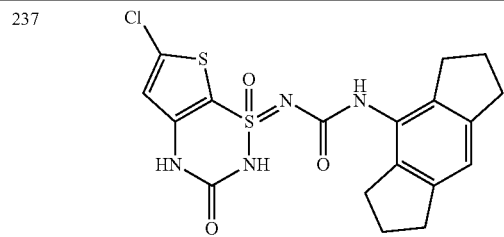 |
| 238 | 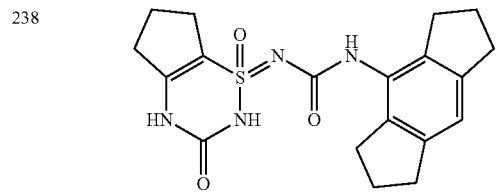 |
| 239 | 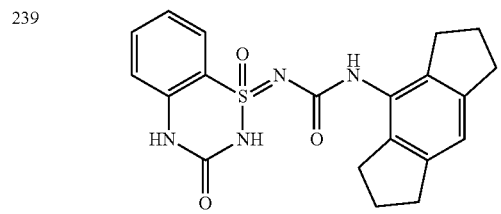 |
| 240 | 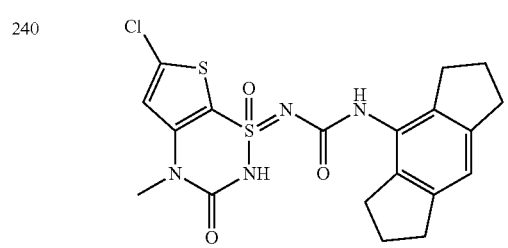 |
| 241 | 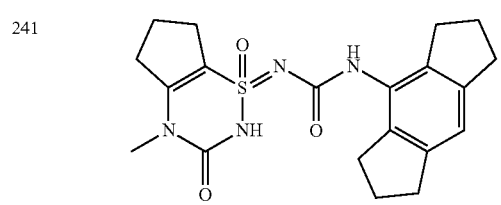 |
| 242 | 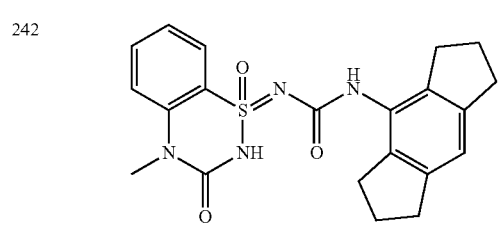 |
| 243 | 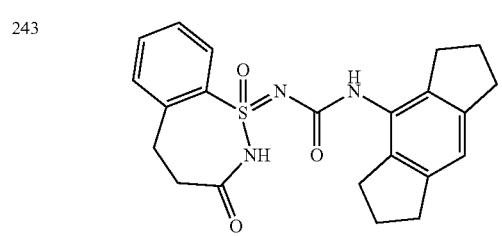 |
| 244 | 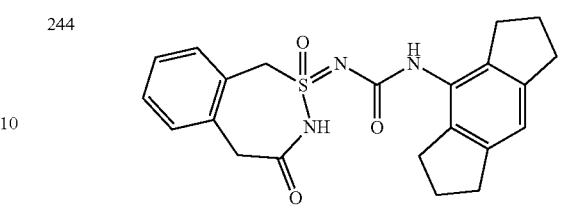 |
| 245 | 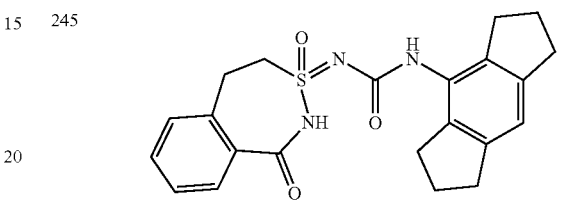 |
| 246 | 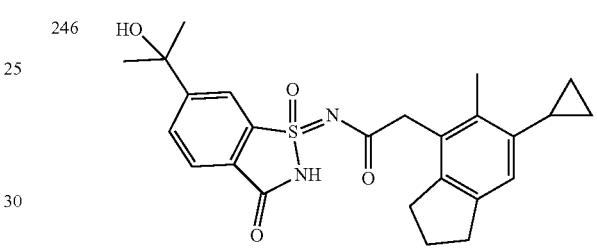 |
| 247 | 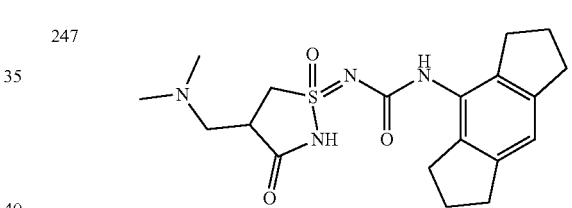 |
| 248 | 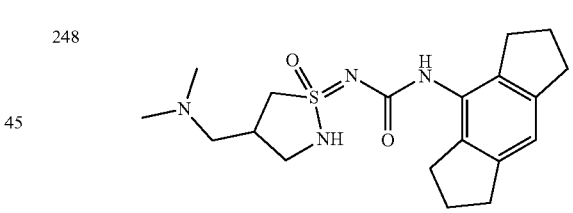 |
| 249 | 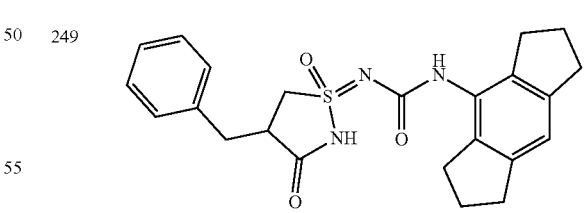 |
| 250 | 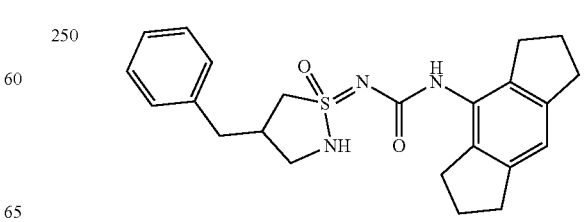 |

| Cmpd # | Structure |
|---|---|
| 251 | 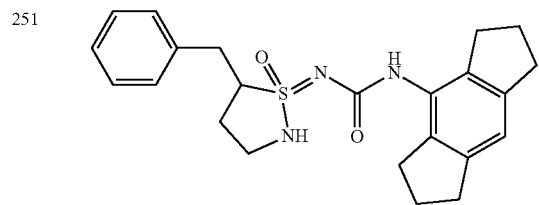 |
| 252 | 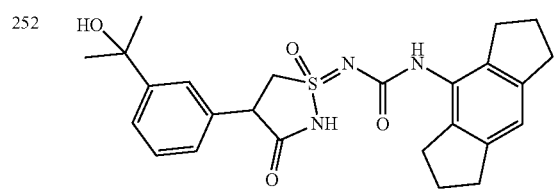 |
| 253 | 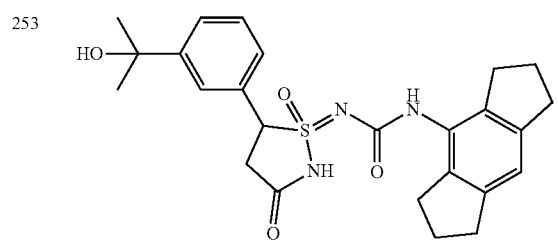 |
| 254 | 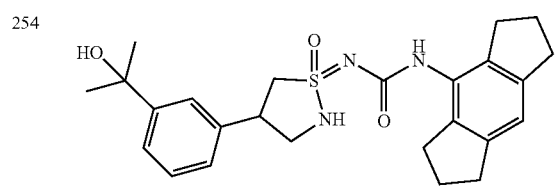 |
| 255 | 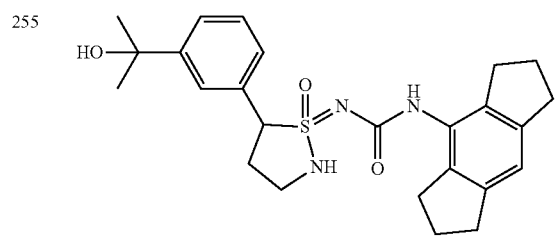 |
| 256 | 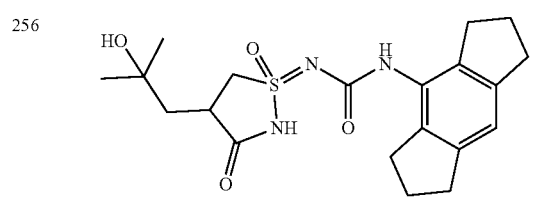 |
| 257 | 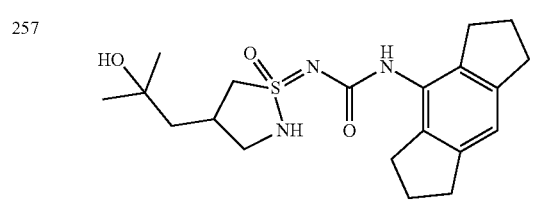 |
| Cmpd # | Structure |
|---|---|
| 258 | 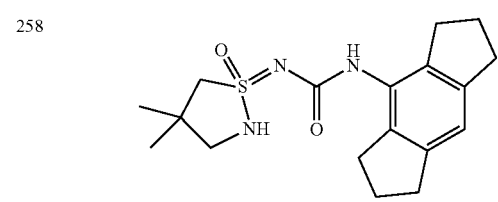 |
| 259 | 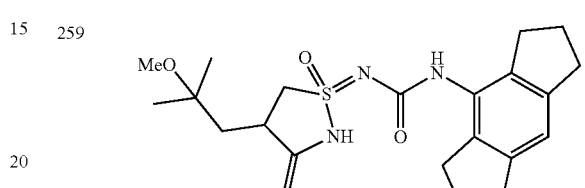 |
| 260 | 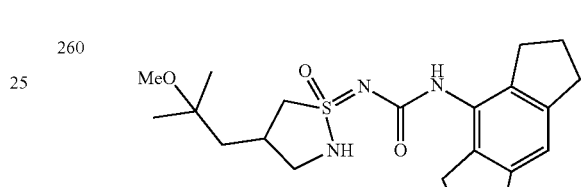 |
| 261 | 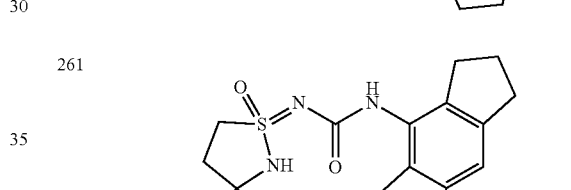 |
| 262 | 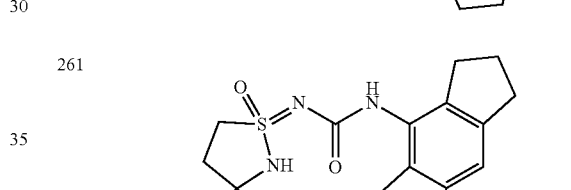 |
| 263 | 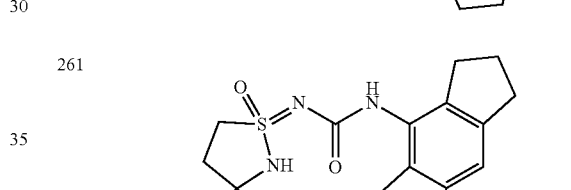 |
| 264 | 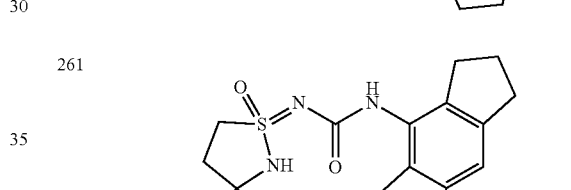 |

-continued

| Cmpd # | Structure |
|---|---|
| 265 | 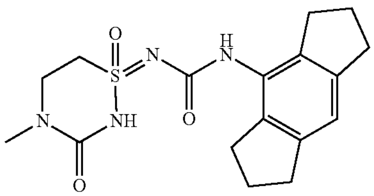 [SMILES: CN1CCS(=O)(=NC(=O)Nc2c3c(cc4c2CCC4)CCC3)NC1=O] |
| 266 | 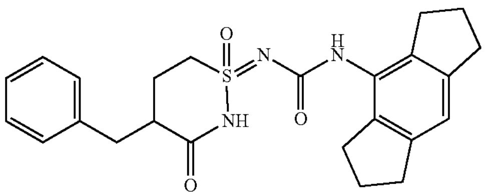 [SMILES: O=C(N=S1(=O)CCC(Cc2ccccc2)C(=O)N1)Nc1c2c(cc3c1CCC3)CCC2] |
| 267 | 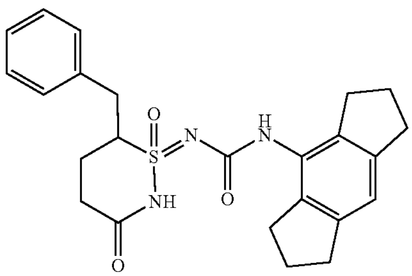 [SMILES: O=C1CCC(Cc2ccccc2)S(=O)(=NC(=O)Nc2c3c(cc4c2CCC4)CCC3)N1] |
| 268 | 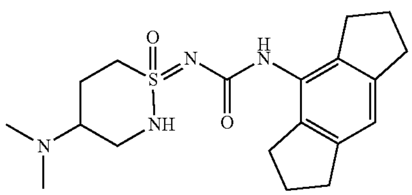 [SMILES: CN(C)C1CCS(=O)(=NC(=O)Nc2c3c(cc4c2CCC4)CCC3)NC1] |
| 269 | 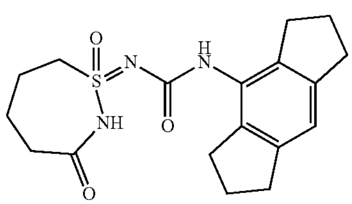 [SMILES: O=C1CCCCS(=O)(=NC(=O)Nc2c3c(cc4c2CCC4)CCC3)N1] |
| 270 | 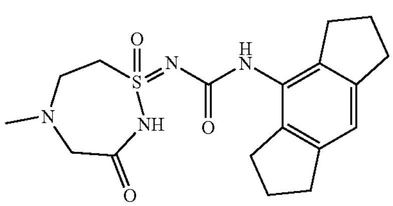 [SMILES: CN1CCS(=O)(=NC(=O)Nc2c3c(cc4c2CCC4)CCC3)NC(=O)C1] |
| 271 | 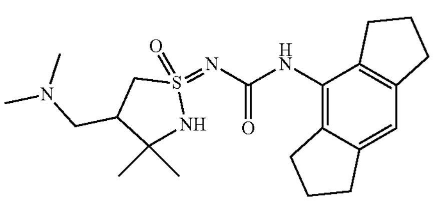 [SMILES: CN(C)CC1CS(=O)(=NC(=O)Nc2c3c(cc4c2CCC4)CCC3)NC1(C)C] |
| 272 | |
| 273 | |
| 274 | |
| 275 | |
| 276 | |
| 277 | |
| 278 | |

367
-continued

| Cmpd # | Structure |
|---|---|
| 279 | 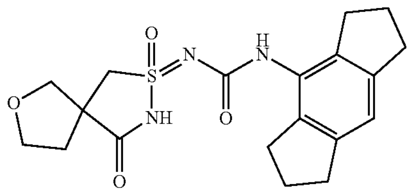 [SMILES: O=C(N=S1(=O)CC2(CCOC2)C(=O)N1)Nc1c2c(cc3c1CCC3)CCC2] |
| 280 | 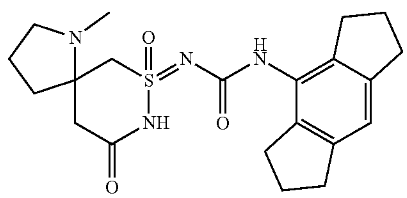 [SMILES: CN1CCCC12CC(=O)NS(=O)(=NC(=O)Nc1c3c(cc4c1CCC4)CCC3)C2] |
| 281 | 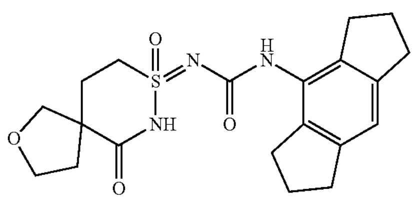 [SMILES: O=C(N=S1(=O)CCC2(CCOC2)C(=O)N1)Nc1c2c(cc3c1CCC3)CCC2] |
| 282 | 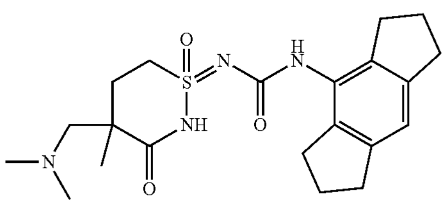 [SMILES: CN(C)CC1(C)CCS(=O)(=NC(=O)Nc2c3c(cc4c2CCC4)CCC3)NC1=O] |
| 283 | 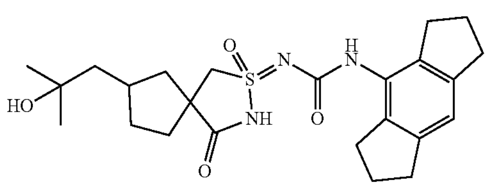 [SMILES: CC(C)(O)CC1CCC2(C1)CS(=O)(=NC(=O)Nc1c3c(cc4c1CCC4)CCC3)NC2=O] |
| 284 | 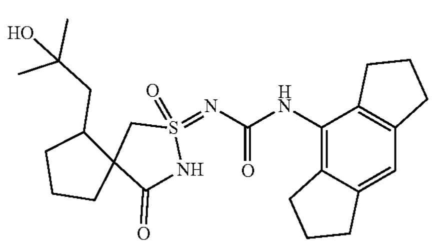 [SMILES: CC(C)(O)CC1CCCC12CS(=O)(=NC(=O)Nc1c3c(cc4c1CCC4)CCC3)NC2=O] |
| 285 | 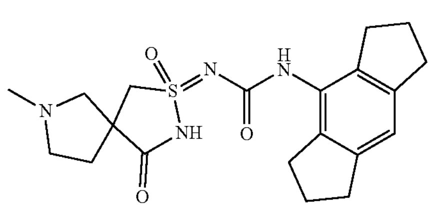 [SMILES: CN1CCC2(C1)CS(=O)(=NC(=O)Nc1c3c(cc4c1CCC4)CCC3)NC2=O] |

368
-continued

| Cmpd # | Structure |
|---|---|
| 286 | 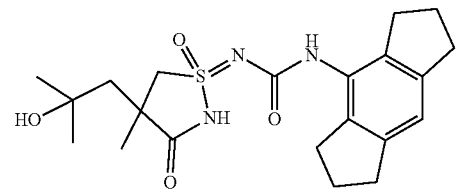 [SMILES: CC(C)(O)CC1(C)CS(=O)(=NC(=O)Nc2c3c(cc4c2CCC4)CCC3)NC1=O] |

| Cmpd # | Structure |
|---|---|
| 102a | 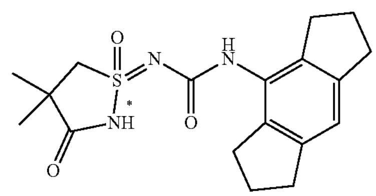 [SMILES: CC1(C)CS(=O)(=NC(=O)Nc2c3c(cc4c2CCC4)CCC3)NC1=O] |
| 102b | 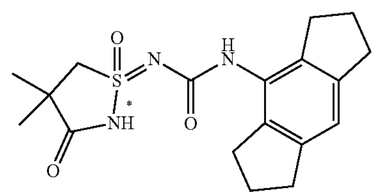 [SMILES: CC1(C)CS(=O)(=NC(=O)Nc2c3c(cc4c2CCC4)CCC3)NC1=O] |
| 103a | 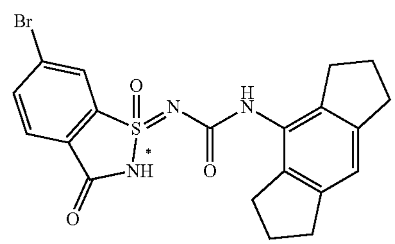 [SMILES: O=C(N=S1(=O)NC(=O)c2ccc(Br)cc21)Nc1c2c(cc3c1CCC3)CCC2] |
| 103b | 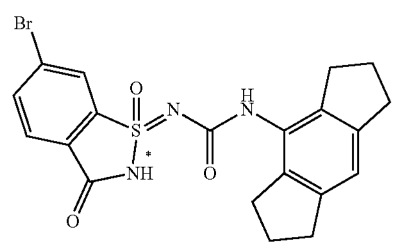 [SMILES: O=C(N=S1(=O)NC(=O)c2ccc(Br)cc21)Nc1c2c(cc3c1CCC3)CCC2] |
| 104a | 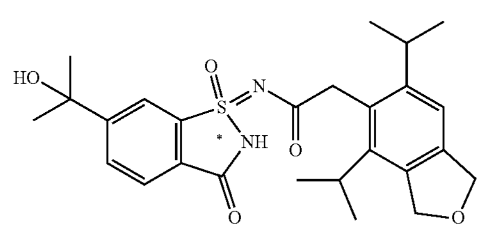 [SMILES: CC(C)c1cc2c(c(C(C)C)c1CC(=O)N=S1(=O)NC(=O)c3ccc(C(C)(C)O)cc31)COC2] |

-continued

| Cmpd # | Structure |
|---|---|
| 113a | 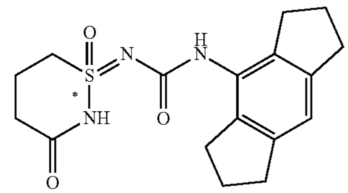 [SMILES: O=C1CCCS(=O)(=NC(=O)Nc2c3c(cc4c2CCC4)CCC3)N1] |
| 115a | 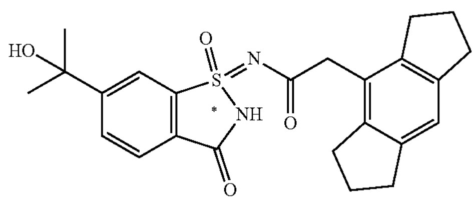 [SMILES: CC(C)(O)c1ccc2c(c1)S(=O)(=NC(=O)Cc1c3c(cc4c1CCC4)CCC3)NC2=O] |
| 132 | 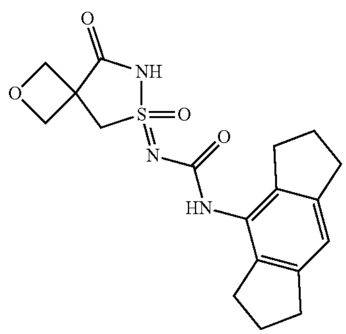 [SMILES: O=C(N=S1(=O)CC2(COC2)C(=O)N1)Nc1c2c(cc3c1CCC3)CCC2] |
| 132a | 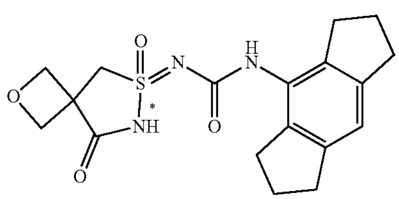 [SMILES: O=C(N=S1(=O)CC2(COC2)C(=O)N1)Nc1c2c(cc3c1CCC3)CCC2] |
| 132b | 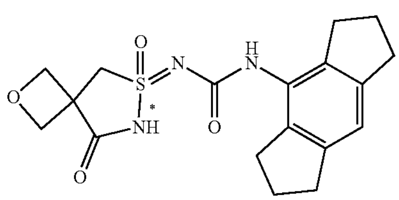 [SMILES: O=C(N=S1(=O)CC2(COC2)C(=O)N1)Nc1c2c(cc3c1CCC3)CCC2] |
| 133 | 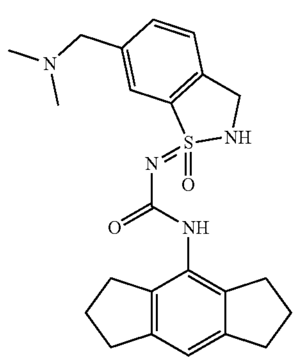 [SMILES: CN(C)Cc1ccc2c(c1)S(=O)(=NC(=O)Nc1c3c(cc4c1CCC4)CCC3)NC2] |

-continued

| Cmpd # | Structure |
|---|---|
| 133a | |
| 133b | |
| 134 | |
| 134a | |
| 134b | |

| Cmpd # | Structure |
|---|---|
| 135 | |
| 136 | |
| 137 | |
| 138 | |
| 139a | 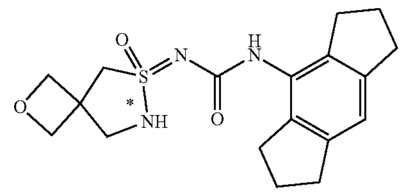 [SMILES: O=C(N=S1(=O)CC2(CN1)COC2)Nc1c2c(cc3c1CCC3)CCC2] |
| 139b | 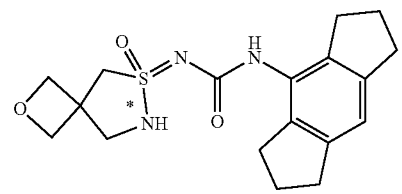 [SMILES: O=C(N=S1(=O)CC2(CN1)COC2)Nc1c2c(cc3c1CCC3)CCC2] |
| 204 | 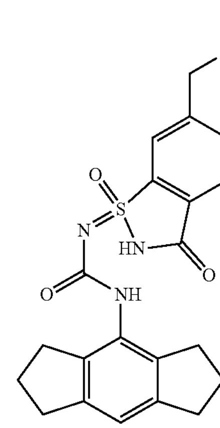 |
| 207 | 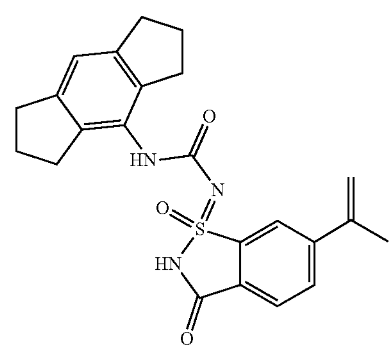 [SMILES: C=C(C)c1ccc2c(c1)S(=O)(=NC(=O)Nc1c3c(cc4c1CCC4)CCC3)NC2=O] |
| 208 | 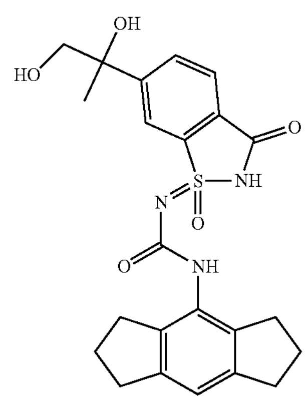 [SMILES: CC(O)(CO)c1ccc2c(c1)S(=O)(=NC(=O)Nc1c3c(cc4c1CCC4)CCC3)NC2=O] |

TABLE-continued
| Cmpd # | Structure |
|---|---|
| 208a | 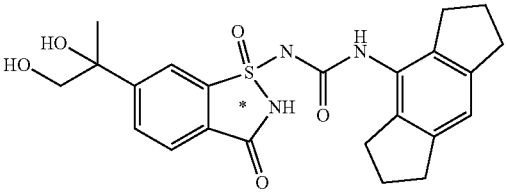 |
| 208b | 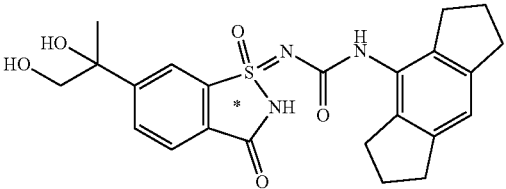 [SMILES: CC(O)(CO)c1ccc2c(c1)S(=O)(=NC(=O)Nc1c3c(cc4c1CCC4)CCC3)NC2=O] |
| 209 | 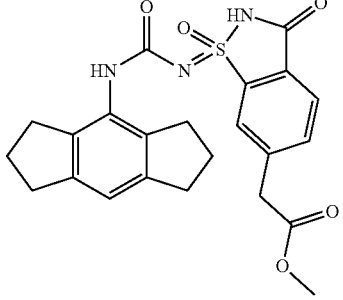 |
| 211 | 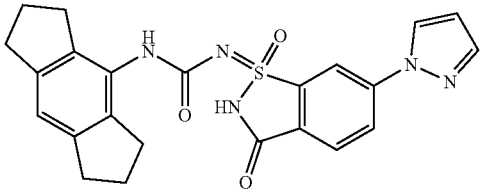 [SMILES: O=C(N=S1(=O)NC(=O)c2ccc(-n3cccn3)cc21)Nc1c2c(cc3c1CCC3)CCC2] |
| 211a | 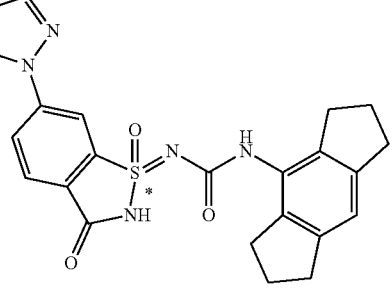 |
| 211b | 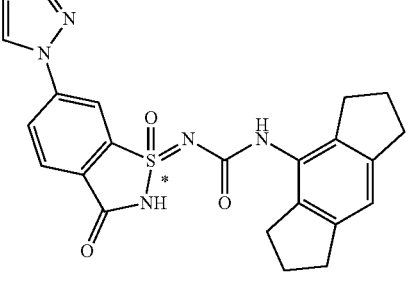 |
| 213 | 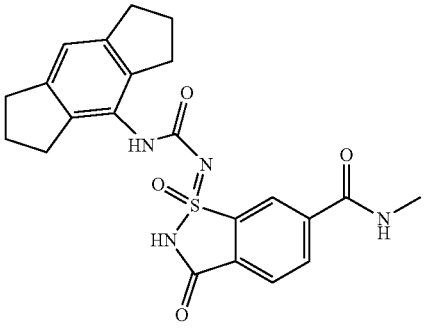 [SMILES: CNC(=O)c1ccc2c(c1)S(=O)(=NC(=O)Nc1c3c(cc4c1CCC4)CCC3)NC2=O] |
| 214 | 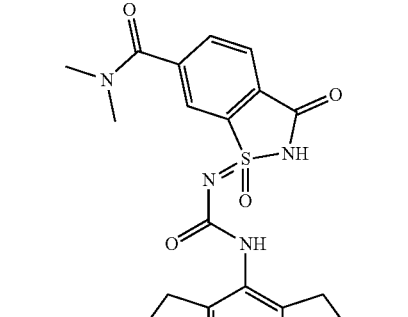 |
| 216 | 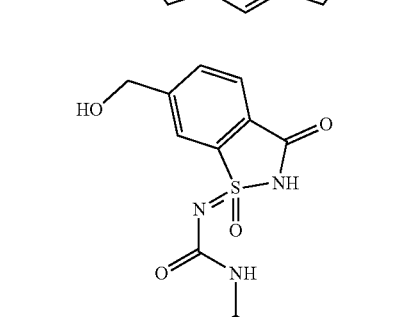 |
| 217 | 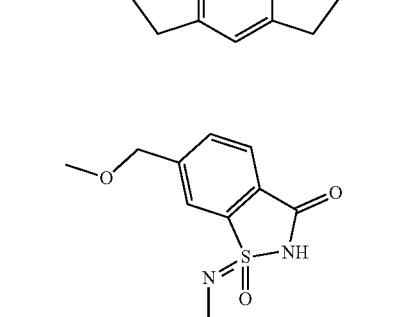 |

| Cmpd # | Structure |
|---|---|
| 218 | 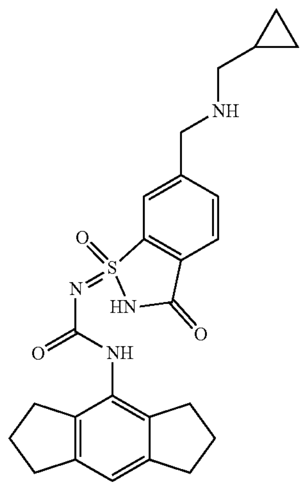 [SMILES: O=C(N=S1(=O)NC(=O)c2ccc(CNCC3CC3)cc21)Nc1c2c(cc3c1CCC3)CCC2] |
| 223 | 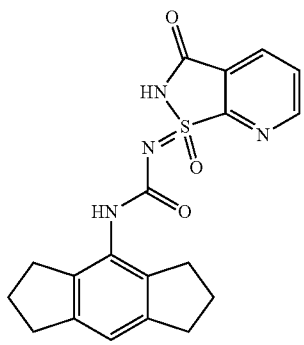 [SMILES: O=C(N=S1(=O)NC(=O)c2cccnc21)Nc1c2c(cc3c1CCC3)CCC2] |
| 223a | 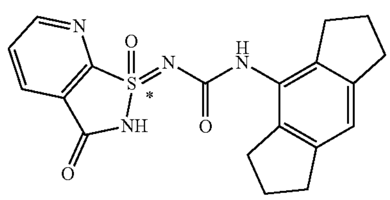 [SMILES: O=C(N=S1(=O)NC(=O)c2cccnc21)Nc1c2c(cc3c1CCC3)CCC2] |
| 223b | |
| 229 | |
| 249a | |

17. A pharmaceutical composition comprising a compound or salt as claimed in claim 1 and one or more pharmaceutically acceptable excipients.

18. A method for modulating NLRP3 activity, the method comprising contacting a subject with an effective amount of a compound as claimed in claim 1.

19. The method of claim 18, wherein the modulating comprises antagonizing NLRP3, in vivo, and the subject is a human.

20. The method of claim 19, further comprising administering a therapeutically effective amount of an anti-TNFα agent to the subject.

* * * * *

UNITED STATES PATENT AND TRADEMARK OFFICE
CERTIFICATE OF CORRECTION

| | | |
|---|---|---|
| PATENT NO. | : 12,134,611 B2 | Page 1 of 1 |
| APPLICATION NO. | : 17/292887 | |
| DATED | : November 5, 2024 | |
| INVENTOR(S) | : Katz et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 731 days.

Signed and Sealed this
Twenty-second Day of July, 2025

Coke Morgan Stewart
*Acting Director of the United States Patent and Trademark Office*